United States Patent
Graham et al.

(10) Patent No.: US 12,215,124 B2
(45) Date of Patent: *Feb. 4, 2025

(54) FLUORINATED NUCLEOTIDES AND USES THEREOF

(71) Applicant: SINGULAR GENOMICS SYSTEMS, INC., La Jolla, CA (US)

(72) Inventors: Ronald Graham, Carlsbad, CA (US); Andrew Spaventa, La Jolla, CA (US); Eli Glezer, Del Mar, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 1128 days.

This patent is subject to a terminal disclaimer.

(21) Appl. No.: 16/969,879

(22) PCT Filed: Feb. 20, 2019

(86) PCT No.: PCT/US2019/018810
§ 371 (c)(1),
(2) Date: Aug. 13, 2020

(87) PCT Pub. No.: WO2019/164977
PCT Pub. Date: Aug. 29, 2019

(65) Prior Publication Data
US 2022/0298201 A1 Sep. 22, 2022

Related U.S. Application Data

(60) Provisional application No. 62/633,505, filed on Feb. 21, 2018.

(51) Int. Cl.
*C07H 21/04* (2006.01)
*C12Q 1/6869* (2018.01)

(52) U.S. Cl.
CPC ........... *C07H 21/04* (2013.01); *C12Q 1/6869* (2013.01); *C12Q 2600/16* (2013.01)

(58) Field of Classification Search
CPC ... C07H 21/04; C12Q 1/6869; C12Q 2600/16
See application file for complete search history.

(56) References Cited

U.S. PATENT DOCUMENTS

| | | | |
|---|---|---|---|
| 5,034,506 A | 7/1991 | Summerton et al. | |
| 5,235,033 A | 8/1993 | Summerton et al. | |
| 5,804,386 A | 9/1998 | Ju | |
| 5,814,454 A | 9/1998 | Ju | |
| 5,876,936 A | 3/1999 | Ju | |
| 5,952,180 A | 9/1999 | Ju | |
| 6,046,005 A | 4/2000 | Ju et al. | |
| 6,485,944 B1 | 11/2002 | Church et al. | |
| 6,627,748 B1 | 9/2003 | Ju et al. | |
| 6,664,079 B2 | 12/2003 | Ju et al. | |
| 7,074,597 B2 | 7/2006 | Ju | |
| 7,279,563 B2 | 10/2007 | Kwiatkowski | |
| 7,345,159 B2 | 3/2008 | Ju et al. | |
| 7,414,116 B2 | 8/2008 | Milton et al. | |
| 7,541,444 B2 | 6/2009 | Milton et al. | |
| 7,566,537 B2 | 7/2009 | Barnes et al. | |
| 7,622,279 B2 | 11/2009 | Ju | |
| 7,635,578 B2 | 12/2009 | Ju et al. | |
| 7,713,698 B2 | 5/2010 | Ju et al. | |
| 7,771,973 B2 | 8/2010 | Milton et al. | |
| 7,790,869 B2 | 9/2010 | Ju et al. | |
| 7,883,869 B2 | 2/2011 | Ju et al. | |
| 7,982,029 B2 | 7/2011 | Ju et al. | |
| 8,071,739 B2 | 12/2011 | Milton et al. | |
| 8,088,575 B2 | 1/2012 | Ju et al. | |
| 8,114,973 B2 | 2/2012 | Siddiqi et al. | |
| 8,298,792 B2 | 10/2012 | Ju et al. | |
| 8,399,188 B2 | 3/2013 | Zhao et al. | |
| 8,597,881 B2 | 12/2013 | Milton et al. | |
| 8,796,432 B2 | 8/2014 | Ju et al. | |
| 8,889,348 B2 | 11/2014 | Ju | |
| 8,900,810 B2 | 12/2014 | Gordon et al. | |
| 9,115,163 B2 | 8/2015 | Ju et al. | |
| 9,121,060 B2 | 9/2015 | Milton et al. | |
| 9,121,062 B2 | 9/2015 | Balasubramanian et al. | |
| 9,133,511 B2 | 9/2015 | Ju et al. | |
| 9,169,510 B2 | 10/2015 | Ju et al. | |
| 9,175,342 B2 | 11/2015 | Ju et al. | |
| 9,255,292 B2 | 2/2016 | Ju et al. | |
| 9,297,042 B2 | 3/2016 | Ju et al. | |
| 9,388,464 B2 | 7/2016 | Milton et al. | |
| 9,410,200 B2 | 8/2016 | Balasubramanian et al. | |
| 9,528,151 B2 | 12/2016 | Ju et al. | |
| 9,593,373 B2 | 3/2017 | Liu et al. | |
| 9,624,539 B2 | 4/2017 | Ju et al. | |

(Continued)

FOREIGN PATENT DOCUMENTS

EP  2876166 A1  5/2015
EP  2876166 B1  5/2015

(Continued)

OTHER PUBLICATIONS

Chu et al. J. Fluorine Chem. 2008, 129, 743-766 (Year: 2008).*
Liu et al. WO-2019071474-A1 English machine translation (online) retrieved on Jan. 22, 2024 from <https://patents.google.com/> (Year: 2024).*
Extended European Examination Report mailed on Aug. 30, 2023, for EP Application No. 21793126.0, PCT/US2021/028839, 8 pages.
Bentley, D.R. et al. (Nov. 6, 2008). "Accurate whole human genome sequencing using reversible terminator chemistry," *Nature* 456(7218):53-59.
Bergen, K. et al. (Jun. 17, 2013, e-published Jun. 3, 2013). "Structures of KOD and 9°N DNA polymerases complexed with primer template duplex," *Chembiochem* 14(9):1058-1062.

(Continued)

*Primary Examiner* — Amanda L. Aguirre
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are compounds, compositions, and methods of use thereof in the sequencing a nucleic acid.

18 Claims, No Drawings

(56) References Cited

U.S. PATENT DOCUMENTS

| | | |
|---|---|---|
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,190,157 B2 | 1/2019 | Wu et al. |
| 10,240,195 B2 | 3/2019 | Fuller et al. |
| 10,246,479 B2 | 4/2019 | Ju et al. |
| 10,260,094 B2 | 4/2019 | Ju et al. |
| 10,273,539 B2 | 4/2019 | Marma et al. |
| 10,336,785 B2 | 7/2019 | Marma et al. |
| 10,738,072 B1 | 8/2020 | Graham et al. |
| 10,822,653 B1* | 11/2020 | Graham .............. C07F 9/65515 |
| 2002/0015961 A1 | 2/2002 | Kwiatkowski |
| 2002/0064782 A1 | 5/2002 | Shinoki et al. |
| 2003/0027140 A1 | 2/2003 | Ju et al. |
| 2006/0003383 A1 | 1/2006 | Graham |
| 2006/0057565 A1 | 3/2006 | Ju et al. |
| 2006/0188901 A1 | 8/2006 | Barnes et al. |
| 2006/0252038 A1 | 11/2006 | Ju |
| 2007/0009980 A1 | 1/2007 | Graham |
| 2007/0219367 A1 | 9/2007 | Shchepinov et al. |
| 2009/0047699 A1 | 2/2009 | Graham |
| 2011/0014611 A1 | 1/2011 | Ju et al. |
| 2012/0142006 A1 | 6/2012 | Ju et al. |
| 2012/0156671 A1 | 6/2012 | Liu et al. |
| 2012/0156680 A1 | 6/2012 | Ju et al. |
| 2013/0264207 A1 | 10/2013 | Ju et al. |
| 2013/0280700 A1 | 10/2013 | Ju et al. |
| 2015/0037788 A1 | 2/2015 | Ju |
| 2015/0080232 A1 | 3/2015 | Ju et al. |
| 2015/0140561 A1 | 5/2015 | Bergmann et al. |
| 2015/0197800 A1 | 7/2015 | Ju et al. |
| 2015/0368710 A1 | 12/2015 | Fuller et al. |
| 2016/0002721 A1* | 1/2016 | Liu .................... C12Q 1/6869 536/28.5 |
| 2016/0024570 A1 | 1/2016 | Ju et al. |
| 2016/0041179 A1 | 2/2016 | Ju et al. |
| 2016/0108382 A1 | 4/2016 | Efcavitch et al. |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0355541 A1 | 12/2016 | Jain et al. |
| 2016/0369336 A1 | 12/2016 | Stupi et al. |
| 2017/0002407 A1 | 1/2017 | Balasubramanian et al. |
| 2017/0058335 A1 | 3/2017 | Tao et al. |
| 2017/0137869 A1 | 5/2017 | Marma et al. |
| 2017/0166961 A1 | 6/2017 | Liu et al. |
| 2017/0211134 A1 | 7/2017 | Marma et al. |
| 2017/0283451 A1 | 10/2017 | Ju et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0208774 A1 | 7/2018 | Marma et al. |
| 2018/0274024 A1 | 9/2018 | Jul et al. |
| 2018/0274025 A1 | 9/2018 | Marma et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0077726 A1 | 3/2019 | Graham et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |
| 2020/0102609 A1 | 4/2020 | Glezer et al. |

FOREIGN PATENT DOCUMENTS

| | | | |
|---|---|---|---|
| EP | 3356381 A1 | 8/2018 | |
| EP | 3356381 A4 | 8/2018 | |
| WO | WO-02/022883 A1 | 3/2002 | |
| WO | WO-02/029003 A2 | 4/2002 | |
| WO | WO-02/029003 A3 | 4/2002 | |
| WO | WO-2008/037568 A2 | 4/2008 | |
| WO | WO-2008/037568 A3 | 4/2008 | |
| WO | WO-2009/054922 A1 | 4/2009 | |
| WO | WO-2012/083249 A2 | 6/2012 | |
| WO | WO-2012/083249 A3 | 6/2012 | |
| WO | WO-2012/162429 A2 | 11/2012 | |
| WO | WO-2012/162429 A3 | 11/2012 | |
| WO | WO-2013/154999 A2 | 10/2013 | |
| WO | WO-2013/154999 A3 | 10/2013 | |
| WO | WO-2013/191793 A1 | 12/2013 | |
| WO | WO-2014/144883 A1 | 9/2014 | |
| WO | WO-2014/144898 A1 | 9/2014 | |
| WO | WO-2015/123430 A2 | 8/2015 | |
| WO | WO-2015/123430 A3 | 8/2015 | |
| WO | WO-2015/148402 A1 | 10/2015 | |
| WO | WO-2016/063059 A1 | 4/2016 | |
| WO | WO-2016/144973 A1 | 9/2016 | |
| WO | WO-2016/154215 A1 | 9/2016 | |
| WO | WO-2017058953 A1 * | 4/2017 | .............. C07H 19/10 |
| WO | WO-2017/079498 A2 | 5/2017 | |
| WO | WO-2017/079498 A3 | 5/2017 | |
| WO | WO-2017/087887 A1 | 5/2017 | |
| WO | WO-2017/176677 A1 | 10/2017 | |
| WO | WO-2017/176679 A1 | 10/2017 | |
| WO | WO-2017/205336 A1 | 11/2017 | |
| WO | WO-2018/165207 A1 | 9/2018 | |
| WO | WO-2018/183538 A1 | 10/2018 | |
| WO | WO-2019071474 A1 * | 4/2019 | .............. C07H 19/10 |
| WO | WO-2019/105421 A1 | 6/2019 | |
| WO | WO-2019/164977 A1 | 8/2019 | |
| WO | WO-2020/086834 A1 | 4/2020 | |
| WO | WO-2020/146497 A1 | 7/2020 | |

OTHER PUBLICATIONS

Bergseid, M. et al. (Nov. 2000). "Small molecule-based chemical affinity system for the purification of proteins," *Bio Techniques* 29(5):1126-1133.

Binauld, S. et al. (Mar. 14, 2013). "Acid-degradable polymers for drug delivery: a decade of innovation," *Chem Commun* 49(21):2082-2102.

Blackman, M.L. et al. (Oct. 15, 2008, e-published Sep. 18, 2008). "Tetrazine ligation: fast bioconjugation based on inverse-electron-demand Diels-Alder reactivity," *J Am Chem Soc* 130(41):13518-13519.

Debets, M.F. et al. (Oct. 14, 2013, e-published Aug. 23, 2013). "Bioorthogonal labelling of biomolecules: new functional handles and ligation methods," *Org Biomol Chem* 11(38):6439-6455.

Extended European Search Report mailed on May 10, 2019, for EP Patent Application No. 16852516.0, 7 pages.

Fuller, C.W et al. (May 10, 2016, e-published Apr. 18, 2016). "Real-time single-molecule electronic DNA sequencing by synthesis using polymer-tagged nucleotides on a nanopore array," *PNAS USA* 113(19):5233-5238.

Guillier, F. et al. (Jun. 14, 2000). "Linkers and cleavage strategies in solid-phase organic synthesis and combinatorial chemistry," *Chem Rev* 100(6):2091-2158.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27):9145-9150.

Hutter, D. et al. (Nov. 2010). "Labeled nucleoside triphosphates with reversibly terminating aminoalkoxyl groups," *Nucleosides Nucleotides Nucleic Acids* 29(11):879-895.

(56) References Cited

OTHER PUBLICATIONS

Inoue, T. et al. (Nov. 2015). "Synthesis of trifluoromethyl ethers and difluoro(methylthio)methyl ethers by the reaction of dithiocarbonates with IF$_5$-pyridine-HF," *Journal of Fluorine Chemistry* 179:48-52.

International Search Report mailed on Dec. 29, 2016, for PCT Application No. PCT/US2016/054236, filed Sep. 28, 2016, 4 pages.

International Search Report mailed on Jun. 1, 2018 for PCT Application No. PCT/US2018/021219, filed Mar. 6, 2018, 3 pages.

International Search Report mailed on Jun. 25, 2019, for PCT Application No. PCT/US2019/018810, filed Feb. 20, 2019, 4 pages.

International Search Report mailed on Jan. 6, 2020 for PCT Application No. PCT/US2019/57842, filed Oct. 24, 2019, 3 pages.

International Search Report mailed on Apr. 2, 2020 for PCT Application No. PCT/US2020/012595, filed Jan. 7, 2020, 3 pages.

Jewett, J.C. et al. (Mar. 24, 2010). "Rapid Cu-free click chemistry with readily synthesized biarylazacyclooctynones," *J Am Chem Soc* 132(11):3688-3690.

Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.

Kumar, S. et al. (2012, e-published Sep. 21, 2012). "PEG-labeled nucleotides and nanopore detection for single molecule DNA sequencing by synthesis," *Sci Rep* 2:684.

Leriche, G. et al. (Jul. 2010). "Optimization of the Azobenzene Scaffold for Reductive Cleavage by Dithionite; Development of an Azobenzene Cleavable Linker for Proteomic Applications," *Eur J Org Chem* 2010(23):4360-4364.

Marcus-Sekura, C.J. et al. (Aug. 1, 1988). "Techniques for using antisense oligodeoxyribonucleotides to study gene expression," *Anal Biochem* 172(2):289-295.

Needleman, S.B .et al. (Mar. 1970). "A general method applicable to the search for similarities in the amino acid sequence of two proteins," *J Mol Biol* 48(3):443-453.

Pearson, W.R. et al. (Apr. 1988). "Improved tools for biological sequence comparison," *PNAS USA* 85(8):2444-2448.

PubChem Compound Summary for CID 121486816 (Aug. 16, 2016). Located at <https:pubchem.ncbi.nlm.nih.gov/compound/121486816> last visited Apr. 22, 2019, 7 pages.

PubChem Compound Summary for CID 69188114 (Nov. 30, 2012). Located at <https:pubchem.ncbi.nlm.nih.gov/compound/69188114> last visited Apr. 22, 2019, 7 pages.

Rathod, K.M. et al. (2013). "Synthesis and Antimicrobial Activity of Azo Compounds Containing m-Cresol Moiety," *Chem Sci Trans* 2(1):25-28.

Rosenblum, B.B. et al. (Nov. 15, 1997). "New dye-labeled terminators for improved DNA sequencing patterns," *Nucleic Acids Res* 25(22):4500-4504.

Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," *PNAS USA* 102(17):5932-5937.

Schumacher, W. et al. (Jun. 16, 1997). "Redox chemistry of cobalamin and iron-sulfur cofactors in the tetrachloroethene reductase of *Dehalobacter restrictus*," *FEBS Lett* 409(3):421-425.

Shenoi, R.A. et al. (Sep. 12, 2012, e-published Aug. 30, 2012). "Branched multifunctional polyether polyketals: variation of ketal group structure enables unprecedented control over polymer degradation in solution and within cells," *J Am Chem Soc* 134(36):14945-14957.

Smith T.F. et al. (Dec. 1981). "Comparison of biosequences," *Advances in Applied Mathematics* 2(4):482-489.

Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11):5281-5285.

Švagera, Z. et al. (Mar. 2012, e-published Feb. 15, 2012). "Study of disulfide reduction and alkyl chloroformate derivatization of plasma sulfur amino acids using gas chromatography-mass spectrometry," *Anal Bioanal Chem* 402(9):2953-2963.

Uhlmann, E. et al. (Jun. 1990). "Antisense oligonucleotides: a new therapeutic principle," *Chemical Reviews* 90(4):543-584.

Weintraub, H.M. (Jan. 1990). "Antisense RNA and DNA," *Sci Am* 262(1):40-46.

Written Opinion mailed on Dec. 29, 2016, for PCT Application No. PCT/US2016/054236, filed Sep. 28, 2016, 4 pages.

Written Opinion mailed on Jun. 1, 2018 for PCT Application No. PCT/US2018/021219, filed Mar. 6, 2018, 9 pages.

Written Opinion mailed on Jun. 25, 2019, for PCT Application No. PCT/US2019/018810, filed Feb. 20, 2019, 5 pages.

Written Opinion mailed on Jan. 6, 2020 for PCT Application No. PCT/US2019/57842, filed Oct. 24, 2019, 11 pages.

Written Opinion mailed on Apr. 2, 2020 for PCT Application No. PCT/US2020/012595, filed Jan. 7, 2020, 3 pages.

Wu, J. et al. (Oct. 16, 2007, e-published Oct. 8, 2007). "3'-O-modified nucleotides as reversible terminators for pyrosequencing," *PNAS USA* 104(42):16462-16467.

Zhu, Z. et al. (Aug. 25, 1994). "Directly labeled DNA probes using fluorescent nucleotides with different length linkers," *Nucleic Acids Res* 22(16):3418-3422.

\* cited by examiner

FLUORINATED NUCLEOTIDES AND USES THEREOF

CROSS-REFERENCES TO RELATED APPLICATIONS

This application is the national stage filing under 35 U.S.C. § 371 of International Application No. PCT/US2019/018810 filed Feb. 20, 2019, which claims the benefit of U.S. Provisional Application No. 62/633,505, filed Feb. 21, 2018, which are incorporated herein by reference in their entirety and for all purposes.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Currently, the widely used high-throughput SBS technology (Bentley D R, et al. Nature, 2008, 456, 53-59) determines DNA sequences during the polymerase reaction using cleavable fluorescently labeled nucleotide reversible terminator (NRT) sequencing chemistry that has been previously developed (Ju J et al. 2003, U.S. Pat. No. 6,664,079; Ju J et al. Proc Natl Acad Sci USA, 2006, 103, 19635-19640). These cleavable fluorescent NRTs were designed based on the rationale that each of the nucleotides is modified by attaching a unique cleavable fluorophore to the specific location of the base and capping the 3'-OH group with a small reversible-blocking moiety so they are still recognized by DNA polymerase as substrates. A disadvantage of the abovementioned SBS approach is the production of a small molecular "scar" (e.g., a propargylamine or a modified propargylamino moiety) at the nucleotide base after cleavage of the fluorescent dye from the incorporated nucleotide in the polymerase reaction. The growing DNA chain accumulates these scars through each successive round of SBS. At some point, the residual scars may be significant enough to interfere with the DNA double helix structure, thereby negatively affecting DNA polymerase recognition and consequently limiting the read length. Accumulated research efforts indicated that the major challenge for this approach is that DNA polymerase has difficulty accepting 3'-O bulky-dye-modified nucleotides as substrates, because the 3' position on the deoxyribose of the nucleotides is very close to the amino acid residues in the active site of the DNA polymerase while in the ternary complex formed by the polymerase with the complementary nucleotide and the primed template.

Accordingly, there is a need for the use in efficient, scarless SBS, and synthesis of, 3'-O modified nucleotides and nucleosides that are effectively recognized as substrates by DNA polymerases, are efficiently and accurately incorporated into growing DNA chains during SBS, have a 3'-O blocking group that is cleavable under mild conditions wherein cleavage results in a 3'-OH, and permit long SBS read-lengths. Disclosed herein, inter alia, are solutions to these and other problems in the art.

BRIEF SUMMARY

In an aspect is a nucleotide analogue of the formula:

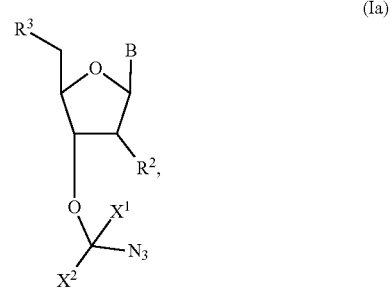

(Ia)

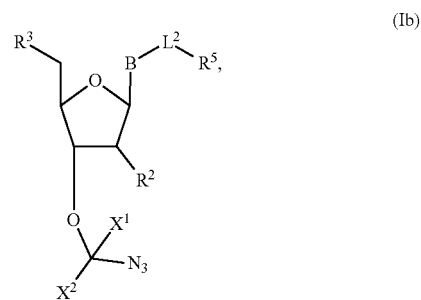

(Ib)

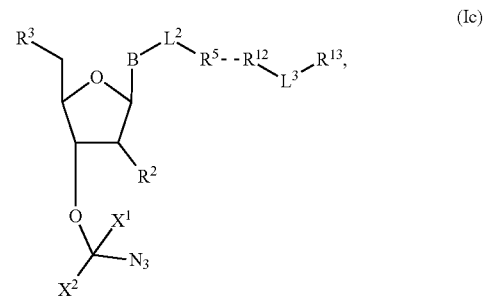

(Ic)

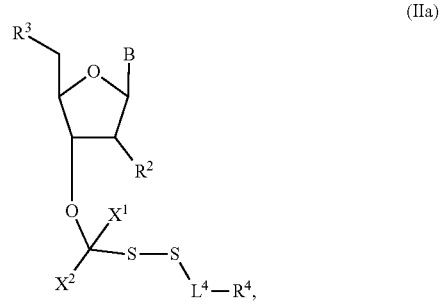

(IIa)

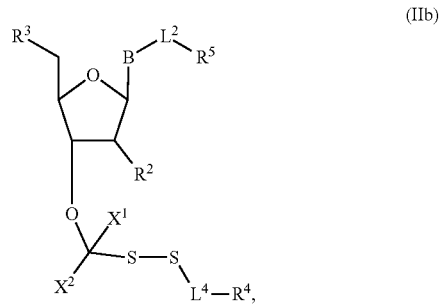

(IIb)

-continued

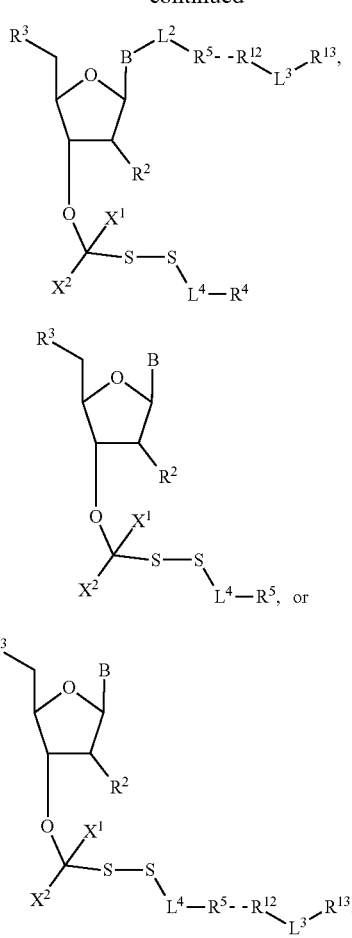

(IIc)

(IIIa)

(IIIb)

The symbol " ---- " is a non-covalent bond. The symbol B is a base or analogue thereof. $L^2$ is a covalent linker (e.g., a cleavable linker). $L^3$ is a covalent linker. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^2$ is hydrogen or —$OR^{2A}$, wherein $R^{2A}$ is hydrogen or a polymerase-compatible cleavable moiety. $R^3$ is —OH, monophosphate, or polyphosphate or a nucleic acid. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, an anchor moiety, or affinity anchor moiety. $R^{12}$ is a complementary affinity anchor moiety binder. $R^{13}$ is a detectable label. The symbols $X^1$ and $X^2$ are independently hydrogen, halogen, —$N_3$, or —CN, wherein at least wherein at least one of $X^1$ or $X^2$ is halogen, —$N_3$, or —CN.

In an aspect is provided a nucleic acid polymerase complex, wherein the nucleic acid polymerase is bound to a nucleotide analogue as described herein, including embodiments.

In another aspect is provided a method for sequencing a nucleic acid, including: (i) incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues include a unique detectable label; and (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues is a nucleotide analogue described herein, including embodiments.

In an aspect is provided a method of incorporating a nucleotide analogue into a primer, the method including combining a polymerase, a primer hybridized to a nucleic acid template and a nucleotide analogue within a reaction vessel and allowing the polymerase to incorporate the nucleotide analogue into the primer thereby forming an extended primer, wherein the nucleotide analogue is of the structure as described herein, including embodiments.

In an aspect is provided a method of incorporating a nucleotide analogue into a primer, the method including combining a polymerase, a primer hybridized to a nucleic acid template and a nucleotide analogue within a reaction vessel and allowing the polymerase to incorporate the nucleotide analogue into the primer thereby forming an extended primer, wherein the nucleotide analogue is a nucleotide analogue described herein, including embodiments.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R'', —OR', —SR', and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

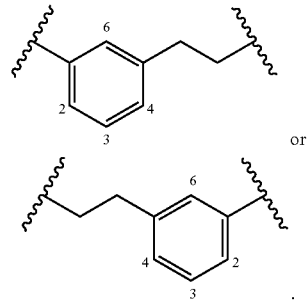

or

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRS₂R', —NR'NR"R'", —ONR'R", —NR'C(O)NR"NR'"R"", —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —R', —N₃, —CH(Ph)₂, fluoro($C_1$-$C_4$)alkoxy, and fluoro($C_1$-$C_4$)alkyl, —NR'SO₂R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCH Br₂, —OCHI₂, —OCHF₂, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(b) alkyl, heteroalkyl, cycloalkyl, heterocycloalkyl, aryl, heteroaryl, substituted with at least one substituent selected from: oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_5$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on a R substituent or L linker or an "openly substituted" R substituent or L linker), the recited R substituent or L linker may, in embodiments, be substituted with one or more "first substituent group(s)" as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$ respectively. In turn, each first substituent group (e.g. $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g. $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L302}$, $R^{L4.2}$, $R^{L5.2}$ ... $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g. $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g. $R^{1.3}$, $R^{2.3}$, $R^{3.3}$, $R^{4.3}$, $R^{5.3}$ ... $R^{100.3}$; $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different.

$R^{WW}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_2$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, $-CX^{WW.2}_3$, $-CHX^{WW.2}_2$, $-CH_2X^{WW.2}$, $-OCX^{WW.2}_3$, $-OCH_2X^{WW.2}$, $-OCHX^{WW.2}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently $-F$, $-Cl$, $-Br$, or $-I$.

$R^{WW.3}$ is independently oxo, halogen, $-CX^{WW.3}_3$, $-CHX^{WW.3}_2$, $-CH_2X^{WW.3}$, $-OCX^{WW.3}_3$, $-OCH_2X^{WW.3}$, $-OCHX^{WW.3}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently $-F$, $-Cl$, $-Br$, or $-I$.

Where two different $R^{WW}$ substituents are joined together to form an openly substituted ring (e.g. substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first ring substituent group is optionally different. Each second ring substituent group is optionally different. Each third ring substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ Bare optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, $-CX^{LWW.1}_3$, $-CHX^{LWW.1}_2$, $-CH_2X^{LWW.1}$, $-OCX^{LWW.1}_3$ $-OCH_2X^{LWW.1}$, $-OCHX^{LWW.1}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $-CX^{LWW.1}_3$, $-CHX^{LWW.1}_2$, $-CH_2X^{LWW.1}$, $-OCX^{LWW.1}_3$ $-OCH_2X^{LWW.1}$, $-OCHX^{LWW.1}_2$ $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently $-F$, $-Cl$, $-Br$, or $-I$.

$R^{LWW.2}$ is independently oxo, halogen, $-CX^{LWW.2}_3$, $CHX^{LWW.2}_2$, $CH_2X^{LWW.2}$, $-OCX^{LWW.2}_3$ $-OCH_2X^{LWW.2}$, $-OCHX^{LWW.2}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $-CX^{LWW.2}_3$, $-CHX^{LWW.2}_2$, $-CH_2X^{LWW.2}$, $-OCX^{LWW.2}_3$, $-OCH_2X^{LWW.2}$, $-OCHX^{LWW.2}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}_3$, —$CHX^{LWW.3}_2$, —$CH_2X^{LWW.3}$, —$OCX^{LWW.3}_3$, —$OCH_2X^{LWW.3}$, —$OCHX^{LWW.3}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}_3$, —$CHX^{WW}_2$, —$CH_2X^{WW}$, —$OCX^{WW}_3$, —$OCH_2X^{WW}$, —$OCHX^{WW}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_2$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). Again, "WW" represents the stated superscript number of the subject R group (e.g. 1, 2, 3, 1A, 2A, 3A, 1B, 2B, 3B, etc.). $R^{WW.1}$, as well as $X^{WW}$, $R^{WW.2}$, and $R^{WW.3}$, are as defined above.

In the event that any L linker group recited in a claim or chemical formula description set forth herein (i.e. an $L^{WW}$ substituent) is not explicitly defined, then that L group ($L^{WW}$ group) is herein defined as independently —O—, —NH—, —COO—, —CONH—, —S—, —$SO_2NH$—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$ is as defined above.

For example, an $R^{WW}$ substituent may be substituted with a first substituent group $R^{WW.1}$. When $R^{WW}$ is phenyl, the said phenyl group is optionally substituted by one or more $R^{WW.1}$. When $R^{WW.1}$ is substituted alkyl (e.g., methyl), the said alkyl group is optionally substituted by one or more $R^{WW.2}$. The compound that could be formed may include, but are not limited to, the compounds depicted below wherein $R^{WW.2}$ is optionally substituted cyclopentyl, optionally substituted pyridyl, $NH_2$, or optionally substituted benzoxazolyl, wherein each such optionally substituted $R^{WW.2}$ substituent group is optionally substituted with one or more $R^{WW.3}$. By way of non-limiting examples, such $R^{WW.3}$ substituents could be independently unsubstituted alkyl (e.g., ethyl), halogen (e.g., fluoro), or OH, as shown below.

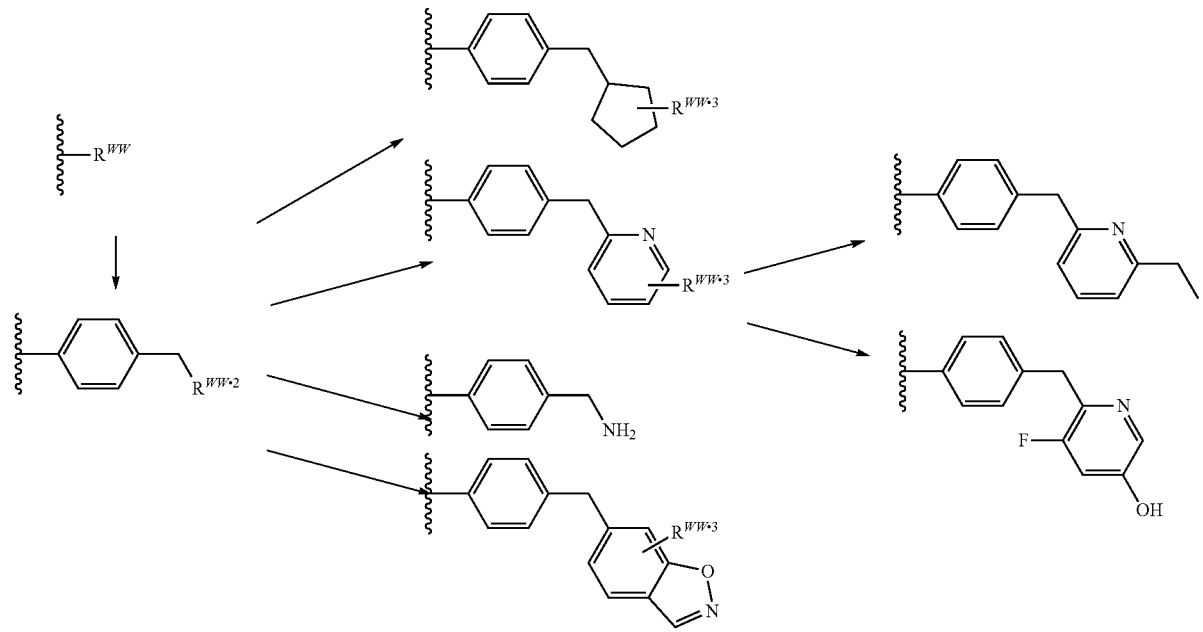

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable compound" or "detectable label" or "detectable moiety" is a composition detectable by spectroscopic, photochemical, biochemical, immunochemical, chemical, magnetic resonance imaging, or other physical means. For example, detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158 1}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$E $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy2 moeity, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, FluoroEmerald moiety, Nissl moiety, Fluorescein dextran pH 8.0 moiety, Rhodamine Green moiety, 5-(and-6)-Carboxy-2',7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(µ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thiol2, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kutzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst- 33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO—Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*-Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DUPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH—CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DUPE, Texas Red-X, ThiolTracker Violet, Thionin acetate, TMRE, TO-PRO-1, TO-PRO-3, Toluene, Topaz (Tsienl998), TOTO-1, TOTO-3, Tris(2,2-Bipyridyl)Ruthenium(II) chloride. Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreenl, or ZsYellowl.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e. cyanine 7 or Cy7).

Descriptions of nucleotide analogues of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "streptavidin" and "" refer to a tetrameric protein (including homologs, isoforms, and functional fragments thereof) capable of binding biotin. The term includes any recombinant or naturally-occurring form of streptavidin variants thereof that maintain streptavidin activity (e.g. within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples.

"Nucleic acid" refers to nucleotides (e.g., deoxyribonucleotides or ribonucleotides) and polymers thereof in either single-, double- or multiple-stranded form, or complements thereof, or nucleosides (e.g., deoxyribonucleosides or ribonucleosides). In embodiments, "nucleic acid" does not include nucleosides. The terms "polynucleotide," "oligonucleotide," "oligo," or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. Nucleosides may be modified at the base and/or and the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. In embodiments, "nucleic acid" or "oligonucleotide" or "polynucleotide" or grammatical equivalents used herein means at least two nucleotides covalently linked together. In embodiments, the term "nucleic acid" includes single-, double-, or multiple-stranded DNA, RNA and analogs (derivatives) thereof.

"Nucleotide," as used herein, refers to a nucleoside-5'-polyphosphate compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as A, C, G, T, U, or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide").

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g., mRNA from DNA), reducing the translation of the target nucleic acid (e.g., mRNA), altering transcript splicing (e.g., single stranded morpholino oligo), or interfering with the endogenous activity of the target nucleic acid. See, e.g., Weintraub, *Scientific American*, 262:40 (1990). Typically, synthetic antisense nucleic acids (e.g., oligonucleotides) are generally between 15 and 25 bases in length. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or precursors, such as nucleotide analogs), short hairpin RNAs (shRNA), micro RNAs (miRNA), saRNAs (small activating RNAs) and small nucleolar RNAs (snoRNA) or certain of their derivatives or precursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of anyone of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. $-NH_2$, $-COOH$, $-N$-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments a bioconjugate is a click chemistry reactant moiety when the association between atoms or molecules of bioconjugate reactive groups is direct (e.g., covalent bond, linker).

In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g. phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The terms "monophosphate" is used in accordance with its ordinary meaning in the arts and refers to a moiety having the formula:

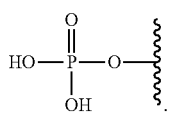

The term "polyphosphate" refers to at least two phosphate groups, having the formula:

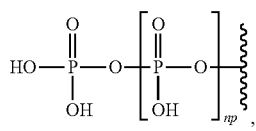

wherein np is an integer of 1 or greater. In embodiments, np is an integer from 0 to 5. In embodiments, np is an integer from 0 to 2. In embodiments, np is 2.

The term "base" as used herein refers to a monovalent or divalent purine or pyrimidine compound or a derivative thereof, that may be a constituent of nucleic acid (i.e. DNA or RNA, or a derivative thereof). In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes a monovalent or divalent cytosine or a derivative thereof (e.g., cytosine analogue), a monovalent or divalent guanine or a derivative thereof (e.g., guanine analogue), a monovalent or divalent adenine or a derivative thereof (e.g., adenine analogue), a monovalent or divalent thymine or a derivative thereof (e.g., thymine analogue), a monovalent or divalent uracil or a derivative thereof (e.g., uracil analogue), a monovalent or divalent hypoxanthine or a derivative thereof (e.g., hypoxanthine analogue), a monovalent or divalent xanthine or a derivative thereof (e.g., xanthine analogue), a monovalent or divalent 7-methylguanine or a derivative thereof (e.g., 7-methylguanine analogue), a monovalent or divalent deaza-adenine or a derivative thereof (e.g., deaza-adenine analogue), a monovalent or divalent deaza-guanine or a derivative thereof (e.g., deaza-guanine), a monovalent or divalent deaza-hypoxanthine or a derivative thereof, a monovalent or divalent 5,6-dihydrouracil or a derivative thereof (e.g., 5,6-dihydrouracil analogue), a monovalent or divalent 5-methylcytosine or a derivative thereof (e.g., 5-methylcytosine analogue), or a monovalent or divalent 5-hydroxymethylcytosine or a derivative thereof (e.g., 5-hydroxymethylcytosine analogue) moieties. In embodiments, the base is a monovalent or divalent adenine, guanine, hypoxanthine, xanthine, theobromine, caffeine, uric acid, or isoguanine. In embodiments, the base is

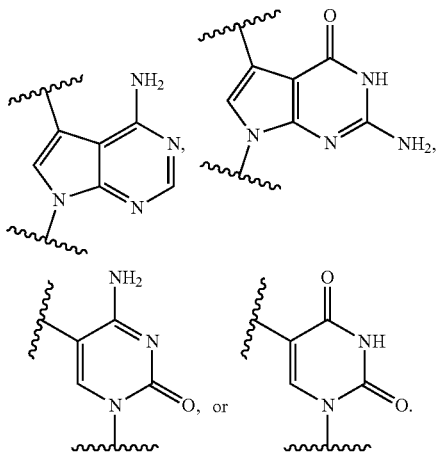

In embodiments, the base is

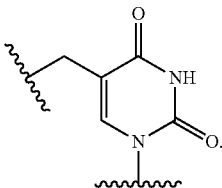 [SMILES: *Cc1cn(*)c(=O)[nH]c1=O]

In embodiments, the base is

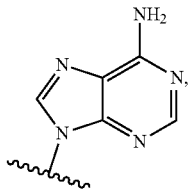

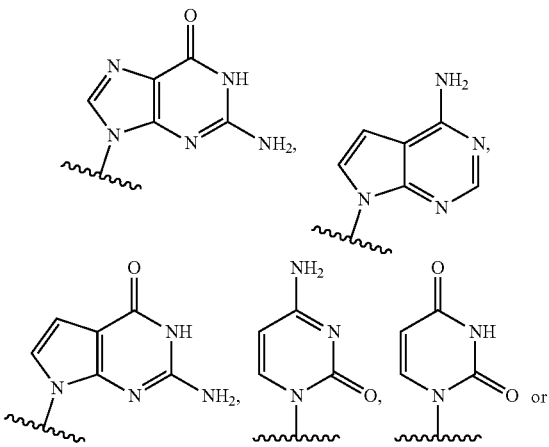

-continued

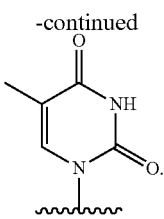

The term "base" as used herein refers to a monovalent purine or pyrimidine compound or a derivative thereof, that may be a constituent of nucleic acid (i.e. DNA or RNA, or a derivative thereof). In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes a monovalent cytosine or a derivative thereof (e.g., cytosine analogue), a monovalent guanine or a derivative thereof (e.g., guanine analogue), a monovalent adenine or a derivative thereof (e.g., adenine analogue), a monovalent thymine or a derivative thereof (e.g., thymine analogue), a monovalent uracil or a derivative thereof (e.g., uracil analogue), a monovalent hypoxanthine or a derivative thereof (e.g., hypoxanthine analogue), a monovalent xanthine or a derivative thereof (e.g., xanthine analogue), a monovalent 7-methylguanine or a derivative thereof (e.g., 7-methylguanine analogue), a monovalent deaza-adenine or a derivative thereof (e.g., deaza-adenine analogue), a monovalent deaza-guanine or a derivative thereof (e.g., deaza-guanine), a monovalent deaza-hypoxanthine or a derivative thereof, a monovalent 5,6-dihydrouracil or a derivative thereof (e.g., 5,6-dihydrouracil analogue), a monovalent 5-methylcytosine or a derivative thereof (e.g., 5-methylcytosine analogue), or a monovalent 5-hydroxymethylcytosine or a derivative thereof (e.g., 5-hydroxymethylcytosine analogue) moieties. In embodiments, the base is a monovalent adenine, guanine, hypoxanthine, xanthine, theobromine, caffeine, uric acid, or isoguanine.

The term "non-covalent linker" is used in accordance with its ordinary meaning and refers to a divalent moiety which includes at least two molecules that are not covalently linked to each other but are capable of interacting with each other via a non-covalent bond (e.g. electrostatic interactions (e.g. ionic bond, hydrogen bond, halogen bond) or van der Waals interactions (e.g. dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) and phenyl boric acid (PBA). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety, tetrazine (TZ) moiety, salicylhydroxamic acid (SHA) moiety).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation).

A photocleavable linker (e.g., including or consisting of a o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent. In embodiments, an orthogonally is a cleavable linker that following cleavage the two separated entities (e.g., fluorescent dye, bioconjugate reactive group) do not further react and form a new orthogonally cleavable linker.

The term "orthogonal binding group" or "orthogonal binding molecule" as used herein refer to a binding group (e.g. anchor moiety or complementary anchor moiety binder) that is capable of binding a first complementary binding group (e.g., complementary anchor moiety binder or anchor moiety) in a mixture of two or more different complementary binding groups and is unable to bind any other different complementary binding group in the mixture of two or more complementary binding groups. For example, two different binding groups are both orthogonal binding groups when a mixture of the two different binding groups are reacted with two complementary binding groups and each binding group binds only one of the complementary binding groups and not the other complementary binding group. An example of a set of four orthogonal binding groups and a set of orthogonal complementary binding groups are the binding groups biotin, azide, trans-cyclooctene (TCO) and phenyl boric acid (PBA), which specifically and efficiently bind or react with the complementary binding groups streptavidin, dibenzocyclooctyne (DBCO), tetrazine (TZ) and salicylhydroxamic acid (SHA) respectively.

The term "orthogonal detectable label" or "orthogonal detectable moiety" as used herein refer to a detectable label (e.g. fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" as used herein refers a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides &Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the polymerase-compatible cleavable moiety comprises a disulfide moiety.

The term "allyl" as described herein refers to an unsubstituted methylene attached to a vinyl group (i.e. —CH=CH$_2$), having the formula

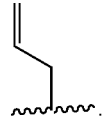

An "allyl linker" refers to a divalent unsubstituted methylene attached to a vinyl group, having the formula

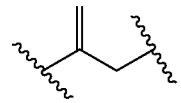

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

The term "polymerase-compatible moiety" as used herein refers a moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218):53-59; or Hutter D. et al. (2010) *Nucleosides Nucleotides &Nucleic Acids* 29:879-895, which are incorporated herein by reference in their entirety for all purposes. In embodiments, a polymerase-compatible moiety includes hydrogen, —N$_3$, —CN, or halogen.

The term "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Taq polymerase, Terminator γ, 9° N polymerase (exo-), Terminator II, Terminator III, or Terminator IX).

The term "thermophilic nucleic acid polymerase" as used herein refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS*. 1996; 93(11):5281-5285). A thermophilic nucleic acid polymerase is a member of the family B DNA polymerases. Site-directed mutagenesis of the 3'-5' exo motif I (Asp-Ile-Glu) to Asp-Ile-Asp resulted in reduction of 3'-5' exonuclease activity to <1% of wild-type, while maintaining other properties of the polymerase including its high strand displacement activity. Subsequent mutagenesis of key amino acids results in an increased ability of the enzyme to incorporate dideoxynucleotides, ribonucleotides and acyclonucleotides (e.g., Terminator II enzyme from New England Biolabs with D141A/E143A/Y409V/A485L mutations); 3'-amino-dNTPs, 3'-azido-dNTPs and other 3'-modified nucleotides (e.g., NEB Terminator III DNA Polymerase with D141A/E143A/L408S/Y409A/P410V mutations, NEB Terminator IX DNA polymerase), or γ-phosphate labeled nucleotides (e.g., Terminator γ: D141A/E143A/W355A/L408W/R460A/Q461S/K464E/D480V/R484W/A485L). Typically these enzymes do not have 5'-3' exonuclease activity. Additional information about thermophilic nucleic acid polymerases may be found in (Southworth M W, et al. *PNAS*. 1996; 93(11):5281-5285; Bergen K, et al. *ChemBioChem*. 2013; 14(9):1058-1062; Kumar S, et al. *Scientific Reports*. 2012; 2:684; Fuller C W, et al. 2016; 113(19):5233-5238; Guo J, et al. *Proceedings of the National Academy of Sciences of the United States of America*. 2008; 105(27):9145-9150), which are incorporated herein in their entirety for all purposes.

The term "primer", as used herein, is defined to be one or more nucleic acid fragments that specifically hybridize to a nucleic acid template. A primer can be of any length depending on the particular technique it will be used for. For example, PCR primers are generally between 10 and 40 nucleotides in length. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

II. Compositions

In an aspect is a nucleotide analogue of the formula:

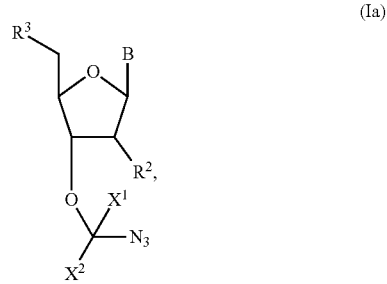

(Ia)

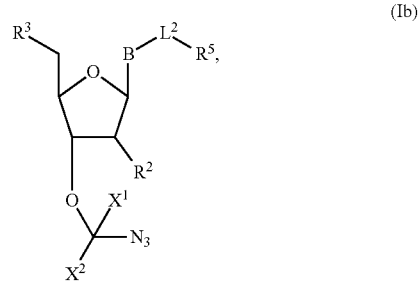

(Ib)

(Ic)

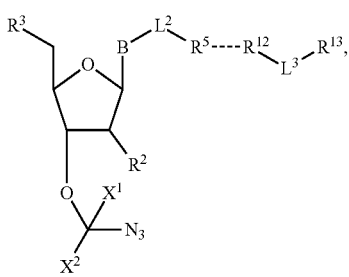

(IIa)

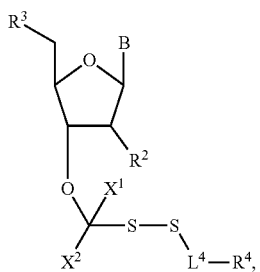

(IIb)

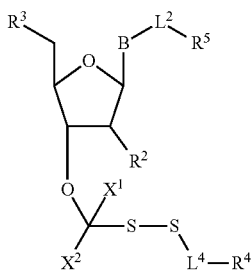

(IIc)

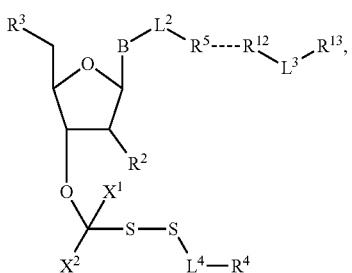

(IIIa)

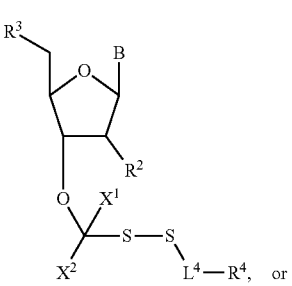

(IIIb)

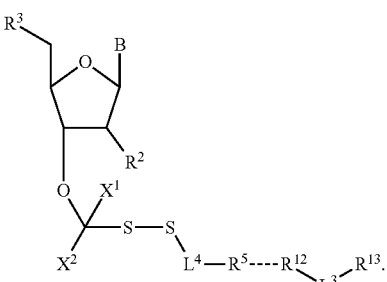

The symbol "----" is a non-covalent bond. The symbol B is a base or analogue thereof. $L^2$ is a covalent linker (e.g., a cleavable linker). $L^3$ is a covalent linker. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^2$ is hydrogen or $-OR^{2A}$, wherein $R^{2A}$ is hydrogen, polymerase-compatible moiety, or polymerase-compatible cleavable moiety. $R^3$ is $-OH$, monophosphate, or polyphosphate or a nucleic acid. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, an anchor moiety, or affinity anchor moiety. $R^{12}$ is a complementary affinity anchor moiety binder. $R^{13}$ is a detectable label. The symbols $X^1$ and $X^2$ are independently hydrogen, halogen, $-N_3$, or $-CN$, wherein at least wherein at least one of $X^1$ or $X^2$ is halogen, $-N_3$, or $-CN$. In embodiments, at least one of $X^1$ or $X^2$ is halogen. In embodiments, if $X^1$ is $-N_3$ then $X^2$ is not $-N_3$ for formula (Ia), (Ib), and (Ic).

In embodiments, the nucleotide analogue has the formula:

(Ia)

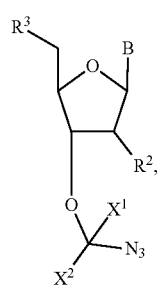

(Ib)

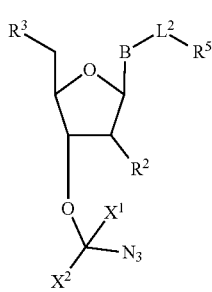

or

51

-continued

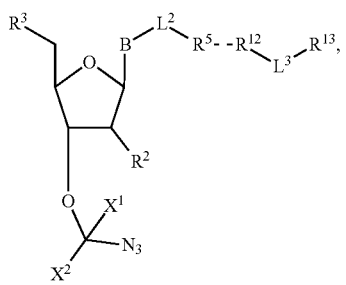
(Ic)

$R^3$, B, $R^2$, $X^1$, $X^2$, $L^2$, $R^5$, $R^{12}$, $L^3$, and $R^{13}$ are as described herein, including embodiments.

In embodiments, the nucleotide analogue has the formula:

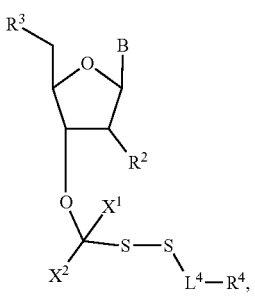
(IIa)

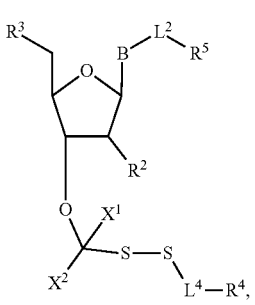
(IIb)

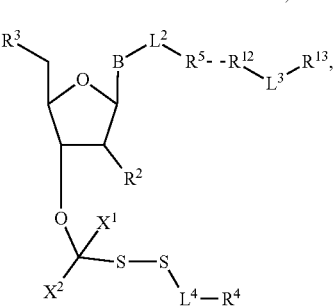
(IIc)

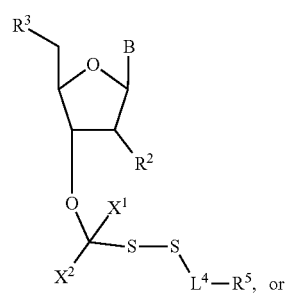
(IIIa)

52

-continued

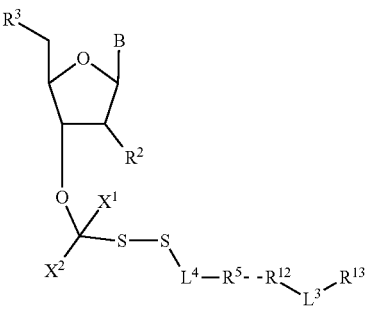
(IIIb)

wherein $R^3$, B, $R^2$, $X^1$, $X^2$, $L^2$, $L^4$, $R^4$, $R^5$, $R^{12}$, $L^3$, and $R^{13}$ are as described herein, including embodiments.

In embodiments, the nucleotide analogue has the formula:

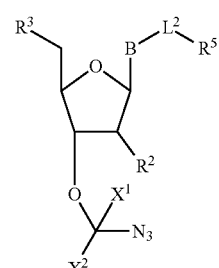
(Ib)

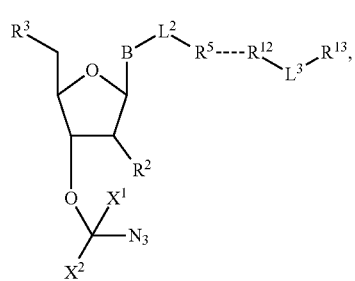
(Ic)

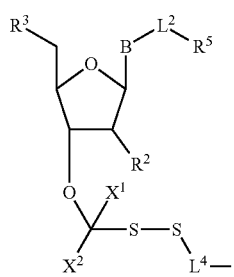
(IIb)

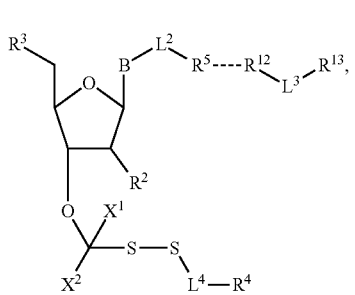
(IIc)

-continued

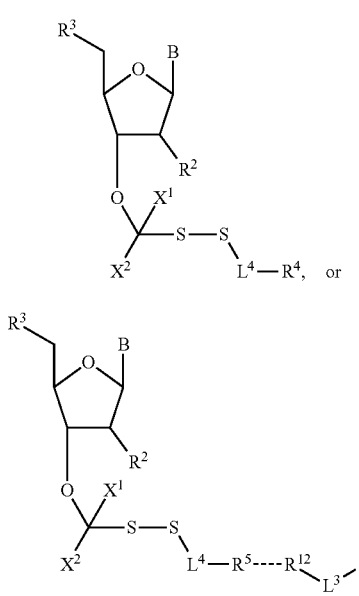

wherein $R^3$, $B$, $R^2$, $X^1$, $X^2$, $L^2$, $L^4$, $R^4$, $R^5$, $R^{12}$, $L^3$, and $R^{13}$ are as described herein, including embodiments.

In embodiments, the nucleotide analogue has the formula:

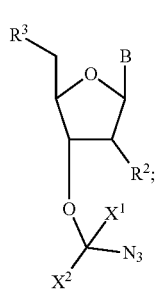

wherein $R^3$, $B$, $R^2$, $X^1$, and $X^2$ are as described herein, including embodiments. In embodiments, the nucleotide analogue has the formula:

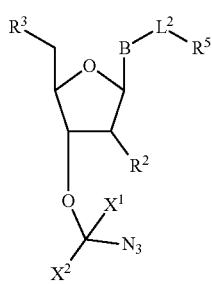

wherein $R^3$, $B$, $L^2$, $R^5$, $R^2$, $X$, and $X^2$ are as described herein, including embodiments. In embodiments, the nucleotide analogue has the formula:

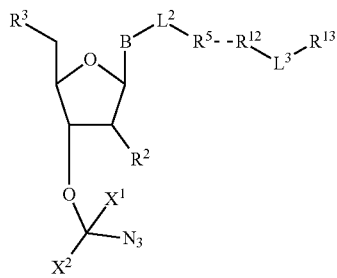

wherein $R^3$, $B$, $L^2$, $R^5$, $R^{12}$, $L^3$, $R^{13}$, $R^2$, $X^1$, and $X^2$ are as described herein, including embodiments. In embodiments, the nucleotide analogue has the formula:

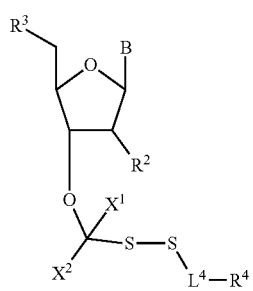

wherein $R^3$, $B$, $R^2$, $X^1$, $X^2$, $L^4$, and $R^4$ are as described herein, including embodiments. In embodiments, the nucleotide analogue has the formula:

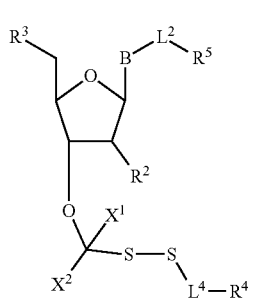

wherein $R^3$, $B$, $L^2$, $R^5$, $R^2$, $X^1$, $X^2$, $L^4$, and $R^4$ are as described herein, including embodiments. In embodiments, the nucleotide analogue has the formula:

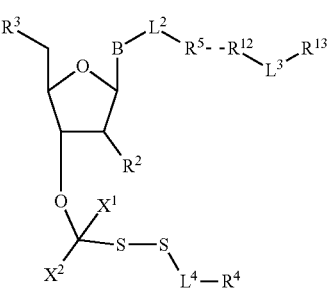

wherein $R^3$, B, $L^2$, $R^5$, $R^{12}$, $L^3$, $R^{13}$, $R^2$, $X^1$, $X^2$, $L^4$ and $R^4$ are as described herein, including embodiments. In embodiments, the nucleotide analogue has the formula:

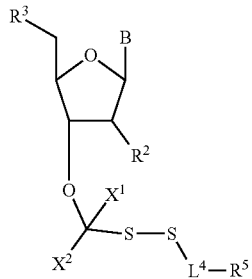

(IIIa)

wherein $R^3$, B, $R^2$, $X^1$, $X^2$, $L^4$ and $R^5$ areas described herein, including embodiments. In embodiments, the nucleotide analogue has the formula:

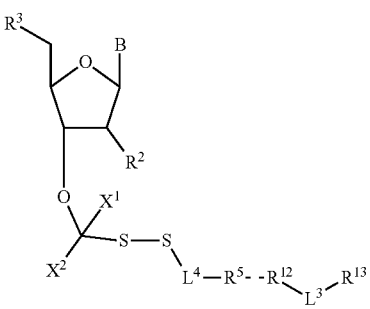

(IIIb)

wherein $R^3$, B, $R^2$, $X^1$, $X^2$, $L^4$, $R^5$, $R^{12}$, $L^3$, and $R^{13}$ are as described herein, including embodiments.

In embodiments, $X^1$ is hydrogen. In embodiments, $X^1$ is halogen (e.g., —F). In embodiments, $X^1$ is —CN. In embodiments, $X^1$ is —N$_3$. In embodiments, $X^1$ is —F. In embodiments, $X^1$ is —Cl. In embodiments, $X^1$ is —Br. In embodiments, $X^1$ is —I. In embodiments, $X^2$ is hydrogen. In embodiments, $X^2$ is halogen (e.g., —F). In embodiments, $X^2$ is —CN. In embodiments, $X^2$ is —N$_3$. In embodiments, $X^2$ is —F. In embodiments, $X^2$ is —Cl. In embodiments, $X^2$ is —Br. In embodiments, $X^2$ is —I.

In embodiments, $X^1$ is hydrogen, and $X^2$ is halogen. In embodiments, $X^1$ is hydrogen, and $X^2$ is —CN. In embodiments, $X^1$ is hydrogen, and $X^2$ is —N$_3$. In embodiments, $X^1$ is halogen, and $X^2$ is hydrogen. In embodiments, $X^1$ is halogen, and $X^2$ is halogen. In embodiments, $X^1$ is halogen, and $X^2$ is —CN. In embodiments, $X^1$ is halogen, and $X^2$ is —N$_3$. In embodiments, $X^1$ is —CN, and $X^2$ is hydrogen. In embodiments, $X^1$ is —CN, and $X^2$ is halogen. In embodiments, $X^1$ is —CN, and $X^2$ is —CN. In embodiments, $X^1$ is —CN, and $X^2$ is —N$_3$. In embodiments, $X^1$ is —N$_3$, and $X^2$ is hydrogen. In embodiments, $X^1$ is —N$_3$, and $X^2$ is halogen. In embodiments, $X^1$ is —N$_3$, and $X^2$ is —CN. In embodiments, $X^1$ is —N$_3$, and $X^2$ is —N$_3$.

In embodiments, $X^1$ is hydrogen, and $X^2$ is —F. In embodiments, $X^1$ is hydrogen, and $X^2$ is —CN. In embodiments, $X^1$ is hydrogen, and $X^2$ is —N$_3$. In embodiments, $X^1$ is —F, and $X^2$ is hydrogen. In embodiments, $X^1$ is —F, and $X^2$ is —F. In embodiments, $X^1$ is —F, and $X^2$ is —CN. In embodiments, $X^1$ is —F, and $X^2$ is —N$_3$. In embodiments, $X^1$ is —CN, and $X^2$ is hydrogen. In embodiments, $X^1$ is —CN, and $X^2$ is —F. In embodiments, $X^1$ is —CN, and $X^2$ is —CN. In embodiments, $X^1$ is —CN, and $X^2$ is —N$_3$. In embodiments, $X^1$ is —N$_3$, and $X^2$ is hydrogen. In embodiments, $X^1$ is —N$_3$, and $X^2$ is —F. In embodiments, $X^1$ is —N$_3$, and $X^2$ is —CN. In embodiments, $X^1$ is —N$_3$, and $X^2$ is —N$_3$.

In embodiments, $X^1$ is H and $X^2$ is —N$_3$. In embodiments, $X^1$ is H and $X^2$ is —CN. In embodiments, $X^1$ is H and $X^2$ is —F. In embodiments, $X^1$ is —F and $X^2$ is —F. In embodiments, $X^1$ is —N$_3$ and $X^2$ is —N$_3$. In embodiments, $X^1$ is —N$_3$ and $X^2$ is —N$_3$. In embodiments, $X^1$ is —N$_3$ and $X^2$ is —CN. In embodiments, $X^1$ is —CN and $X^2$ is —CN.

In embodiments, $X^1$ is H and $X^2$ is —N$_3$ for formula (Ia), (Ib), and (Ic). In embodiments, $X^1$ is H and $X^2$ is —CN for formula (Ia), (Ib), and (Ic). In embodiments, $X^1$ is H and $X^2$ is —F for formula (Ia), (Ib), and (Ic). In embodiments, $X^1$ is —F and $X^2$ is —F for formula (Ia), (Ib), and (Ic). In embodiments, $X^1$ is —N$_3$ and $X^2$ is —N$_3$ for formula (Ia), (Ib), and (Ic). In embodiments, $X^1$ is —N$_3$ and $X^2$ is —N$_3$ for formula (Ia), (Ib), and (Ic). In embodiments, $X^1$ is —N$_3$ and $X^2$ is —CN for formula (Ia), (Ib), and (Ic). In embodiments, $X^1$ is —CN and $X^2$ is —CN for formula (Ia), (Ib), and (Ic).

In embodiments, $X^1$ is not —N$_3$ and $X^2$ is not —N$_3$ for formula (Ia), (Ib), and (Ic). In embodiments, $X^1$ is not —CN and $X^2$ is not —N$_3$ for formula (Ia), (Ib), and (Ic). In embodiments, $X^1$ is not —CN and $X^2$ is not —CN for formula (Ia), (Ib), and (Ic).

In embodiments, $X^1$ is not —N$_3$ and $X^2$ is not —N$_3$ for formula (IIa), (IIb), (IIc), (IIIa), or (IIIb). In embodiments, $X^1$ is not —N$_3$ and $X^2$ is not —CN for formula (IIa), (IIb), (IIc), (IIIa), or (IIIb). In embodiments, $X^1$ is not —CN and $X^2$ is not —CN for formula (IIa), (IIb), (IIc), (IIIa), or (IIIb).

In embodiments of formula (Ia), (IIa), (IIIa), or (IIIb), B is cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, deaza-adenine or a derivative thereof, deaza-guanine or a derivative thereof, deaza-hypoxanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

In embodiments of formula (Ia), (IIa), (IIIa), or (IIIb), B is a monovalent cytosine or a derivative thereof, a monovalent guanine or a derivative thereof, a monovalent adenine or a derivative thereof, a monovalent thymine or a derivative thereof, a monovalent uracil or a derivative thereof, a monovalent hypoxanthine or a derivative thereof, a monovalent xanthine or a derivative thereof, a monovalent deaza-adenine or a derivative thereof, a monovalent deaza-guanine or a derivative thereof, a monovalent deaza-hypoxanthine or a derivative thereof, a monovalent 7-methylguanine or a derivative thereof, a monovalent 5,6-dihydrouracil or a derivative thereof, 5-methylcytosine or a derivative thereof, or a monovalent 5-hydroxymethylcytosine or a derivative thereof.

In embodiments of formula (Ia), (IIa), (IIIa), or (IIIb), B is cytosine or a derivative thereof. In embodiments of formula (Ia), (IIa), (IIIa), or (IIIb), B is guanine or a derivative thereof. In embodiments of formula (Ia), (IIa), (IIIa), or (IIIb), B is adenine or a derivative thereof. In embodiments of formula (Ia), (IIa), (IIIa), or (IIIb), B is thymine or a derivative thereof. In embodiments of formula (Ia), (IIa), (IIIa), or (IIIb), B is uracil or a derivative thereof. In embodiments of formula (Ia), (IIa), (IIIa), or (IIIb), B is hypoxanthine or a derivative thereof. In embodiments of formula (Ia), (IIa), (IIIa), or (IIIb), B is xanthine or a derivative thereof. In embodiments of formula (Ia), (IIa), (IIIa), or (IIIb), B is deaza-adenine or a derivative thereof. In embodiments of formula (Ia), (IIa), (IIIa), or (IIIb), B is deaza-guanine or a derivative thereof. In embodiments of formula (Ia), (IIa), (IIIa), or (IIIb), B is deaza-hypoxanthine or a derivative thereof. In embodiments of formula (Ia), (IIa), (IIIa), or (IIIb), B is 7-methylguanine or a derivative thereof. In embodiments of formula (Ia), (IIa), (IIIa), or (IIIb), B is 5,6-dihydrouracil or a derivative thereof. In embodiments of formula (Ia), (IIa), (IIIa), or (IIIb), B is 5-methylcytosine or a derivative thereof. In embodiments of formula (Ia), (IIa), (IIIa), or (IIIb), B is 5-hydroxymethyl-cytosine or a derivative thereof.

In embodiments of formula (Ia), (IIa), (IIIa), or (IIIb), B is a monovalent cytosine or a derivative thereof. In embodiments of formula (Ia), (IIa), (IIIa), or (IIIb), B is a monovalent guanine or a derivative thereof. In embodiments of formula (Ia), (IIa), (IIIa), or (IIIb), B is a monovalent adenine or a derivative thereof. In embodiments of formula (Ia), (IIa), (IIIa), or (IIIb), B is a monovalent thymine or a derivative thereof. In embodiments of formula (Ia), (IIa), (IIIa), or (IIIb), B is a monovalent uracil or a derivative thereof. In embodiments of formula (Ia), (IIa), (IIIa), or (IIIb), B is a monovalent hypoxanthine or a derivative thereof. In embodiments of formula (Ia), (IIa), (IIIa), or (IIIb), B is a monovalent xanthine or a derivative thereof. In embodiments of formula (Ia), (IIa), (IIIa), or (IIIb), B is a monovalent deaza-adenine or a derivative thereof. In embodiments of formula (Ia), (IIa), (IIa), or (IIIb), B is a monovalent deaza-guanine or a derivative thereof. In embodiments of formula (Ia), (IIa), (IIIa), or (IIIb), B is a monovalent deaza-hypoxanthine or a derivative thereof. In embodiments of formula (Ia), (IIa), (IIIa), or (IIIb), B is a monovalent 7-methylguanine or a derivative thereof. In embodiments of formula (Ia), (IIa), (IIIa), or (IIIb), B is a monovalent 5,6-dihydrouracil or a derivative thereof. In embodiments of formula (Ia), (IIa), (IIIa), or (IIIb), B is a monovalent 5-methylcytosine or a derivative thereof. In embodiments of formula (Ia), (IIa), (IIIa), or (IIIb), B is a monovalent 5-hydroxymethylcytosine or a derivative thereof.

In embodiments of formula (Ia), (IIa), (IIIa), or (IIIb), B is

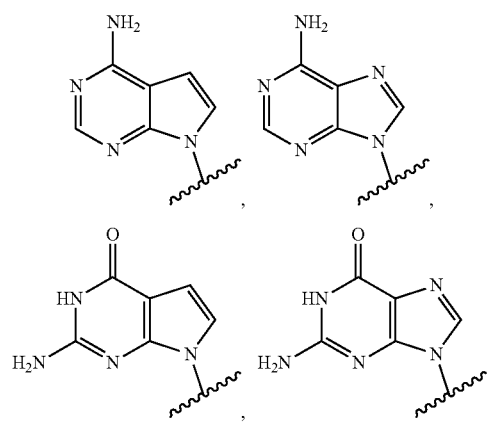

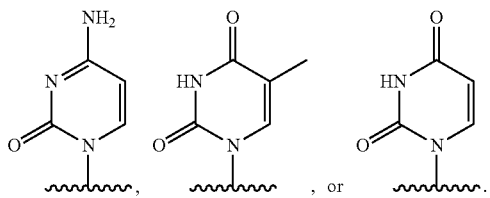

In embodiments of formula (Ia), (IIa), (IIIa), or (IIIb), B is

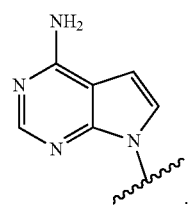 [SMILES: *n1ccc2c(N)ncnc21]

In embodiments of formula (Ia), (IIa), (IIIa), or (IIIb), B is

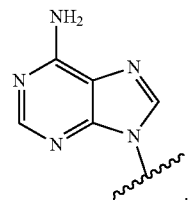 [SMILES: *n1cnc2c(N)ncnc21]

In embodiments of formula (Ia), (IIa), (IIIa), or (IIIb), B is

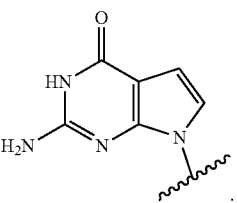 [SMILES: *n1ccc2c(=O)[nH]c(N)nc21]

In embodiments of formula (Ia), (IIa), (IIIa), or (IIIb), B is

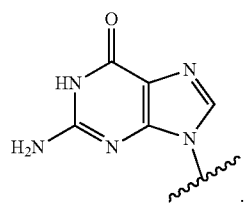 [SMILES: *n1cnc2c(=O)[nH]c(N)nc21]

In embodiments of formula (Ia), (IIa), (IIIa), or (IIIb), B is

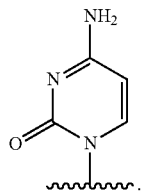 [SMILES: *n1ccc(N)nc1=O]

In embodiments of formula (Ia), (IIa), (IIIa), or (IIIb), B is

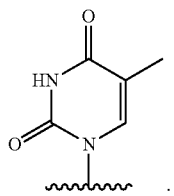

In embodiments of formula (Ia), (IIa), (IIIa), or (IIIb), B is

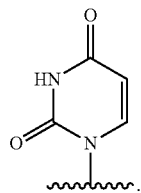

In embodiments of formula (Ib), (Ic), (IIb), (IIc), B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

In embodiments of formula (Ib), (Ic), (IIb), (IIc), B is a divalent cytosine or a derivative thereof. In embodiments of formula (Ib), (Ic), (IIb), (IIc), B is divalent guanine or a derivative thereof. In embodiments of formula (Ib), (Ic), (IIb), (IIc), B is divalent adenine or a derivative thereof. In embodiments of formula (Ib), (Ic), (IIb), (IIc), B is divalent thymine or a derivative thereof. In embodiments of formula (Ib), (Ic), (IIb), (IIc), B is divalent uracil or a derivative thereof. In embodiments of formula (Ib), (Ic), (IIb), (IIc), B is divalent hypoxanthine or a derivative thereof. In embodiments of formula (Ib), (Ic), (Ib), (Ic), B is divalent xanthine or a derivative thereof. In embodiments of formula (Ib), (Ic), (IIb), (IIc), B is divalent 7-methylguanine or a derivative thereof. In embodiments of formula (Ib), (Ic), (IIb), (IIc), B is divalent 5,6-dihydrouracil or a derivative thereof. In embodiments of formula (Ib), (Ic), (IIb), (IIc), B is divalent 5-methylcytosine or a derivative thereof. In embodiments of formula (Ib), (Ic), (IIb), (IIc), B is divalent 5-hydroxymethylcytosine or a derivative thereof.

In embodiments of formula (Ib), (Ic), (IIb), (IIc), B is a divalent cytosine. In embodiments of formula (Ib), (Ic), (IIb), (IIc), B is divalent guanine. In embodiments of formula (Ib), (Ic), (IIb), (IIc), B is divalent adenine. In embodiments of formula (Ib), (Ic), (IIb), (IIc), B is divalent thymine. In embodiments of formula (Ib), (Ic), (Ib), (IIc), B is divalent uracil. In embodiments of formula (Ib), (Ic), (IIb), (IIc), B is divalent hypoxanthine. In embodiments of formula (Ib), (Ic), (IIb), (IIc), B is divalent xanthine. In embodiments of formula (Ib), (Ic), (IIb), (IIc), B is divalent 7-methylguanine. In embodiments of formula (Ib), (Ic), (IIb), (IIc), B is divalent 5,6-dihydrouracil. In embodiments of formula (Ib), (Ic), (IIb), (IIc), B is divalent 5-methylcytosine. In embodiments of formula (Ib), (Ic), (Ib), (Ic), B is divalent 5-hydroxymethyleytosine.

In embodiments of formula (Ib), (Ic), (IIb), (IIc), B is

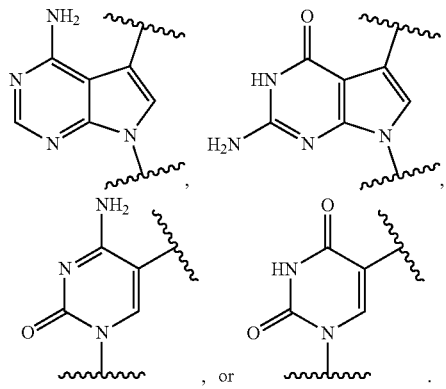

In embodiments of formula (Ib), (Ic), (IIb), (IIc), B is

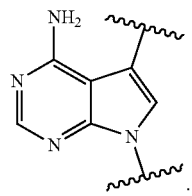

in embodiments of formula (Ib), (Ic), (Ib), (Ic), B is

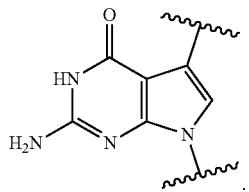 [SMILES: *c1cn(*)c2nc(N)[nH]c(=O)c12]

In embodiments of formula (Ib), (Ic), (Ib), (Ic), B is

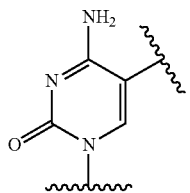

In embodiments of formula (Ib), (Ic), (IIb), (IIc), B is

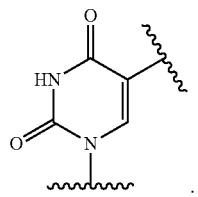 [SMILES: *c1cn(*)c(=O)[nH]c1=O]

In embodiments, $R^3$ is —OH. In embodiments, $R^3$ is a monophosphate. In embodiments, $R^3$ is triphosphate, tetraphosphate, pentaphosphate, or hexaphosphate. In embodiments, $R^3$ is a diphosphate. In embodiments, $R^3$ is triphosphate. In embodiments, $R^3$ is a polyphosphate. In embodiments, $R^3$ is monophosphate, diphosphate, triphosphate, tetraphosphate, pentaphosphate, or hexaphosphate. In embodiments, $R^3$ is tetraphosphate, pentaphosphate, or hexaphosphate. In embodiments, $R^3$ is tetraphosphate. In embodiments, $R^3$ is pentaphosphate. In embodiments, $R^3$ is hexaphosphate. In embodiments, $R^3$ is a phosphodiester derivative of a monophosphate. In embodiments, $R^3$ is a phosphodiester derivative of a diphosphate. In embodiments, $R^3$ is a phosphodiester derivative of a triphosphate. In embodiments, $R^3$ is a phosphodiester derivative of a tetraphosphate. In embodiments, $R^3$ is a phosphodiester derivative of a pentaphosphate. In embodiments, $R^3$ is a phosphodiester derivative of a hexaphosphate.

In embodiments, $R^3$ is a nucleic acid. In embodiments, $R^3$ is a residue of a nucleic acid. In embodiments, $R^3$ is a 10 to 10,000 base of a nucleic acid. In embodiments, $R^3$ is a 100 to 10,000 base of a nucleic acid. In embodiments, $R^3$ is a 1000 to 10,000 base of a nucleic acid. In embodiments, $R^3$ is a 10 to 8,000 base of a nucleic acid. In embodiments, $R^3$ is a 10 to 9,000 base of a nucleic acid. In embodiments, $R^3$ is a 10 to 7,000 base of a nucleic acid. In embodiments, $R^3$ is a 10 to 6,000 base of a nucleic acid. In embodiments, $R^3$ is a 10 to 5,000 base of a nucleic acid. In embodiments, $R^3$ is a 10 to 4,000 base of a nucleic acid. In embodiments, $R^3$ is a 10 to 3,000 base of a nucleic acid. In embodiments, $R^3$ is a 10 to 2,000 base of a nucleic acid. In embodiments, $R^3$ is a 10 to 1,000 base of a nucleic acid. In embodiments, $R^3$ is a 10 to 900 base of a nucleic acid. In embodiments, $R^3$ is a 10 to 800 base of a nucleic acid. In embodiments, $R^3$ is a 10 to 700 base of a nucleic acid. In embodiments, $R^3$ is a 10 to 600 base of a nucleic acid. In embodiments, $R^3$ is a 10 to 500 base of a nucleic acid. In embodiments, $R^3$ is a 10 to 400 base of a nucleic acid. In embodiments, $R^3$ is a 10 to 300 base of a nucleic acid. In embodiments, $R^3$ is a 10 to 200 base of a nucleic acid. In embodiments, $R^3$ is a 10 to 90 base of a nucleic acid. In embodiments, $R^3$ is a 10 to 75 base of a nucleic acid.

In embodiments, $R^3$ is a nucleic acid. In embodiments, $R^3$ is a residue of a nucleic acid. In embodiments, $R^3$ is a 10 to 10,000 base nucleic acid. In embodiments, $R^3$ is a 100 to 10,000 base nucleic acid. In embodiments, $R^3$ is a 1000 to 10,000 base nucleic acid. In embodiments, $R^3$ is a 10 to 8,000 base nucleic acid. In embodiments, $R^3$ is a 10 to 9,000 base nucleic acid. In embodiments, $R^3$ is a 10 to 7,000 base nucleic acid. In embodiments, $R^3$ is a 10 to 6,000 base nucleic acid. In embodiments, $R^3$ is a 10 to 5,000 base nucleic acid. In embodiments, $R^3$ is a 10 to 4,000 base nucleic acid. In embodiments, $R^3$ is a 10 to 3,000 base nucleic acid. In embodiments, $R^3$ is a 10 to 2,000 base nucleic acid. In embodiments, $R^3$ is a 10 to 1,000 base nucleic acid. In embodiments, $R^3$ is a 10 to 900 base nucleic acid. In embodiments, $R^3$ is a 10 to 800 base nucleic acid. In embodiments, $R^3$ is a 10 to 700 base nucleic acid. In embodiments, $R^3$ is a 10 to 600 base nucleic acid. In embodiments, $R^3$ is a 10 to 500 base nucleic acid. In embodiments, $R^3$ is a 10 to 400 base nucleic acid. In embodiments, $R^3$ is a 10 to 300 base nucleic acid. In embodiments, $R^3$ is a 10 to 200 base nucleic acid. In embodiments, $R^3$ is a 10 to 90 base nucleic acid. In embodiments, $R^3$ is a 10 to 75 base nucleic acid.

In embodiments, $R^2$ is hydrogen or —OH. In embodiments, $R^2$ is hydrogen. In embodiments, $R^2$ is —OH. In embodiments, $R^2$ is-$OR^{2A}$; and $R^{2A}$ is hydrogen. In embodiments, $R^2$ is —$OR^{2A}$; and $R^{2A}$ is a polymerase-compatible cleavable moiety. In embodiments, $R^2$ is-$OR^{2A}$; and $R^{2A}$ is a polymerase-compatible cleavable moiety including an azido moiety. In embodiments, $R^2$ is-$OR^{2A}$; and $R^{2A}$ is a polymerase-compatible cleavable moiety including a dithiol linker. In embodiments, $R^2$ is-$OR^{2A}$; $R^{2A}$ is a polymerase-compatible cleavable moiety; and the polymerase-compatible cleavable moiety is —$CH_2N_3$. In embodiments, $R^2$ is-$OR^{2A}$; and $R^{2A}$ is a polymerase-compatible moiety including a dithiol linker, an allyl group, an azo group, or a 2-nitrobenzyl group. In embodiments, $R^{2A}$ is hydrogen.

In embodiments, $R^2$ is-$OR^{2A}$. In embodiments, $R^{2A}$ is hydrogen, polymerase-compatible moiety, or polymerase-compatible cleavable moiety. In embodiments, $R^{2A}$ is hydrogen. In embodiments, $R^{2A}$ is polymerase-compatible moiety. In embodiments, $R^{2A}$ is a polymerase-compatible cleavable moiety. In embodiments, $R^{2A}$ is a polymerase-compatible cleavable moiety including an azido moiety. In embodiments, $R^{2A}$ is a polymerase-compatible cleavable moiety including a dithiol linker, an allyl group, an azo group, or a 2-nitrobenzyl group. In embodiments, $R^{2A}$ is a polymerase-compatible cleavable moiety including a dithiol linker. In embodiments, $R^{2A}$ is a polymerase-compatible cleavable moiety including an allyl group. In embodiments, $R^{2A}$ is a polymerase-compatible cleavable moiety including an azo group. In embodiments, $R^{2A}$ is a polymerase-compatible cleavable moiety including a 2-nitrobenzyl group.

In embodiments, $R^{2A}$ is hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{2A}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{2A}$ is an unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{2A}$ is substituted (e.g., substituted with a substituent group, a size-limited substituent group, or lower substituent group) or unsubstituted alkyl. In embodiments, $R^{2A}$ is an alkyl substituted with a substituent group. In embodiments, $R^{2A}$ is an alkyl substituted with a size-limited substituent group. In embodiments, $R^{2A}$ is an alkyl substituted with a lower substituent group. In embodiments, $R^{2A}$ is an unsubstituted alkyl.

In embodiments, $R^{2A}$ is substituted (e.g., substituted with a substituent group, a size-limited substituent group, or lower substituent group) or unsubstituted heteroalkyl. In embodiments, $R^{2A}$ is a heteroalkyl substituted with a substituent group. In embodiments, $R^{2A}$ is a heteroalkyl substituted with a size-limited substituent group. In embodiments, $R^{2A}$ is a heteroalkyl substituted with a lower substituent group. In embodiments, $R^{2A}$ is an unsubstituted heteroalkyl.

In embodiments, $R^{2A}$ is substituted (e.g., substituted with a substituent group, a size-limited substituent group, or lower substituent group) or unsubstituted cycloalkyl. In embodiments, $R^{2A}$ is a cycloalkyl substituted with a substituent group. In embodiments, $R^{2A}$ is a cycloalkyl substituted with a size-limited substituent group. In embodiments, $R^{2A}$ is a cycloalkyl substituted with a lower substituent group. In embodiments, $R^{2A}$ is an unsubstituted cycloalkyl.

In embodiments, $R^{2A}$ is substituted (e.g., substituted with a substituent group, a size-limited substituent group, or lower substituent group) or unsubstituted heterocycloalkyl. In embodiments, $R^{2A}$ is a heterocycloalkyl substituted with a substituent group. In embodiments, $R^{2A}$ is a heterocycloalkyl substituted with a size-limited substituent group. In embodiments, $R^{2A}$ is a heterocycloalkyl substituted with a lower substituent group. In embodiments, $R^{2A}$ is an unsubstituted heterocycloalkyl.

In embodiments, $R^{2A}$ is substituted (e.g., substituted with a substituent group, a size-limited substituent group, or lower substituent group) or unsubstituted aryl. In embodiments, $R^{2A}$ is an aryl substituted with a substituent group. In embodiments, $R^{2A}$ is an aryl substituted with a size-limited substituent group. In embodiments, $R^{2A}$ is an aryl substituted with a lower substituent group. In embodiments, $R^{2A}$ is an unsubstituted aryl.

In embodiments, $R^{2A}$ is substituted (e.g., substituted with a substituent group, a size-limited substituent group, or lower substituent group) or unsubstituted heteroaryl. In embodiments, $R^{2A}$ is a heteroaryl substituted with a substituent group. In embodiments, $R^{2A}$ is a heteroaryl substituted with a size-limited substituent group. In embodiments, $R^{2A}$ is a heteroaryl substituted with a lower substituent group. In embodiments, $R^{2A}$ is an unsubstituted heteroaryl.

In embodiments, $L^2$ is a cleavable linker. In embodiments, $L^2$ is a non-cleavable linker. In embodiments, $L^2$ is a chemically cleavable linker. In embodiments, $L^2$ is a photocleavable linker, an acid-cleavable linker, a base-cleavable linker, an oxidant-cleavable linker, a reductant-cleavable linker, or a fluoride-cleavable linker. In embodiments, $L^2$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^2$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^2$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^2$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^2$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenylene, or substituted (e.g., substituted with a substituent group, size-limited substituent group, or lower substituent group) or unsubstituted 5 to 6 membered heteroarylene.

In embodiments, $L^2$ is substituted or unsubstituted methylene. In embodiments, $L^2$ is substituted or unsubstituted $C_2$ alkylene. In embodiments, $L^2$ is substituted or unsubstituted $C_3$ alkylene. In embodiments, $L^2$ is substituted or unsubstituted $C_4$ alkylene. In embodiments, $L^2$ is substituted or unsubstituted $C_5$ alkylene. In embodiments, $L^2$ is substituted or unsubstituted $C_6$ alkylene. In embodiments, $L^2$ is substituted or unsubstituted $C_7$ alkylene. In embodiments, $L^2$ is substituted or unsubstituted $C_8$ alkylene. In embodiments, $L^2$ is substituted methylene. In embodiments, $L^2$ is substituted $C_2$ alkylene. In embodiments, $L^2$ is substituted $C_3$ alkylene. In embodiments, $L^2$ is substituted $C_4$ alkylene. In embodiments, $L^2$ is substituted $C_5$ alkylene. In embodiments, $L^2$ is substituted $C_6$ alkylene. In embodiments, $L^2$ is substituted $C_7$ alkylene. In embodiments, $L^2$ is substituted $C_8$ alkylene. In embodiments, $L^2$ is an unsubstituted methylene. In embodiments, $L^2$ is an unsubstituted $C_2$ alkylene. In embodiments, $L^2$ is an unsubstituted $C_3$ alkylene. In embodiments, $L^2$ is an unsubstituted $C_4$ alkylene. In embodiments, $L^2$ is an unsubstituted $C_5$ alkylene. In embodiments, $L^2$ is an unsubstituted $C_6$ alkylene. In embodiments, $L^2$ is an unsubstituted $C_7$ alkylene. In embodiments, $L^2$ is an unsubstituted $C_8$ alkylene.

In embodiments, $L^2$ is substituted or unsubstituted $C_9$ alkylene. In embodiments, $L^2$ is substituted or unsubstituted $C_{10}$ alkylene. In embodiments, $L^2$ is substituted or unsubstituted $C_{11}$ alkylene. In embodiments, $L^2$ is substituted or unsubstituted Cu alkylene. In embodiments, $L^2$ is substituted or unsubstituted $C_{13}$ alkylene. In embodiments, $L^2$ is substituted or unsubstituted $C_{14}$ alkylene. In embodiments, $L^2$ is substituted or unsubstituted $C_{18}$ alkylene. In embodiments, $L^2$ is substituted or unsubstituted $C_{16}$ alkylene. In embodiments, $L^2$ is substituted or unsubstituted $C_{17}$ alkylene. In embodiments, $L^2$ is substituted or unsubstituted $C_{18}$ alkylene. In embodiments, $L^2$ is substituted or unsubstituted $C_{19}$ alkylene. In embodiments, $L^2$ is substituted or unsubstituted $C_2$ alkylene.

In embodiments, $L^2$ is substituted $C_9$ alkylene. In embodiments, $L^2$ is substituted $C_{10}$ alkylene. In embodiments, $L^2$ is substituted $C_{11}$ alkylene. In embodiments, $L^2$ is substituted Cu alkylene. In embodiments, $L^2$ is substituted $C_{13}$ alkylene. In embodiments, $L^2$ is substituted $C_{14}$ alkylene. In embodiments, $L^2$ is substituted $C_{18}$ alkylene. In embodiments, $L^2$ is substituted $C_{16}$ alkylene. In embodiments, $L^2$ is substituted $C_{17}$ alkylene. In embodiments, $L^2$ is substituted $C_{18}$ alkylene. In embodiments, $L^2$ is substituted $C_{19}$ alkylene. In embodiments, $L^2$ is substituted $C_{20}$ alkylene. In embodiments, $L^2$ is an unsubstituted $C_9$ alkylene. In embodiments, $L^2$ is an unsubstituted $C_{10}$ alkylene. In embodiments, $L^2$ is an unsubstituted $C_{11}$ alkylene. In embodiments, $L^2$ is an unsubstituted Cu alkylene. In embodiments, $L^2$ is an unsubstituted $C_{13}$ alkylene. In embodiments, $L^2$ is an unsubstituted $C_{14}$ alkylene. In embodiments, $L^2$ is an unsubstituted $C_{15}$ alkylene. In embodiments, $L^2$ is an unsubstituted $C_{16}$ alkylene. In embodiments, $L^2$ is an unsubstituted $C_{17}$ alkylene. In embodiments, $L^2$ is an unsubstituted $C_{18}$ alkylene. In embodiments, $L^2$ is an unsubstituted $C_{19}$ alkylene. In embodiments, $L^2$ is an unsubstituted $C_{20}$ alkylene.

In embodiments, $L^2$ is substituted or unsubstituted $C_1$-$C_6$ alkylene. In embodiments, $L^2$ is substituted $C_1$-$C_6$ alkylene. In embodiments, $L^2$ is unsubstituted $C_1$-$C_6$ alkylene. In embodiments, $L^2$ is substituted or unsubstituted $C_2$-$C_6$ alkylene. In embodiments, $L^2$ is substituted $C_2$-$C_6$ alkylene. In embodiments, $L^2$ is unsubstituted $C_2$-$C_6$ alkylene. In embodiments, $L^2$ is substituted or unsubstituted $C_1$ alkylene. In embodiments, $L^2$ is substituted $C_1$ alkylene. In embodiments, $L^2$ is unsubstituted $C_1$ alkylene. In embodiments, $L^2$ is substituted or unsubstituted $C_2$ alkylene. In embodiments, $L^2$ is substituted $C_2$ alkylene. In embodiments, $L^2$ is unsubstituted $C_2$ alkylene. In embodiments, $L^2$ is substituted or unsubstituted $C_3$ alkylene. In embodiments, $L^2$ is substituted $C_3$ alkylene. In embodiments, $L^2$ is unsubstituted $C_3$ alkylene. In embodiments, $L^2$ is substituted or unsubstituted $C_4$ alkylene. In embodiments, $L^2$ is substituted $C_4$ alkylene. In embodiments, $L^2$ is unsubstituted $C_4$ alkylene. In embodiments, $L^2$ is substituted or unsubstituted $C_5$ alkylene. In embodiments, $L^2$ is substituted $C_5$ alkylene. In embodiments, $L^2$ is unsubstituted $C_5$ alkylene. In embodiments, $L^2$ is substituted or unsubstituted $C_6$ alkylene. In embodiments, $L^2$ is substituted $C_6$ alkylene. In embodiments, $L^2$ is unsubstituted $C_6$ alkylene.

In embodiments, $L^2$ is substituted or unsubstituted 2 to 20 membered heteroalkylene. In embodiments, $L^2$ is substituted or unsubstituted 2 to 18 membered heteroalkylene. In embodiments, $L^2$ is substituted or unsubstituted 2 to 16 membered heteroalkylene. In embodiments, $L^2$ is substituted or unsubstituted 2 to 14 membered heteroalkylene. In embodiments, $L^2$ is substituted or unsubstituted 2 to 12 membered heteroalkylene. In embodiments, $L^2$ is substituted or unsubstituted 2 to 10 membered heteroalkylene. In embodiments, $L^2$ is substituted or unsubstituted 2 to 8 membered heteroalkylene. In embodiments, $L^2$ is substituted 2 to 8 membered heteroalkylene. In embodiments, $L^2$ is unsubstituted 2 to 8 membered heteroalkylene. In embodiments, $L^2$ is substituted or unsubstituted 2 membered heteroalkylene. In embodiments, $L^2$ is substituted 2 membered heteroalkylene. In embodiments, $L^2$ is unsubstituted 2 membered heteroalkylene. In embodiments, $L^2$ is substituted or unsubstituted 3 membered heteroalkylene. In embodiments, $L^2$ is substituted 3 membered heteroalkylene. In embodiments, $L^2$ is unsubstituted 3 membered heteroalkylene. In embodiments, $L^2$ is substituted or unsubstituted 4 membered heteroalkylene. In embodiments, $L^2$ is substituted 4 membered heteroalkylene. In embodiments, $L^2$ is unsubstituted 4 membered heteroalkylene. In embodiments, $L^2$ is substituted or unsubstituted 5 membered heteroalkylene. In embodiments, $L^2$ is substituted 5 membered heteroalkylene. In embodiments, $L^2$ is unsubstituted 5 membered heteroalkylene. In embodiments, $L^2$ is substituted or unsubstituted 6 membered heteroalkylene. In embodiments, $L^2$ is substituted 6 membered heteroalkylene. In embodiments, $L^2$ is unsubstituted 6 membered heteroalkylene. In embodiments, $L^2$ is substituted or unsubstituted 7 membered heteroalkylene. In embodiments, $L^2$ is substituted 7 membered heteroalkylene. In embodiments, $L^2$ is unsubstituted 7 membered heteroalkylene. In embodiments, $L^2$ is substituted or unsubstituted 8 membered heteroalkylene. In embodiments, $L^2$ is substituted 8 membered heteroalkylene. In embodiments, $L^2$ is unsubstituted 8 membered heteroalkylene.

In embodiments, $L^2$ is substituted or unsubstituted 9 membered heteroalkylene. In embodiments, $L^2$ is substituted 9 membered heteroalkylene. In embodiments, $L^2$ is unsubstituted 9 membered heteroalkylene. In embodiments, $L^2$ is substituted or unsubstituted 10 membered heteroalkylene. In embodiments, $L^2$ is substituted 10 membered heteroalkylene. In embodiments, $L^2$ is unsubstituted 10 membered heteroalkylene. In embodiments, $L^2$ is substituted or unsubstituted 11 membered heteroalkylene. In embodiments, $L^2$ is substituted 11 membered heteroalkylene. In embodiments, $L^2$ is unsubstituted 11 membered heteroalkylene. In embodiments, $L^2$ is substituted or unsubstituted 12 membered heteroalkylene. In embodiments, $L^2$ is substituted 12 membered heteroalkylene. In embodiments, $L^2$ is unsubstituted 12 membered heteroalkylene. In embodiments, $L^2$ is substituted or unsubstituted 13 membered heteroalkylene. In embodiments, $L^2$ is substituted 13 membered heteroalkylene. In embodiments, $L^2$ is unsubstituted 13 membered heteroalkylene. In embodiments, $L^2$ is substituted or unsubstituted 14 membered heteroalkylene. In embodiments, $L^2$ is substituted 14 membered heteroalkylene. In embodiments, $L^2$ is unsubstituted 14 membered heteroalkylene. In embodiments, $L^2$ is substituted or unsubstituted 15 membered heteroalkylene. In embodiments, $L^2$ is substituted 15 membered heteroalkylene. In embodiments, $L^2$ is unsubstituted 15 membered heteroalkylene. In embodiments, $L^2$ is substituted or unsubstituted 16 membered heteroalkylene. In embodiments, $L^2$ is substituted 16 membered heteroalkylene. In embodiments, $L^2$ is unsubstituted 16 membered heteroalkylene. In embodiments, $L^2$ is substituted or unsubstituted 17 membered heteroalkylene. In embodiments, $L^2$ is substituted 17 membered heteroalkylene. In embodiments, $L^2$ is unsubstituted 17 membered heteroalkylene. In embodiments, $L^2$ is substituted or unsubstituted 18 membered heteroalkylene. In embodiments, $L^2$ is substituted 18 membered heteroalkylene. In embodiments, $L^2$ is unsubstituted 18 membered heteroalkylene. In embodiments, $L^2$ is substituted or unsubstituted 19 membered heteroalkylene. In embodiments, $L^2$ is substituted 19 membered heteroalkylene. In embodiments, $L^2$ is unsubstituted 19 membered heteroalkylene. In embodiments, $L^2$ is substituted or unsubstituted 20 membered heteroalkylene. In embodiments, $L^2$ is substituted 20 membered heteroalkylene. In embodiments, $L^2$ is unsubstituted 20 membered heteroalkylene.

In embodiments, $L^2$ is substituted or unsubstituted $C_4$-$C_6$ cycloalkylene. In embodiments, $L^2$ is substituted $C_4$-$C_6$ cycloalkylene. In embodiments, $L^2$ is substituted $C_4$-$C_6$ cycloalkylene. In embodiments, $L^2$ is substituted or unsubstituted $C_4$ cycloalkylene. In embodiments, $L^2$ is substituted $C_4$ cycloalkylene. In embodiments, $L^2$ is substituted $C_4$ cycloalkylene. In embodiments, $L^2$ is substituted or unsubstituted $C_5$ cycloalkylene. In embodiments, $L^2$ is substituted $C_5$ cycloalkylene. In embodiments, $L^2$ is substituted $C_5$ cycloalkylene.

In embodiments, $L^2$ is substituted or unsubstituted 5 to 6 membered heterocycloalkylene. In embodiments, $L^2$ is substituted 5 to 6 membered heterocycloalkylene. In embodiments, $L^2$ is unsubstituted 5 to 6 membered heterocycloalkylene. In embodiments, $L^2$ is substituted or unsubstituted 5 membered heterocycloalkylene. In embodiments, $L^2$ is substituted 5 membered heterocycloalkylene. In embodiments, $L^2$ is unsubstituted 5 membered heterocycloalkylene. In embodiments, $L^2$ is substituted or unsubstituted 6 membered heterocycloalkylene. In embodiments, $L^2$ is substituted 6 membered heterocycloalkylene. In embodiments, $L^2$ is unsubstituted 6 membered heterocycloalkylene.

In embodiments, $L^2$ is substituted or unsubstituted phenylene. In embodiments, $L^2$ is substituted phenylene. In embodiments, $L^2$ is unsubstituted phenylene.

In embodiments, $L^2$ is substituted or unsubstituted 5 to 6 membered heteroarylene. In embodiments, $L^2$ is substituted 5 to 6 membered heteroarylene. In embodiments, $L^2$ is unsubstituted 5 to 6 membered heteroarylene. In embodiments, $L^2$ is substituted or unsubstituted 5 membered heteroarylene. In embodiments, $L^2$ is substituted 5 membered heteroarylene. In embodiments, $L^2$ is unsubstituted 5 membered heteroarylene. In embodiments, $L^2$ is substituted or unsubstituted 6 membered heteroarylene. In embodiments, $L^2$ is substituted 6 membered heteroarylene. In embodiments, $L^2$ is unsubstituted 6 membered heteroarylene.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$, and $L^{2E}$ are independently a bond, —SS—, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$ $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$, and $L^{2E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; $L^{2A}$ is a bond, substituted or unsubstituted alkylene, substituted or unsubstituted heteroalkylene; $L^{2B}$ is a bond, substituted or unsubstituted cycloalkylene, substituted or unsubstituted heterocycloalkylene, substituted or unsubstituted arylene, substituted or unsubstituted heteroarylene; $L^{2C}$ is a bond, substituted or unsubstituted cycloalkylene, substituted or unsubstituted heterocycloalkylene, substituted or unsubstituted arylene, substituted or unsubstituted heteroarylene; $L^{2D}$ is a bond, substituted or unsubstituted alkylene, substituted or unsubstituted heteroalkylene; and $L^{2E}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$, and $L^{2E}$ is not a bond.

In embodiments, $L^{2A}$ is a bond, substituted (e.g., substituted with a substituent group, size-limited substituent group, or lower substituent group) or unsubstituted alkynylene, or substituted (e.g., substituted with a substituent group, size-limited substituent group, or lower substituent group) or unsubstituted heteroalkynylene. In embodiments, $L^{2A}$ is a bond, substituted (e.g., substituted with a substituent group, size-limited substituent group, or lower substituent group) or unsubstituted $C_2$-$C_8$ alkynylene, or substituted (e.g., substituted with a substituent group, size-limited substituent group, or lower substituent group) or unsubstituted 3 to 8 membered heteroalkynylene. In embodiments, $L^{2A}$ is a bond, substituted (e.g., substituted with a substituent group, size-limited substituent group, or lower substituent group) or unsubstituted $C_2$-$C_6$ alkynylene, or substituted (e.g., substituted with a substituent group, size-limited substituent group, or lower substituent group) or unsubstituted 3 to 6 membered heteroalkynylene.

In embodiments, $L^{2A}$ is a substituted (e.g., substituted with a substituent group, size-limited substituent group, or lower substituent group) or unsubstituted $C_1$-$C_6$ alkylene (e.g., alkylene, alkenylene, or alkynylene), alkenylene, or alkynylene) or substituted (e.g., substituted with a substituent group, size-limited substituent group, or lower substituent group) or unsubstituted 2 to 6 membered heteroalkylene (e.g., heteroalkylene, heteroalkenylene, or heteroalkynylene). In embodiments, $L^{2A}$ is an unsubstituted $C_1$-$C_4$ alkylene (e.g., alkylene, alkenylene, or alkynylene). In embodiments, $L^{2A}$ is —C≡C—CH$_2$—.

In embodiments, $L^{2A}$ is substituted or unsubstituted methylene. In embodiments, $L^{2A}$ is substituted or unsubstituted $C_2$ alkylene. In embodiments, $L^{2A}$ is substituted or unsubstituted $C_3$ alkylene. In embodiments, $L^{2A}$ is substituted or unsubstituted $C_4$ alkylene. In embodiments, $L^{2A}$ is substituted or unsubstituted $C_5$ alkylene. In embodiments, $L^{2A}$ is substituted or unsubstituted $C_6$ alkylene. In embodiments, $L^{2A}$ is substituted or unsubstituted $C_7$ alkylene. In embodiments, $L^{2A}$ is substituted or unsubstituted $C_8$ alkylene. In embodiments, $L^{2A}$ is substituted methylene. In embodiments, $L^{2A}$ is substituted $C_2$ alkylene. In embodiments, $L^{2A}$ is substituted $C_3$ alkylene. In embodiments, $L^{2A}$ is substituted $C_4$ alkylene. In embodiments, $L^{2A}$ is substituted $C_5$ alkylene. In embodiments, $L^{2A}$ is substituted $C_6$ alkylene. In embodiments, $L^{2A}$ is substituted $C_7$ alkylene. In embodiments, $L^{2A}$ is substituted $C_8$ alkylene. In embodiments, $L^{2A}$ is an unsubstituted methylene. In embodiments, $L^{2A}$ is an unsubstituted $C_2$ alkylene. In embodiments, $L^{2A}$ is an unsubstituted $C_3$ alkylene. In embodiments, $L^{2A}$ is an unsubstituted $C_4$ alkylene. In embodiments, $L^{2A}$ is an unsubstituted $C_5$ alkylene. In embodiments, $L^{2A}$ is an unsubstituted $C_6$ alkylene. In embodiments, $L^{2A}$ is an unsubstituted $C_7$ alkylene. In embodiments, $L^{2A}$ is an unsubstituted $C_8$ alkylene.

In embodiments, $L^{2A}$ is substituted or unsubstituted $C_1$-$C_6$ alkylene. In embodiments, $L^{2A}$ is substituted $C_1$-$C_6$ alkylene. In embodiments, $L^{2A}$ is unsubstituted $C_1$-$C_6$ alkylene. In embodiments, $L^{2A}$ is substituted or unsubstituted $C_2$-$C_6$ alkylene. In embodiments, $L^{2A}$ is substituted $C_2$-$C_6$ alkylene. In embodiments, $L^{2A}$ is unsubstituted $C_2$-$C_6$ alkylene. In embodiments, $L^{2A}$ is substituted or unsubstituted $C_1$ alkylene. In embodiments, $L^{2A}$ is substituted or unsubstituted $C_1$ alkylene. In embodiments, $L^{2A}$ is unsubstituted $C_1$ alkylene. In embodiments, $L^{2A}$ is substituted or unsubstituted $C_2$ alkylene. In embodiments, $L^{2A}$ is substituted $C_2$ alkylene. In embodiments, $L^{2A}$ is unsubstituted $C_2$ alkylene. In embodiments, $L^{2A}$ is substituted or unsubstituted $C_3$ alkylene. In embodiments, $L^{2A}$ is substituted $C_3$ alkylene. In embodiments, $L^{2A}$ is unsubstituted $C_3$ alkylene. In embodiments, $L^{2A}$ is substituted or unsubstituted $C_4$ alkylene. In embodiments, $L^{2A}$ is substituted $C_4$ alkylene. In embodiments, $L^{2A}$ is unsubstituted $C_4$ alkylene. In embodiments, $L^{2A}$ is substituted or unsubstituted $C_5$ alkylene. In embodiments, $L^{2A}$ is substituted $C_5$ alkylene. In embodiments, $L^{2A}$ is unsubstituted $C_5$ alkylene. In embodiments, $L^{2A}$ is substituted or unsubstituted $C_6$ alkylene. In embodiments, $L^{2A}$ is substituted $C_6$ alkylene. In embodiments, $L^{2A}$ is unsubstituted $C_6$ alkylene.

In embodiments, $L^{2A}$ is substituted or unsubstituted 2 to 8 membered heteroalkylene. In embodiments, $L^{2A}$ is substituted 2 to 8 membered heteroalkylene. In embodiments, $L^{2A}$ is unsubstituted 2 to 8 membered heteroalkylene. In embodiments, $L^{2A}$ is substituted or unsubstituted 2 membered heteroalkylene. In embodiments, $L^{2A}$ is substituted 2 membered heteroalkylene. In embodiments, $L^{2A}$ is unsubstituted 2 membered heteroalkylene. In embodiments, $L^{2A}$ is substituted or unsubstituted 3 membered heteroalkylene. In embodiments, $L^{2A}$ is substituted 3 membered heteroalkylene. In embodiments, $L^{2A}$ is unsubstituted 3 membered heteroalkylene. In embodiments, $L^{2A}$ is substituted or unsubstituted 4 membered heteroalkylene. In embodiments, $L^{2A}$ is substituted 4 membered heteroalkylene. In embodiments, $L^{2A}$ is unsubstituted 4 membered heteroalkylene. In embodiments, $L^{2A}$ is substituted or unsubstituted 5 membered heteroalkylene. In embodiments, $L^{2A}$ is substituted 5 membered heteroalkylene. In embodiments, $L^{2A}$ is unsubstituted 5 membered heteroalkylene. In embodiments, $L^{2A}$ is substituted or unsubstituted 6 membered heteroalkylene. In embodiments, $L^{2A}$ is substituted 6 membered heteroalkylene. In embodiments, $L^{2A}$ is unsubstituted 6 membered heteroalkylene.

In embodiments, $L^{2A}$ is substituted or unsubstituted $C_4$-$C_6$ cycloalkylene. In embodiments, $L^{2A}$ is substituted $C_4$-$C_6$ cycloalkylene. In embodiments, $L^{2A}$ is substituted $C_4$-$C_6$ cycloalkylene. In embodiments, $L^{2A}$ is substituted or unsubstituted $C_4$ cycloalkylene. In embodiments, $L^{2A}$ is substituted $C_4$ cycloalkylene. In embodiments, $L^{2A}$ is substituted $C_4$ cycloalkylene. In embodiments, $L^{2A}$ is substituted or unsubstituted $C_5$ cycloalkylene. In embodiments, $L^{2A}$ is substituted $C_5$ cycloalkylene. In embodiments, $L^{2A}$ is substituted $C_5$ cycloalkylene.

In embodiments, $L^{2A}$ is substituted or unsubstituted 5 to 6 membered heterocycloalkylene. In embodiments, $L^{2A}$ is substituted 5 to 6 membered heterocycloalkylene. In embodiments, $L^{2A}$ is unsubstituted 5 to 6 membered heterocycloalkylene. In embodiments, $L^{2A}$ is substituted or unsubstituted 5 membered heterocycloalkylene. In embodiments, $L^{2A}$ is substituted 5 membered heterocycloalkylene. In embodiments, $L^{2A}$ is unsubstituted 5 membered heterocycloalkylene. In embodiments, $L^{2A}$ is substituted or unsubstituted 6 membered heterocycloalkylene. In embodiments, $L^{2A}$ is substituted 6 membered heterocycloalkylene. In embodiments, $L^{2A}$ is unsubstituted 6 membered heterocycloalkylene.

In embodiments, $L^{2A}$ is substituted or unsubstituted phenylene. In embodiments, $L^{2A}$ is substituted phenylene. In embodiments, $L^{2A}$ is unsubstituted phenylene.

In embodiments, $L^{2A}$ is substituted or unsubstituted 5 to 6 membered heteroarylene. In embodiments, $L^{2A}$ is substituted 5 to 6 membered heteroarylene. In embodiments, $L^{2A}$ is unsubstituted 5 to 6 membered heteroarylene. In embodiments, $L^{2A}$ is substituted or unsubstituted 5 membered heteroarylene. In embodiments, $L^{2A}$ is substituted 5 membered heteroarylene. In embodiments, $L^{2A}$ is unsubstituted 5 membered heteroarylene. In embodiments, $L^{2A}$ is substituted or unsubstituted 6 membered heteroarylene. In embodiments, $L^{2A}$ is substituted 6 membered heteroarylene. In embodiments, $L^{2A}$ is unsubstituted 6 membered heteroarylene.

In embodiments, $L^{2A}$ is a polymer.

In embodiments, $L^{2B}$ is substituted or unsubstituted methylene. In embodiments, $L^{2B}$ is substituted or unsubstituted $C_2$ alkylene. In embodiments, $L^{2B}$ is substituted or unsubstituted $C_3$ alkylene. In embodiments, $L^{2B}$ is substituted or unsubstituted $C_4$ alkylene. In embodiments, $L^{2B}$ is substituted or unsubstituted $C_5$ alkylene. In embodiments, $L^{2B}$ is substituted or unsubstituted $C_6$ alkylene. In embodiments, $L^{2B}$ is substituted or unsubstituted $C_7$ alkylene. In embodiments, $L^{2B}$ is substituted or unsubstituted $C_8$ alkylene. In embodiments, $L^{2B}$ is substituted methylene. In embodiments, $L^{2B}$ is substituted $C_2$ alkylene. In embodiments, $L^{2B}$ is substituted $C_3$ alkylene. In embodiments, $L^{2B}$ is substituted $C_4$ alkylene. In embodiments, $L^{2B}$ is substituted $C_5$ alkylene. In embodiments, $L^{2B}$ is substituted $C_6$ alkylene. In embodiments, $L^{2B}$ is substituted $C_7$ alkylene. In embodiments, $L^{2B}$ is substituted $C_8$ alkylene. In embodiments, $L^{2B}$ is an unsubstituted methylene. In embodiments, $L^{2B}$ is an unsubstituted $C_2$ alkylene. In embodiments, $L^{2B}$ is an unsubstituted $C_3$ alkylene. In embodiments, $L^{2B}$ is an unsubstituted $C_4$ alkylene. In embodiments $L^{2B}$ is an unsubstituted $C_5$ alkylene. In embodiments, $L^{2B}$ is an unsubstituted $C_6$ alkylene. In embodiments, $L^{2B}$ is an unsubstituted $C_7$ alkylene. In embodiments, $L^{2B}$ is an unsubstituted $C_8$ alkylene.

In embodiments, $L^{2B}$ is substituted or unsubstituted $C_1$-$C_6$ alkylene. In embodiments, $L^{2B}$ is substituted $C_1$-$C_6$ alkylene. In embodiments, $L^{2B}$ is unsubstituted $C_1$-$C_6$ alkylene. In embodiments, $L^{2B}$ is substituted or unsubstituted $C_2$-$C_6$ alkylene. In embodiments, $L^{2B}$ is substituted $C_2$-$C_6$ alkylene. In embodiments, $L^{2B}$ is unsubstituted $C_2$-$C_6$ alkylene. In embodiments, $L^{2B}$ is substituted or unsubstituted $C_1$ alkylene. In embodiments, $L^{2B}$ is substituted $C_1$ alkylene. In embodiments, $L^{2B}$ is unsubstituted $C_1$ alkylene. In embodiments, $L^{2B}$ is substituted or unsubstituted $C_2$ alkylene. In embodiments, $L^{2B}$ is substituted $C_2$ alkylene. In embodiments, $L^{2B}$ is unsubstituted $C_2$ alkylene. In embodiments, $L^{2B}$ is substituted or unsubstituted $C_3$ alkylene. In embodiments, $L^{2B}$ is substituted $C_3$ alkylene. In embodiments, $L^{2B}$ is unsubstituted $C_3$ alkylene. In embodiments, $L^{2B}$ is substituted or unsubstituted $C_4$ alkylene. In embodiments, $L^{2B}$ is substituted $C_4$ alkylene. In embodiments, $L^{2B}$ is unsubstituted $C_4$ alkylene. In embodiments, $L^{2B}$ is substituted or unsubstituted $C_5$ alkylene. In embodiments, $L^{2B}$ is substituted $C_5$ alkylene. In embodiments, $L^{2B}$ is unsubstituted $C_5$ alkylene. In embodiments, $L^{2B}$ is substituted or unsubstituted $C_6$ alkylene. In embodiments, $L^{2B}$ is substituted $C_6$ alkylene. In embodiments, $L^{2B}$ is unsubstituted $C_6$ alkylene.

In embodiments, $L^{2B}$ is substituted or unsubstituted 2 to 8 membered heteroalkylene. In embodiments, $L^{2B}$ is substituted 2 to 8 membered heteroalkylene. In embodiments, $L^{2B}$ is unsubstituted 2 to 8 membered heteroalkylene. In embodiments, $L^{2B}$ is substituted or unsubstituted 2 membered heteroalkylene. In embodiments, $L^{2B}$ is substituted 2 membered heteroalkylene. In embodiments, $L^{2B}$ is unsubstituted 2 membered heteroalkylene. In embodiments, $L^{2B}$ is substituted or unsubstituted 3 membered heteroalkylene. In embodiments, $L^{2B}$ is substituted 3 membered heteroalkylene. In embodiments, $L^{2B}$ is unsubstituted 3 membered heteroalkylene. In embodiments, $L^{2B}$ is substituted or unsubstituted 4 membered heteroalkylene. In embodiments, $L^{2B}$ is substituted 4 membered heteroalkylene. In embodiments, $L^{2B}$ is unsubstituted 4 membered heteroalkylene. In embodiments, $L^{2B}$ is substituted or unsubstituted 5 membered heteroalkylene. In embodiments, $L^{2B}$ is substituted 5 membered heteroalkylene. In embodiments, $L^{2B}$ is unsubstituted 5 membered heteroalkylene. In embodiments, $L^{2B}$ is substituted or unsubstituted 6 membered heteroalkylene. In embodiments, $L^{2B}$ is substituted 6 membered heteroalkylene. In embodiments, $L^{2B}$ is unsubstituted 6 membered heteroalkylene.

In embodiments, $L^{2B}$ is substituted or unsubstituted $C_4$-$C_6$ cycloalkylene. In embodiments, $L^{2B}$ is substituted $C_4$-$C_6$ cycloalkylene. In embodiments, $L^{2B}$ is substituted $C_4$-$C_6$ cycloalkylene. In embodiments, $L^{2B}$ is substituted or unsubstituted $C_4$ cycloalkylene. In embodiments, $L^{2B}$ is substituted $C_4$ cycloalkylene. In embodiments, $L^{2B}$ is substituted $C_4$ cycloalkylene. In embodiments, $L^{2B}$ is substituted or unsubstituted $C_5$ cycloalkylene. In embodiments, $L^{2B}$ is substituted $C_5$ cycloalkylene. In embodiments, $L^{2B}$ is substituted $C_5$ cycloalkylene.

In embodiments, $L^{2B}$ is substituted or unsubstituted 5 to 6 membered heterocycloalkylene. In embodiments, $L^{2B}$ is substituted 5 to 6 membered heterocycloalkylene. In embodiments, $L^{2B}$ is unsubstituted 5 to 6 membered heterocycloalkylene. In embodiments, $L^{2B}$ is substituted or unsubstituted 5 membered heterocycloalkylene. In embodiments, $L^{2B}$ is substituted 5 membered heterocycloalkylene. In embodiments, $L^{2B}$ is unsubstituted 5 membered heterocycloalkylene. In embodiments, $L^{2B}$ is substituted or unsubstituted 6 membered heterocycloalkylene. In embodiments, $L^{2B}$ is substituted 6 membered heterocycloalkylene. In embodiments, $L^{2B}$ is unsubstituted 6 membered heterocycloalkylene.

In embodiments, $L^{2B}$ is substituted or unsubstituted phenylene. In embodiments, $L^{2B}$ is substituted phenylene. In embodiments, $L^{2B}$ is unsubstituted phenylene.

In embodiments, $L^{2B}$ is substituted or unsubstituted 5 to 6 membered heteroarylene. In embodiments, $L^{2B}$ is substituted 5 to 6 membered heteroarylene. In embodiments, $L^{2B}$ is unsubstituted 5 to 6 membered heteroarylene. In embodiments, $L^{2B}$ is substituted or unsubstituted 5 membered heteroarylene. In embodiments, $L^{2B}$ is substituted 5 membered heteroarylene. In embodiments, $L^{2B}$ is unsubstituted 5 membered heteroarylene. In embodiments, $L^{2B}$ is substituted or unsubstituted 6 membered heteroarylene. In embodiments, $L^{2B}$ is substituted 6 membered heteroarylene. In embodiments, $L^{2B}$ is unsubstituted 6 membered heteroarylene.

In embodiments, $L^{2C}$ is substituted or unsubstituted methylene. In embodiments, $L^{2C}$ is substituted or unsubstituted $C_2$ alkylene. In embodiments, $L^{2C}$ is substituted or unsubstituted $C_3$ alkylene. In embodiments, $L^{2C}$ is substituted or unsubstituted $C_4$ alkylene. In embodiments, $L^{2C}$ is substituted or unsubstituted $C_5$ alkylene. In embodiments, $L^{2C}$ is substituted or unsubstituted $C_6$ alkylene. In embodiments, $L^{2C}$ is substituted or unsubstituted $C_7$ alkylene. In embodiments, $L^{2C}$ is substituted or unsubstituted $C_8$ alkylene. In embodiments, $L^{2C}$ is substituted methylene. In embodiments, $L^{2C}$ is substituted $C_2$ alkylene. In embodiments, $L^{2C}$ is substituted $C_3$ alkylene. In embodiments, $L^{2C}$ is substituted $C_4$ alkylene. In embodiments, $L^{2C}$ is substituted $C_5$ alkylene. In embodiments, $L^{2C}$ is substituted $C_6$ alkylene. In embodiments, $L^{2C}$ is substituted $C_7$ alkylene. In embodiments, $L^{2C}$ is substituted $C_8$ alkylene. In embodiments, $L^{2C}$ is an unsubstituted methylene. In embodiments, $L^{2C}$ is an unsubstituted $C_2$ alkylene. In embodiments, $L^{2C}$ is an unsubstituted $C_3$ alkylene. In embodiments, $L^{2C}$ is an unsubstituted $C_4$ alkylene. In embodiments, $L^{2C}$ is an unsubstituted $C_5$ alkylene. In embodiments, $L^{2C}$ is an unsubstituted $C_6$ alkylene. In embodiments, $L^{2C}$ is an unsubstituted $C_7$ alkylene. In embodiments, $L^{2C}$ is an unsubstituted $C_8$ alkylene.

In embodiments, $L^{2C}$ is substituted or unsubstituted $C_1$-$C_6$ alkylene. In embodiments, $L^{2C}$ is substituted $C_1$-$C_6$ alkylene. In embodiments, $L^{2C}$ is unsubstituted $C_1$-$C_6$ alkylene. In embodiments, $L^{2C}$ is substituted or unsubstituted $C_2$-$C_6$ alkylene. In embodiments, $L^{2C}$ is substituted $C_2$-$C_6$ alkylene. In embodiments, $L^{2C}$ is unsubstituted $C_2$-$C_6$ alkylene. In embodiments, $L^{2C}$ is substituted or unsubstituted $C_1$ alkylene. In embodiments, $L^{2C}$ is substituted $C_1$ alkylene. In embodiments, $L^{2C}$ is unsubstituted $C_1$ alkylene. In embodiments, $L^{2C}$ is substituted or unsubstituted $C_2$ alkylene. In embodiments, $L^{2C}$ is substituted $C_2$ alkylene. In embodiments, $L^{2C}$ is unsubstituted $C_2$ alkylene. In embodiments, $L^{2C}$ is substituted or unsubstituted $C_3$ alkylene. In embodiments, $L^{2C}$ is substituted $C_3$ alkylene. In embodiments, $L^{2C}$ is unsubstituted $C_3$ alkylene. In embodiments, $L^{2C}$ is substituted or unsubstituted $C_4$ alkylene. In embodiments, $L^{2C}$ is substituted $C_4$ alkylene. In embodiments, $L^{2C}$ is unsubstituted $C_4$ alkylene. In embodiments, $L^{2C}$ is substituted or unsubstituted $C_5$ alkylene. In embodiments, $L^{2C}$ is substituted $C_5$ alkylene. In embodiments, $L^{2C}$ is unsubstituted $C_5$ alkylene. In embodiments, $L^{2C}$ is substituted or unsubstituted $C_6$ alkylene. In embodiments, $L^{2C}$ is substituted $C_6$ alkylene. In embodiments, $L^{2C}$ is unsubstituted $C_6$ alkylene.

In embodiments, $L^{2C}$ is substituted or unsubstituted 2 to 8 membered heteroalkylene. In embodiments, $L^{2C}$ is substituted 2 to 8 membered heteroalkylene. In embodiments, $L^{2C}$ is unsubstituted 2 to 8 membered heteroalkylene. In embodiments, $L^{2C}$ is substituted or unsubstituted 2 membered heteroalkylene. In embodiments, $L^{2C}$ is substituted 2 membered heteroalkylene. In embodiments, $L^{2C}$ is unsubstituted 2 membered heteroalkylene. In embodiments, $L^{2C}$ is substituted or unsubstituted 3 membered heteroalkylene. In embodiments, $L^{2C}$ is substituted 3 membered heteroalkylene. In embodiments, $L^{2C}$ is unsubstituted 3 membered heteroalkylene. In embodiments, $L^{2C}$ is substituted or unsubstituted 4 membered heteroalkylene. In embodiments, $L^{2C}$ is substituted 4 membered heteroalkylene. In embodiments, $L^{2C}$ is unsubstituted 4 membered heteroalkylene. In embodiments, $L^{2C}$ is substituted or unsubstituted 5 membered heteroalkylene. In embodiments, $L^{2C}$ is substituted 5 membered heteroalkylene. In embodiments, $L^{2C}$ is unsubstituted 5 membered heteroalkylene. In embodiments, $L^{2C}$ is substituted or unsubstituted 6 membered heteroalkylene. In embodiments, $L^{2C}$ is substituted 6 membered heteroalkylene. In embodiments, $L^{2C}$ is unsubstituted 6 membered heteroalkylene.

In embodiments, $L^{2C}$ is substituted or unsubstituted $C_4$-$C_6$ cycloalkylene. In embodiments, $L^{2C}$ is substituted $C_4$-$C_6$ cycloalkylene. In embodiments, $L^{2C}$ is substituted $C_4$-$C_6$ cycloalkylene. In embodiments, $L^{2C}$ is substituted or unsubstituted $C_4$ cycloalkylene. In embodiments, $L^{2C}$ is substituted $C_4$ cycloalkylene. In embodiments, $L^{2C}$ is substituted $C_4$ cycloalkylene. In embodiments, $L^{2C}$ is substituted or unsubstituted $C_5$ cycloalkylene. In embodiments, $L^{2C}$ is substituted $C_5$ cycloalkylene. In embodiments, $L^{2C}$ is substituted $C_5$ cycloalkylene.

In embodiments, $L^{2C}$ is substituted or unsubstituted 5 to 6 membered heterocycloalkylene. In embodiments, $L^{2C}$ is substituted 5 to 6 membered heterocycloalkylene. In embodiments, $L^{2C}$ is unsubstituted 5 to 6 membered heterocycloalkylene. In embodiments, $L^{2C}$ is substituted or unsubstituted 5 membered heterocycloalkylene. In embodiments, $L^{2C}$ is substituted 5 membered heterocycloalkylene. In embodiments, $L^{2C}$ is unsubstituted 5 membered heterocycloalkylene. In embodiments, $L^{2C}$ is substituted or unsubstituted 6 membered heterocycloalkylene. In embodiments, $L^{2C}$ is substituted 6 membered heterocycloalkylene. In embodiments, $L^{2C}$ is unsubstituted 6 membered heterocycloalkylene.

In embodiments, $L^{2C}$ is substituted or unsubstituted phenylene. In embodiments, $L^{2C}$ is substituted phenylene. In embodiments, $L^{2C}$ is unsubstituted phenylene.

In embodiments, $L^{2C}$ is substituted or unsubstituted 5 to 6 membered heteroarylene. In embodiments, $L^{2C}$ is substituted 5 to 6 membered heteroarylene. In embodiments, $L^{2C}$ is unsubstituted 5 to 6 membered heteroarylene. In embodiments, $L^{2C}$ is substituted or unsubstituted 5 membered heteroarylene. In embodiments, $L^{2C}$ is substituted 5 membered heteroarylene. In embodiments, $L^{2C}$ is unsubstituted 5 membered heteroarylene. In embodiments, $L^{2C}$ is substituted or unsubstituted 6 membered heteroarylene. In embodiments, $L^{2C}$ is substituted 6 membered heteroarylene. In embodiments, $L^{2C}$ is unsubstituted 6 membered heteroarylene.

In embodiments, $L^{2D}$ is substituted or unsubstituted methylene. In embodiments, $L^{2D}$ is substituted or unsubstituted $C_2$ alkylene. In embodiments, $L^{2D}$ is substituted or unsubstituted $C_3$ alkylene. In embodiments, $L^{2D}$ is substituted or unsubstituted $C_4$ alkylene. In embodiments, $L^{2D}$ is substituted or unsubstituted $C_5$ alkylene. In embodiments, $L^{2D}$ is substituted or unsubstituted $C_6$ alkylene. In embodiments, $L^{2D}$ is substituted or unsubstituted $C_7$ alkylene. In embodiments, $L^{2D}$ is substituted or unsubstituted $C_8$ alkylene. In embodiments, $L^{2D}$ is substituted methylene. In embodiments, $L^{2D}$ is substituted $C_2$ alkylene. In embodiments, $L^{2D}$ is substituted $C_3$ alkylene. In embodiments, $L^{2D}$ is substituted $C_4$ alkylene. In embodiments, $L^{2D}$ is substituted $C_8$ alkylene. In embodiments, $L^{2D}$ is substituted $C_6$ alkylene. In embodiments, $L^{2D}$ is substituted $C_7$ alkylene. In embodiments, $L^{2D}$ is substituted $C_8$ alkylene. In embodiments, $L^{2D}$ is an unsubstituted methylene. In embodiments, $L^{2D}$ is an unsubstituted $C_2$ alkylene. In embodiments, $L^{2D}$ is an unsubstituted $C_3$ alkylene. In embodiments, $L^{2D}$ is an unsubstituted $C_4$ alkylene. In embodiments $L^{2D}$ is an unsubstituted $C_5$ alkylene. In embodiments, $L^{2D}$ is an unsubstituted $C_6$ alkylene. In embodiments, $L^{2D}$ is an unsubstituted $C_7$ alkylene. In embodiments, $L^{2D}$ is an unsubstituted $C_8$ alkylene.

In embodiments, $L^{2D}$ is substituted or unsubstituted $C_1$-$C_6$ alkylene. In embodiments, $L^{2D}$ is substituted $C_1$-$C_6$ alkylene. In embodiments, $L^{2D}$ is unsubstituted $C_1$-$C_6$ alkylene. In embodiments, $L^{2D}$ is substituted or unsubstituted $C_2$-$C_6$ alkylene. In embodiments, $L^{2D}$ is substituted $C_2$-$C_6$ alkylene. In embodiments, $L^{2D}$ is unsubstituted $C_2$-$C_6$ alkylene. In embodiments, $L^{2D}$ is substituted or unsubstituted $C_1$ alkylene. In embodiments, $L^{2D}$ is substituted $C_1$ alkylene. In embodiments, $L^{2D}$ is unsubstituted $C_1$ alkylene. In embodiments, $L^{2D}$ is substituted or unsubstituted $C_2$ alkylene. In embodiments, $L^{2D}$ is substituted $C_2$ alkylene. In embodiments, $L^{2D}$ is unsubstituted $C_2$ alkylene. In embodiments, $L^{2D}$ is substituted or unsubstituted $C_3$ alkylene. In embodiments, $L^{2D}$ is substituted $C_3$ alkylene. In embodiments, $L^{2D}$ is unsubstituted $C_3$ alkylene. In embodiments, $L^{2D}$ is substituted or unsubstituted $C_4$ alkylene. In embodiments, $L^{2D}$ is substituted $C_4$ alkylene. In embodiments, $L^{2D}$ is unsubstituted $C_4$ alkylene. In embodiments, $L^{2D}$ is substituted or unsubstituted $C_5$ alkylene. In embodiments, $L^{2D}$ is substituted $C_8$ alkylene. In embodiments, $L^{2D}$ is unsubstituted $C_8$ alkylene. In embodiments, $L^{2D}$ is substituted or unsubstituted $C_6$ alkylene. In embodiments, $L^{2D}$ is substituted $C_6$ alkylene. In embodiments, $L^{2D}$ is unsubstituted $C_6$ alkylene.

In embodiments, $L^{2D}$ is substituted or unsubstituted 2 to 8 membered heteroalkylene. In embodiments, $L^{2D}$ is substituted 2 to 8 membered heteroalkylene. In embodiments, $L^{2D}$ is unsubstituted 2 to 8 membered heteroalkylene. In embodiments, $L^{2D}$ is substituted or unsubstituted 2 membered heteroalkylene. In embodiments, $L^{2D}$ is substituted 2 membered heteroalkylene. In embodiments, $L^{2D}$ is unsubstituted 2 membered heteroalkylene. In embodiments, $L^{2D}$ is substituted or unsubstituted 3 membered heteroalkylene. In embodiments, $L^{2D}$ is substituted 3 membered heteroalkylene. In embodiments, $L^{2D}$ is unsubstituted 3 membered heteroalkylene. In embodiments, $L^{2D}$ is substituted or unsubstituted 4 membered heteroalkylene. In embodiments, $L^{2D}$ is substituted 4 membered heteroalkylene. In embodiments, $L^{2D}$ is unsubstituted 4 membered heteroalkylene. In embodiments, $L^{2D}$ is substituted or unsubstituted 5 membered heteroalkylene. In embodiments, $L^{2D}$ is substituted 5 membered heteroalkylene. In embodiments, $L^{2D}$ is unsubstituted 5 membered heteroalkylene. In embodiments, $L^{2D}$ is substituted or unsubstituted 6 membered heteroalkylene. In embodiments, $L^{2D}$ is substituted 6 membered heteroalkylene. In embodiments, $L^{2D}$ is unsubstituted 6 membered heteroalkylene.

In embodiments, $L^{2D}$ is substituted or unsubstituted $C_4$-$C_6$ cycloalkylene. In embodiments, $L^{2D}$ is substituted $C_4$-$C_6$ cycloalkylene. In embodiments, $L^{2D}$ is unsubstituted $C_4$-$C_6$ cycloalkylene. In embodiments, $L^{2D}$ is substituted or unsubstituted $C_4$ cycloalkylene. In embodiments, $L^{2D}$ is substituted $C_4$ cycloalkylene. In embodiments, $L^{2D}$ is unsubstituted $C_4$ cycloalkylene. In embodiments, $L^{2D}$ is substituted or unsubstituted $C_5$ cycloalkylene. In embodiments, $L^{2D}$ is substituted $C_5$ cycloalkylene. In embodiments, $L^{2D}$ is unsubstituted $C_5$ cycloalkylene.

In embodiments, $L^{2D}$ is substituted or unsubstituted 5 to 6 membered heterocycloalkylene. In embodiments, $L^{2D}$ is substituted 5 to 6 membered heterocycloalkylene. In embodiments, $L^{2D}$ is unsubstituted 5 to 6 membered heterocycloalkylene. In embodiments, $L^{2D}$ is substituted or unsubstituted 5 membered heterocycloalkylene. In embodiments, $L^{2D}$ is substituted 5 membered heterocycloalkylene. In embodiments, $L^{2D}$ is unsubstituted 5 membered heterocycloalkylene. In embodiments, $L^{2D}$ is substituted or unsubstituted 6 membered heterocycloalkylene. In embodiments, $L^{2D}$ is substituted 6 membered heterocycloalkylene. In embodiments, $L^{2D}$ is unsubstituted 6 membered heterocycloalkylene.

In embodiments, $L^{2D}$ is substituted or unsubstituted phenylene. In embodiments, $L^{2D}$ is substituted phenylene. In embodiments, $L^{2D}$ is unsubstituted phenylene.

In embodiments, $L^{2D}$ is substituted or unsubstituted 5 to 6 membered heteroarylene. In embodiments, $L^{2D}$ is substituted 5 to 6 membered heteroarylene. In embodiments, $L^{2D}$ is unsubstituted 5 to 6 membered heteroarylene. In embodiments, $L^{2D}$ is substituted or unsubstituted 5 membered heteroarylene. In embodiments, $L^{2D}$ is substituted 5 membered heteroarylene. In embodiments, $L^{2D}$ is unsubstituted 5 membered heteroarylene. In embodiments, $L^{2D}$ is substituted or unsubstituted 6 membered heteroarylene. In embodiments, $L^{2D}$ is substituted 6 membered heteroarylene. In embodiments, $L^{2D}$ is unsubstituted 6 membered heteroarylene.

In embodiments, $L^{2E}$ is substituted or unsubstituted methylene. In embodiments, $L^{2E}$ is substituted or unsubstituted $C_2$ alkylene. In embodiments, $L^{2E}$ is substituted or unsubstituted $C_3$ alkylene. In embodiments, $L^{2E}$ is substituted or unsubstituted $C_4$ alkylene. In embodiments, $L^{2E}$ is substituted or unsubstituted $C_5$ alkylene. In embodiments, $L^{2E}$ is substituted or unsubstituted $C_6$ alkylene. In embodiments, $L^{2E}$ is substituted or unsubstituted $C_7$ alkylene. In embodiments, $L^{2E}$ is substituted or unsubstituted $C_8$ alkylene. In embodiments, $L^{2E}$ is substituted methylene. In embodiments, $L^{2E}$ is substituted $C_2$ alkylene. In embodiments, $L^{2E}$ is substituted $C_3$ alkylene. In embodiments, $L^{2E}$ is substituted $C_4$ alkylene. In embodiments, $L^{2E}$ is substituted $C_5$ alkylene. In embodiments, $L^{2E}$ is substituted $C_6$ alkylene. In embodiments, $L^{2E}$ is substituted $C_7$ alkylene. In embodiments, $L^{2E}$ is substituted $C_8$ alkylene. In embodiments, $L^{2E}$ is an unsubstituted methylene. In embodiments, $L^{2E}$ is an unsubstituted $C_2$ alkylene. In embodiments, $L^{2E}$ is an unsubstituted $C_3$ alkylene. In embodiments, $L^{2E}$ is an unsubstituted $C_4$ alkylene. In embodiments, $L^{2E}$ is an unsubstituted $C_5$ alkylene. In embodiments, $L^{2E}$ is an unsubstituted $C_6$ alkylene. In embodiments, $L^{2E}$ is an unsubstituted $C_7$ alkylene. In embodiments, $L^{2E}$ is an unsubstituted $C_8$ alkylene.

In embodiments, $L^{2E}$ is substituted or unsubstituted $C_1$-$C_6$ alkylene. In embodiments, $L^{2E}$ is substituted $C_1$-$C_6$ alkylene. In embodiments, $L^{2E}$ is unsubstituted $C_1$-$C_6$ alkylene. In embodiments, $L^{2E}$ is substituted or unsubstituted $C_2$-$C_6$ alkylene. In embodiments, $L^{2E}$ is substituted $C_2$-$C_6$ alkylene. In embodiments, $L^{2E}$ is unsubstituted $C_2$-$C_6$ alkylene. In embodiments, $L^{2E}$ is substituted or unsubstituted $C_1$ alkylene. In embodiments, $L^{2E}$ is substituted $C_1$ alkylene. In embodiments, $L^{2E}$ is unsubstituted $C_1$ alkylene. In embodiments, $L^{2E}$ is substituted or unsubstituted $C_2$ alkylene. In embodiments, $L^{2E}$ is substituted $C_2$ alkylene. In embodiments, $L^{2E}$ is unsubstituted $C_2$ alkylene. In embodiments, $L^{2E}$ is substituted or unsubstituted $C_3$ alkylene. In embodiments, $L^{2E}$ is substituted $C_3$ alkylene. In embodiments, $L^{2E}$ is unsubstituted $C_3$ alkylene. In embodiments, $L^{2E}$ is substituted or unsubstituted $C_4$ alkylene. In embodiments, $L^{2E}$ is substituted $C_4$ alkylene. In embodiments, $L^{2E}$ is unsubstituted $C_4$ alkylene. In embodiments, $L^{2E}$ is substituted or unsubstituted $C_5$ alkylene. In embodiments, $L^{2E}$ is substituted $C_5$ alkylene. In embodiments, $L^{2E}$ is unsubstituted $C_5$ alkylene. In embodiments, $L^{2E}$ is substituted or unsubstituted $C_6$ alkylene. In embodiments, $L^{2E}$ is substituted $C_6$ alkylene. In embodiments, $L^{2E}$ is unsubstituted $C_6$ alkylene.

In embodiments, $L^{2E}$ is substituted or unsubstituted 2 to 8 membered heteroalkylene. In embodiments, $L^{2E}$ is substituted 2 to 8 membered heteroalkylene. In embodiments, $L^{2E}$ is unsubstituted 2 to 8 membered heteroalkylene. In embodiments, $L^{2E}$ is substituted or unsubstituted 2 membered heteroalkylene. In embodiments, $L^{2E}$ is substituted 2 membered heteroalkylene. In embodiments, $L^{2E}$ is unsubstituted 2 membered heteroalkylene. In embodiments, $L^{2E}$ is substituted or unsubstituted 3 membered heteroalkylene. In embodiments, $L^{2E}$ is substituted 3 membered heteroalkylene. In embodiments, $L^{2E}$ is unsubstituted 3 membered heteroalkylene. In embodiments, $L^{2E}$ is substituted or unsubstituted 4 membered heteroalkylene. In embodiments, $L^{2E}$ is substituted 4 membered heteroalkylene. In embodiments, $L^{2E}$ is unsubstituted 4 membered heteroalkylene. In embodiments, $L^{2E}$ is substituted or unsubstituted 5 membered heteroalkylene. In embodiments, $L^{2E}$ is substituted 5 membered heteroalkylene. In embodiments, $L^{2E}$ is unsubstituted 5 membered heteroalkylene. In embodiments, $L^{2E}$ is substituted or unsubstituted 6 membered heteroalkylene. In embodiments, $L^{2E}$ is substituted 6 membered heteroalkylene. In embodiments, $L^{2E}$ is unsubstituted 6 membered heteroalkylene.

In embodiments, $L^{2E}$ is substituted or unsubstituted $C_4$-$C_6$ cycloalkylene. In embodiments, $L^{2E}$ is substituted $C_4$-$C_6$ cycloalkylene. In embodiments, $L^{2E}$ is substituted $C_4$-$C_6$ cycloalkylene. In embodiments, $L^{2E}$ is substituted or unsubstituted $C_4$ cycloalkylene. In embodiments, $L^{2E}$ is substituted $C_4$ cycloalkylene. In embodiments, $L^{2E}$ is substituted $C_4$ cycloalkylene. In embodiments, $L^{2E}$ is substituted or unsubstituted $C_5$ cycloalkylene. In embodiments, $L^{2E}$ is substituted $C_5$ cycloalkylene. In embodiments, $L^{2E}$ is substituted $C_5$ cycloalkylene.

In embodiments, $L^{2E}$ is substituted or unsubstituted 5 to 6 membered heterocycloalkylene. In embodiments, $L^{2E}$ is substituted 5 to 6 membered heterocycloalkylene. In embodiments, $L^{2E}$ is unsubstituted 5 to 6 membered heterocycloalkylene. In embodiments, $L^{2E}$ is substituted or unsubstituted 5 membered heterocycloalkylene. In embodiments, $L^{2E}$ is substituted 5 membered heterocycloalkylene. In embodiments, $L^{2E}$ is unsubstituted 5 membered heterocycloalkylene. In embodiments, $L^{2E}$ is substituted or unsubstituted 6 membered heterocycloalkylene. In embodiments, $L^{2E}$ is substituted 6 membered heterocycloalkylene. In embodiments, $L^{2E}$ is unsubstituted 6 membered heterocycloalkylene.

In embodiments, $L^{2E}$ is substituted or unsubstituted phenylene. In embodiments, $L^{2E}$ is substituted phenylene. In embodiments, $L^{2E}$ is unsubstituted phenylene.

In embodiments, $L^{2E}$ is substituted or unsubstituted 5 to 6 membered heteroarylene. In embodiments, $L^{2E}$ is substituted 5 to 6 membered heteroarylene. In embodiments, $L^{2E}$ is unsubstituted 5 to 6 membered heteroarylene. In embodiments, $L^{2E}$ is substituted or unsubstituted 5 membered heteroarylene. In embodiments, $L^{2E}$ is substituted 5 membered heteroarylene. In embodiments, $L^{2E}$ is unsubstituted 5 membered heteroarylene. In embodiments, $L^{2E}$ is substituted or unsubstituted 6 membered heteroarylene. In embodiments, $L^{2E}$ is substituted 6 membered heteroarylene. In embodiments, $L^{2E}$ is unsubstituted 6 membered heteroarylene.

In embodiments, $L^{2A}$ is a bond. In embodiments, $L^{2B}$ is a bond. In embodiments, $L^{2C}$ is a bond. In embodiments, $L^{2D}$ is a bond. In embodiments, $L^{2E}$ is a bond.

In embodiments, $L^{2A}$ is —NN—. In embodiments, $L^{2B}$ is —NN—. In embodiments, $L^{2C}$ is —NN—. In embodiments, $L^{2D}$ is —NN—. In embodiments, $L^{2E}$ is —NN—. In embodiments, $L^{2A}$ is —SS—. In embodiments, $L^{2B}$ is —SS—. In embodiments, $L^{2C}$ is —SS—. In embodiments, $L^{2D}$ is —SS—. In embodiments, $L^{2E}$ is —SS—.

In embodiments, $L^{2A}$ is —NHC(O)—. In embodiments, $L^{2B}$ is —NHC(O)—. In embodiments, $L^{2C}$ is —NHC(O)—. In embodiments, $L^{2D}$ is —NHC(O)—. In embodiments, $L^{2E}$ is —NHC(O)—.

In embodiments, $L^{2A}$ is —C(O)NH—. In embodiments, $L^{2B}$ is —C(O)NH—. In embodiments, $L^{2C}$ is —C(O)NH—. In embodiments, $L^{2D}$ is —C(O)NH—. In embodiments, $L^{2E}$ is —C(O)NH—.

In embodiments, $L^2$ is

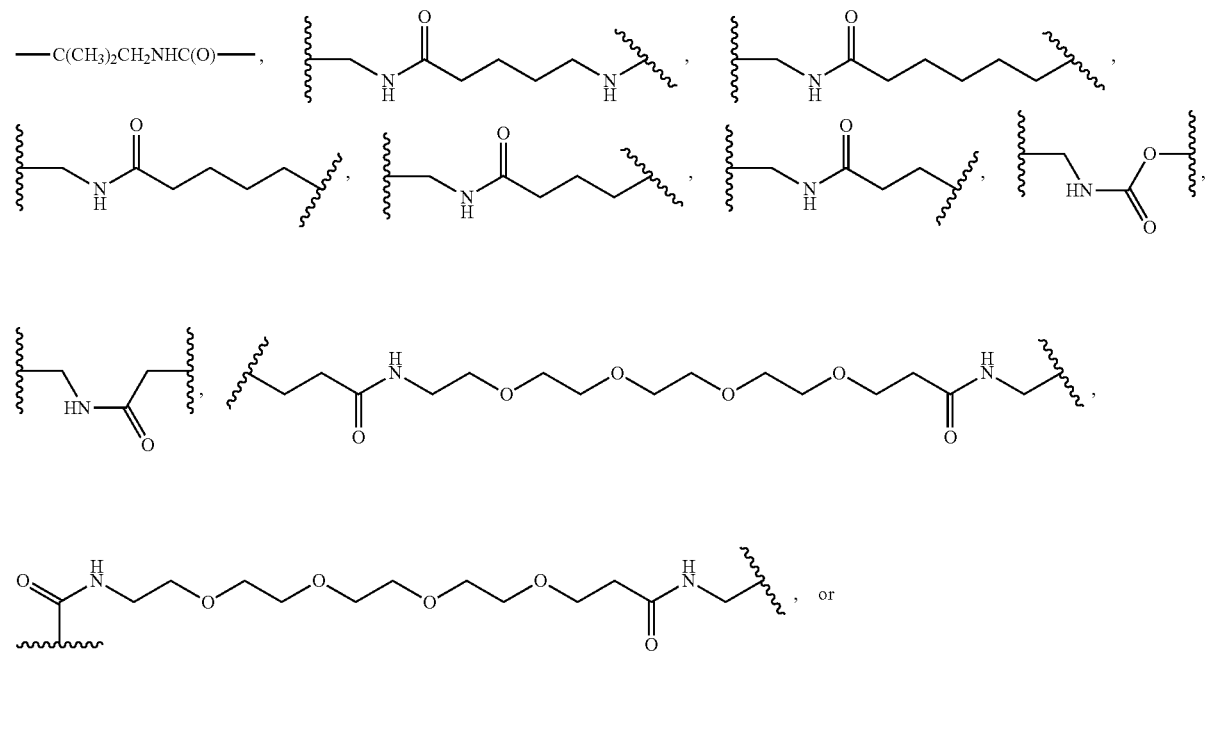

In embodiments, $L^2$ is
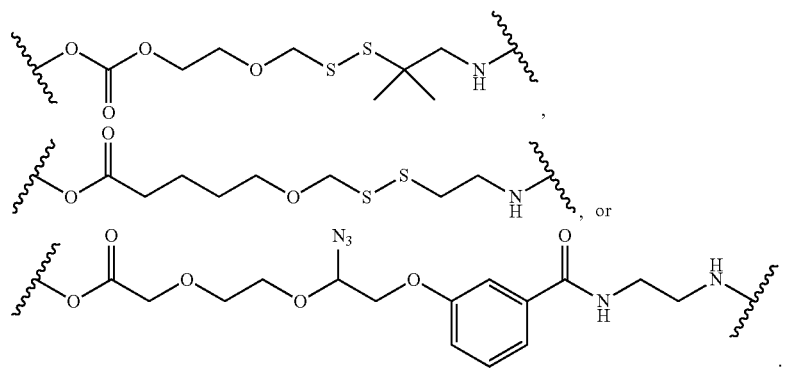
In embodiments, $L^2$ is
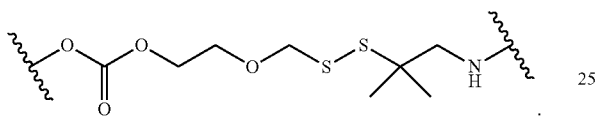
In embodiments, $L^2$ is
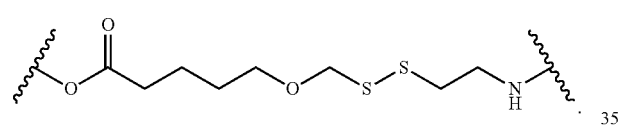
In embodiments, $L^2$ is
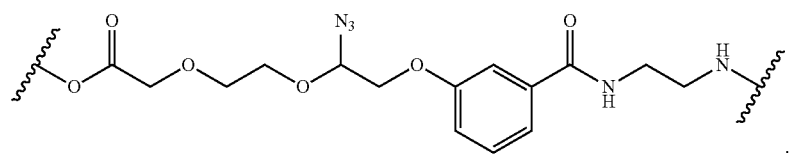 [SMILES: *NCCNC(=O)c1cccc(OCC(N=[N+]=[N-])OCCOCC(=O)O*)c1]
In embodiments, $L^2$ is
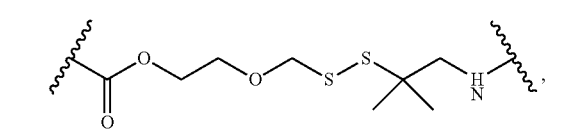
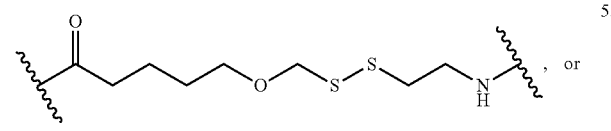
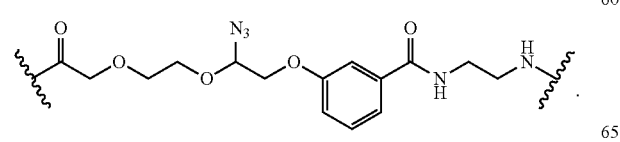

In embodiments, L² is
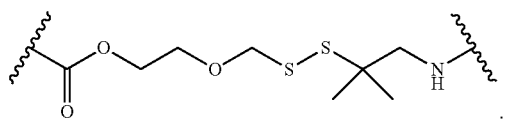 [SMILES: *NCC(C)(C)SSCOCCOC(*)=O]
In embodiments, L² is
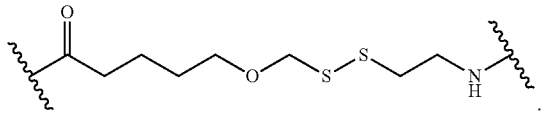 [SMILES: *NCCSSCOCCCCC(*)=O]
In embodiments, L² is
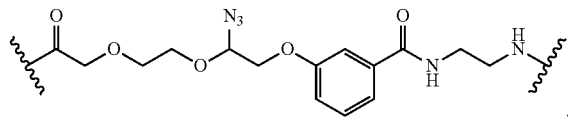 [SMILES: *NCCNC(=O)c1cccc(OCC(N=[N+]=[N-])OCCOCC(*)=O)c1]
In embodiments, L² is
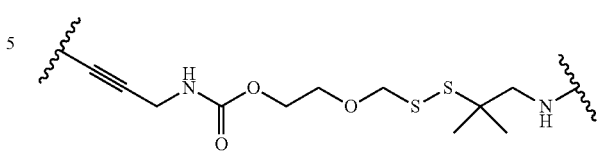
In embodiments, L² is
In embodiments, L² is
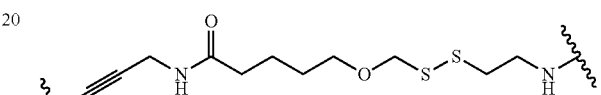
In embodiments, L² is
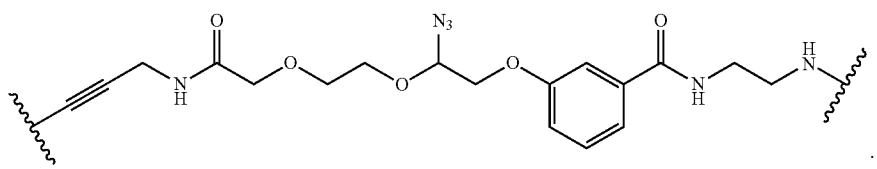 [SMILES: *C#CCNC(=O)COCCOC(COc1cccc(C(=O)NCCN*)c1)N=[N+]=[N-]]
In embodiments, L² is
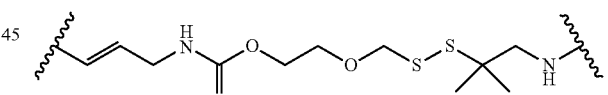
In embodiments, L² is
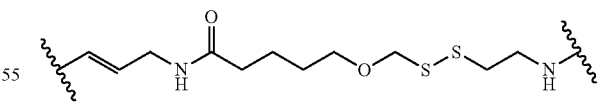
In embodiments, L² is
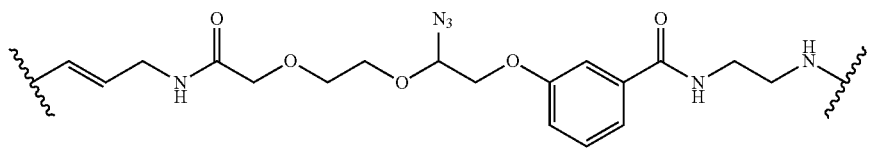 [SMILES: */C=C/CNC(=O)COCCOC(COc1cccc(C(=O)NCCN*)c1)N=[N+]=[N-]]

In embodiments, L² is
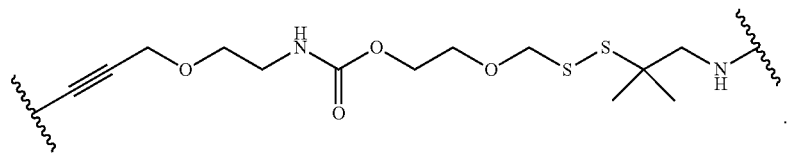 [SMILES: *C#CCOCCNC(=O)OCCOCSSC(C)(C)CN*]
In embodiments, L² is
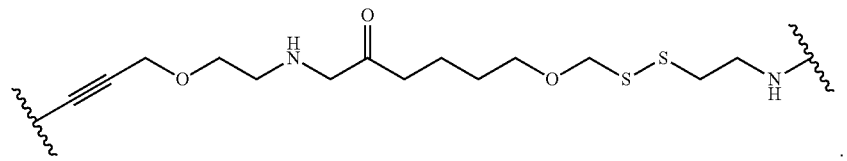 [SMILES: *C#CCOCCNCC(=O)CCCCOCSSCCN*]
In embodiments, L² is
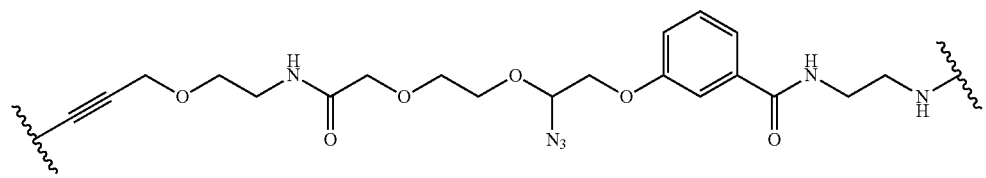 [SMILES: *C#CCOCCNC(=O)COCCOC(COc1cccc(C(=O)NCCN*)c1)N=[N+]=[N-]]
In embodiments, L² is
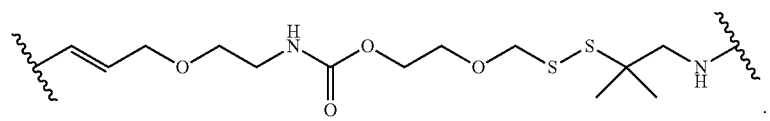 [SMILES: */C=C/COCCNC(=O)OCCOCSSC(C)(C)CN*]
In embodiments, L² is
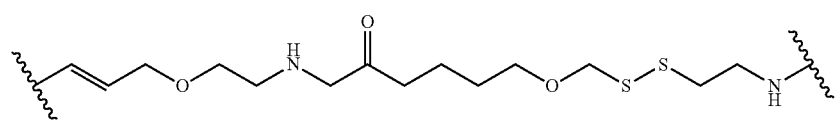
In embodiments, L² is
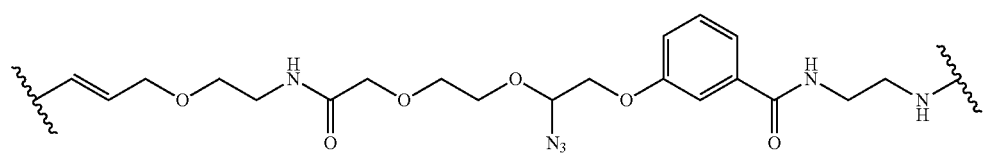

In embodiments, L² is
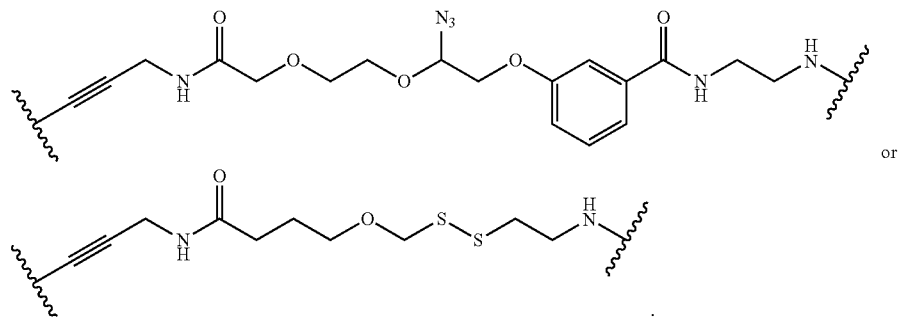
or
In embodiments, L² is
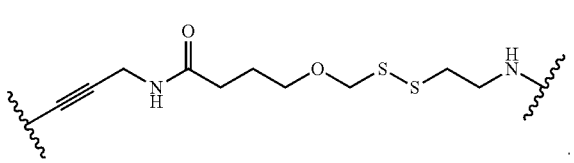 [SMILES: *C#CCNC(=O)CCCOCSSCCN*]
In embodiments, L² is
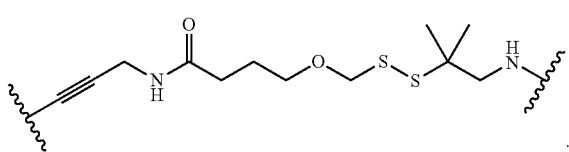 [SMILES: *C#CCNC(=O)CCCOCSSC(C)(C)CN*]
In embodiments, L² is
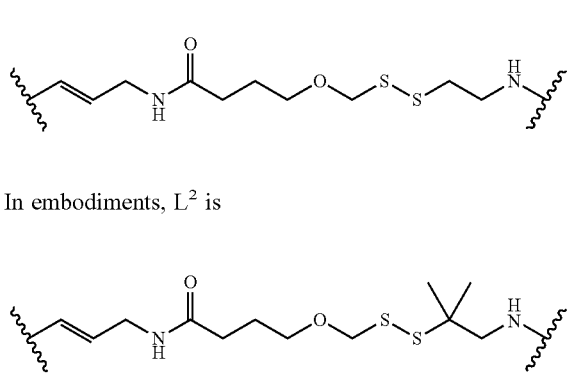
In embodiments, L² is
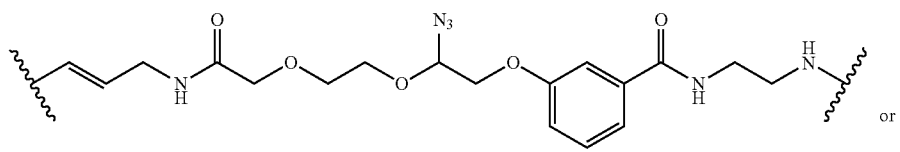
or
In embodiments, L² is
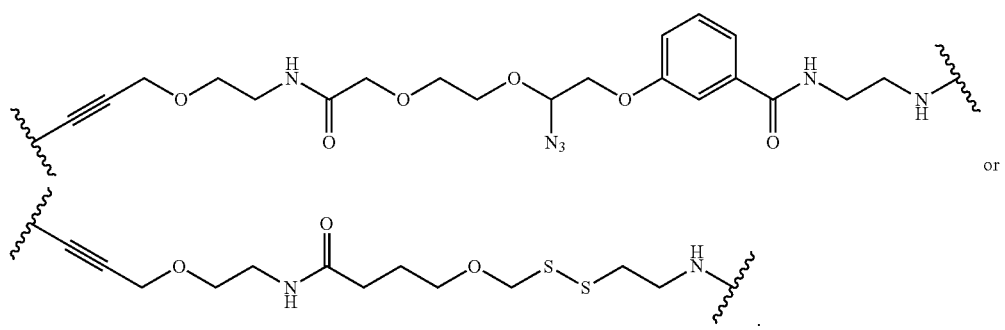
or In embodiments, $L^2$ is
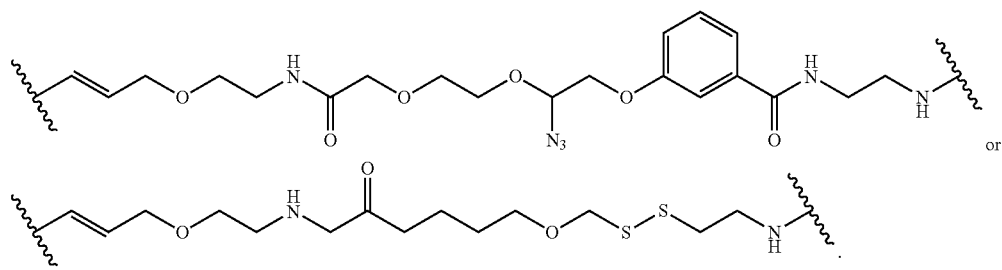
or
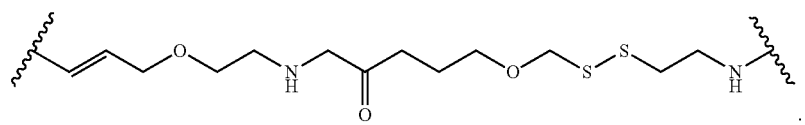 [SMILES: */C=C/COCCNCC(=O)CCCOCSSCCN*]
In embodiments, $L^2$ is
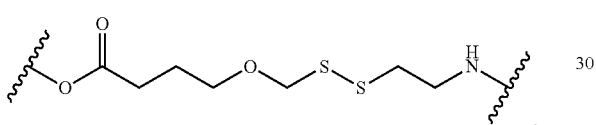
In embodiments, $L^2$ is
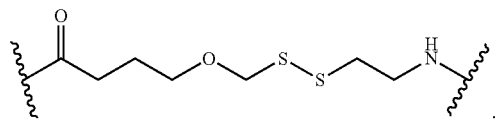 [SMILES: *NCCSSCOCCCC(*)=O]
In embodiments, $L^2$ is
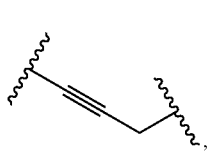
In embodiments, $L^{2A}$ is
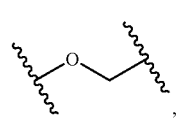 [SMILES: *CO*]
$L^{2B}$ is
$L^{2C}$ is
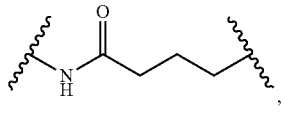 [SMILES: *CCCC(=O)N*]
$L^{2D}$ is
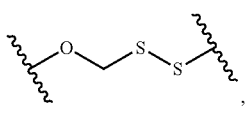 [SMILES: *OCSS*]
and $L^{2E}$ is
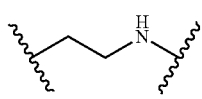
In embodiments, $L^{2A}$ is
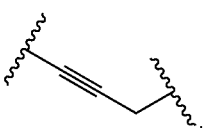 [SMILES: *C#CC*]
In embodiments, $L^{2A}$ is
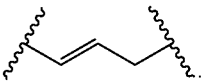 [SMILES: */C=C/C*]

In embodiments, $L^{2B}$ is
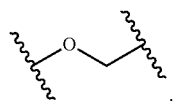 [SMILES: *CO*]
In embodiments, $L^{2C}$ is
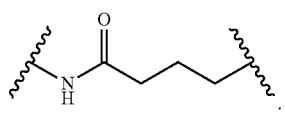
In embodiments, $L^{2D}$ is
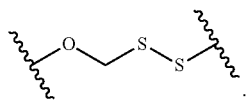 [SMILES: *OCSS*]
In embodiments, $L^{2E}$ is
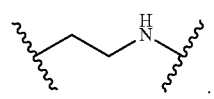 [SMILES: *CCN*]
In embodiments, $L^{2A}$ is
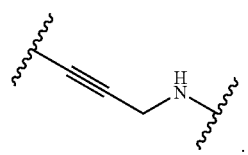 [SMILES: *C#CCN*]
In embodiments, $L^{2A}$ is
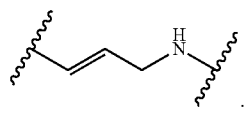 [SMILES: */C=C/CN*]
In embodiments, $L^{2A}$ is
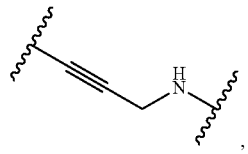 [SMILES: *C#CCN*]
$L^{2B}$ is
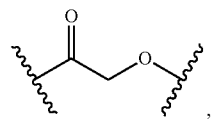
$L^{2C}$ is
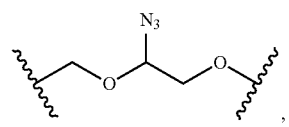 [SMILES: *COC(CO*)N=[N+]=[N-]]
$L^{2D}$ is
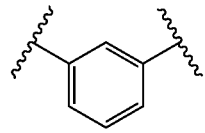
and $L^{2E}$ is
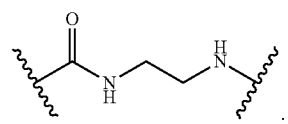 [SMILES: *NCCNC(*)=O]
In embodiments, $L^{2A}$ is
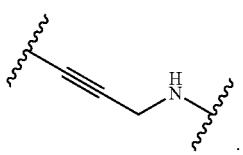 [SMILES: *C#CCN*]
In embodiments, $L^{2A}$ is
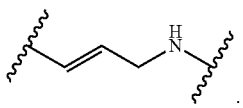 [SMILES: */C=C/CN*]
In embodiments, $L^{2B}$ is
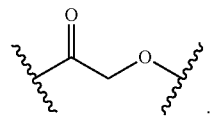

In embodiments, $L^{2C}$ is

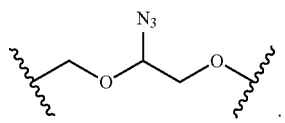 [SMILES: *COC(CO*)N=[N+]=[N-]]

In embodiments, $L^{2D}$ is

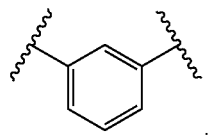 [SMILES: *c1cccc(*)c1]

In embodiments, $L^{2E}$ is

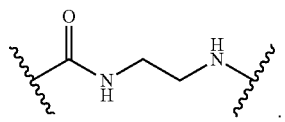 [SMILES: *NCCNC(*)=O]

In embodiments, $L^{2A}$ is substituted or unsubstituted $C_1$-$C_8$ alkylene. In embodiments, $L^{2A}$ is substituted or unsubstituted $C_1$-$C_4$ alkylene. In embodiments, $L^{2A}$ is substituted or unsubstituted $C_2$-$C_4$ alkenylene. In embodiments, $L^{2A}$ is substituted or unsubstituted $C_2$-$C_4$ alkynylene. In embodiments, $L^{2A}$ is unsubstituted $C_2$-$C_4$ alkynylene. In embodiments, $L^{2A}$ is oxo substituted $C_1$-$C_8$ alkylene. In embodiments, $L^{2A}$ is oxo substituted $C_1$-$C_4$ alkylene. In embodiments, $L^{2A}$ is substituted or unsubstituted 2 to 25 membered heteroalkylene. In embodiments, $L^{2A}$ is substituted or unsubstituted 2 to 20 membered heteroalkylene. In embodiments, $L^{2A}$ is substituted or unsubstituted 2 to 8 membered heteroalkylene. In embodiments, $L^{2A}$ is substituted or unsubstituted 2 to 5 membered heteroalkylene. In embodiments, $L^{2A}$ is oxo substituted 2 to 25 membered heteroalkylene. In embodiments, $L^{2A}$ is oxo substituted 2 to 20 membered heteroalkylene. In embodiments, $L^{2A}$ is oxo substituted 2 to 8 membered heteroalkylene. In embodiments, $L^{2A}$ is oxo substituted 2 to 5 membered heteroalkylene.

In embodiments, $L^{2B}$ is substituted or unsubstituted 2 to 10 membered heteroalkylene. In embodiments, $L^{2B}$ is substituted or unsubstituted 2 to 6 membered heteroalkylene. In embodiments, $L^{2B}$ is substituted or unsubstituted 2 to 4 membered heteroalkylene. In embodiments, $L^{2B}$ is oxo substituted 2 to 10 membered heteroalkylene. In embodiments, $L^{2B}$ is oxo substituted 2 to 6 membered heteroalkylene. In embodiments, $L^{2B}$ is oxo substituted 2 to 4 membered heteroalkylene.

In embodiments, $L^{2C}$ is substituted or unsubstituted $C_1$-$C_8$ alkylene. In embodiments, $L^{2C}$ is substituted or unsubstituted $C_1$-$C_4$ alkylene. In embodiments, $L^{2C}$ is oxo substituted $C_1$-$C_8$ alkylene. In embodiments, $L^{2C}$ is oxo substituted $C_1$-$C_4$ alkylene. In embodiments, $L^{2C}$ is substituted or unsubstituted 2 to 10 membered heteroalkylene. In embodiments, $L^{2C}$ is substituted or unsubstituted 2 to 6 membered heteroalkylene. In embodiments, $L^{2C}$ is substituted or unsubstituted 2 to 4 membered heteroalkylene. In embodiments, $L^{2C}$ is substituted or unsubstituted 2 membered heteroalkylene. In embodiments, $L^{2C}$ is oxo substituted 2 to 10 membered heteroalkylene. In embodiments, $L^{2C}$ is oxo substituted 2 to 6 membered heteroalkylene. In embodiments, $L^{2C}$ is oxo substituted 2 to 4 membered heteroalkylene. In embodiments, $L^{2C}$ is oxo substituted 2 membered heteroalkylene. In embodiments, $L^{2C}$ is $N_3$ substituted 2 to 10 membered heteroalkylene. In embodiments, $L^{2C}$ is $N_3$ substituted 2 to 6 membered heteroalkylene. In embodiments, $L^{2C}$ is $N_3$ substituted 2 to 4 membered heteroalkylene. In embodiments, $L^{2C}$ is $N_3$ substituted 2 membered heteroalkylene.

In embodiments, $L^{2D}$ is substituted or unsubstituted 2 to 8 membered heteroalkylene. In embodiments, $L^{2D}$ is substituted or unsubstituted 2 to 6 membered heteroalkylene. In embodiments, $L^{2D}$ is substituted or unsubstituted 2 to 4 membered heteroalkylene. In embodiments, $L^{2D}$ is substituted or unsubstituted 2 membered heteroalkylene. In embodiments, $L^{2D}$ is unsubstituted 2 to 8 membered heteroalkylene. In embodiments, $L^{2D}$ is unsubstituted 2 to 6 membered heteroalkylene. In embodiments, $L^{2D}$ is unsubstituted 2 to 4 membered heteroalkylene. In embodiments, $L^{2D}$ is unsubstituted 2 membered heteroalkylene. In embodiments, $L^{2D}$ is alkyl substituted 2 to 8 membered heteroalkylene. In embodiments, $L^{2D}$ is alkyl substituted 2 to 6 membered heteroalkylene. In embodiments, $L^{2D}$ is alkyl substituted 2 to 4 membered heteroalkylene. In embodiments, $L^{2D}$ is alkyl substituted 2 membered heteroalkylene. In embodiments, $L^{2D}$ is substituted or unsubstituted arylene. In embodiments, $L^{2D}$ is unsubstituted arylene. In embodiments, $L^{2D}$ is substituted or unsubstituted phenylene. In embodiments, $L^{2D}$ is unsubstituted phenylene.

In embodiments, $L^{2C}$ is substituted or unsubstituted 2 to 8 membered heteroalkylene. In embodiments, $L^{2C}$ is substituted or unsubstituted 2 to 6 membered heteroalkylene. In embodiments, $L^{2C}$ is substituted or unsubstituted 2 to 4 membered heteroalkylene. In embodiments, $L^{2C}$ is substituted or unsubstituted 2 membered heteroalkylene. In embodiments, $L^{2C}$ is oxo substituted 2 to 8 membered heteroalkylene. In embodiments, $L^{2C}$ is oxo substituted 2 to 6 membered heteroalkylene. In embodiments, $L^{2C}$ is oxo substituted 2 to 4 membered heteroalkylene. In embodiments, $L^{2C}$ is oxo substituted 2 membered heteroalkylene. In embodiments, $L^{2C}$ is alkyl substituted 2 to 8 membered heteroalkylene. In embodiments, $L^{2C}$ is alkyl substituted 2 to 6 membered heteroalkylene. In embodiments, $L^{2C}$ is alkyl substituted 2 to 4 membered heteroalkylene. In embodiments, $L^{2C}$ is alkyl substituted 2 membered heteroalkylene.

In embodiments, $L^{2A}$ is

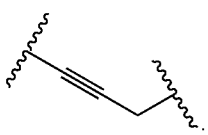 [SMILES: *C#CC*]

In embodiments, $L^{2A}$ is

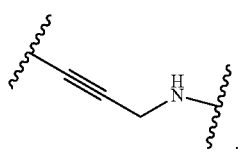 [SMILES: *C#CCN*]

In embodiments, $L^{2A}$ is
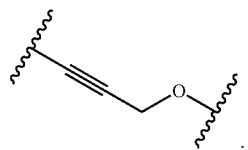 [SMILES: *C#CCO*]
In embodiments, $L^{2A}$ is
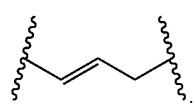 [SMILES: */C=C/C*]
In embodiments, $L^{2A}$ is
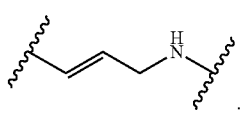 [SMILES: */C=C/CN*]
In embodiments, $L^{2A}$ is
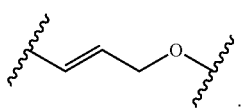
In embodiments, $L^{2A}$ is
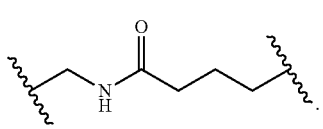 [SMILES: *CCCC(=O)NC*]
In embodiments, $L^{2A}$ is
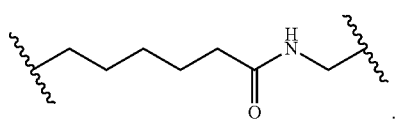 [SMILES: *CCCCCC(=O)NC*]
In embodiments, $L^{2A}$ is
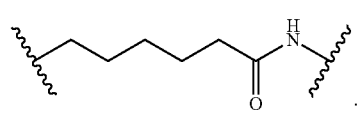 [SMILES: *CCCCCC(=O)N*]
In embodiments, $L^{2A}$ is
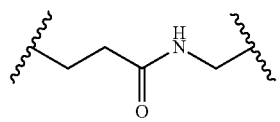
In embodiments, $L^{2A}$ is
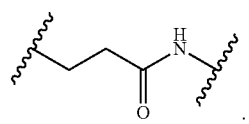 [SMILES: *CCC(=O)N*]
In embodiments, $L^{2A}$ is
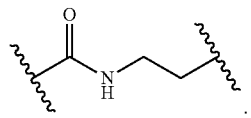 [SMILES: *CCNC(*)=O]
In embodiments, $L^{2A}$ is
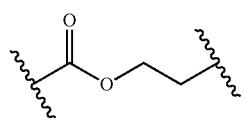
In embodiments, $L^{2A}$ is
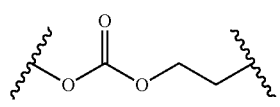
In embodiments, $L^{2A}$ is
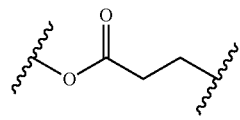
In embodiments, $L^{2A}$ is
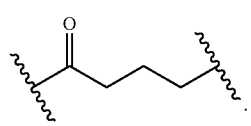 [SMILES: *CCCC(*)=O]

In embodiments, $L^{2A}$ is

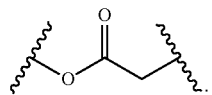 [SMILES: *CC(=O)O*]

In embodiments, $L^{2A}$ is

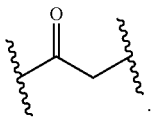 [SMILES: *CC(*)=O]

In embodiments, $L^{2B}$ is

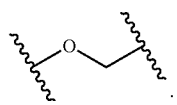 [SMILES: *CO*]

In embodiments, $L^{2B}$ is

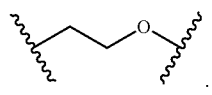 [SMILES: *CCO*]

In embodiments, $L^{2B}$ is

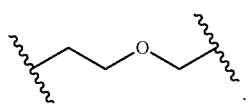 [SMILES: *CCOC*]

In embodiments, $L^{2B}$ is

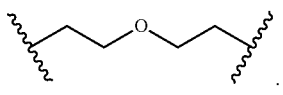 [SMILES: *CCOCC*]

In embodiments, $L^{2B}$ is

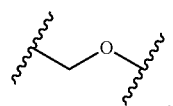

In embodiments, $L^{2B}$ is

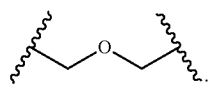 [SMILES: *COC*]

In embodiments, $L^{2B}$ is

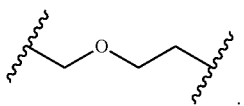 [SMILES: *CCOC*]

In embodiments, $L^{2B}$ is

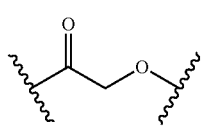

In embodiments, $L^{2B}$ is

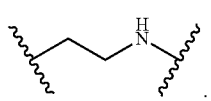

In embodiments, $L^{2B}$ is

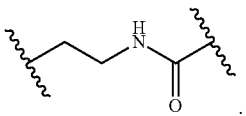 [SMILES: *CCNC(*)=O]

In embodiments, $L^{2B}$ is

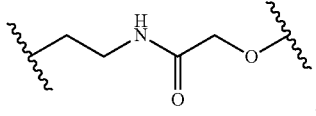

In embodiments, $L^{2B}$ is

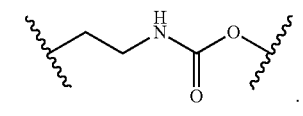 [SMILES: *CCNC(=O)O*]

In embodiments, $L^{2B}$ is

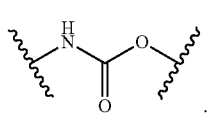

In embodiments, $L^{2B}$ is

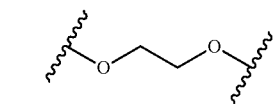

In embodiments, $L^{2C}$ is

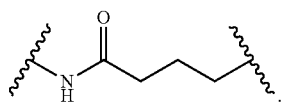 [SMILES: *CCCC(=O)N*]

In embodiments, $L^{2C}$ is

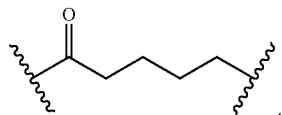 [SMILES: *CCCCC(*)=O]

In embodiments, $L^{2C}$ is

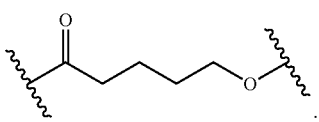 [SMILES: *OCCCCC(*)=O]

In embodiments, $L^{2C}$ is

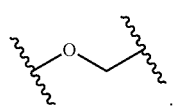

In embodiments, $L^{2C}$ is

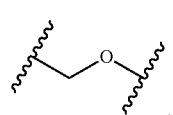

In embodiments $L^{2C}$ is

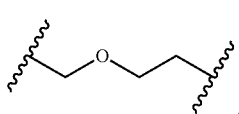

In embodiments, $L^{2C}$ is

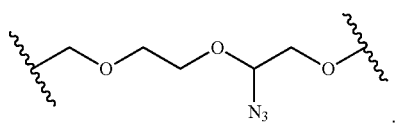 [SMILES: *COCCOC(CO*)N=[N+]=[N-]]

In embodiments, $L^{2C}$ is

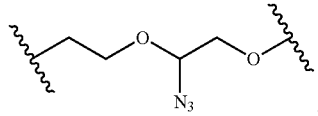

In embodiments, $L^{2C}$ is

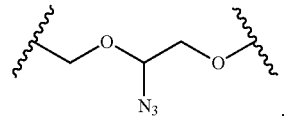 [SMILES: *COC(CO*)N=[N+]=[N-]]

In embodiments, $L^{2C}$ is

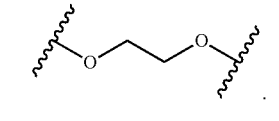 [SMILES: *OCCO*]

In embodiments, $L^{2D}$ is

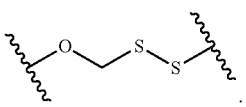

In embodiments, $L^{2D}$ is

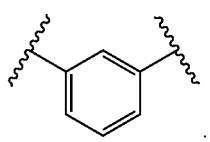 [SMILES: *c1cccc(*)c1]

In embodiments, $L^{2D}$ is

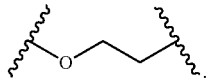 [SMILES: *CCO*]

In embodiments, $L^{2D}$ is

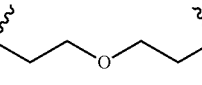

In embodiments, $L^{2D}$ is

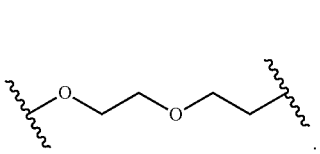 [SMILES: *CCOCCO*]

In embodiments, $L^{2D}$ is

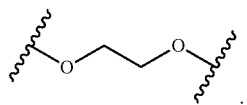 [SMILES: *OCCO*]

In embodiments, $L^{2E}$ is

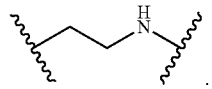 [SMILES: *CCN*]

In embodiments, $L^{2E}$ is

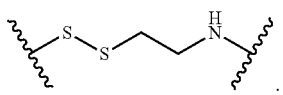 [SMILES: *NCCSS*]

In embodiments, $L^{2E}$ is

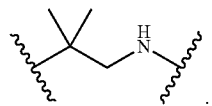

In embodiments, $L^{2E}$ is

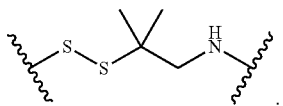 [SMILES: *NCC(C)(C)SS*]

In embodiments, $L^{2E}$ is

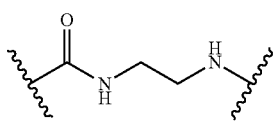

In embodiments, $L^{2E}$ is

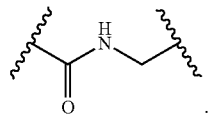

In embodiments, $L^{2E}$ is

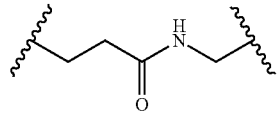

In embodiments, $L^{2E}$ is

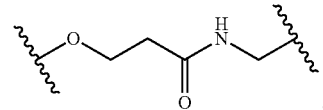

In embodiments, —B-$L^{2A}$-$L^{2B}$-$L^{2C}$-$L^{2D}$-$L^{2E}$-$R^5$ has the formula:

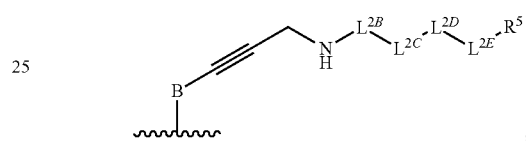

wherein B, $L^{2B}$, $L^{2C}$, $L^{2D}$, $L^{2E}$, and $R^5$ are as described herein, including embodiments.

In embodiments, —B-$L^{2A}$-$L^{2B}$-$L^{2C}$-$L^{2D}$-$L^{2E}$-$R^5$----$R^{12}$-$L^3$-$R^{13}$ has the formula:

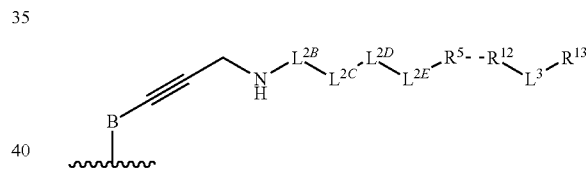

herein B, $L^{2B}$, $L^{2C}$, $L^{2D}$, $L^{2E}$, $R^5$, $R^{12}$, $L^3$, and $R^{13}$ are as described herein including embodiments.

In embodiments, —B-$L^{2A}$-$L^{2B}$-$L^{2C}$-$L^{2D}$-$L^{2E}$-$R^5$ has the formula:

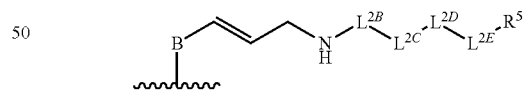

wherein B, $L^{2B}$, $L^{2C}$, $L^{2D}$, $L^{2E}$, and $R^5$ areas described herein, including embodiments.

In embodiments, —B-$L^{2A}$-$L^{2B}$-$L^{2C}$-$L^{2D}$-$L^{2E}$-R----$R^{12}$-$L^3$-$R^{13}$ has the formula:

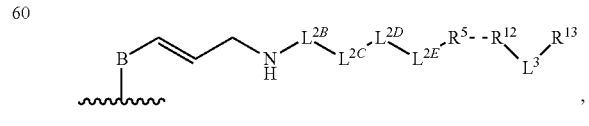

wherein B, $L^{2B}$, $L^{2C}$, $L^{2D}$, $L^{2E}$, $R^5$, $R^{12}$, $L^3$, and $R^{13}$ are as described herein including embodiments.

In embodiments, —B-L² is
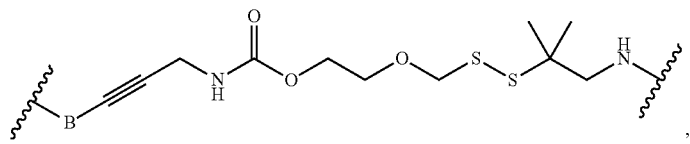
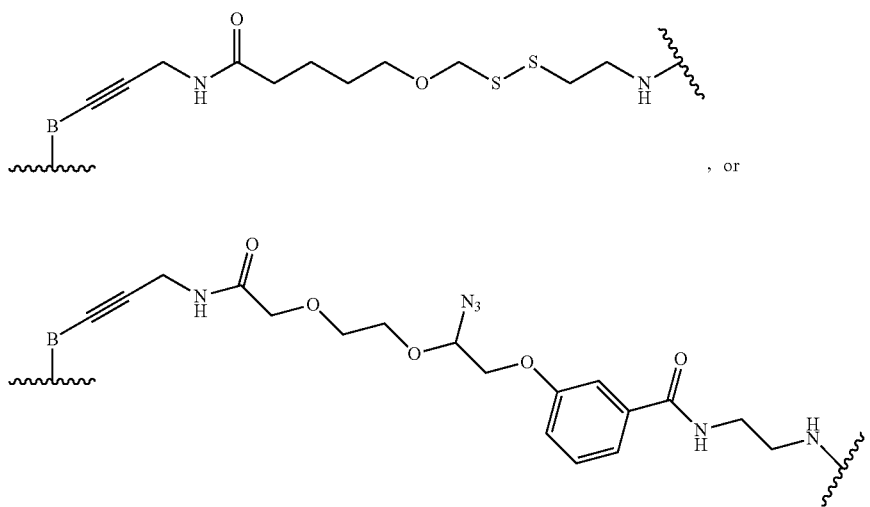
, or
wherein B is as described herein, including embodiments. In embodiments, —B-L² is
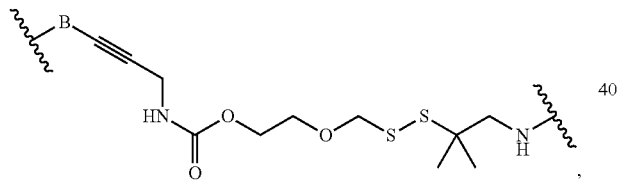
wherein B is as described herein, including embodiments. In embodiments, —B-L² is
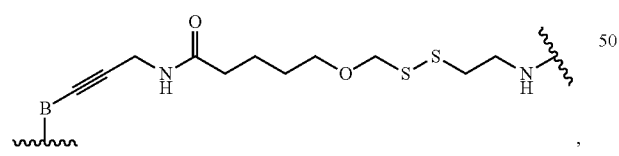
wherein B is as described herein, including embodiments. In embodiments, —B-L² is
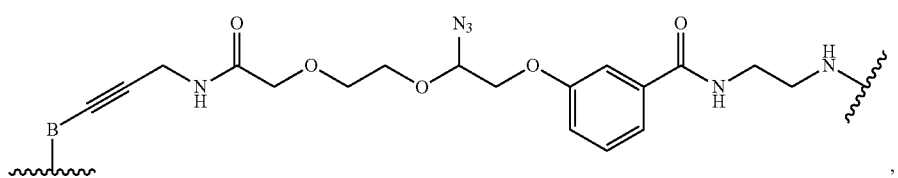

wherein B is as described herein, including embodiments.
In embodiments, —B-L² is

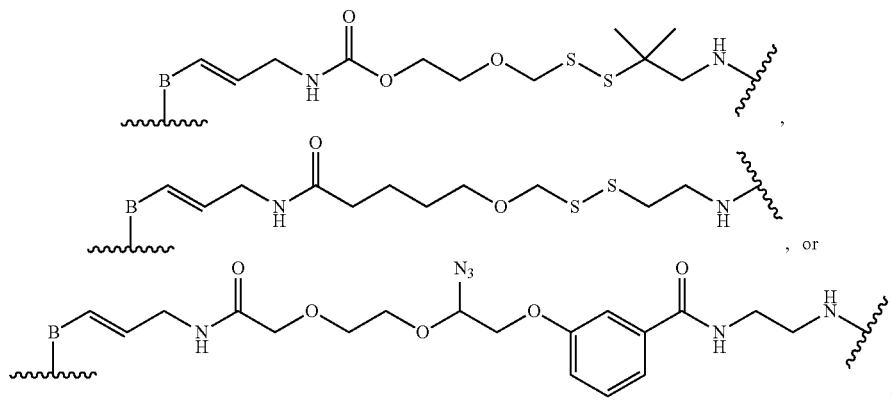

wherein B is as described herein, including embodiments. In embodiments, —B-L² is

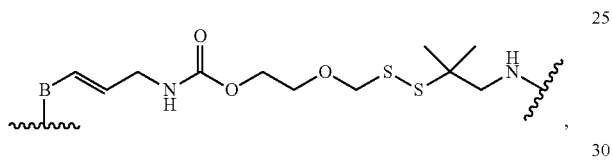

wherein B is as described herein, including embodiments. In embodiments, —B-L² is

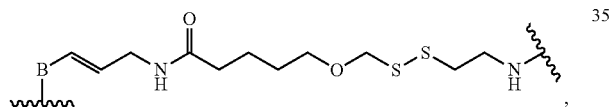

wherein B is as described herein, including embodiments. In embodiments, —B-L² is

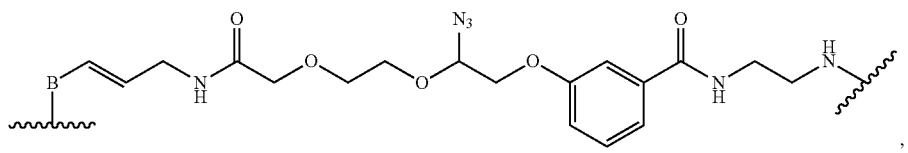

wherein B is as described herein, including embodiments.

In embodiments, —B-$L^{2A}$-$L^{2B}$-$L^{2C}$-$L^{2D}$-$L^{2E}$-$R^5$ has the formula:

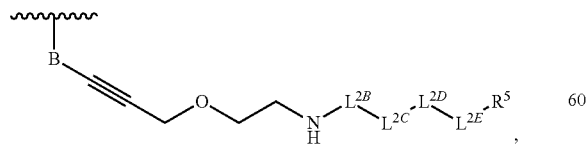

wherein B, $L^{2B}$, $L^{2C}$, $L^{2D}$, $L^{2E}$, and $R^5$ areas described herein, including embodiments.

In embodiments, —B-L$^{2A}$-L$^{2B}$-L$^{2C}$-L$^{2D}$-L$^{2E}$-R$^5$----R$^{12}$-L$^3$-R$^{13}$ has the formula:

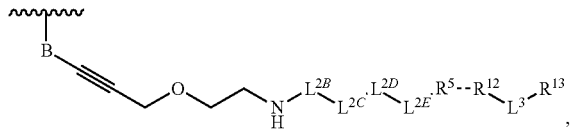

wherein B, L$^{2B}$, L$^{2C}$, L$^{2D}$, L$^{2E}$, R$^5$, R$^{12}$, L$^3$, and R$^{13}$ are as described herein including embodiments.

In embodiments, —B-L$^{2A}$-L$^{2B}$-L$^{2C}$-L$^{2D}$-L$^{2E}$-R$^5$ has the formula:

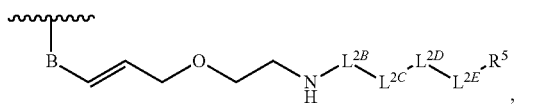

wherein B, L$^{2B}$, L$^{2C}$, L$^{2D}$, L$^{2E}$, and R$^5$ are as described herein, including embodiments.

In embodiments, —B-L$^{2A}$-L$^{2B}$-L$^{2C}$-L$^{2D}$-L$^{2E}$-R$^5$----R$^{12}$-L$^3$-R$^{13}$ has the formula:

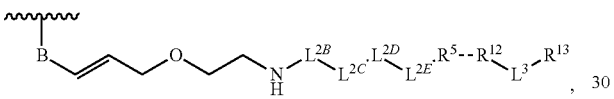

wherein B, L$^{2B}$, L$^{2C}$, L$^{2D}$, L$^{2E}$, R$^5$, R$^{12}$, L$^3$, and R$^{13}$ are as described herein including embodiments.

In embodiments —B-L$^2$ is

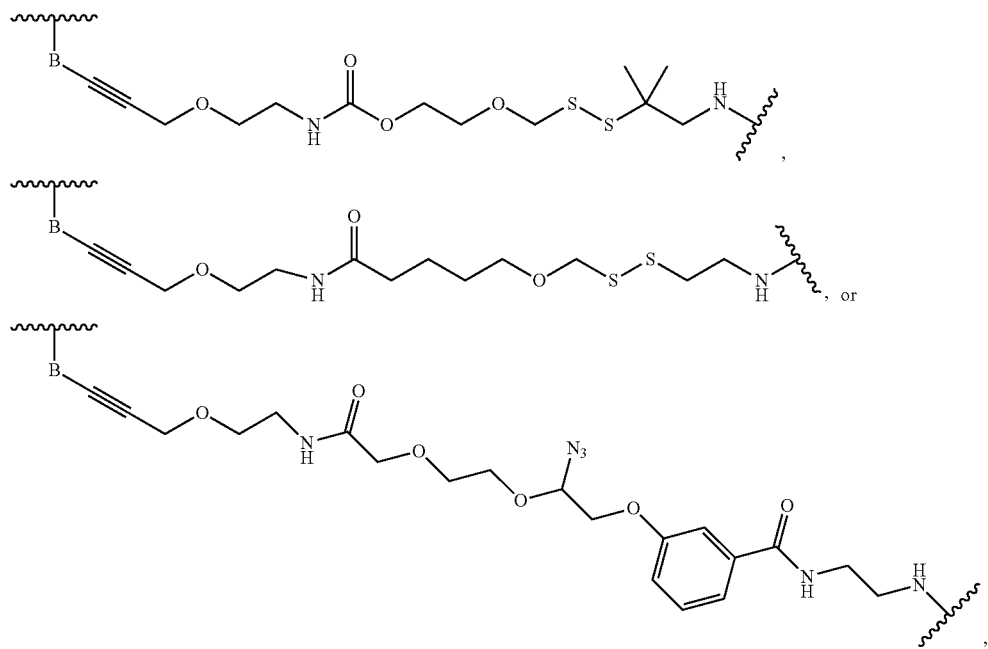

wherein B is as described herein, including embodiments. In embodiments, —B-L² is

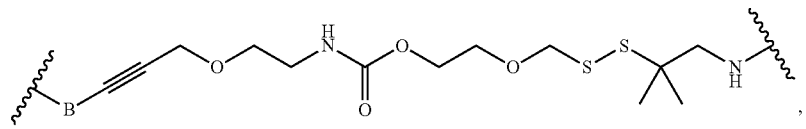

, wherein B is as described herein, including embodiments. In embodiments, —B-L² is

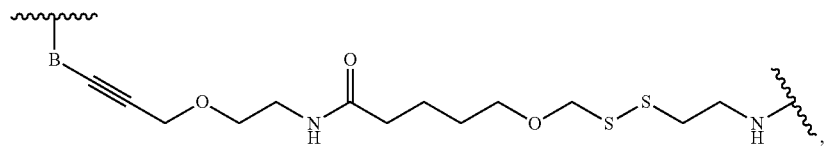

, wherein B is as described herein, including embodiments. In embodiments, —B-L² is

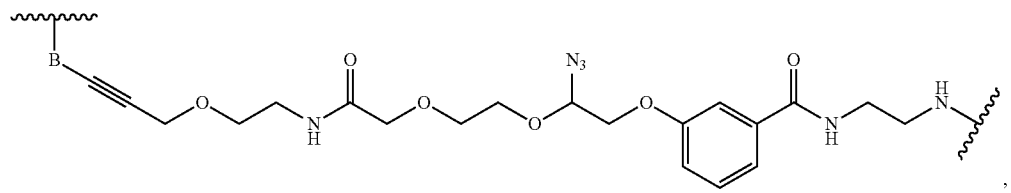

, wherein B is as described herein, including embodiments. In embodiments, —B-L² is

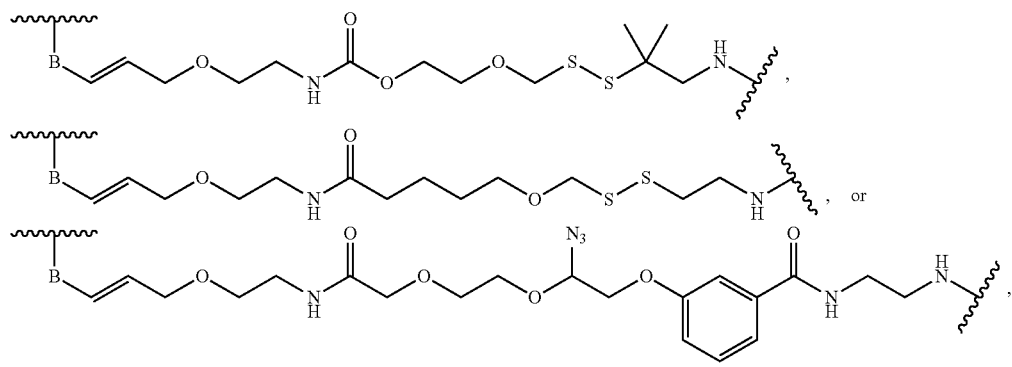

, or wherein B is as described herein, including embodiments. In embodiments, —B-L² is

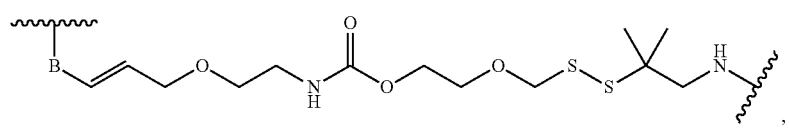

, wherein B is as described herein, including embodiments. In embodiments, —B-L² is

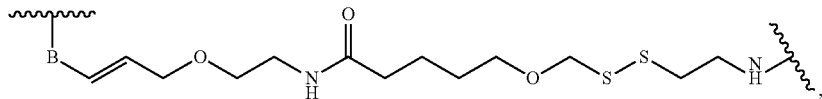

wherein B is as described herein, including embodiments. In embodiments, —B-L² is

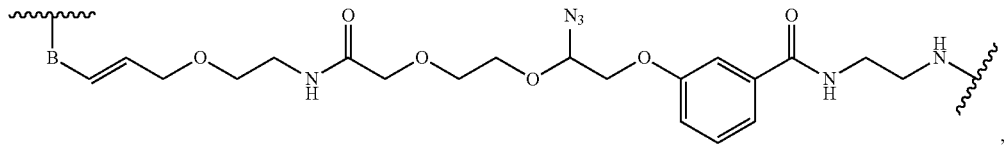

wherein B is as described herein, including embodiments.

In embodiments, L² is a cleavable linker. In embodiments, L² is a chemically cleavable linker. In embodiments, L² is a photocleavable linker, an acid-cleavable linker, a base-cleavable linker, an oxidant-cleavable linker, a reductant-cleavable linker, or a fluoride-cleavable linker.

In embodiments, L² includes a cleavable linker. In embodiments, L² includes a chemically cleavable linker. In embodiments, L² includes a photocleavable linker, an acid-cleavable linker, a base-cleavable linker, an oxidant-cleavable linker, a reductant-cleavable linker, or a fluoride-cleavable linker.

In embodiments, L² is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, L² is a cleavable linker including a dialkylketal linker. In embodiments, L² is a cleavable linker including an azo linker. In embodiments, L² is a cleavable linker including an allyl linker. In embodiments, L² is a cleavable linker including a cyanoethyl linker. In embodiments, L² is a cleavable linker including a 1-(4,4-dimethyl-2,6-dioxocyclohex-1-ylidene)ethyl linker. In embodiments, L² is a cleavable linker including a nitrobenzyl linker.

In embodiments, L² is $L^{2A}$-$L^{2B}$-$L^{2C}$-$L^{2D}$-$L^{2E}$; and $L^{2A}$, $L^{2B}$, $L^{2C}$, $L^{2D}$, and $L^{2E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$, and $L^{2E}$ is not a bond.

In embodiments, L² is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{2A}$, $L^{2B}$, $L^{2C}$, $L^{2D}$, and $L^{2E}$ is not a bond.

In embodiments, L² is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{2A}$, $L^{2B}$, $L^{2C}$, $L^{2D}$, and $L^{2E}$ is not a bond.

In embodiments, L² is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{2A}$, $L^{2B}$, $L^{2C}$, $L^{2D}$, and $L^{2E}$ is not a bond.

In embodiments, $L^2$ is $L^{2A}$-$L^{2B}$-$L^{2C}$-$L^{2D}$-$L^{2E}$; $L^{2A}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{2B}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2C}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2D}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{2E}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$ and $L^{2E}$ is not a bond.

In embodiments, $L^2$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene. In embodiments, $L^2$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene. In embodiments, $L^2$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene. In embodiments, $L^2$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^2$ is a substituted (e.g., substituted with a substituent group, size-limited substituent group, or lower substituent group) or unsubstituted 4 to 10 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 4 to 8 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 4 to 6 membered heteroalkylene (e.g., heteroalkylene, heteroalkenylene, or heteroalkynylene).

In embodiments, $L^2$ is $-C(CH_3)_2CH_2NHC(O)-$. In embodiments, $L^2$ is an orthogonally cleavable linker or a non-covalent linker. In embodiments, $L^2$ includes an orthogonally cleavable linker or a non-covalent linker. In embodiments, $L^2$ is an orthogonally cleavable linker. In embodiments, $L^2$ is a non-covalent linker. In embodiments, $L^2$ includes an alkyne.

In embodiments, $-L^2-R^5$ is

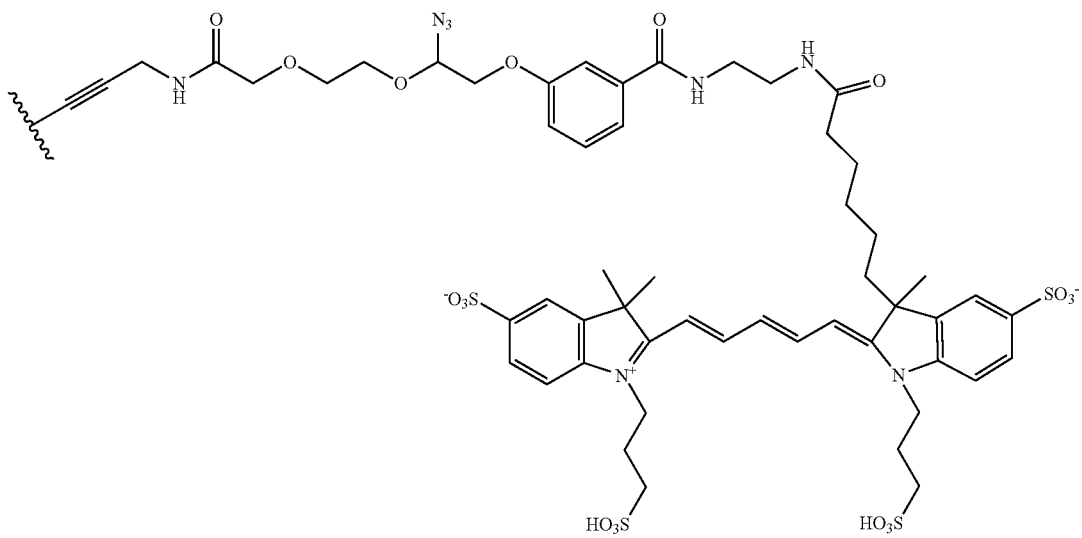

In embodiments, $-L^2-R^5$ is

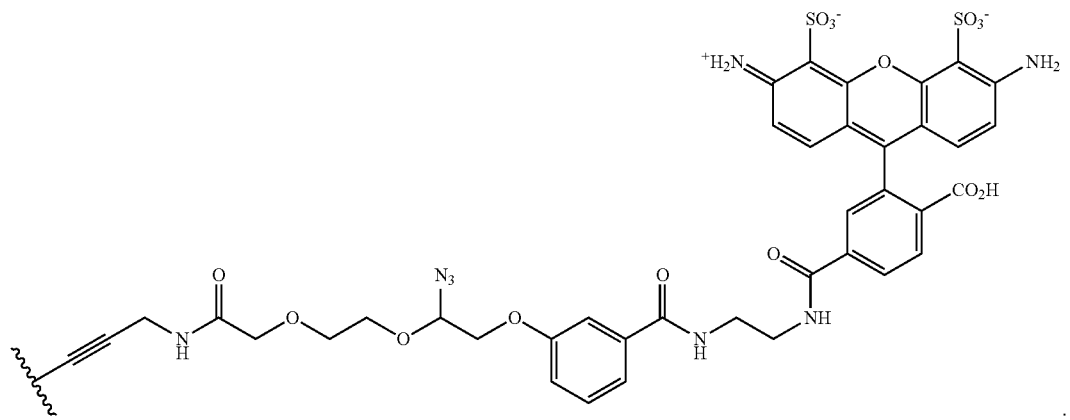

In embodiments, -L²-R⁵ is
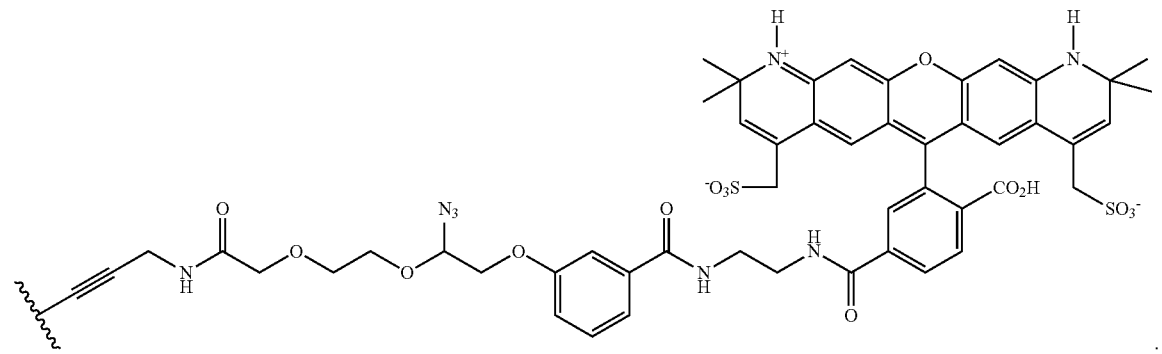
20
In embodiments, -L²-R⁵ is
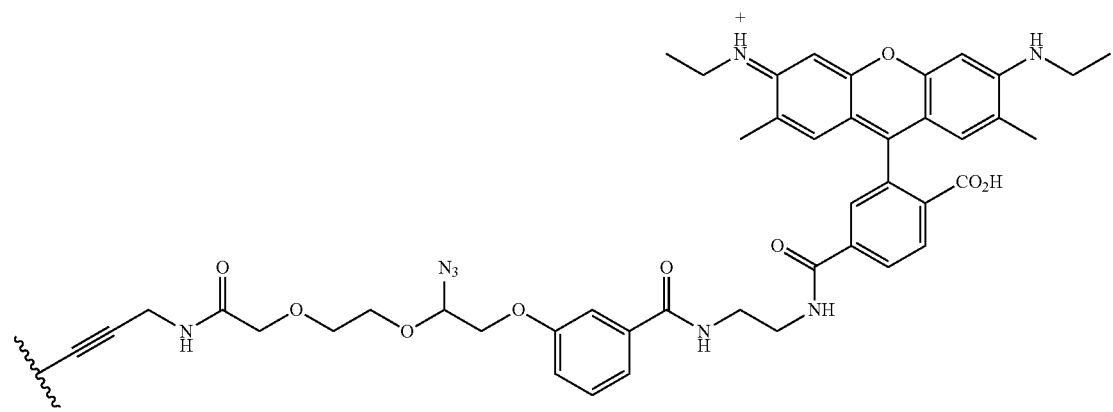
In embodiments, -L²-R⁵ is
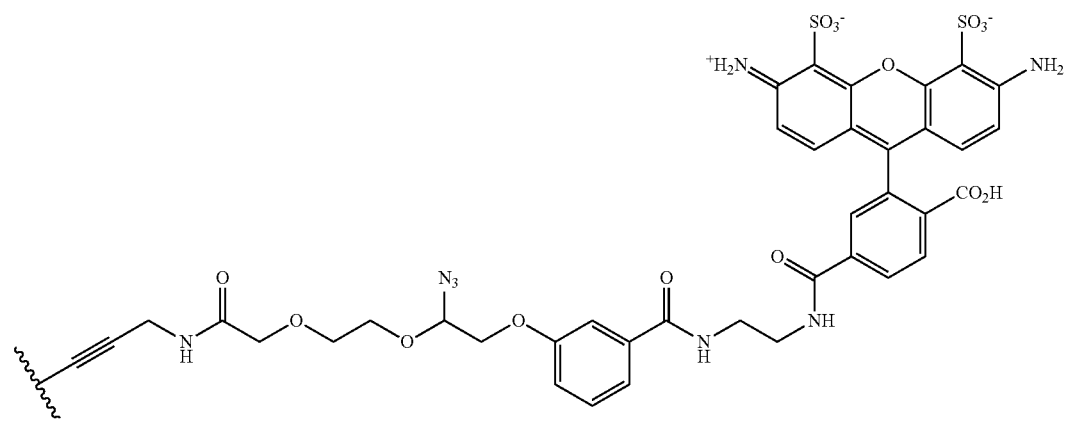

In embodiments, -L²-R⁵ is
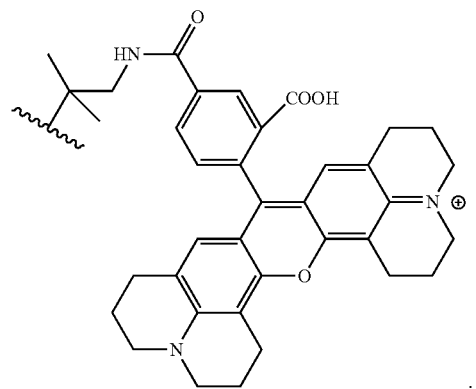 [SMILES: *C(C)(C)CNC(=O)c1ccc(C2=c3cc4c5c(c3Oc3c2cc2c6c3CCCN6CCC2)CCC[N+]=5CCC4)c(C(=O)O)c1]
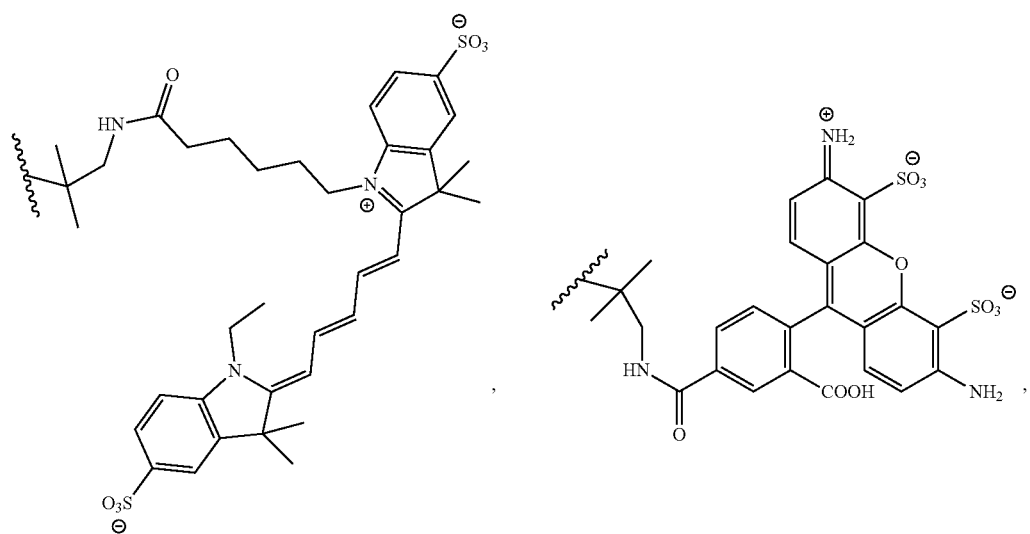
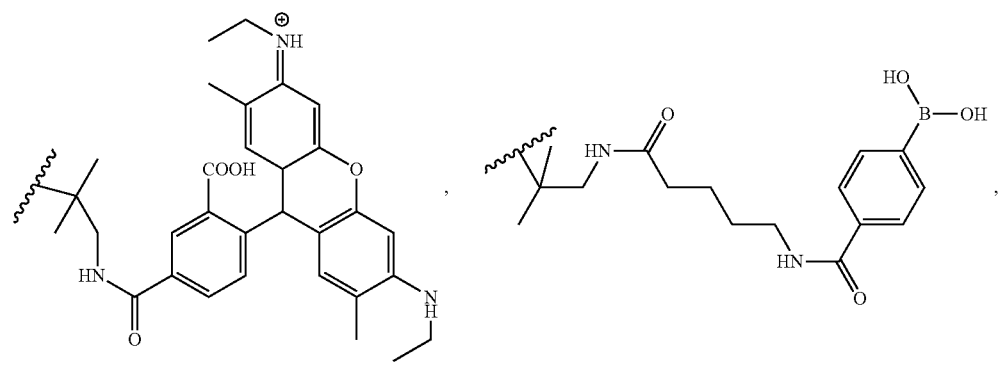

-continued
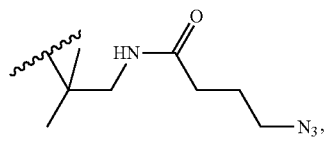
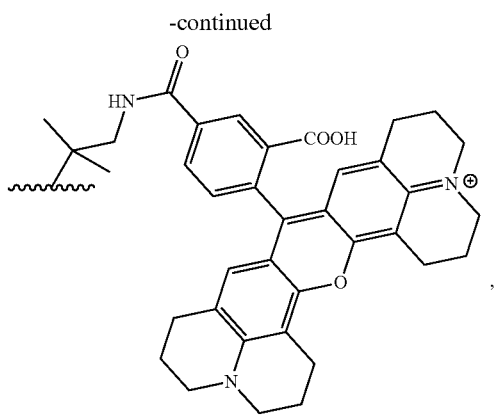
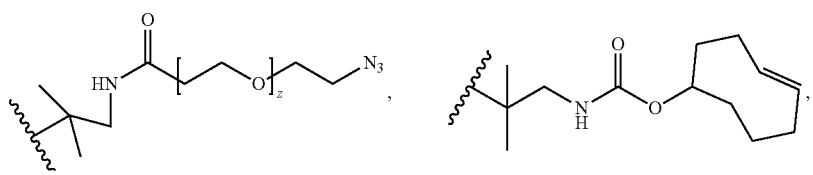
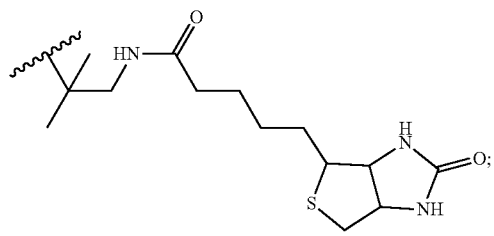
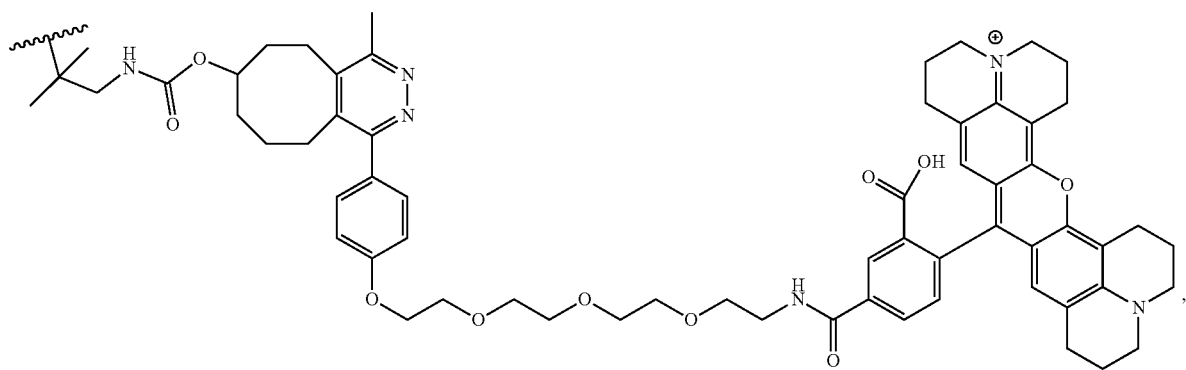

-continued
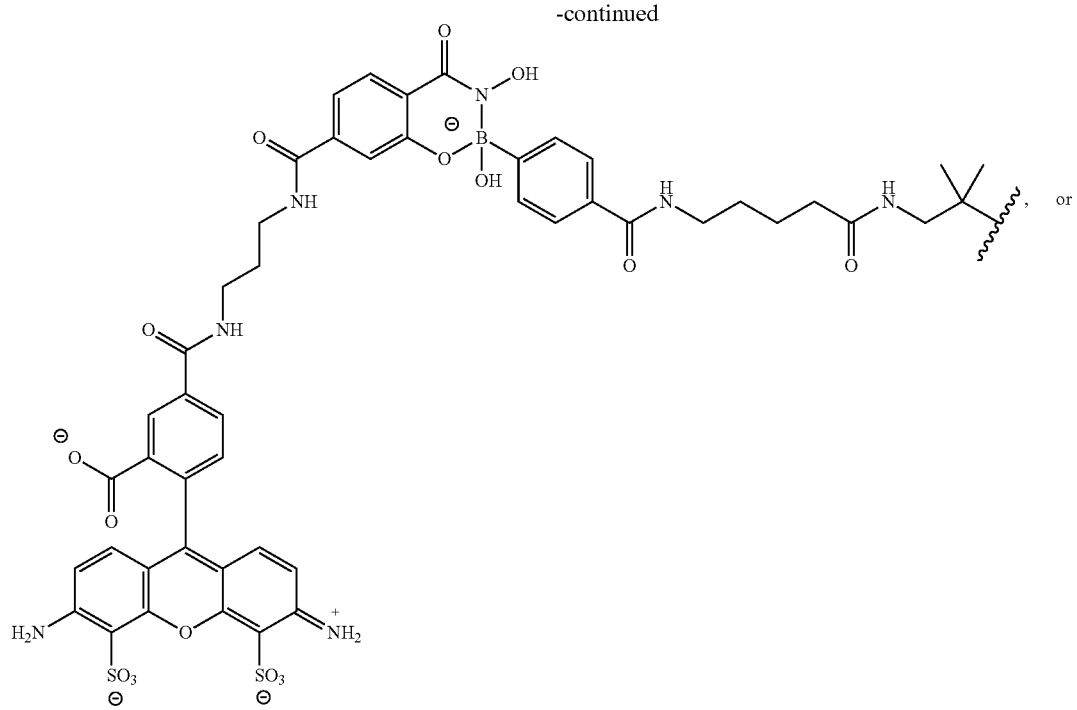
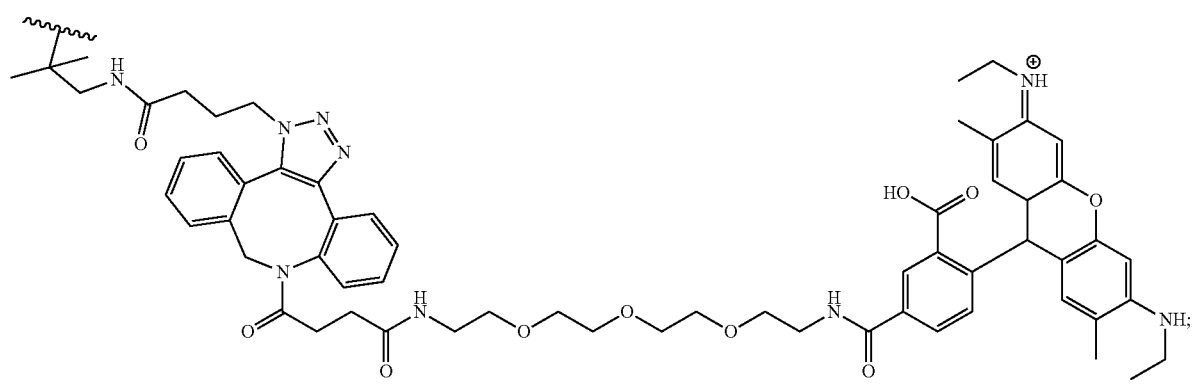
and z is an integer from 0 to 10.
In embodiments, -L$^2$-R$^5$ is
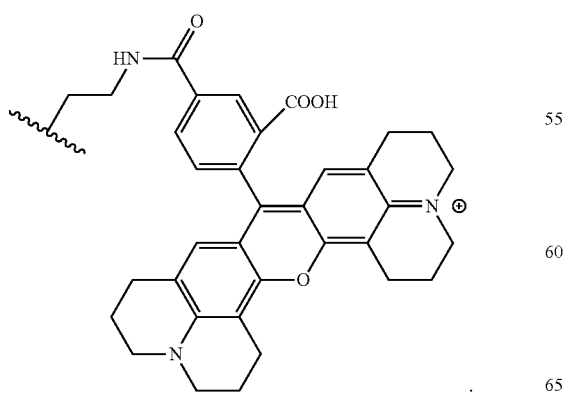

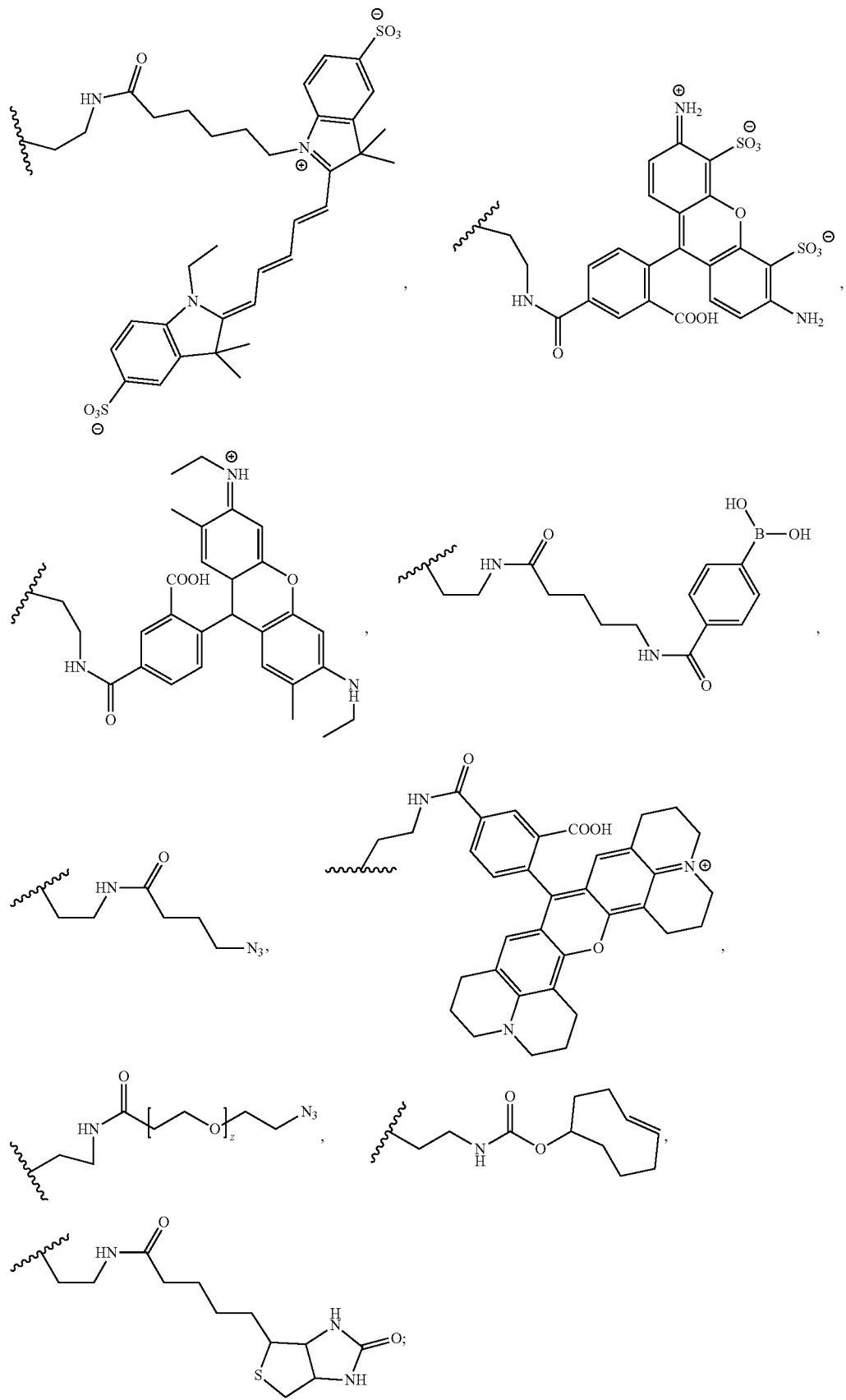

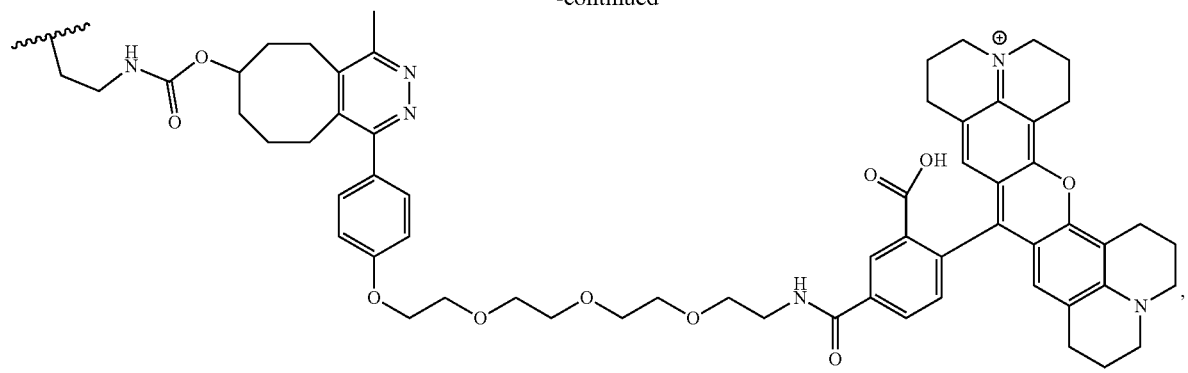

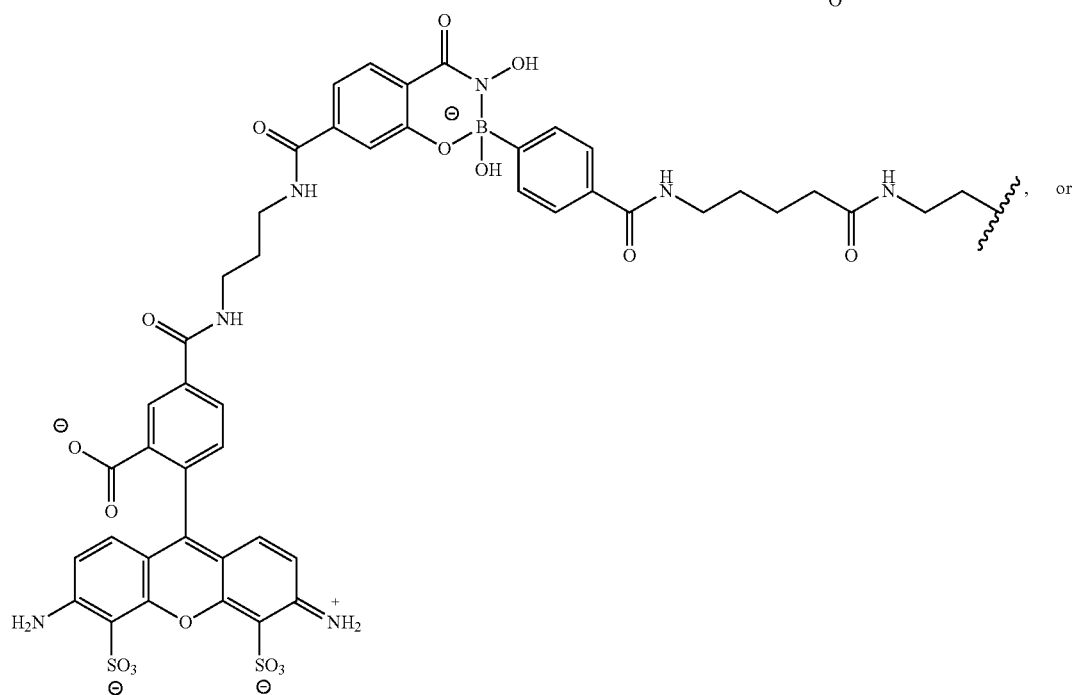

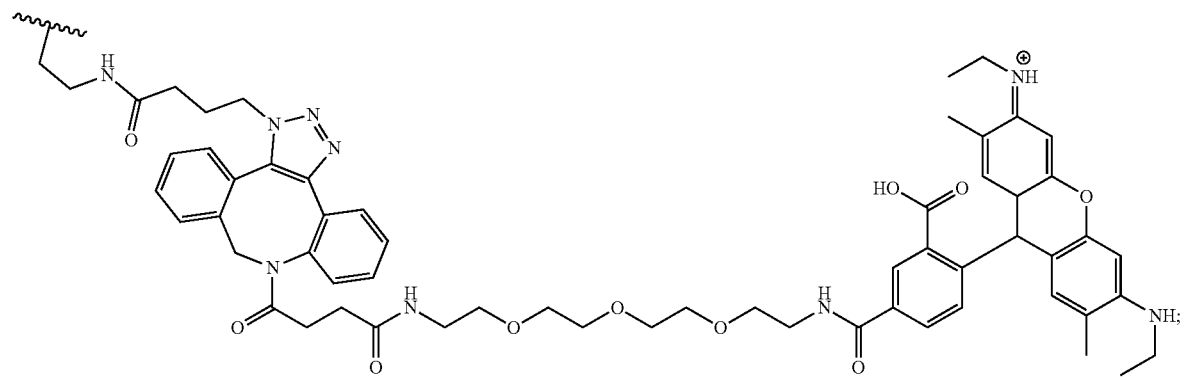

and z is an integer from 0 to 10.

In embodiments, z is an integer from 0 to 20. In embodiments, z is an integer from 0 to 10. In embodiments, z is an integer from 0 to 15. In embodiments, z is an integer from 5 to 10. In embodiments, z is 0. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9. In embodiments, z is 10. In embodiments, z is 11. In embodiments, z is 12. In embodiments, z is 13. In embodiments, z is 14. In embodiments, z is 15. In embodiments, z is 16. In embodiments, z is 17. In embodiments, z is 18. In embodiments, z is 19. In embodiments, z is 20.

In embodiments, $L^{2A}$, $L^{2B}$, $L^{2C}$, $L^{2D}$, and $L^{2E}$ are each independently

—C(CH₃)₂CH₂NHC(O)—,

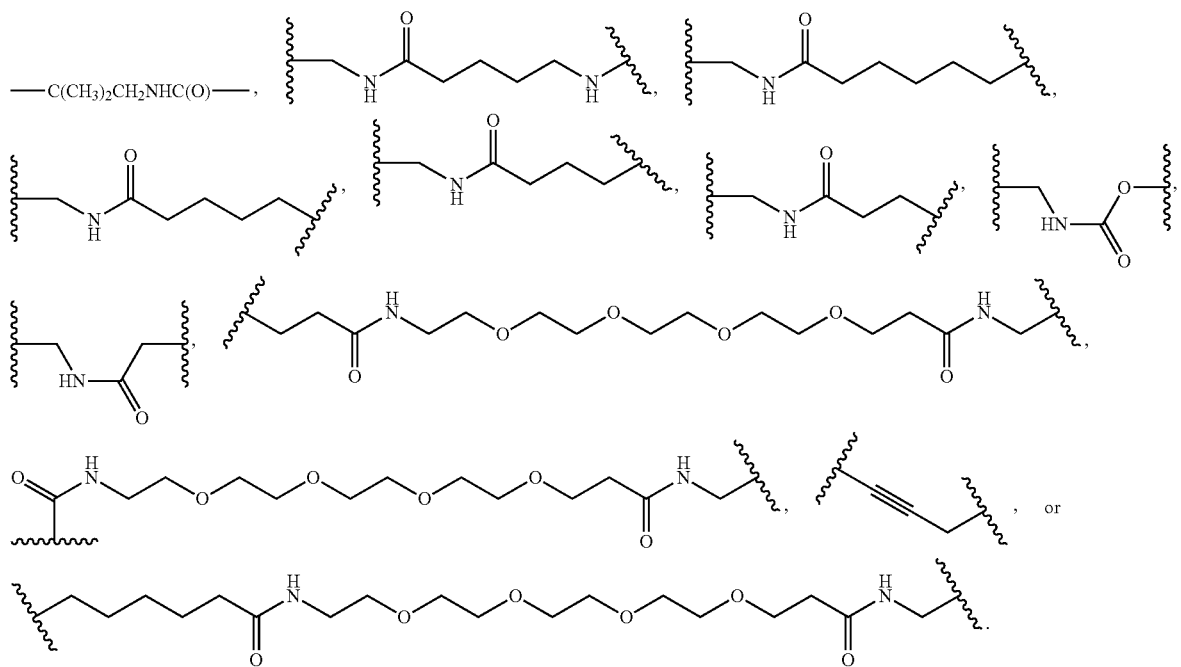

In embodiments, $L^{2A}$, $L^{2B}$, $L^{2C}$, $L^{2D}$ and $L^{2E}$ are each independently

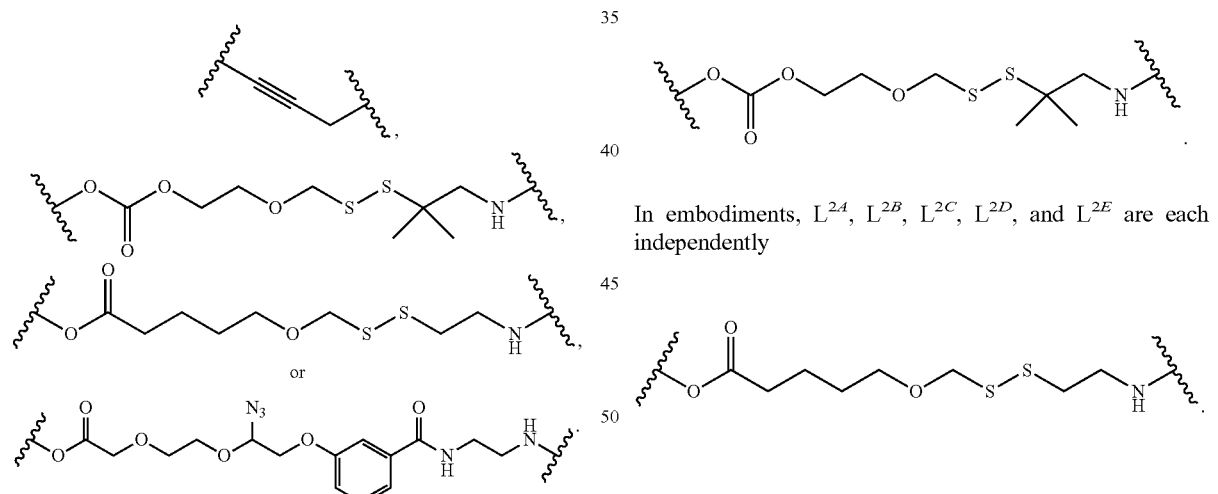

In embodiments, $L^{2A}$, $L^{2B}$, $L^{2C}$, $L^{2D}$, and $L^{2E}$ are each independently In embodiments, $L^{2A}$, $L^{2B}$, $L^{2C}$, $L^{2D}$, and $L^{2E}$ are each independently In embodiments, $L^{2A}$, $L^{2B}$, $L^{2C}$, $L^{2D}$, and $L^{2E}$ are each independently

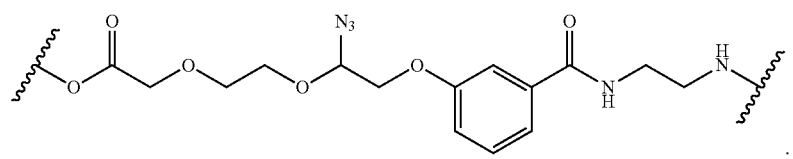 [SMILES: *NCCNC(=O)c1cccc(OCC(N=[N+]=[N-])OCCOCC(=O)O*)c1]

In embodiments, $L^{2A}$, $L^{2B}$, $L^{2C}$, $L^{2D}$, and $L^{2E}$ are each independently

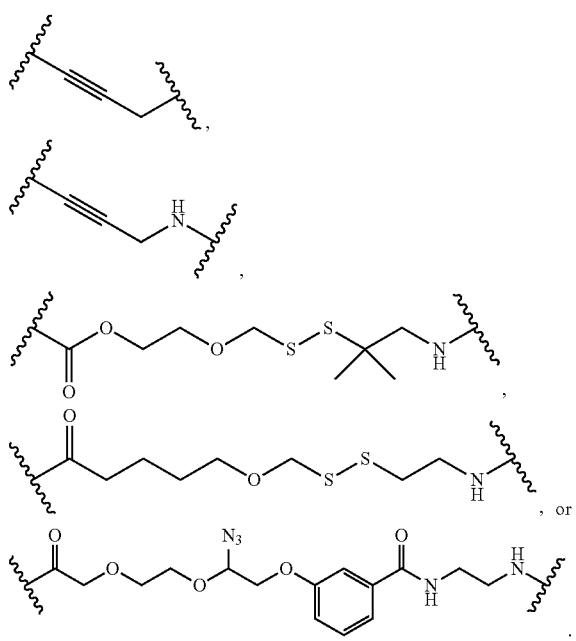

In embodiments, $L^{2A}$, $L^{2B}$, $L^{2C}$, $L^{2D}$, and $L^{2E}$ are each independently

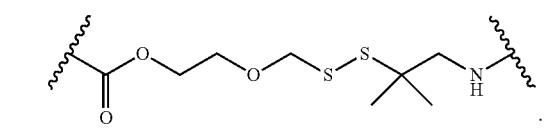 [SMILES: *NCC(C)(C)SSCOCCOC(*)=O]

In embodiments, $L^{2A}$, $L^{2B}$, $L^{2C}$, $L^{2D}$, and $L^{2E}$ are each independently

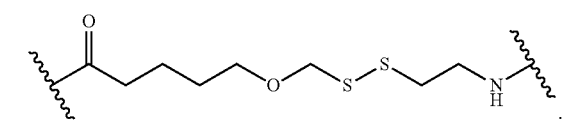 [SMILES: *NCCSSCOCCCCC(*)=O]

In embodiments, $L^{2A}$, $L^{2B}$, $L^{2C}$, $L^{2D}$, and $L^{2E}$ are each independently

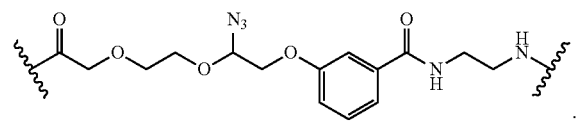 [SMILES: *NCCNC(=O)c1cccc(OCC(N=[N+]=[N-])OCCOCC(*)=O)c1]

In embodiments, $L^{2B}$ is

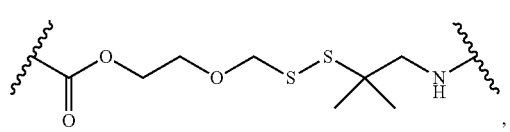 [SMILES: *NCC(C)(C)SSCOCCOC(*)=O]

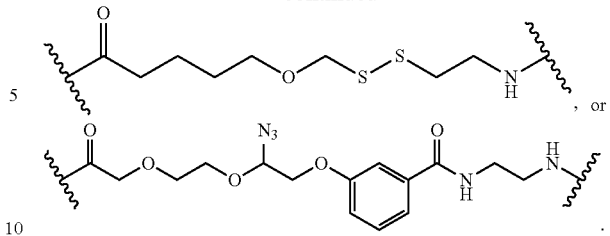, or

In embodiments, $L^{2B}$ is

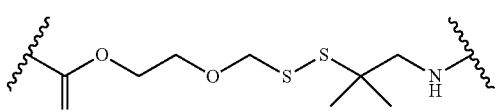

In embodiments, $L^{2B}$ is

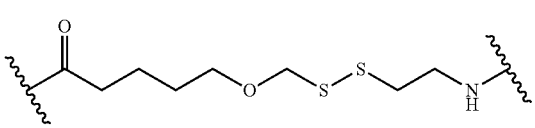

In embodiments, $L^{2B}$ is

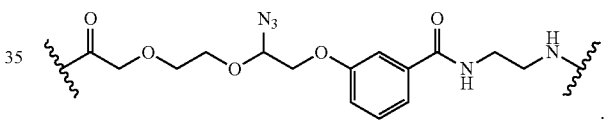

In embodiments, $L^{2C}$ is

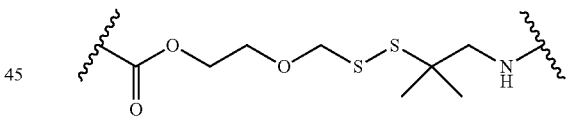

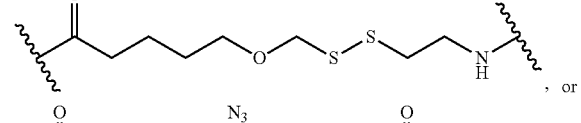, or

In embodiments, $L^{2C}$ is

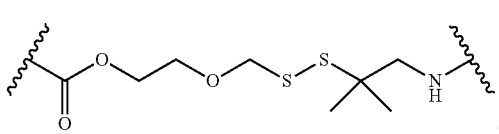

In embodiments, $L^{2C}$ is

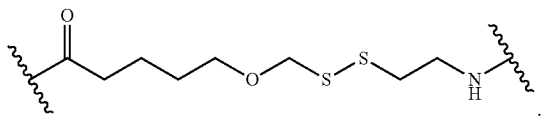 [SMILES: *NCCSSCOCCCCC(*)=O]

In embodiments, $L^{2C}$ is

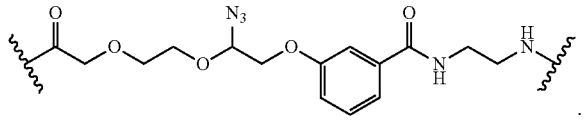 [SMILES: *NCCNC(=O)c1cccc(OCC(N=[N+]=[N-])OCCOCC(*)=O)c1]

In embodiments, $L^{2D}$ is

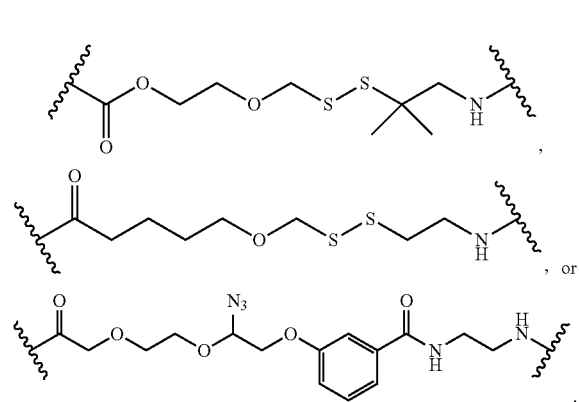

, or

In embodiments, $L^{2D}$ is

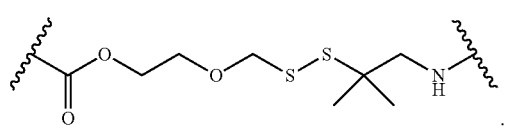 [SMILES: *NCC(C)(C)SSCOCCOC(*)=O]

In embodiments, $L^{2D}$ is

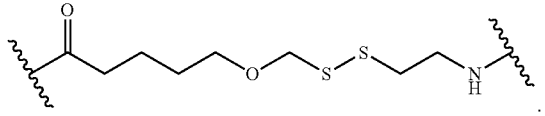 [SMILES: *NCCSSCOCCCCC(*)=O]

In embodiments, $L^{2D}$ is

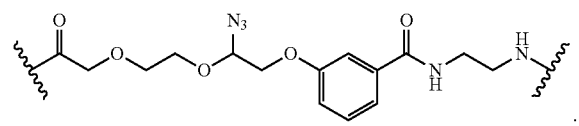 [SMILES: *NCCNC(=O)c1cccc(OCC(N=[N+]=[N-])OCCOCC(*)=O)c1]

In embodiments, $L^{2E}$ is

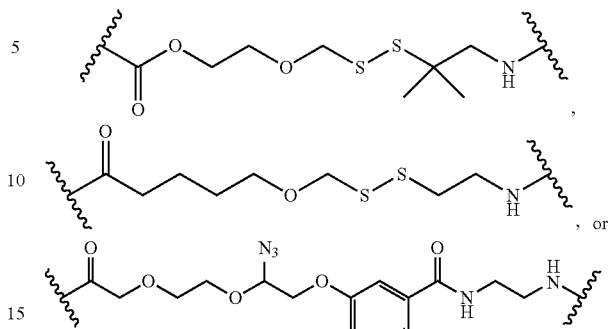

, or

In embodiments, $L^{2E}$ is

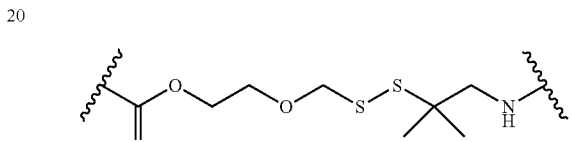

In embodiments, $L^{2E}$ is

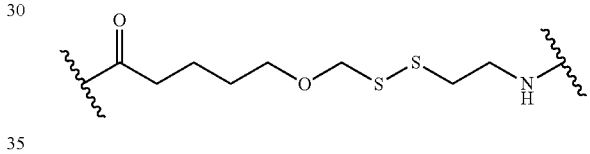

In embodiments, $L^{2E}$ is

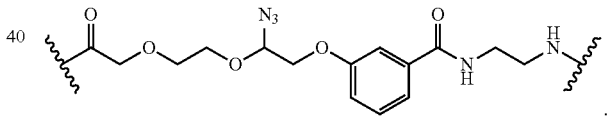

In embodiments, $L^{2B}$ is a bond. In embodiments, $L^{2C}$ is a bond. In embodiments, $L^{2D}$ is a bond. In embodiments, $L^{2E}$ is a bond.

In embodiments, $L^3$ is an orthogonally cleavable linker. In embodiments, $L^3$ is a cleavable linker. In embodiments, $L^3$ is a chemically cleavable linker. In embodiments, $L^3$ is a photocleavable linker, an acid-cleavable linker, a base-cleavable linker, an oxidant-cleavable linker, a reductant-cleavable linker, or a fluoride-cleavable linker. In embodiments, $L^3$ is a photocleavable linker. In embodiments, $L^3$ is an acid-cleavable linker. In embodiments, $L^3$ is a base-cleavable linker. In embodiments, $L^3$ is an oxidant-cleavable linker. In embodiments, $L^3$ is a reductant-cleavable linker. In embodiments, $L^3$ is a fluoride-cleavable linker. In embodiments, $L^3$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^3$ includes an orthogonally cleavable linker. In embodiments, L includes a cleavable linker. In embodiments, $L^3$ includes a chemically cleavable linker. In embodiments, $L^3$ includes a photocleavable linker, an acid-cleavable linker, a base-cleavable linker, an oxidant-cleavable linker, a reductant-cleavable linker, or a fluoride-cleavable linker. In embodiments, $L^3$ includes a photocleavable linker. In embodiments, $L^3$ includes an acid-cleavable linker. In embodiments, $L^3$ includes a base-cleavable linker. In embodiments, $L^3$ includes an oxidant-cleavable linker. In embodiments, L includes a reductant-cleavable linker. In embodiments, $L^3$ includes a fluoride-cleavable linker. In embodiments, L includes a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^3$ is $L^{3A}$-$L^{3B}$-$L^{3C}$-$L^{3D}$-$L^{3E}$. $L^{3A}$, $L^{3B}$, $L^{3C}$, $L^{3D}$, or $L^{3E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{3A}$, $L^{3B}$, $L^{3C}$, $L^{3D}$, and $L^{3E}$ is not a bond.

In embodiments, $L^3$ is $L^{3A}$-$L^{3B}$-$L^{3C}$-$L^{3D}$-$L^{3E}$; and $L^{3A}$, $L^{3B}$, $L^{3C}$, $L^{3D}$, or $L^{3E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{3A}$, $L^{3B}$, $L^{3C}$, $L^{3D}$, and $L^{3E}$ is not a bond.

In embodiments, $L^3$ is $L^{3A}$-$L^{3B}$-$L^{3C}$-$L^{3D}$-$L^{3E}$; and $L^{3A}$, $L^{3B}$, $L^{3C}$, $L^{3D}$, or $L^{3E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{3A}$, $L^{3B}$, $L^{3C}$, $L^{3D}$, and $L^{3E}$ is not a bond.

In embodiments, $L^3$ is $L^{3A}$-$L^{3B}$-$L^{3C}$-$L^{3D}$-$L^{3E}$; and $L^{3A}$, $L^{3B}$, $L^{3C}$, $L^{3D}$, or $L^{3E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{3A}$, $L^{3B}$, $L^{3C}$, $L^{3D}$, and $L^{3E}$ is not a bond.

In embodiments, $L^3$ is $L^{3A}$-$L^{3B}$-$L^{3C}$-$L^{3D}$-$L^{3E}$; wherein $L^{3A}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{3B}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{3C}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{3D}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{3E}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{3A}$, $L^{3B}$, $L^{3C}$, $L^{3D}$, and $L^{3E}$ is not a bond.

In embodiments, $L^3$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^3$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^3$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^3$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^3$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^3$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^3$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $L^3$ is substituted or unsubstituted methylene. In embodiments, $L^3$ is substituted or unsubstituted $C_2$ alkylene. In embodiments, $L^3$ is substituted or unsubstituted $C_3$ alkylene. In embodiments, $L^3$ is substituted or unsubstituted $C_4$ alkylene. In embodiments, $L^3$ is substituted or unsubstituted $C_5$ alkylene. In embodiments, $L^3$ is substituted or unsubstituted $C_6$ alkylene. In embodiments, $L^3$ is substituted or unsubstituted $C_7$ alkylene. In embodiments, $L^3$ is substituted or unsubstituted $C_8$ alkylene. In embodiments, $L^3$ is substituted methylene. In embodiments, $L^3$ is substituted $C_2$ alkylene. In embodiments, $L^3$ is substituted $C_3$ alkylene. In embodiments, $L^3$ is substituted $C_4$ alkylene. In embodiments, $L^3$ is substituted $C_5$ alkylene. In embodiments, $L^3$ is substituted $C_6$ alkylene. In embodiments, $L^3$ is substituted $C_7$ alkylene. In embodiments, $L^3$ is substituted $C_8$ alkylene. In embodiments, $L^3$ is an unsubstituted methylene. In embodiments, $L^3$ is an unsubstituted $C_2$ alkylene. In embodiments, $L^3$ is an unsubstituted $C_3$ alkylene. In embodiments, $L^3$ is an unsubstituted $C_4$ alkylene. In embodiments, $L^3$ is an unsubstituted $C_5$ alkylene. In embodiments, $L^3$ is an unsubstituted $C_6$ alkylene. In embodiments, $L^3$ is an unsubstituted $C_7$ alkylene. In embodiments, $L^3$ is an unsubstituted $C_8$ alkylene.

In embodiments, $L^3$ is substituted or unsubstituted $C_1$-$C_6$ alkylene. In embodiments, $L^3$ is substituted $C_1$-$C_6$ alkylene.

In embodiments, $L^3$ is unsubstituted $C_1$-$C_6$ alkylene. In embodiments, $L^3$ is substituted or unsubstituted $C_2$-$C_6$ alkylene. In embodiments, $L^3$ is substituted $C_2$-$C_6$ alkylene. In embodiments, $L^3$ is unsubstituted $C_2$-$C_6$ alkylene. In embodiments, $L^3$ is substituted or unsubstituted $C_1$ alkylene. In embodiments, $L^3$ is substituted $C_1$ alkylene. In embodiments, $L^3$ is unsubstituted $C_1$ alkylene. In embodiments, $L^3$ is substituted or unsubstituted $C_2$ alkylene. In embodiments, $L^3$ is substituted $C_2$ alkylene. In embodiments, $L^3$ is unsubstituted $C_2$ alkylene. In embodiments, $L^3$ is substituted or unsubstituted $C_3$ alkylene. In embodiments, $L^3$ is substituted $C_3$ alkylene. In embodiments, $L^3$ is unsubstituted $C_3$ alkylene. In embodiments, $L^3$ is substituted or unsubstituted $C_4$ alkylene. In embodiments, $L^3$ is substituted $C_4$ alkylene. In embodiments, $L^3$ is unsubstituted $C_4$ alkylene. In embodiments, $L^3$ is substituted or unsubstituted $C_5$ alkylene. In embodiments, $L^3$ is substituted $C_5$ alkylene. In embodiments, $L^3$ is unsubstituted $C_5$ alkylene. In embodiments, $L^3$ is substituted or unsubstituted $C_6$ alkylene. In embodiments, $L^3$ is substituted $C_6$ alkylene. In embodiments, $L^3$ is unsubstituted $C_6$ alkylene.

In embodiments, $L^3$ is substituted or unsubstituted $C_9$ alkylene. In embodiments, $L^3$ is substituted or unsubstituted $C_{10}$ alkylene. In embodiments, $L^3$ is substituted or unsubstituted $C_1$ alkylene. In embodiments, $L^3$ is substituted or unsubstituted $C_2$ alkylene. In embodiments, $L^3$ is substituted or unsubstituted $C_{13}$ alkylene. In embodiments, $L^3$ is substituted or unsubstituted $C_{14}$ alkylene. In embodiments, $L^3$ is substituted or unsubstituted $C_{15}$ alkylene. In embodiments, $L^3$ is substituted or unsubstituted $C_{16}$ alkylene. In embodiments, $L^3$ is substituted or unsubstituted $C_7$ alkylene. In embodiments, $L^3$ is substituted or unsubstituted $C_{18}$ alkylene. In embodiments, $L^3$ is substituted or unsubstituted $C_{19}$ alkylene. In embodiments, $L^3$ is substituted or unsubstituted $C_2$ alkylene.

In embodiments, $L^3$ is substituted or unsubstituted 2 to 8 membered heteroalkylene. In embodiments, $L^3$ is substituted 2 to 8 membered heteroalkylene. In embodiments, $L^3$ is unsubstituted 2 to 8 membered heteroalkylene. In embodiments, $L^3$ is substituted or unsubstituted 2 membered heteroalkylene. In embodiments, $L^3$ is substituted 2 membered heteroalkylene. In embodiments, $L^3$ is unsubstituted 2 membered heteroalkylene. In embodiments, $L^3$ is substituted or unsubstituted 3 membered heteroalkylene. In embodiments, $L^3$ is substituted 3 membered heteroalkylene. In embodiments, $L^3$ is unsubstituted 3 membered heteroalkylene. In embodiments, $L^3$ is substituted or unsubstituted 4 membered heteroalkylene. In embodiments, $L^3$ is substituted 4 membered heteroalkylene. In embodiments, $L^3$ is unsubstituted 4 membered heteroalkylene. In embodiments, $L^3$ is substituted or unsubstituted 5 membered heteroalkylene. In embodiments, $L^3$ is substituted 5 membered heteroalkylene. In embodiments, $L^3$ is unsubstituted 5 membered heteroalkylene. In embodiments, $L^3$ is substituted or unsubstituted 6 membered heteroalkylene. In embodiments, $L^3$ is substituted 6 membered heteroalkylene. In embodiments, $L^3$ is unsubstituted 6 membered heteroalkylene. In embodiments, $L^3$ is substituted or unsubstituted 7 membered heteroalkylene. In embodiments, $L^3$ is substituted 7 membered heteroalkylene. In embodiments, $L^3$ is unsubstituted 7 membered heteroalkylene. In embodiments, $L^3$ is substituted or unsubstituted 8 membered heteroalkylene. In embodiments, $L^3$ is substituted 8 membered heteroalkylene. In embodiments, $L^3$ is unsubstituted 8 membered heteroalkylene. In embodiments, $L^3$ is substituted or unsubstituted 9 membered heteroalkylene. In embodiments, $L^3$ is substituted 9 membered heteroalkylene. In embodiments, $L^3$ is unsubstituted 9 membered heteroalkylene. In embodiments, $L^3$ is substituted or unsubstituted 10 membered heteroalkylene. In embodiments, $L^3$ is substituted 10 membered heteroalkylene. In embodiments, $L^3$ is unsubstituted 10 membered heteroalkylene. In embodiments, $L^3$ is substituted or unsubstituted 11 membered heteroalkylene. In embodiments, $L^3$ is substituted 11 membered heteroalkylene. In embodiments, $L^3$ is unsubstituted 11 membered heteroalkylene. In embodiments, $L^3$ is substituted or unsubstituted 12 membered heteroalkylene. In embodiments, $L^3$ is substituted 12 membered heteroalkylene. In embodiments, $L^3$ is unsubstituted 12 membered heteroalkylene. In embodiments, $L^3$ is substituted or unsubstituted 13 membered heteroalkylene. In embodiments, $L^3$ is substituted 13 membered heteroalkylene. In embodiments, $L^3$ is unsubstituted 13 membered heteroalkylene. In embodiments, $L^3$ is substituted or unsubstituted 14 membered heteroalkylene. In embodiments, $L^3$ is substituted 14 membered heteroalkylene. In embodiments, $L^3$ is unsubstituted 14 membered heteroalkylene. In embodiments, $L^3$ is substituted or unsubstituted 15 membered heteroalkylene. In embodiments, $L^3$ is substituted 15 membered heteroalkylene. In embodiments, $L^3$ is unsubstituted 15 membered heteroalkylene. In embodiments, $L^3$ is substituted or unsubstituted 16 membered heteroalkylene. In embodiments, $L^3$ is substituted 16 membered heteroalkylene. In embodiments, $L^3$ is unsubstituted 16 membered heteroalkylene. In embodiments, $L^3$ is substituted or unsubstituted 17 membered heteroalkylene. In embodiments, $L^3$ is substituted 17 membered heteroalkylene. In embodiments, $L^3$ is unsubstituted 17 membered heteroalkylene. In embodiments, $L^3$ is substituted or unsubstituted 18 membered heteroalkylene. In embodiments, $L^3$ is substituted 18 membered heteroalkylene. In embodiments, $L^3$ is unsubstituted 18 membered heteroalkylene. In embodiments, $L^3$ is substituted or unsubstituted 19 membered heteroalkylene. In embodiments, $L^3$ is substituted 19 membered heteroalkylene. In embodiments, $L^3$ is unsubstituted 19 membered heteroalkylene. In embodiments, $L^3$ is substituted or unsubstituted 20 membered heteroalkylene. In embodiments, $L^3$ is substituted 20 membered heteroalkylene. In embodiments, $L^3$ is unsubstituted 20 membered heteroalkylene.

In embodiments, $L^3$ is substituted or unsubstituted $C_4$-$C_6$ cycloalkylene. In embodiments, $L^3$ is substituted $C_4$-$C_6$ cycloalkylene. In embodiments, $L^3$ is substituted $C_4$-$C_6$ cycloalkylene. In embodiments, $L^3$ is substituted or unsubstituted $C_4$ cycloalkylene. In embodiments, $L^3$ is substituted $C_4$ cycloalkylene. In embodiments, $L^3$ is substituted $C_4$ cycloalkylene. In embodiments, $L^3$ is substituted or unsubstituted $C_5$ cycloalkylene. In embodiments, $L^3$ is substituted $C_5$ cycloalkylene. In embodiments, $L^3$ is substituted $C_5$ cycloalkylene.

In embodiments, $L^3$ is substituted or unsubstituted 5 to 6 membered heterocycloalkylene. In embodiments, $L^3$ is substituted 5 to 6 membered heterocycloalkylene. In embodiments, $L^3$ is unsubstituted 5 to 6 membered heterocycloalkylene. In embodiments, $L^3$ is substituted or unsubstituted 5 membered heterocycloalkylene. In embodiments, $L^3$ is substituted 5 membered heterocycloalkylene. In embodiments, $L^3$ is unsubstituted 5 membered heterocycloalkylene. In embodiments, $L^3$ is substituted or unsubstituted 6 membered heterocycloalkylene. In embodiments, $L^3$ is substituted 6 membered heterocycloalkylene. In embodiments, $L^3$ is unsubstituted 6 membered heterocycloalkylene.

In embodiments, $L^3$ is substituted or unsubstituted phenylene. In embodiments, $L^3$ is substituted phenylene. In embodiments, $L^3$ is unsubstituted phenylene.

In embodiments, $L^3$ is substituted or unsubstituted 5 to 6 membered heteroarylene. In embodiments, $L^3$ is substituted 5 to 6 membered heteroarylene. In embodiments, $L^3$ is unsubstituted 5 to 6 membered heteroarylene. In embodiments, $L^3$ is substituted or unsubstituted 5 membered heteroarylene. In embodiments, $L^3$ is substituted 5 membered heteroarylene. In embodiments, $L^3$ is unsubstituted 5 membered heteroarylene. In embodiments, $L^3$ is substituted or unsubstituted 6 membered heteroarylene. In embodiments, $L^3$ is substituted 6 membered heteroarylene. In embodiments, $L^3$ is unsubstituted 6 membered heteroarylene.

In embodiments, $L^3$ is a polymer.

In embodiments, $L^{3A}$ is substituted or unsubstituted methylene. In embodiments, $L^{3A}$ is substituted or unsubstituted $C_2$ alkylene. In embodiments, $L^{3A}$ is substituted or unsubstituted $C_3$ alkylene. In embodiments, $L^{3A}$ is substituted or unsubstituted $C_4$ alkylene. In embodiments, $L^{3A}$ is substituted or unsubstituted $C_5$ alkylene. In embodiments, $L^{3A}$ is substituted or unsubstituted $C_6$ alkylene. In embodiments, $L^{3A}$ is substituted or unsubstituted $C_7$ alkylene. In embodiments, $L^{3A}$ is substituted or unsubstituted $C_8$ alkylene. In embodiments, $L^{3A}$ is substituted methylene. In embodiments, $L^{3A}$ is substituted $C_2$ alkylene. In embodiments, $L^{3A}$ is substituted $C_3$ alkylene. In embodiments, $L^{3A}$ is substituted $C_4$ alkylene. In embodiments, $L^{3A}$ is substituted $C_5$ alkylene. In embodiments, $L^{3A}$ is substituted $C_6$ alkylene. In embodiments, $L^{3A}$ is substituted $C_7$ alkylene. In embodiments, $L^{3A}$ is substituted $C_8$ alkylene. In embodiments, $L^{3A}$ is an unsubstituted methylene. In embodiments, $L^{3A}$ is an unsubstituted $C_2$ alkylene. In embodiments, $L^{3A}$ is an unsubstituted $C_3$ alkylene. In embodiments, $L^{3A}$ is an unsubstituted $C_4$ alkylene. In embodiments, $L^{3A}$ is an unsubstituted $C_5$ alkylene. In embodiments, $L^{3A}$ is an unsubstituted $C_6$ alkylene. In embodiments, $L^{3A}$ is an unsubstituted $C_7$ alkylene. In embodiments, $L^{3A}$ is an unsubstituted $C_8$ alkylene.

In embodiments, $L^{3A}$ is substituted or unsubstituted $C_1$-$C_6$ alkylene. In embodiments, $L^{3A}$ is substituted $C_1$-$C_6$ alkylene. In embodiments, $L^{3A}$ is unsubstituted $C_1$-$C_6$ alkylene. In embodiments, $L^{3A}$ is substituted or unsubstituted $C_2$-$C_6$ alkylene. In embodiments, $L^{3A}$ is substituted $C_2$-$C_6$ alkylene. In embodiments, $L^{3A}$ is unsubstituted $C_2$-$C_6$ alkylene. In embodiments, $L^{3A}$ is substituted or unsubstituted $C_1$ alkylene. In embodiments, $L^{3A}$ is substituted $C_1$ alkylene. In embodiments, $L^{3A}$ is unsubstituted $C_1$ alkylene. In embodiments, $L^{3A}$ is substituted or unsubstituted $C_2$ alkylene. In embodiments, $L^{3A}$ is substituted $C_2$ alkylene. In embodiments, $L^{3A}$ is unsubstituted $C_2$ alkylene. In embodiments, $L^{3A}$ is substituted or unsubstituted $C_3$ alkylene. In embodiments, $L^{3A}$ is substituted $C_3$ alkylene. In embodiments, $L^{3A}$ is unsubstituted $C_3$ alkylene. In embodiments, $L^{3A}$ is substituted or unsubstituted $C_4$ alkylene. In embodiments, $L^{3A}$ is substituted $C_4$ alkylene. In embodiments, $L^{3A}$ is unsubstituted $C_4$ alkylene. In embodiments, $L^{3A}$ is substituted or unsubstituted $C_5$ alkylene. In embodiments, $L^{3A}$ is substituted $C_5$ alkylene. In embodiments, $L^{3A}$ is unsubstituted $C_5$ alkylene. In embodiments, $L^{3A}$ is substituted or unsubstituted $C_6$ alkylene. In embodiments, $L^{3A}$ is substituted $C_6$ alkylene. In embodiments, $L^{3A}$ is unsubstituted $C_6$ alkylene.

In embodiments, $L^{3A}$ is substituted or unsubstituted 2 to 8 membered heteroalkylene. In embodiments, $L^{3A}$ is substituted 2 to 8 membered heteroalkylene. In embodiments, $L^{3A}$ is unsubstituted 2 to 8 membered heteroalkylene. In embodiments, $L^{3A}$ is substituted or unsubstituted 2 membered heteroalkylene. In embodiments, $L^{3A}$ is substituted 2 membered heteroalkylene. In embodiments, $L^{3A}$ is unsubstituted 2 membered heteroalkylene. In embodiments, $L^{3A}$ is substituted or unsubstituted 3 membered heteroalkylene. In embodiments, $L^{3A}$ is substituted 3 membered heteroalkylene. In embodiments, $L^{3A}$ is unsubstituted 3 membered heteroalkylene. In embodiments, $L^{3A}$ is substituted or unsubstituted 4 membered heteroalkylene. In embodiments, $L^{3A}$ is substituted 4 membered heteroalkylene. In embodiments, $L^{3A}$ is unsubstituted 4 membered heteroalkylene. In embodiments, $L^{3A}$ is substituted or unsubstituted 5 membered heteroalkylene. In embodiments, $L^{3A}$ is substituted 5 membered heteroalkylene. In embodiments, $L^{3A}$ is unsubstituted 5 membered heteroalkylene. In embodiments, $L^{3A}$ is substituted or unsubstituted 6 membered heteroalkylene. In embodiments, $L^{3A}$ is substituted 6 membered heteroalkylene. In embodiments, $L^{3A}$ is unsubstituted 6 membered heteroalkylene.

In embodiments, $L^{3A}$ is substituted or unsubstituted $C_4$-$C_6$ cycloalkylene. In embodiments, $L^{3A}$ is substituted $C_4$-$C_6$ cycloalkylene. In embodiments, $L^{3A}$ is unsubstituted $C_4$-$C_6$ cycloalkylene. In embodiments, $L^{3A}$ is substituted or unsubstituted $C_4$ cycloalkylene. In embodiments, $L^{3A}$ is substituted $C_4$ cycloalkylene. In embodiments, $L^{3A}$ is unsubstituted $C_4$ cycloalkylene. In embodiments, $L^{3A}$ is substituted or unsubstituted $C_5$ cycloalkylene. In embodiments, $L^{3A}$ is substituted $C_5$ cycloalkylene. In embodiments, $L^{3A}$ is unsubstituted $C_5$ cycloalkylene.

In embodiments, $L^{3A}$ is substituted or unsubstituted 5 to 6 membered heterocycloalkylene. In embodiments, $L^{3A}$ is substituted 5 to 6 membered heterocycloalkylene. In embodiments, $L^{3A}$ is unsubstituted 5 to 6 membered heterocycloalkylene. In embodiments, $L^{3A}$ is substituted or unsubstituted 5 membered heterocycloalkylene. In embodiments, $L^{3A}$ is substituted 5 membered heterocycloalkylene. In embodiments, $L^{3A}$ is unsubstituted 5 membered heterocycloalkylene. In embodiments, $L^{3A}$ is substituted or unsubstituted 6 membered heterocycloalkylene. In embodiments, $L^{3A}$ is substituted 6 membered heterocycloalkylene. In embodiments, $L^{3A}$ is unsubstituted 6 membered heterocycloalkylene.

In embodiments, $L^{3A}$ is substituted or unsubstituted phenylene. In embodiments, $L^{3A}$ is substituted phenylene. In embodiments, $L^{3A}$ is unsubstituted phenylene.

In embodiments, $L^{3A}$ is substituted or unsubstituted 5 to 6 membered heteroarylene. In embodiments, $L^{3A}$ is substituted 5 to 6 membered heteroarylene. In embodiments, $L^{3A}$ is unsubstituted 5 to 6 membered heteroarylene. In embodiments, $L^{3A}$ is substituted or unsubstituted 5 membered heteroarylene. In embodiments, $L^{3A}$ is substituted 5 membered heteroarylene. In embodiments, $L^{3A}$ is unsubstituted 5 membered heteroarylene. In embodiments, $L^{3A}$ is substituted or unsubstituted 6 membered heteroarylene. In embodiments, $L^{3A}$ is substituted 6 membered heteroarylene. In embodiments, $L^{3A}$ is unsubstituted 6 membered heteroarylene.

In embodiments, $L^{3A}$ is a polymer.

In embodiments, $L^{3B}$ is substituted or unsubstituted methylene. In embodiments, $L^{3B}$ is substituted or unsubstituted $C_2$ alkylene. In embodiments, $L^{3B}$ is substituted or unsubstituted $C_3$ alkylene. In embodiments, $L^{3B}$ is substituted or unsubstituted $C_4$ alkylene. In embodiments, $L^{3B}$ is substituted or unsubstituted $C_5$ alkylene. In embodiments, $L^{3B}$ is substituted or unsubstituted $C_6$ alkylene. In embodiments, $L^{3B}$ is substituted or unsubstituted $C_7$ alkylene. In embodiments, $L^{3B}$ is substituted or unsubstituted $C_8$ alkylene. In embodiments, $L^{3B}$ is substituted methylene. In embodiments, $L^{3B}$ is substituted $C_2$ alkylene. In embodiments, $L^{3B}$ is substituted $C_3$ alkylene. In embodiments, $L^{3B}$ is substituted $C_4$ alkylene. In embodiments, $L^{3B}$ is substituted $C_5$ alkylene. In embodiments, $L^{3B}$ is substituted $C_6$ alkylene. In embodiments, $L^{3B}$ is substituted $C_7$ alkylene. In embodiments, $L^{3B}$ is substituted $C_8$ alkylene. In embodiments, $L^{3B}$ is an unsubstituted methylene. In embodiments, $L^{3B}$ is an unsubstituted $C_2$ alkylene. In embodiments, $L^{3B}$ is an unsubstituted $C_3$ alkylene. In embodiments, $L^{3B}$ is an unsubstituted $C_4$ alkylene. In embodiments $L^{3B}$ is an unsubstituted $C_5$ alkylene. In embodiments, $L^{3B}$ is an unsubstituted $C_6$ alkylene. In embodiments, $L^{3B}$ is an unsubstituted $C_7$ alkylene. In embodiments, $L^{3B}$ is an unsubstituted $C_8$ alkylene.

In embodiments, $L^{3B}$ is substituted or unsubstituted $C_1$-$C_6$ alkylene. In embodiments, $L^{3B}$ is substituted $C_1$-$C_6$ alkylene. In embodiments, $L^{3B}$ is unsubstituted $C_1$-$C_6$ alkylene. In embodiments, $L^{3B}$ is substituted or unsubstituted $C_2$-$C_6$ alkylene. In embodiments, $L^{3B}$ is substituted $C_2$-$C_6$ alkylene. In embodiments, $L^{3B}$ is unsubstituted $C_2$-$C_6$ alkylene. In embodiments, $L^{3B}$ is substituted or unsubstituted $C_1$ alkylene. In embodiments, $L^{3B}$ is substituted $C_1$ alkylene. In embodiments, $L^{3B}$ is unsubstituted $C_1$ alkylene. In embodiments, $L^{3B}$ is substituted or unsubstituted $C_2$ alkylene. In embodiments, $L^{3B}$ is substituted $C_2$ alkylene. In embodiments, $L^{3B}$ is unsubstituted $C_2$ alkylene. In embodiments, $L^{3B}$ is substituted or unsubstituted $C_3$ alkylene. In embodiments, $L^{3B}$ is substituted $C_3$ alkylene. In embodiments, $L^{3B}$ is unsubstituted $C_3$ alkylene. In embodiments, $L^{3B}$ is substituted or unsubstituted $C_4$ alkylene. In embodiments, $L^{3B}$ is substituted $C_4$ alkylene. In embodiments, $L^{3B}$ is unsubstituted $C_4$ alkylene. In embodiments, $L^{3B}$ is substituted or unsubstituted $C_5$ alkylene. In embodiments, $L^{3B}$ is substituted $C_5$ alkylene. In embodiments, $L^{3B}$ is unsubstituted $C_5$ alkylene. In embodiments, $L^{3B}$ is substituted or unsubstituted $C_6$ alkylene. In embodiments, $L^{3B}$ is substituted $C_6$ alkylene. In embodiments, $L^{3B}$ is unsubstituted $C_6$ alkylene.

In embodiments, $L^{3B}$ is substituted or unsubstituted 2 to 8 membered heteroalkylene. In embodiments, $L^{3B}$ is substituted 2 to 8 membered heteroalkylene. In embodiments, $L^{3B}$ is unsubstituted 2 to 8 membered heteroalkylene. In embodiments, $L^{3B}$ is substituted or unsubstituted 2 membered heteroalkylene. In embodiments, $L^{3B}$ is substituted 2 membered heteroalkylene. In embodiments, $L^{3B}$ is unsubstituted 2 membered heteroalkylene. In embodiments, $L^{3B}$ is substituted or unsubstituted 3 membered heteroalkylene. In embodiments, $L^{3B}$ is substituted 3 membered heteroalkylene. In embodiments, $L^{3B}$ is unsubstituted 3 membered heteroalkylene. In embodiments, $L^{3B}$ is substituted or unsubstituted 4 membered heteroalkylene. In embodiments, $L^{3B}$ is substituted 4 membered heteroalkylene. In embodiments, $L^{3B}$ is unsubstituted 4 membered heteroalkylene. In embodiments, $L^{3B}$ is substituted or unsubstituted 5 membered heteroalkylene. In embodiments, $L^{3B}$ is substituted 5 membered heteroalkylene. In embodiments, $L^{3B}$ is unsubstituted 5 membered heteroalkylene. In embodiments, $L^{3B}$ is substituted or unsubstituted 6 membered heteroalkylene. In embodiments, $L^{3B}$ is substituted 6 membered heteroalkylene. In embodiments, $L^{3B}$ is unsubstituted 6 membered heteroalkylene.

In embodiments, $L^{3B}$ is substituted or unsubstituted $C_4$-$C_6$ cycloalkylene. In embodiments, $L^{3B}$ is substituted $C_4$-$C_6$ cycloalkylene. In embodiments, $L^{3B}$ is substituted $C_4$-$C_6$ cycloalkylene. In embodiments, $L^{3B}$ is substituted or unsubstituted $C_4$ cycloalkylene. In embodiments, $L^{3B}$ is substituted $C_4$ cycloalkylene. In embodiments, $L^{3B}$ is substituted $C_4$ cycloalkylene. In embodiments, $L^{3B}$ is substituted or unsubstituted $C_5$ cycloalkylene. In embodiments, $L^{3B}$ is substituted $C_5$ cycloalkylene. In embodiments, $L^{3B}$ is substituted $C_5$ cycloalkylene.

In embodiments, $L^{3B}$ is substituted or unsubstituted 5 to 6 membered heterocycloalkylene. In embodiments, $L^{3B}$ is substituted 5 to 6 membered heterocycloalkylene. In embodiments, $L^{3B}$ is unsubstituted 5 to 6 membered heterocycloalkylene. In embodiments, $L^{3B}$ is substituted or unsubstituted 5 membered heterocycloalkylene. In embodiments, $L^{3B}$ is substituted 5 membered heterocycloalkylene. In embodiments, $L^{3B}$ is unsubstituted 5 membered heterocycloalkylene. In embodiments, $L^{3B}$ is substituted or unsubstituted 6 membered heterocycloalkylene. In embodiments, $L^{3B}$ is substituted 6 membered heterocycloalkylene. In embodiments, $L^{3B}$ is unsubstituted 6 membered heterocycloalkylene.

In embodiments, $L^{3B}$ is substituted or unsubstituted phenylene. In embodiments, $L^{3B}$ is substituted phenylene. In embodiments, $L^{3B}$ is unsubstituted phenylene.

In embodiments, $L^{3B}$ is substituted or unsubstituted 5 to 6 membered heteroarylene. In embodiments, $L^{3B}$ is substituted 5 to 6 membered heteroarylene. In embodiments, $L^{3B}$ is unsubstituted 5 to 6 membered heteroarylene. In embodiments, $L^{3B}$ is substituted or unsubstituted 5 membered heteroarylene. In embodiments, $L^{3B}$ is substituted 5 membered heteroarylene. In embodiments, $L^{3B}$ is unsubstituted 5 membered heteroarylene. In embodiments, $L^{3B}$ is substituted or unsubstituted 6 membered heteroarylene. In embodiments, $L^{3B}$ is substituted 6 membered heteroarylene. In embodiments, $L^{3B}$ is unsubstituted 6 membered heteroarylene.

In embodiments, $L^{3C}$ is substituted or unsubstituted methylene. In embodiments, $L^{3C}$ is substituted or unsubstituted $C_2$ alkylene. In embodiments, $L^{3C}$ is substituted or unsubstituted $C_3$ alkylene. In embodiments, $L^{3C}$ is substituted or unsubstituted $C_4$ alkylene. In embodiments, $L^{3C}$ is substituted or unsubstituted $C_5$ alkylene. In embodiments, $L^{3C}$ is substituted or unsubstituted $C_6$ alkylene. In embodiments, $L^{3C}$ is substituted or unsubstituted $C_7$ alkylene. In embodiments, $L^{3C}$ is substituted or unsubstituted $C_8$ alkylene. In embodiments, $L^{3C}$ is substituted methylene. In embodiments, $L^{3C}$ is substituted $C_2$ alkylene. In embodiments, $L^{3C}$ is substituted $C_3$ alkylene. In embodiments, $L^{3C}$ is substituted $C_4$ alkylene. In embodiments, $L^{3C}$ is substituted $C_5$ alkylene. In embodiments, $L^{3C}$ is substituted $C_6$ alkylene. In embodiments, $L^{3C}$ is substituted $C_7$ alkylene. In embodiments, $L^{3C}$ is substituted $C_8$ alkylene. In embodiments, $L^{3C}$ is an unsubstituted methylene. In embodiments, $L^{3C}$ is an unsubstituted $C_2$ alkylene. In embodiments, $L^{3C}$ is an unsubstituted $C_3$ alkylene. In embodiments, $L^{3C}$ is an unsubstituted $C_4$ alkylene. In embodiments, $L^{3C}$ is an unsubstituted $C_5$ alkylene. In embodiments, $L^{3C}$ is an unsubstituted $C_6$ alkylene. In embodiments, $L^{3C}$ is an unsubstituted $C_7$ alkylene. In embodiments, $L^{3C}$ is an unsubstituted $C_8$ alkylene.

In embodiments, $L^{3C}$ is substituted or unsubstituted $C_1$-$C_6$ alkylene. In embodiments, $L^{3C}$ is substituted $C_1$-$C_6$ alkylene. In embodiments, $L^{3C}$ is unsubstituted $C_1$-$C_6$ alkylene. In embodiments, $L^{3C}$ is substituted or unsubstituted $C_2$-$C_6$ alkylene. In embodiments, $L^{3C}$ is substituted $C_2$-$C_6$ alkylene. In embodiments, $L^{3C}$ is unsubstituted $C_2$-$C_6$ alkylene. In embodiments, $L^{3C}$ is substituted or unsubstituted $C_1$ alkylene. In embodiments, $L^{3C}$ is substituted $C_1$ alkylene. In embodiments, $L^{3C}$ is unsubstituted $C_1$ alkylene. In embodiments, $L^{3C}$ is substituted or unsubstituted $C_2$ alkylene. In embodiments, $L^{3C}$ is substituted $C_2$ alkylene. In embodiments, $L^{3C}$ is unsubstituted $C_2$ alkylene. In embodiments, $L^{3C}$ is substituted or unsubstituted $C_3$ alkylene. In embodiments, $L^{3C}$ is substituted $C_3$ alkylene. In embodiments, $L^{3C}$ is unsubstituted $C_3$ alkylene. In embodiments, $L^{3C}$ is substituted or unsubstituted $C_4$ alkylene. In embodiments, $L^{3C}$ is substituted $C_4$ alkylene. In embodiments, $L^{3C}$ is unsubstituted $C_4$ alkylene. In embodiments, $L^{3C}$ is substituted or unsubstituted $C_5$ alkylene. In embodiments, $L^{3C}$ is substituted $C_5$ alkylene. In embodiments, $L^{3C}$ is unsubstituted $C_5$ alkylene. In embodiments, $L^{3C}$ is substituted or unsubstituted $C_6$ alkylene. In embodiments, $L^{3C}$ is substituted $C_6$ alkylene. In embodiments, $L^{3C}$ is unsubstituted $C_6$ alkylene.

In embodiments, $L^{3C}$ is substituted or unsubstituted 2 to 8 membered heteroalkylene. In embodiments, $L^{3C}$ is substituted 2 to 8 membered heteroalkylene. In embodiments, $L^{3C}$ is unsubstituted 2 to 8 membered heteroalkylene. In embodiments, $L^{3C}$ is substituted or unsubstituted 2 membered heteroalkylene. In embodiments, $L^{3C}$ is substituted 2 membered heteroalkylene. In embodiments, $L^{3C}$ is unsubstituted 2 membered heteroalkylene. In embodiments, $L^{3C}$ is substituted or unsubstituted 3 membered heteroalkylene. In embodiments, $L^{3C}$ is substituted 3 membered heteroalkylene. In embodiments, $L^{3C}$ is unsubstituted 3 membered heteroalkylene. In embodiments, $L^{3C}$ is substituted or unsubstituted 4 membered heteroalkylene. In embodiments, $L^{3C}$ is substituted 4 membered heteroalkylene. In embodiments, $L^{3C}$ is unsubstituted 4 membered heteroalkylene. In embodiments, $L^{3C}$ is substituted or unsubstituted 5 membered heteroalkylene. In embodiments, $L^{3C}$ is substituted 5 membered heteroalkylene. In embodiments, $L^{3C}$ is unsubstituted 5 membered heteroalkylene. In embodiments, $L^{3C}$ is substituted or unsubstituted 6 membered heteroalkylene. In embodiments, $L^{3C}$ is substituted 6 membered heteroalkylene. In embodiments, $L^{3C}$ is unsubstituted 6 membered heteroalkylene.

In embodiments, $L^{3C}$ is substituted or unsubstituted $C_4$-$C_6$ cycloalkylene. In embodiments, $L^{3C}$ is substituted $C_4$-$C_6$ cycloalkylene. In embodiments, $L^{3C}$ is substituted $C_4$-$C_6$ cycloalkylene. In embodiments, $L^{3C}$ is substituted or unsubstituted $C_4$ cycloalkylene. In embodiments, $L^{3C}$ is substituted $C_4$ cycloalkylene. In embodiments, $L^{3C}$ is substituted $C_4$ cycloalkylene. In embodiments, $L^{3C}$ is substituted or unsubstituted $C_5$ cycloalkylene. In embodiments, $L^{3C}$ is substituted $C_5$ cycloalkylene. In embodiments, $L^{3C}$ is substituted $C_5$ cycloalkylene.

In embodiments, $L^{3C}$ is substituted or unsubstituted 5 to 6 membered heterocycloalkylene. In embodiments, $L^{3C}$ is substituted 5 to 6 membered heterocycloalkylene. In embodiments, $L^{3C}$ is unsubstituted 5 to 6 membered heterocycloalkylene. In embodiments, $L^{3C}$ is substituted or unsubstituted 5 membered heterocycloalkylene. In embodiments, $L^{3C}$ is substituted 5 membered heterocycloalkylene. In embodiments, $L^{3C}$ is unsubstituted 5 membered heterocycloalkylene. In embodiments, $L^{3C}$ is substituted or unsubstituted 6 membered heterocycloalkylene. In embodiments, $L^{3C}$ is substituted 6 membered heterocycloalkylene. In embodiments, $L^{3C}$ is unsubstituted 6 membered heterocycloalkylene.

In embodiments, $L^{3C}$ is substituted or unsubstituted phenylene. In embodiments, $L^{3C}$ is substituted phenylene. In embodiments, $L^{3C}$ is unsubstituted phenylene.

In embodiments, $L^{3C}$ is substituted or unsubstituted 5 to 6 membered heteroarylene. In embodiments, $L^{3C}$ is substituted 5 to 6 membered heteroarylene. In embodiments, $L^{3C}$ is unsubstituted 5 to 6 membered heteroarylene. In embodiments, $L^{3C}$ is substituted or unsubstituted 5 membered heteroarylene. In embodiments, $L^{3C}$ is substituted 5 membered heteroarylene. In embodiments, $L^{3C}$ is unsubstituted 5 membered heteroarylene. In embodiments, $L^{3C}$ is substituted or unsubstituted 6 membered heteroarylene. In embodiments, $L^{3C}$ is substituted 6 membered heteroarylene. In embodiments, $L^{3C}$ is unsubstituted 6 membered heteroarylene.

In embodiments, $L^{3D}$ is substituted or unsubstituted methylene. In embodiments, $L^{3D}$ is substituted or unsubstituted $C_2$ alkylene. In embodiments, $L^{3D}$ is substituted or unsubstituted $C_3$ alkylene. In embodiments, $L^{3D}$ is substituted or unsubstituted $C_4$ alkylene. In embodiments, $L^{3D}$ is substituted or unsubstituted $C_5$ alkylene. In embodiments, $L^{3D}$ is substituted or unsubstituted $C_6$ alkylene. In embodiments, $L^{3D}$ is substituted or unsubstituted $C_7$ alkylene. In embodiments, $L^{3D}$ is substituted or unsubstituted $C_8$ alkylene. In embodiments, $L^{3D}$ is substituted methylene. In embodiments, $L^{3D}$ is substituted $C_2$ alkylene. In embodiments, $L^{3D}$ is substituted $C_3$ alkylene. In embodiments, $L^{3D}$ is substituted $C_4$ alkylene. In embodiments, $L^{3D}$ is substituted $C_5$ alkylene. In embodiments, $L^{3D}$ is substituted $C_6$ alkylene. In embodiments, $L^{3D}$ is substituted $C_7$ alkylene. In embodiments, $L^{3D}$ is substituted $C_8$ alkylene. In embodiments, $L^{3D}$ is an unsubstituted methylene. In embodiments, $L^{3D}$ is an unsubstituted $C_2$ alkylene. In embodiments, $L^{3D}$ is an unsubstituted $C_3$ alkylene. In embodiments, $L^{3D}$ is an unsubstituted $C_4$ alkylene. In embodiments, $L^{3D}$ is an unsubstituted $C_5$ alkylene. In embodiments, $L^{3D}$ is an unsubstituted $C_6$ alkylene. In embodiments, $L^{3D}$ is an unsubstituted $C_7$ alkylene. In embodiments, $L^{3D}$ is an unsubstituted $C_8$ alkylene.

In embodiments, $L^{3D}$ is substituted or unsubstituted $C_1$-$C_6$ alkylene. In embodiments, $L^{3D}$ is substituted $C_1$-$C_6$ alkylene. In embodiments, $L^{3D}$ is unsubstituted $C_1$-$C_6$ alkylene. In embodiments, $L^{3D}$ is substituted or unsubstituted $C_2$-$C_6$ alkylene. In embodiments, $L^{3D}$ is substituted $C_2$-$C_6$ alkylene. In embodiments, $L^{3D}$ is unsubstituted $C_2$-$C_6$ alkylene. In embodiments, $L^{3D}$ is substituted or unsubstituted $C_1$ alkylene. In embodiments, $L^{3D}$ is substituted $C_1$ alkylene. In embodiments, $L^{3D}$ is unsubstituted $C_1$ alkylene. In embodiments, $L^{3D}$ is substituted or unsubstituted $C_2$ alkylene. In embodiments, $L^{3D}$ is substituted $C_2$ alkylene. In embodiments, $L^{3D}$ is unsubstituted $C_2$ alkylene. In embodiments, $L^{3D}$ is substituted or unsubstituted $C_3$ alkylene. In embodiments, $L^{3D}$ is substituted $C_3$ alkylene. In embodiments, $L^{3D}$ is unsubstituted $C_3$ alkylene. In embodiments, $L^{3D}$ is substituted or unsubstituted $C_4$ alkylene. In embodiments, $L^{3D}$ is substituted $C_4$ alkylene. In embodiments, $L^{3D}$ is unsubstituted $C_4$ alkylene. In embodiments, $L^{3D}$ is substituted or unsubstituted $C_5$ alkylene. In embodiments, $L^{3D}$ is substituted $C_5$ alkylene. In embodiments, $L^{3D}$ is unsubstituted $C_5$ alkylene. In embodiments, $L^{3D}$ is substituted or unsubstituted $C_6$ alkylene. In embodiments, $L^{3D}$ is substituted $C_6$ alkylene. In embodiments, $L^{3D}$ is unsubstituted $C_6$ alkylene.

In embodiments, $L^{3D}$ is substituted or unsubstituted 2 to 8 membered heteroalkylene. In embodiments, $L^{3D}$ is substituted 2 to 8 membered heteroalkylene. In embodiments, $L^{3D}$ is unsubstituted 2 to 8 membered heteroalkylene. In embodiments, $L^{3D}$ is substituted or unsubstituted 2 membered heteroalkylene. In embodiments, $L^{3D}$ is substituted 2 membered heteroalkylene. In embodiments, $L^{3D}$ is unsubstituted 2 membered heteroalkylene. In embodiments, $L^{3D}$ is substituted or unsubstituted 3 membered heteroalkylene. In embodiments, $L^{3D}$ is substituted 3 membered heteroalkylene. In embodiments, $L^{3D}$ is unsubstituted 3 membered heteroalkylene. In embodiments, $L^{3D}$ is substituted or unsubstituted 4 membered heteroalkylene. In embodiments, $L^{3D}$ is substituted 4 membered heteroalkylene. In embodiments, $L^{3D}$ is unsubstituted 4 membered heteroalkylene. In embodiments, $L^{3D}$ is substituted or unsubstituted 5 membered heteroalkylene. In embodiments, $L^{3D}$ is substituted 5 membered heteroalkylene. In embodiments, $L^{3D}$ is unsubstituted 5 membered heteroalkylene. In embodiments, $L^{3D}$ is substituted or unsubstituted 6 membered heteroalkylene. In embodiments, $L^{3D}$ is substituted 6 membered heteroalkylene. In embodiments, $L^{3D}$ is unsubstituted 6 membered heteroalkylene.

In embodiments, $L^{3D}$ is substituted or unsubstituted $C_4$-$C_6$ cycloalkylene. In embodiments, $L^{3D}$ is substituted $C_4$-$C_6$ cycloalkylene. In embodiments, $L^{3D}$ is substituted $C_4$-$C_6$ cycloalkylene. In embodiments, $L^{3D}$ is substituted or unsubstituted $C_4$ cycloalkylene. In embodiments, $L^{3D}$ is substituted $C_4$ cycloalkylene. In embodiments, $L^{3D}$ is substituted $C_4$ cycloalkylene. In embodiments, $L^{3D}$ is substituted or unsubstituted $C_5$ cycloalkylene. In embodiments, $L^{3D}$ is substituted $C_5$ cycloalkylene. In embodiments, $L^{3D}$ is substituted $C_5$ cycloalkylene.

In embodiments, $L^{3D}$ is substituted or unsubstituted 5 to 6 membered heterocycloalkylene. In embodiments, $L^{3D}$ is substituted 5 to 6 membered heterocycloalkylene. In embodiments, $L^{3D}$ is unsubstituted 5 to 6 membered heterocycloalkylene. In embodiments, $L^{3D}$ is substituted or unsubstituted 5 membered heterocycloalkylene. In embodiments, $L^{3D}$ is substituted 5 membered heterocycloalkylene. In embodiments, $L^{3D}$ is unsubstituted 5 membered heterocycloalkylene. In embodiments, $L^{3D}$ is substituted or unsubstituted 6 membered heterocycloalkylene. In embodiments, $L^{3D}$ is substituted 6 membered heterocycloalkylene. In embodiments, $L^{3D}$ is unsubstituted 6 membered heterocycloalkylene.

In embodiments, $L^{3D}$ is substituted or unsubstituted phenylene. In embodiments, $L^{3D}$ is substituted phenylene. In embodiments, $L^{3D}$ is unsubstituted phenylene.

In embodiments, $L^{3D}$ is substituted or unsubstituted 5 to 6 membered heteroarylene. In embodiments, $L^{3D}$ is substituted 5 to 6 membered heteroarylene. In embodiments, $L^{3D}$ is unsubstituted 5 to 6 membered heteroarylene. In embodiments, $L^{3D}$ is substituted or unsubstituted 5 membered heteroarylene. In embodiments, $L^{3D}$ is substituted 5 membered heteroarylene. In embodiments, $L^{3D}$ is unsubstituted 5 membered heteroarylene. In embodiments, $L^{3D}$ is substituted or unsubstituted 6 membered heteroarylene. In embodiments, $L^{3D}$ is substituted 6 membered heteroarylene. In embodiments, $L^{3D}$ is unsubstituted 6 membered heteroarylene.

In embodiments, $L^{3E}$ is substituted or unsubstituted methylene. In embodiments, $L^{3E}$ is substituted or unsubstituted $C_2$ alkylene. In embodiments, $L^{3E}$ is substituted or unsubstituted $C_3$ alkylene. In embodiments, $L^{3E}$ is substituted or unsubstituted $C_4$ alkylene. In embodiments, $L^{3E}$ is substituted or unsubstituted $C_5$ alkylene. In embodiments, $L^{3E}$ is substituted or unsubstituted $C_6$ alkylene. In embodiments, $L^{3E}$ is substituted or unsubstituted $C_7$ alkylene. In embodiments, $L^{3E}$ is substituted or unsubstituted $C_8$ alkylene. In embodiments, $L^{3E}$ is substituted methylene. In embodiments, $L^{3E}$ is substituted $C_2$ alkylene. In embodiments, $L^{3E}$ is substituted $C_3$ alkylene. In embodiments, $L^{3E}$ is substituted $C_4$ alkylene. In embodiments, $L^{3E}$ is substituted $C_5$ alkylene. In embodiments, $L^{3E}$ is substituted $C_6$ alkylene. In embodiments, $L^{3E}$ is substituted $C_7$ alkylene. In embodiments, $L^{3E}$ is substituted $C_8$ alkylene. In embodiments, $L^{3E}$ is an unsubstituted methylene. In embodiments, $L^{3E}$ is an unsubstituted $C_2$ alkylene. In embodiments, $L^{3E}$ is an unsubstituted $C_3$ alkylene. In embodiments, $L^{3E}$ is an unsubstituted $C_4$ alkylene. In embodiments, $L^{3E}$ is an unsubstituted $C_5$ alkylene. In embodiments, $L^{3E}$ is an unsubstituted $C_6$ alkylene. In embodiments, $L^{3E}$ is an unsubstituted $C_7$ alkylene. In embodiments, $L^{3E}$ is an unsubstituted $C_8$ alkylene.

In embodiments, $L^{3E}$ is substituted or unsubstituted $C_1$-$C_6$ alkylene. In embodiments, $L^{3E}$ is substituted $C_1$-$C_6$ alkylene. In embodiments, $L^{3E}$ is unsubstituted $C_1$-$C_6$ alkylene. In embodiments, $L^{3E}$ is substituted or unsubstituted $C_2$-$C_6$ alkylene. In embodiments, $L^{3E}$ is substituted $C_2$-$C_6$ alkylene. In embodiments, $L^{3E}$ is unsubstituted $C_2$-$C_6$ alkylene. In embodiments, $L^{3E}$ is substituted or unsubstituted $C_1$ alkylene. In embodiments, $L^{3E}$ is substituted $C_1$ alkylene. In embodiments, $L^{3E}$ is unsubstituted $C_1$ alkylene. In embodiments, $L^{3E}$ is substituted or unsubstituted $C_2$ alkylene. In embodiments, $L^{3E}$ is substituted $C_2$ alkylene. In embodiments, $L^{3E}$ is unsubstituted $C_2$ alkylene. In embodiments, $L^{3E}$ is substituted or unsubstituted $C_3$ alkylene. In embodiments, $L^{3E}$ is substituted $C_3$ alkylene. In embodiments, $L^{3E}$ is unsubstituted $C_3$ alkylene. In embodiments, $L^{3E}$ is substituted or unsubstituted $C_4$ alkylene. In embodiments, $L^{3E}$ is substituted $C_4$ alkylene. In embodiments, $L^{3E}$ is unsubstituted $C_4$ alkylene. In embodiments, $L^{3E}$ is substituted or unsubstituted $C_5$ alkylene. In embodiments, $L^{3E}$ is substituted $C_5$ alkylene. In embodiments, $L^{3E}$ is unsubstituted $C_5$ alkylene. In embodiments, $L^{3E}$ is substituted or unsubstituted $C_6$ alkylene. In embodiments, $L^{3E}$ is substituted $C_6$ alkylene. In embodiments, $L^{3E}$ is unsubstituted $C_6$ alkylene.

In embodiments, $L^{3E}$ is substituted or unsubstituted 2 to 8 membered heteroalkylene. In embodiments, $L^{3E}$ is substituted 2 to 8 membered heteroalkylene. In embodiments, $L^{3E}$ is unsubstituted 2 to 8 membered heteroalkylene. In embodiments, $L^{3E}$ is substituted or unsubstituted 2 membered heteroalkylene. In embodiments, $L^{3E}$ is substituted 2 membered heteroalkylene. In embodiments, $L^{3E}$ is unsubstituted 2 membered heteroalkylene. In embodiments, $L^{3E}$ is substituted or unsubstituted 3 membered heteroalkylene. In embodiments, $L^{3E}$ is substituted 3 membered heteroalkylene. In embodiments, $L^{3E}$ is unsubstituted 3 membered heteroalkylene. In embodiments, $L^{3E}$ is substituted or unsubstituted 4 membered heteroalkylene. In embodiments, $L^{3E}$ is substituted 4 membered heteroalkylene. In embodiments, $L^{3E}$ is unsubstituted 4 membered heteroalkylene. In embodiments, $L^{3E}$ is substituted or unsubstituted 5 membered heteroalkylene. In embodiments, $L^{3E}$ is substituted 5 membered heteroalkylene. In embodiments, $L^{3E}$ is unsubstituted 5 membered heteroalkylene. In embodiments, $L^{3E}$ is substituted or unsubstituted 6 membered heteroalkylene. In embodiments, $L^{3E}$ is substituted 6 membered heteroalkylene. In embodiments, $L^{3E}$ is unsubstituted 6 membered heteroalkylene.

In embodiments, $L^{3E}$ is substituted or unsubstituted $C_4$-$C_6$ cycloalkylene. In embodiments, $L^{3E}$ is substituted $C_4$-$C_6$ cycloalkylene. In embodiments, $L^{3E}$ is substituted $C_4$-$C_6$ cycloalkylene. In embodiments, $L^{3E}$ is substituted or unsubstituted $C_4$ cycloalkylene. In embodiments, $L^{3E}$ is substituted $C_4$ cycloalkylene. In embodiments, $L^{3E}$ is substituted $C_4$ cycloalkylene. In embodiments, $L^{3E}$ is substituted or unsubstituted $C_5$ cycloalkylene. In embodiments, $L^{3E}$ is substituted $C_5$ cycloalkylene. In embodiments, $L^{3E}$ is substituted $C_5$ cycloalkylene.

In embodiments, $L^{3E}$ is substituted or unsubstituted 5 to 6 membered heterocycloalkylene. In embodiments, $L^{3E}$ is substituted 5 to 6 membered heterocycloalkylene. In embodiments, $L^{3E}$ is unsubstituted 5 to 6 membered heterocycloalkylene. In embodiments, $L^{3E}$ is substituted or unsubstituted 5 membered heterocycloalkylene. In embodiments, $L^{3E}$ is substituted 5 membered heterocycloalkylene. In embodiments, $L^{3E}$ is unsubstituted 5 membered heterocycloalkylene. In embodiments, $L^{3E}$ is substituted or unsubstituted 6 membered heterocycloalkylene. In embodiments, $L^{3E}$ is substituted 6 membered heterocycloalkylene. In embodiments, $L^{3E}$ is unsubstituted 6 membered heterocycloalkylene.

In embodiments, $L^{3E}$ is substituted or unsubstituted phenylene. In embodiments, $L^{3E}$ is substituted phenylene. In embodiments, $L^{3E}$ is unsubstituted phenylene.

In embodiments, $L^{3E}$ is substituted or unsubstituted 5 to 6 membered heteroarylene. In embodiments, $L^{3E}$ is substituted 5 to 6 membered heteroarylene. In embodiments, $L^{3E}$ is unsubstituted 5 to 6 membered heteroarylene. In embodiments, $L^{3E}$ is substituted or unsubstituted 5 membered heteroarylene. In embodiments, $L^{3E}$ is substituted 5 membered heteroarylene. In embodiments, $L^{3E}$ is unsubstituted 5 membered heteroarylene. In embodiments, $L^{3E}$ is substituted or unsubstituted 6 membered heteroarylene. In embodiments, $L^{3E}$ is substituted 6 membered heteroarylene. In embodiments, $L^{3E}$ is unsubstituted 6 membered heteroarylene.

In embodiments, $L^{3A}$ is a bond. In embodiments, $L^{3B}$ is a bond. In embodiments, $L^{3C}$ is a bond. In embodiments, $L^{3D}$ is a bond. In embodiments, $L^{3E}$ is a bond.

In embodiments, $X^1$ is hydrogen and $X^2$ is halogen. In embodiments, $X^1$ is halogen and $X^2$ is hydrogen. In embodiments, $X^1$ is hydrogen and $X^2$ is —F. In embodiments, $X^1$ is —F and $X^2$ is hydrogen. In embodiments, $X^1$ and $X^2$ are halogen. In embodiments, $X^1$ and $X^2$ are —F. In embodiments, $X^1$ is hydrogen. In embodiments, $X^1$ is halogen. In embodiments, $X^1$ is —F. In embodiments, $X^2$ is hydrogen. In embodiments, $X^2$ is halogen. In embodiments, $X^2$ is —F.

In embodiments, $X^1$ is —N$_3$ and $X^2$ is halogen. In embodiments, $X^1$ is halogen and $X^2$ is —N$_3$. In embodiments, $X^1$ is —N$_3$ and $X^2$ is —F. In embodiments, $X^1$ is —F and $X^2$ is —N$_3$. In embodiments, $X^1$ is —N$_3$ and $X^2$ is hydrogen. In embodiments, $X^1$ is hydrogen and $X^2$ is —N$_3$. In embodiments, $X^1$ is —N$_3$. In embodiments, $X^2$ is —N$_3$. In embodiments, but not of formula (Ia), (Ib), or (Ic), $X^1$ is —N$_3$ and $X^2$ is —N$_3$.

In embodiments, $R^5$ is a detectable label. In embodiments, $R^5$ is a fluorescent dye.

In embodiments, $R^5$ is a streptavidin moiety. In embodiments, $R^5$ is an anchor moiety, or affinity anchor moiety. In embodiments, $R^5$ is an anchor moiety. In embodiments, $R^5$ is an affinity anchor moiety.

In embodiments, $R^5$ is

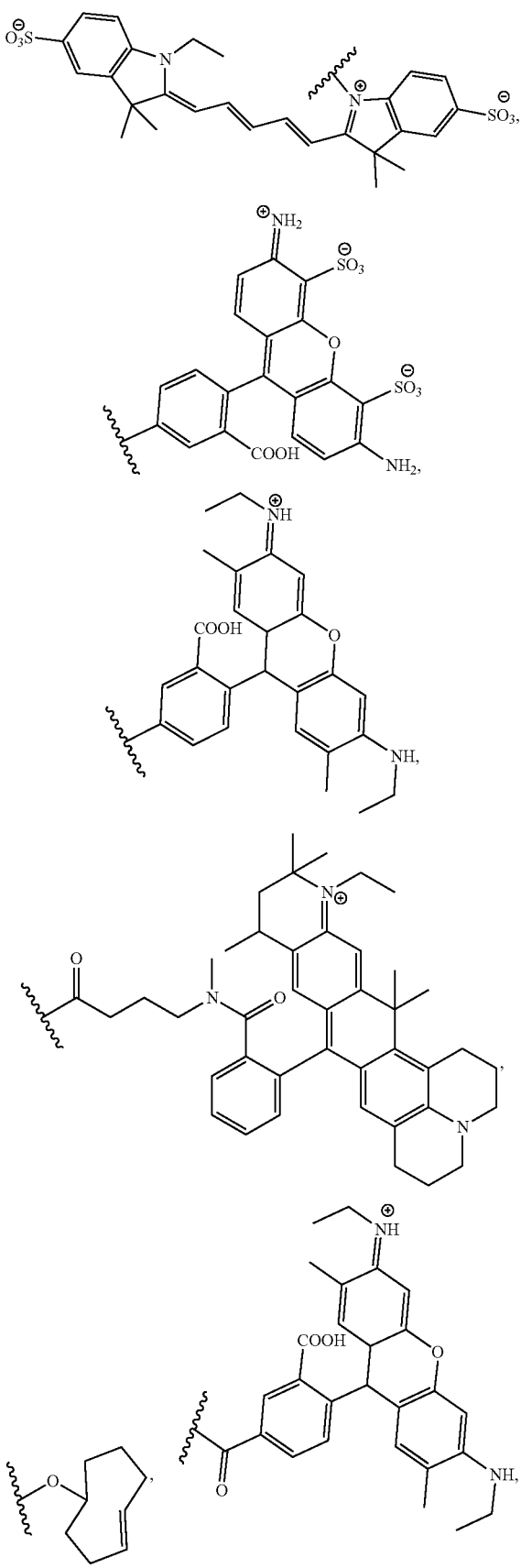

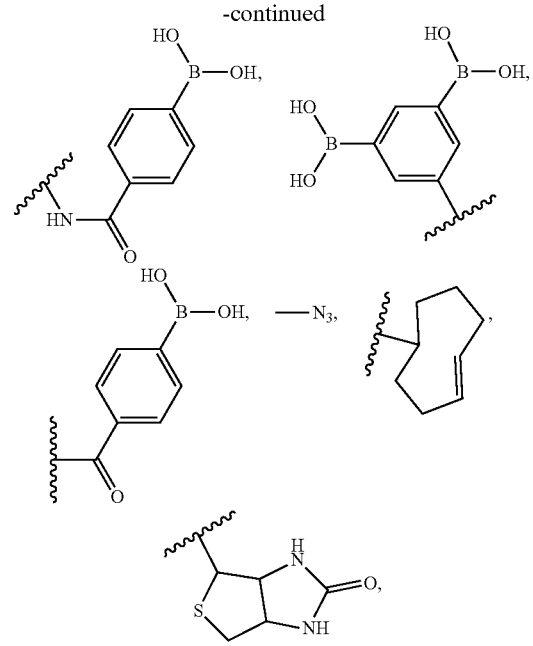
unsubstituted ethynyl,
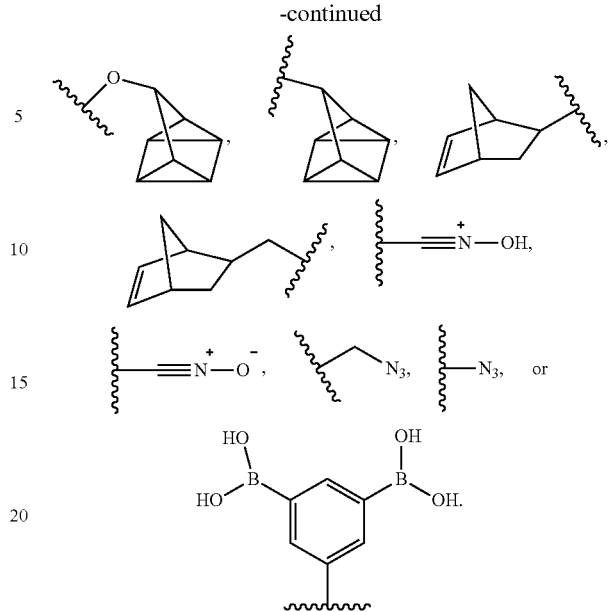
In embodiments, $R^5$
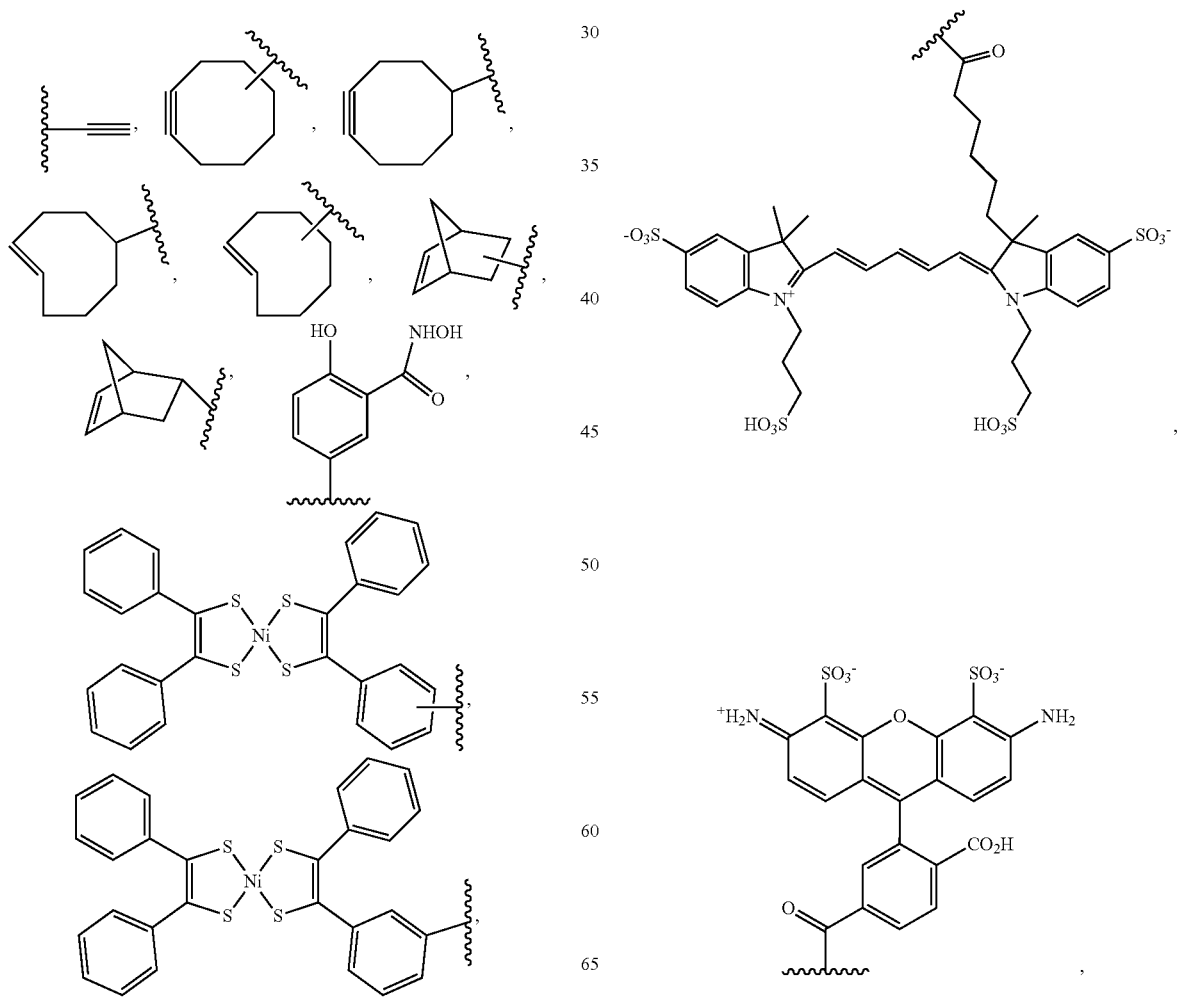

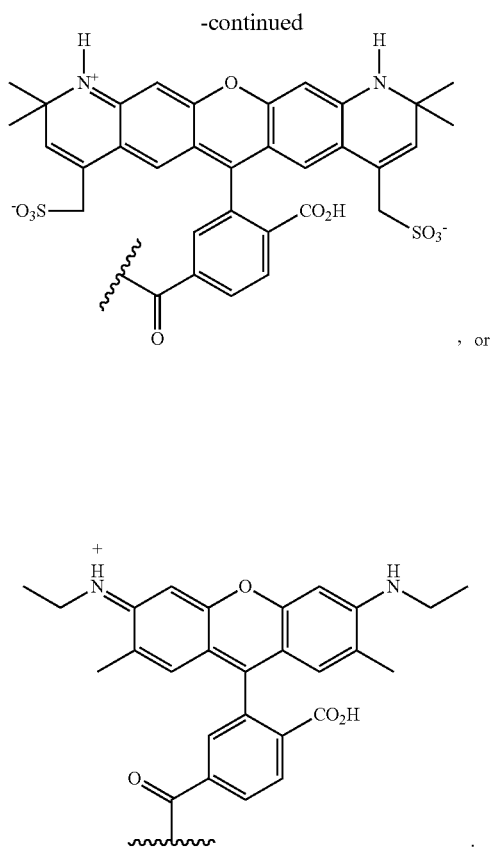
, or

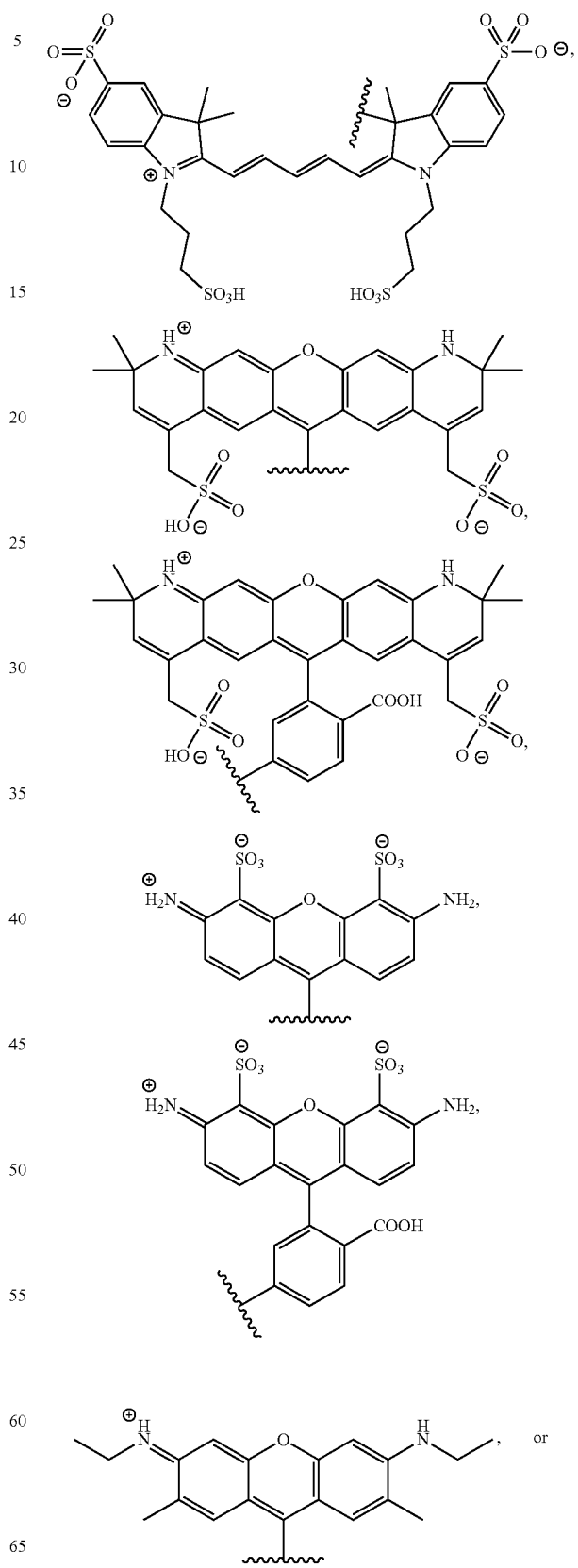

In embodiments, $R^5$ is a detectable label. In embodiments, $R^5$ is a fluorescent dye. In embodiments, $R^5$ is an anchor moiety. In embodiments, $R^5$ is a click chemistry reactant moiety. In embodiments, $R^5$ is a trans-cyclooctene moiety or azide moiety. In embodiments, $R^5$ is an affinity anchor moiety. In embodiments, $R^5$ is a biotin moiety. In embodiments, $R^5$ is a reactant for a bioconjugate reaction that forms a covalent bond between $R^5$ and a second bioconjugate reaction reactant (e.g., $R^{12}$).

In embodiments, $R^5$ is a fluorescent dye. In embodiments $R^5$ is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R6G) moiety, ROX Reference Dye (ROX) moiety, or Cy5 moiety.

In embodiments $R^5$ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R6G) moiety, ROX Reference Dye (ROX) moiety, Sulfo-Cy5, or Cy5 moiety. In embodiments $R^5$ is a Rhodamine 6G (R6G) moiety, ROX Reference Dye (ROX) moiety, Sulfo-Cy5, or Cy5 moiety.

In embodiments, $R^5$ is a biotin moiety. In embodiments, $R^5$ is a biotin moiety and $R^{12}$ is a streptavidin moiety.

153
-continued
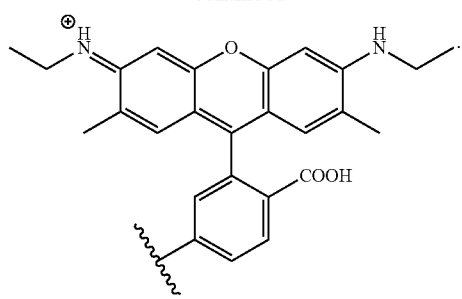
In embodiments, R⁵ is
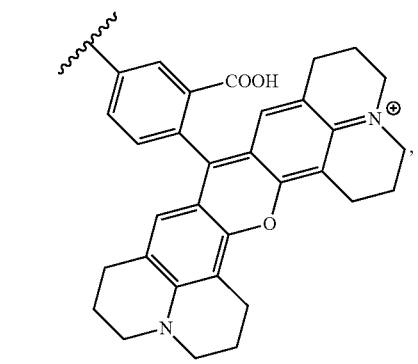
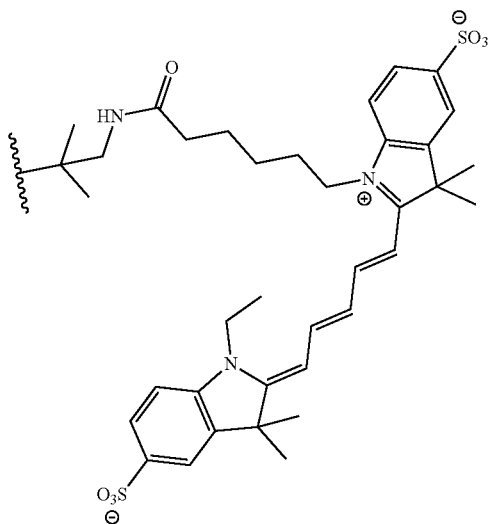
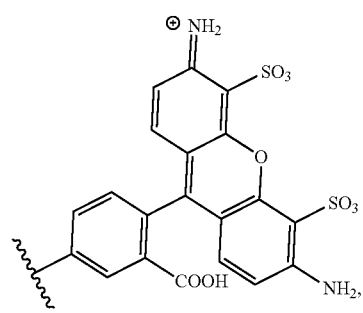
154
-continued
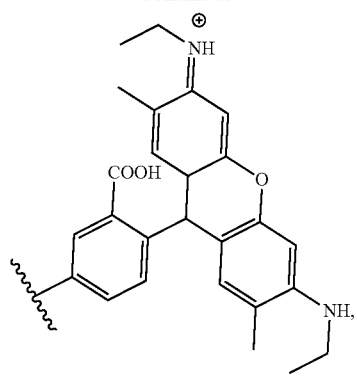
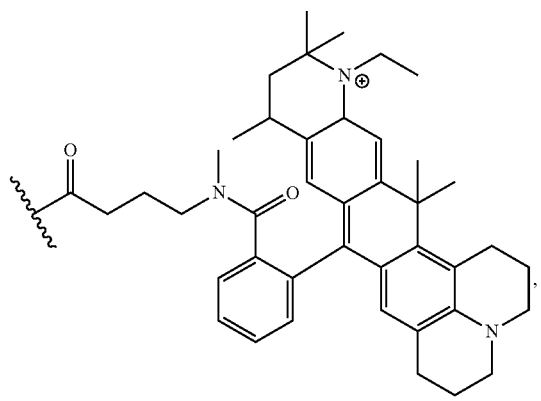
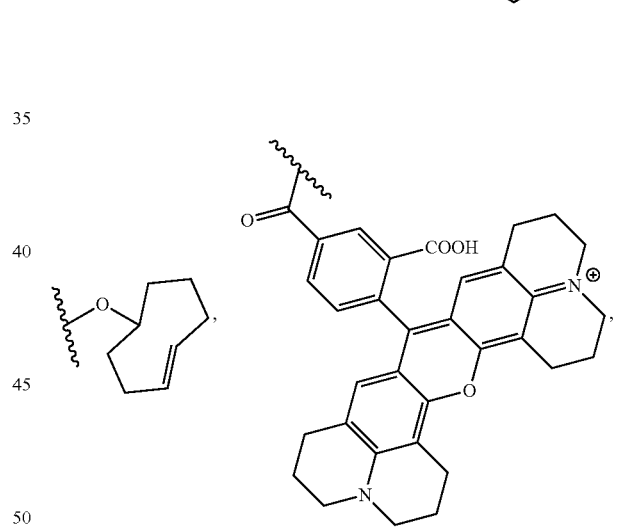
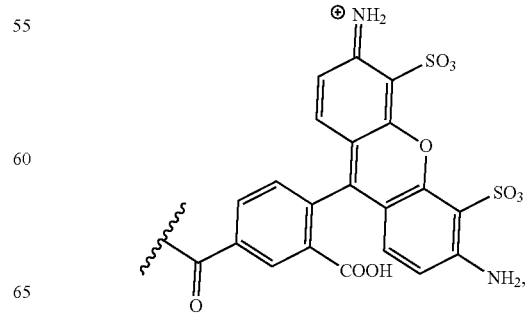

-continued
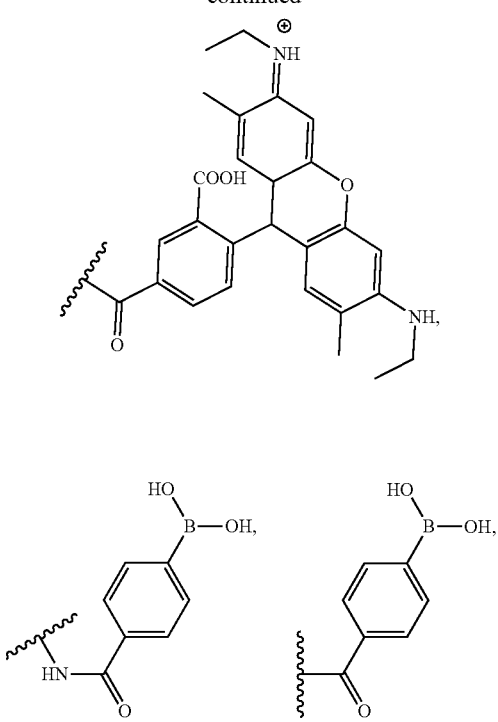
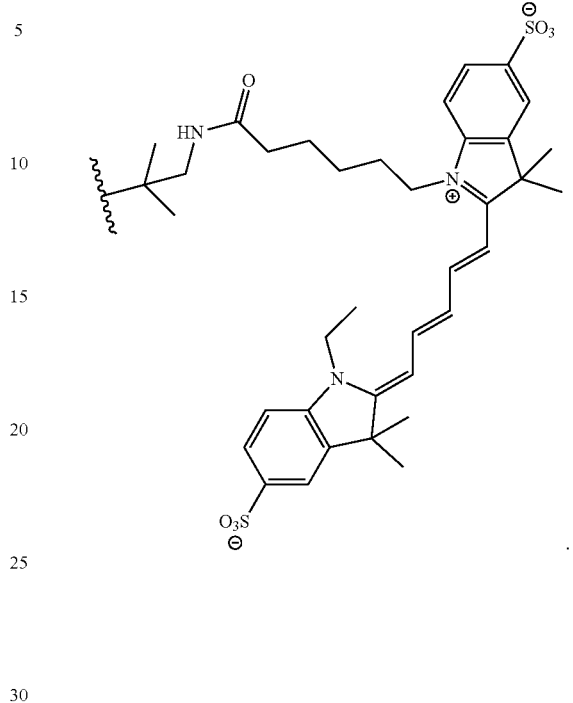
In embodiments, $R^5$ is
In embodiments, $R^5$ is
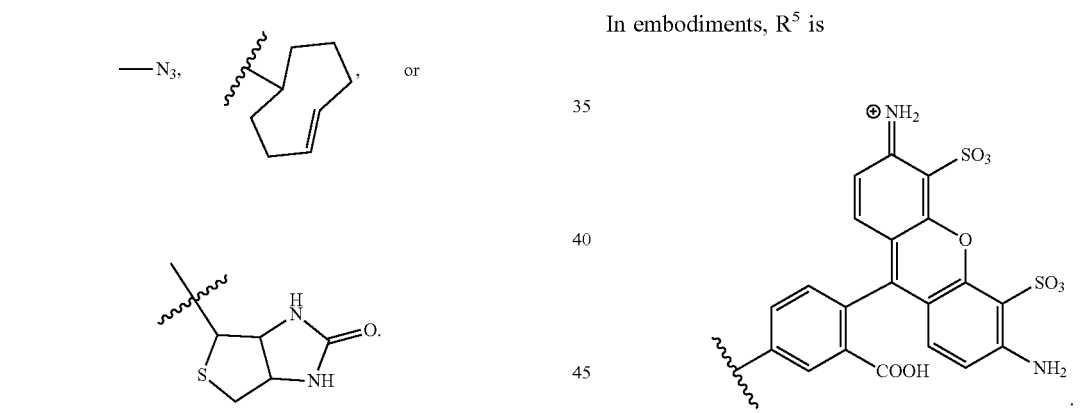
In embodiments, $R^5$ is
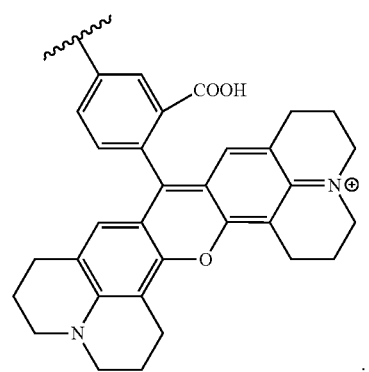 [SMILES: *c1ccc(C2=c3cc4c5c(c3Oc3c2cc2c6c3CCCN6CCC2)CCC[N+]=5CCC4)c(C(=O)O)c1]
In embodiments, $R^5$ is
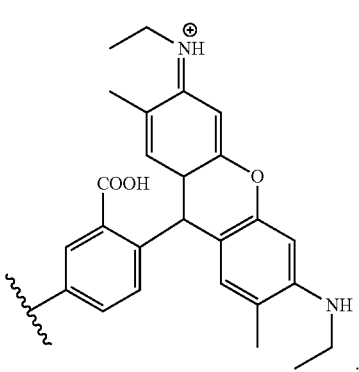 [SMILES: *c1ccc(C2c3cc(C)c(NCC)cc3OC3=C/C(=[NH+]/CC)C(C)=CC32)c(C(=O)O)c1]

In embodiments, R⁵ is
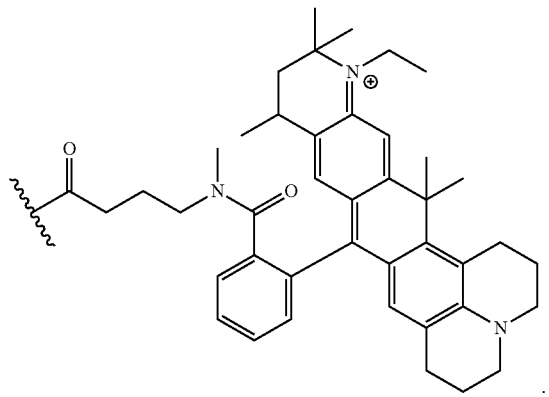 [SMILES: *C(=O)CCCN(C)C(=O)c1ccccc1C1=c2cc3c(cc2C(C)(C)c2c1cc1c4c2CCCN4CCC1)=[N+](CC)C(C)(C)CC3C]
In embodiments, R⁵ is
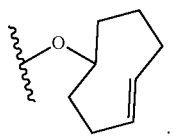
In embodiments, R⁵ is
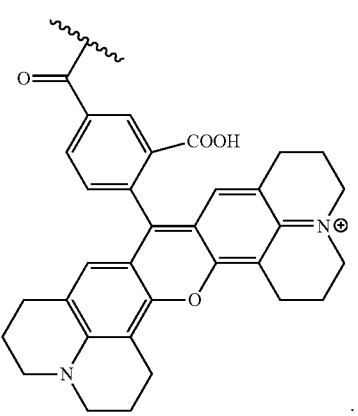 [SMILES: *C(=O)c1ccc(C2=c3cc4c5c(c3Oc3c2cc2c6c3CCCN6CCC2)CCC[N+]=5CCC4)c(C(=O)O)c1]
In embodiments, R⁵ is
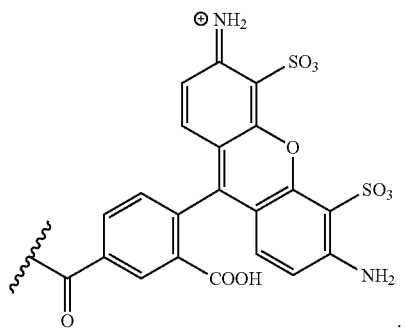
In embodiments, R⁵ is
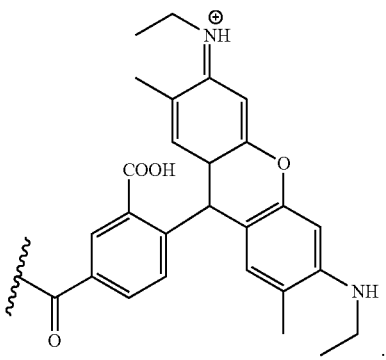 [SMILES: *C(=O)c1ccc(C2c3cc(C)c(NCC)cc3OC3=C/C(=[NH+]/CC)C(C)=CC32)c(C(=O)O)c1]
In embodiments, R⁵ is
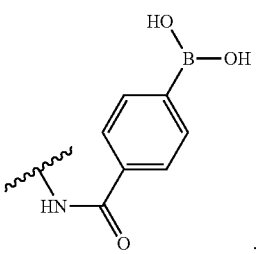 [SMILES: *NC(=O)c1ccc(B(O)O)cc1]
In embodiments, R⁵ is
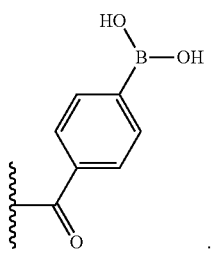 [SMILES: *C(=O)c1ccc(B(O)O)cc1]
In embodiments, R⁵ is —N₃. In embodiments, R⁵ is
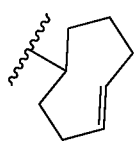
In embodiments, R⁵ is
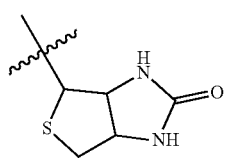
In embodiments, R⁵ is biotin, azide, trans-cyclooctene (TCO), or phenyl boric acid (PBA). In embodiments, R⁵ is biotin, azide, trans-cyclooctene (TCO), phenylboronic acid (PBA), quadricyclane, or norbornene.

In embodiments, $R^5$ is fluorescent dye with a molecular weight of at least about 130 Daltons. In embodiments, $R^5$ is fluorescent dye with a molecular weight of at least about 135 Daltons. In embodiments, $R^5$ is fluorescent dye with a molecular weight of at least about 140 Daltons. In embodiments, $R^5$ is fluorescent dye with a molecular weight of at least about 145 Daltons. In embodiments, $R^5$ is fluorescent dye with a molecular weight of at least about 150 Daltons. In embodiments, $R^5$ is fluorescent dye with a molecular weight of about 130 Daltons. In embodiments, $R^5$ is fluorescent dye with a molecular weight of about 135 Daltons. In embodiments, $R^5$ is fluorescent dye with a molecular weight of about 140 Daltons. In embodiments, $R^5$ is fluorescent dye with a molecular weight of about 145 Daltons. In embodiments, $R^5$ is fluorescent dye with a molecular weight of about 150 Daltons. In embodiments, $R^5$ is fluorescent dye with a molecular weight of about 146 Daltons.

In embodiments, $R^5$ is fluorescent dye with a molecular weight of about 140 to about 3000 Daltons. In embodiments, $R^5$ is fluorescent dye with a molecular weight of about 140 to about 2500 Daltons. In embodiments, $R^5$ is fluorescent dye with a molecular weight of about 140 to about 2000 Daltons. In embodiments, $R^5$ is fluorescent dye with a molecular weight of about 140 to about 1000 Daltons. In embodiments, $R^5$ is fluorescent dye with a molecular weight of about 140 to about 900 Daltons. In embodiments, $R^5$ is fluorescent dye with a molecular weight of about 140 to about 800 Daltons. In embodiments, $R^5$ is fluorescent dye with a molecular weight of about 140 to about 700 Daltons. In embodiments, $R^5$ is fluorescent dye with a molecular weight of about 140 to about 600 Daltons. In embodiments, $R^5$ is fluorescent dye with a molecular weight of about 140 to about 500 Daltons. In embodiments, $R^5$ is fluorescent dye with a molecular weight of about 140 to about 400 Daltons. In embodiments, $R^5$ is fluorescent dye with a molecular weight of about 140 to about 300 Daltons. In embodiments, $R^5$ is fluorescent dye with a molecular weight of about 140 to about 200 Daltons.

In embodiments, $R^5$ is fluorescent dye with a molecular weight of about 200 to about 3000 Daltons. In embodiments, $R^5$ is fluorescent dye with a molecular weight of about 200 to about 2500 Daltons. In embodiments, $R^5$ is fluorescent dye with a molecular weight of about 200 to about 2000 Daltons. In embodiments, $R^5$ is fluorescent dye with a molecular weight of about 200 to about 1000 Daltons. In embodiments, $R^5$ is fluorescent dye with a molecular weight of about 200 to about 900 Daltons. In embodiments, $R^5$ is fluorescent dye with a molecular weight of about 200 to about 800 Daltons. In embodiments, $R^5$ is fluorescent dye with a molecular weight of about 200 to about 700 Daltons. In embodiments, $R^5$ is fluorescent dye with a molecular weight of about 200 to about 600 Daltons. In embodiments, $R^5$ is fluorescent dye with a molecular weight of about 200 to about 500 Daltons. In embodiments, $R^5$ is fluorescent dye with a molecular weight of about 200 to about 400 Daltons. In embodiments, $R^5$ is fluorescent dye with a molecular weight of about 200 to about 300 Daltons.

In embodiments, $R^5$ is fluorescent dye with a molecular weight of about 300 to about 3000 Daltons. In embodiments, $R^5$ is fluorescent dye with a molecular weight of about 300 to about 2500 Daltons. In embodiments, $R^5$ is fluorescent dye with a molecular weight of about 300 to about 2000 Daltons. In embodiments, $R^5$ is fluorescent dye with a molecular weight of about 300 to about 1000 Daltons. In embodiments, $R^5$ is fluorescent dye with a molecular weight of about 300 to about 900 Daltons. In embodiments, $R^5$ is fluorescent dye with a molecular weight of about 300 to about 800 Daltons. In embodiments, $R^5$ is fluorescent dye with a molecular weight of about 300 to about 700 Daltons. In embodiments, $R^5$ is fluorescent dye with a molecular weight of about 300 to about 600 Daltons. In embodiments, $R^5$ is fluorescent dye with a molecular weight of about 300 to about 500 Daltons. In embodiments, $R^5$ is fluorescent dye with a molecular weight of about 300 to about 400 Daltons.

In embodiments, $R^5$ is a detectable label. In embodiments, $R^5$ is a fluorescent dye. In embodiments, $R^5$ is an anchor moiety. In embodiments, $R^5$ is a click chemistry reactant moiety. In embodiments, $R^5$ is a trans-cyclooctene moiety or azide moiety. In embodiments, $R^5$ is an affinity anchor moiety. In embodiments, $R^5$ is a biotin moiety. In embodiments, $R^5$ is a reactant for a bioconjugate reaction that forms a covalent bond between $R^5$ and a second bioconjugate reaction reactant (e.g., with an $R^{12}$ substituent).

In embodiments, $R^5$ is unsubstituted ethynyl,

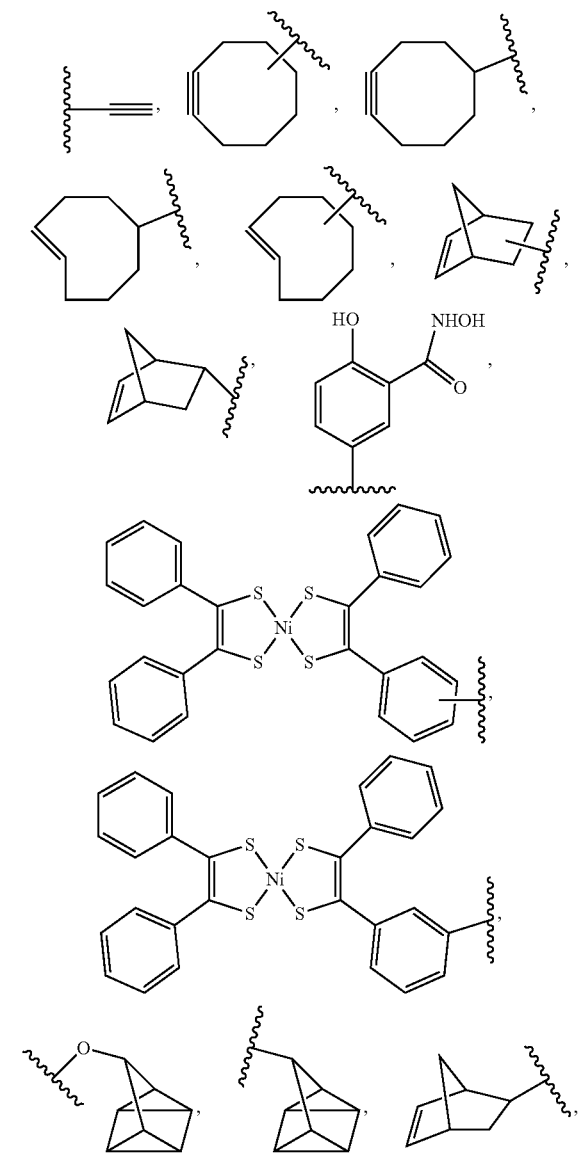

-continued
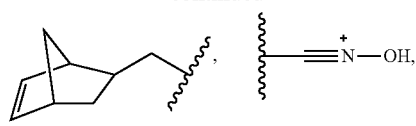
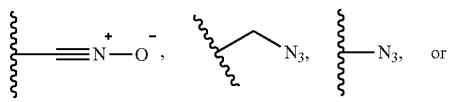
In embodiments, $R^5$ is unsubstituted ethynyl. In embodiments, $R^5$ is
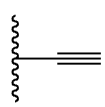
embodiments, $R^5$ is
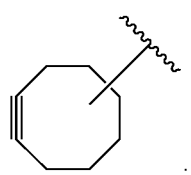
In embodiments, $R^5$ is
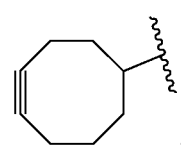
In embodiments, $R^5$ is
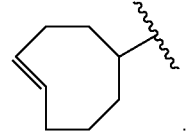
In embodiments, $R^5$ is
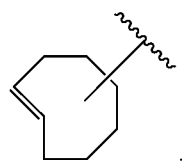
In embodiments, $R^5$ is
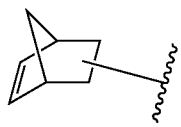
In embodiments, $R^5$ is
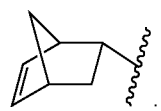
In embodiments, $R^5$ is
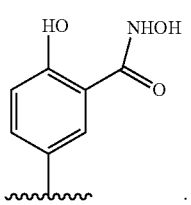
In embodiments, $R^5$ is
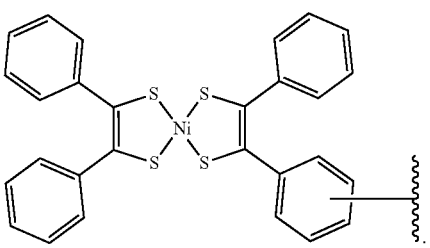

In embodiments, R⁵ is

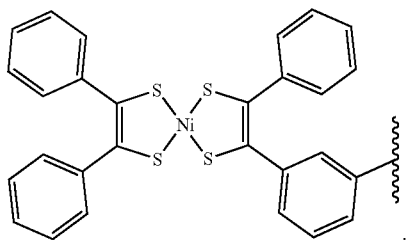

In embodiments, R⁵ is

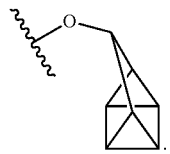 [SMILES: *OC1C2C3C2C2C1C32]

In embodiments, R⁵ is

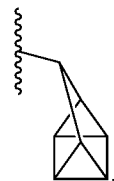

In embodiments, R⁵ is

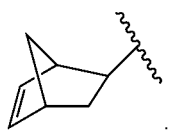 [SMILES: *C1CC2C=CC1C2]

In embodiments, R⁵ is

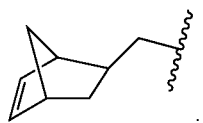 [SMILES: *CC1CC2C=CC1C2]

In embodiments, R⁵ is

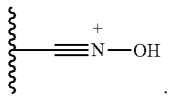

In embodiments, R⁵ is

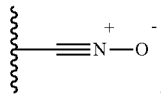

In embodiments, R⁵ is

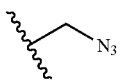

In embodiments, R⁵ is

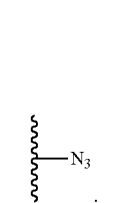

In embodiments, R⁵ is

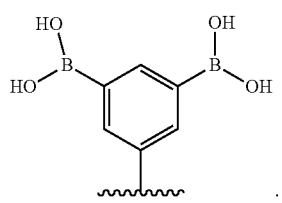 [SMILES: *c1cc(B(O)O)cc(B(O)O)c1]

In embodiments, R⁵ is a modified oligonucleotide. In embodiments, R⁵ is a modified oligonucleotide as described in Kumar et al Scientific Reports (2012) 2, 684; Fuller et al, PNAS USA (2016) 113, 5233-5238; US Patent Application US20150368710, which are incorporated herein by reference for all purposes.

In embodiments, R¹² is a streptavidin moiety.

In embodiments, R¹² is selected from the group consisting of

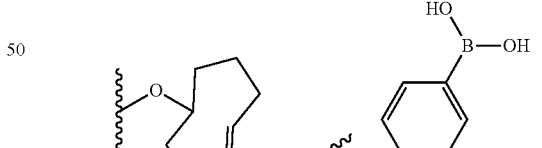
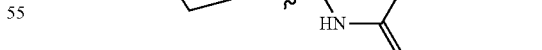

165
-continued
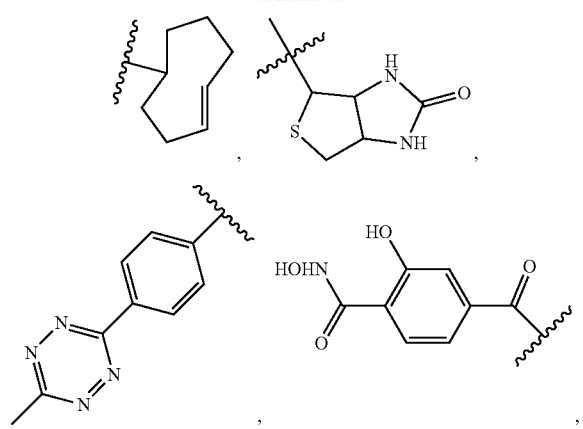
a streptavidin moiety,
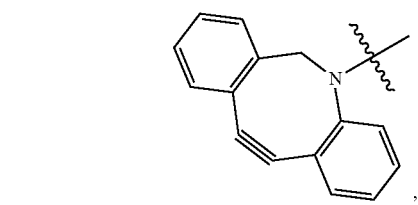 [SMILES: *N1Cc2ccccc2C#Cc2ccccc21]
unsubstituted ethynyl,
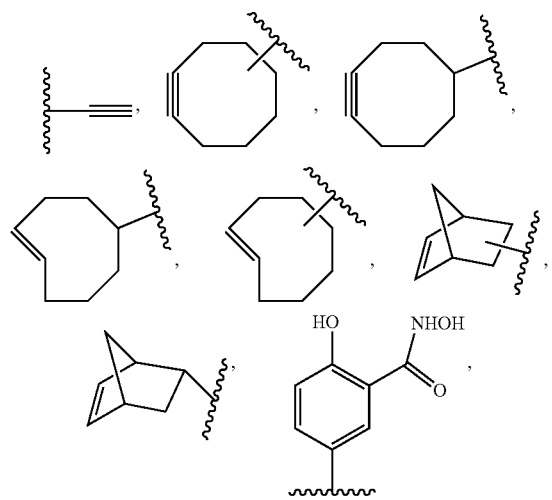
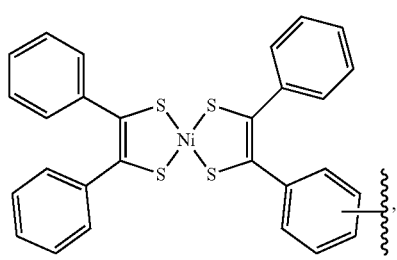
166
-continued
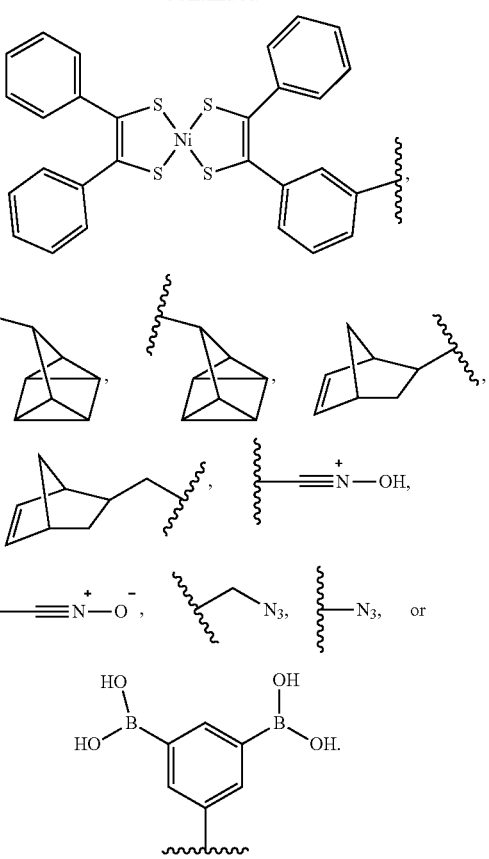
In embodiments, $R^{12}$ is selected from the group consisting of:
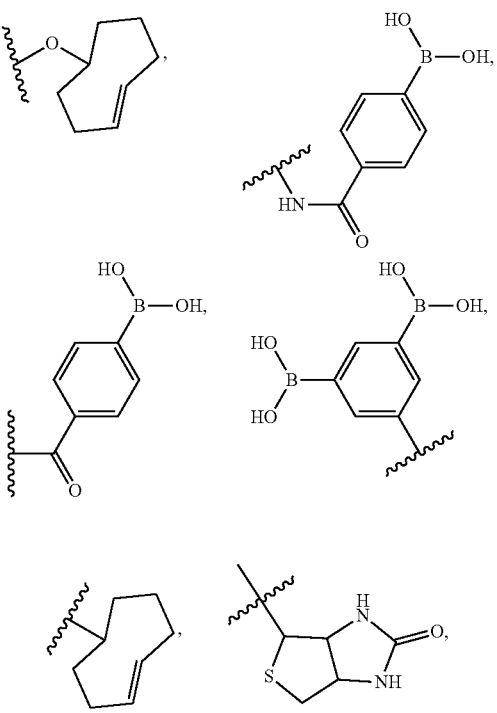

-continued

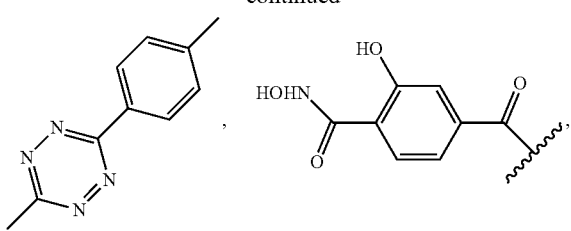

a streptavidin moiety, or

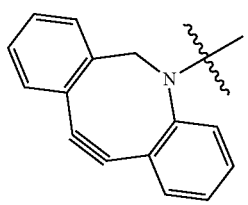

In embodiments, R$^{12}$ is

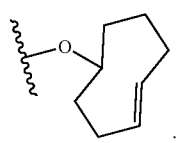 [SMILES: *OC1CC/C=C/CCC1]

In embodiments, R$^{12}$ is

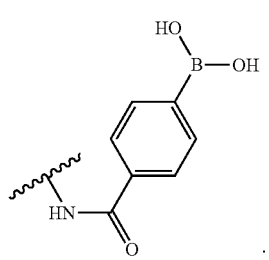 [SMILES: *NC(=O)c1ccc(B(O)O)cc1]

In embodiments, R$^{12}$ is

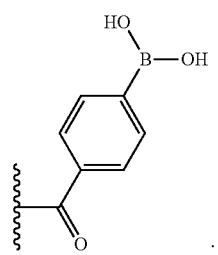 [SMILES: *C(=O)c1ccc(B(O)O)cc1]

In embodiments, R$^{12}$ is

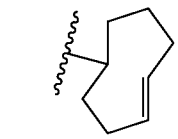

In embodiments, R$^{12}$ is

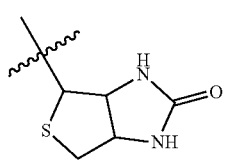

In embodiments, R$^{12}$ is

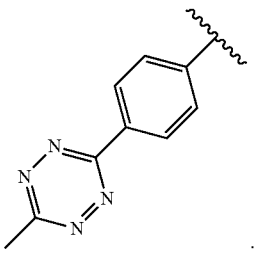 [SMILES: *c1ccc(-c2nnc(C)nn2)cc1]

In embodiments, R$^{12}$ is

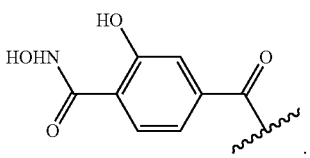

In embodiments, R$^{12}$ is a streptavidin moiety. In embodiments, R$^{12}$ is

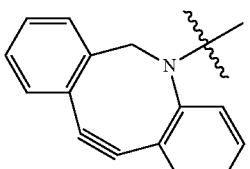

In embodiments, R$^{12}$ streptavidin, dibenzocyclooctyne (DBCO), tetrazine (TZ), or salicylhydroxamic acid (SHA).

In embodiments, $R^{12}$ is unsubstituted ethynyl,
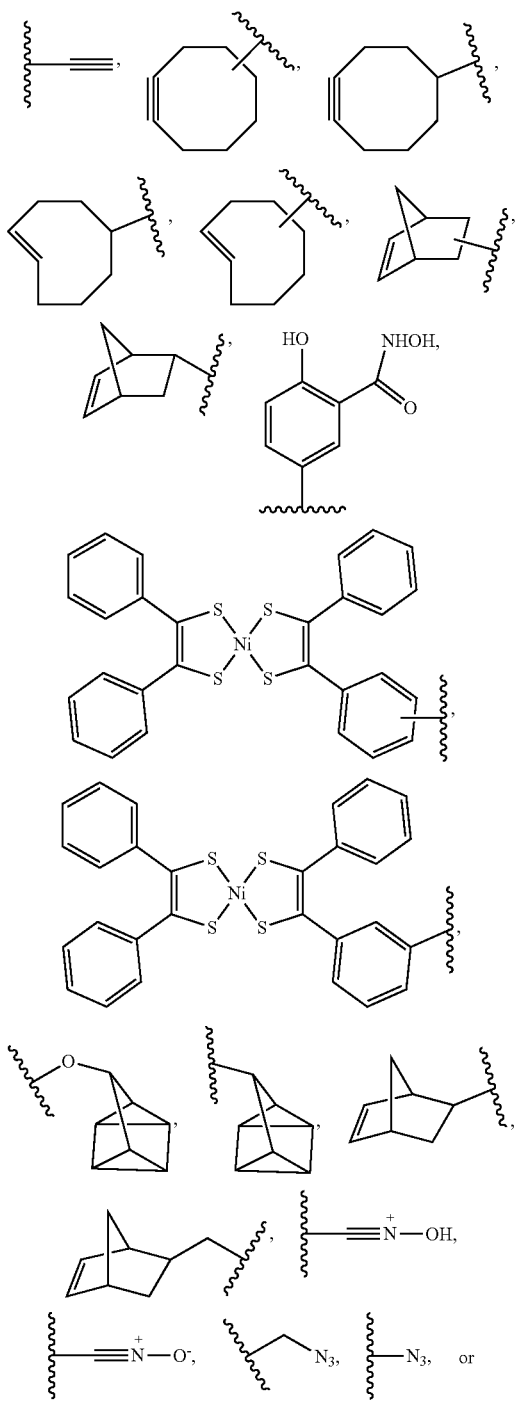
In embodiments, $R^{12}$ is unsubstituted ethynyl. In embodiments, $R^{12}$ is
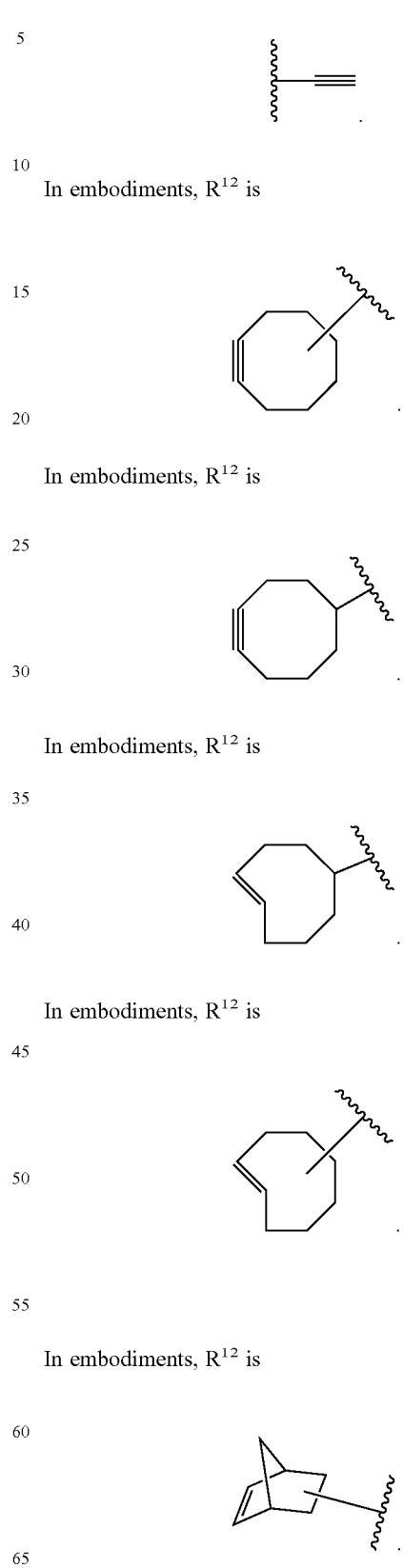

In embodiments, $R^{12}$ is
In embodiments, $R^{12}$ is
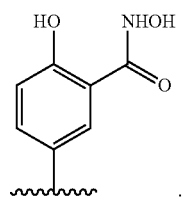
In embodiments, $R^{12}$ is
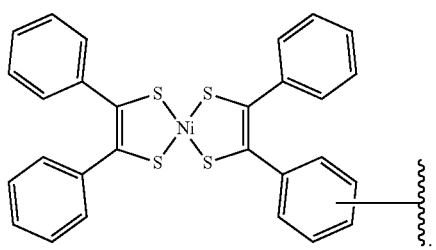
In embodiments, $R^{12}$ is
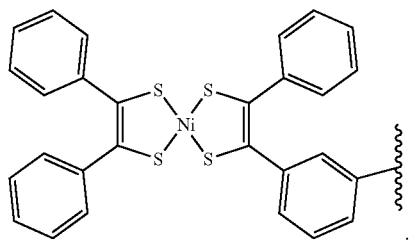
In embodiments, $R^{12}$ is
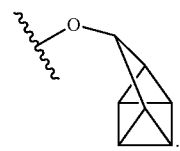
In embodiments, $R^{12}$ is
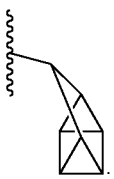
In embodiments, $R^{12}$ is
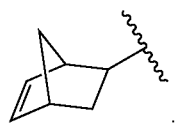 [SMILES: *C1CC2C=CC1C2]
In embodiments, $R^{12}$ is
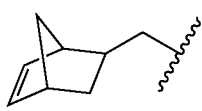
In embodiments, $R^{12}$ is
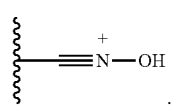
In embodiments, $R^{12}$ is
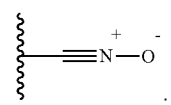
In embodiments, $R^{12}$ is
In embodiments, $R^{12}$ is
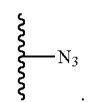

In embodiments, $R^{12}$ is

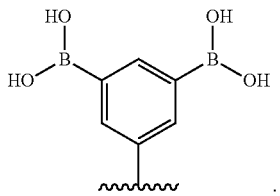 [SMILES: *c1cc(B(O)O)cc(B(O)O)c1]

In embodiments, $R^{12}$ is streptavidin, dibenzylcyclooctene (DBCO), tetrazine, salicylhydroxamic acid (SHA), bis(dithiobenzil)nickel(II), or nitrile oxide.

In embodiments, $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is an orthogonally cleavable linker. In embodiments, $L^3$ is a photocleavable linker, an acid-cleavable linker, a base-cleavable linker, an oxidant-cleavable linker, a reductant-cleavable linker, or a fluoride-cleavable linker. In embodiments, $L^3$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^3$ is $L^{3A}$-$L^{3B}$-$L^{3C}$-$L^{3D}$-$L^{3E}$; and $L^{3A}$, $L^{3B}$, $L^{3C}$, $L^{3D}$, and $L^{3E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{3A}$, $L^{3B}$, $L^{3C}$, $L^{3D}$, and $L^{3E}$ is not a bond.

In embodiments, $L^3$ is $L^{3A}$-$L^{3B}$-$L^{3C}$-$L^{3D}$-$L^{3E}$; $L^{3A}$ is a bond, —NN—, —NHC(O)—, —C(O)NH—, substituted or unsubstituted alkylene, substituted or unsubstituted heteroalkylene; $L^{3B}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene; $L^{3C}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene; $L^{3D}$ is a bond, —NN—, —NHC(O)—, —C(O)NH—, substituted or unsubstituted alkylene, substituted or unsubstituted heteroalkylene; and $L^{3E}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{3A}$, $L^{3B}$, $L^{3C}$, $L^{3D}$, and $L^{3E}$ is not a bond.

In embodiments, $R^{13}$ is a detectable label. In embodiments, $R^{13}$ is a fluorescent dye.

In embodiments, $R^{13}$ is

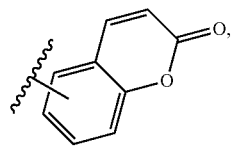

-continued

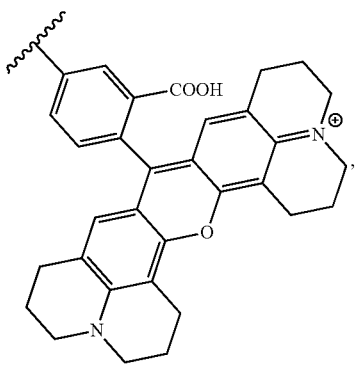

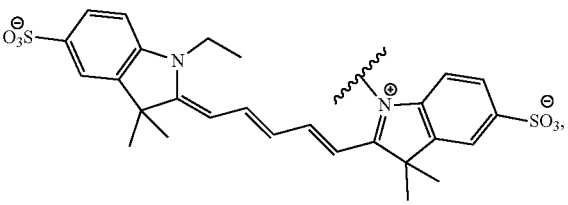

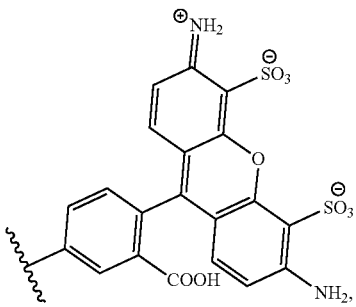

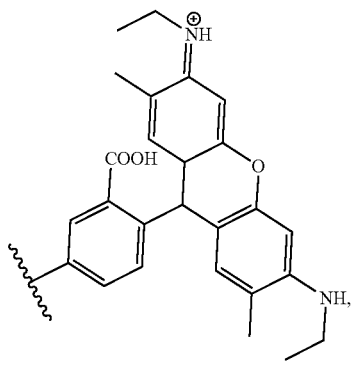

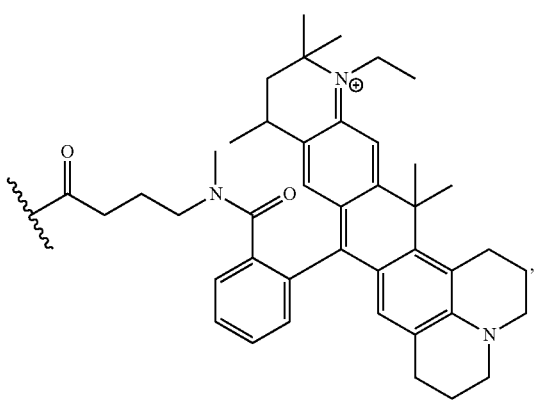

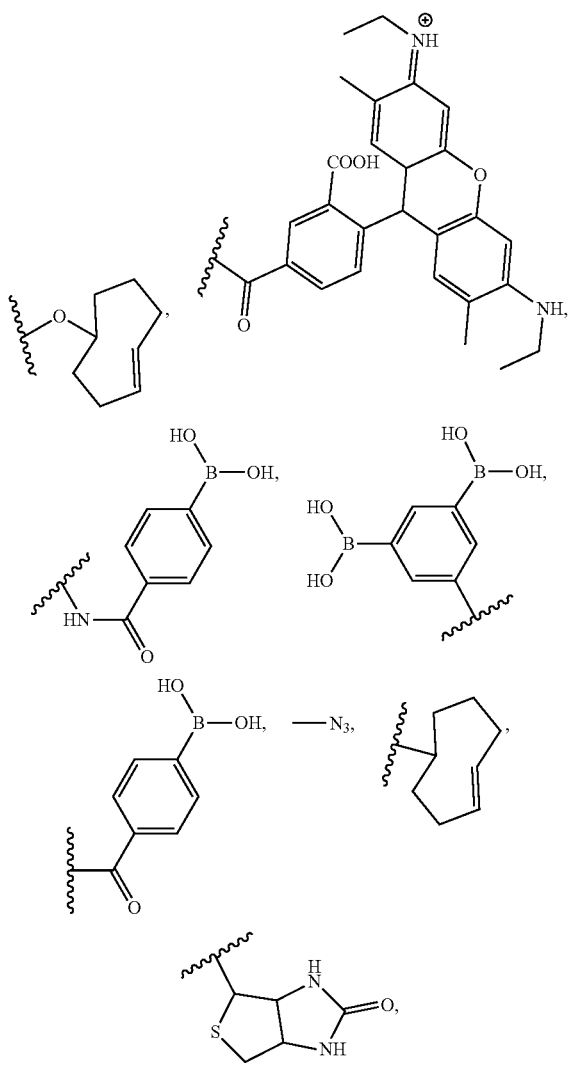

unsubstituted ethynyl,

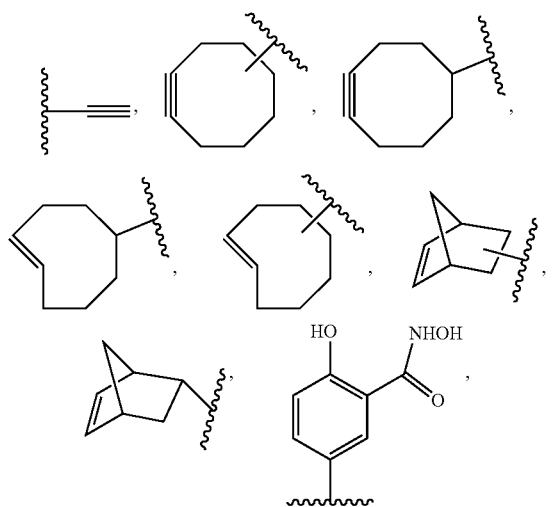

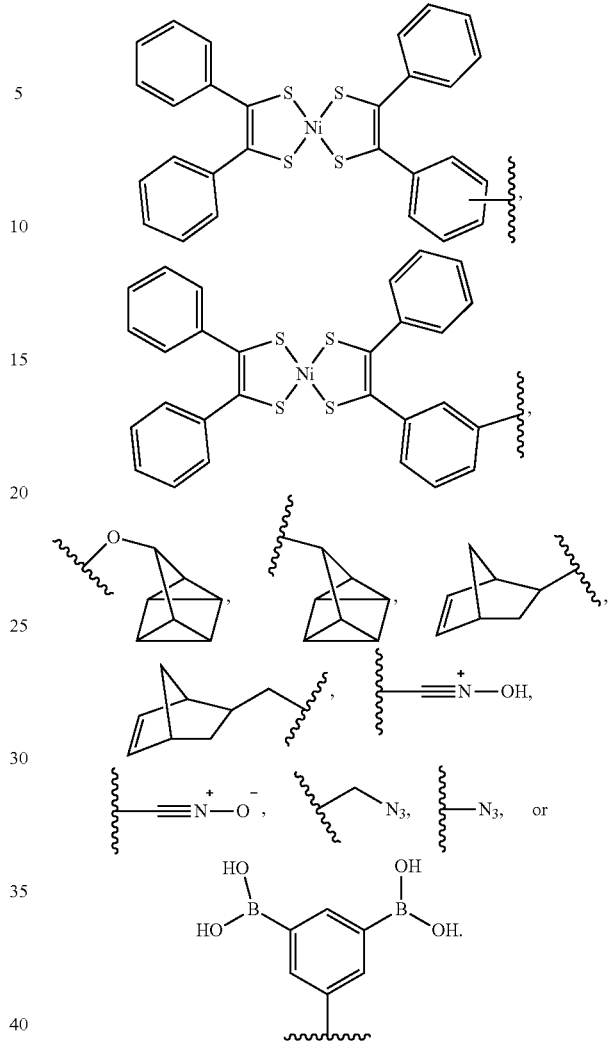

In embodiments, $R^{13}$ is a fluorescent dye. In embodiments $R^{13}$ is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R6G) moiety, ROX Reference Dye (ROX) moiety, or Cy5 moiety.

In embodiments $R^{13}$ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R6G) moiety, ROX Reference Dye (ROX) moiety, Sulfo-Cy5, or Cy5 moiety. In embodiments $R^{13}$ is a Rhodamine 6G (R6G) moiety, ROX Reference Dye (ROX) moiety, Sulfo-Cy5, or Cy5 moiety.

In embodiments, $R^{13}$ is fluorescent dye with a molecular weight of about 140 to about 3000 Daltons. In embodiments, $R^{13}$ is fluorescent dye with a molecular weight of about 140 to about 2500 Daltons. In embodiments, $R^{13}$ is fluorescent dye with a molecular weight of about 140 to about 2000

Daltons. In embodiments, $R^{13}$ is fluorescent dye with a molecular weight of about 140 to about 1000 Daltons. In embodiments, $R^{13}$ is fluorescent dye with a molecular weight of about 140 to about 900 Daltons. In embodiments, $R^{13}$ is fluorescent dye with a molecular weight of about 140 to about 800 Daltons. In embodiments, $R^{13}$ is fluorescent dye with a molecular weight of about 140 to about 700 Daltons. In embodiments, $R^{13}$ is fluorescent dye with a molecular weight of about 140 to about 600 Daltons. In embodiments, $R^{13}$ is fluorescent dye with a molecular weight of about 140 to about 500 Daltons. In embodiments, $R^{13}$ is fluorescent dye with a molecular weight of about 140 to about 400 Daltons. In embodiments, $R^{13}$ is fluorescent dye with a molecular weight of about 140 to about 300 Daltons. In embodiments, $R^{13}$ is fluorescent dye with a molecular weight of about 140 to about 200 Daltons.

In embodiments, $R^{13}$ is fluorescent dye with a molecular weight of about 200 to about 3000 Daltons. In embodiments, $R^{13}$ is fluorescent dye with a molecular weight of about 200 to about 2500 Daltons. In embodiments, $R^{13}$ is fluorescent dye with a molecular weight of about 200 to about 2000 Daltons. In embodiments, $R^{13}$ is fluorescent dye with a molecular weight of about 200 to about 1000 Daltons. In embodiments, $R^{13}$ is fluorescent dye with a molecular weight of about 200 to about 900 Daltons. In embodiments, $R^{13}$ is fluorescent dye with a molecular weight of about 200 to about 800 Daltons. In embodiments, $R^{13}$ is fluorescent dye with a molecular weight of about 200 to about 700 Daltons. In embodiments, $R^{13}$ is fluorescent dye with a molecular weight of about 200 to about 600 Daltons. In embodiments, $R^{13}$ is fluorescent dye with a molecular weight of about 200 to about 500 Daltons. In embodiments, $R^{13}$ is fluorescent dye with a molecular weight of about 200 to about 400 Daltons. In embodiments, $R^{13}$ is fluorescent dye with a molecular weight of about 200 to about 300 Daltons.

In embodiments, $R^{13}$ is fluorescent dye with a molecular weight of about 300 to about 3000 Daltons. In embodiments, $R^{13}$ is fluorescent dye with a molecular weight of about 300 to about 2500 Daltons. In embodiments, $R^{13}$ is fluorescent dye with a molecular weight of about 300 to about 2000 Daltons. In embodiments, $R^{13}$ is fluorescent dye with a molecular weight of about 300 to about 1000 Daltons. In embodiments, $R^{13}$ is fluorescent dye with a molecular weight of about 300 to about 900 Daltons. In embodiments, $R^{13}$ is fluorescent dye with a molecular weight of about 300 to about 800 Daltons. In embodiments, $R^{13}$ is fluorescent dye with a molecular weight of about 300 to about 700 Daltons. In embodiments, $R^{13}$ is fluorescent dye with a molecular weight of about 300 to about 600 Daltons. In embodiments, $R^{13}$ is fluorescent dye with a molecular weight of about 300 to about 500 Daltons. In embodiments, $R^{13}$ is fluorescent dye with a molecular weight of about 300 to about 400 Daltons.

In embodiments, $R^{13}$ is

In embodiments, $R^{13}$ is
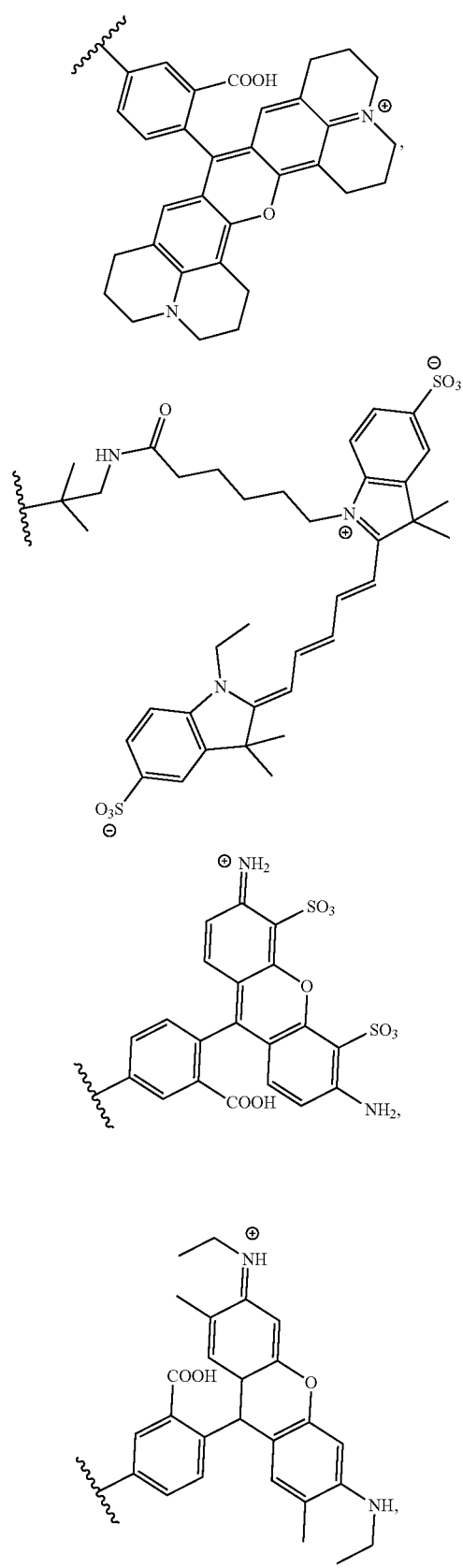
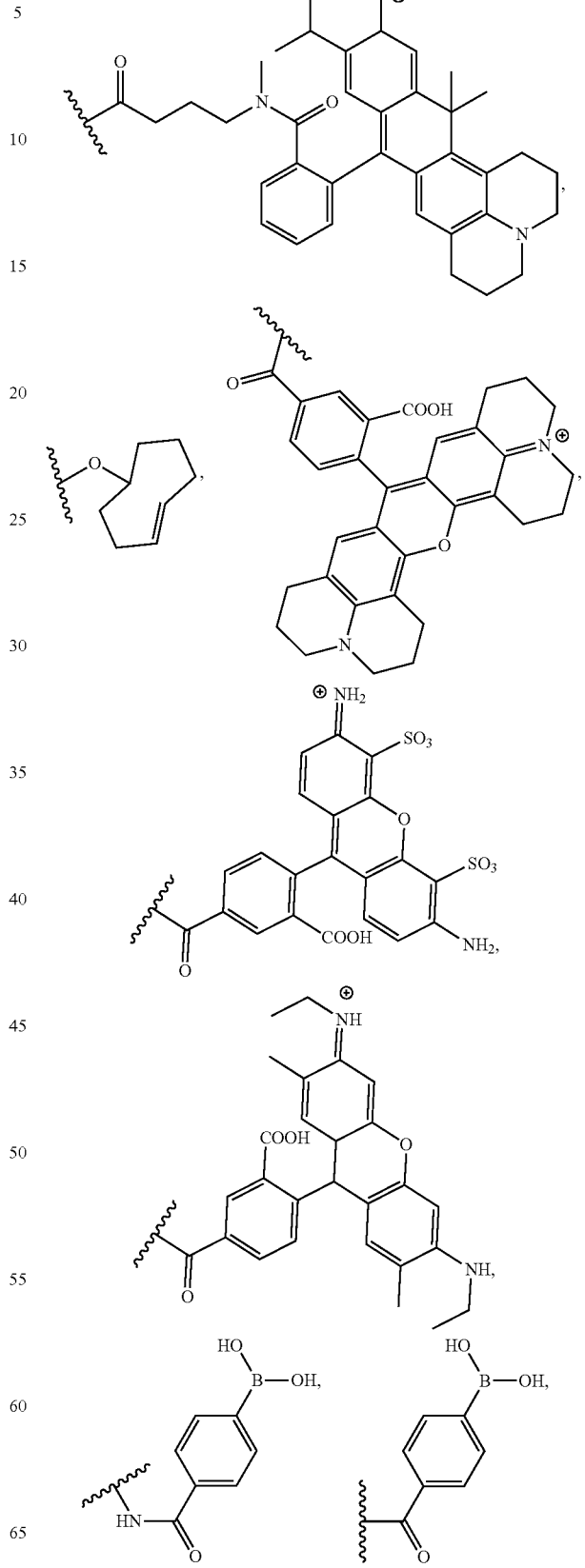

-continued
—N₃, 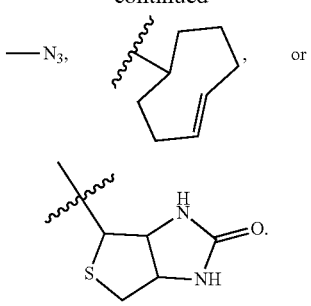 or
In embodiments, R¹³ is
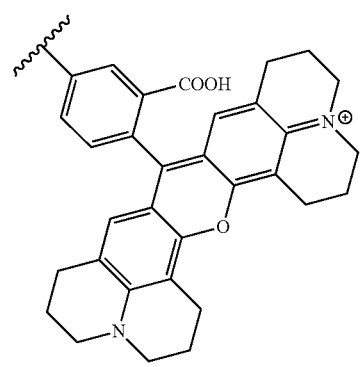
In embodiments, R¹³ is
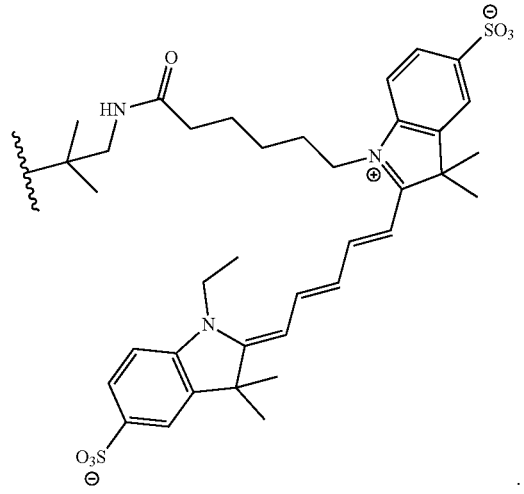
In embodiments, R¹³ is
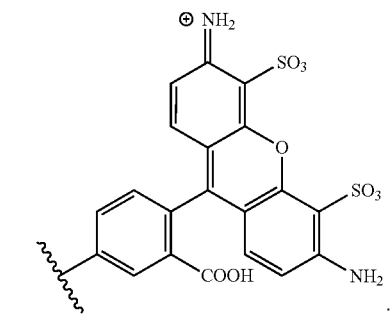
In embodiments, R¹³ is
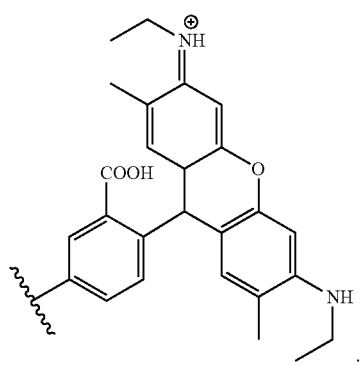 [SMILES: *c1ccc(C2c3cc(C)c(NCC)cc3OC3=C/C(=[NH+]/CC)C(C)=CC32)c(C(=O)O)c1]
In embodiments, R¹³ is
In embodiments, R¹³ is
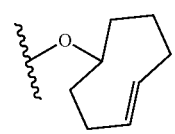

In embodiments, $R^{13}$ is
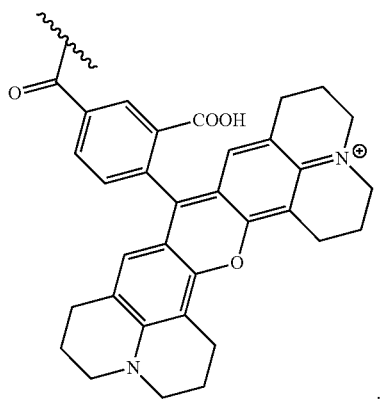 [SMILES: *C(=O)c1ccc(C2=c3cc4c5c(c3Oc3c2cc2c6c3CCCN6CCC2)CCC[N+]=5CCC4)c(C(=O)O)c1]
In embodiments, $R^{13}$ is
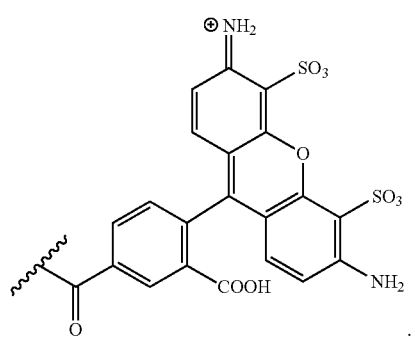
In embodiments, $R^{13}$ is
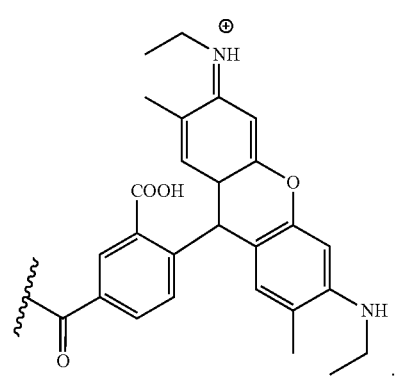 [SMILES: *C(=O)c1ccc(C2c3cc(C)c(NCC)cc3OC3=C/C(=[NH+]/CC)C(C)=CC32)c(C(=O)O)c1]
In embodiments, $R^{13}$ is
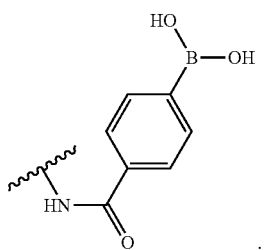 [SMILES: *NC(=O)c1ccc(B(O)O)cc1]
In embodiments, $R^{13}$ is
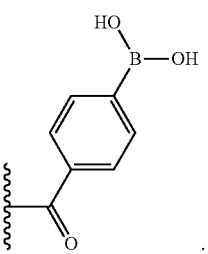 [SMILES: *C(=O)c1ccc(B(O)O)cc1]
In embodiments, $R^{13}$ is —$N_3$. In embodiments, $R^{13}$ is
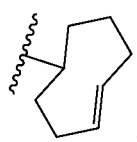
In embodiments, $R^{13}$ is
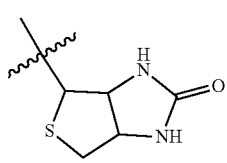

In embodiments, $R^{12}$-$L^3$-$R^{13}$ has the formula:
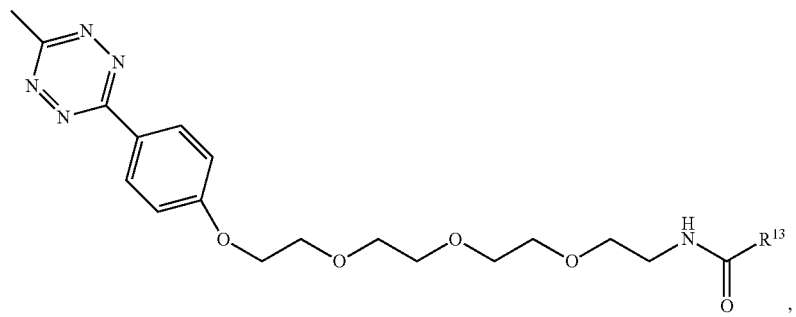
wherein $R^{13}$ is as described herein.
In embodiments, $R^{12}$-$L^3$-$R^{13}$ has the formula:
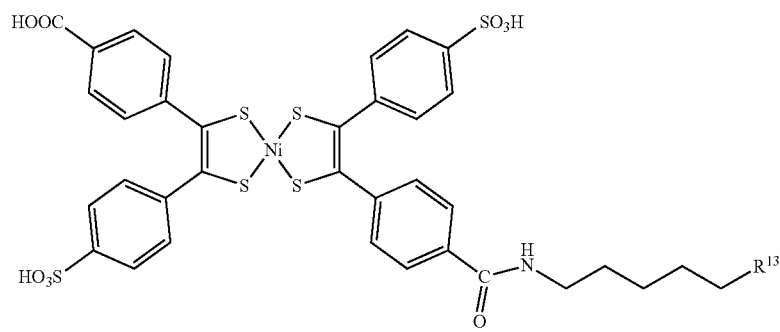
wherein $R^{13}$ is as described herein.
In embodiments, $R^{12}$-$L^3$-$R^{13}$ has the formula:
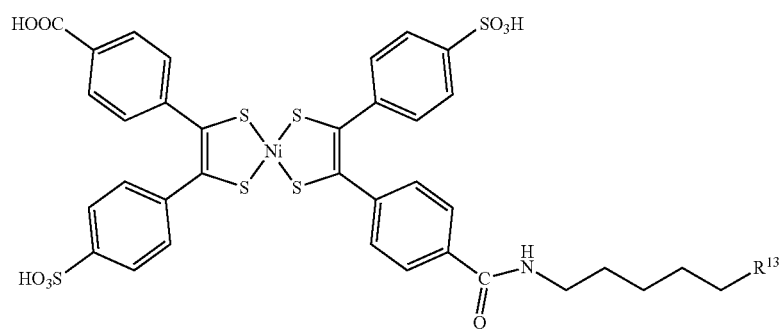
wherein $R^{13}$ is as described herein.
In embodiments, $R^{12}$-$L^3$-$R^{13}$ has the formula:
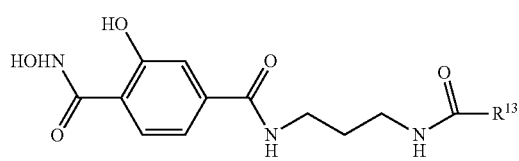
wherein $R^{13}$ is as described herein.

In embodiments, $R^{12}$-$L^3$-$R^{13}$ has the formula:

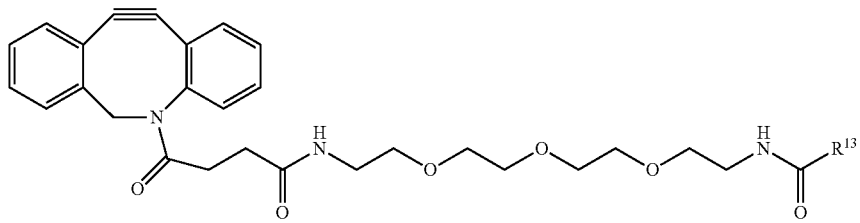

wherein $R^{13}$ is as described herein.

In embodiments, $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^4$ is a substituted or unsubstituted $C_1$-$C_6$ alkylene or substituted or unsubstituted 2 to 6 membered heteroalkylene. In embodiments, $L^4$ is an unsubstituted $C_1$-$C_4$ alkylene. In embodiments, $L^4$ is a bond.

In embodiments, $L^4$ is a substituted or unsubstituted methylene. In embodiments, $L^4$ is substituted with a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene. In embodiments, $L^4$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

In embodiments, $L^4$ is substituted with a substituted or unsubstituted $C_1$-$C_6$ alkylene or substituted or unsubstituted 2 to 6 membered heteroalkylene. In embodiments, $L^4$ is a substituted or unsubstituted $C_1$-$C_6$ alkylene or substituted or unsubstituted 2 to 6 membered heteroalkylene. In embodiments, $L^4$ is a substituted or unsubstituted methylene. In embodiments, $L^4$ is substituted with a substituted or unsubstituted $C_1$-$C_6$ alkylene. In embodiments, $L^4$ is an unsubstituted methylene.

In embodiments, $L^4$ is a bond, substituted (e.g., substituted with a substituent group, size-limited substituent group, or lower substituent group) or unsubstituted alkynylene, or substituted (e.g., substituted with a substituent group, size-limited substituent group, or lower substituent group) or unsubstituted heteroalkynylene. In embodiments, $L^4$ is a bond, substituted (e.g., substituted with a substituent group, size-limited substituent group, or lower substituent group) or unsubstituted $C_2$-$C_8$ alkynylene, or substituted (e.g., substituted with a substituent group, size-limited substituent group, or lower substituent group) or unsubstituted 3 to 8 membered heteroalkynylene. In embodiments, $L^4$ is a bond, substituted (e.g., substituted with a substituent group, size-limited substituent group, or lower substituent group) or unsubstituted $C_2$-$C_6$ alkynylene, or substituted (e.g., substituted with a substituent group, size-limited substituent group, or lower substituent group) or unsubstituted 3 to 6 membered heteroalkynylene.

In embodiments, $L^4$ is a substituted (e.g., substituted with a substituent group, size-limited substituent group, or lower substituent group) or unsubstituted $C_1$-$C_6$ alkelyene (e.g., alkylene (e.g., alkylene, alkenylene, or alkynylene), alkenylene, or alkynylene) or substituted (e.g., substituted with a substituent group, size-limited substituent group, or lower substituent group) or unsubstituted 2 to 6 membered heteroalkylene (e.g., heteroalkylene, heteroalkenylene, or heteroalkynylene). In embodiments, $L^4$ is an unsubstituted $C_1$-$C_4$ alkylene (e.g., alkylene, alkenylene, or alkynylene). In embodiments, $L^4$ is not substituted with a cleavable moiety. In embodiments, $L^4$ is not substituted with a monovalent cleavable moiety.

In embodiments, $L^4$ is $L^{4A}$-$L^{4B}$-$L^{4C}$-$L^{4D}$-$L^{4E}$ $L^{4A}$ $L^{4B}$ $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4A}$ $L^{4B}$ $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; and $L^{4A}$ $L^{4B}$ $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{4A}$ $L^{4B}$ $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; and $L^{4A}$ $L^{4B}$ $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{4A}$ $L^{4B}$ $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; and $L^{4A}$ $L^{4B}$ $L^{4C}$, $L^{4D}$, or $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{4A}$ $L^{4B}$ $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; wherein $L^{4A}$ is a
bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{4B}$ is a
bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4C}$ is a
bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4D}$ is a
bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{4E}$ is a
bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4A}$ $L^{4B}$ $L^{4C}$, $L^{4D}$, and $L^{4E}$ is not a bond.

In embodiments, $L^4$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^4$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^4$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^4$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^4$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^4$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^4$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $L^4$ is substituted or unsubstituted methylene. In embodiments, $L^4$ is substituted or unsubstituted $C_2$ alkylene. In embodiments, $L^4$ is substituted or unsubstituted $C_3$ alkylene. In embodiments, $L^4$ is substituted or unsubstituted $C_4$ alkylene. In embodiments, $L^4$ is substituted or unsubstituted $C_5$ alkylene. In embodiments, $L^4$ is substituted or unsubstituted $C_6$ alkylene. In embodiments, $L^4$ is substituted or unsubstituted $C_7$ alkylene. In embodiments, $L^4$ is substituted or unsubstituted $C_8$ alkylene. In embodiments, $L^4$ is substituted methylene. In embodiments, $L^4$ is substituted $C_2$ alkylene. In embodiments, $L^4$ is substituted $C_3$ alkylene. In embodiments, $L^4$ is substituted $C_4$ alkylene. In embodiments, $L^4$ is substituted $C_5$ alkylene. In embodiments, $L^4$ is substituted $C_6$ alkylene. In embodiments, $L^4$ is substituted $C_7$ alkylene. In embodiments, $L^4$ is substituted $C_8$ alkylene. In embodiments, $L^4$ is an unsubstituted methylene. In embodiments, $L^4$ is an unsubstituted $C_2$ alkylene. In embodiments, $L^4$ is an unsubstituted $C_3$ alkylene. In embodiments, $L^4$ is an unsubstituted $C_4$ alkylene. In embodiments, $L^4$ is an unsubstituted $C_5$ alkylene. In embodiments, $L^4$ is an unsubstituted $C_6$ alkylene. In embodiments, $L^4$ is an unsubstituted $C_7$ alkylene. In embodiments, $L^4$ is an unsubstituted $C_8$ alkylene.

In embodiments, $L^4$ is substituted or unsubstituted $C_9$ alkylene. In embodiments, $L^4$ is substituted or unsubstituted $C_{10}$ alkylene. In embodiments, $L^4$ is substituted or unsubstituted $C_{11}$ alkylene. In embodiments, $L^4$ is substituted or unsubstituted $C_{12}$ alkylene. In embodiments, $L^4$ is substituted or unsubstituted $C_{13}$ alkylene. In embodiments, $L^4$ is substituted or unsubstituted $C_{14}$ alkylene. In embodiments, $L^4$ is substituted or unsubstituted $C_{18}$ alkylene. In embodiments, $L^4$ is substituted or unsubstituted $C_{16}$ alkylene. In embodiments, $L^4$ is substituted or unsubstituted $C_{17}$ alkylene. In embodiments, $L^4$ is substituted or unsubstituted $C_{18}$ alkylene. In embodiments, $L^4$ is substituted or unsubstituted $C_{19}$ alkylene. In embodiments, $L^4$ is substituted or unsubstituted $C_2$ alkylene.

In embodiments, $L^4$ is substituted or unsubstituted $C_1$-$C_6$ alkylene. In embodiments, $L^4$ is substituted $C_1$-$C_6$ alkylene. In embodiments, $L^4$ is unsubstituted $C_1$-$C_6$ alkylene. In embodiments, $L^4$ is substituted or unsubstituted $C_2$-$C_6$ alkylene. In embodiments, $L^4$ is substituted $C_2$-$C_6$ alkylene. In embodiments, $L^4$ is unsubstituted $C_2$-$C_6$ alkylene. In embodiments, $L^4$ is substituted or unsubstituted $C_1$ alkylene. In embodiments, $L^4$ is substituted $C_1$ alkylene. In embodiments, $L^4$ is unsubstituted $C_1$ alkylene. In embodiments, $L^4$ is substituted or unsubstituted $C_2$ alkylene. In embodiments, $L^4$ is substituted $C_2$ alkylene. In embodiments, $L^4$ is unsubstituted $C_2$ alkylene. In embodiments, $L^4$ is substituted or unsubstituted $C_3$ alkylene. In embodiments, $L^4$ is substituted $C_3$ alkylene. In embodiments, $L^4$ is unsubstituted $C_3$ alkylene. In embodiments, $L^4$ is substituted or unsubstituted $C_4$ alkylene. In embodiments, $L^4$ is substituted $C_4$ alkylene. In embodiments, $L^4$ is unsubstituted $C_4$ alkylene. In embodiments, $L^4$ is substituted or unsubstituted $C_5$ alkylene. In embodiments, $L^4$ is substituted $C_5$ alkylene. In embodiments, $L^4$ is unsubstituted $C_5$ alkylene. In embodiments, $L^4$ is substituted or unsubstituted $C_6$ alkylene. In embodiments, $L^4$ is substituted $C_6$ alkylene. In embodiments, $L^4$ is unsubstituted $C_6$ alkylene.

In embodiments, $L^4$ is substituted or unsubstituted 2 to 8 membered heteroalkylene. In embodiments, $L^4$ is substituted 2 to 8 membered heteroalkylene. In embodiments, $L^4$ is unsubstituted 2 to 8 membered heteroalkylene. In embodiments, $L^4$ is substituted or unsubstituted 2 membered heteroalkylene. In embodiments, $L^4$ is substituted 2 membered heteroalkylene. In embodiments, $L^4$ is unsubstituted 2 membered heteroalkylene. In embodiments, $L^4$ is substituted or unsubstituted 3 membered heteroalkylene. In embodiments, $L^4$ is substituted 3 membered heteroalkylene. In embodiments, $L^4$ is unsubstituted 3 membered heteroalkylene. In embodiments, $L^4$ is substituted or unsubstituted 4 membered heteroalkylene. In embodiments, $L^4$ is substituted 4 membered heteroalkylene. In embodiments, $L^4$ is unsubstituted 4 membered heteroalkylene. In embodiments, $L^4$ is substituted or unsubstituted 5 membered heteroalkylene. In embodiments, $L^4$ is substituted 5 membered heteroalkylene. In embodiments, $L^4$ is unsubstituted 5 membered heteroalkylene. In embodiments, $L^4$ is substituted or unsubstituted 6 membered heteroalkylene. In embodiments, $L^4$ is substituted 6 membered heteroalkylene. In embodiments, $L^4$ is unsubstituted 6 membered heteroalkylene. In embodiments, $L^4$ is substituted or unsubstituted 7 membered heteroalkylene. In embodiments, $L^4$ is substituted 7 membered heteroalkylene. In embodiments, $L^4$ is unsubstituted 7 membered heteroalkylene. In embodiments, $L^4$ is substituted or unsubstituted 8 membered heteroalkylene. In embodiments, $L^4$ is substituted 8 membered heteroalkylene. In embodiments, $L^4$ is unsubstituted 8 membered heteroalkylene.

In embodiments, $L^4$ is substituted or unsubstituted 9 membered heteroalkylene. In embodiments, $L^4$ is substituted 9 membered heteroalkylene. In embodiments, $L^4$ is unsubstituted 9 membered heteroalkylene. In embodiments, $L^4$ is substituted or unsubstituted 10 membered heteroalkylene. In embodiments, $L^4$ is substituted 10 membered heteroalkylene. In embodiments, $L^4$ is unsubstituted 10 membered heteroalkylene. In embodiments, $L^4$ is substituted or unsubstituted 11 membered heteroalkylene. In embodiments, $L^4$ is substituted 11 membered heteroalkylene. In embodiments, $L^4$ is unsubstituted 11 membered heteroalkylene. In embodiments, $L^4$ is substituted or unsubstituted 12 membered heteroalkylene. In embodiments, $L^4$ is substituted 12 membered heteroalkylene. In embodiments, $L^4$ is unsubstituted 12 membered heteroalkylene. In embodiments, $L^4$ is substituted or unsubstituted 13 membered heteroalkylene. In embodiments, $L^4$ is substituted 13 membered heteroalkylene. In embodiments, $L^4$ is unsubstituted 13 membered heteroalkylene. In embodiments, $L^4$ is substituted or unsubstituted 14 membered heteroalkylene. In embodiments, $L^4$ is substituted 14 membered heteroalkylene. In embodiments, $L^4$ is unsubstituted 14 membered heteroalkylene. In embodiments, $L^4$ is substituted or unsubstituted 15 membered heteroalkylene. In embodiments, $L^4$ is substituted 15 membered heteroalkylene. In embodiments, $L^4$ is unsubstituted 15 membered heteroalkylene. In embodiments, $L^4$ is substituted or unsubstituted 16 membered heteroalkylene. In embodiments, $L^4$ is substituted 16 membered heteroalkylene. In embodiments, $L^4$ is unsubstituted 16 membered heteroalkylene. In embodiments, $L^4$ is substituted or unsubstituted 17 membered heteroalkylene. In embodiments, $L^4$ is substituted 17 membered heteroalkylene. In embodiments, $L^4$ is unsubstituted 17 membered heteroalkylene. In embodiments, $L^4$ is substituted or unsubstituted 18 membered heteroalkylene. In embodiments, $L^4$ is substituted 18 membered heteroalkylene. In embodiments, $L^4$ is unsubstituted 18 membered heteroalkylene. In embodiments, $L^4$ is substituted or unsubstituted 19 membered heteroalkylene. In embodiments, $L^4$ is substituted 19 membered heteroalkylene. In embodiments, $L^4$ is unsubstituted 19 membered heteroalkylene. In embodiments, $L^4$ is substituted or unsubstituted 20 membered heteroalkylene. In embodiments, $L^4$ is substituted 20 membered heteroalkylene. In embodiments, $L^4$ is unsubstituted 20 membered heteroalkylene.

In embodiments, $L^4$ is substituted or unsubstituted $C_4$-$C_6$ cycloalkylene. In embodiments, $L^4$ is substituted $C_4$-$C_6$ cycloalkylene. In embodiments, $L^4$ is unsubstituted $C_4$-$C_6$ cycloalkylene. In embodiments, $L^4$ is substituted or unsubstituted $C_4$ cycloalkylene. In embodiments, $L^4$ is substituted $C_4$ cycloalkylene. In embodiments, $L^4$ is substituted $C_4$ cycloalkylene. In embodiments, $L^4$ is substituted or unsubstituted $C_5$ cycloalkylene. In embodiments, $L^4$ is substituted $C_5$ cycloalkylene. In embodiments, $L^4$ is substituted $C_5$ cycloalkylene.

In embodiments, $L^4$ is substituted or unsubstituted 5 to 6 membered heterocycloalkylene. In embodiments, $L^4$ is substituted 5 to 6 membered heterocycloalkylene. In embodiments, $L^4$ is unsubstituted 5 to 6 membered heterocycloalkylene. In embodiments, $L^4$ is substituted or unsubstituted 5 membered heterocycloalkylene. In embodiments, $L^4$ is substituted 5 membered heterocycloalkylene. In embodiments, $L^4$ is unsubstituted 5 membered heterocycloalkylene. In embodiments, $L^4$ is substituted or unsubstituted 6 membered heterocycloalkylene. In embodiments, $L^4$ is substituted 6 membered heterocycloalkylene. In embodiments, $L^4$ is unsubstituted 6 membered heterocycloalkylene.

In embodiments, $L^4$ is substituted or unsubstituted phenylene. In embodiments, $L^4$ is substituted phenylene. In embodiments, $L^4$ is unsubstituted phenylene.

In embodiments, $L^4$ is substituted or unsubstituted 5 to 6 membered heteroarylene. In embodiments, $L^4$ is substituted 5 to 6 membered heteroarylene. In embodiments, $L^4$ is unsubstituted 5 to 6 membered heteroarylene. In embodiments, $L^4$ is substituted or unsubstituted 5 membered heteroarylene. In embodiments, $L^4$ is substituted 5 membered heteroarylene. In embodiments, $L^4$ is unsubstituted 5 membered heteroarylene. In embodiments, $L^4$ is substituted or unsubstituted 6 membered heteroarylene. In embodiments, $L^4$ is substituted 6 membered heteroarylene. In embodiments, $L^4$ is unsubstituted 6 membered heteroarylene.

In embodiments, $L^4$ is a polymer.

In embodiments, $L^{4A}$ is substituted or unsubstituted methylene. In embodiments, $L^{4A}$ is substituted or unsubstituted $C_2$ alkylene. In embodiments, $L^{4A}$ is substituted or unsubstituted $C_3$ alkylene. In embodiments, $L^{4A}$ is substituted or unsubstituted $C_4$ alkylene. In embodiments, $L^{4A}$ is substituted or unsubstituted $C_5$ alkylene. In embodiments, $L^{4A}$ is substituted or unsubstituted $C_6$ alkylene. In embodiments, $L^{4A}$ is substituted or unsubstituted $C_7$ alkylene. In embodiments, $L^{4A}$ is substituted or unsubstituted $C_8$ alkylene. In embodiments, $L^{4A}$ is substituted methylene. In embodiments, $L^{4A}$ is substituted $C_2$ alkylene. In embodiments, $L^{4A}$ is substituted $C_3$ alkylene. In embodiments, $L^{4A}$ is substituted $C_4$ alkylene. In embodiments, $L^{4A}$ is substituted $C_5$ alkylene. In embodiments, $L^{4A}$ is substituted $C_6$ alkylene. In embodiments, $L^{4A}$ is substituted $C_7$ alkylene. In embodiments, $L^{4A}$ is substituted $C_8$ alkylene. In embodiments, $L^{4A}$ is an unsubstituted methylene. In embodiments, $L^{4A}$ is an unsubstituted $C_2$ alkylene. In embodiments, $L^{4A}$ is an unsubstituted $C_3$ alkylene. In embodiments, $L^{4A}$ is an unsubstituted $C_4$ alkylene. In embodiments, $L^{4A}$ is an unsubstituted $C_5$ alkylene. In embodiments, $L^{4A}$ is an unsubstituted $C_6$ alkylene. In embodiments, $L^{4A}$ is an unsubstituted $C_7$ alkylene. In embodiments, $L^{4A}$ is an unsubstituted $C_8$ alkylene.

In embodiments, $L^{4A}$ is substituted or unsubstituted $C_1$-$C_6$ alkylene. In embodiments, $L^{4A}$ is substituted $C_1$-$C_6$ alkylene. In embodiments, $L^{4A}$ is unsubstituted $C_1$-$C_6$ alkylene. In embodiments, $L^{4A}$ is substituted or unsubstituted $C_2$-$C_6$ alkylene. In embodiments, $L^{4A}$ is substituted $C_2$-$C_6$ alkylene. In embodiments, $L^{4A}$ is unsubstituted $C_2$-$C_6$ alkylene. In embodiments, $L^{4A}$ is substituted or unsubstituted $C_1$ alkylene. In embodiments, $L^{4A}$ is substituted $C_1$ alkylene. In embodiments, $L^{4A}$ is unsubstituted $C_1$ alkylene. In embodiments, $L^{4A}$ is substituted or unsubstituted $C_2$ alkylene. In embodiments, $L^{4A}$ is substituted $C_2$ alkylene. In embodiments, $L^{4A}$ is unsubstituted $C_2$ alkylene. In embodiments, $L^{4A}$ is substituted or unsubstituted $C_3$ alkylene. In embodiments, $L^{4A}$ is substituted $C_3$ alkylene. In embodiments, $L^{4A}$ is unsubstituted $C_3$ alkylene. In embodiments, $L^{4A}$ is substituted or unsubstituted $C_4$ alkylene. In embodiments, $L^{4A}$ is substituted $C_4$ alkylene. In embodiments, $L^{4A}$ is unsubstituted $C_4$ alkylene. In embodiments, $L^{4A}$ is substituted or unsubstituted $C_5$ alkylene. In embodiments, $L^{4A}$ is substituted $C_8$ alkylene. In embodiments, $L^{4A}$ is unsubstituted $C_8$ alkylene. In embodiments, $L^{4A}$ is substituted or unsubstituted $C_6$ alkylene. In embodiments, $L^{4A}$ is substituted $C_6$ alkylene. In embodiments, $L^{4A}$ is unsubstituted $C_6$ alkylene.

In embodiments, $L^{4A}$ is substituted or unsubstituted 2 to 8 membered heteroalkylene. In embodiments, $L^{4A}$ is substituted 2 to 8 membered heteroalkylene. In embodiments, $L^{4A}$ is unsubstituted 2 to 8 membered heteroalkylene. In embodiments, $L^{4A}$ is substituted or unsubstituted 2 membered heteroalkylene. In embodiments, $L^{4A}$ is substituted 2 membered heteroalkylene. In embodiments, $L^{4A}$ is unsubstituted 2 membered heteroalkylene. In embodiments, $L^{4A}$ is substituted or unsubstituted 3 membered heteroalkylene. In embodiments, $L^{4A}$ is substituted 3 membered heteroalkylene. In embodiments, $L^{4A}$ is unsubstituted 3 membered heteroalkylene. In embodiments, $L^{4A}$ is substituted or unsubstituted 4 membered heteroalkylene. In embodiments, $L^{4A}$ is substituted 4 membered heteroalkylene. In embodiments, $L^{4A}$ is unsubstituted 4 membered heteroalkylene. In embodiments, $L^{4A}$ is substituted or unsubstituted 5 membered heteroalkylene. In embodiments, $L^{4A}$ is substituted 5 membered heteroalkylene. In embodiments, $L^{4A}$ is unsubstituted 5 membered heteroalkylene. In embodiments, $L^{4A}$ is substituted or unsubstituted 6 membered heteroalkylene. In embodiments, $L^{4A}$ is substituted 6 membered heteroalkylene. In embodiments, $L^{4A}$ is unsubstituted 6 membered heteroalkylene.

In embodiments, $L^{4A}$ is substituted or unsubstituted $C_4$-$C_6$ cycloalkylene. In embodiments, $L^{4A}$ is substituted $C_4$-$C_6$ cycloalkylene. In embodiments, $L^{4A}$ is substituted $C_4$-$C_6$ cycloalkylene. In embodiments, $L^{4A}$ is substituted or unsubstituted $C_4$ cycloalkylene. In embodiments, $L^{4A}$ is substituted $C_4$ cycloalkylene. In embodiments, $L^{4A}$ is substituted $C_4$ cycloalkylene. In embodiments, $L^{4A}$ is substituted or unsubstituted $C_5$ cycloalkylene. In embodiments, $L^{4A}$ is substituted $C_5$ cycloalkylene. In embodiments, $L^{4A}$ is substituted $C_5$ cycloalkylene.

In embodiments, $L^{4A}$ is substituted or unsubstituted 5 to 6 membered heterocycloalkylene. In embodiments, $L^{4A}$ is substituted 5 to 6 membered heterocycloalkylene. In embodiments, $L^{4A}$ is unsubstituted 5 to 6 membered heterocycloalkylene. In embodiments, $L^{4A}$ is substituted or unsubstituted 5 membered heterocycloalkylene. In embodiments, $L^{4A}$ is substituted 5 membered heterocycloalkylene. In embodiments, $L^{4A}$ is unsubstituted 5 membered heterocycloalkylene. In embodiments, $L^{4A}$ is substituted or unsubstituted 6 membered heterocycloalkylene. In embodiments, $L^{4A}$ is substituted 6 membered heterocycloalkylene. In embodiments, $L^{4A}$ is unsubstituted 6 membered heterocycloalkylene.

In embodiments, $L^{4A}$ is substituted or unsubstituted phenylene. In embodiments, $L^{4A}$ is substituted phenylene. In embodiments, $L^{4A}$ is unsubstituted phenylene.

In embodiments, $L^{4A}$ is substituted or unsubstituted 5 to 6 membered heteroarylene. In embodiments, $L^{4A}$ is substituted 5 to 6 membered heteroarylene. In embodiments, $L^{4A}$ is unsubstituted 5 to 6 membered heteroarylene. In embodiments, $L^{4A}$ is substituted or unsubstituted 5 membered heteroarylene. In embodiments, $L^{4A}$ is substituted 5 membered heteroarylene. In embodiments, $L^{4A}$ is unsubstituted 5 membered heteroarylene. In embodiments, $L^{4A}$ is substituted or unsubstituted 6 membered heteroarylene. In embodiments, $L^{4A}$ is substituted 6 membered heteroarylene. In embodiments, $L^{4A}$ is unsubstituted 6 membered heteroarylene.

In embodiments, $L^{4A}$ is a polymer.

In embodiments, $L^{4B}$ is substituted or unsubstituted methylene. In embodiments, $L^{4B}$ is substituted or unsubstituted $C_2$ alkylene. In embodiments, $L^{4B}$ is substituted or unsubstituted $C_3$ alkylene. In embodiments, $L^{4B}$ is substituted or unsubstituted $C_4$ alkylene. In embodiments, $L^{4B}$ is substituted or unsubstituted $C_5$ alkylene. In embodiments, $L^{4B}$ is substituted or unsubstituted $C_6$ alkylene. In embodiments, $L^{4B}$ is substituted or unsubstituted $C_7$ alkylene. In embodiments, $L^{4B}$ is substituted or unsubstituted $C_8$ alkylene. In embodiments, $L^{4B}$ is substituted methylene. In embodiments, $L^{4B}$ is substituted $C_2$ alkylene. In embodiments, $L^{4B}$ is substituted $C_3$ alkylene. In embodiments, $L^{4B}$ is substituted $C_4$ alkylene. In embodiments, $L^{4B}$ is substituted $C_5$ alkylene. In embodiments, $L^{4B}$ is substituted $C_6$ alkylene. In embodiments, $L^{4B}$ is substituted $C_7$ alkylene. In embodiments, $L^{4B}$ is substituted $C_8$ alkylene. In embodiments, $L^{4B}$ is an unsubstituted methylene. In embodiments, $L^{4B}$ is an unsubstituted $C_2$ alkylene. In embodiments, $L^{4B}$ is an unsubstituted $C_3$ alkylene. In embodiments, $L^{4B}$ is an unsubstituted $C_4$ alkylene. In embodiments $L^{4B}$ is an unsubstituted $C_5$ alkylene. In embodiments, $L^{4B}$ is an unsubstituted $C_6$ alkylene. In embodiments, $L^{4B}$ is an unsubstituted $C_7$ alkylene. In embodiments, $L^{4B}$ is an unsubstituted $C_8$ alkylene.

In embodiments, $L^{4B}$ is substituted or unsubstituted $C_1$-$C_6$ alkylene. In embodiments, $L^{4B}$ is substituted $C_1$-$C_6$ alkylene. In embodiments, $L^{4B}$ is unsubstituted $C_1$-$C_6$ alkylene. In embodiments, $L^{4B}$ is substituted or unsubstituted $C_2$-$C_6$ alkylene. In embodiments, $L^{4B}$ is substituted $C_2$-$C_6$ alkylene. In embodiments, $L^{4B}$ is unsubstituted $C_2$-$C_6$ alkylene. In embodiments, $L^{4B}$ is substituted or unsubstituted $C_1$ alkylene. In embodiments, $L^{4B}$ is substituted $C_1$ alkylene. In embodiments, $L^{4B}$ is unsubstituted $C_1$ alkylene. In embodiments, $L^{4B}$ is substituted or unsubstituted $C_2$ alkylene. In embodiments, $L^{4B}$ is substituted $C_2$ alkylene. In embodiments, $L^{4B}$ is unsubstituted $C_2$ alkylene. In embodiments, $L^{4B}$ is substituted or unsubstituted $C_3$ alkylene. In embodiments, $L^{4B}$ is substituted $C_3$ alkylene. In embodiments, $L^{4B}$ is unsubstituted $C_3$ alkylene. In embodiments, $L^{4B}$ is substituted or unsubstituted $C_4$ alkylene. In embodiments, $L^{4B}$ is substituted $C_4$ alkylene. In embodiments, $L^{4B}$ is unsubstituted $C_4$ alkylene. In embodiments, $L^{4B}$ is substituted or unsubstituted $C_5$ alkylene. In embodiments, $L^{4B}$ is substituted $C_5$ alkylene. In embodiments, $L^{4B}$ is unsubstituted $C_5$ alkylene. In embodiments, $L^{4B}$ is substituted or unsubstituted $C_6$ alkylene. In embodiments, $L^{4B}$ is substituted $C_6$ alkylene. In embodiments, $L^{4B}$ is unsubstituted $C_6$ alkylene.

In embodiments, $L^{4B}$ is substituted or unsubstituted 2 to 8 membered heteroalkylene. In embodiments, $L^{4B}$ is substituted 2 to 8 membered heteroalkylene. In embodiments, $L^{4B}$ is unsubstituted 2 to 8 membered heteroalkylene. In embodiments, $L^{4B}$ is substituted or unsubstituted 2 membered heteroalkylene. In embodiments, $L^{4B}$ is substituted 2 membered heteroalkylene. In embodiments, $L^{4B}$ is unsubstituted 2 membered heteroalkylene. In embodiments, $L^{4B}$ is substituted or unsubstituted 3 membered heteroalkylene. In embodiments, $L^{4B}$ is substituted 3 membered heteroalkylene. In embodiments, $L^{4B}$ is unsubstituted 3 membered heteroalkylene. In embodiments, $L^{4B}$ is substituted or unsubstituted 4 membered heteroalkylene. In embodiments, $L^{4B}$ is substituted 4 membered heteroalkylene. In embodiments, $L^{4B}$ is unsubstituted 4 membered heteroalkylene. In embodiments, $L^{4B}$ is substituted or unsubstituted 5 membered heteroalkylene. In embodiments, $L^{4B}$ is substituted 5 membered heteroalkylene. In embodiments, $L^{4B}$ is unsubstituted 5 membered heteroalkylene. In embodiments, $L^{4B}$ is substituted or unsubstituted 6 membered heteroalkylene. In embodiments, $L^{4B}$ is substituted 6 membered heteroalkylene. In embodiments, $L^{4B}$ is unsubstituted 6 membered heteroalkylene.

In embodiments, $L^{4B}$ is substituted or unsubstituted $C_4$-$C_6$ cycloalkylene. In embodiments, $L^{4B}$ is substituted $C_4$-$C_6$ cycloalkylene. In embodiments, $L^{4B}$ is substituted $C_4$-$C_6$ cycloalkylene. In embodiments, $L^{4B}$ is substituted or unsubstituted $C_4$ cycloalkylene. In embodiments, $L^{4B}$ is substituted $C_4$ cycloalkylene. In embodiments, $L^{4B}$ is substituted $C_4$ cycloalkylene. In embodiments, $L^{4B}$ is substituted or unsubstituted $C_5$ cycloalkylene. In embodiments, $L^{4B}$ is substituted $C_5$ cycloalkylene. In embodiments, $L^{4B}$ is substituted $C_5$ cycloalkylene.

In embodiments, $L^{4B}$ is substituted or unsubstituted 5 to 6 membered heterocycloalkylene. In embodiments, $L^{4B}$ is substituted 5 to 6 membered heterocycloalkylene. In embodiments, $L^{4B}$ is unsubstituted 5 to 6 membered heterocycloalkylene. In embodiments, $L^{4B}$ is substituted or unsubstituted 5 membered heterocycloalkylene. In embodiments, $L^{4B}$ is substituted 5 membered heterocycloalkylene. In embodiments, $L^{4B}$ is unsubstituted 5 membered heterocycloalkylene. In embodiments, $L^{4B}$ is substituted or unsubstituted 6 membered heterocycloalkylene. In embodiments, $L^{4B}$ is substituted 6 membered heterocycloalkylene. In embodiments, $L^{4B}$ is unsubstituted 6 membered heterocycloalkylene.

In embodiments, $L^{4B}$ is substituted or unsubstituted phenylene. In embodiments, $L^{4B}$ is substituted phenylene. In embodiments, $L^{4B}$ is unsubstituted phenylene.

In embodiments, $L^{4B}$ is substituted or unsubstituted 5 to 6 membered heteroarylene. In embodiments, $L^{4B}$ is substituted 5 to 6 membered heteroarylene. In embodiments, $L^{4B}$ is unsubstituted 5 to 6 membered heteroarylene. In embodiments, $L^{4B}$ is substituted or unsubstituted 5 membered heteroarylene. In embodiments, $L^{4B}$ is substituted 5 membered heteroarylene. In embodiments, $L^{4B}$ is unsubstituted 5 membered heteroarylene. In embodiments, $L^{4B}$ is substituted or unsubstituted 6 membered heteroarylene. In embodiments, $L^{4B}$ is substituted 6 membered heteroarylene. In embodiments, $L^{4B}$ is unsubstituted 6 membered heteroarylene.

In embodiments, $L^{4C}$ is substituted or unsubstituted methylene. In embodiments, $L^{4C}$ is substituted or unsubstituted $C_2$ alkylene. In embodiments, $L^{4C}$ is substituted or unsubstituted $C_3$ alkylene. In embodiments, $L^{4C}$ is substituted or unsubstituted $C_4$ alkylene. In embodiments, $L^{4C}$ is substituted or unsubstituted $C_5$ alkylene. In embodiments, $L^{4C}$ is substituted or unsubstituted $C_6$ alkylene. In embodiments, $L^{4C}$ is substituted or unsubstituted $C_7$ alkylene. In embodiments, $L^{4C}$ is substituted or unsubstituted $C_8$ alkylene. In embodiments, $L^{4C}$ is substituted methylene. In embodiments, $L^{4C}$ is substituted $C_2$ alkylene. In embodiments, $L^{4C}$ is substituted $C_3$ alkylene. In embodiments, $L^{4C}$ is substituted $C_4$ alkylene. In embodiments, $L^{4C}$ is substituted $C_5$ alkylene. In embodiments, $L^{4C}$ is substituted $C_6$ alkylene. In embodiments, $L^{4C}$ is substituted $C_7$ alkylene. In embodiments, $L^{4C}$ is substituted $C_8$ alkylene. In embodiments, $L^{4C}$ is an unsubstituted methylene. In embodiments, $L^{4C}$ is an unsubstituted $C_2$ alkylene. In embodiments, $L^{4C}$ is an unsubstituted $C_3$ alkylene. In embodiments, $L^{4C}$ is an unsubstituted $C_4$ alkylene. In embodiments, $L^{4C}$ is an unsubstituted $C_5$ alkylene. In embodiments, $L^{4C}$ is an unsubstituted $C_6$ alkylene. In embodiments, $L^{4C}$ is an unsubstituted $C_7$ alkylene. In embodiments, $L^{4C}$ is an unsubstituted $C_8$ alkylene.

In embodiments, $L^{4C}$ is substituted or unsubstituted $C_1$-$C_6$ alkylene. In embodiments, $L^{4C}$ is substituted $C_1$-$C_6$ alkylene. In embodiments, $L^{4C}$ is unsubstituted $C_1$-$C_6$ alkylene. In embodiments, $L^{4C}$ is substituted or unsubstituted $C_2$-$C_6$ alkylene. In embodiments, $L^{4C}$ is substituted $C_2$-$C_6$ alkylene. In embodiments, $L^{4C}$ is unsubstituted $C_2$-$C_6$ alkylene. In embodiments, $L^{4C}$ is substituted or unsubstituted $C_1$ alkylene. In embodiments, $L^{4C}$ is substituted $C_1$ alkylene. In embodiments, $L^{4C}$ is unsubstituted $C_1$ alkylene. In embodiments, $L^{4C}$ is substituted or unsubstituted $C_2$ alkylene. In embodiments, $L^{4C}$ is substituted $C_2$ alkylene. In embodiments, $L^{4C}$ is unsubstituted $C_2$ alkylene. In embodiments, $L^{4C}$ is substituted or unsubstituted $C_3$ alkylene. In embodiments, $L^{4C}$ is substituted $C_3$ alkylene. In embodiments, $L^{4C}$ is unsubstituted $C_3$ alkylene. In embodiments, $L^{4C}$ is substituted or unsubstituted $C_4$ alkylene. In embodiments, $L^{4C}$ is substituted $C_4$ alkylene. In embodiments, $L^{4C}$ is unsubstituted $C_4$ alkylene. In embodiments, $L^{4C}$ is substituted or unsubstituted $C_5$ alkylene. In embodiments, $L^{4C}$ is substituted $C_5$ alkylene. In embodiments, $L^{4C}$ is unsubstituted $C_5$ alkylene. In embodiments, $L^{4C}$ is substituted or unsubstituted $C_6$ alkylene. In embodiments, $L^{4C}$ is substituted $C_6$ alkylene. In embodiments, $L^{4C}$ is unsubstituted $C_6$ alkylene.

In embodiments, $L^{4C}$ is substituted or unsubstituted 2 to 8 membered heteroalkylene. In embodiments, $L^{4C}$ is substituted 2 to 8 membered heteroalkylene. In embodiments, $L^{4C}$ is unsubstituted 2 to 8 membered heteroalkylene. In embodiments, $L^{4C}$ is substituted or unsubstituted 2 membered heteroalkylene. In embodiments, $L^{4C}$ is substituted 2 membered heteroalkylene. In embodiments, $L^{4C}$ is unsubstituted 2 membered heteroalkylene. In embodiments, $L^{4C}$ is substituted or unsubstituted 3 membered heteroalkylene. In embodiments, $L^{4C}$ is substituted 3 membered heteroalkylene. In embodiments, $L^{4C}$ is unsubstituted 3 membered heteroalkylene. In embodiments, $L^{4C}$ is substituted or unsubstituted 4 membered heteroalkylene. In embodiments, $L^{4C}$ is substituted 4 membered heteroalkylene. In embodiments, $L^{4C}$ is unsubstituted 4 membered heteroalkylene. In embodiments, $L^{4C}$ is substituted or unsubstituted 5 membered heteroalkylene. In embodiments, $L^{4C}$ is substituted 5 membered heteroalkylene. In embodiments, $L^{4C}$ is unsubstituted 5 membered heteroalkylene. In embodiments, $L^{4C}$ is substituted or unsubstituted 6 membered heteroalkylene. In embodiments, $L^{4C}$ is substituted 6 membered heteroalkylene. In embodiments, $L^{4C}$ is unsubstituted 6 membered heteroalkylene.

In embodiments, $L^{4C}$ is substituted or unsubstituted $C_4$-$C_6$ cycloalkylene. In embodiments, $L^{4C}$ is substituted $C_4$-$C_6$ cycloalkylene. In embodiments, $L^{4C}$ is unsubstituted $C_4$-$C_6$ cycloalkylene. In embodiments, $L^{4C}$ is substituted or unsubstituted $C_4$ cycloalkylene. In embodiments, $L^{4C}$ is substituted $C_4$ cycloalkylene. In embodiments, $L^{4C}$ is unsubstituted $C_4$ cycloalkylene. In embodiments, $L^{4C}$ is substituted or unsubstituted $C_5$ cycloalkylene. In embodiments, $L^{4C}$ is substituted $C_5$ cycloalkylene. In embodiments, $L^{4C}$ is unsubstituted $C_5$ cycloalkylene.

In embodiments, $L^{4C}$ is substituted or unsubstituted 5 to 6 membered heterocycloalkylene. In embodiments, $L^{4C}$ is substituted 5 to 6 membered heterocycloalkylene. In embodiments, $L^{4C}$ is unsubstituted 5 to 6 membered heterocycloalkylene. In embodiments, $L^{4C}$ is substituted or unsubstituted 5 membered heterocycloalkylene. In embodiments, $L^{4C}$ is substituted 5 membered heterocycloalkylene. In embodiments, $L^{4C}$ is unsubstituted 5 membered heterocycloalkylene. In embodiments, $L^{4C}$ is substituted or unsubstituted 6 membered heterocycloalkylene. In embodiments, $L^{4C}$ is substituted 6 membered heterocycloalkylene. In embodiments, $L^{4C}$ is unsubstituted 6 membered heterocycloalkylene.

In embodiments, $L^{4C}$ is substituted or unsubstituted phenylene. In embodiments, $L^{4C}$ is substituted phenylene. In embodiments, $L^{4C}$ is unsubstituted phenylene.

In embodiments, $L^{4C}$ is substituted or unsubstituted 5 to 6 membered heteroarylene. In embodiments, $L^{4C}$ is substituted 5 to 6 membered heteroarylene. In embodiments, $L^{4C}$ is unsubstituted 5 to 6 membered heteroarylene. In embodiments, $L^{4C}$ is substituted or unsubstituted 5 membered heteroarylene. In embodiments, $L^{4C}$ is substituted 5 membered heteroarylene. In embodiments, $L^{4C}$ is unsubstituted 5 membered heteroarylene. In embodiments, $L^{4C}$ is substituted or unsubstituted 6 membered heteroarylene. In embodiments, $L^{4C}$ is substituted 6 membered heteroarylene. In embodiments, $L^{4C}$ is unsubstituted 6 membered heteroarylene.

In embodiments, $L^{4D}$ is substituted or unsubstituted methylene. In embodiments, $L^{4D}$ is substituted or unsubstituted $C_2$ alkylene. In embodiments, $L^{4D}$ is substituted or unsubstituted $C_3$ alkylene. In embodiments, $L^{4D}$ is substituted or unsubstituted $C_4$ alkylene. In embodiments, $L^{4D}$ is substituted or unsubstituted $C_5$ alkylene. In embodiments, $L^{4D}$ is substituted or unsubstituted $C_6$ alkylene. In embodiments, $L^{4D}$ is substituted or unsubstituted $C_7$ alkylene. In embodiments, $L^{4D}$ is substituted or unsubstituted $C_8$ alkylene. In embodiments, $L^{4D}$ is substituted methylene. In embodiments, $L^{4D}$ is substituted $C_2$ alkylene. In embodiments, $L^{4D}$ is substituted $C_3$ alkylene. In embodiments, $L^{4D}$ is substituted $C_4$ alkylene. In embodiments, $L^{4D}$ is substituted $C_5$ alkylene. In embodiments, $L^{4D}$ is substituted $C_6$ alkylene. In embodiments, $L^{4D}$ is substituted $C_7$ alkylene. In embodiments, $L^{4D}$ is substituted $C_8$ alkylene. In embodiments, $L^{4D}$ is an unsubstituted methylene. In embodiments, $L^{4D}$ is an unsubstituted $C_2$ alkylene. In embodiments, $L^{4D}$ is an unsubstituted $C_3$ alkylene. In embodiments, $L^{4D}$ is an unsubstituted $C_4$ alkylene. In embodiments, $L^{4D}$ is an unsubstituted $C_5$ alkylene. In embodiments, $L^{4D}$ is an unsubstituted $C_6$ alkylene. In embodiments, $L^{4D}$ is an unsubstituted $C_7$ alkylene. In embodiments, $L^{4D}$ is an unsubstituted $C_8$ alkylene.

In embodiments, $L^{4D}$ is substituted or unsubstituted $C_1$-$C_6$ alkylene. In embodiments, $L^{4D}$ is substituted $C_1$-$C_6$ alkylene. In embodiments, $L^{4D}$ is unsubstituted $C_1$-$C_6$ alkylene. In embodiments, $L^{4D}$ is substituted or unsubstituted $C_2$-$C_6$ alkylene. In embodiments, $L^{4D}$ is substituted $C_2$-$C_6$ alkylene. In embodiments, $L^{4D}$ is unsubstituted $C_2$-$C_6$ alkylene. In embodiments, $L^{4D}$ is substituted or unsubstituted $C_1$ alkylene. In embodiments, $L^{4D}$ is substituted $C_1$ alkylene. In embodiments, $L^{4D}$ is unsubstituted $C_1$ alkylene. In embodiments, $L^{4D}$ is substituted or unsubstituted $C_2$ alkylene. In embodiments, $L^{4D}$ is substituted $C_2$ alkylene. In embodiments, $L^{4D}$ is unsubstituted $C_2$ alkylene. In embodiments, $L^{4D}$ is substituted or unsubstituted $C_3$ alkylene. In embodiments, $L^{4D}$ is substituted $C_3$ alkylene. In embodiments, $L^{4D}$ is unsubstituted $C_3$ alkylene. In embodiments, $L^{4D}$ is substituted or unsubstituted $C_4$ alkylene. In embodiments, $L^{4D}$ is substituted $C_4$ alkylene. In embodiments, $L^{4D}$ is unsubstituted $C_4$ alkylene. In embodiments, $L^{4D}$ is substituted or unsubstituted $C_5$ alkylene. In embodiments, $L^{4D}$ is substituted $C_5$ alkylene. In embodiments, $L^{4D}$ is unsubstituted $C_5$ alkylene. In embodiments, $L^{4D}$ is substituted or unsubstituted $C_6$ alkylene. In embodiments, $L^{4D}$ is substituted $C_6$ alkylene. In embodiments, $L^{4D}$ is unsubstituted $C_6$ alkylene.

In embodiments, $L^{4D}$ is substituted or unsubstituted 2 to 8 membered heteroalkylene. In embodiments, $L^{4D}$ is substituted 2 to 8 membered heteroalkylene. In embodiments, $L^{4D}$ is unsubstituted 2 to 8 membered heteroalkylene. In embodiments, $L^{4D}$ is substituted or unsubstituted 2 membered heteroalkylene. In embodiments, $L^{4D}$ is substituted 2 membered heteroalkylene. In embodiments, $L^{4D}$ is unsubstituted 2 membered heteroalkylene. In embodiments, $L^{4D}$ is substituted or unsubstituted 3 membered heteroalkylene. In embodiments, $L^{4D}$ is substituted 3 membered heteroalkylene. In embodiments, $L^{4D}$ is unsubstituted 3 membered heteroalkylene. In embodiments, $L^{4D}$ is substituted or unsubstituted 4 membered heteroalkylene. In embodiments, $L^{4D}$ is substituted 4 membered heteroalkylene. In embodiments, $L^{4D}$ is unsubstituted 4 membered heteroalkylene. In embodiments, $L^{4D}$ is substituted or unsubstituted 5 membered heteroalkylene. In embodiments, $L^{4D}$ is substituted 5 membered heteroalkylene. In embodiments, $L^{4D}$ is unsubstituted 5 membered heteroalkylene. In embodiments, $L^{4D}$ is substituted or unsubstituted 6 membered heteroalkylene. In embodiments, $L^{4D}$ is substituted 6 membered heteroalkylene. In embodiments, $L^{4D}$ is unsubstituted 6 membered heteroalkylene.

In embodiments, $L^{4D}$ is substituted or unsubstituted $C_4$-$C_6$ cycloalkylene. In embodiments, $L^{4D}$ is substituted $C_4$-$C_6$ cycloalkylene. In embodiments, $L^{4D}$ is unsubstituted $C_4$-$C_6$ cycloalkylene. In embodiments, $L^{4D}$ is substituted or unsubstituted $C_4$ cycloalkylene. In embodiments, $L^{4D}$ is substituted $C_4$ cycloalkylene. In embodiments, $L^{4D}$ is unsubstituted $C_4$ cycloalkylene. In embodiments, $L^{4D}$ is substituted or unsubstituted $C_5$ cycloalkylene. In embodiments, $L^{4D}$ is substituted $C_5$ cycloalkylene. In embodiments, $L^{4D}$ is unsubstituted $C_5$ cycloalkylene.

In embodiments, $L^{4D}$ is substituted or unsubstituted 5 to 6 membered heterocycloalkylene. In embodiments, $L^{4D}$ is substituted 5 to 6 membered heterocycloalkylene. In embodiments, $L^{4D}$ is unsubstituted 5 to 6 membered heterocycloalkylene. In embodiments, $L^{4D}$ is substituted or unsubstituted 5 membered heterocycloalkylene. In embodiments, $L^{4D}$ is substituted 5 membered heterocycloalkylene. In embodiments, $L^{4D}$ is unsubstituted 5 membered heterocycloalkylene. In embodiments, $L^{4D}$ is substituted or unsubstituted 6 membered heterocycloalkylene. In embodiments, $L^{4D}$ is substituted 6 membered heterocycloalkylene. In embodiments, $L^{4D}$ is unsubstituted 6 membered heterocycloalkylene.

In embodiments, $L^{4D}$ is substituted or unsubstituted phenylene. In embodiments, $L^{4D}$ is substituted phenylene. In embodiments, $L^{4D}$ is unsubstituted phenylene.

In embodiments, $L^{4D}$ is substituted or unsubstituted 5 to 6 membered heteroarylene. In embodiments, $L^{4D}$ is substituted 5 to 6 membered heteroarylene. In embodiments, $L^{4D}$ is unsubstituted 5 to 6 membered heteroarylene. In embodiments, $L^{4D}$ is substituted or unsubstituted 5 membered heteroarylene. In embodiments, $L^{4D}$ is substituted 5 membered heteroarylene. In embodiments, $L^{4D}$ is unsubstituted 5 membered heteroarylene. In embodiments, $L^{4D}$ is substituted or unsubstituted 6 membered heteroarylene. In embodiments, $L^{4D}$ is substituted 6 membered heteroarylene. In embodiments, $L^{4D}$ is unsubstituted 6 membered heteroarylene.

In embodiments, $L^{4E}$ is substituted or unsubstituted methylene. In embodiments, $L^{4E}$ is substituted or unsubstituted $C_2$ alkylene. In embodiments, $L^{4E}$ is substituted or unsubstituted $C_3$ alkylene. In embodiments, $L^{4E}$ is substituted or unsubstituted $C_4$ alkylene. In embodiments, $L^{4E}$ is substituted or unsubstituted $C_5$ alkylene. In embodiments, $L^{4E}$ is substituted or unsubstituted $C_6$ alkylene. In embodiments, $L^{4E}$ is substituted or unsubstituted $C_7$ alkylene. In embodiments, $L^{4E}$ is substituted or unsubstituted $C_8$ alkylene. In embodiments, $L^{4E}$ is substituted methylene. In embodiments, $L^{4E}$ is substituted $C_2$ alkylene. In embodiments, $L^{4E}$ is substituted $C_3$ alkylene. In embodiments, $L^{4E}$ is substituted $C_4$ alkylene. In embodiments, $L^{4E}$ is substituted $C_5$ alkylene. In embodiments, $L^{4E}$ is substituted $C_6$ alkylene. In embodiments, $L^{4E}$ is substituted $C_7$ alkylene. In embodiments, $L^{4E}$ is substituted $C_8$ alkylene. In embodiments, $L^{4E}$ is an unsubstituted methylene. In embodiments, $L^{4E}$ is an unsubstituted $C_2$ alkylene. In embodiments, $L^{4E}$ is an unsubstituted $C_3$ alkylene. In embodiments, $L^{4E}$ is an unsubstituted $C_4$ alkylene. In embodiments, $L^{4E}$ is an unsubstituted $C_5$ alkylene. In embodiments, $L^{4E}$ is an unsubstituted $C_6$ alkylene. In embodiments, $L^{4E}$ is an unsubstituted $C_7$ alkylene. In embodiments, $L^{4E}$ is an unsubstituted $C_8$ alkylene.

In embodiments, $L^{4E}$ is substituted or unsubstituted $C_1$-$C_6$ alkylene. In embodiments, $L^{4E}$ is substituted $C_1$-$C_6$ alkylene. In embodiments, $L^{4E}$ is unsubstituted $C_1$-$C_6$ alkylene. In embodiments, $L^{4E}$ is substituted or unsubstituted $C_2$-$C_6$ alkylene. In embodiments, $L^{4E}$ is substituted $C_2$-$C_6$ alkylene. In embodiments, $L^{4E}$ is unsubstituted $C_2$-$C_6$ alkylene. In embodiments, $L^{4E}$ is substituted or unsubstituted $C_1$ alkylene. In embodiments, $L^{4E}$ is substituted $C_1$ alkylene. In embodiments, $L^{4E}$ is unsubstituted $C_1$ alkylene. In embodiments, $L^{4E}$ is substituted or unsubstituted $C_2$ alkylene. In embodiments, $L^{4E}$ is substituted $C_2$ alkylene. In embodiments, $L^{4E}$ is unsubstituted $C_2$ alkylene. In embodiments, $L^{4E}$ is substituted or unsubstituted $C_3$ alkylene. In embodiments, $L^{4E}$ is substituted $C_3$ alkylene. In embodiments, $L^{4E}$ is unsubstituted $C_3$ alkylene. In embodiments, $L^{4E}$ is substituted or unsubstituted $C_4$ alkylene. In embodiments, $L^{4E}$ is substituted $C_4$ alkylene. In embodiments, $L^{4E}$ is unsubstituted $C_4$ alkylene. In embodiments, $L^{4E}$ is substituted or unsubstituted $C_5$ alkylene. In embodiments, $L^{4E}$ is substituted $C_5$ alkylene. In embodiments, $L^{4E}$ is unsubstituted $C_5$ alkylene. In embodiments, $L^{4E}$ is substituted or unsubstituted $C_6$ alkylene. In embodiments, $L^{4E}$ is substituted $C_6$ alkylene. In embodiments, $L^{4E}$ is unsubstituted $C_6$ alkylene.

In embodiments, $L^{4E}$ is substituted or unsubstituted 2 to 8 membered heteroalkylene. In embodiments, $L^{4E}$ is substituted 2 to 8 membered heteroalkylene. In embodiments, $L^{4E}$ is unsubstituted 2 to 8 membered heteroalkylene. In embodiments, $L^{4E}$ is substituted or unsubstituted 2 membered heteroalkylene. In embodiments, $L^{4E}$ is substituted 2 membered heteroalkylene. In embodiments, $L^{4E}$ is unsubstituted 2 membered heteroalkylene. In embodiments, $L^{4E}$ is substituted or unsubstituted 3 membered heteroalkylene. In embodiments, $L^{4E}$ is substituted 3 membered heteroalkylene. In embodiments, $L^{4E}$ is unsubstituted 3 membered heteroalkylene. In embodiments, $L^{4E}$ is substituted or unsubstituted 4 membered heteroalkylene. In embodiments, $L^{4E}$ is substituted 4 membered heteroalkylene. In embodiments, $L^{4E}$ is unsubstituted 4 membered heteroalkylene. In embodiments, $L^{4E}$ is substituted or unsubstituted 5 membered heteroalkylene. In embodiments, $L^{4E}$ is substituted 5 membered heteroalkylene. In embodiments, $L^{4E}$ is unsubstituted 5 membered heteroalkylene. In embodiments, $L^{4E}$ is substituted or unsubstituted 6 membered heteroalkylene. In embodiments, $L^{4E}$ is substituted 6 membered heteroalkylene. In embodiments, $L^{4E}$ is unsubstituted 6 membered heteroalkylene.

In embodiments, $L^{4E}$ is substituted or unsubstituted $C_4$-$C_6$ cycloalkylene. In embodiments, $L^{4E}$ is substituted $C_4$-$C_6$ cycloalkylene. In embodiments, $L^{4E}$ is unsubstituted $C_4$-$C_6$ cycloalkylene. In embodiments, $L^{4E}$ is substituted or unsubstituted $C_4$ cycloalkylene. In embodiments, $L^{4E}$ is substituted $C_4$ cycloalkylene. In embodiments, $L^{4E}$ is unsubstituted $C_4$ cycloalkylene. In embodiments, $L^{4E}$ is substituted or unsubstituted $C_5$ cycloalkylene. In embodiments, $L^{4E}$ is substituted $C_5$ cycloalkylene. In embodiments, $L^{4E}$ is unsubstituted $C_5$ cycloalkylene.

In embodiments, $L^{4E}$ is substituted or unsubstituted 5 to 6 membered heterocycloalkylene. In embodiments, $L^{4E}$ is substituted 5 to 6 membered heterocycloalkylene. In embodiments, $L^{4E}$ is unsubstituted 5 to 6 membered heterocycloalkylene. In embodiments, $L^{4E}$ is substituted or unsubstituted 5 membered heterocycloalkylene. In embodiments, $L^{4E}$ is substituted 5 membered heterocycloalkylene. In embodiments, $L^{4E}$ is unsubstituted 5 membered heterocycloalkylene. In embodiments, $L^{4E}$ is substituted or unsubstituted 6 membered heterocycloalkylene. In embodiments, $L^{4E}$ is substituted 6 membered heterocycloalkylene. In embodiments, $L^{4E}$ is unsubstituted 6 membered heterocycloalkylene.

In embodiments, $L^{4E}$ is substituted or unsubstituted phenylene. In embodiments, $L^{4E}$ is substituted phenylene. In embodiments, $L^{4E}$ is unsubstituted phenylene.

In embodiments, $L^{4E}$ is substituted or unsubstituted 5 to 6 membered heteroarylene. In embodiments, $L^{4E}$ is substituted 5 to 6 membered heteroarylene. In embodiments, $L^{4E}$ is unsubstituted 5 to 6 membered heteroarylene. In embodiments, $L^{4E}$ is substituted or unsubstituted 5 membered heteroarylene. In embodiments, $L^{4E}$ is substituted 5 membered heteroarylene. In embodiments, $L^{4E}$ is unsubstituted 5 membered heteroarylene. In embodiments, $L^{4E}$ is substituted or unsubstituted 6 membered heteroarylene. In embodiments, $L^{4E}$ is substituted 6 membered heteroarylene. In embodiments, $L^{4E}$ is unsubstituted 6 membered heteroarylene.

In embodiments, $L^{4A}$ is a bond. In embodiments, $L^{4B}$ is a bond. In embodiments, $L^{4C}$ is a bond. In embodiments, $L^{4D}$ is a bond. In embodiments, $L^{4E}$ is a bond.

In embodiments, $R^4$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is substituted or unsubstituted $C_1$-$C_6$ alkyl, or substituted or unsubstituted phenyl. In embodiments, $R^4$ is an unsubstituted $C_1$-$C_6$ alkyl.

In embodiments, $R^4$ is substituted (e.g., substituted with a substituent group, a size-limited substituent group, or lower substituent group) or unsubstituted alkyl. In embodiments, $R^4$ is substituted (e.g., substituted with a substituent group, a size-limited substituent group, or lower substituent group) alkyl. In embodiments, $R^4$ is unsubstituted alkyl. In embodiments, $R^4$ is substituted or unsubstituted alkyl (e.g., $C_1$-$C_8$, $C_1$-$C_6$, $C_1$-$C_4$, or $C_1$-$C_2$). In embodiments, $R^4$ is substituted alkyl (e.g., $C_1$-$C_8$, $C_1$-$C_6$, $C_1$-$C_4$, or $C_1$-$C_2$). In embodiments, $R^4$ is unsubstituted alkyl (e.g., $C_1$-$C_8$, $C_1$-$C_6$, $C_1$-$C_4$, or $C_1$-$C_2$).

In embodiments, $R^4$ is substituted (e.g., substituted with a substituent group, a size-limited substituent group, or lower substituent group) or unsubstituted heteroalkyl. In embodiments, $R^4$ is substituted (e.g., substituted with a substituent group, a size-limited substituent group, or lower substituent group) heteroalkyl. In embodiments, $R^4$ is unsubstituted heteroalkyl. In embodiments, $R^4$ is substituted or unsubstituted heteroalkyl (e.g., 2 to 8 membered, 2 to 6 membered, 4 to 6 membered, 2 to 3 membered, or 4 to 5 membered). In embodiments, $R^4$ is substituted heteroalkyl (e.g., 2 to 8 membered, 2 to 6 membered, 4 to 6 membered, 2 to 3 membered, or 4 to 5 membered). In embodiments, $R^4$ is an unsubstituted heteroalkyl (e.g., 2 to 8 membered, 2 to 6 membered, 4 to 6 membered, 2 to 3 membered, or 4 to 5 membered).

In embodiments, $R^4$ is substituted (e.g., substituted with a substituent group, a size-limited substituent group, or lower substituent group) or unsubstituted cycloalkyl. In embodiments, $R^4$ is substituted (e.g., substituted with a substituent group, a size-limited substituent group, or lower substituent group) cycloalkyl. In embodiments, $R^4$ is an unsubstituted cycloalkyl. In embodiments, $R^4$ is substituted or unsubstituted cycloalkyl (e.g., $C_3$-$C_8$, $C_3$-$C_6$, $C_4$-$C_6$, or $C_5$-$C_6$). In embodiments, $R^4$ is substituted cycloalkyl (e.g., $C_3$-$C_8$, $C_3$—$C_6$, $C_4$-$C_6$, or $C_5$-$C_6$). In embodiments, $R^4$ is unsubstituted cycloalkyl (e.g., $C_3$-$C_8$, $C_3$-$C_6$, $C_4$-$C_6$, or $C_5$-$C_6$).

In embodiments, $R^4$ is substituted (e.g., substituted with a substituent group, a size-limited substituent group, or lower substituent group) or unsubstituted heterocycloalkyl. In embodiments, $R^4$ is substituted (e.g., substituted with a substituent group, a size-limited substituent group, or lower substituent group) heterocycloalkyl. In embodiments, $R^4$ is an unsubstituted heterocycloalkyl. In embodiments, $R^4$ is substituted or unsubstituted heterocycloalkyl (e.g., 3 to 8 membered, 3 to 6 membered, 4 to 6 membered, 4 to 5 membered, or 5 to 6 membered). In embodiments, $R^4$ is substituted heterocycloalkyl (e.g., 3 to 8 membered, 3 to 6 membered, 4 to 6 membered, 4 to 5 membered, or 5 to 6 membered). In embodiments, $R^4$ an unsubstituted heterocycloalkyl (e.g., 3 to 8 membered, 3 to 6 membered, 4 to 6 membered, 4 to 5 membered, or 5 to 6 membered).

In embodiments, $R^4$ is substituted (e.g., substituted with a substituent group, a size-limited substituent group, or lower substituent group) or unsubstituted aryl. In embodiments, $R^4$ is substituted (e.g., substituted with a substituent group, a size-limited substituent group, or lower substituent group) aryl. In embodiments, $R^4$ is an unsubstituted aryl. In embodiments, $R^4$ is substituted or unsubstituted aryl (e.g., $C_6$-$C_{10}$ or phenyl). In embodiments, $R^4$ is substituted aryl (e.g., $C_6$-$C_{10}$ or phenyl). In embodiments, $R^4$ is an unsubstituted aryl (e.g., $C_6$-$C_{10}$ or phenyl).

In embodiments, $R^4$ is substituted (e.g., substituted with a substituent group, a size-limited substituent group, or lower substituent group) or unsubstituted heteroaryl. In embodiments, $R^4$ is substituted (e.g., substituted with a substituent group, a size-limited substituent group, or lower substituent group) heteroaryl. In embodiments, $R^4$ is an unsubstituted heteroaryl. In embodiments, $R^4$ is substituted or unsubstituted heteroaryl (e.g., 5 to 10 membered, 5 to 9 membered, or 5 to 6 membered). In embodiments, $R^4$ is substituted heteroaryl (e.g., 5 to 10 membered, 5 to 9 membered, or 5 to 6 membered). In embodiments, $R^4$ is an unsubstituted heteroaryl (e.g., 5 to 10 membered, 5 to 9 membered, or 5 to 6 membered).

In embodiments, $R^4$ is substituted (e.g., substituted with a substituent group, a size-limited substituent group, or lower substituent group) or unsubstituted alkyl. In embodiments, $R^4$ is an alkyl substituted with a substituent group. In embodiments, $R^4$ is an alkyl substituted with a size-limited substituent group. In embodiments, $R^4$ is an alkyl substituted with a lower substituent group. In embodiments, $R^4$ is unsubstituted alkyl.

In embodiments, $R^4$ is substituted (e.g., substituted with a substituent group, a size-limited substituent group, or lower substituent group) or unsubstituted heteroalkyl. In embodiments, $R^4$ is a heteroalkyl substituted with a substituent group. In embodiments, $R^4$ is a heteroalkyl substituted with a size-limited substituent group. In embodiments, $R^4$ is a heteroalkyl substituted with a lower substituent group. In embodiments, $R^4$ is unsubstituted heteroalkyl.

In embodiments, $R^4$ is substituted (e.g., substituted with a substituent group, a size-limited substituent group, or lower substituent group) or unsubstituted cycloalkyl. In embodiments, $R^4$ is a cycloalkyl substituted with a substituent group. In embodiments, $R^4$ is a cycloalkyl substituted with a size-limited substituent group. In embodiments, $R^4$ is a cycloalkyl substituted with a lower substituent group. In embodiments, $R^4$ is unsubstituted cycloalkyl.

In embodiments, $R^4$ is substituted (e.g., substituted with a substituent group, a size-limited substituent group, or lower substituent group) or unsubstituted heterocycloalkyl. In embodiments, $R^4$ is a heterocycloalkyl substituted with a substituent group. In embodiments, $R^4$ is a heterocycloalkyl substituted with a size-limited substituent group. In embodiments, $R^4$ is a heterocycloalkyl substituted with a lower substituent group. In embodiments, $R^4$ is unsubstituted heterocycloalkyl.

In embodiments, $R^4$ is substituted (e.g., substituted with a substituent group, a size-limited substituent group, or lower substituent group) or unsubstituted aryl. In embodiments, $R^4$ is an aryl substituted with a substituent group. In embodiments, $R^4$ is an aryl substituted with a size-limited substituent group. In embodiments, $R^4$ is an aryl substituted with a lower substituent group. In embodiments, $R^4$ is unsubstituted aryl.

In embodiments, $R^4$ is substituted (e.g., substituted with a substituent group, a size-limited substituent group, or lower substituent group) or unsubstituted heteroaryl. In embodiments, $R^4$ is a heteroaryl substituted with a substituent group. In embodiments, $R^4$ is a heteroaryl substituted with a size-limited substituent group. In embodiments, $R^4$ is a heteroaryl substituted with a lower substituent group. In embodiments, $R^4$ is unsubstituted heteroaryl.

In embodiments, $R^4$ is substituted or unsubstituted alkyl (e.g., $C_1$-$C_8$ alkyl, $C_1$-$C_6$ alkyl, or $C_1$-$C_4$ alkyl). In embodiments, $R^4$ is substituted alkyl (e.g., $C_1$-$C_8$ alkyl, $C_1$-$C_6$ alkyl, or $C_1$-$C_4$ alkyl). In embodiments, $R^4$ is an unsubstituted alkyl (e.g., $C_1$-$C_8$ alkyl, $C_1$-$C_6$ alkyl, or $C_1$-$C_4$ alkyl). In embodiments, $R^4$ is substituted or unsubstituted methyl. In embodiments, $R^4$ is substituted or unsubstituted $C_2$ alkyl. In embodiments, $R^4$ is substituted or unsubstituted $C_3$ alkyl. In embodiments, $R^4$ is substituted or unsubstituted $C_4$ alkyl. In embodiments, $R^4$ is substituted or unsubstituted $C_5$ alkyl. In embodiments, $R^4$ is substituted or unsubstituted $C_6$ alkyl. In embodiments, $R^4$ is substituted or unsubstituted $C_7$ alkyl. In embodiments, $R^4$ is substituted or unsubstituted $C_8$ alkyl. In embodiments, $R^4$ is substituted methyl. In embodiments, $R^4$ is substituted $C_2$ alkyl. In embodiments, $R^4$ is substituted $C_3$ alkyl. In embodiments, $R^4$ is substituted $C_4$ alkyl. In embodiments, $R^4$ is substituted $C_5$ alkyl. In embodiments, $R^4$ is substituted $C_6$ alkyl. In embodiments, $R^4$ is substituted $C_7$ alkyl. In embodiments, $R^4$ is substituted C alkyl. In embodiments, $R^4$ is an unsubstituted methyl. In embodiments, $R^4$ is an unsubstituted $C_2$ alkyl. In embodiments, $R^4$ is an unsubstituted $C_3$ alkyl. In embodiments, $R^4$ is an unsubstituted $C_4$ alkyl (e.g., t-butyl). In embodiments, $R^4$ is an unsubstituted $C_5$ alkyl. In embodiments, $R^4$ is an unsubstituted $C_6$ alkyl. In embodiments, $R^4$ is an unsubstituted $C_7$ alkyl. In embodiments, $R^4$ is an unsubstituted $C_8$ alkyl.

In embodiments, the nucleotide analogue has the formula:

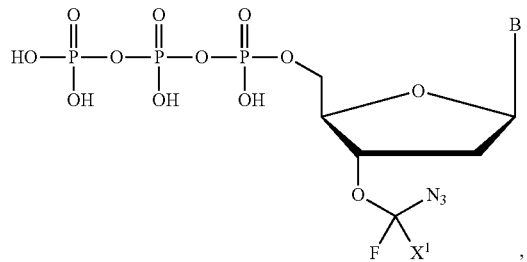

wherein B and $X^1$ are as described herein, including embodiments.

In embodiments, the nucleotide analogue has the formula:

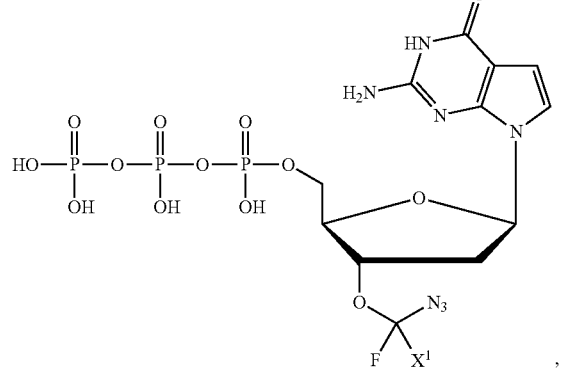

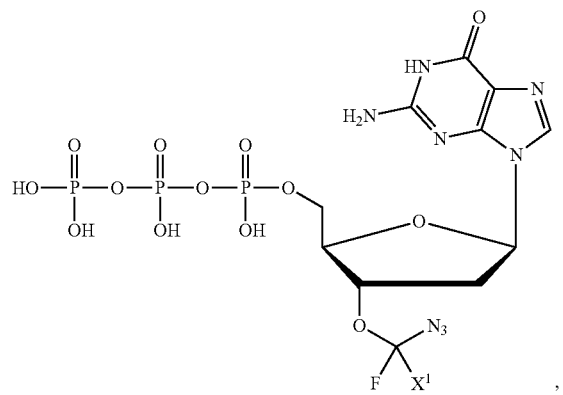

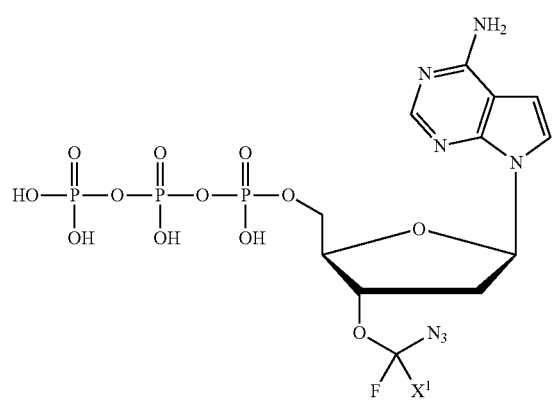

-continued

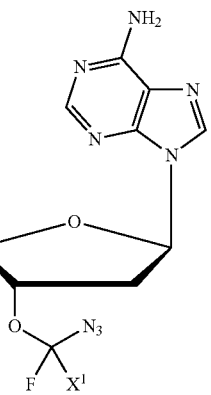

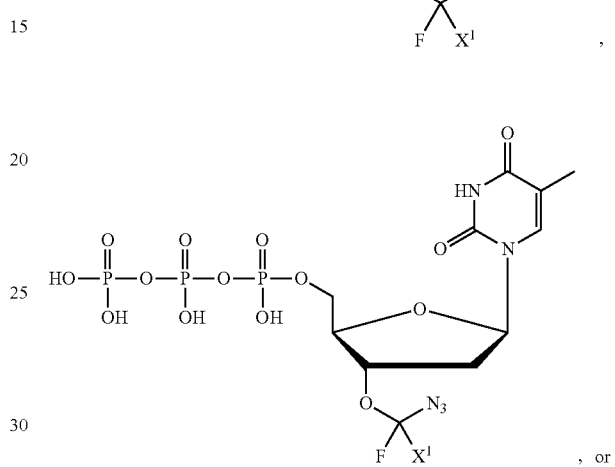

, or

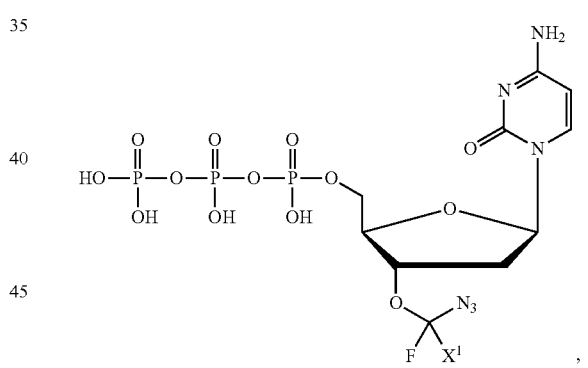

wherein $X^1$ is as described herein, including embodiments.

In embodiments, the nucleotide analogue has the formula:

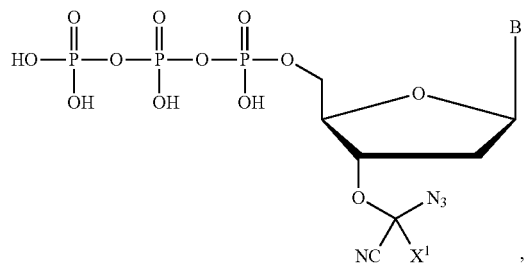

wherein B and $X^1$ are as described herein, including embodiments.

In embodiments, the nucleotide analogue has the formula:
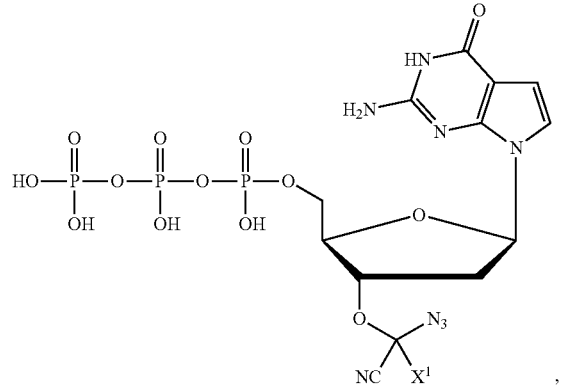
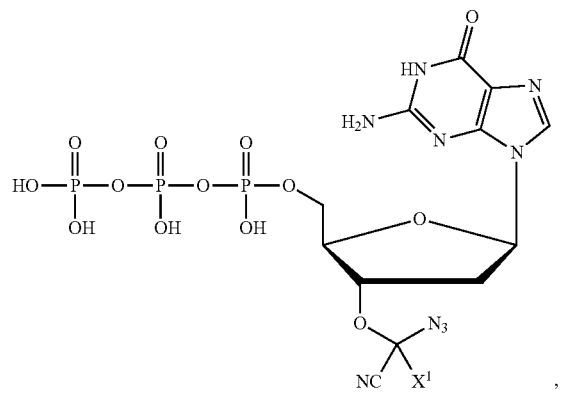
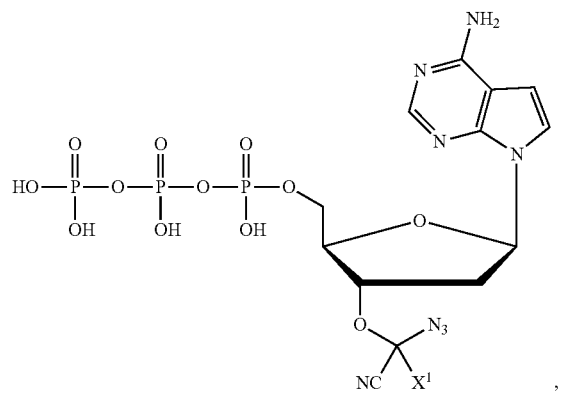
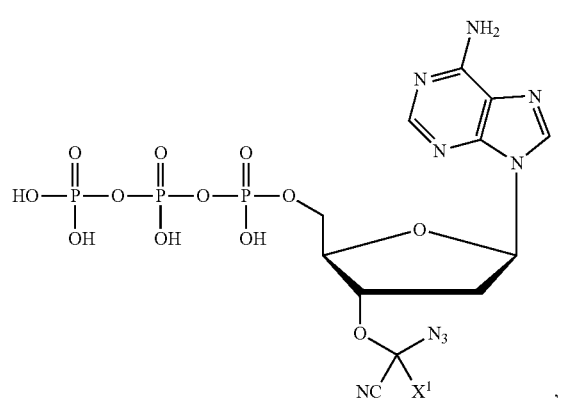
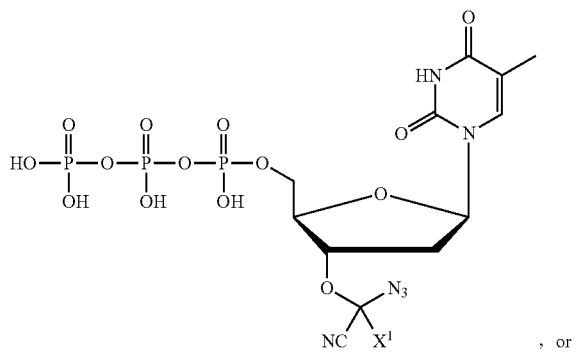
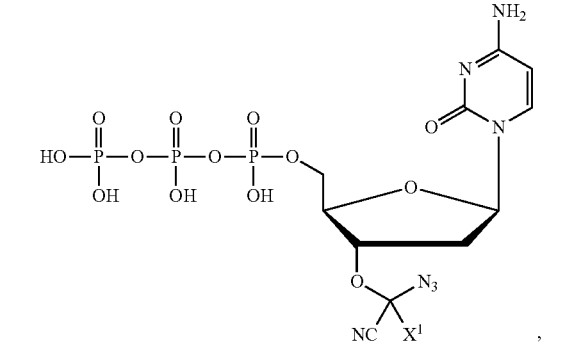
wherein $X^1$ is as described herein, including embodiments.
In embodiments, the nucleotide analogue has the formula:
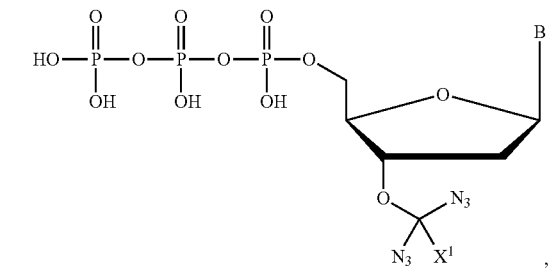
wherein B and $X^1$ are as described herein, including embodiments.
In embodiments, the nucleotide analogue has the formula:
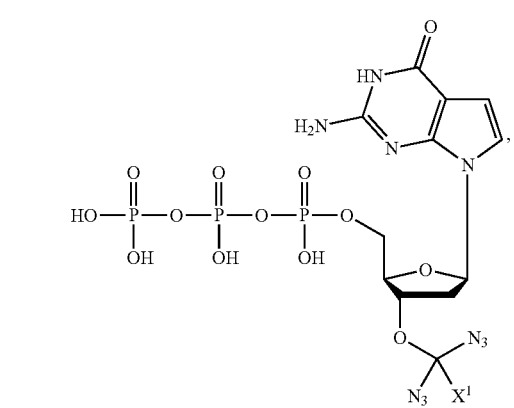

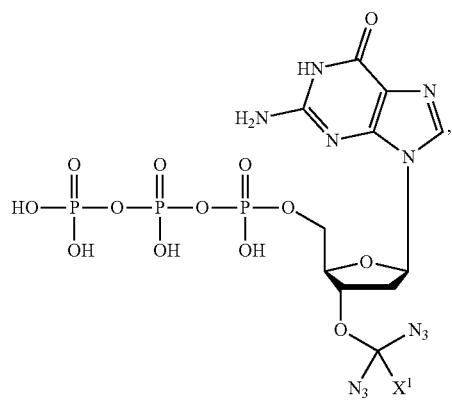
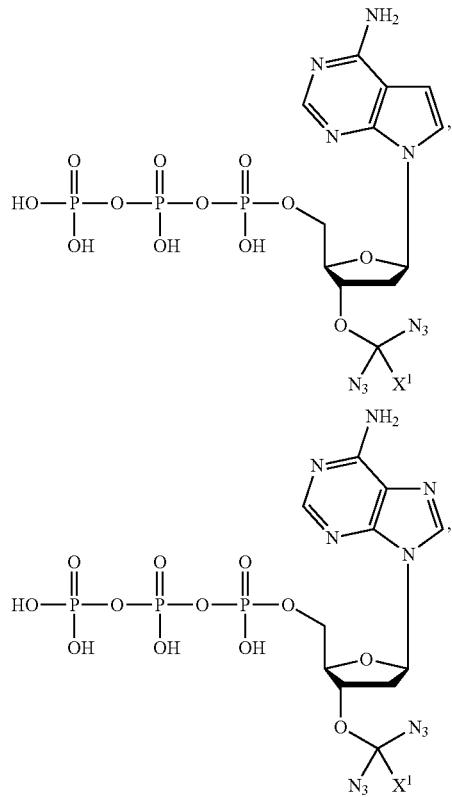
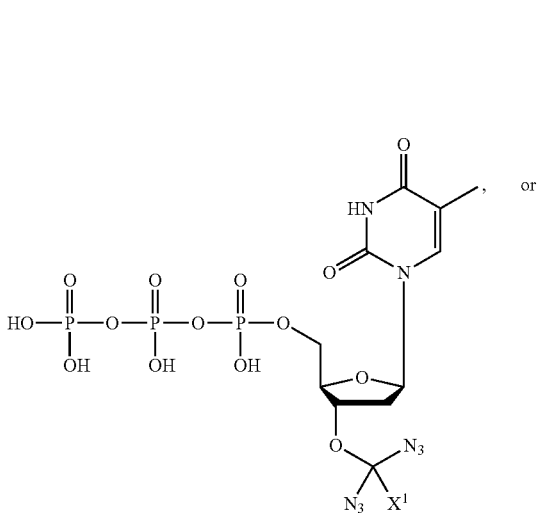
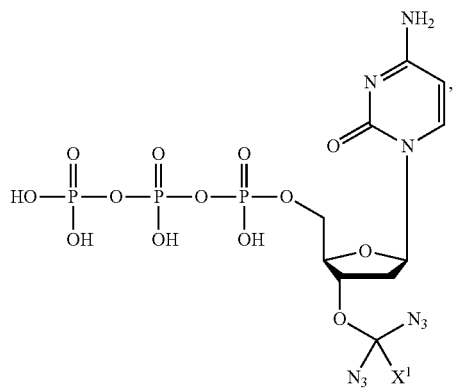
wherein $X^1$ is as described herein, including embodiments.
In embodiments, the nucleotide analogue has the formula:
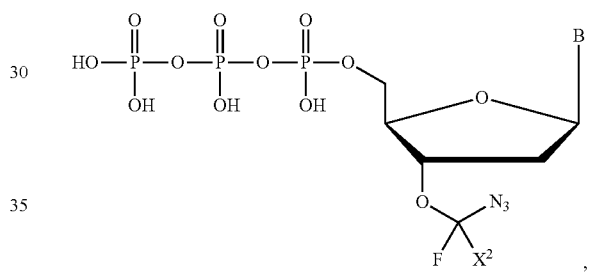
wherein B and $X^2$ are as described herein, including embodiments.
In embodiments, the nucleotide analogue has the formula:
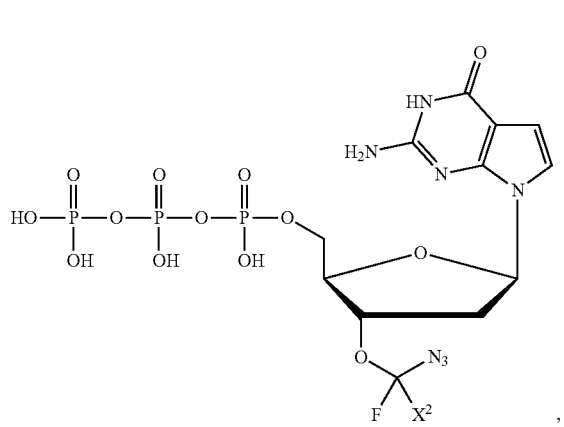

211
-continued
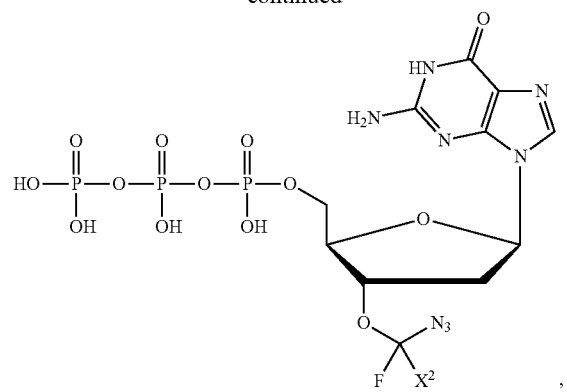
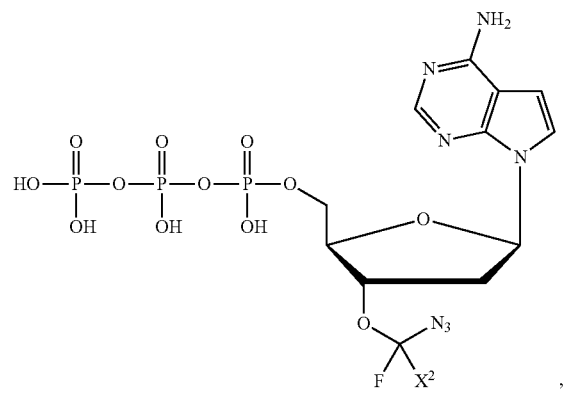
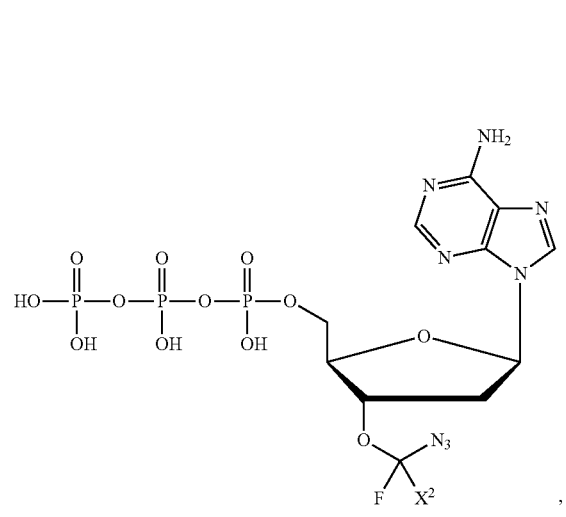
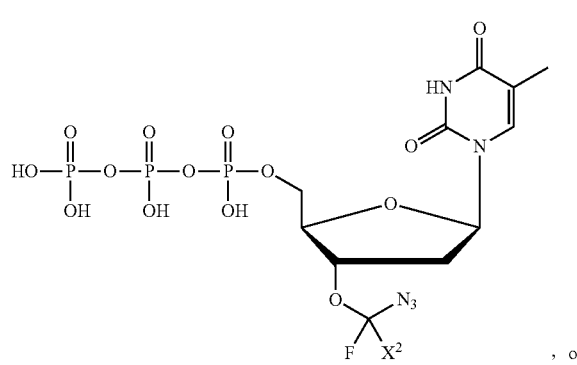
212
-continued
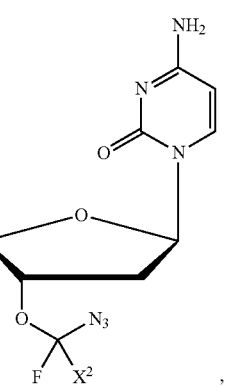
wherein $X^2$ is as described herein, including embodiments.
In embodiments, the nucleotide analogue has the formula:

-continued
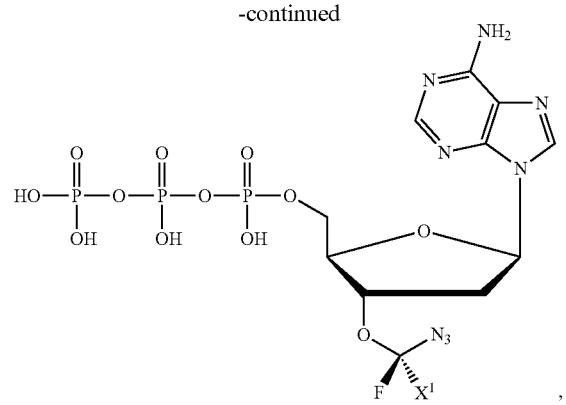
,
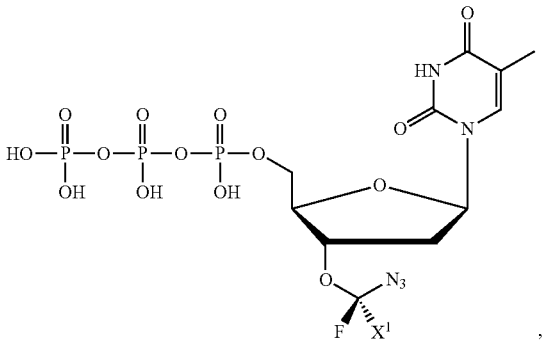
, or
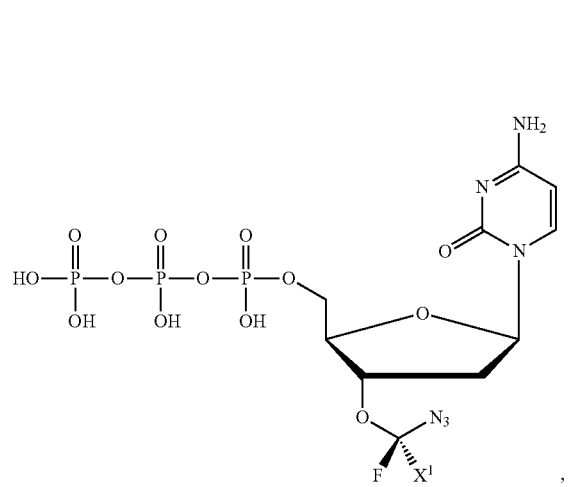
,
wherein $X^1$ is as described herein, including embodiments.
In embodiments, the nucleotide analogue has the formula:
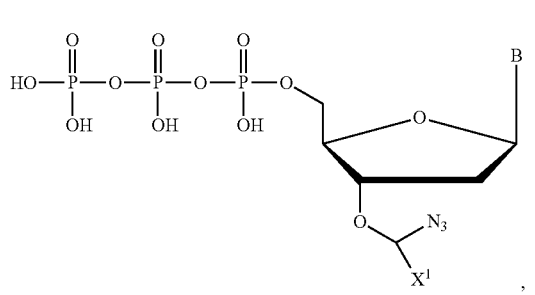
,
wherein B and $X^1$ are as described herein, including embodiments.
In embodiments, the nucleotide analogue has the formula:
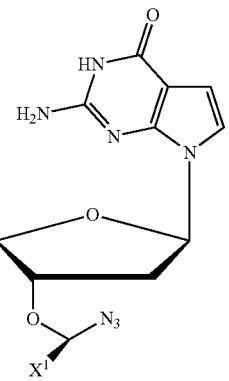
,
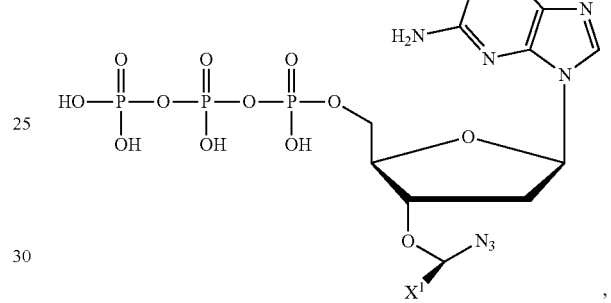
,
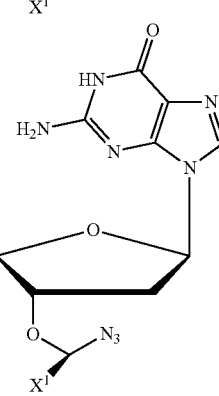
,
,
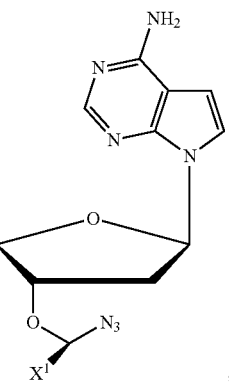
, -continued

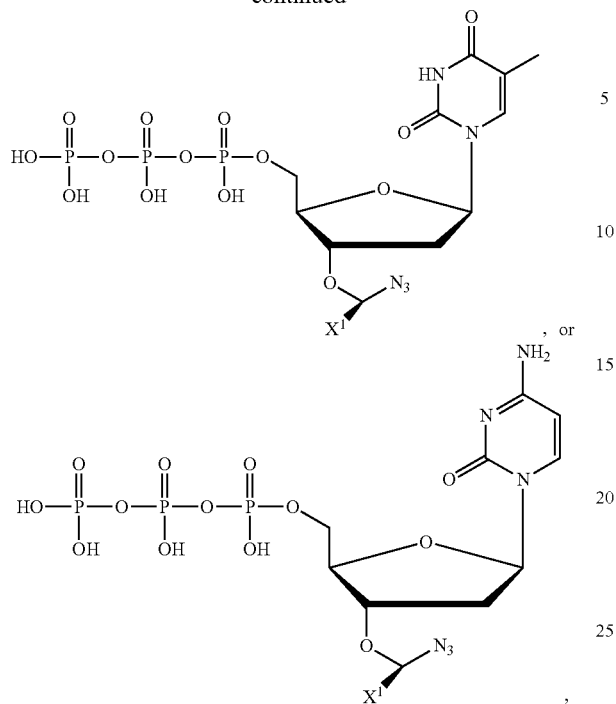

, or wherein X¹ is as described herein, including embodiments.
In embodiments, the nucleotide analogue has the formula:

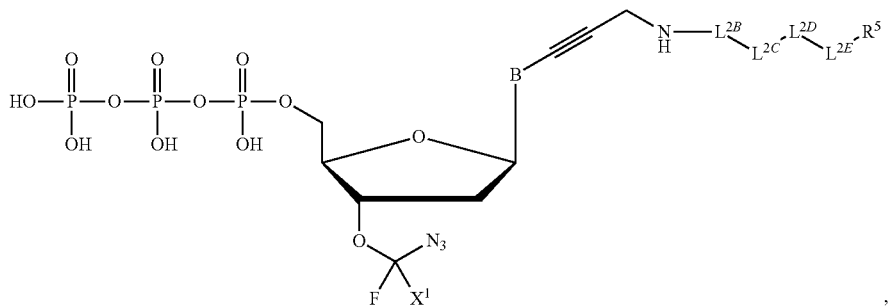

wherein $X^1$, B, $L^{2B}$, $L^{2C}$, $L^{2D}$, $L^{2E}$, and $R^5$ are as described herein, including embodiments.

In embodiments, the nucleotide analogue has the formula:

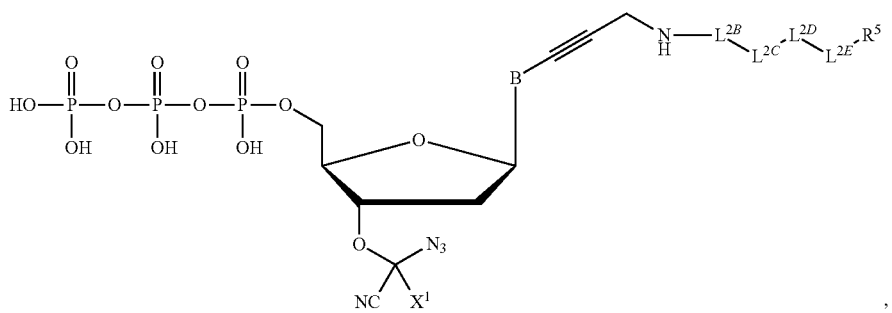

wherein $X^1$, B, $L^{2B}$, $L^{2C}$, $L^{2D}$, $L^{2E}$, and $R^5$ are as described herein, including embodiments.

In embodiments, the nucleotide analogue has the formula:

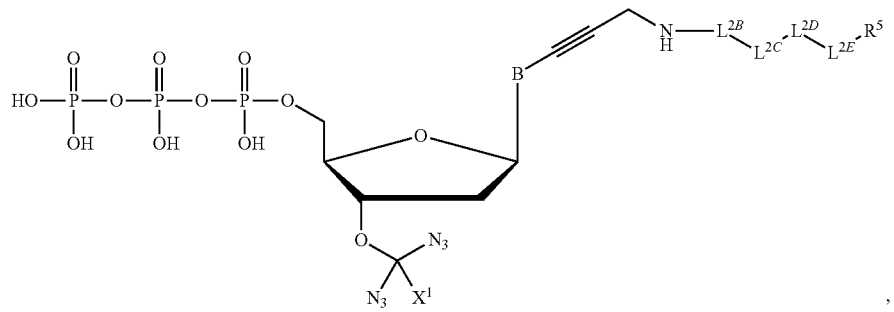

wherein $X^1$, B, $L^{2B}$, $L^{2C}$, $L^{2D}$, $L^{2E}$, and $R^5$ are as described herein, including embodiments.

In embodiments, the nucleotide analogue has the formula:

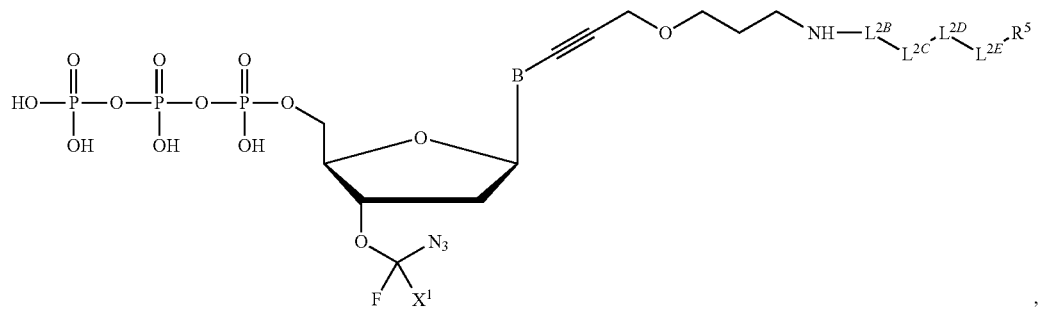

wherein $X^1$, B, $L^{2B}$, $L^{2C}$, $L^{2D}$, $L^{2E}$, and $R^5$ are as described herein, including embodiments.

In embodiments, the nucleotide analogue has the formula:

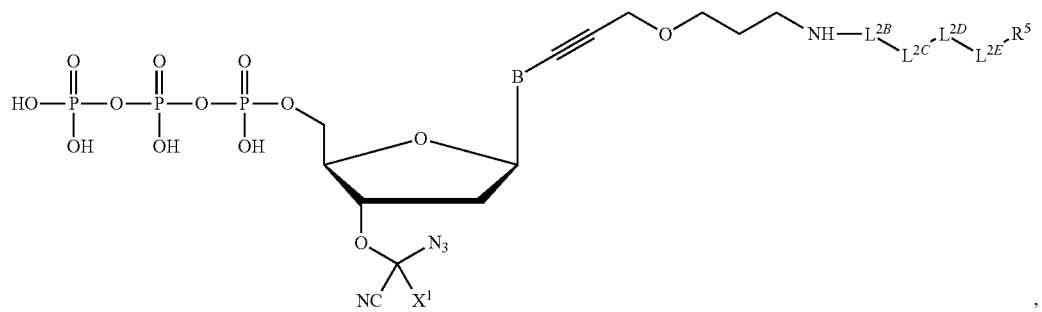

wherein $X^1$, B, $L^{2B}$, $L^{2C}$, $L^{2D}$, $L^{2E}$, and $R^5$ areas described herein, including embodiments.

In embodiments, the nucleotide analogue has the formula:
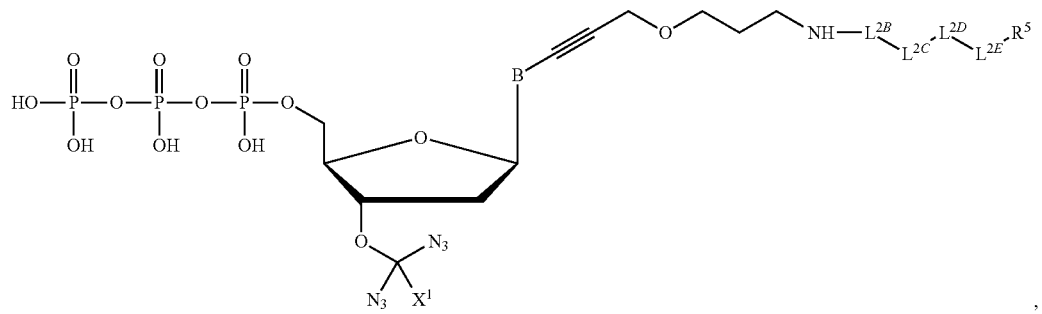
wherein $X^1$, B, $L^{2B}$, $L^{2C}$, $L^{2D}$, $L^{2E}$, and $R^5$ are as described herein, including embodiments.
In embodiments, the nucleotide analogue has the formula:
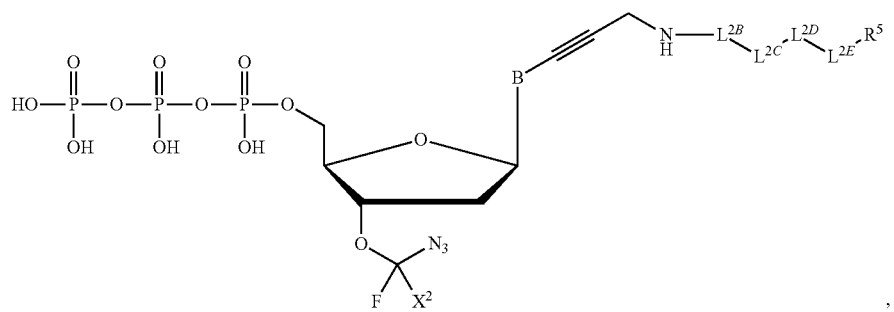
wherein $X^2$, B, $L^{2B}$, $L^{2C}$, $L^{2D}$, $L^{2E}$, and $R^5$ are as described herein, including embodiments.
In embodiments, the nucleotide analogue has the formula:
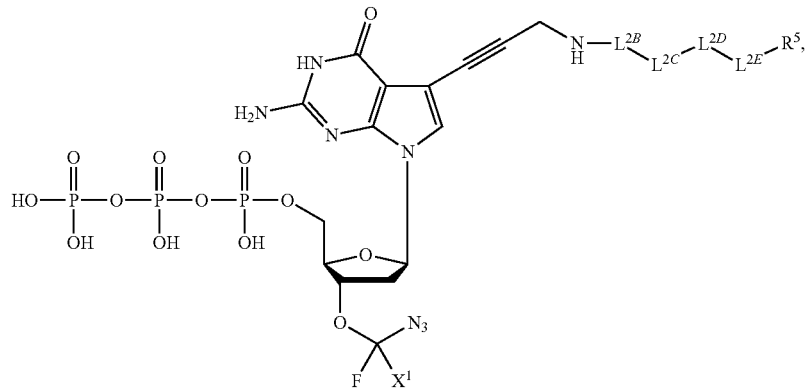

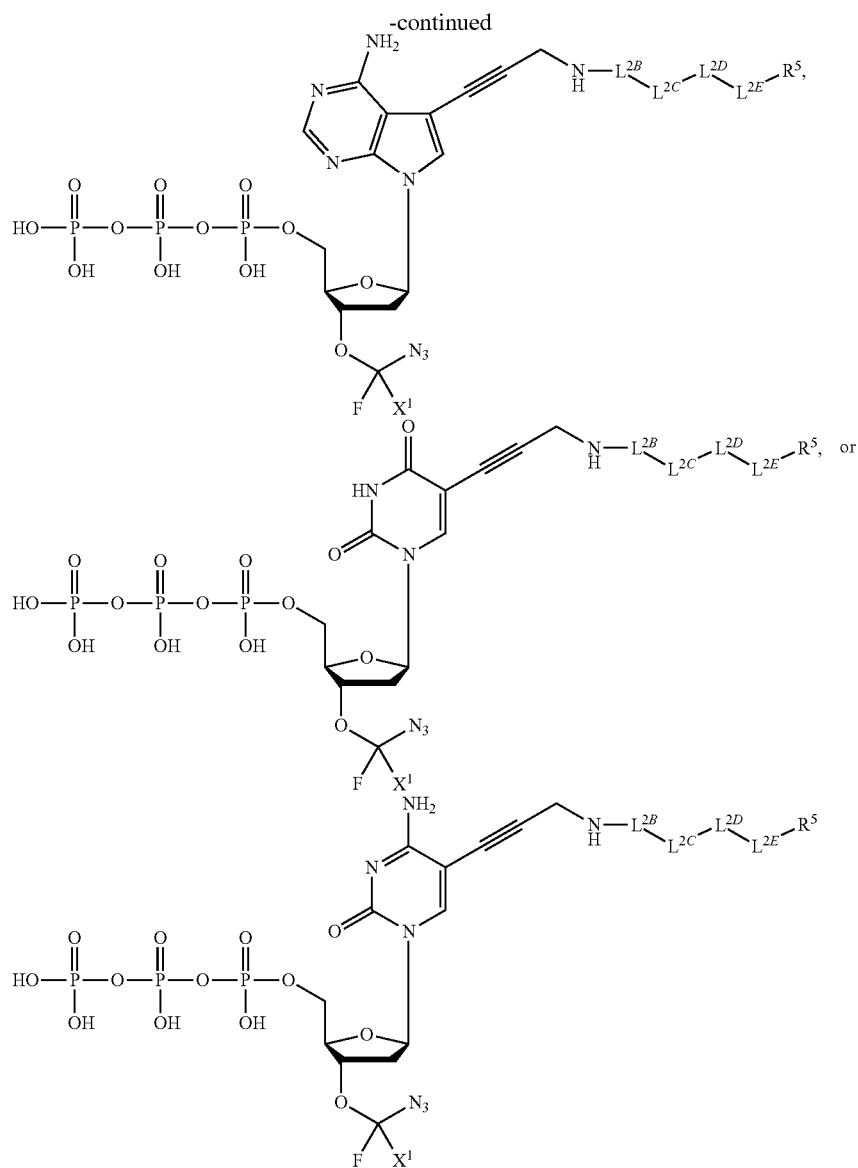
wherein $X^1$, $L^{2B}$, $L^{2C}$, $L^{2D}$, $L^{2E}$, and $R^5$ are as described herein, including embodiments.
In embodiments, the nucleotide analogue has the formula:
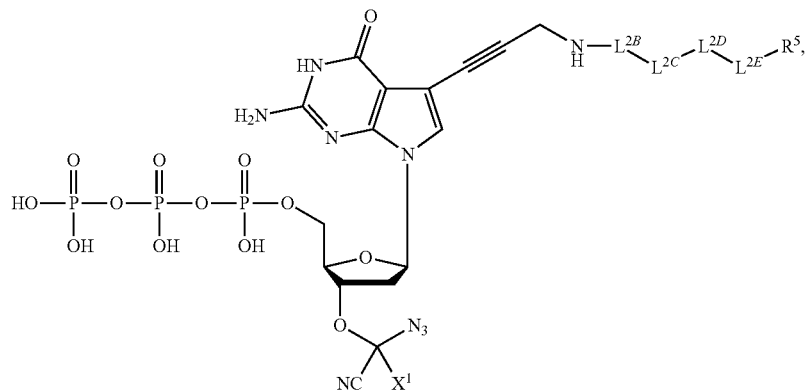

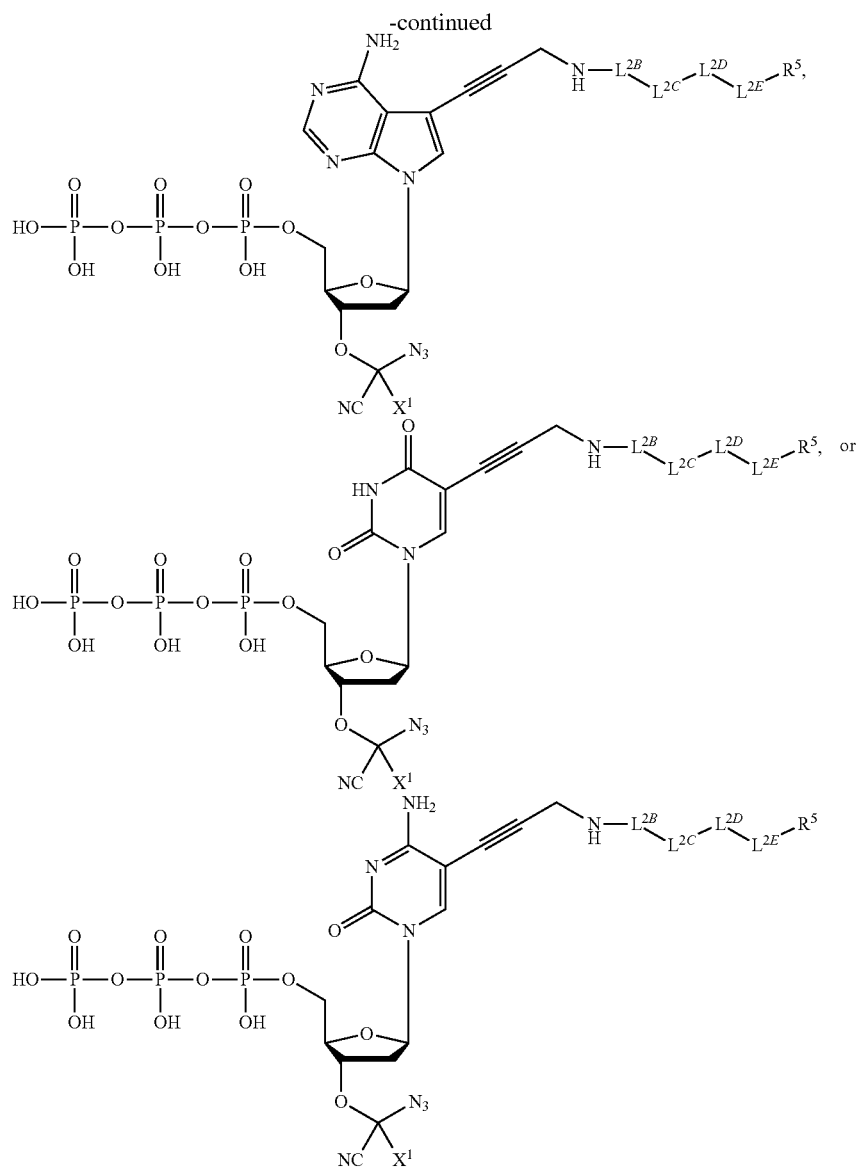
wherein $X^1$, $L^{2B}$, $L^{2C}$, $L^{2D}$, $L^{2E}$, and $R^5$ are as described herein, including embodiments.
In embodiments, the nucleotide analogue has the formula:
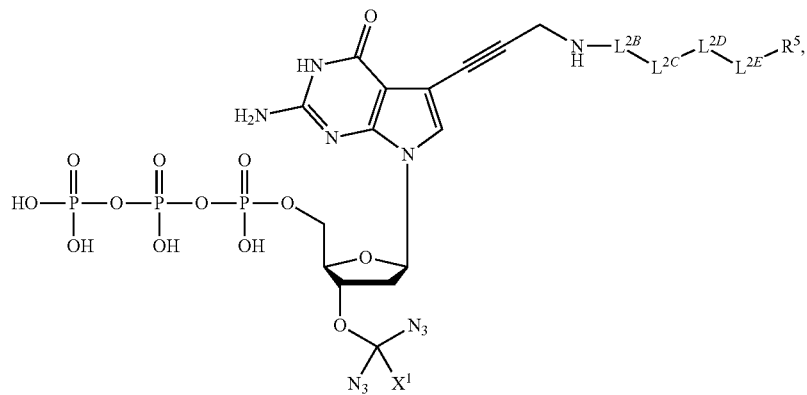

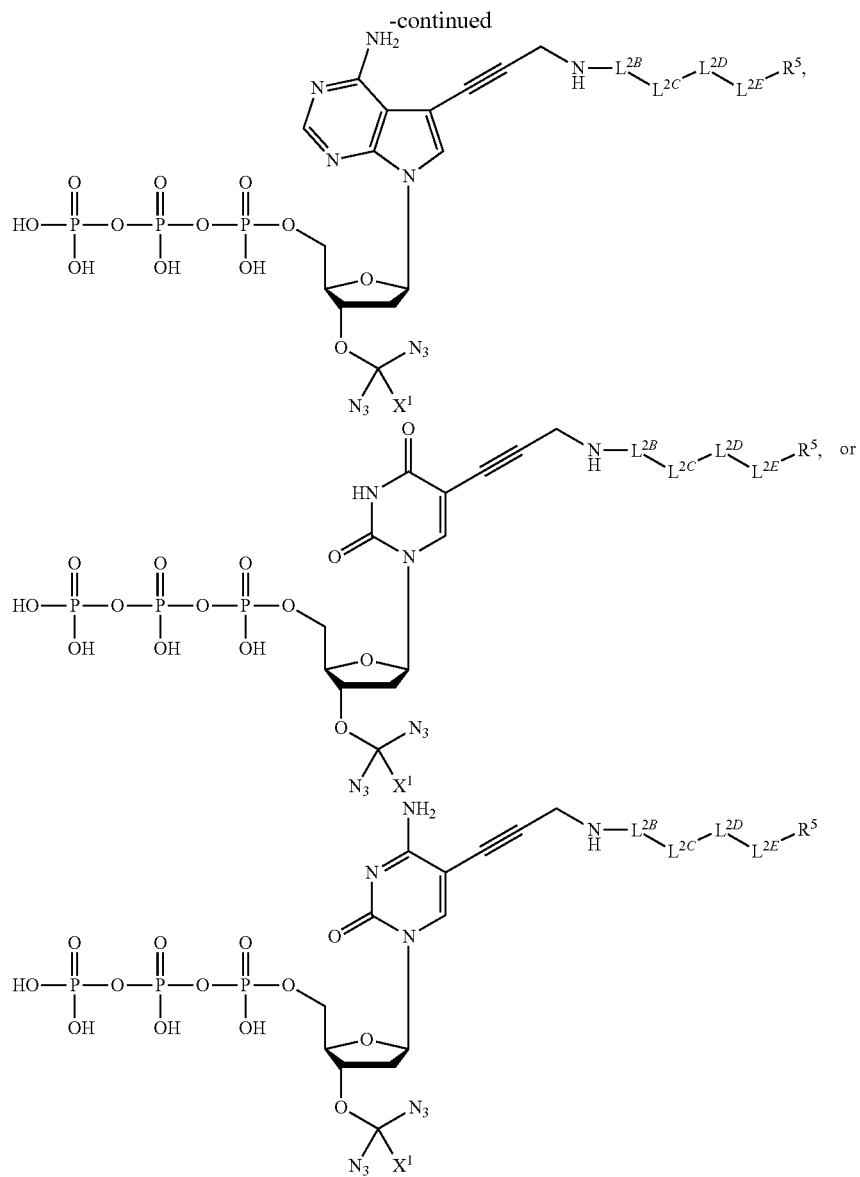
wherein $X^1$, $L^{2B}$, $L^{2C}$, $L^{2D}$, $L^{2E}$, and $R^5$ are as described herein, including embodiments.
In embodiments, the nucleotide analogue has the formula:
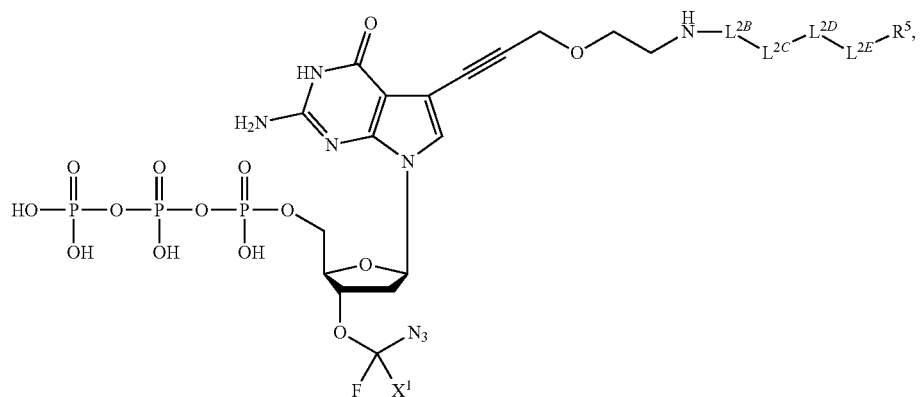

-continued
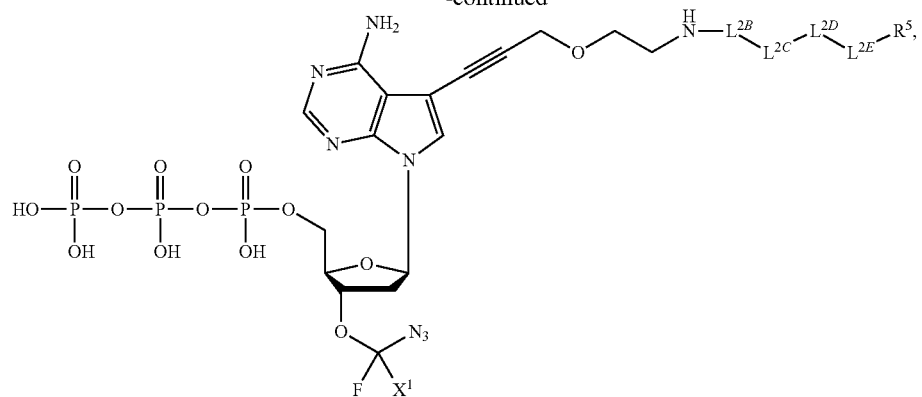
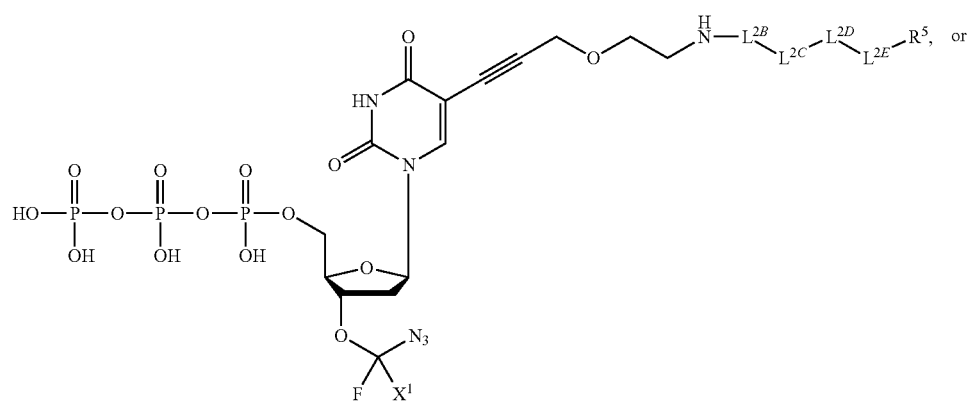
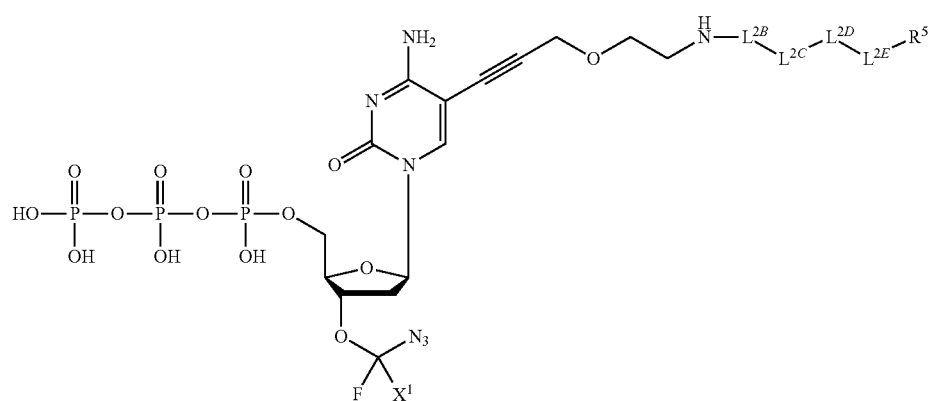
wherein $X^1$, $L^{2B}$, $L^{2C}$, $L^{2D}$, $L^{2E}$, and $R^5$ are as described herein, including embodiments.

In embodiments, the nucleotide analogue has the formula:
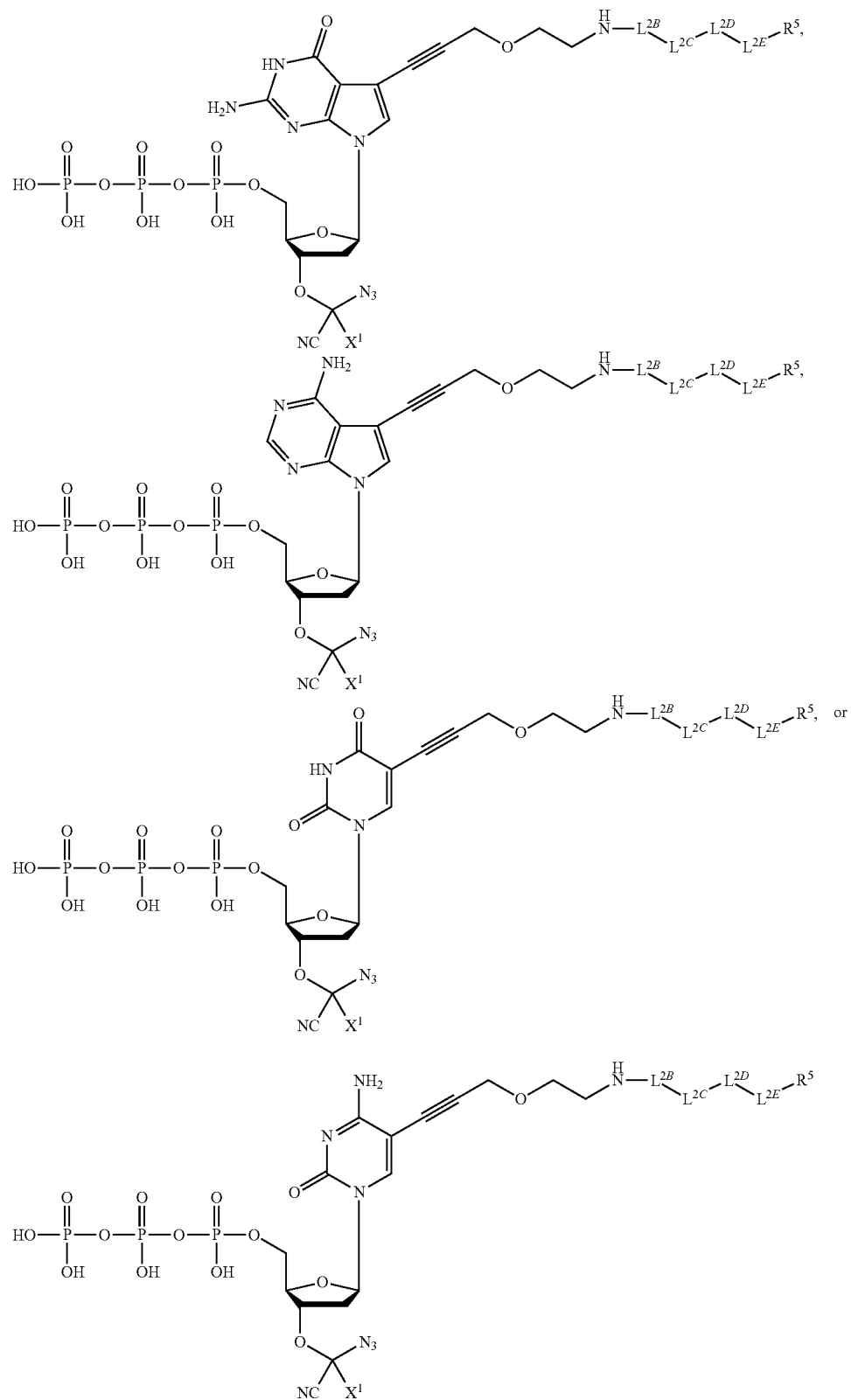
wherein $X^1$, $L^{2B}$, $L^{2C}$, $L^{2D}$, $L^{2E}$, and $R^5$ are as described herein, including embodiments.

In embodiments, the nucleotide analogue has the formula:
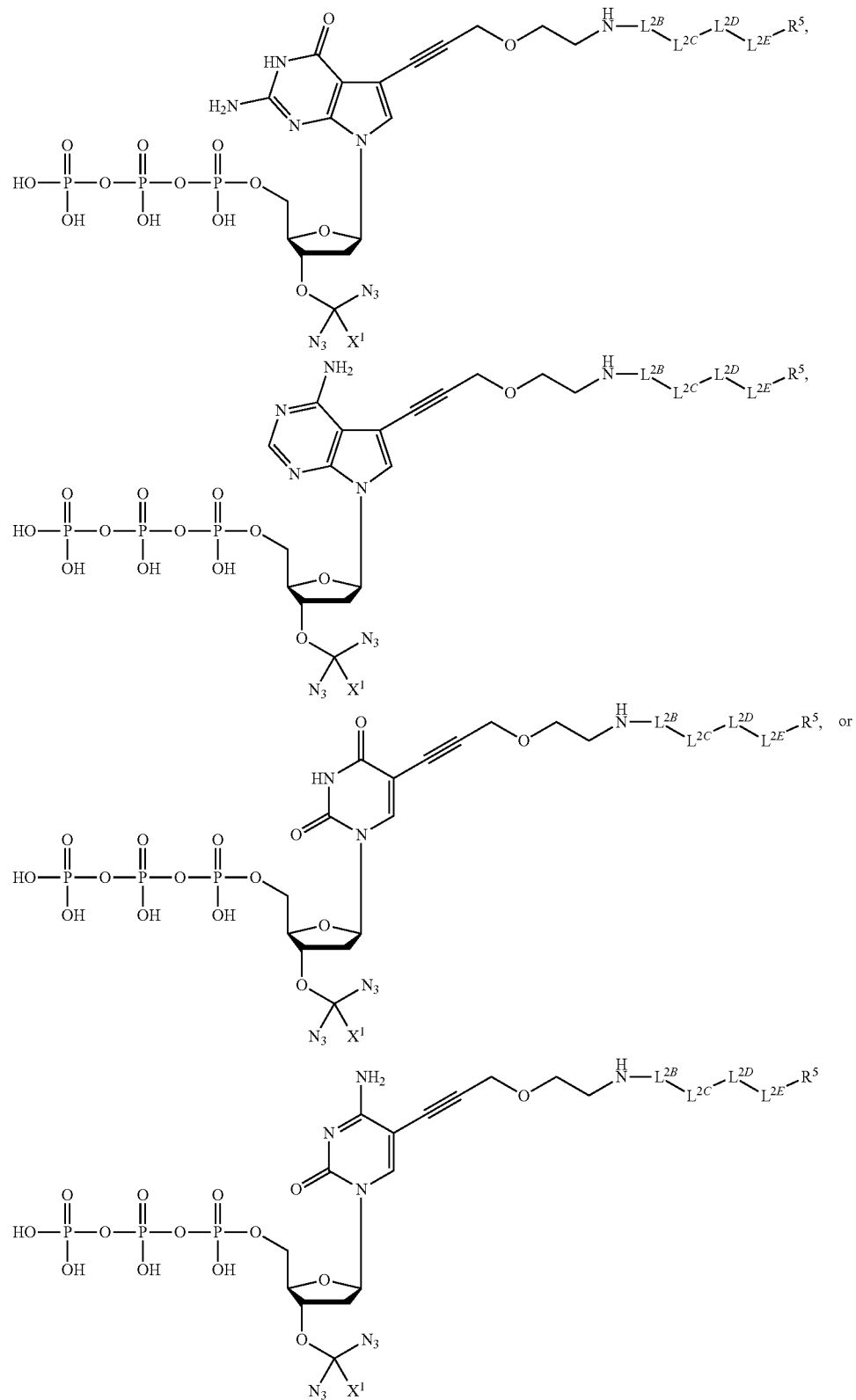
wherein $X^1$, $L^{2B}$, $L^{2C}$, $L^{2D}$, $L^{2E}$, and $R^5$ are as described herein, including embodiments.

In embodiments, the nucleotide analogue has the formula:
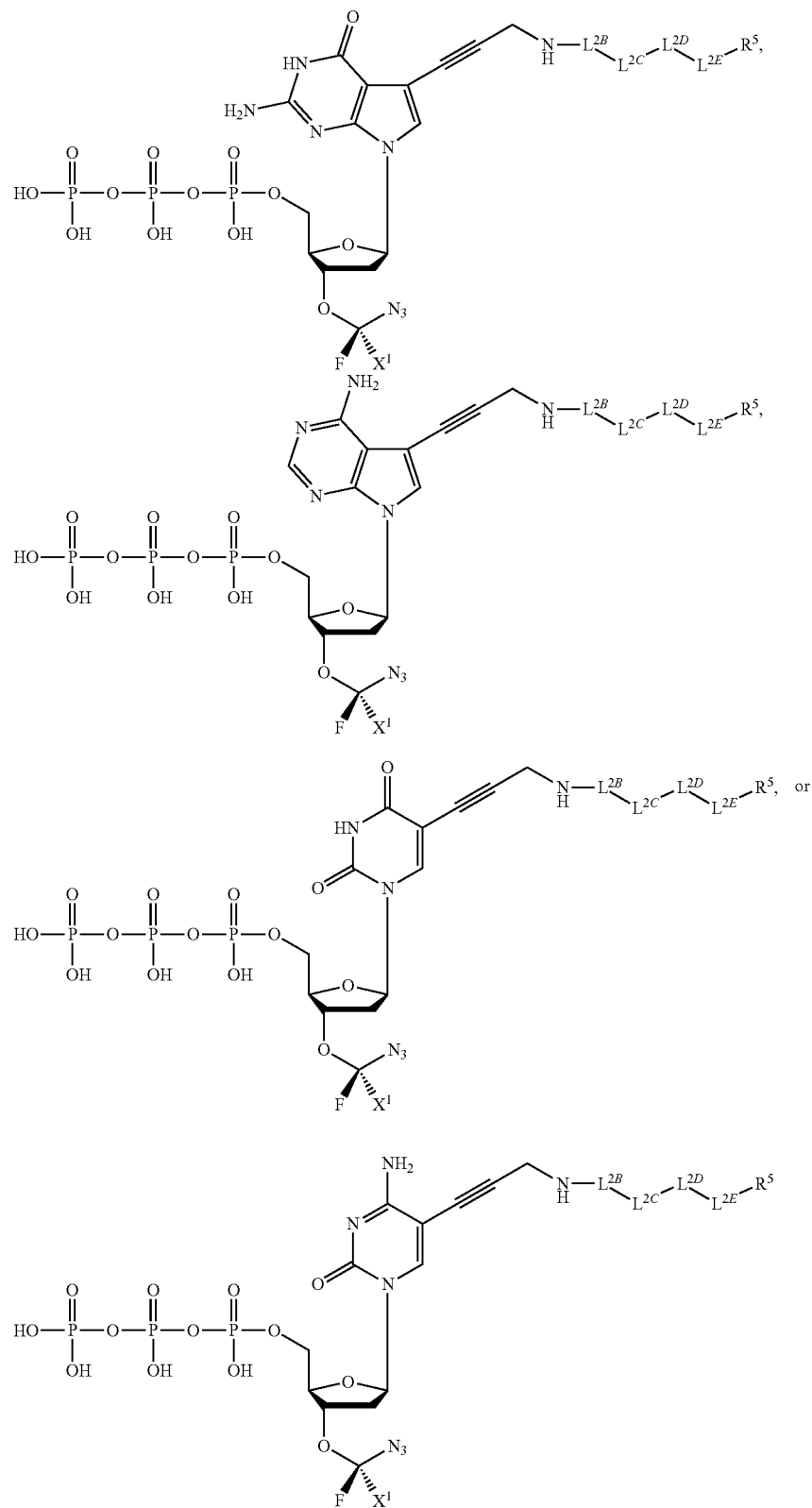
wherein $X^1$, $L^{2B}$, $L^{2C}$, $L^{2D}$, $L^{2E}$, and $R^5$ are as described herein, including embodiments.

In embodiments, the nucleotide analogue has the formula:
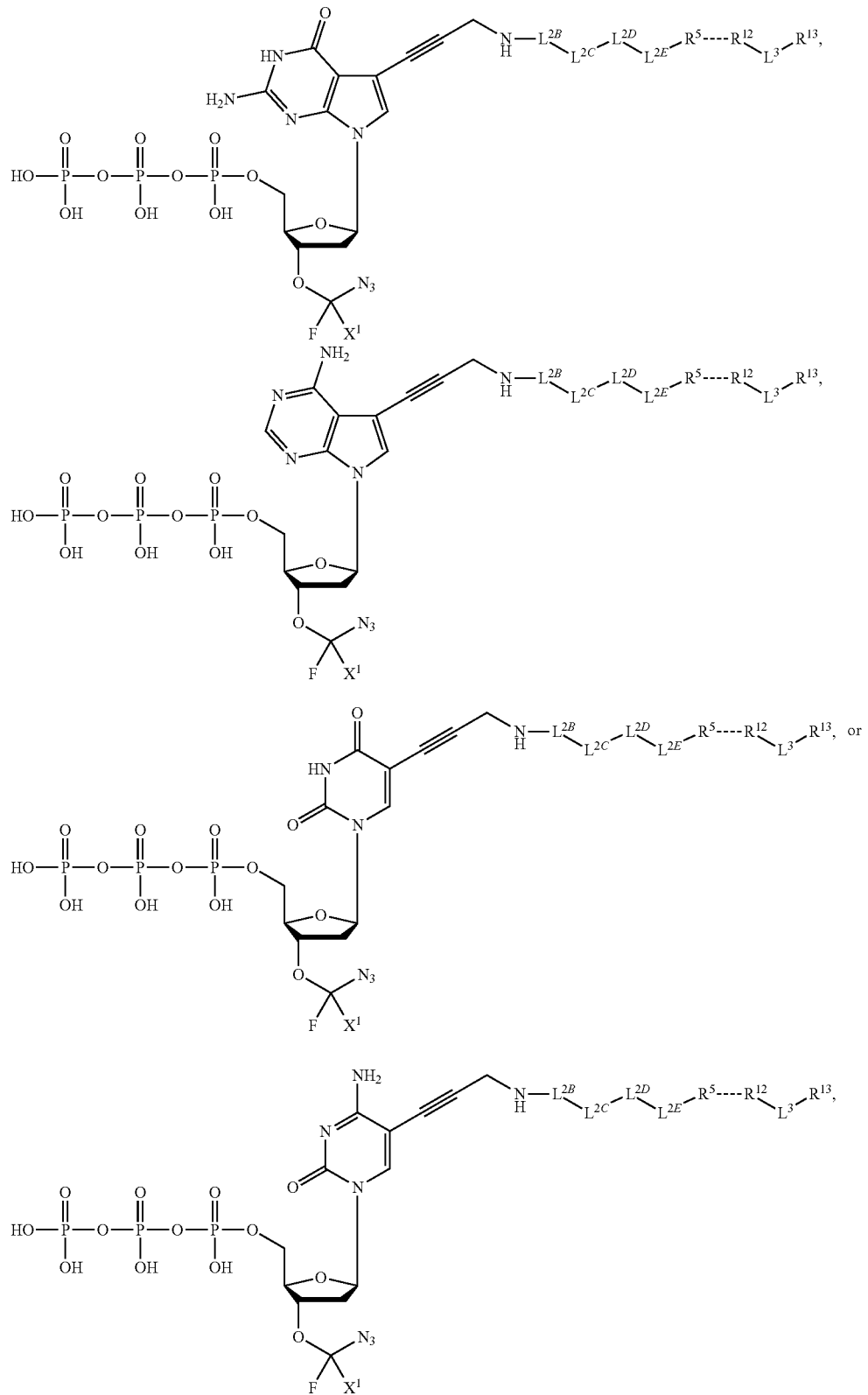
wherein $X^1$, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:
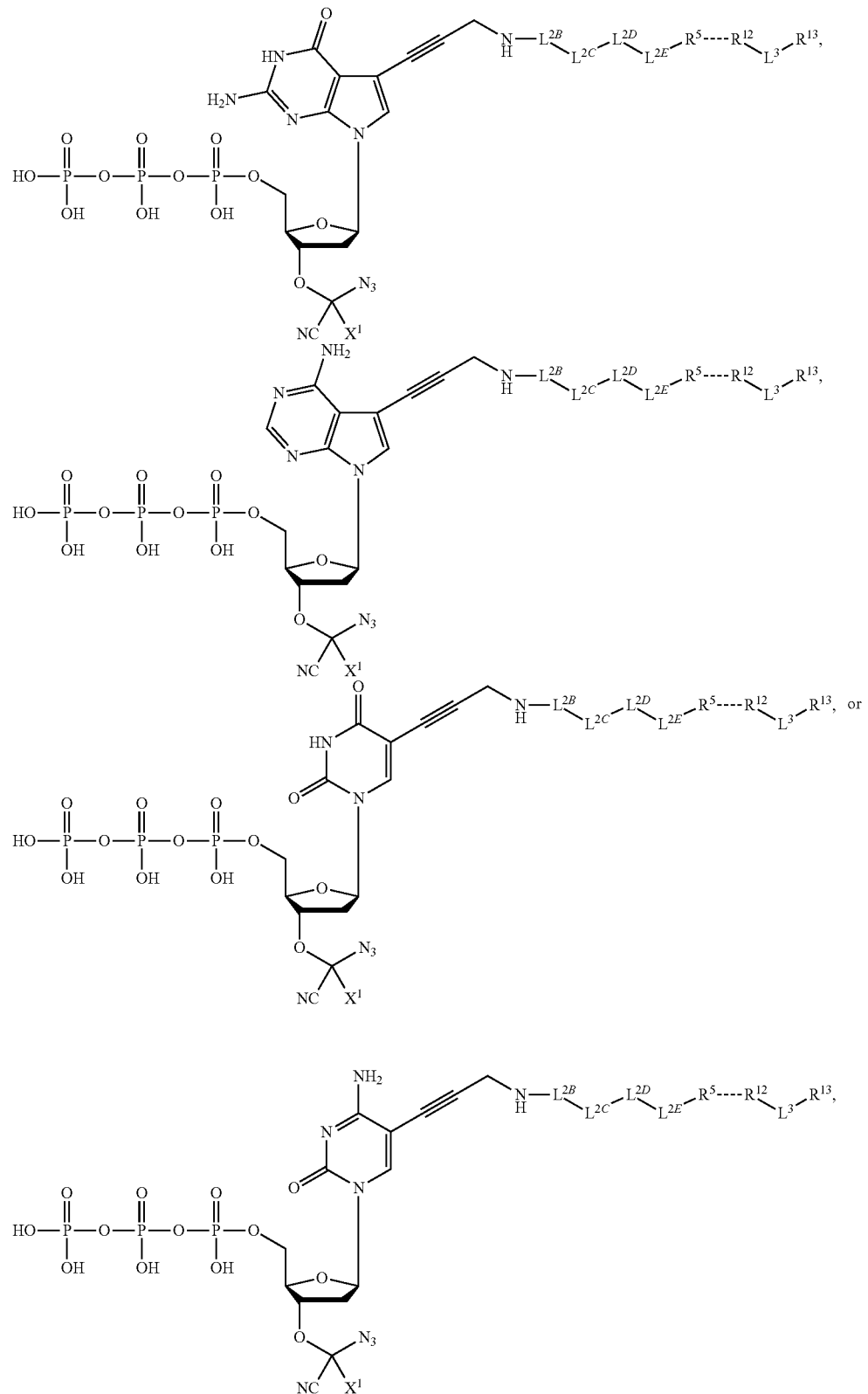
wherein $X^1$, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:
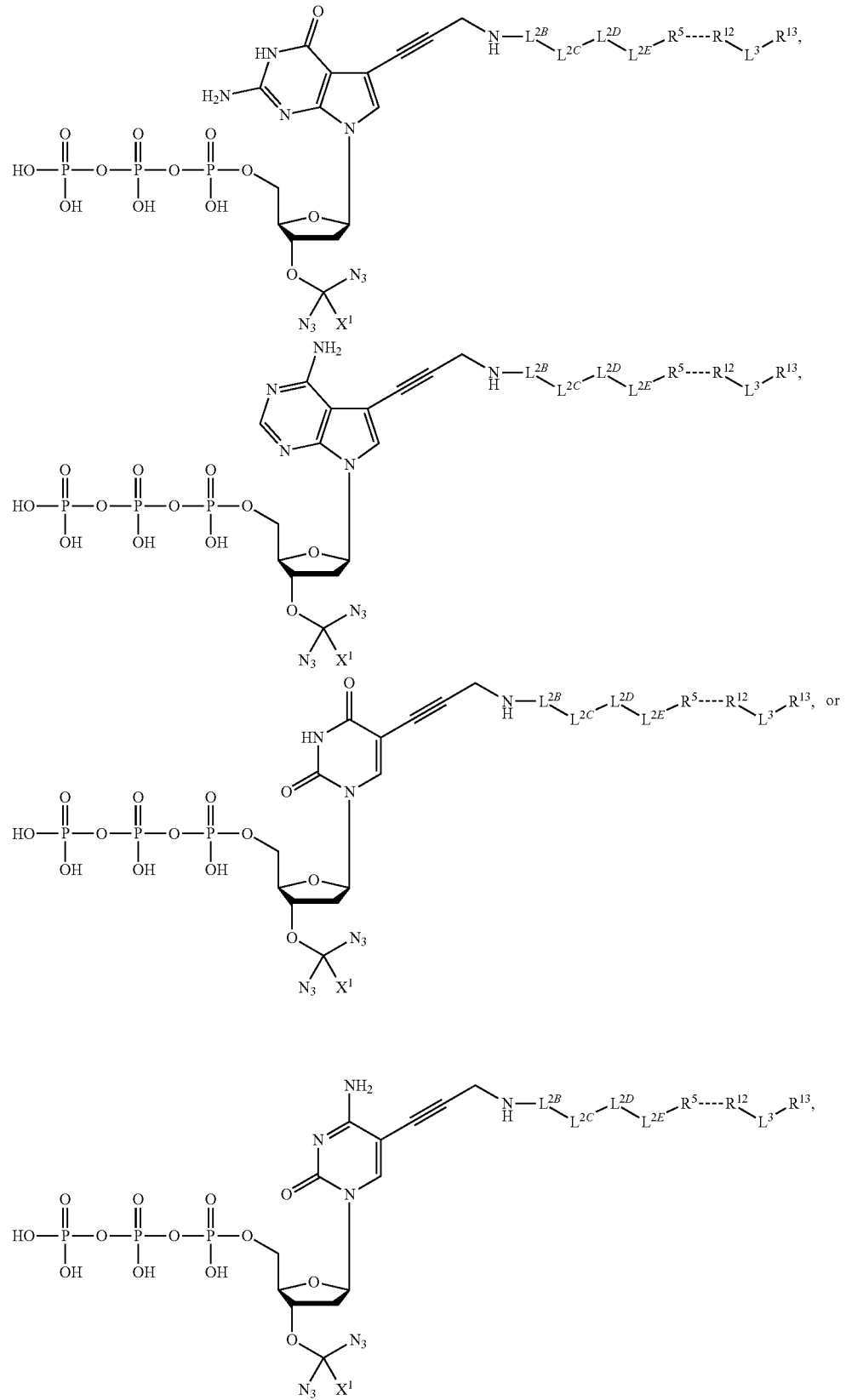

wherein $X^1$, $L^{2B}$, $L^{2C}$, $L^{2D}$, $L^{2E}$, $R^{12}$, $L^3$, $R^{13}$, and $R^5$ are as described herein, including embodiments.
In embodiments, the nucleotide analogue has the formula:
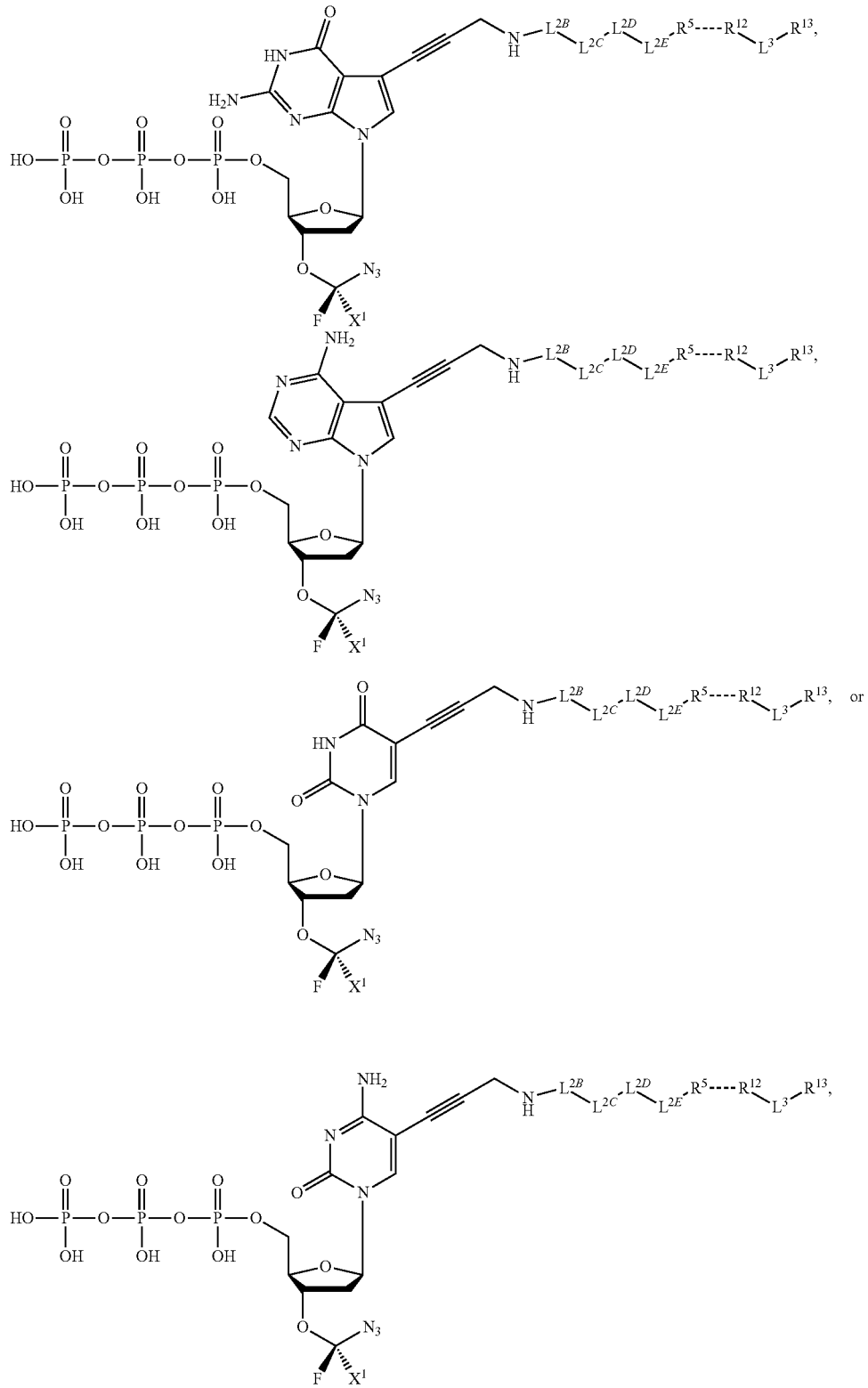
wherein $X^1$, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:
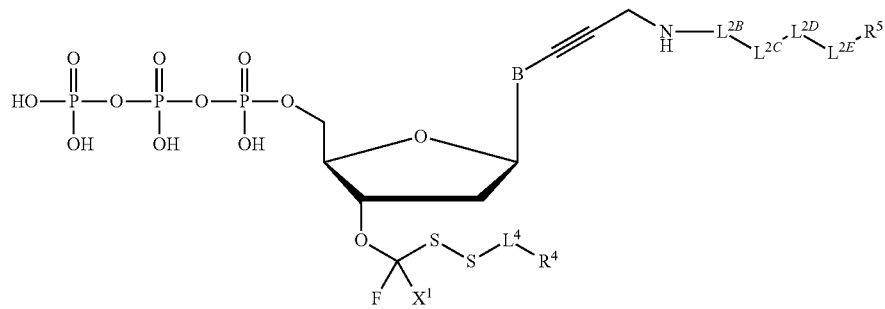
wherein B, $X^1$, $L^{2B}L^{2C}$, $L^{2D}$, $L^{2E}$, $R^5$, $L^4$, and $R^4$ are as described herein, including embodiments.
In embodiments, the nucleotide analogue has the formula:
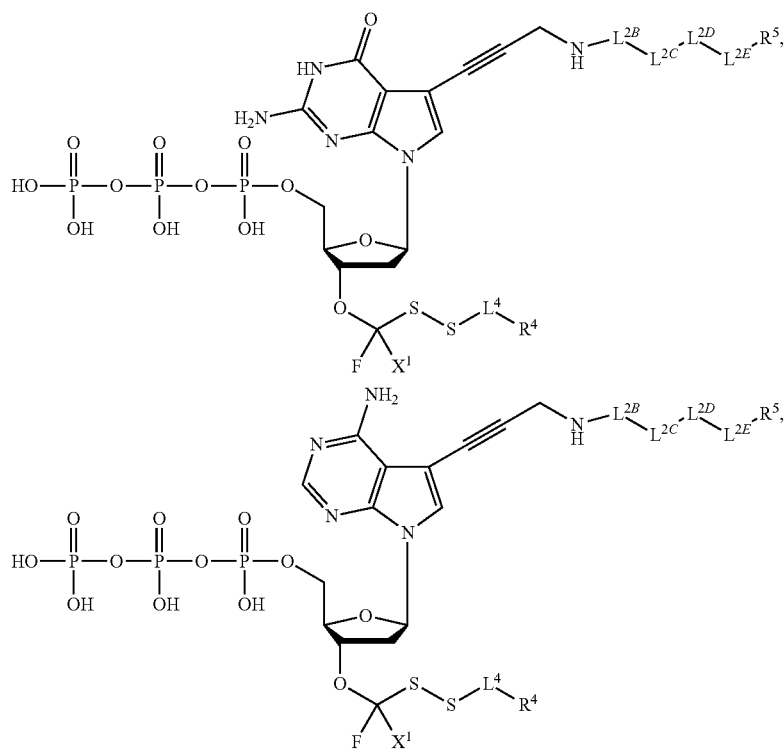
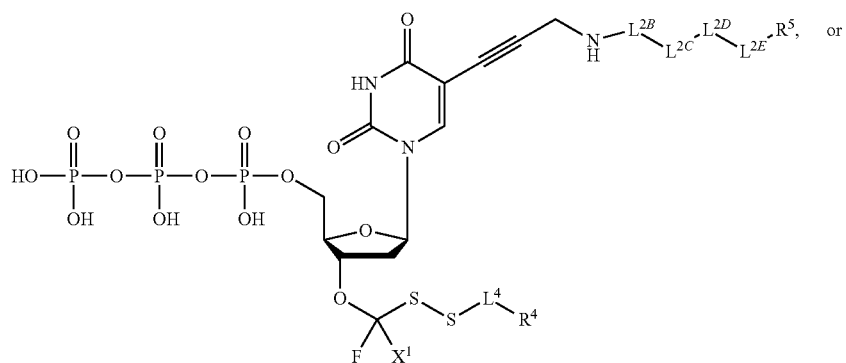

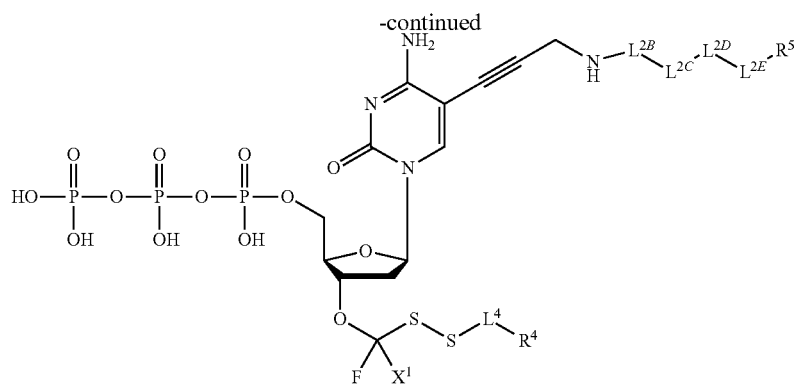
wherein $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
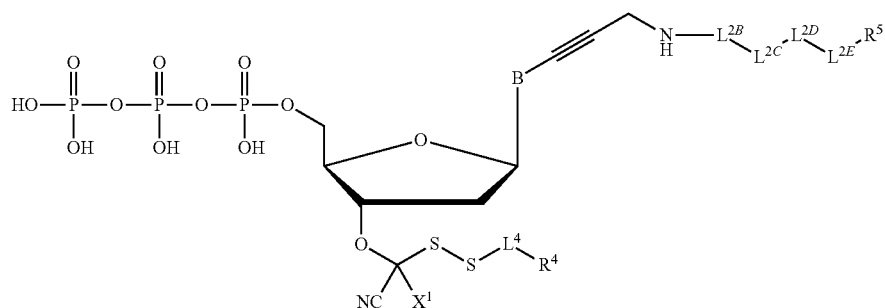
wherein B, $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
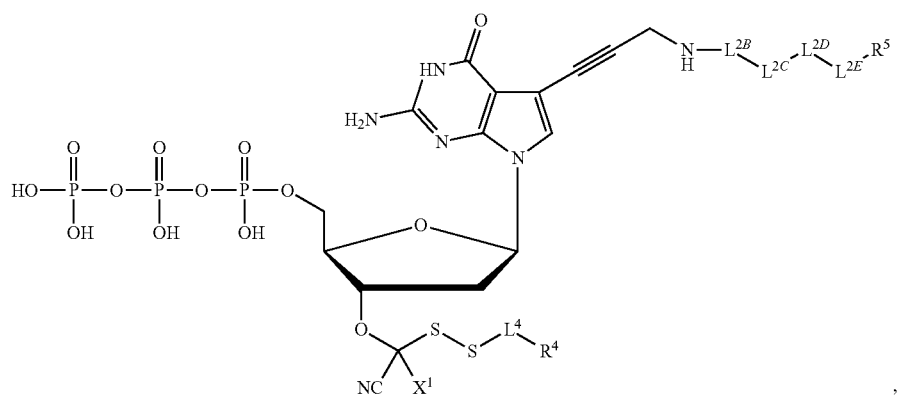
,

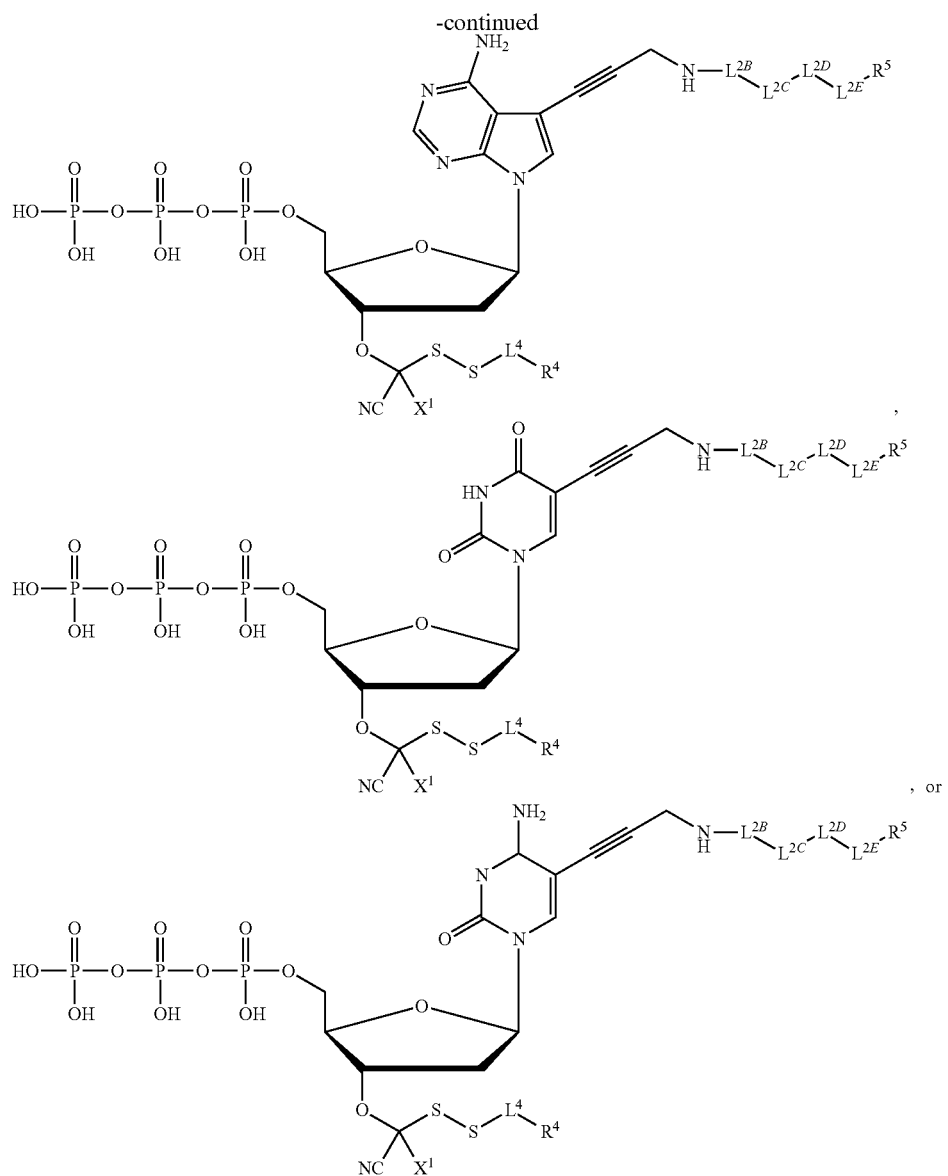
wherein $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
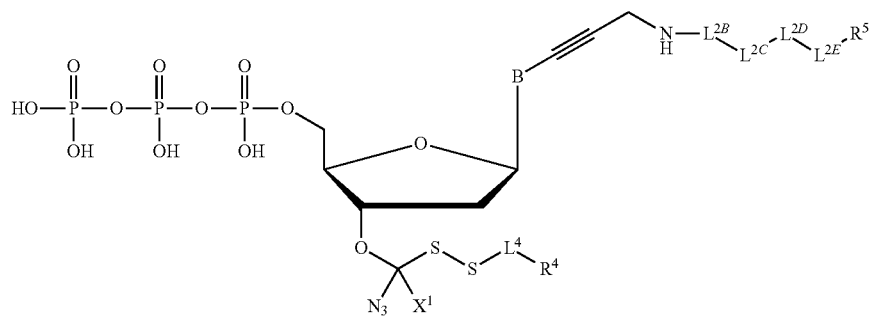

wherein B, $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
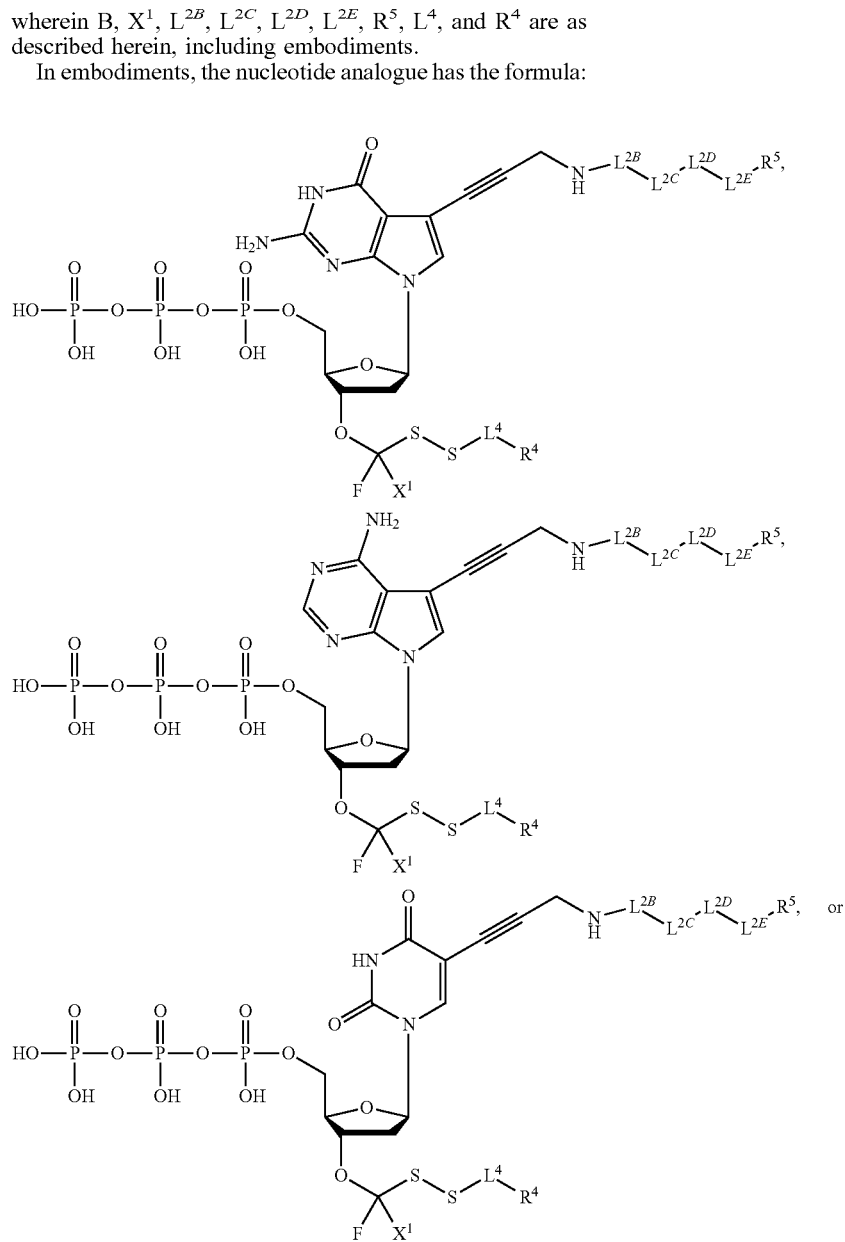

wherein $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
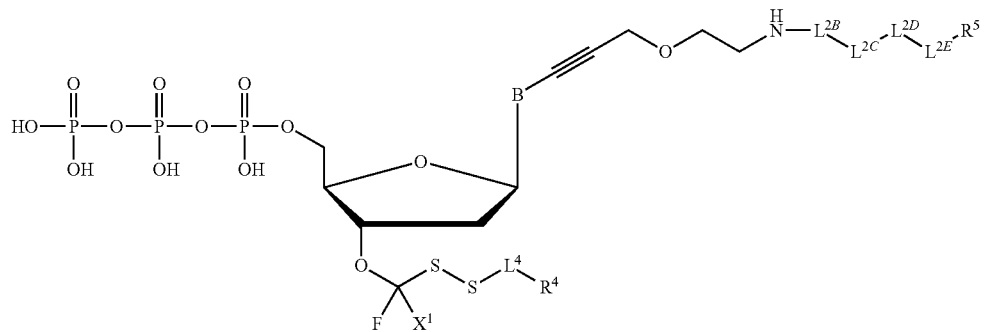
wherein B, $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
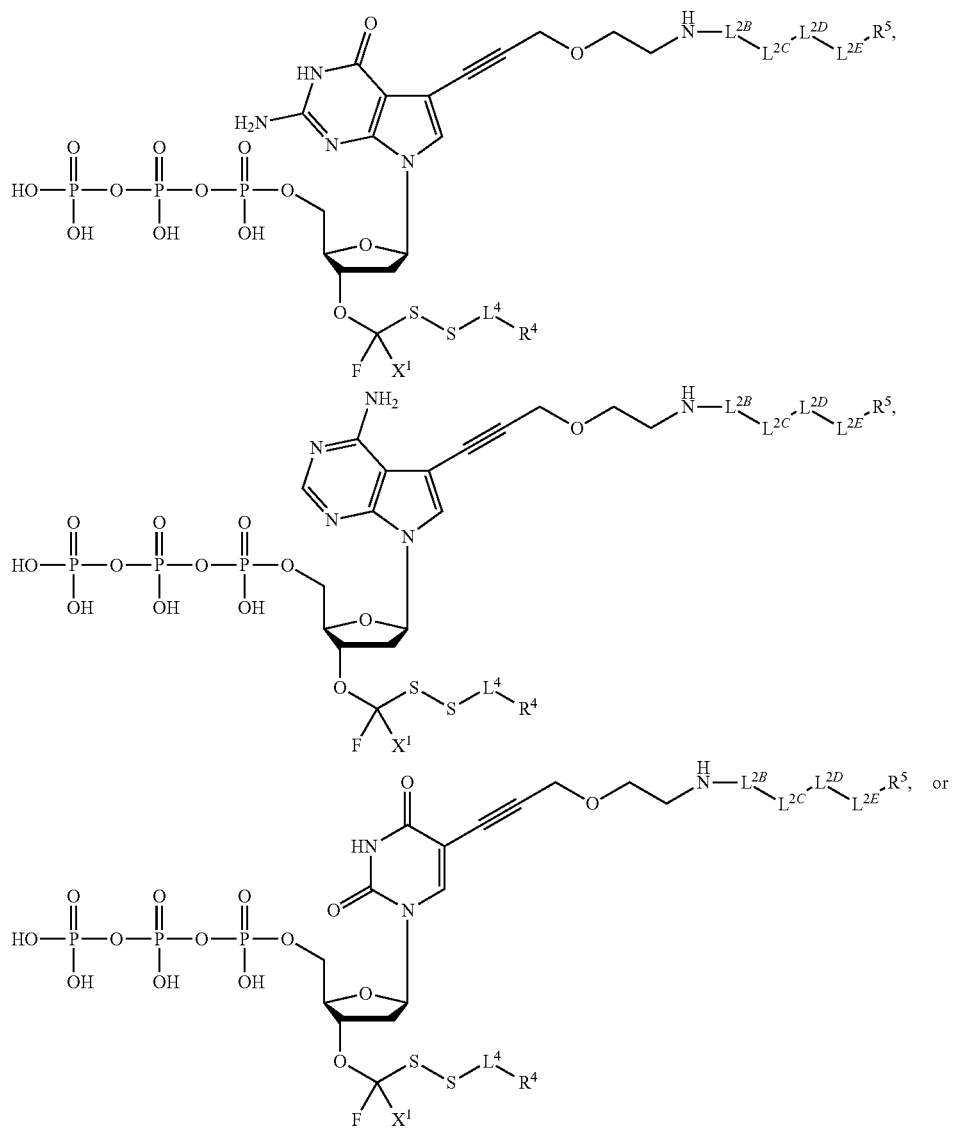

-continued
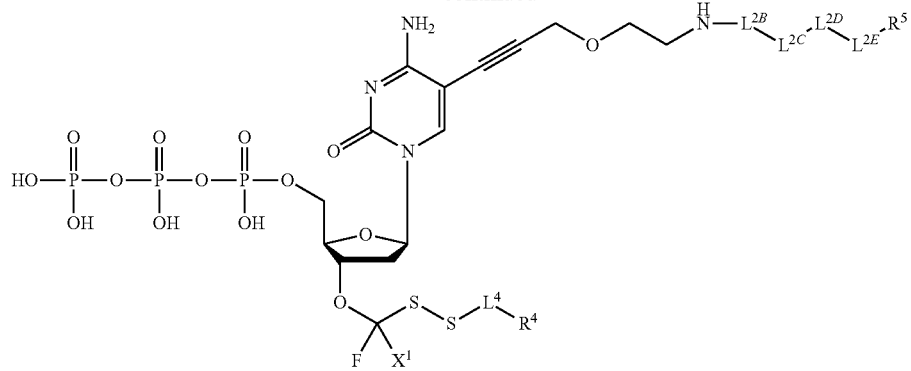
wherein $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
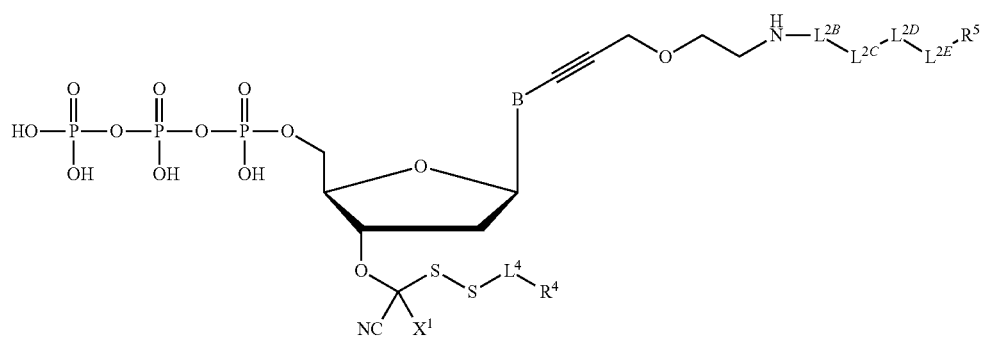
wherein B, $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
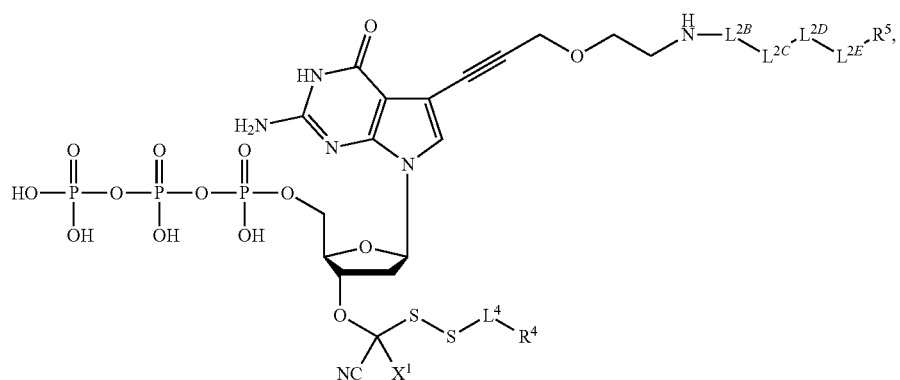

-continued
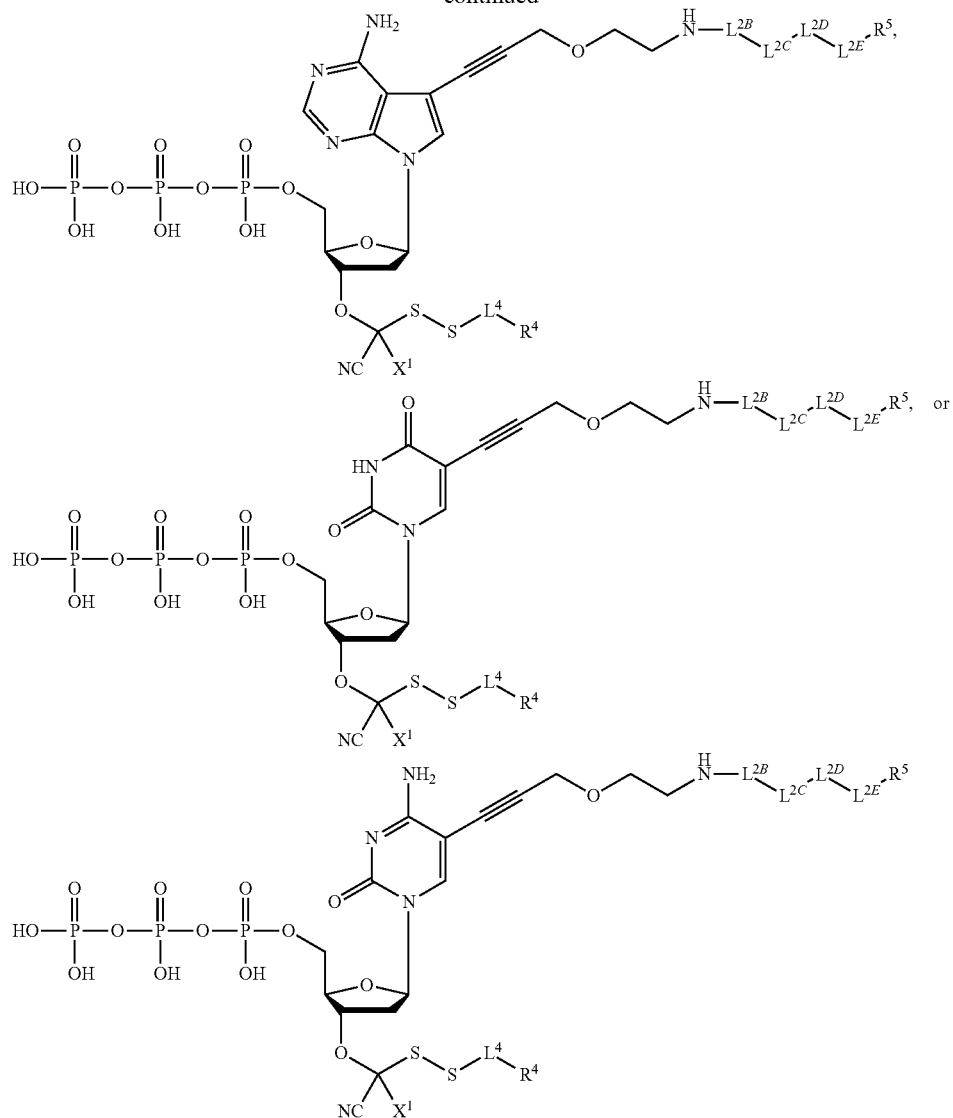
wherein $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
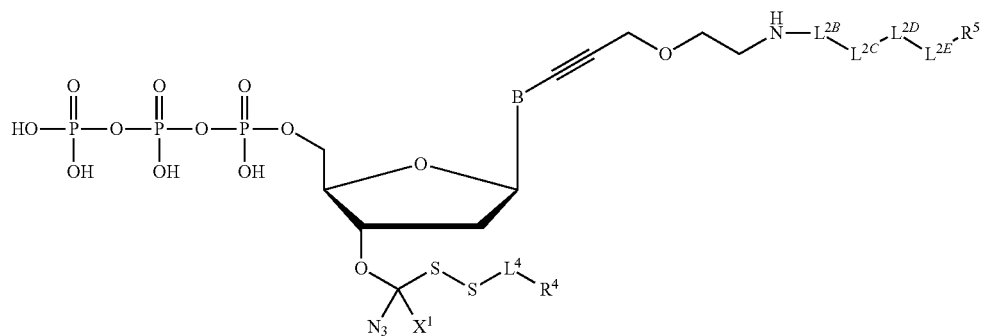
wherein B, $X^1$, $L^{2B}$, $L^{2C}$, $L^{2D}$, $L^{2E}$, $R^5$, $L^4$, and $R^4$ are as described herein, including embodiments.

In embodiments, the nucleotide analogue has the formula:
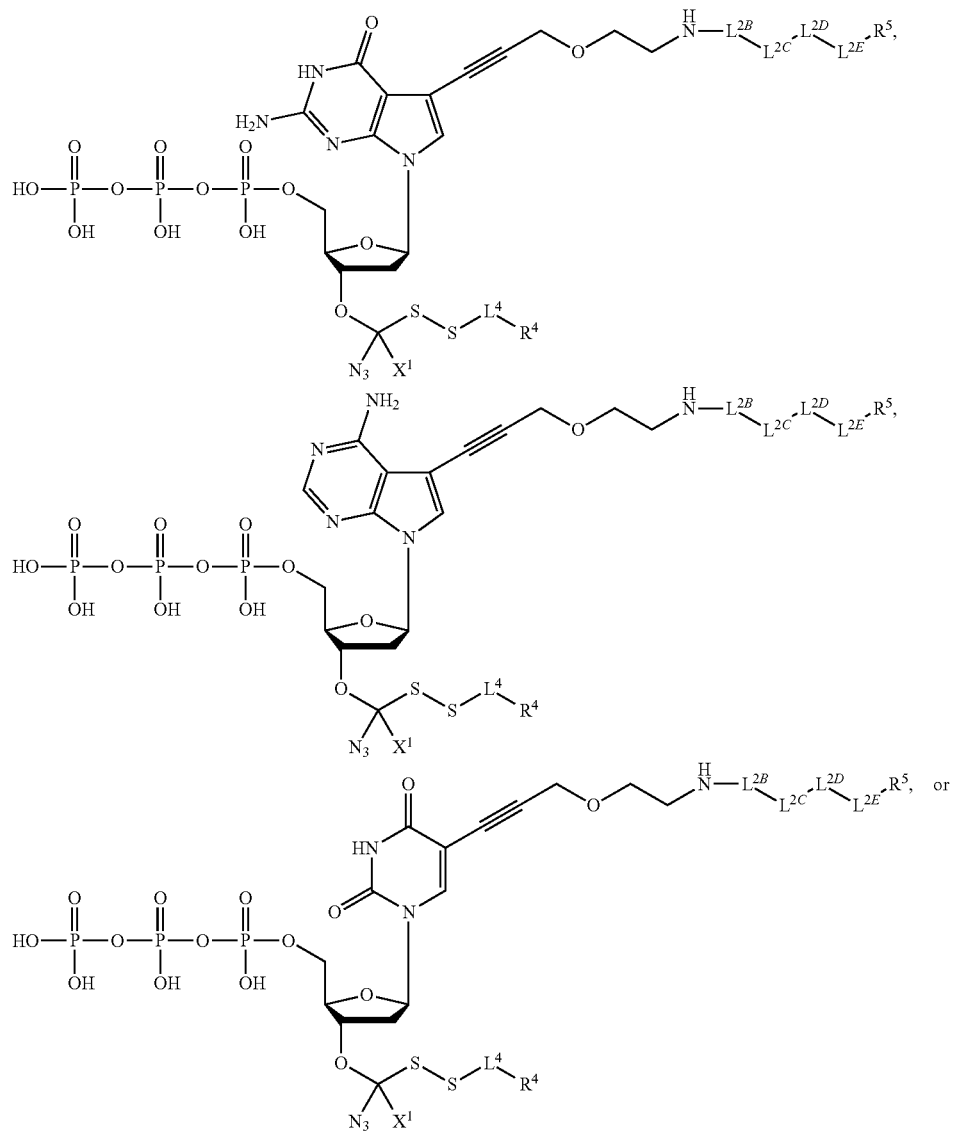
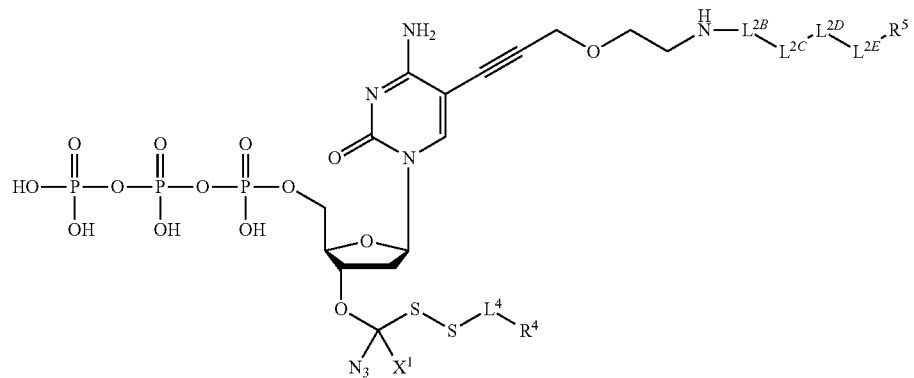

wherein $X^1$, $L^{2B}$, $L^{2C}$, $L^{2D}$, $L^{2E}$, $R^5$, $L^4$, and $R^4$ are as described herein, including embodiments.
In embodiments, the nucleotide analogue has the formula:
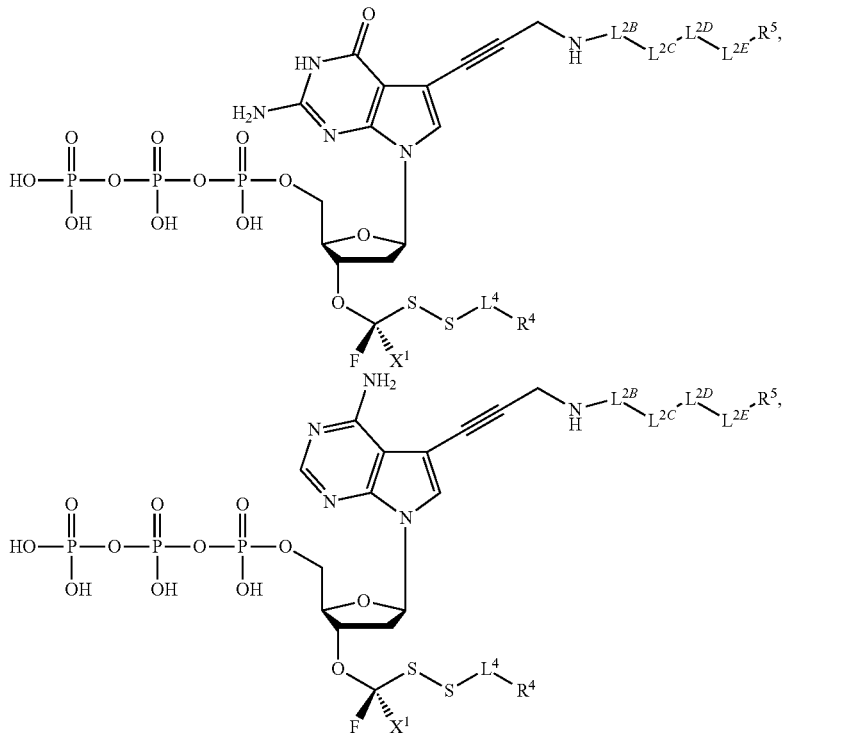
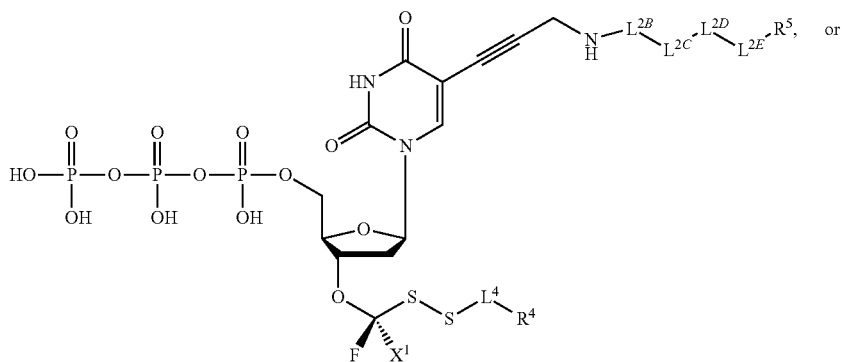
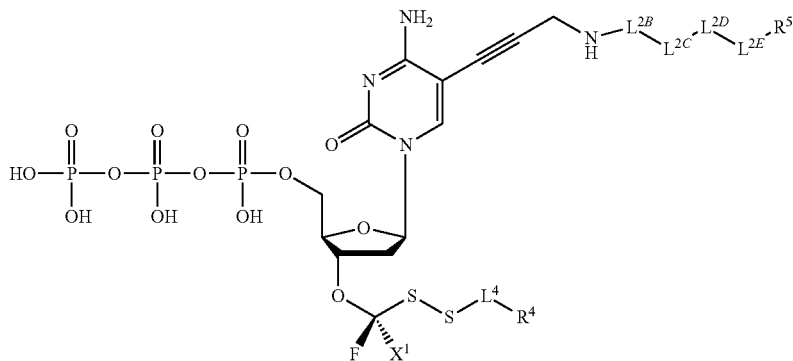
wherein $X^1$, $L^{2B}$, $L^{2C}$, $L^{2D}$, $L^{2E}$, $R^5$, $L^4$, and $R^4$ are as described herein, including embodiments.

In embodiments, the nucleotide analogue has the formula:

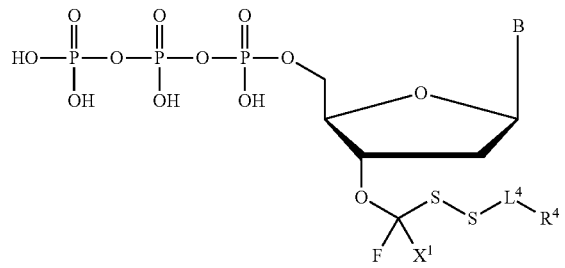

wherein $X^1$, B, $L^4$, and $R^4$ are as described herein, including embodiments.

In embodiments, the nucleotide analogue has the formula:

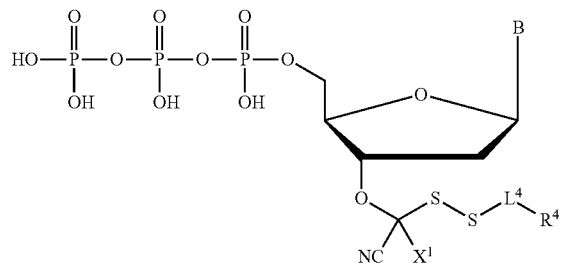

wherein $X^1$, B, $L^4$, and $R^4$ are as described herein, including embodiments.

In embodiments, the nucleotide analogue has the formula:

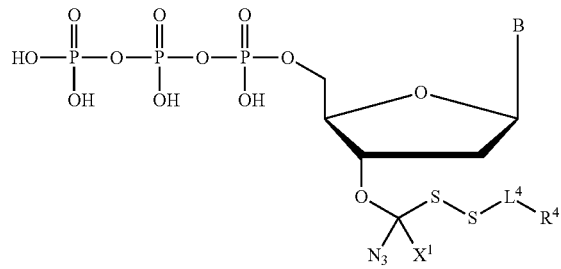

wherein $X^1$, B, $L^4$, and $R^4$ are as described herein, including embodiments.

In embodiments, the nucleotide analogue has the formula:

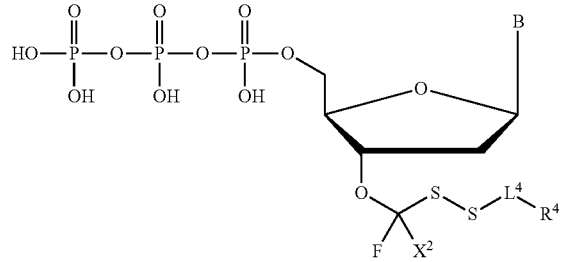

wherein $X^2$, B, $L^4$, and $R^4$ are as described herein, including embodiments.

In embodiments, the nucleotide analogue has the formula:

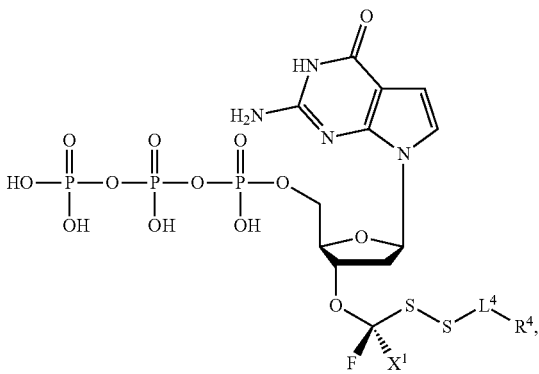

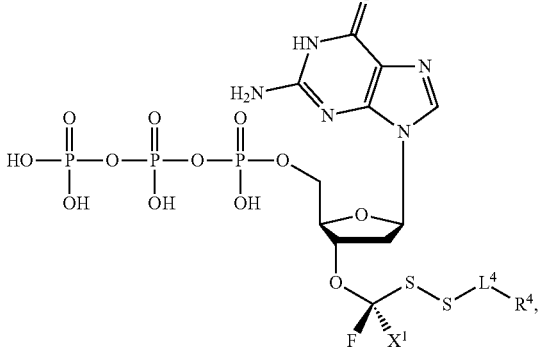

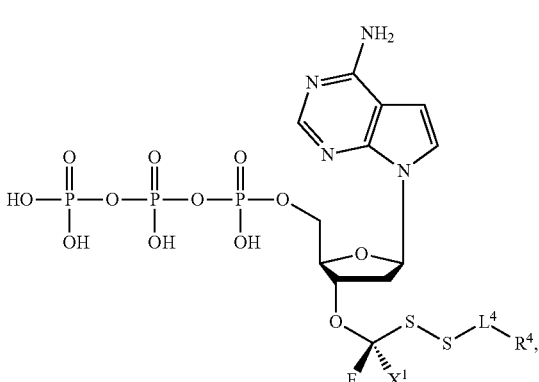

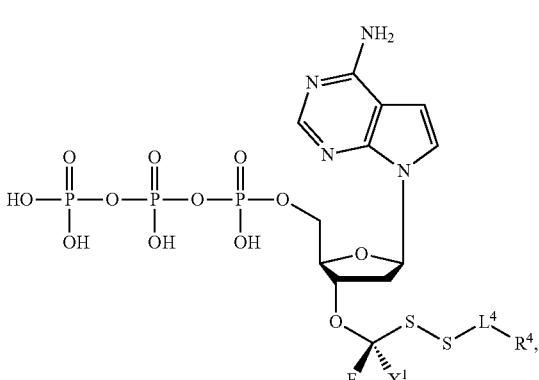

-continued

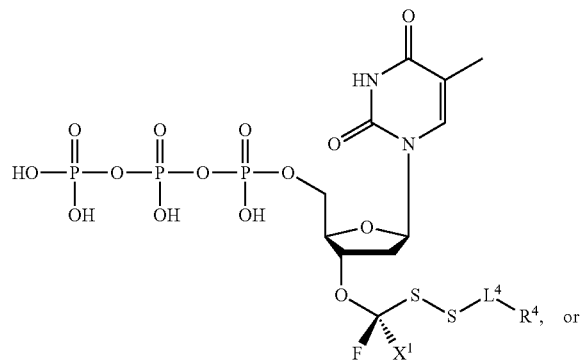

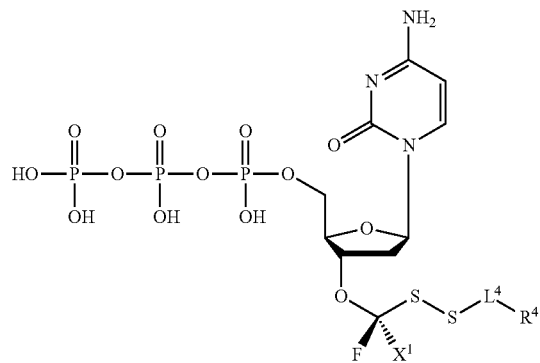

wherein $X^1$, $L^4$, and $R^4$ are as described herein, including embodiments.

In embodiments, the nucleotide analogue has the formula:

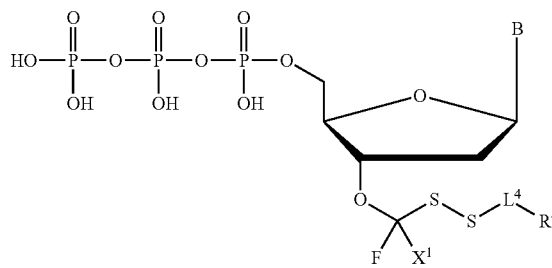

wherein $X^1$, B, $L^4$, and $R^5$ are as described herein, including embodiments.

In embodiments, the nucleotide analogue has the formula:

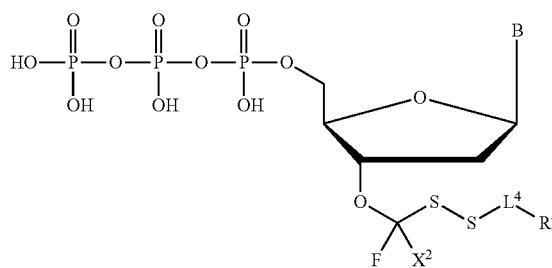

wherein $X^2$, B, $L^4$, and $R^5$ are as described herein, including embodiments.

In embodiments, the nucleotide analogue has the formula:

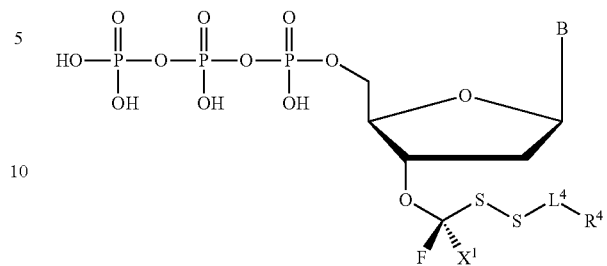

wherein $X^1$, B, $L^4$, and $R^5$ are as described herein, including embodiments.

In embodiments, the nucleotide analogue has the formula:

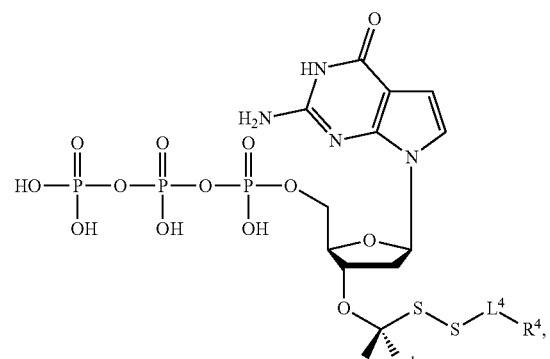

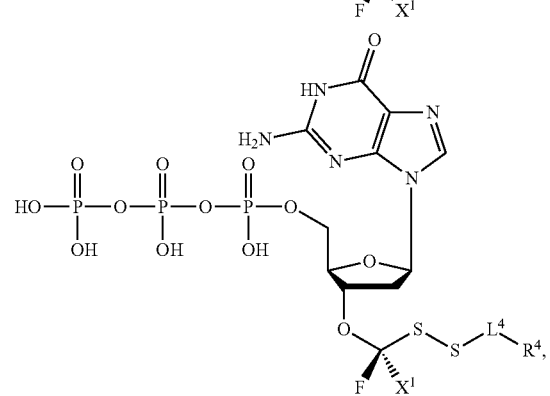

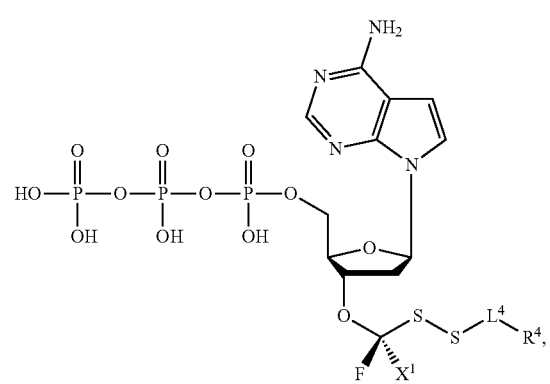

-continued
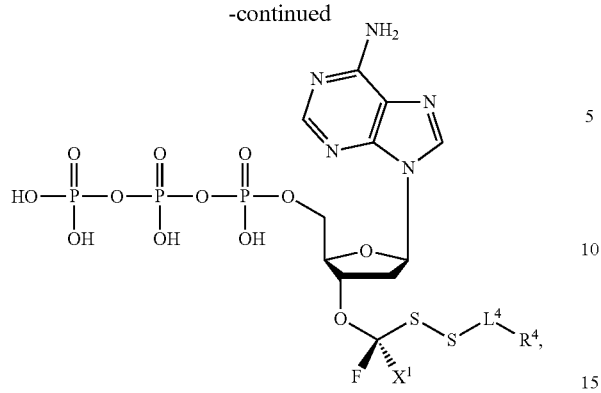
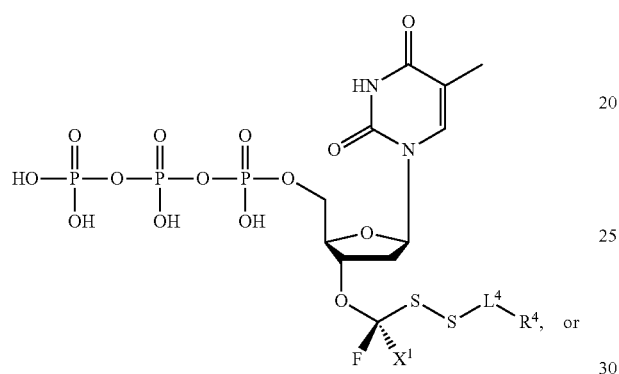
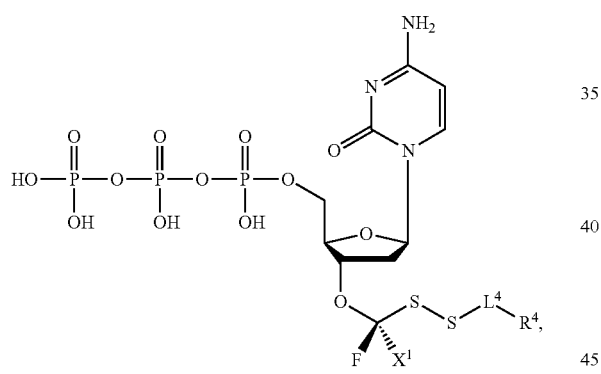
wherein $X^1$, $L^4$, and $R^5$ are as described herein, including embodiments.
In embodiments, the nucleotide analogue has the formula:
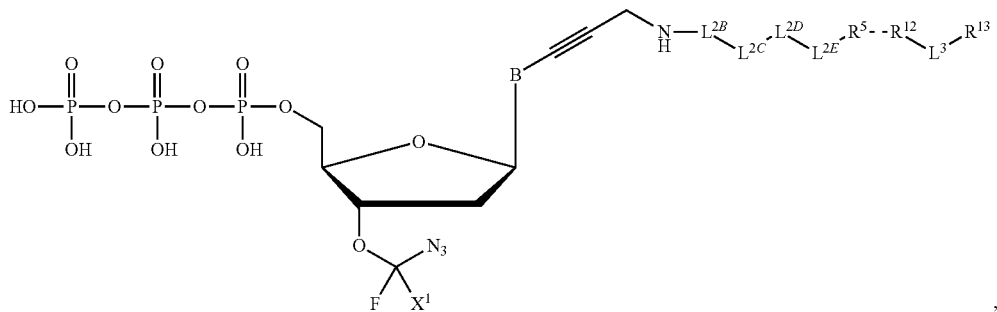
wherein $X^1$, B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

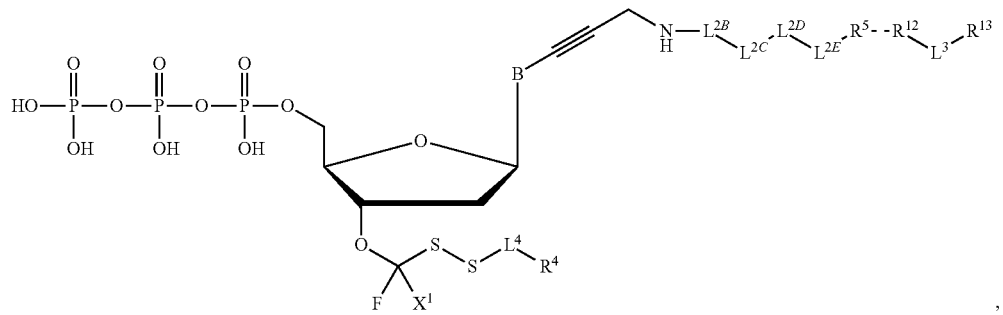

wherein $X^1$, B, $L^{2B}$, $L^{2C}$, $L^{2D}$, $L^{2E}$, $R^{12}$, $L^3$, $R^{13}$, $R^5$, $L^4$, and $R^4$ are as described herein, including embodiments.

In embodiments, the nucleotide analogue has the formula:

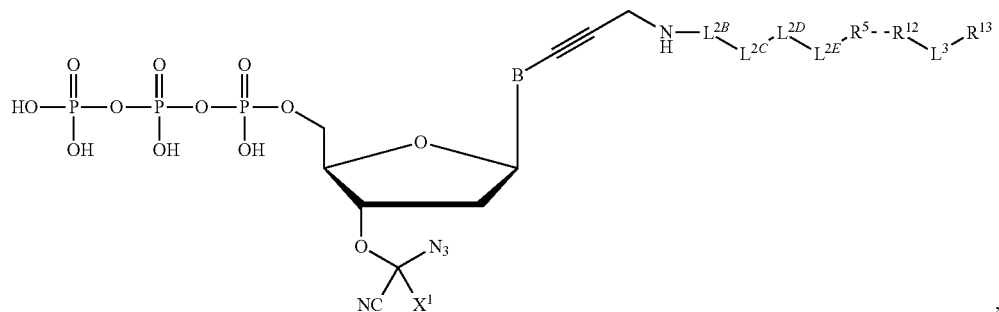

wherein $X^1$, B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

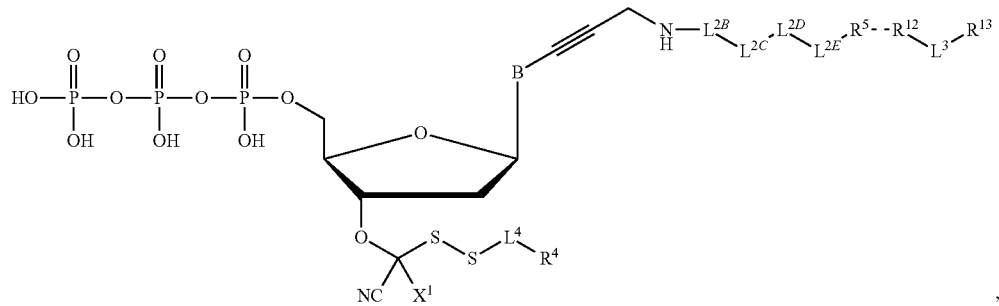

wherein $X^1$, B, $L^{2B}$, $L^{2C}$, $L^{2D}$, $L^{2E}$, $R^{12}$, $L^3$, $R^{13}$, $R^5$, $L^4$, and $R^5$ are as described herein, including embodiments.

In embodiments, the nucleotide analogue has the formula:

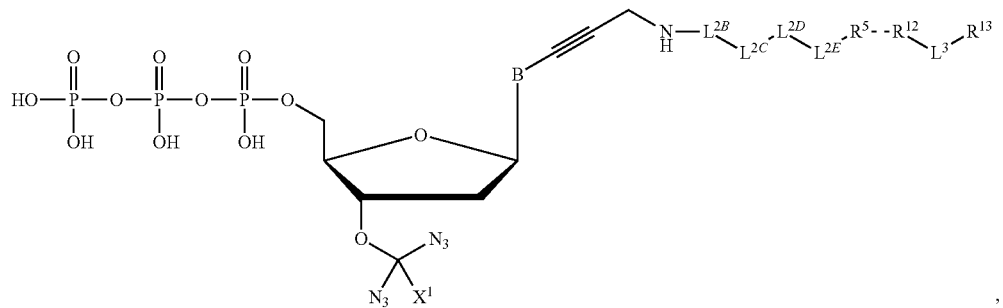

wherein $X^1$, B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

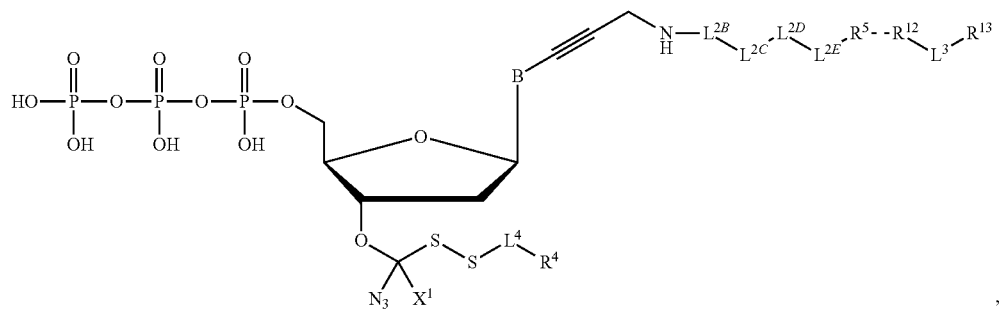

wherein $X^1$, B, $L^{2B}$, $L^{2C}$, $L^{2D}$, $L^{2E}$, $R^{12}$, $L^3$, $R^{13}$, $R^5$, $L^4$, and $R^4$ are as described herein, including embodiments.

In embodiments, the nucleotide analogue has the formula:

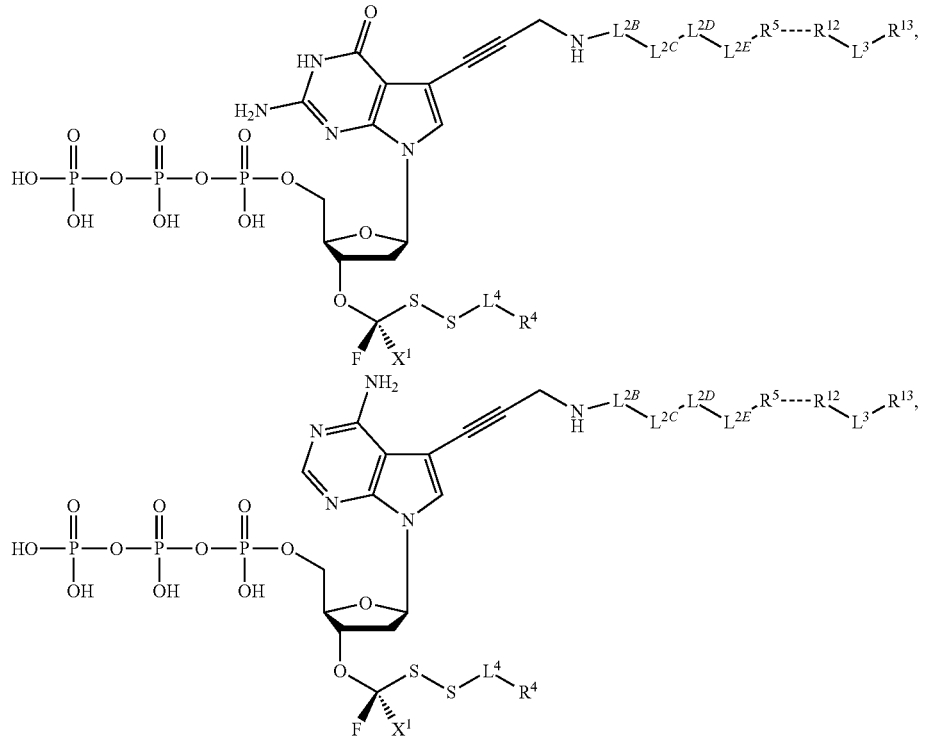

-continued
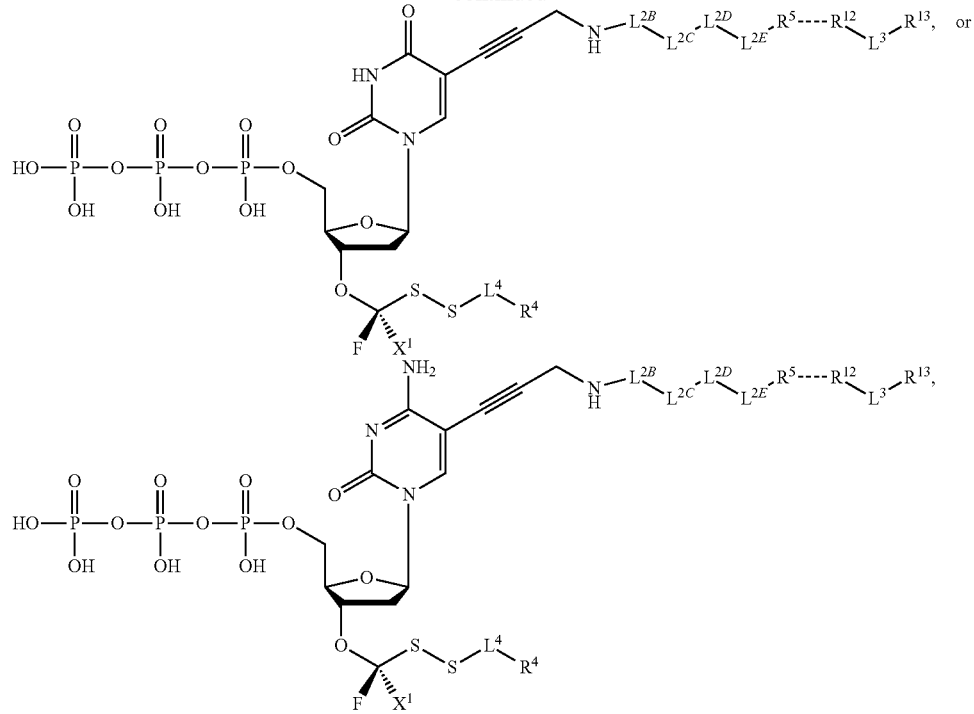
wherein $X^1$, $L^{2B}$, $L^{2C}$, $L^{2D}$, $L^{2E}$, $R^{12}$, $L^3$, $R^{13}$, $R^5$, $L^4$, and $R^4$ are as described herein, including embodiments.
In embodiments, the nucleotide analogue has the formula:
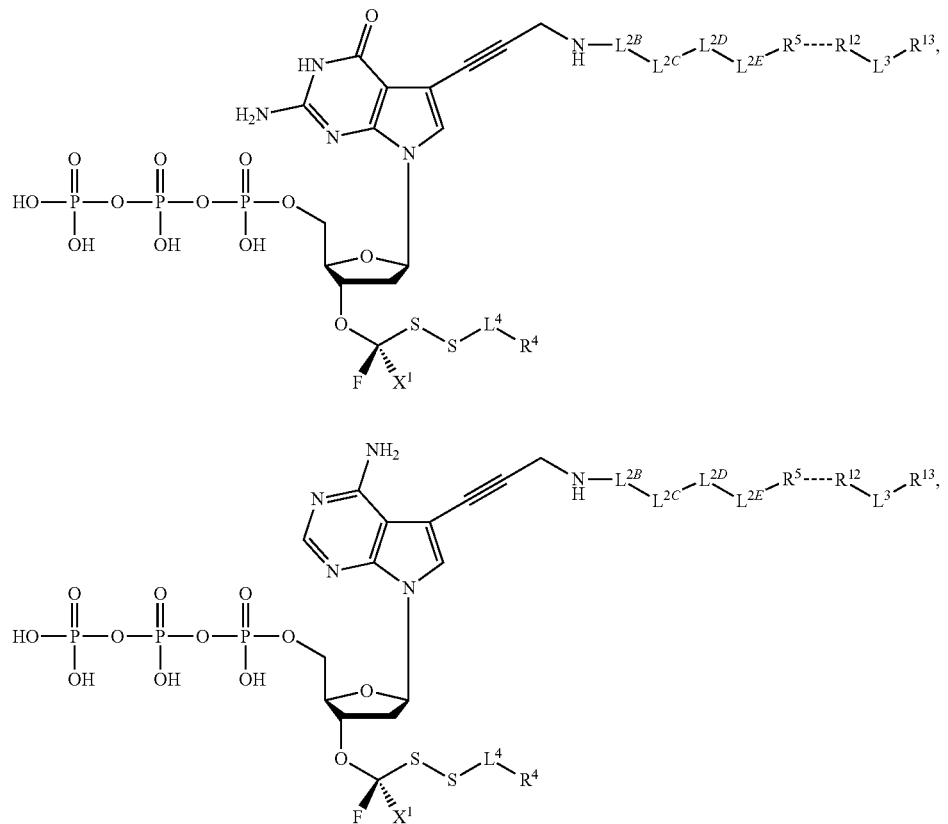

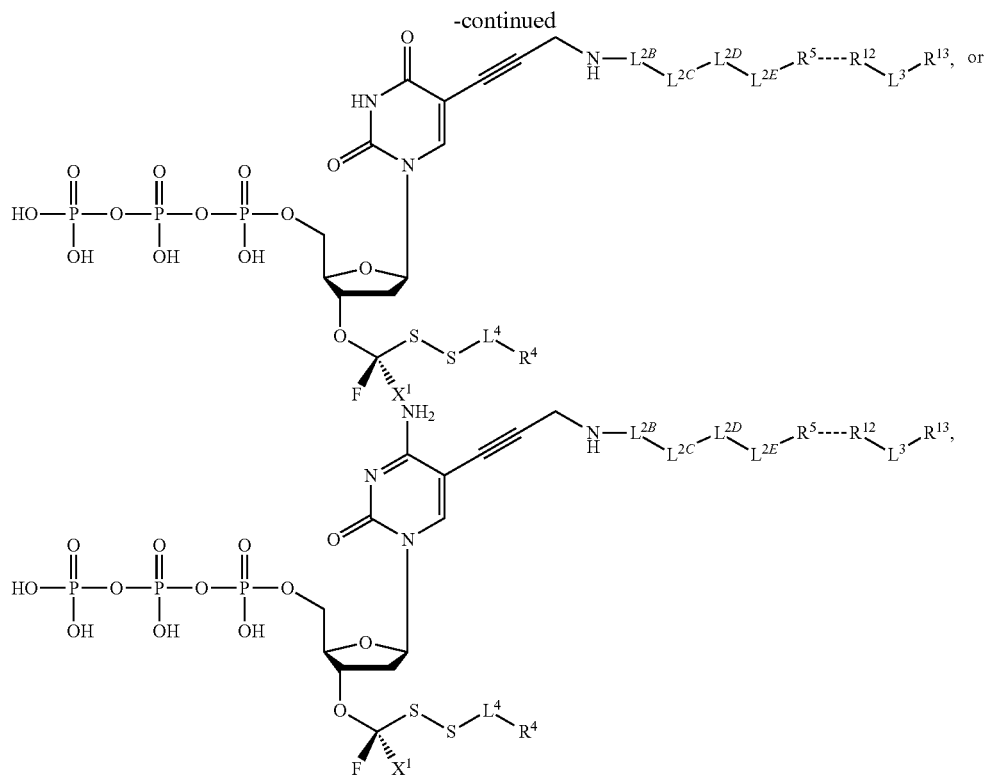

wherein $X^1$, $L^{2B}$, $L^{2C}$, $L^{2D}$, $L^{2E}$, $R^{12}$, $L^3$, $R^{13}$, $R^5$, $L^4$, and $R^4$ are as described herein, including embodiments.

In embodiments, the nucleotide analogue has the formula:

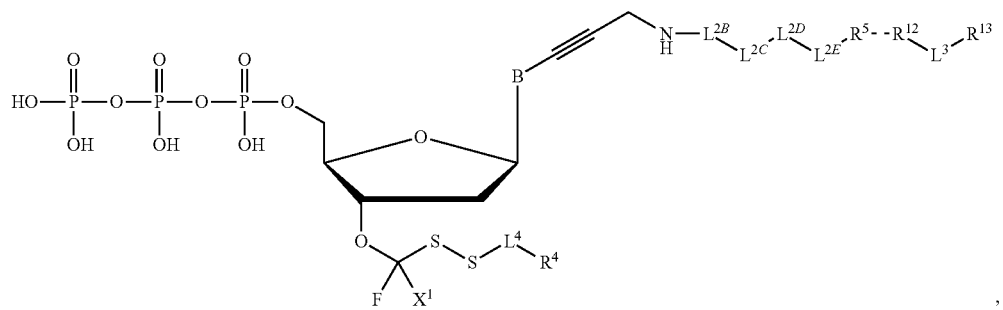

wherein $X^1$, B, $L^{2B}$, $L^{2C}$, $L^{2D}$, $L^{2E}$, $R^{12}$, $L^3$, $R^{13}$, $R^5$, $L^4$, and $R^4$ are as described herein, including embodiments.

In embodiments, the nucleotide analogue has the formula:

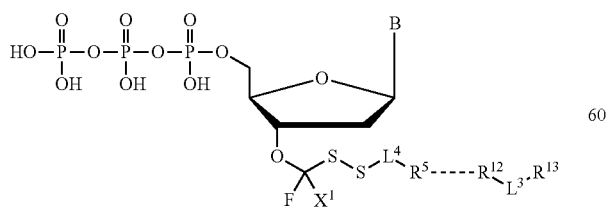

wherein $X^1$, B, $R^{12}$, $L^3$, $R^{13}$, $R^5$, and $L^4$ are as described herein, including embodiments.

In embodiments, the nucleotide analogue has the formula:

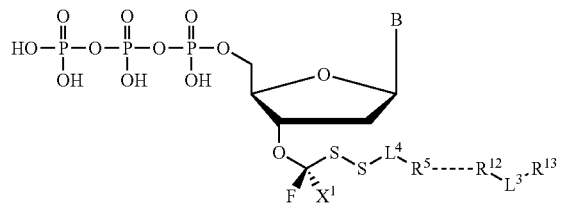

wherein $X^1$, B, $R^{12}$, $L^3$, $R^{13}$, $R^5$ and $L^4$ are as described herein, including embodiments.

In embodiments, the nucleotide analogue has the formula:

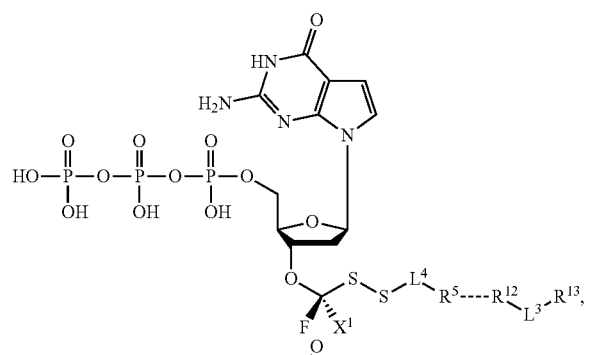

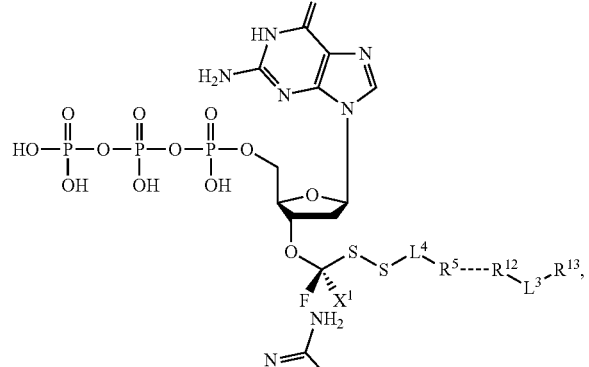

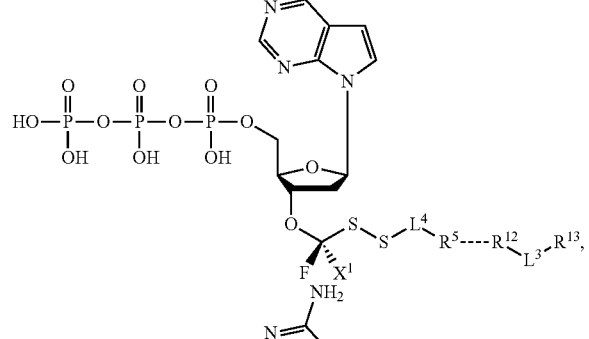

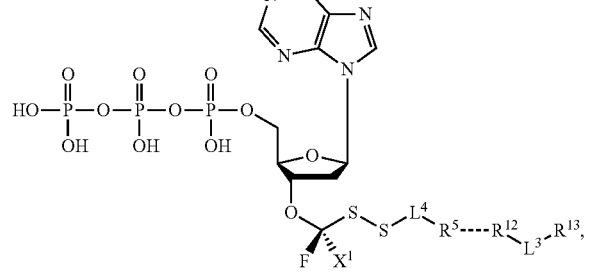

-continued

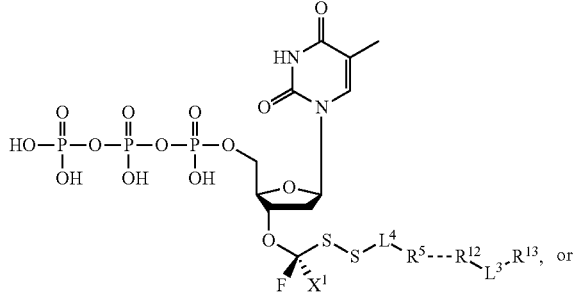

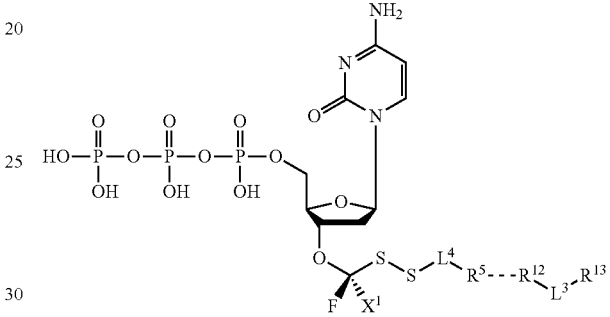

wherein $X^1$, $R^{12}$, $L^3$, $R^{13}$, $R^5$, and $L^4$ are as described herein, including embodiments.

In embodiments, the nucleotide analogue has the formula:

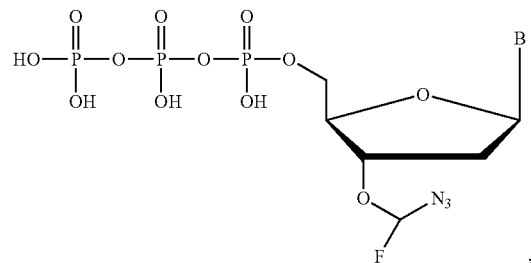

wherein B is as described herein, including embodiments.

In embodiments, the nucleotide analogue has the formula:

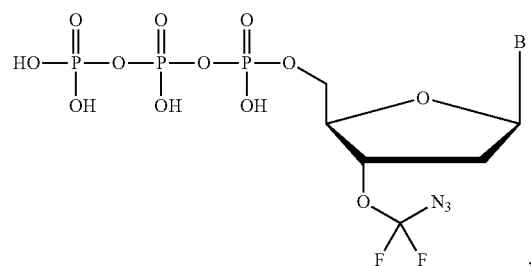

wherein B is as described herein, including embodiments.

In embodiments, the nucleotide analogue has the formula:

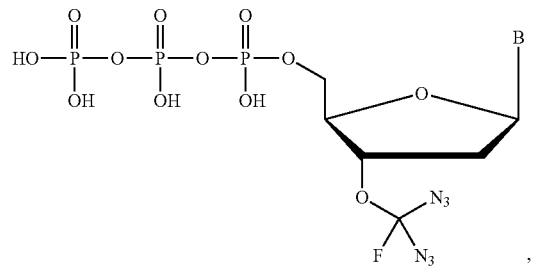

wherein B is as described herein, including embodiments.

In embodiments, the nucleotide analogue has the formula:

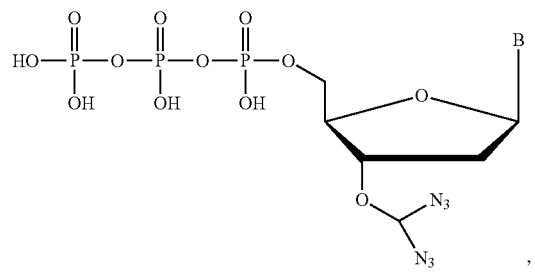

wherein B is as described herein, including embodiments.

In embodiments, the nucleotide analogue has the formula:

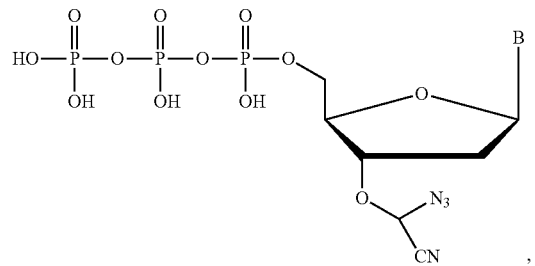

wherein B is as described herein, including embodiments.

In embodiments, the nucleotide analogue has the formula:

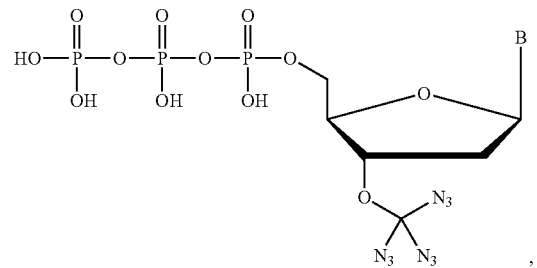

wherein B is as described herein, including embodiments.

In embodiments, the nucleotide analogue has the formula:

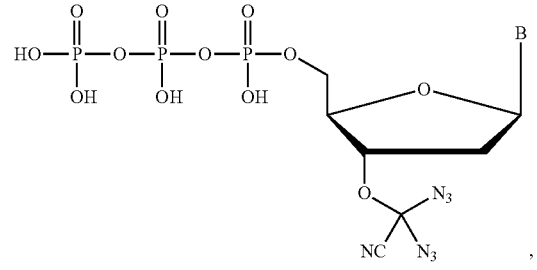

wherein B is as described herein, including embodiments.

In embodiments, the nucleotide analogue has the formula:

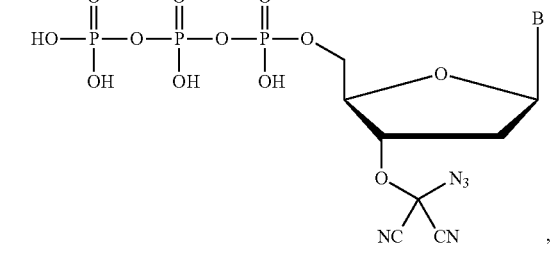

wherein B is as described herein, including embodiments.

In embodiments, the nucleotide analogue has the formula:

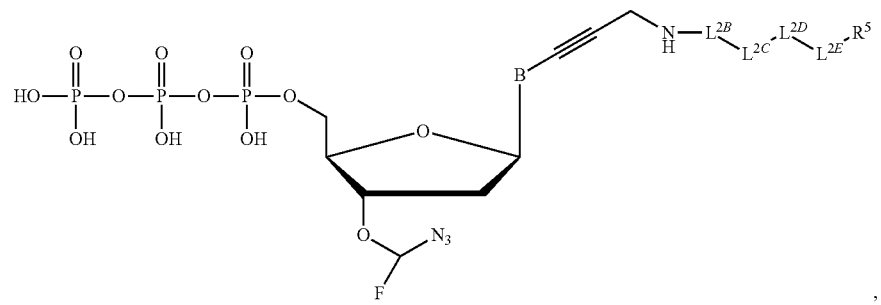

wherein B, $L^{2B}$, $L^{2C}$, $L^{2D}$, $L^{2E}$, and $R^5$ are as described herein, including embodiments.

In embodiments, the nucleotide analogue has the formula:

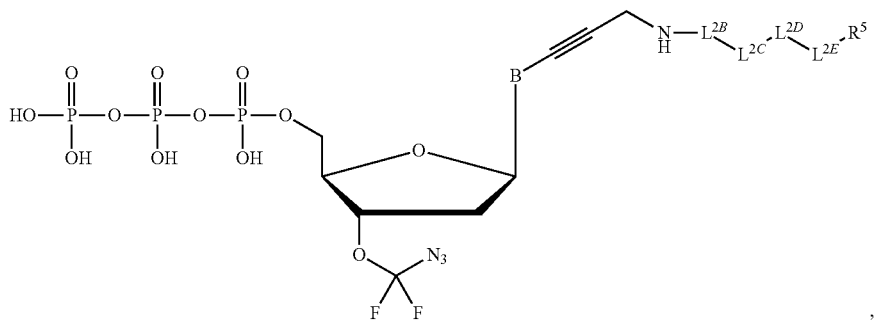

, wherein B, $L^{2B}$, $L^{2C}$, $L^{2D}$, $L^{2E}$, and $R^5$ are as described herein, including embodiments.

In embodiments, the nucleotide analogue has the formula:

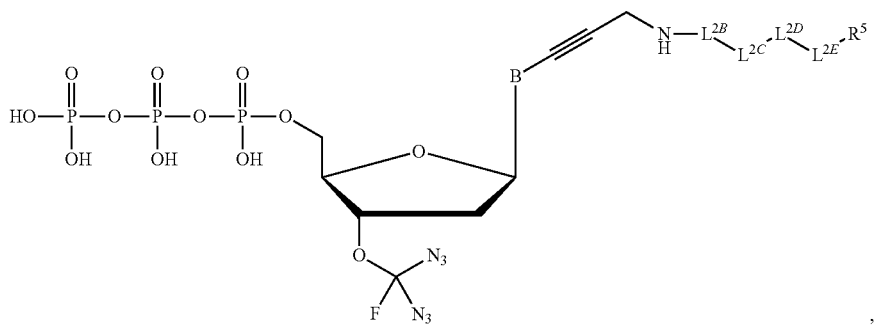

, wherein B, $L^{2B}$, $L^{2C}$, $L^{2D}$, $L^{2E}$, and $R^5$ are as described herein, including embodiments.

In embodiments, the nucleotide analogue has the formula:

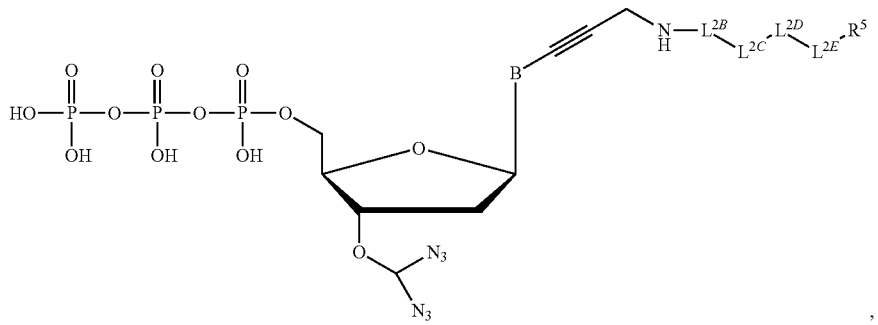

, wherein B, $L^{2B}$, $L^{2C}$, $L^{2D}$, $L^{2E}$, and $R^5$ are as described herein, including embodiments.

In embodiments, the nucleotide analogue has the formula:

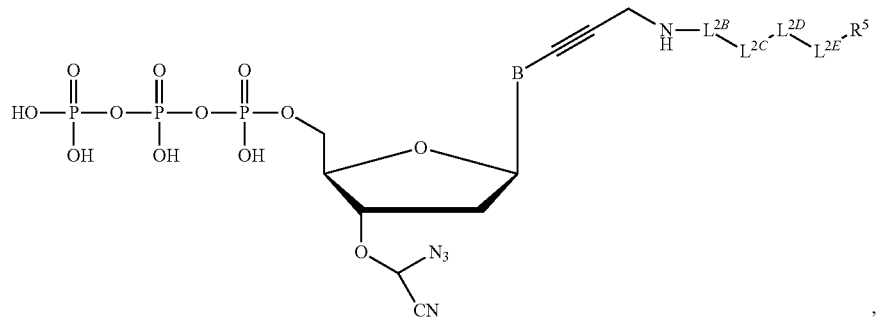

wherein B, $L^{2B}$, $L^{2C}$, $L^{2D}$, $L^{2E}$, and $R^5$ are as described herein, including embodiments.

In embodiments, the nucleotide analogue has the formula:

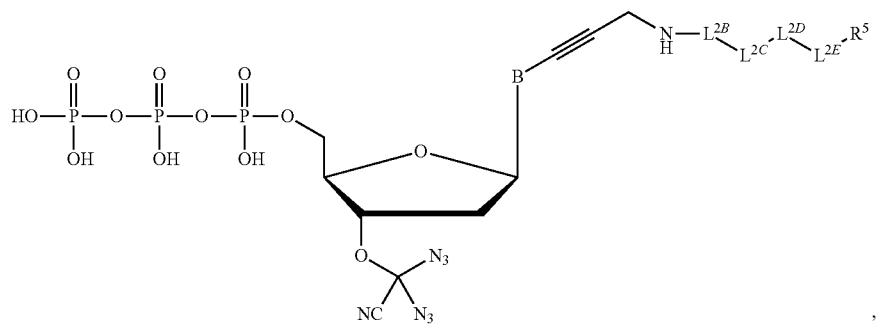

wherein B, $L^{2B}$, $L^{2C}$, $L^{2D}$, $L^{2E}$, and $R^5$ are as described herein, including embodiments.

In embodiments, the nucleotide analogue has the formula:

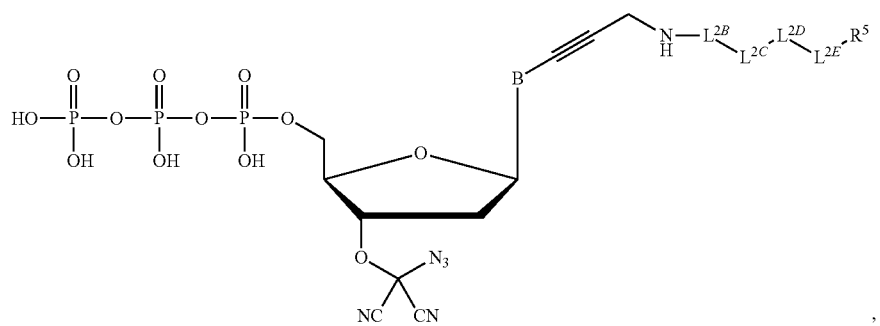

wherein B, $L^{2B}$, $L^{2C}$, $L^{2D}$, $L^{2E}$, and $R^5$ are as described herein, including embodiments.

In embodiments, the nucleotide analogue has the formula:

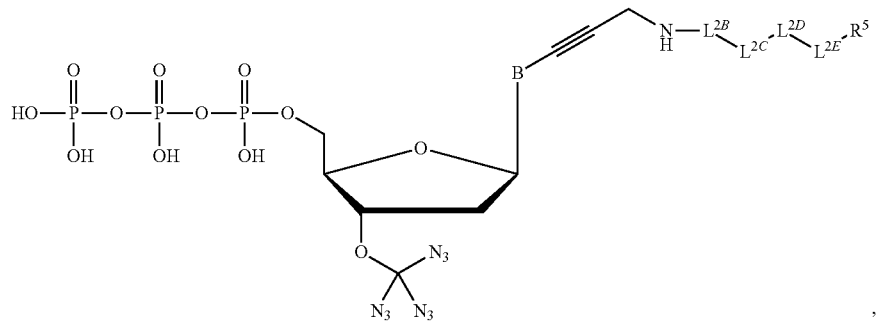

wherein B, $L^{2B}$, $L^{2C}$, $L^{2D}$, $L^{2E}$, and $R^5$ are as described herein, including embodiments.

In embodiments, the nucleotide analogue has the formula:

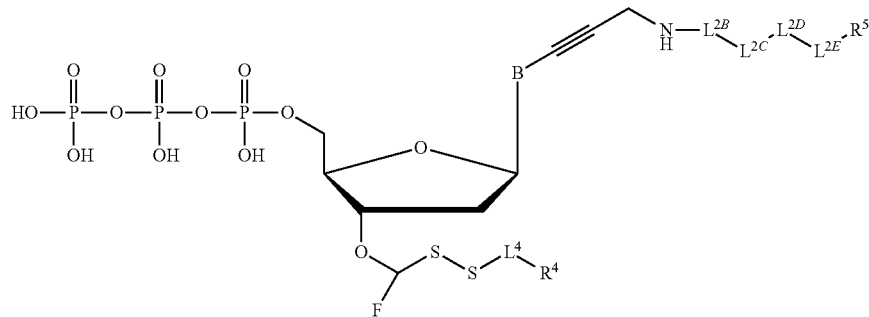

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

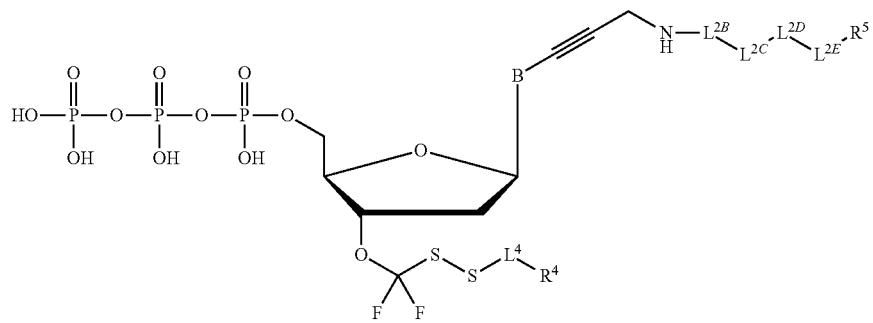

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

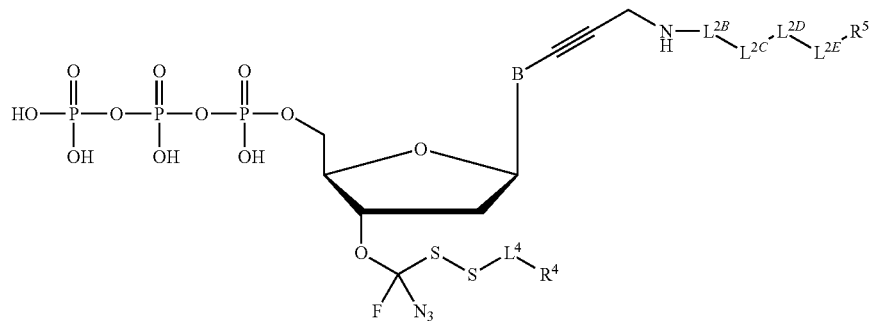

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

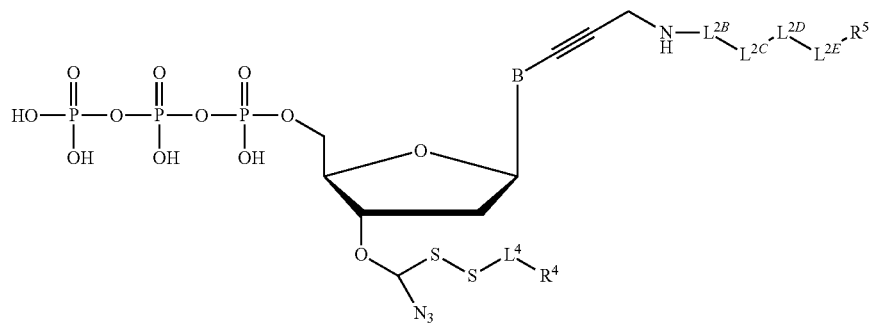

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

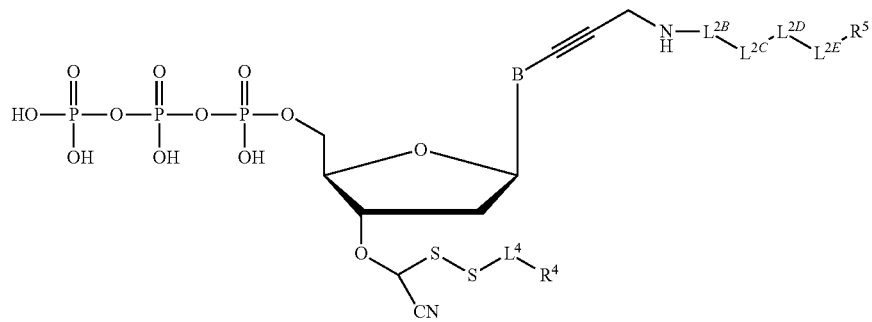

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

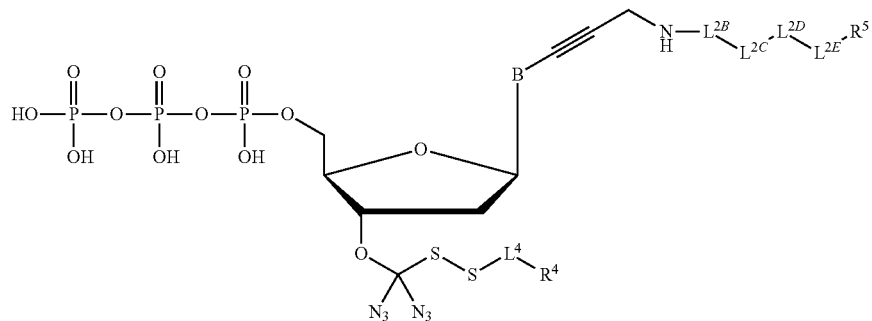

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

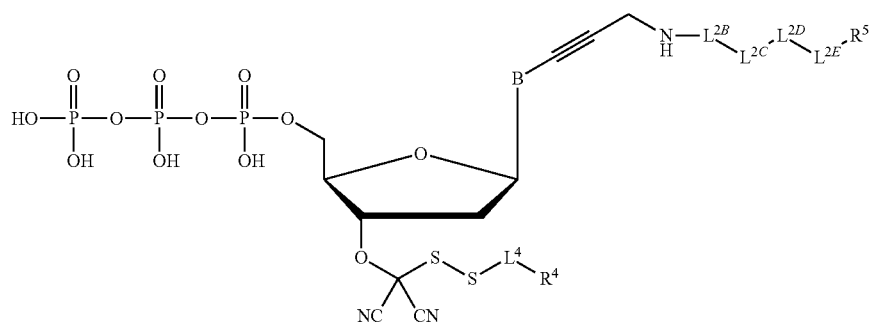

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

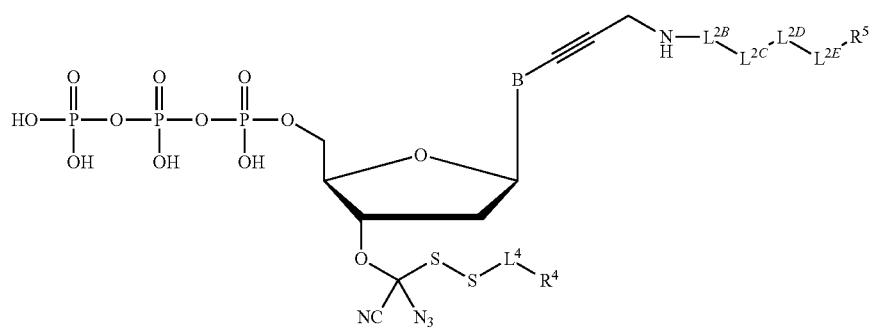

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

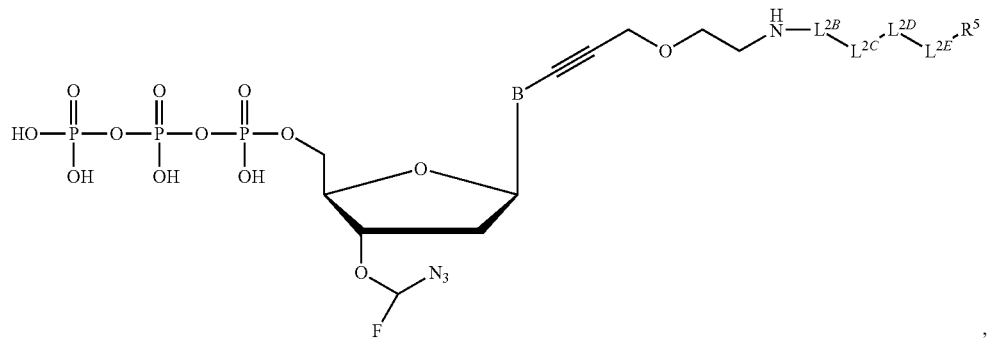

wherein $X^2$, B, $L^{2B}$, $L^{2C}$, $L^{2D}$, $L^{2E}$, and $R^5$ are as described herein, including embodiments.

In embodiments, the nucleotide analogue has the formula:

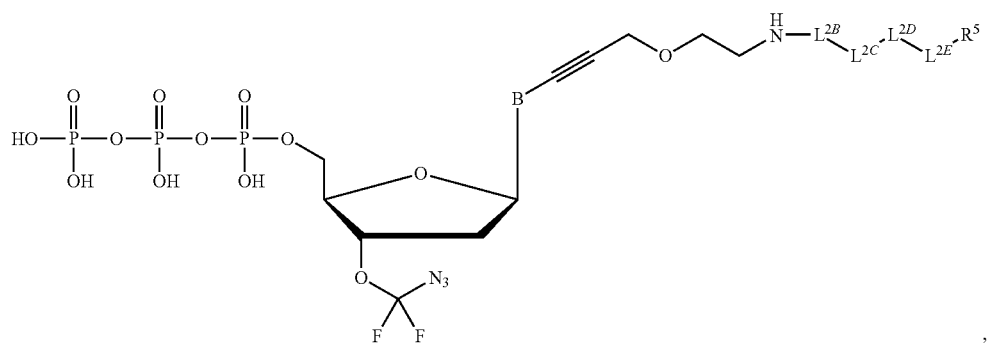

wherein B, $L^{2B}$, $L^{2C}$, $L^{2D}$, $L^{2E}$, and $R^5$ are as described herein, including embodiments.

In embodiments, the nucleotide analogue has the formula:

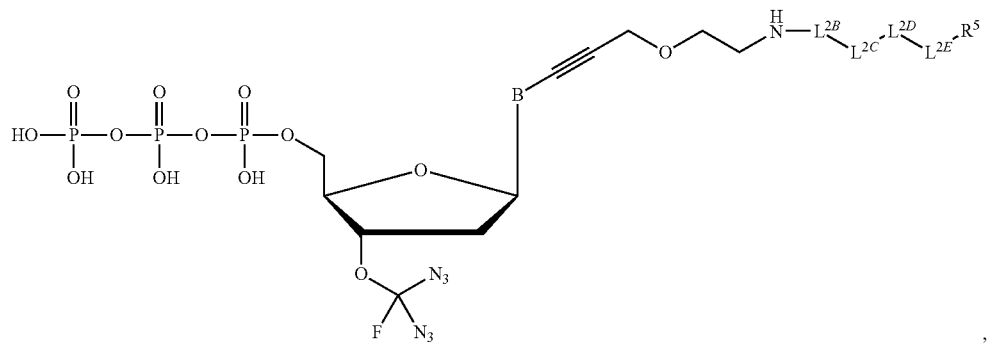

wherein B, $L^{2B}$, $L^{2C}$, $L^{2D}$, $L^{2E}$, and $R^5$ are as described herein, including embodiments.

In embodiments, the nucleotide analogue has the formula:

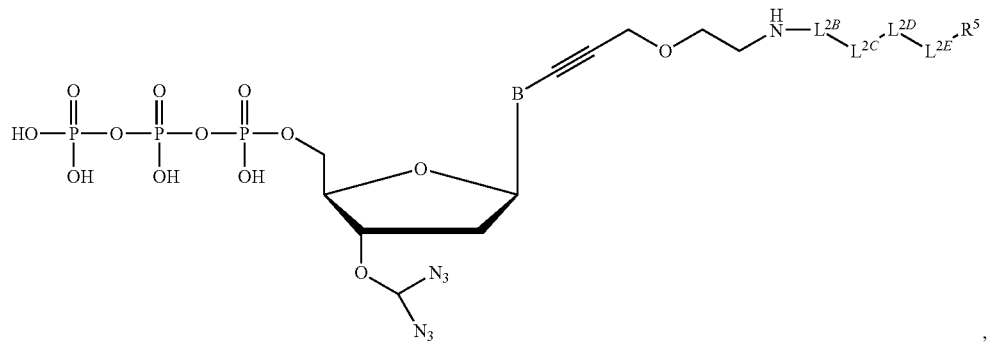

wherein B, $L^{2B}$, $L^{2C}$, $L^{2D}$, $L^{2E}$, and $R^5$ are as described herein, including embodiments.

In embodiments, the nucleotide analogue has the formula:

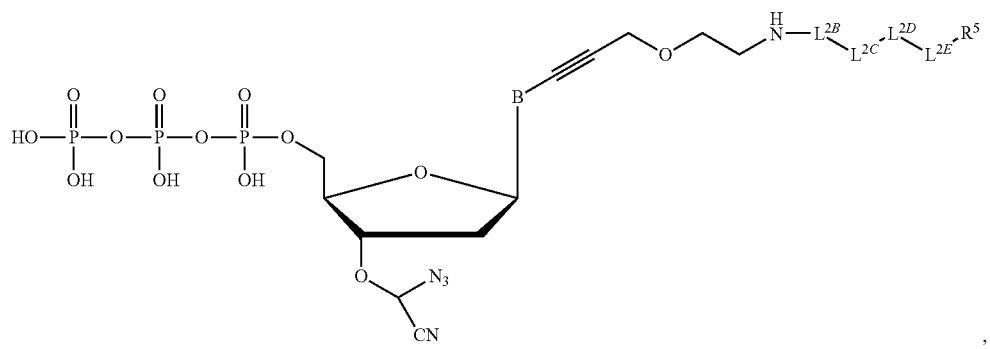

wherein B, $L^{2B}$, $L^{2C}$, $L^{2D}$, $L^{2E}$, and $R^5$ are as described herein, including embodiments.

In embodiments, the nucleotide analogue has the formula:

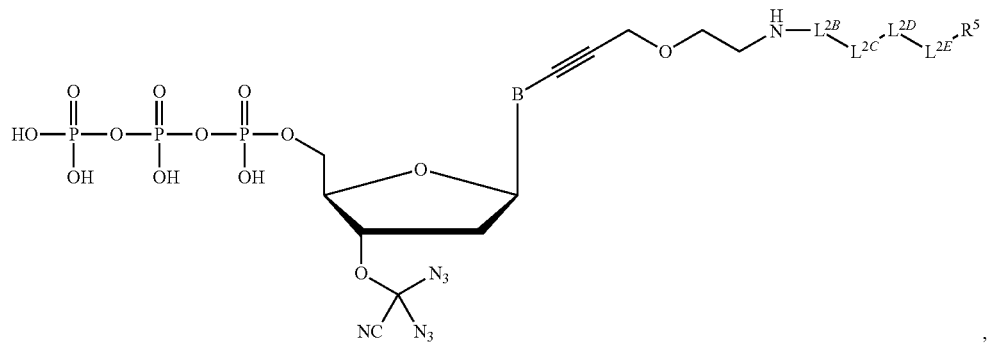

wherein B, $L^{2B}$, $L^{2C}$, $L^{2D}$, $L^{2E}$, and $R^5$ are as described herein, including embodiments.

In embodiments, the nucleotide analogue has the formula:

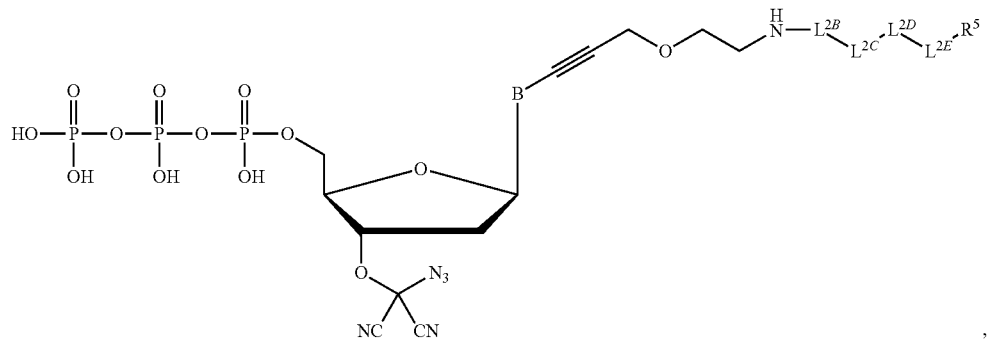

wherein B, $L^{2B}$, $L^{2C}$, $L^{2D}$, $L^{2E}$, and $R^5$ are as described herein, including embodiments.

In embodiments, the nucleotide analogue has the formula:

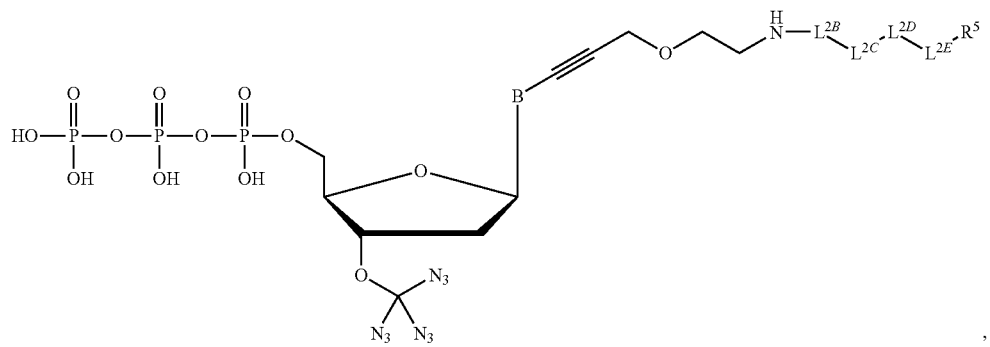

wherein B, $L^{2B}$, $L^{2C}$, $L^{2D}$, $L^{2E}$, and $R^5$ are as described herein, including embodiments.

In embodiments, the nucleotide analogue has the formula:

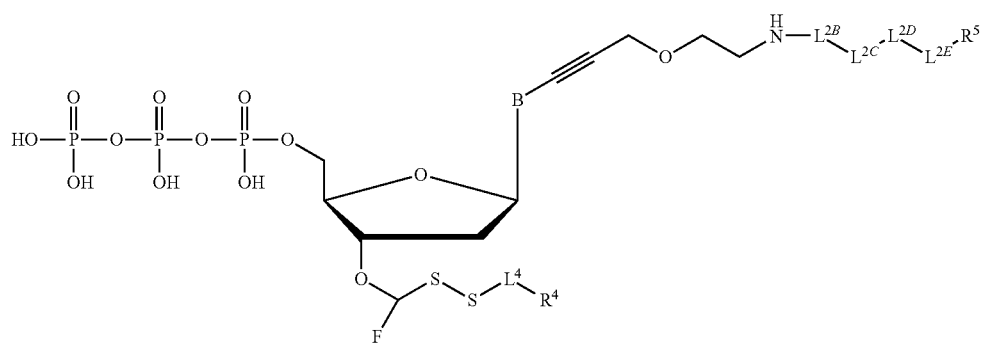

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

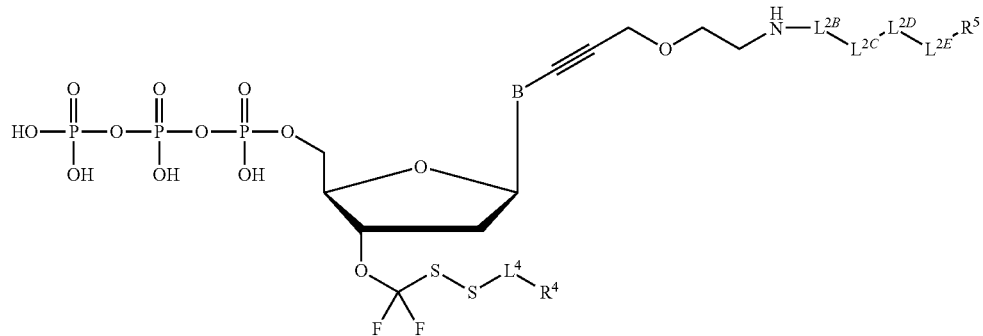

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

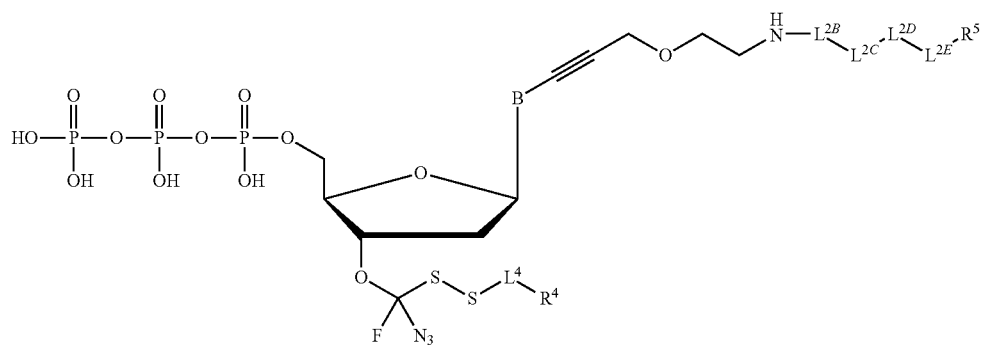

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

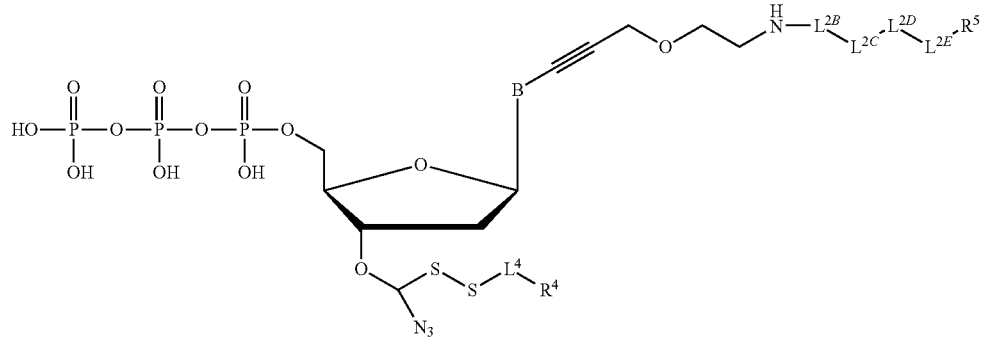

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

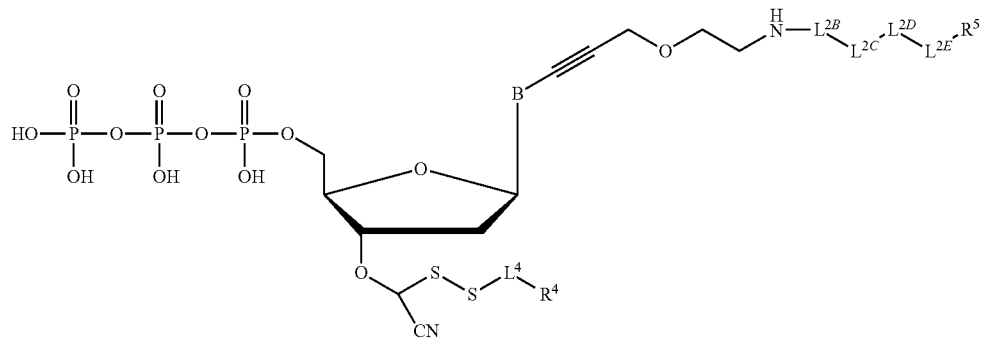

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

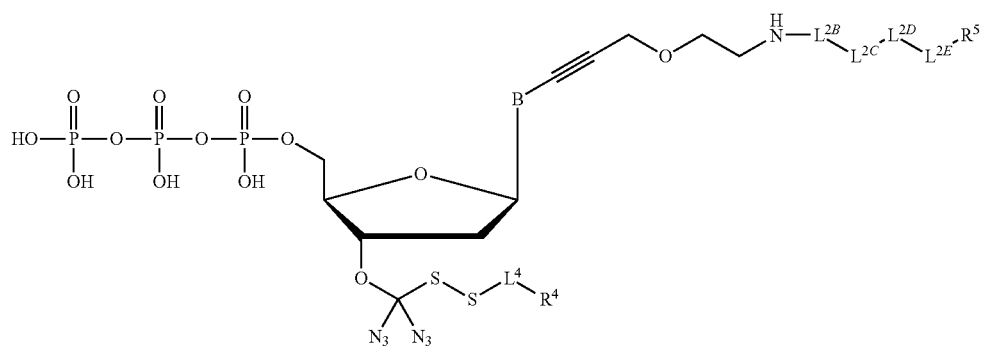

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

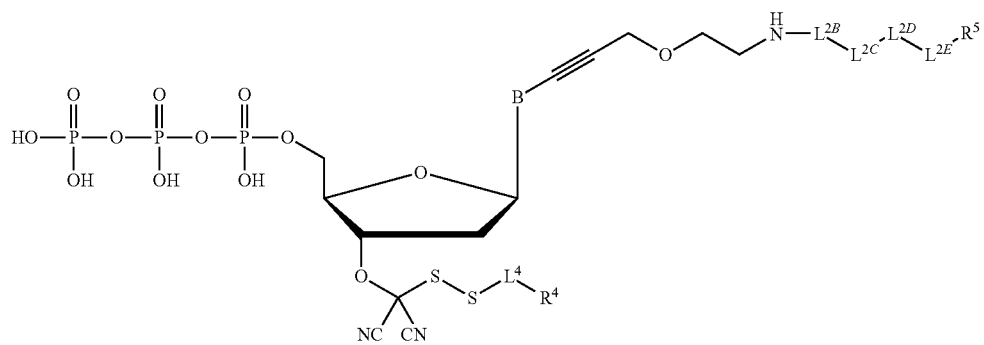

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

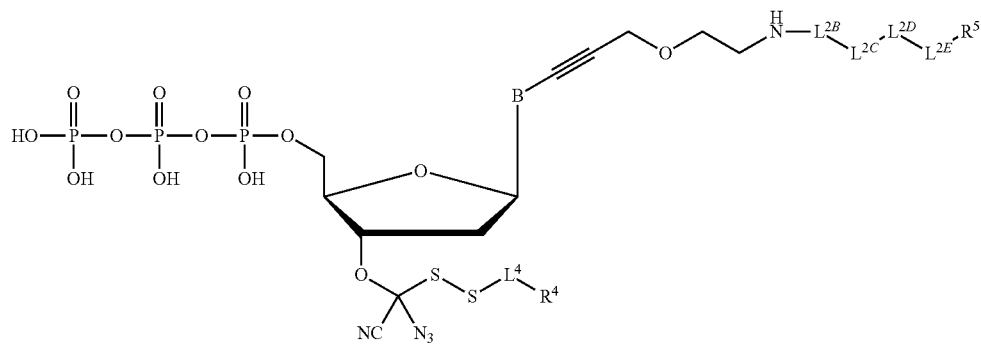

wherein B, $L^{2B}$, $L^{2C}$, $L^{2D}$, $L^{2E}$, $R^5$, $L^4$ and $R^4$ are as described herein, including embodiments.

In embodiments, the nucleotide analogue has the formula:

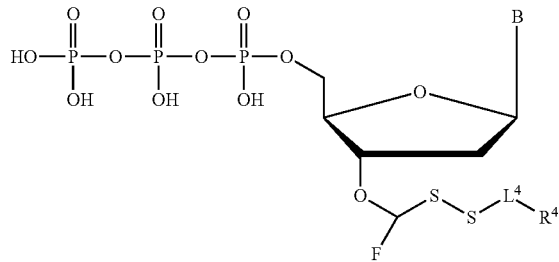

wherein B, $L^4$ and $R^4$ are as described herein, including embodiments.

In embodiments, the nucleotide analogue has the formula:

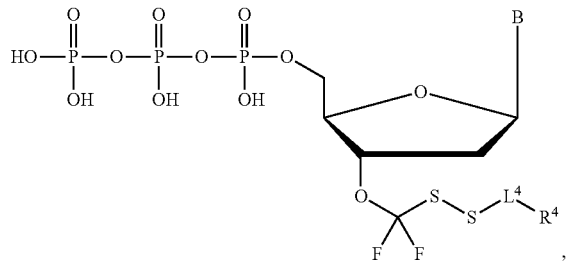

wherein B, $L^4$ and $R^4$ are as described herein, including embodiments.

In embodiments, the nucleotide analogue has the formula:

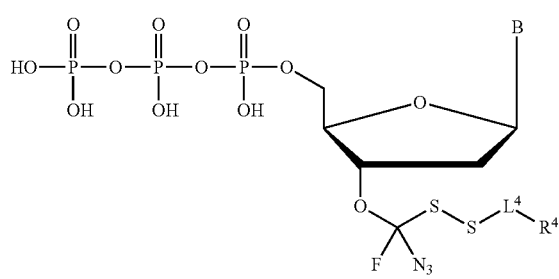

wherein B, $L^4$ and $R^4$ are as described herein, including embodiments.

In embodiments, the nucleotide analogue has the formula:

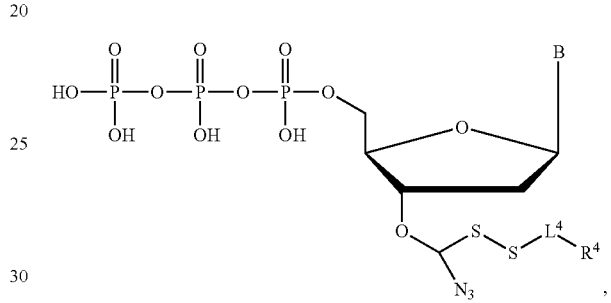

wherein B, $L^4$ and $R^4$ are as described herein, including embodiments.

In embodiments, the nucleotide analogue has the formula:

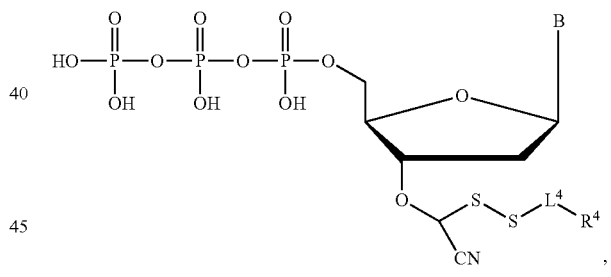

wherein B, $L^4$ and $R^4$ are as described herein, including embodiments.

In embodiments, the nucleotide analogue has the formula:

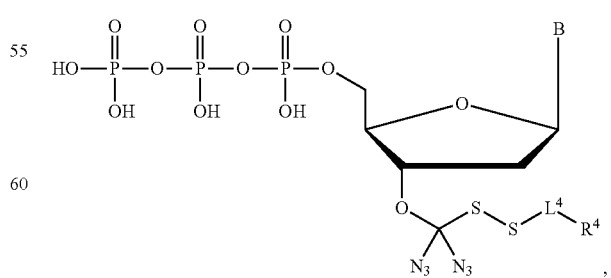

wherein B, $L^4$ and $R^4$ are as described herein, including embodiments.

In embodiments, the nucleotide analogue has the formula:

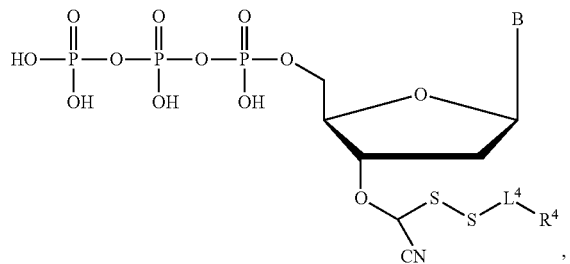

wherein B, $L^4$ and $R^4$ are as described herein, including embodiments.

In embodiments, the nucleotide analogue has the formula:

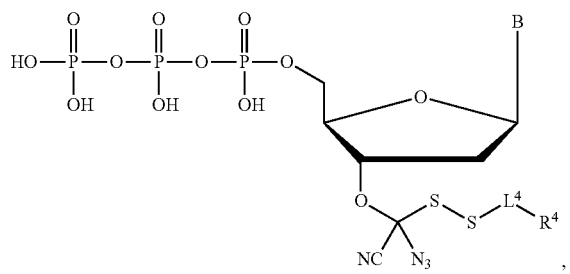

wherein B, $L^4$ and $R^4$ are as described herein, including embodiments.

In embodiments, the nucleotide analogue has the formula:

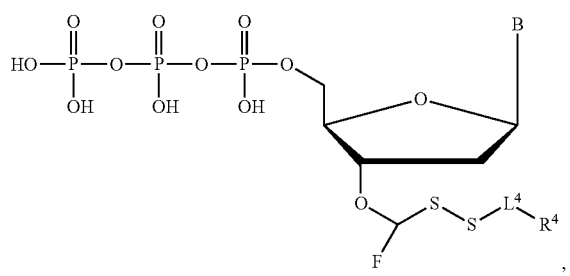

wherein B, $L^4$ and $R^4$ are as described herein, including embodiments.

In embodiments, the nucleotide analogue has the formula:

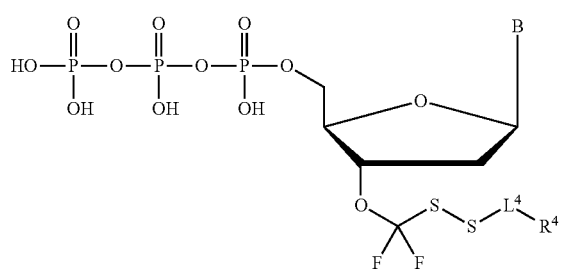

wherein B, $L^4$ and $R^4$ areas described herein, including embodiments.

In embodiments, the nucleotide analogue has the formula:

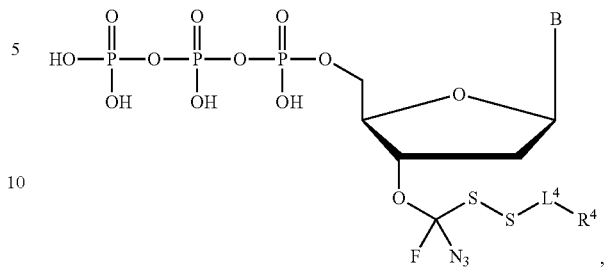

wherein B, $L^4$ and $R^5$ are as described herein, including embodiments.

In embodiments, the nucleotide analogue has the formula:

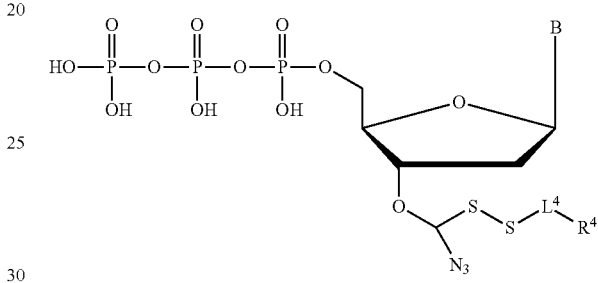

wherein B, $L^4$ and $R^5$ are as described herein, including embodiments.

In embodiments, the nucleotide analogue has the formula:

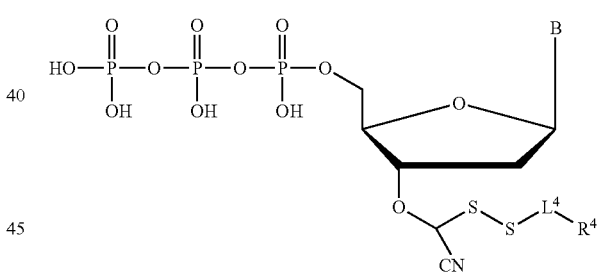

wherein B, $L^4$ and $R^5$ are as described herein, including embodiments.

In embodiments, the nucleotide analogue has the formula:

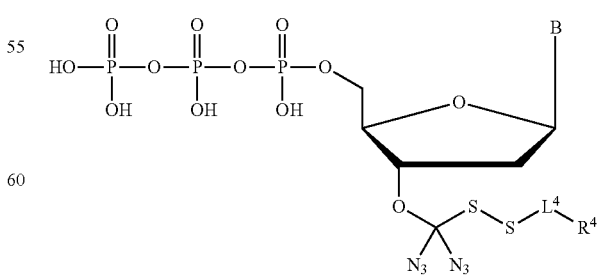

wherein B, $L^4$ and $R^5$ are as described herein, including embodiments.

In embodiments, the nucleotide analogue has the formula:

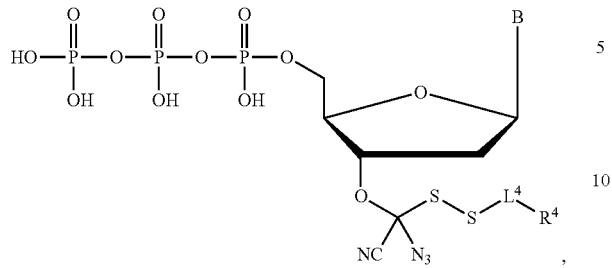

wherein B, $L^4$ and R' are as described herein, including embodiments.

In embodiments, the nucleotide analogue has the formula:

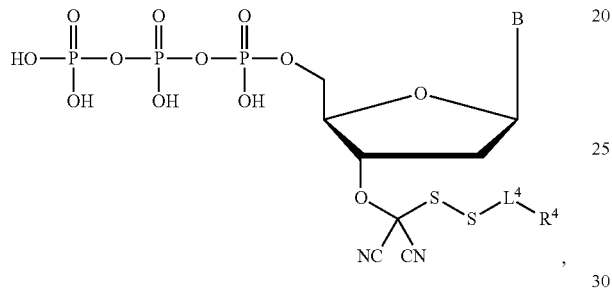

wherein B, $L^4$ and $R^5$ are as described herein, including embodiments.

In embodiments, the nucleotide analogue has the formula:

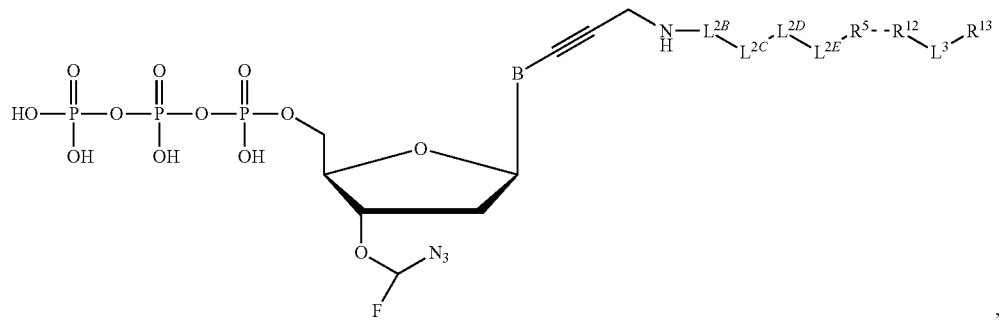

wherein B, $L^{2B}$, $L^{2C}$, $L^{2D}$, $L^{2E}$, $R^{12}$, $L^3$, $R^{13}$ and $R^5$ areas described herein, including embodiments.

In embodiments, the nucleotide analogue has the formula:

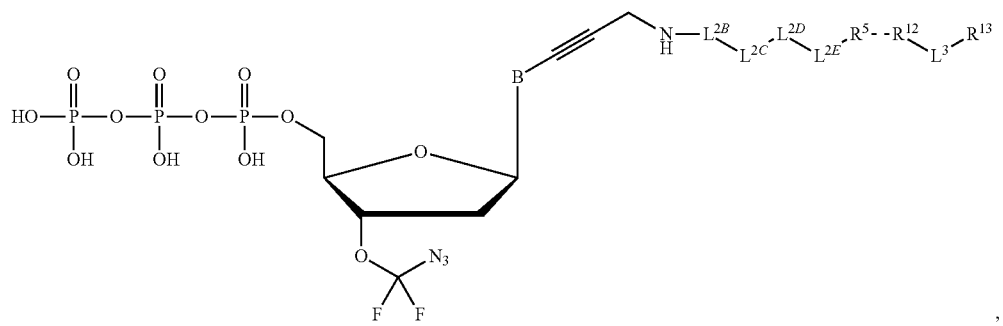

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

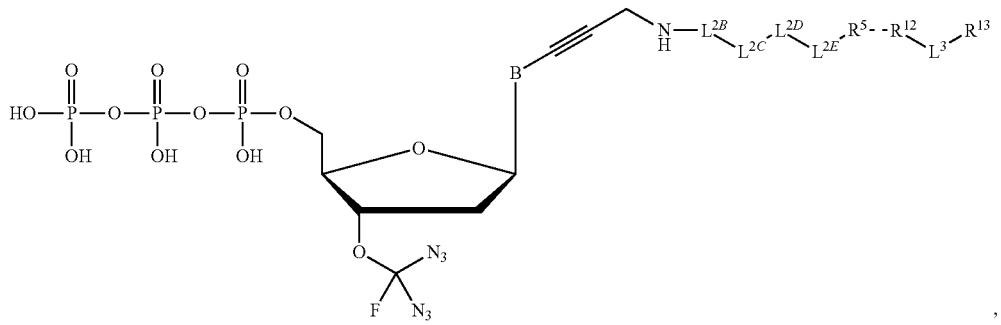

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

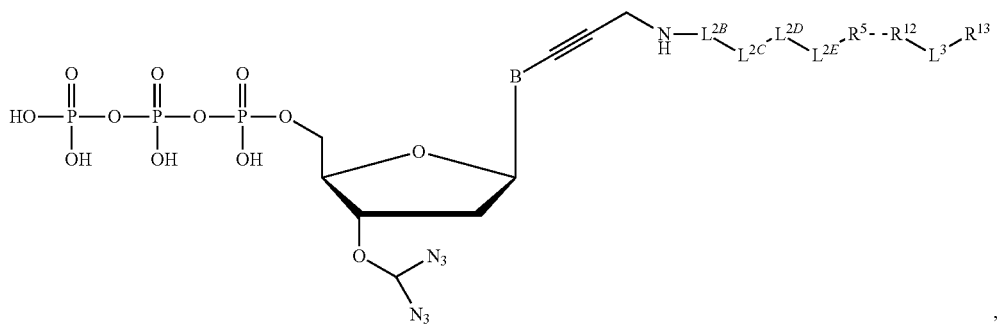

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

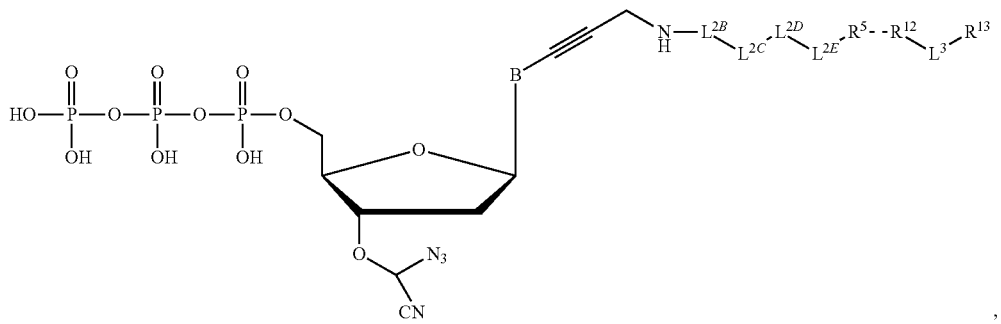

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

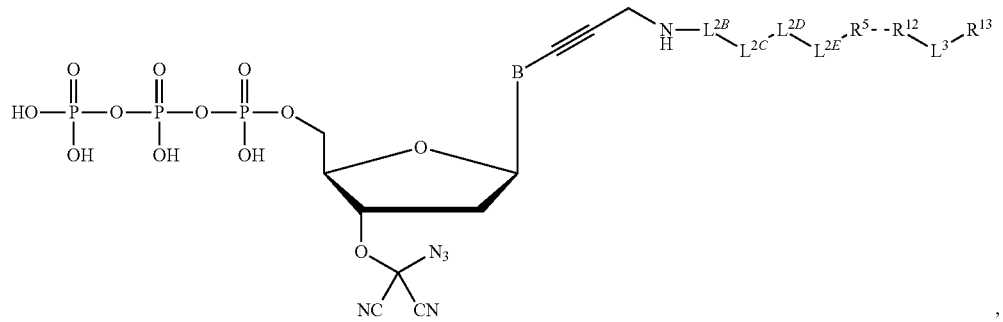

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

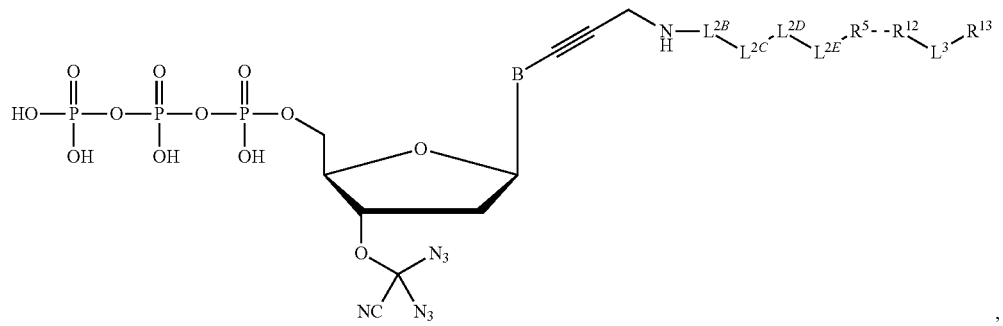

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

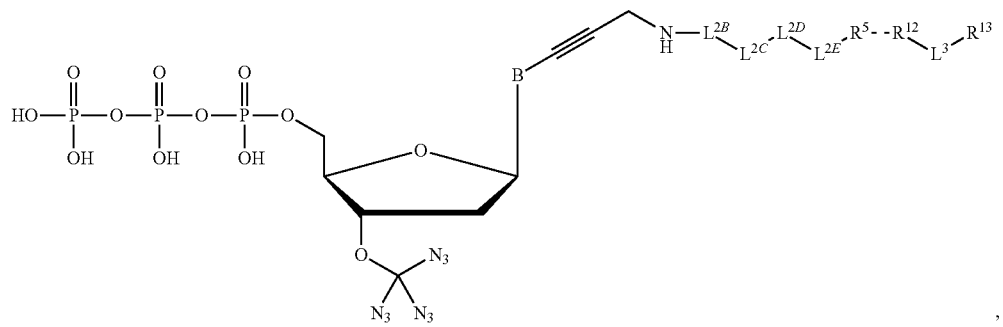

wherein B, $L^{2B}$, $L^{2C}$, $L^{2D}$, $L^{2E}$, $R^{12}$, $L^3$, $R^{13}$, and $R^5$ are as described herein, including embodiments.

In embodiments, the nucleotide analogue has the formula:

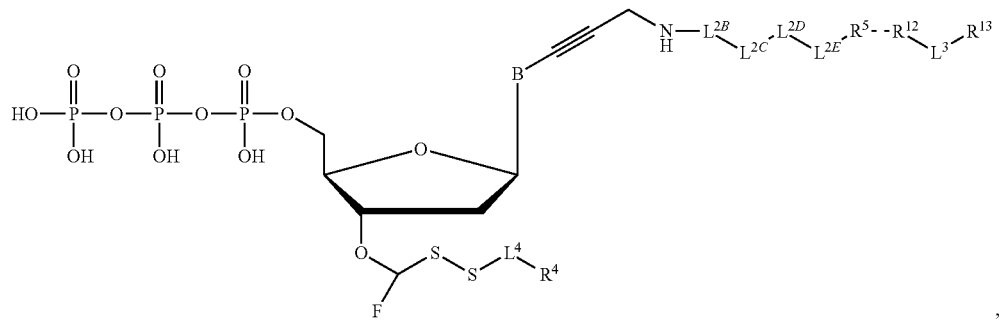

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

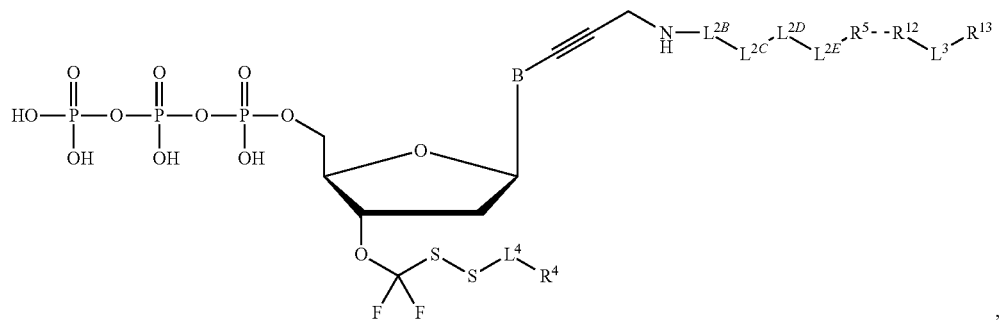

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

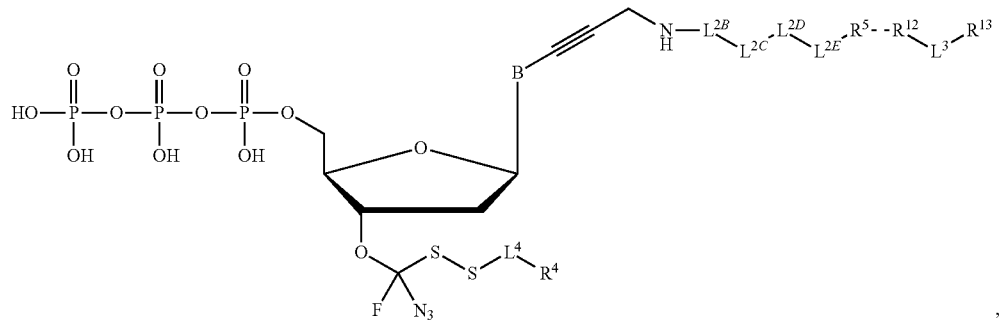

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

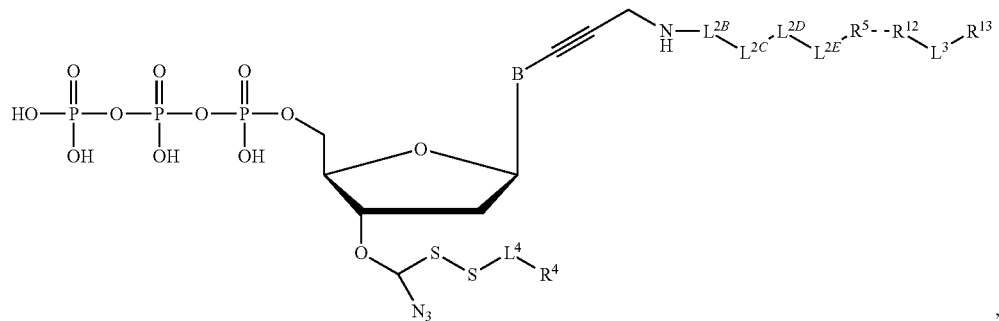

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

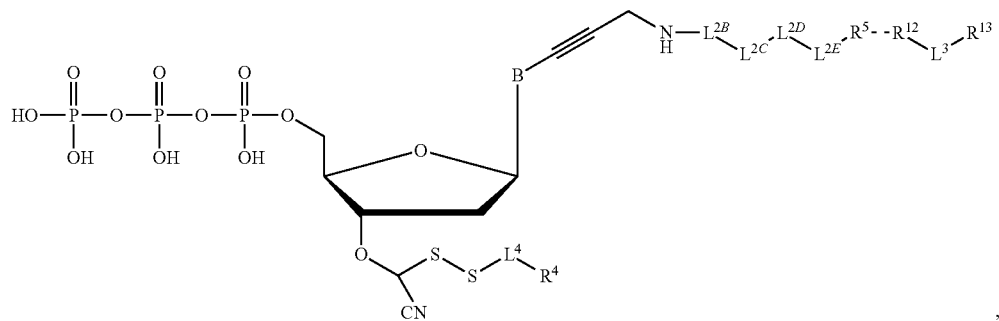

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

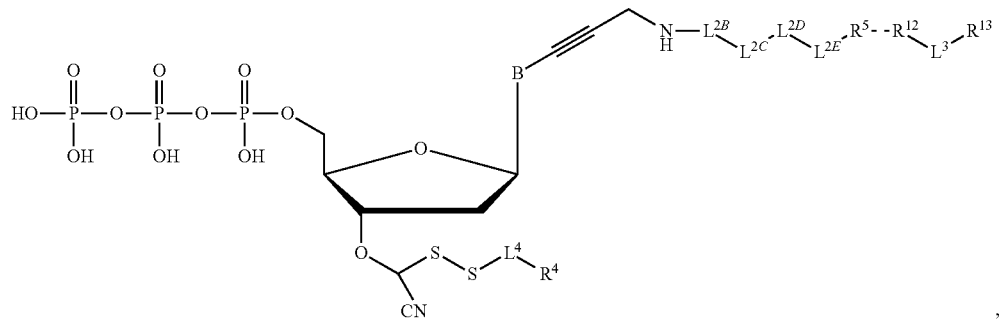

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

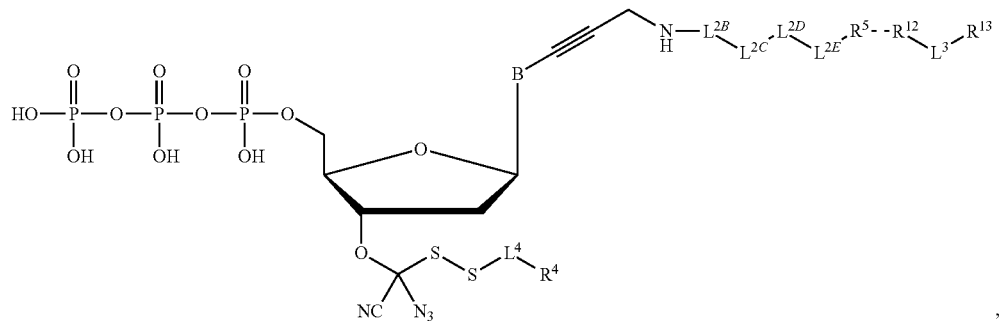

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

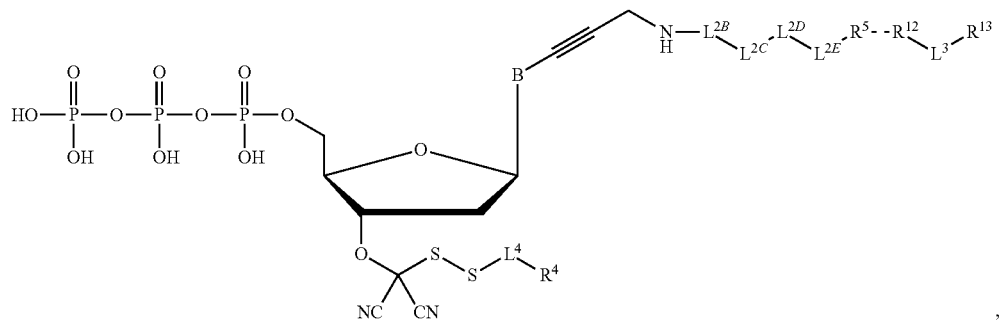

wherein B, $L^{2B}$, $L^{2C}$, $L^{2D}$, $L^{2E}$, $R^{12}$, $L^3$, $R^{13}$, $R^5$, $L^4$ and $R^4$ are as described herein, including embodiments.

In embodiments, the nucleotide analogue has the formula:

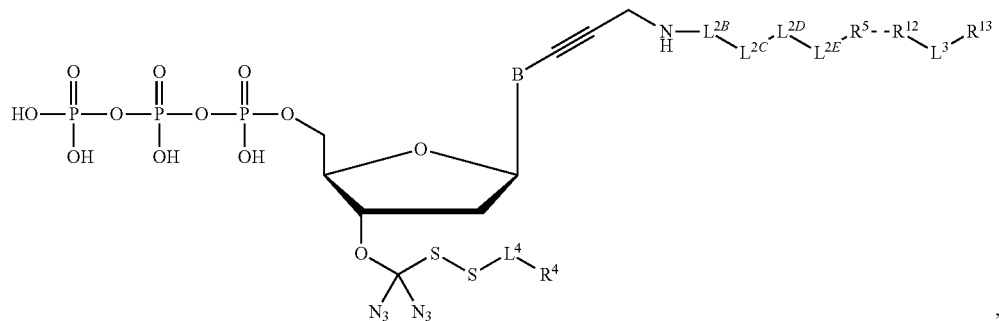

wherein B, $L^{2B}$, $L^{2C}$, $L^{2D}$, $L^{2E}$, $R^{12}$, $L^3$, $R^{13}$, $R^5$, $L^4$ and $R^4$ areas described herein, including embodiments.

In embodiments, the nucleotide analogue has the formula:

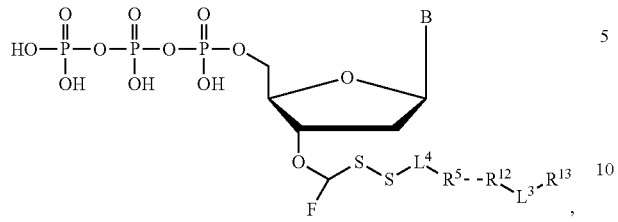

wherein B, $R^{12}$, $L^3$, $R^{13}$, $R^5$, and $L^4$ are as described herein, including embodiments.

In embodiments, the nucleotide analogue has the formula:

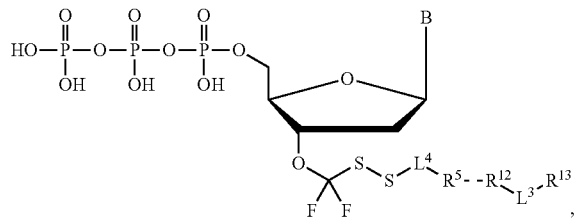

wherein B, $R^{12}$, $L^3$, $R^{13}$, $R^5$, and $L^4$ are as described herein, including embodiments.

In embodiments, the nucleotide analogue has the formula:

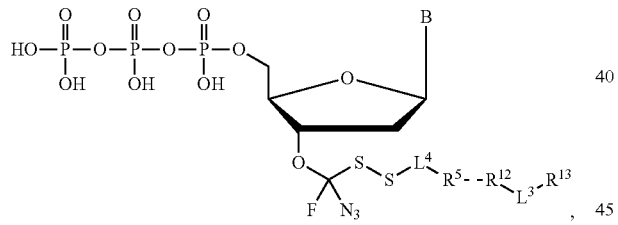

wherein B, $R^{12}$, $L^3$, $R^{13}$, $R^5$, and $L^4$ are as described herein, including embodiments.

In embodiments, the nucleotide analogue has the formula:

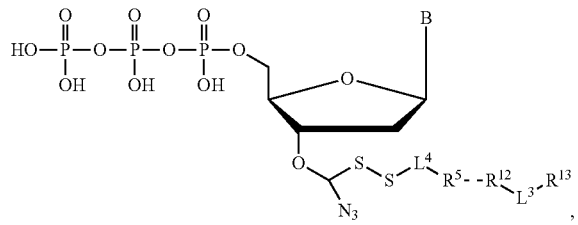

wherein B, $R^{12}$, $L^3$, $R^{13}$, $R^5$, and $L^4$ are as described herein, including embodiments.

In embodiments, the nucleotide analogue has the formula:

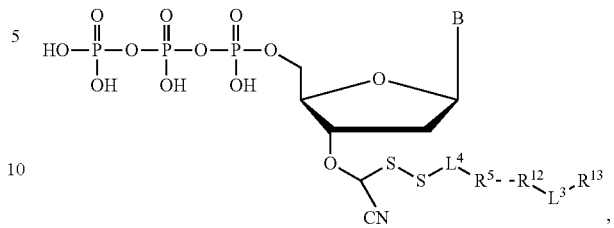

wherein B, $R^{12}$, $L^3$, $R^{13}$, $R^5$, and $L^4$ are as described herein, including embodiments.

In embodiments, the nucleotide analogue has the formula:

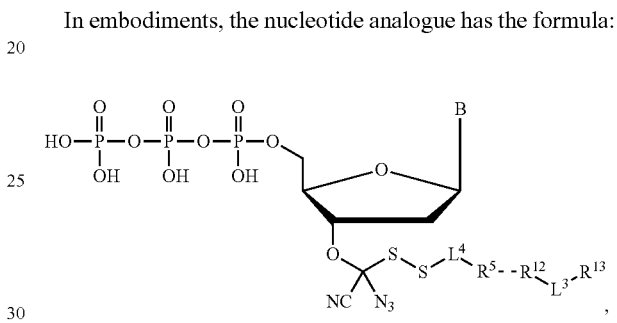

wherein B, $R^{12}$, $L^3$, $R^{13}$, $R^5$, and $L^4$ are as described herein, including embodiments.

In embodiments, the nucleotide analogue has the formula:

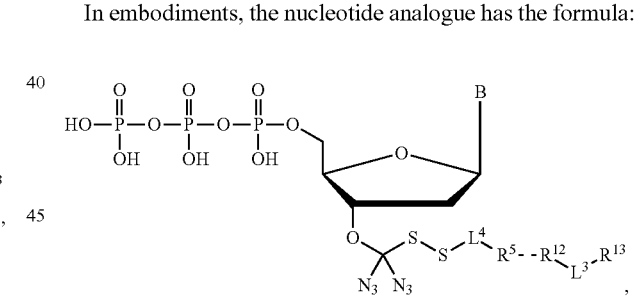

wherein B, $R^{12}$, $L^3$, $R^{13}$, $R^5$, and $L^4$ are as described herein, including embodiments.

In embodiments, the nucleotide analogue has the formula:

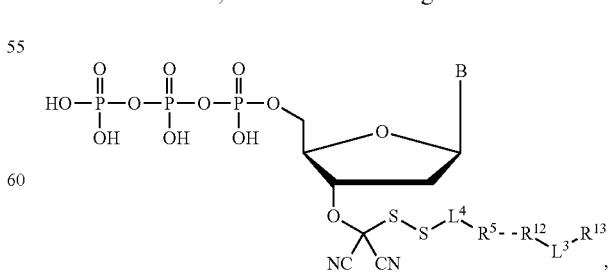

wherein B, $R^{12}$, $L^3$, $R^{13}$, $R^5$, and $L^4$ are as described herein, including embodiments.

In embodiments, the nucleotide analogue has the formula:
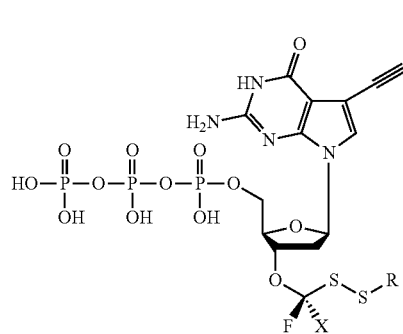
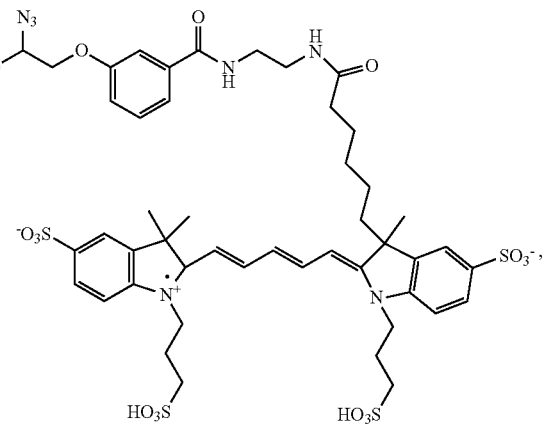
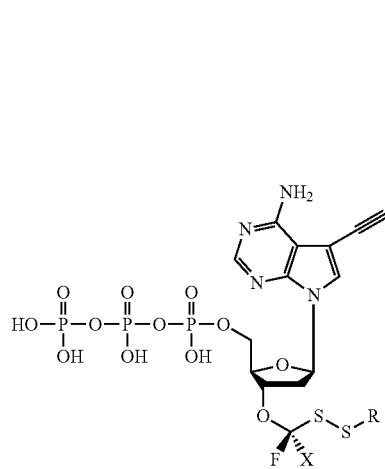
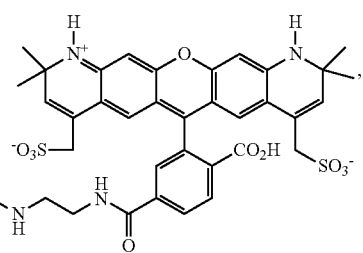
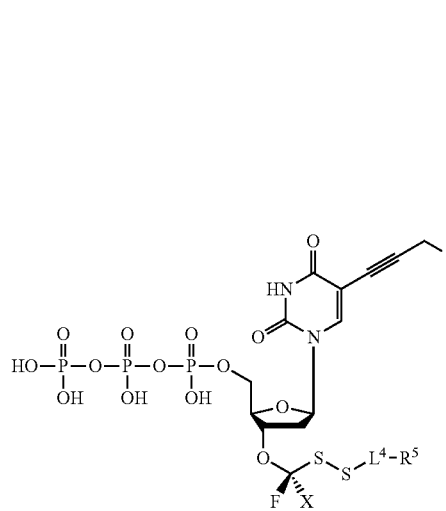
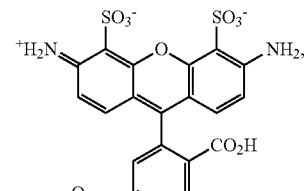

319 320
-continued
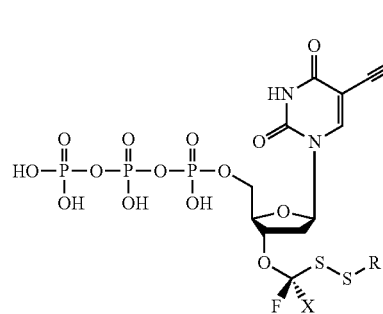
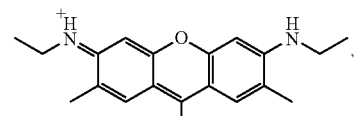
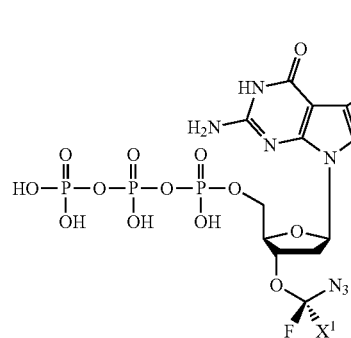
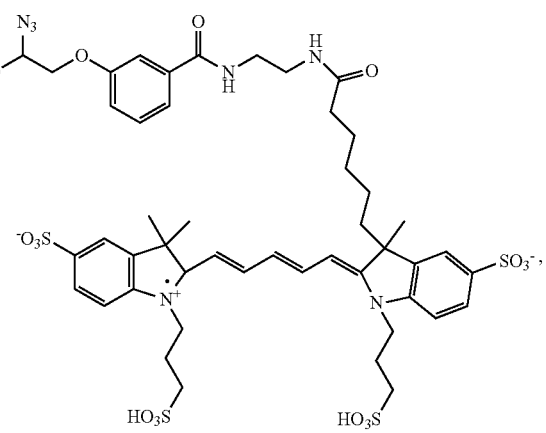
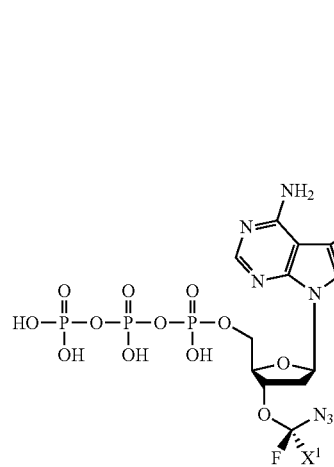

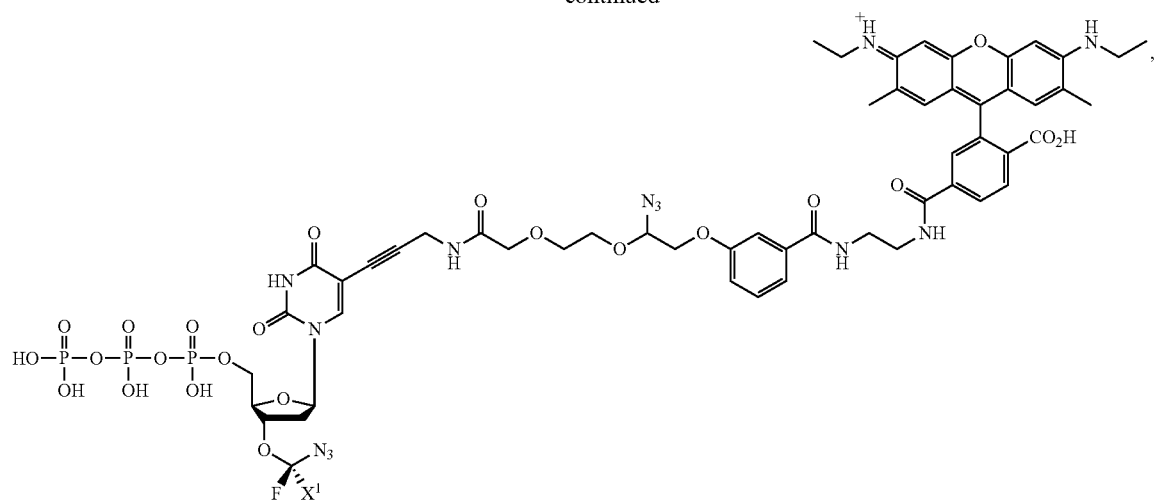
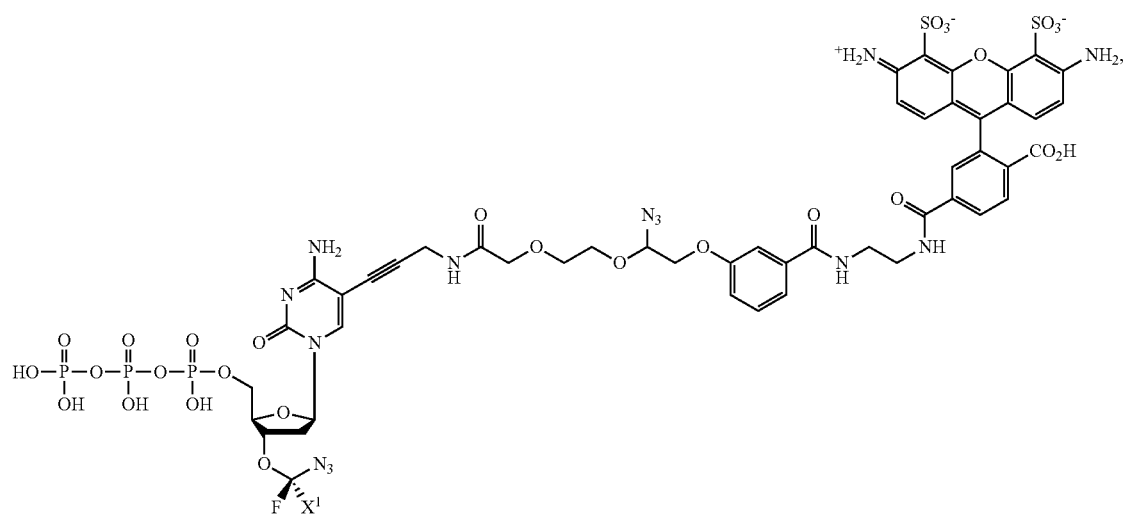
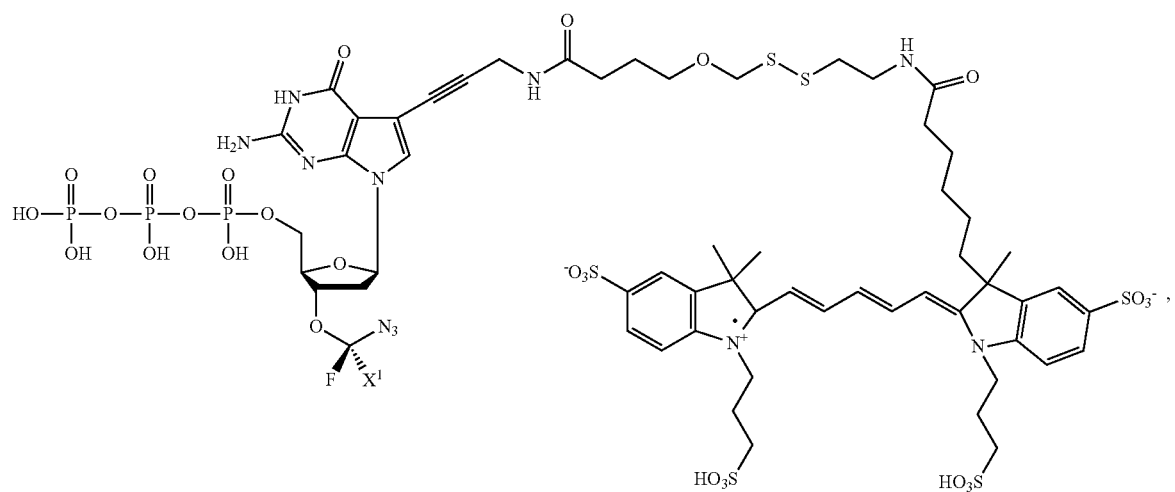

323
324
-continued
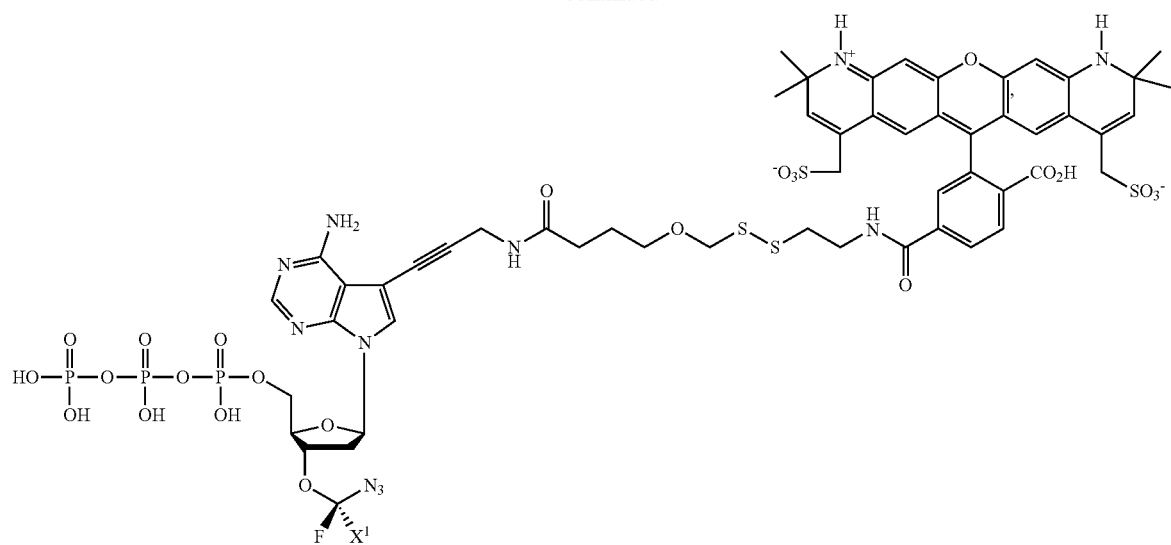
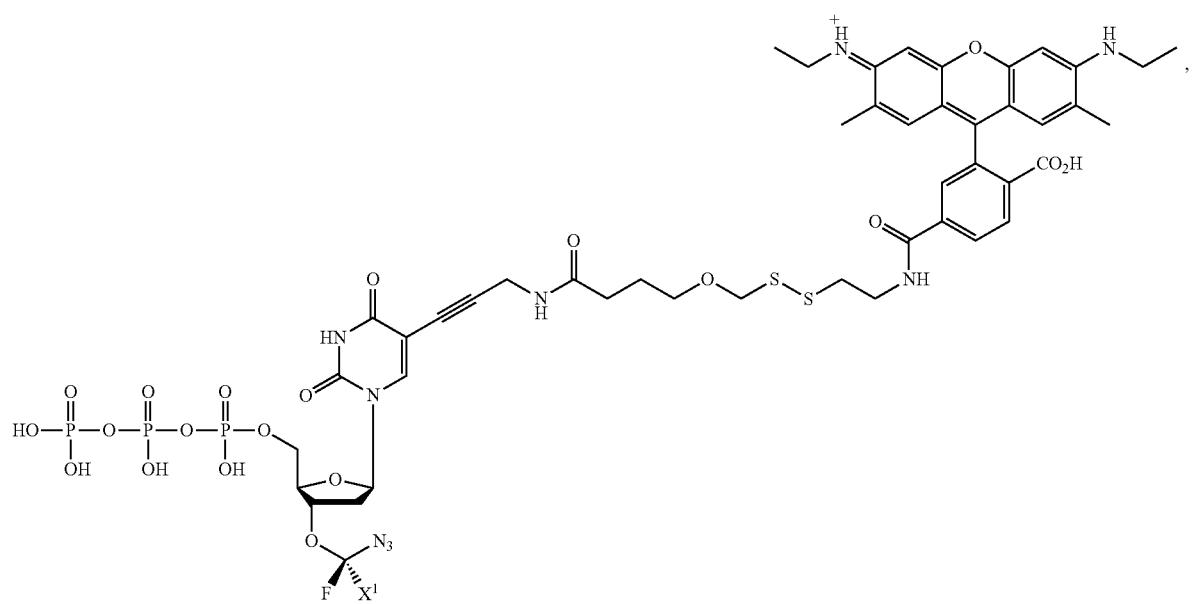

325 326
-continued
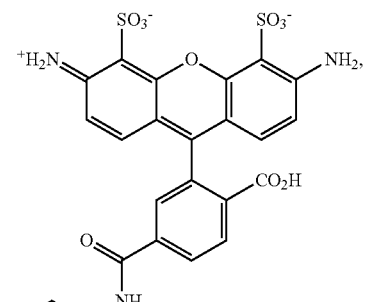
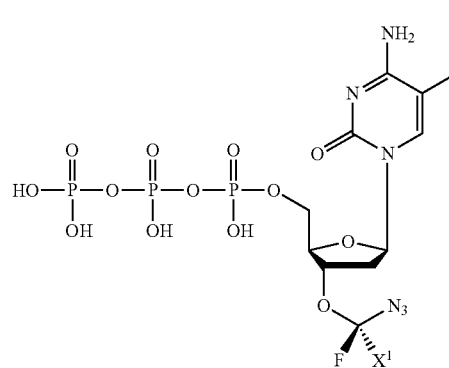
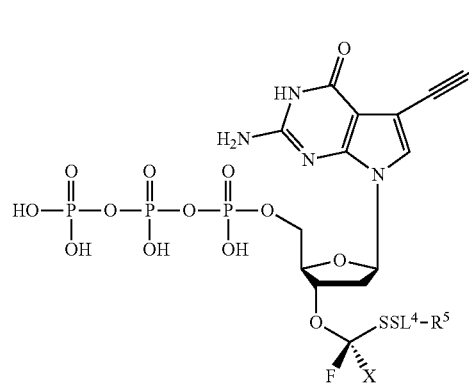
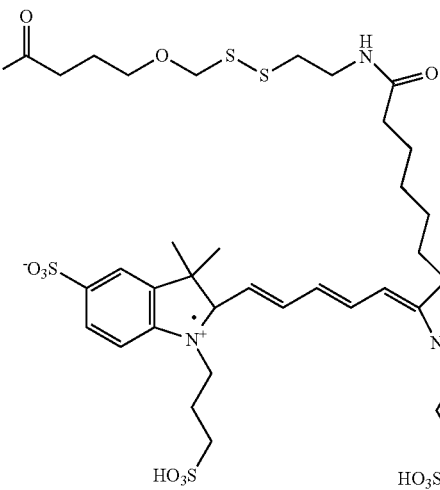
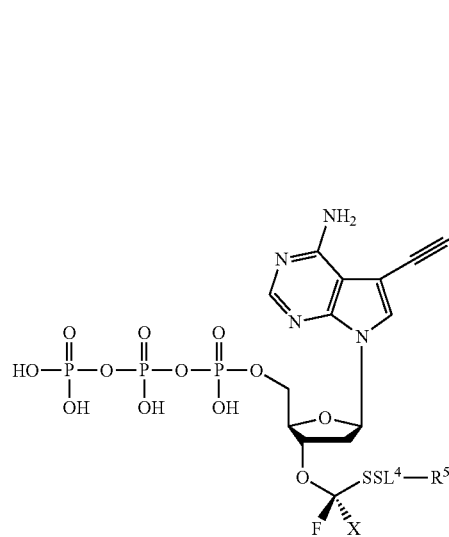
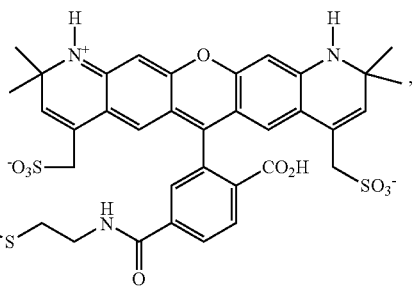

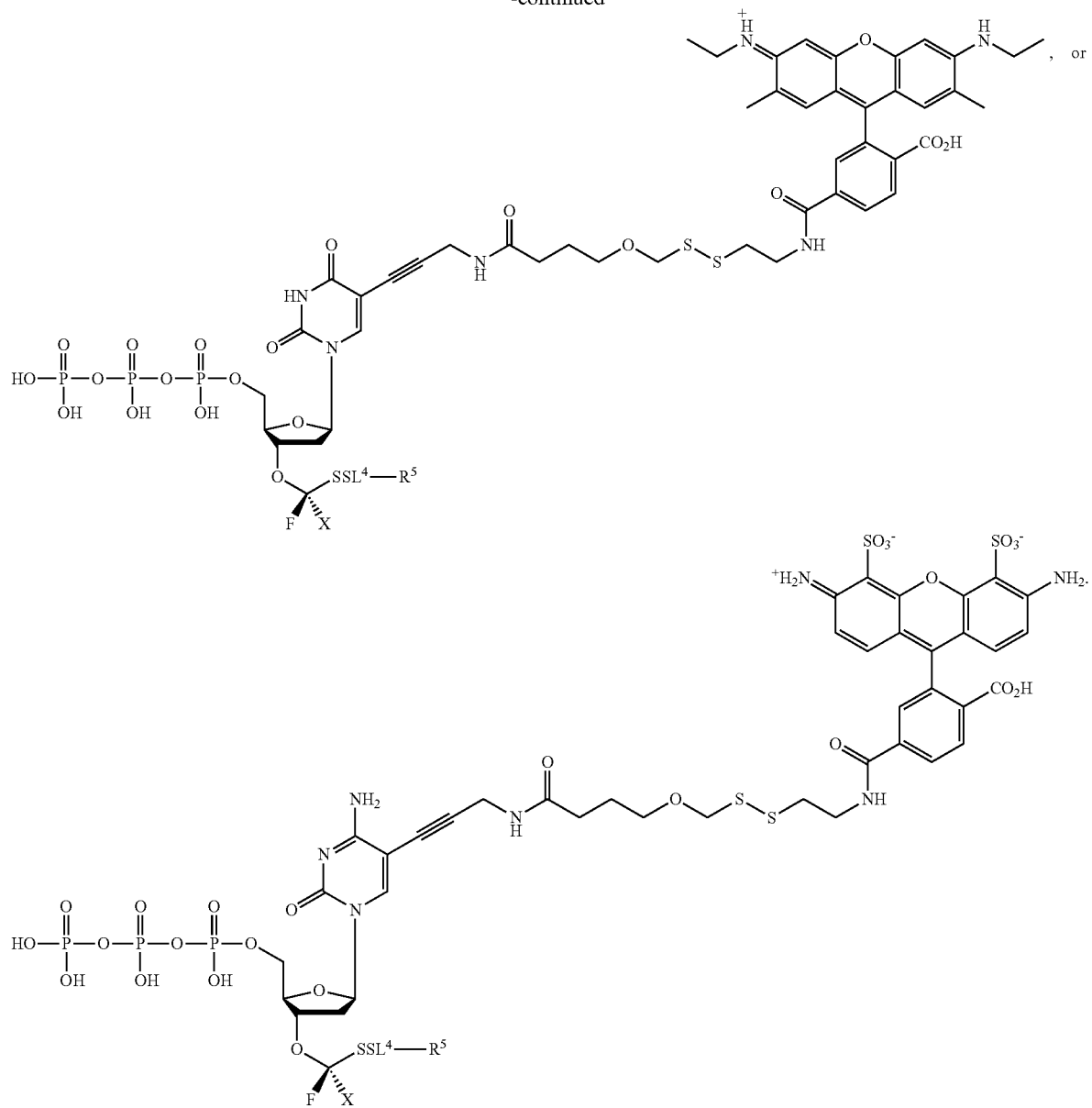

In an aspect is provided a nucleic acid polymerase complex, wherein the nucleic acid polymerase is bound (e.g., nocovalently bound) to a nucleotide analogue as described herein, including embodiments.

In embodiments, the nucleic acid polymerase is a Taq polymerase, Terminator γ, 9° N polymerase (exo-), Terminator II, Terminator III, or Terminator IX. In embodiments, the nucleic acid polymerase is Therminator γ. In embodiments, the nucleic acid polymerase is 9° N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9° N and mutants thereof. In embodiments, the nucleic acid polymerase is Phi29 and mutants thereof.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when $L^2$ is substituted, $L^2$ is substituted with one or more first substituent groups denoted by $R^{L2.1}$ as explained in the definitions section above in the description of "first substituent group(s)". In embodiments, when an $R^{L2.1}$ substituent group is substituted, the $R^{L2.1}$ substituent group is substituted with one or more second substituent groups denoted by $R^{L2.2}$ as explained in the definitions section above in the description of "first substituent group(s)". In embodiments, when an $R^{L2.2}$ substituent group is substituted, the $R^{L2.2}$ substituent group is substituted with one or more third substituent groups denoted by $R^{L2.3}$ as explained in the definitions section above in the description of "first substituent group(s)". In the above embodiments, $L^2$, $R^{L2.1}$, $R^{L2.2}$, and $R^{L2.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^2$, $R^{L2.1}$, $R^{L2.2}$, and $R^{L2.3}$, respectively.

In embodiments, when $L^3$ is substituted, $L^3$ is substituted with one or more first substituent groups denoted by $R^{L3.1}$ as explained in the definitions section above in the description of "first substituent group(s)". In embodiments, when an $R^{L3.1}$ substituent group is substituted, the $R^{L3.1}$ substituent group is substituted with one or more second substituent groups denoted by $R^{L3.2}$ as explained in the definitions section above in the description of "first substituent group(s)". In embodiments, when an $R^{L3.2}$ substituent group is substituted, the $R^{L3.2}$ substituent group is substituted with one or more third substituent groups denoted by $R^{L3.3}$ as explained in the definitions section above in the description of "first substituent group(s)". In the above embodiments, $L^3$, $R^{L3.1}$, $R^{L3.2}$, and $R^{L3.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^3$, $R^{L3.1}$, $R^{L3.2}$, and $R^{L3.3}$, respectively.

In embodiments, when $L^4$ is substituted, $L^4$ is substituted with one or more first substituent groups denoted by $R^{L4.1}$ as explained in the definitions section above in the description of "first substituent group(s)". In embodiments, when an $R^{L4.1}$ substituent group is substituted, the $R^{L4.1}$ substituent group is substituted with one or more second substituent groups denoted by $R^{L4.2}$ as explained in the definitions section above in the description of "first substituent group(s)". In embodiments, when an $R^{L4.2}$ substituent group is substituted, the $R^{L4.2}$ substituent group is substituted with one or more third substituent groups denoted by $R^{L4.3}$ as explained in the definitions section above in the description of "first substituent group(s)". In the above embodiments, $L^4$, $R^{L4.1}$, $R^{L4.2}$, and $R^{L4.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^4$, $R^{L4.1}$, $R^{L4.2}$, and $R^{L4.3}$, respectively.

In embodiments, when $L^{2A}$ is substituted, $L^{2A}$ is substituted with one or more first substituent groups denoted by $R^{L2A.1}$ as explained in the definitions section above in the description of "first substituent group(s)". In embodiments, when an $R^{L2A.1}$ substituent group is substituted, the $R^{L2A.1}$ substituent group is substituted with one or more second substituent groups denoted by $R^{L2A.2}$ as explained in the definitions section above in the description of "first substituent group(s)". In embodiments, when an $R^{L2A.2}$ substituent group is substituted, the $R^{L2A.2}$ substituent group is substituted with one or more third substituent groups denoted by $R^{L2A.3}$ as explained in the definitions section above in the description of "first substituent group(s)". In the above embodiments, $L^{2A}$, $R^{L2A.1}$, $R^{L2A.2}$, and $R^{L2A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2A}$, $R^{L2A.1}$, $R^{L2A.2}$, and $R^{L2A.3}$, respectively.

In embodiments, when $L^{2B}$ is substituted, $L^{2B}$ is substituted with one or more first substituent groups denoted by $R^{L2B.1}$ as explained in the definitions section above in the description of "first substituent group(s)". In embodiments, when an $R^{L2B.1}$ substituent group is substituted, the $R^{L2B.1}$ substituent group is substituted with one or more second substituent groups denoted by $R^{L2B.2}$ as explained in the definitions section above in the description of "first substituent group(s)". In embodiments, when an $R^{L2B.2}$ substituent group is substituted, the $R^{L2B.2}$ substituent group is substituted with one or more third substituent groups denoted by $R^{L2B.3}$ as explained in the definitions section above in the description of "first substituent group(s)". In the above embodiments, $L^{2B}$, $R^{L2B.1}$, $R^{L2B.2}$, and $R^{L2B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2B}$, $R^{L2B.1}$, $R^{L2B.2}$, and $R^{L2B.3}$, respectively.

In embodiments, when $L^{2C}$ is substituted, $L^{2C}$ is substituted with one or more first substituent groups denoted by $R^{L2C.1}$ as explained in the definitions section above in the description of "first substituent group(s)". In embodiments, when an $R^{L2C.1}$ substituent group is substituted, the $R^{L2C.1}$ substituent group is substituted with one or more second substituent groups denoted by $R^{L2C.2}$ as explained in the definitions section above in the description of "first substituent group(s)". In embodiments, when an $R^{L2C.2}$ substituent group is substituted, the $R^{L2C.2}$ substituent group is substituted with one or more third substituent groups denoted by $R^{L2C.3}$ as explained in the definitions section above in the description of "first substituent group(s)". In the above embodiments, $L^{2C}$, $R^{L2C.1}$, $R^{L2C.2}$, and $R^{L2C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2C}$, $R^{L2C.1}$, $R^{L2C.2}$, and $R^{L2C.3}$, respectively.

In embodiments, when $L^{2D}$ is substituted, $L^{2D}$ is substituted with one or more first substituent groups denoted by $R^{L2D.1}$ as explained in the definitions section above in the description of "first substituent group(s)". In embodiments, when an $R^{L2D.1}$ substituent group is substituted, the $R^{L2D.1}$ substituent group is substituted with one or more second substituent groups denoted by $R^{L2D.2}$ as explained in the definitions section above in the description of "first substituent group(s)". In embodiments, when an $R^{L2D.2}$ substituent group is substituted, the $R^{L2D.2}$ substituent group is substituted with one or more third substituent groups denoted by $R^{L2D.3}$ as explained in the definitions section above in the description of "first substituent group(s)". In the above embodiments, $L^{2D}$, $R^{L2D.1}$, $R^{L2D.2}$, and $R^{L2D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2D}$, $R^{L2D.1}$, $R^{L2D.2}$, and $R^{L2D.3}$, respectively.

In embodiments, when $L^{2E}$ is substituted, $L^{2E}$ is substituted with one or more first substituent groups denoted by $R^{L2E.1}$ as explained in the definitions section above in the description of "first substituent group(s)". In embodiments, when an $R^{L2E.1}$ substituent group is substituted, the $R^{L2E.1}$ substituent group is substituted with one or more second substituent groups denoted by $R^{L2E.2}$ as explained in the definitions section above in the description of "first substituent group(s)". In embodiments, when an $R^{L2E.2}$ substituent group is substituted, the $R^{L2E.2}$ substituent group is substituted with one or more third substituent groups denoted by $R^{L2E.3}$ as explained in the definitions section above in the description of "first substituent group(s)". In the above embodiments, $L^{2E}$, $R^{L2E.1}$, $R^{L2E.2}$, and $R^{L2E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{2E}$, $R^{L2E.1}$, $R^{L2E.2}$, and $R^{L2E.3}$, respectively.

In embodiments, when $L^{3A}$ is substituted, $L^{3A}$ is substituted with one or more first substituent groups denoted by $R^{L3A.1}$ as explained in the definitions section above in the description of "first substituent group(s)". In embodiments, when an $R^{L3A.1}$ substituent group is substituted, the $R^{L3A.1}$ substituent group is substituted with one or more second substituent groups denoted by $R^{L3A.2}$ as explained in the definitions section above in the description of "first substituent group(s)". In embodiments, when an $R^{L3A.2}$ substituent group is substituted, the $R^{L3A.2}$ substituent group is substituted with one or more third substituent groups denoted by $R^{L3A.3}$ as explained in the definitions section above in the description of "first substituent group(s)". In the above embodiments, $L^{3A}$, $R^{L3A.1}$, $R^{L3A.2}$, and $R^{L3A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{3A}$, $R^{L3A.1}$, $R^{L3A.2}$, and $R^{L3A.3}$, respectively.

In embodiments, when $L^{3B}$ is substituted, $L^{3B}$ is substituted with one or more first substituent groups denoted by $R^{L3B.1}$ as explained in the definitions section above in the description of "first substituent group(s)". In embodiments, when an $R^{L3B.1}$ substituent group is substituted, the $R^{L3B.1}$ substituent group is substituted with one or more second substituent groups denoted by $R^{L3B.2}$ as explained in the definitions section above in the description of "first substituent group(s)". In embodiments, when an $R^{L3B.2}$ substituent group is substituted, the $R^{L3B.2}$ substituent group is substituted with one or more third substituent groups denoted by $R^{L3B.3}$ as explained in the definitions section above in the description of "first substituent group(s)". In the above embodiments, $L^{3B}$, $R^{L3B.1}$, $R^{L3B.2}$, and $R^{L3B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{3B}$, $R^{L3B.1}$, $R^{L3B.2}$, and $R^{L3B.3}$, respectively.

In embodiments, when $L^{3C}$ is substituted, $L^{3C}$ is substituted with one or more first substituent groups denoted by $R^{L3C.1}$ as explained in the definitions section above in the description of "first substituent group(s)". In embodiments, when an $R^{L3C.1}$ substituent group is substituted, the $R^{L3C.1}$ substituent group is substituted with one or more second substituent groups denoted by $R^{L3C.2}$ as explained in the definitions section above in the description of "first substituent group(s)". In embodiments, when an $R^{L3C.2}$ substituent group is substituted, the $R^{L3C.2}$ substituent group is substituted with one or more third substituent groups denoted by $R^{L3C.3}$ as explained in the definitions section above in the description of "first substituent group(s)". In the above embodiments, $L^{3C}$, $R^{L3C.1}$, $R^{L3C.2}$, and $R^{L3C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{3C}$, $R^{L3C.1}$, $R^{L3C.2}$, and $R^{L3C.3}$, respectively.

In embodiments, when $L^{3D}$ is substituted, $L^{3D}$ is substituted with one or more first substituent groups denoted by $R^{L3D.1}$ as explained in the definitions section above in the description of "first substituent group(s)". In embodiments, when an $R^{L3D.1}$ substituent group is substituted, the $R^{L3D.1}$ substituent group is substituted with one or more second substituent groups denoted by $R^{L3D.2}$ as explained in the definitions section above in the description of "first substituent group(s)". In embodiments, when an $R^{L3D.2}$ substituent group is substituted, the $R^{L3D.2}$ substituent group is substituted with one or more third substituent groups denoted by $R^{L3D.3}$ as explained in the definitions section above in the description of "first substituent group(s)". In the above embodiments, $L^{3D}$, $R^{L3D.1}$, $R^{L3D.2}$, and $R^{L3D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{3D}$, $R^{L3D.1}$, $R^{L3D.2}$, and $R^{L3D.3}$, respectively.

In embodiments, when $L^{3E}$ is substituted, $L^{3E}$ is substituted with one or more first substituent groups denoted by $R^{L3E.1}$ as explained in the definitions section above in the description of "first substituent group(s)". In embodiments, when an $R^{L3E.1}$ substituent group is substituted, the $R^{L3E.1}$ substituent group is substituted with one or more second substituent groups denoted by $R^{L3E.2}$ as explained in the definitions section above in the description of "first substituent group(s)". In embodiments, when an $R^{L3E.2}$ substituent group is substituted, the $R^{L3E.2}$ substituent group is substituted with one or more third substituent groups denoted by $R^{L3E.3}$ as explained in the definitions section above in the description of "first substituent group(s)". In the above embodiments, $L^{3E}$, $R^{L3E.1}$, $R^{L3E.2}$, and $R^{L3E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{3E}$, $R^{L3E.1}$, $R^{L3E.2}$, and $R^{L3E.3}$, respectively.

In embodiments, when $L^{4A}$ is substituted, $L^{4A}$ is substituted with one or more first substituent groups denoted by $R^{L4A.1}$ as explained in the definitions section above in the description of "first substituent group(s)". In embodiments, when an $R^{L4A.1}$ substituent group is substituted, the $R^{L4A.1}$ substituent group is substituted with one or more second substituent groups denoted by $R^{L4A.2}$ as explained in the definitions section above in the description of "first substituent group(s)". In embodiments, when an $R^{L4A.2}$ substituent group is substituted, the $R^{L4A.2}$ substituent group is substituted with one or more third substituent groups denoted by $R^{L4A.3}$ as explained in the definitions section above in the description of "first substituent group(s)". In the above embodiments, $L^{4A}$, $R^{L4A.1}$, $R^{L4A.2}$, and $R^{L4A.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{4A}$, $R^{L4A.1}$, $R^{L4A.2}$, and $R^{L4A.3}$, respectively.

In embodiments, when $L^{4B}$ is substituted, $L^{4B}$ is substituted with one or more first substituent groups denoted by $R^{L4B.1}$ as explained in the definitions section above in the description of "first substituent group(s)". In embodiments, when an $R^{L4B.1}$ substituent group is substituted, the $R^{L4B.1}$ substituent group is substituted with one or more second substituent groups denoted by $R^{L4B.2}$ as explained in the definitions section above in the description of "first substituent group(s)". In embodiments, when an $R^{L4B.2}$ substituent group is substituted, the $R^{L4B.2}$ substituent group is substituted with one or more third substituent groups denoted by $R^{L4B.3}$ as explained in the definitions section above in the description of "first substituent group(s)". In the above embodiments, $L^{4B}$, $R^{L4B.1}$, $R^{L4B.2}$, and $R^{L4B.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{4B}$, $R^{L4B.1}$, $R^{L4B.2}$, and $R^{L4B.3}$, respectively.

In embodiments, when $L^{4C}$ is substituted, $L^{4C}$ is substituted with one or more first substituent groups denoted by $R^{L4C.1}$ as explained in the definitions section above in the description of "first substituent group(s)". In embodiments, when an $R^{L4C.1}$ substituent group is substituted, the $R^{L4C.1}$ substituent group is substituted with one or more second substituent groups denoted by $R^{L4C.2}$ as explained in the definitions section above in the description of "first substituent group(s)". In embodiments, when an $R^{L4C.2}$ substituent group is substituted, the $R^{L4C.2}$ substituent group is substituted with one or more third substituent groups denoted by $R^{L4C.3}$ as explained in the definitions section above in the description of "first substituent group(s)". In the above embodiments, $L^{4C}$, $R^{L4C.1}$, $R^{L4C.2}$, and $R^{L4C.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{4C}$, $R^{L4C.1}$, $R^{L4C.2}$, and $R^{L4C.3}$, respectively.

In embodiments, when $L^{4D}$ is substituted, $L^{4D}$ is substituted with one or more first substituent groups denoted by $R^{L4D.1}$ as explained in the definitions section above in the description of "first substituent group(s)". In embodiments, when an $R^{L4D.1}$ substituent group is substituted, the $R^{L4D.1}$ substituent group is substituted with one or more second substituent groups denoted by $R^{L4D.2}$ as explained in the definitions section above in the description of "first substituent group(s)". In embodiments, when an $R^{L4D.2}$ substituent group is substituted, the $R^{L4D.2}$ substituent group is substituted with one or more third substituent groups denoted by $R^{L4D.3}$ as explained in the definitions section above in the description of "first substituent group(s)". In the above embodiments, $L^{4D}$, $R^{L4D.1}$, $R^{L4D.2}$, and $R^{L4D.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{4D}$, $R^{L4D.1}$, $R^{L4D.2}$, and $R^{L4D.3}$, respectively.

In embodiments, when $L^{4E}$ is substituted, $L^{4E}$ is substituted with one or more first substituent groups denoted by $R^{L4E.1}$ as explained in the definitions section above in the description of "first substituent group(s)". In embodiments, when an $R^{L4E.1}$ substituent group is substituted, the $R^{L4E.1}$ substituent group is substituted with one or more second substituent groups denoted by $R^{L4E.2}$ as explained in the definitions section above in the description of "first substituent group(s)". In embodiments, when an $R^{L4E.2}$ substituent group is substituted, the $R^{L4E.2}$ substituent group is substituted with one or more third substituent groups denoted by $R^{L4E.3}$ as explained in the definitions section above in the description of "first substituent group(s)". In the above embodiments, $L^{4E}$, $R^{L4E.1}$, $R^{L4E.2}$, and $R^{L4E.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{4E}$, $R^{L4E.1}$, $R^{L4E.2}$, and $R^{L4E.3}$, respectively.

III. Methods of Use

In another aspect is provided method for sequencing a nucleic acid, including: (i) incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues include a unique detectable label; and (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues is a nucleotide analogue described herein, including embodiments. In embodiments, the removal of the cleavable moiety

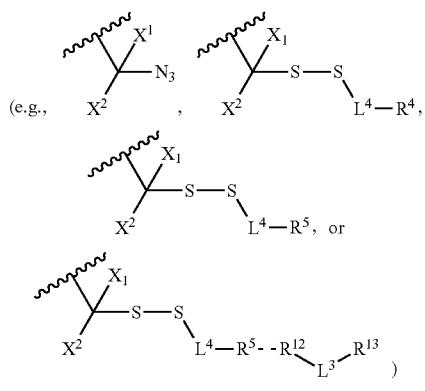

is increased relative to a control (e.g., a native nucleotide, or a nucleotide without a cleavable moiety with the formula

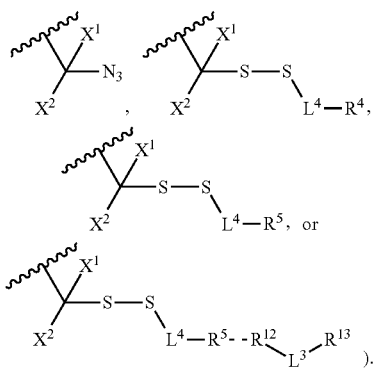

).

In embodiments, at least one of the four different labeled nucleotide analogues is an orthogonally cleavable labeled nucleotide analogue including a cleavable moiety, the orthogonally cleavable labeled nucleotide analogue having the structure as described herein, and wherein the method further includes, after each of the incorporating steps, adding to the reaction vessel a cleaving reagent capable of cleaving the cleavable moiety. In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the cleaving reagent includes an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$).

In embodiments, at least one of the four different labeled nucleotide analogues is an orthogonally cleavable labeled nucleotide analogue including a cleavable linker (e.g., DTM), the orthogonally cleavable labeled nucleotide analogue having the structure as described herein, and wherein the method further includes, after each of the incorporating steps, adding to the reaction vessel a cleaving reagent capable of cleaving the cleavable linker (e.g., DTM). In embodiments the nucleic acid sequence is single-stranded DNA.

In an aspect is provided a method of incorporating a nucleotide analogue into a primer, the method including combining a polymerase, a primer hybridized to a nucleic acid template and a nucleotide analogue within a reaction vessel and allowing the polymerase to incorporate the nucleotide analogue into the primer thereby forming an extended primer, wherein the nucleotide analogue is a nucleotide analogue described herein, including embodiments.

In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In an aspect is provided a method of incorporating a nucleotide analogue into a primer, the method including combining a polymerase, a primer hybridized to a nucleic acid template and a nucleotide analogue within a reaction vessel and allowing the polymerase to incorporate the nucleotide analogue into the primer thereby forming an extended primer, wherein the nucleotide analogue is of the structure as described herein, including embodiments.

In embodiments, $L^2$ is a cleavable moiety and $R^5$ is a detectable label, the method further including, after the incorporating, cleaving the cleavable moiety with a cleaving reagent.

In embodiments, $R^5$ is an anchor moiety, said method further including, after the incorporating, labeling the nucleotide analog with a detectable label.

In an aspect is provided a method for sequencing a nucleic acid, including: (i) incorporating in series with a nucleic acid polymerase (e.g., thermophilic, 9° N and mutants thereof, Phi29 and mutants thereof), within a reaction vessel, one of four different labeled nucleotide analogues into a primer to create an extension strand, wherein the primer is hybridized to the nucleic acid and wherein each of the four different labeled nucleotide analogues include a unique detectable label; (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues are of the structure formula:

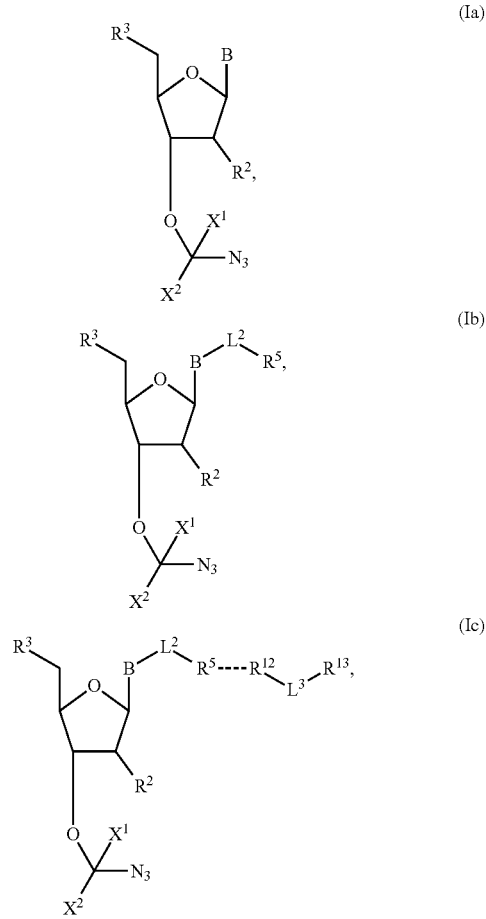

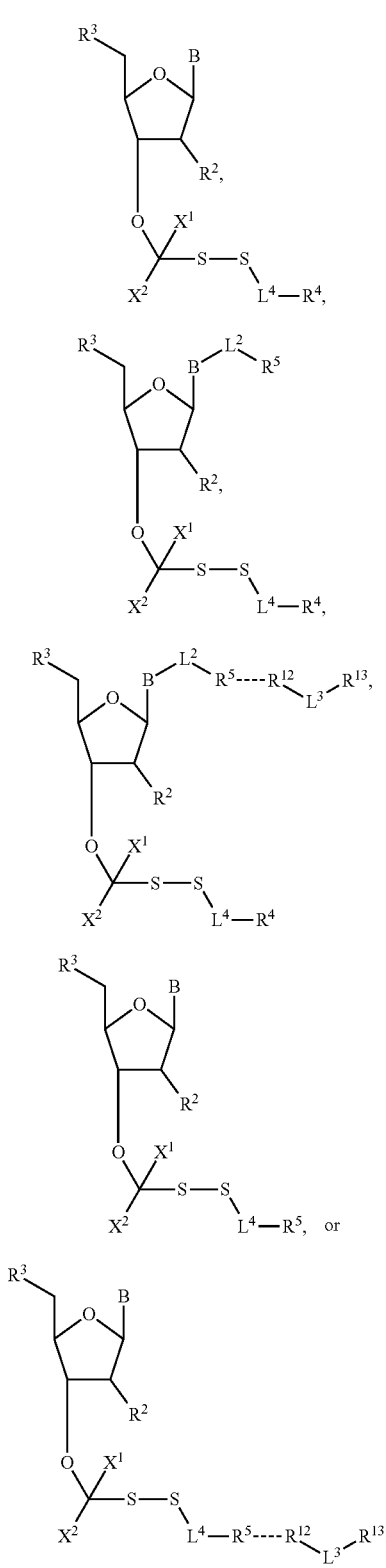

The symbol "----" is a non-covalent bond. The symbol B is a base (e.g., monovalent or divalent) or analogue thereof. $L^2$ is a covalent linker (e.g., a cleavable linker). $L^3$ is a covalent linker. $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^2$ is hydrogen or —$OR^{2A}$, wherein $R^{2A}$ is hydrogen, polymerase-compatible moiety, or polymerase-compatible cleavable moiety. $R^3$ is —OH, monophosphate, or polyphosphate or a nucleic acid. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is a detectable label, an anchor moiety, or affinity anchor moiety. $R^{12}$ is a complementary affinity anchor moiety binder. $R^{13}$ is a detectable label. The symbols $X^1$ and $X^2$ are independently hydrogen, halogen, —$N_3$, or —CN, wherein at least wherein at least one of $X^1$ or $X^2$ is halogen, —$N_3$, or —CN. In embodiments, at least one of $X^1$ or $X^2$ is halogen. In embodiments, if $X^1$ is —$N_3$ then $X^2$ is not —$N_3$ for formula (Ia), (Ib), and (Ic).

In an aspect is provided a method of incorporating a nucleotide analogue into a nucleic acid sequence comprising combining a nucleic acid polymerase, a primer hybridized to a nucleic acid template, and a nucleotide analogue, within a reaction vessel and allowing said nucleic acid polymerase to incorporate said nucleotide analogue into said primer thereby incorporating a nucleotide analogue into a nucleic acid sequence, wherein said nucleotide analogue comprises a fluorescent dye (e.g., a fluorescent dye with a molecular weight of at least about 140 Daltons), wherein the fluorescent dye is covalently bound at the 3' position of said nucleotide analogue for sequence determination, and wherein after removal of the fluorescent dye by cleaving the 3'-O linker to regenerate the 3'-OH on the DNA extension product allows continuous nucleotide analogue incorporation and detection of multiple bases.

In embodiments, the method includes contacting the single-stranded DNA, wherein the single-stranded DNA is bound to a polymerase which is in turn attached to a membrane-embedded nanopore in an electrolyte solution, wherein the single-stranded DNA has a primer hybridized to a portion thereof, and determining the sequence of the single stranded DNA template, following the steps of: (a) addition of four nucleotides including 3'-O-cleavable linkers (DTM) attached with anchor moieties. The appropriate nucleotide analogue complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-O-being blocked by a cleavable linker and anchor moiety, preventing further incorporation in this step; (b) addition to the extended primer of 4 different nanopore tags attached with different binding molecules corresponding to the 4 anchors; the appropriate binding molecule with tag will either covalently bind or complex with the 3'-O-anchor nucleotide incorporated in step (a); (c) application of a voltage across the membrane and measuring an electronic (ionic current) change across the nanopore resulting from the tag attached thereto generated in step (b) translocating through the nanopore, wherein the electronic change is different for each different type of tag, thereby identifying the nucleotide residue in the single-stranded template DNA, which is complementary to the incorporated tagged nucleotide; (d) cleavage of the 3'-O-cleavable linker-attached tag by treatment with an appropriate cleaving agent, thus generating a free 3'-OH ready for the next extension reaction; and (e)

Iteratively performing steps (a)-(d) for each nucleotide residue of the single-stranded DNA being sequenced, wherein in each iteration of step (a) the 3'-O-cleavable anchor nucleotide is incorporated into the DNA extension product resulting from the previous iteration of step (d) if it is complementary to the nucleotide residue of the single-stranded (template) DNA which is immediately 5' to a nucleotide residue of the single-stranded DNA hybridized to the 3' terminal nucleotide residue of the DNA extension product, thereby determining the nucleotide sequence of the single-stranded DNA.

In embodiments, the method includes contacting the single-stranded DNA template, wherein the single-strand DNA to be sequenced hybridizes to the primer, wherein the single-stranded primer is conjugated to a membrane-embedded nanopore in an electrolyte solution, and determining the sequence of the single stranded DNA template, following the steps of: (a) addition of polymerase and four nucleotides including 3'-O-cleavable linkers (DTM) attached with anchor moieties. The appropriate nucleotide analogue complementary to the nucleotide residue of the single-stranded DNA (template) which is immediately 5' to a nucleotide residue of the single-stranded DNA will be incorporated by DNA polymerase at the 3' terminal nucleotide residue of the primer, so as to form a DNA extension product. Only a single 3'-O-anchor-cleavable linker (DTM) nucleotide will add to the primer due to the 3'-0-being blocked by a cleavable linker and anchor moiety, preventing further incorporation in this step; (b) addition to the extended primer of 4 different nanopore tags attached with different binding molecules corresponding to the 4 anchors; the appropriate binding molecule with tag will either covalently bind or complex with the 3'-O-anchor nucleotide incorporated in step (a); (c) application of a voltage across the membrane and measuring an electronic (ionic current) change across the nanopore resulting from the tag attached thereto generated in step (b) translocating through the nanopore, wherein the electronic change is different for each different type of tag, thereby identifying the nucleotide residue in the single-stranded template DNA, which is complementary to the incorporated tagged nucleotide; (d) cleavage of the 3'-O-cleavable linker-attached tag by treatment with an appropriate cleaving agent, thus generating a free 3'-OH ready for the next extension reaction; and (e) iteratively performing steps (a)-(d) for each nucleotide residue of the single-stranded DNA being sequenced, wherein in each iteration of step (a) the 3'-O-cleavable anchor nucleotide is incorporated into the DNA extension product resulting from the previous iteration of step (d) if it is complementary to the nucleotide residue of the single-stranded (template) DNA which is immediately 5' to a nucleotide residue of the single-stranded DNA hybridized to the 3' terminal nucleotide residue of the DNA extension product, thereby determining the nucleotide sequence of the single-stranded DNA.

In embodiments, the method includes sequencing nucleic acid including: a) providing a nucleic acid template hybridized to a primer; b) extending the primer hybridized to the nucleic acid template with a labeled nucleotide or nucleotide analog, wherein the labeled nucleotide or nucleotide analog includes nucleotide analogs with a label linked to the base and a blocking group on the 3-hydroxyl group, and nucleotides or nucleotide analogs with a cleavable label blocking the 3' OH; and c) identifying the labeled nucleotide, so as to sequence the nucleic acid. In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof.

In embodiments, at least four of the nucleotide analogues (e.g., 3'-O-Anchor-Cleavable Linker nucleotides) include a triphosphate or a polyphosphate, a base which is adenine, guanine, cytosine, thymine, or uracil, or a derivative of each thereof, and an anchor molecule covalently coupled to the 3'-O-position of the nucleotide sugar moiety including a cleavable linker at the 3'-O-position.

In embodiments, the method includes simultaneously sequencing a plurality of different nucleic acids, including: a) extending a plurality of priming DNA strands hybridized to template DNAs, each of which includes one of the priming DNA strands, by incorporating a labeled nucleotide (e.g., a nucleotide analogue described herein); and b) identifying each labeled nucleotide (e.g., a nucleotide analogue described herein), so as to simultaneously sequence the plurality of different nucleic acids.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. Embodiments

Embodiment P1. A nucleotide analogue of the formula:

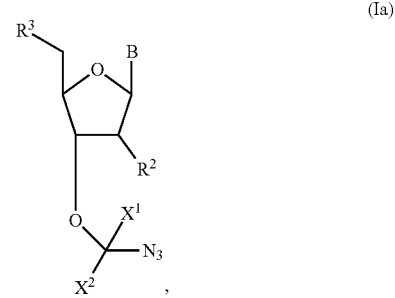

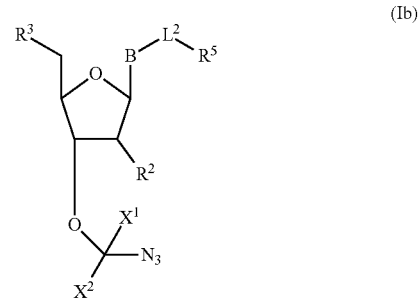

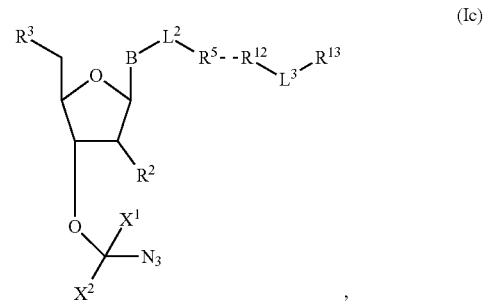

-continued

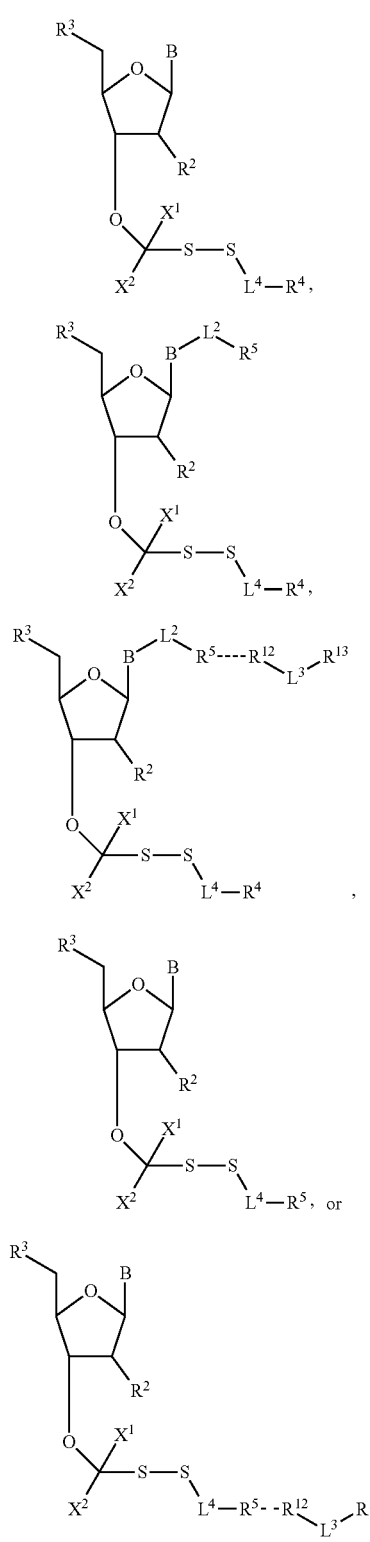

wherein
the symbol " --- " is a non-covalent bond;
B is a base or analogue thereof;
L² is a covalent linker;
L³ is a covalent linker;

L⁴ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R² is hydrogen or —OR$^{2A}$, wherein R$^{2A}$ is hydrogen or a polymerase-compatible cleavable moiety;

R³ is —OH, monophosphate, or polyphosphate or a nucleic acid;

R⁴ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is a detectable label, an anchor moiety, or affinity anchor moiety;

R¹² is a complementary affinity anchor moiety binder; and

R¹³ is a detectable label; and

X¹ and X² are independently hydrogen, halogen, —N₃, or —CN; wherein at least wherein at least one of X¹ or X² is halogen, —N₃, or —CN.

Embodiment P2. The nucleotide analogue of embodiment P1, wherein the nucleotide analogue has the formula:

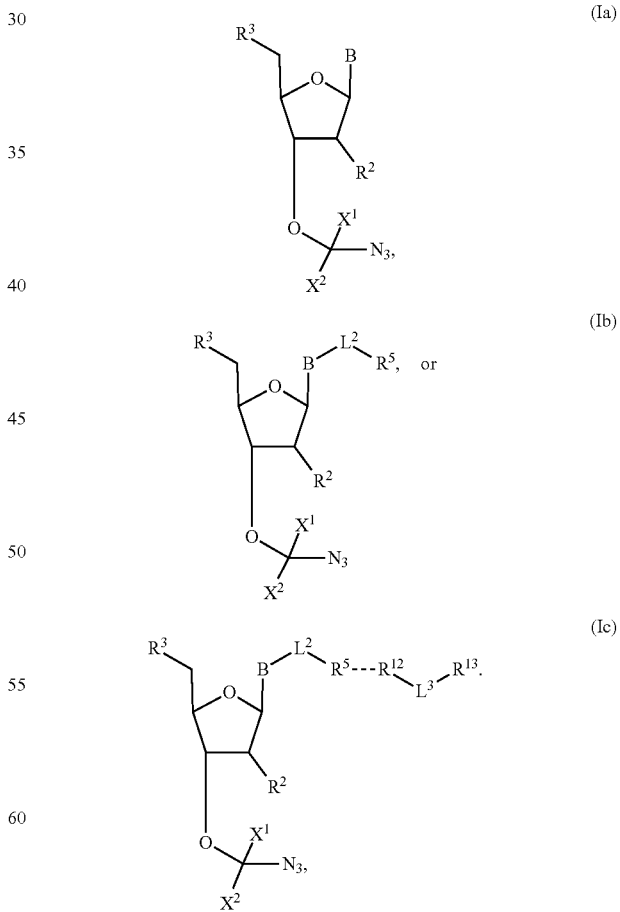

Embodiment P3. The nucleotide analogue of embodiment P1, wherein the nucleotide analogue has the formula:

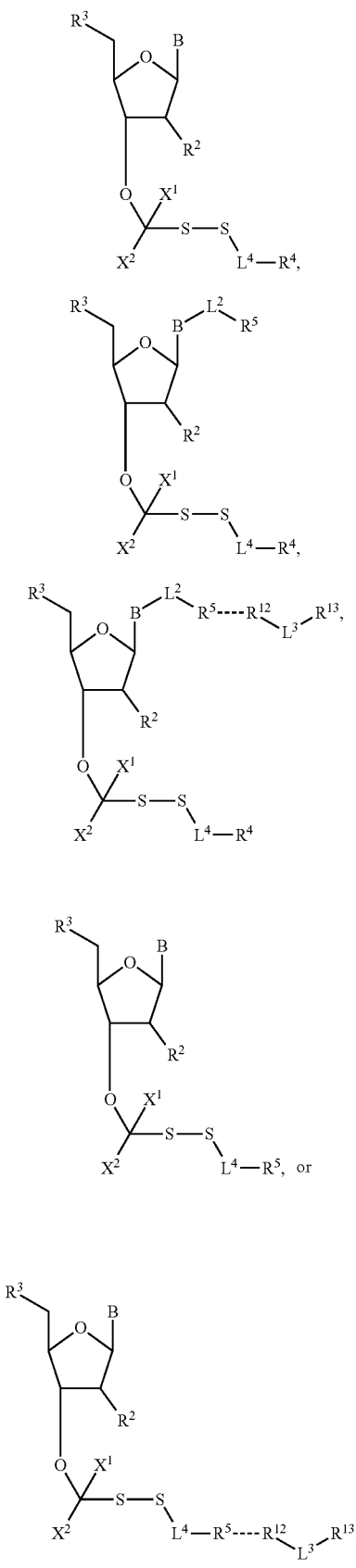
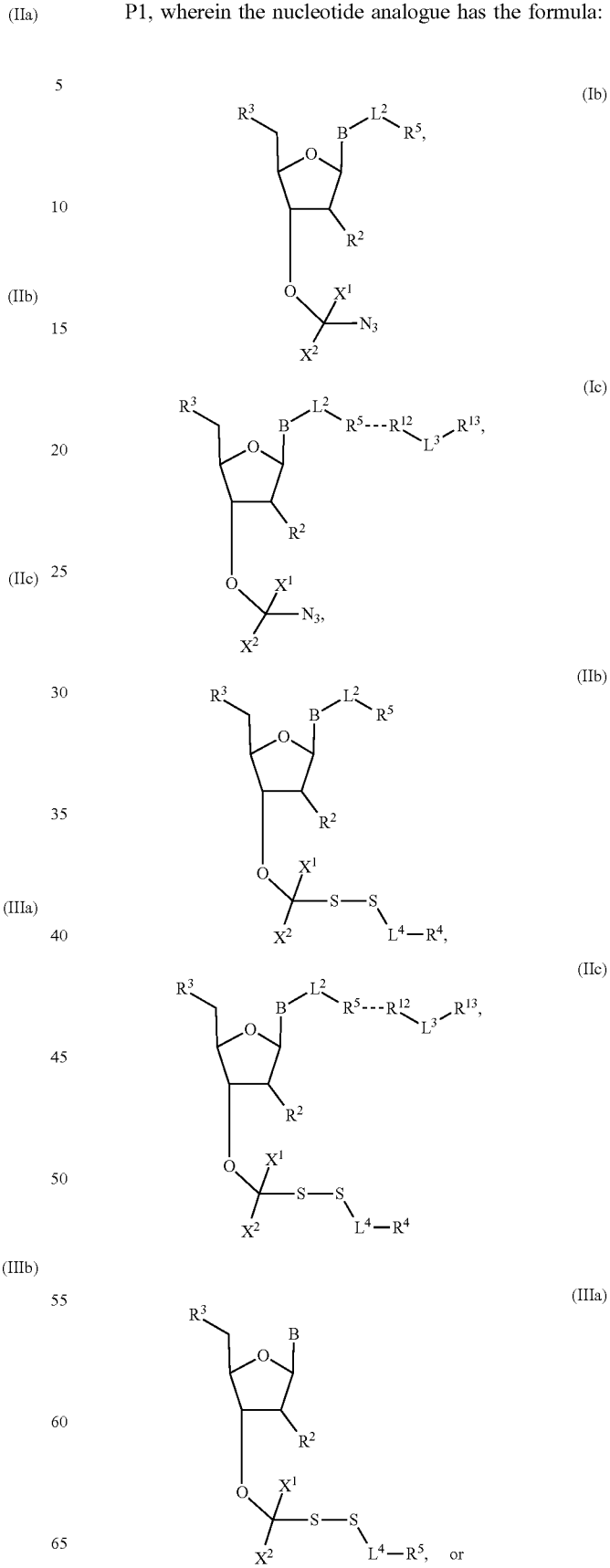
Embodiment P4. The nucleotide analogue of embodiment P1, wherein the nucleotide analogue has the formula:

-continued (IIIb)

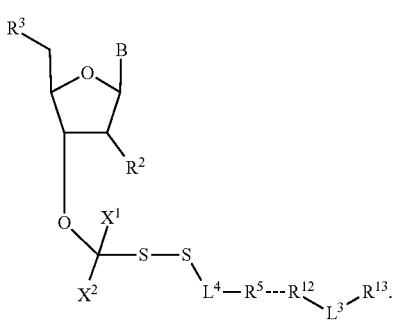

Embodiment P5. The nucleotide analogue of any one of embodiments P1 to P4 having the formula (Ia), (IIa), (IIIa), or (IIIb), wherein B is cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, deaza-adenine or a derivative thereof, deaza-guanine or a derivative thereof, deaza-hypoxanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment P6. The nucleotide analogue of any one of embodiments P1 to P4 having the formula (Ia), (IIa), (IIIa), or (IIIb), wherein B is

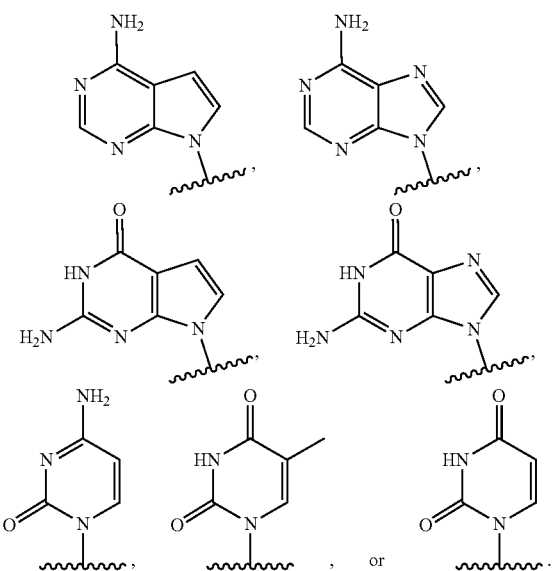

Embodiment P7. The nucleotide analogue of any one of embodiments P1 to P4 having the formula (Ib), (Ic), (IIb), (IIc), B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment P8. The nucleotide analogue of any one of c embodiments P1 to P4 having the formula (Ib), (Ic), (IIb), (IIc), wherein B is

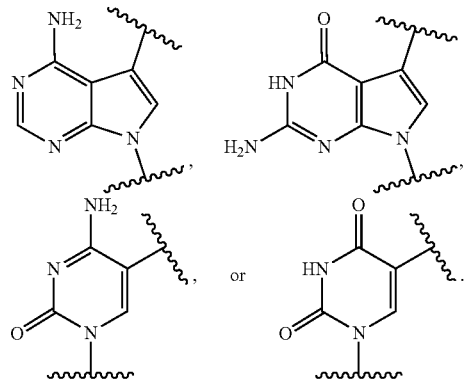

Embodiment P9. The nucleotide analogue of any one of embodiments P1 to P8, wherein $R^3$ is —OH.

Embodiment P10. The nucleotide analogue of anyone of embodiments P1 to P8, wherein $R^3$ is monophosphate.

Embodiment P11. The nucleotide analogue of anyone of embodiments P1 to P8, wherein $R^3$ is triphosphate, tetraphosphate, pentaphosphate, or hexaphosphate.

Embodiment P12. The nucleotide analogue of anyone of embodiments P1 to P11, wherein $R^2$ is hydrogen or —OH.

Embodiment P13. The nucleotide analogue of anyone of embodiments P1 to P11, wherein $R^2$ is hydrogen.

Embodiment P14. The nucleotide analogue of anyone of embodiments P1 to P13, wherein $L^2$ is a cleavable linker.

Embodiment P15. The nucleotide analogue of anyone of embodiments P1 to P14, wherein $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P16. The nucleotide analogue of anyone of embodiments P1 to P14, wherein $L^2$ is a non-cleavable linker.

Embodiment P17. The nucleotide analogue of anyone of embodiments P1 to P14, wherein $L^2$ is a chemically cleavable linker.

Embodiment P18. The nucleotide analogue of anyone of embodiments P1 to P14, wherein $L^2$ is a photocleavable linker, an acid-cleavable linker, a base-cleavable linker, an oxidant-cleavable linker, a reductant-cleavable linker, or a fluoride-cleavable linker.

Embodiment P19. The nucleotide analogue of anyone of embodiments P1 to P14, wherein $L^2$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment P20. The nucleotide analogue of anyone of embodiments P1 to P14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$, and $L^{2E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{2A}$, $L^{2B}$, $L^{2C}$, $L^{2D}$, and $L^{2E}$ is not a bond.

Embodiment P21. The nucleotide analogue of anyone of embodiments P1 to P14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene;
wherein at least one of $L^{2A}$, $L^{2B}$, $L^{2C}$, $L^{2D}$, and $L^{2E}$ is not a bond.

Embodiment P22. The nucleotide analogue of anyone of embodiments P1 to P14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_5$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene;
wherein at least one of $L^{2A}$, $L^{2B}$, $L^{2C}$, $L^{2D}$, and $L^{2E}$ is not a bond.

Embodiment P23. The nucleotide analogue of anyone of embodiments P1 to P14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{2A}$, $L^{2B}$, $L^{2C}$, $L^{2D}$, and $L^{2E}$ is not a bond.

Embodiment P24. The nucleotide analogue of anyone of embodiments P1 to P14, wherein
$L^2$ is $L^{2A}$-$L^{2B}$-$L^{2C}$-$L^{2D}$-$L^{2E}$.
$L^{2A}$ is a bond, substituted or unsubstituted alkylene, substituted or unsubstituted heteroalkylene;
$L^{2B}$ is a bond, substituted or unsubstituted cycloalkylene, substituted or unsubstituted heterocycloalkylene, substituted or unsubstituted arylene, substituted or unsubstituted heteroarylene;
$L^{2C}$ is a bond, substituted or unsubstituted cycloalkylene, substituted or unsubstituted heterocycloalkylene, substituted or unsubstituted arylene, substituted or unsubstituted heteroarylene;
$L^{2D}$ is a bond, substituted or unsubstituted alkylene, substituted or unsubstituted heteroalkylene; and
$L^{2E}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{2A}$, $L^{2B}$, $L^{2C}$, $L^{2D}$, and $L^{2E}$ is not a bond.

Embodiment P25. The nucleotide analogue of anyone of embodiments P1 to P14, wherein $L^2$ is

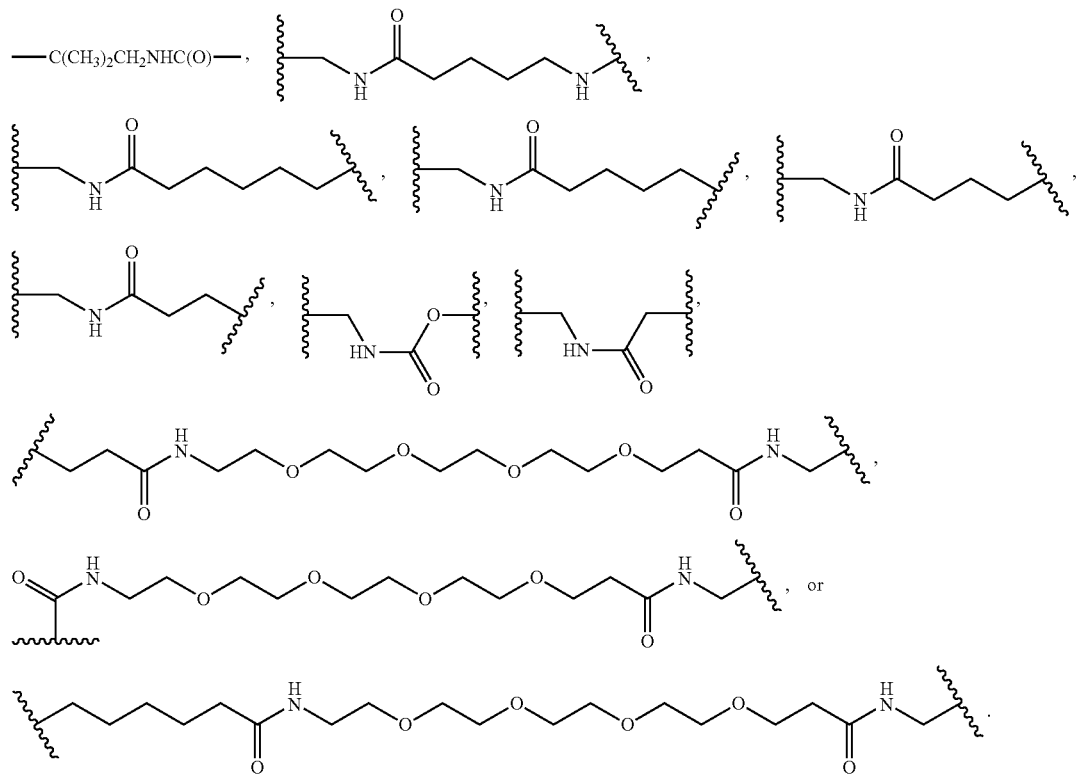

Embodiment P26. The nucleotide analogue of anyone of embodiments P1 to P14, wherein —B-L$^{2A}$-L$^{2B}$-L$^{2C}$-L$^{2D}$-L$^{2E}$-R$^5$ has the formula:

Embodiment P27. The nucleotide analogue of anyone of embodiments P1 to P14, wherein —B-L$^{2A}$-L$^{2B}$-L$^{2C}$-L$^{2D}$-L$^{2E}$-R$^5$----R$^{12}$-L$^3$-R$^{13}$ has the formula:

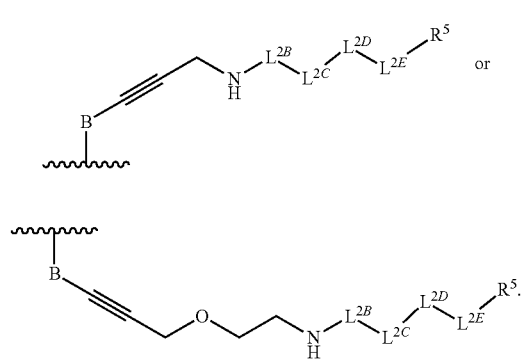

or

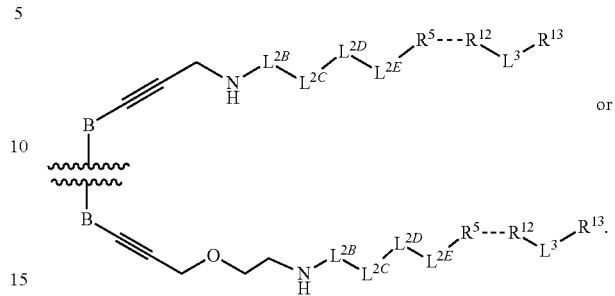

or

Embodiment P28. The nucleotide analogue of anyone of embodiments P1 to P14, wherein —B-L$^2$ is

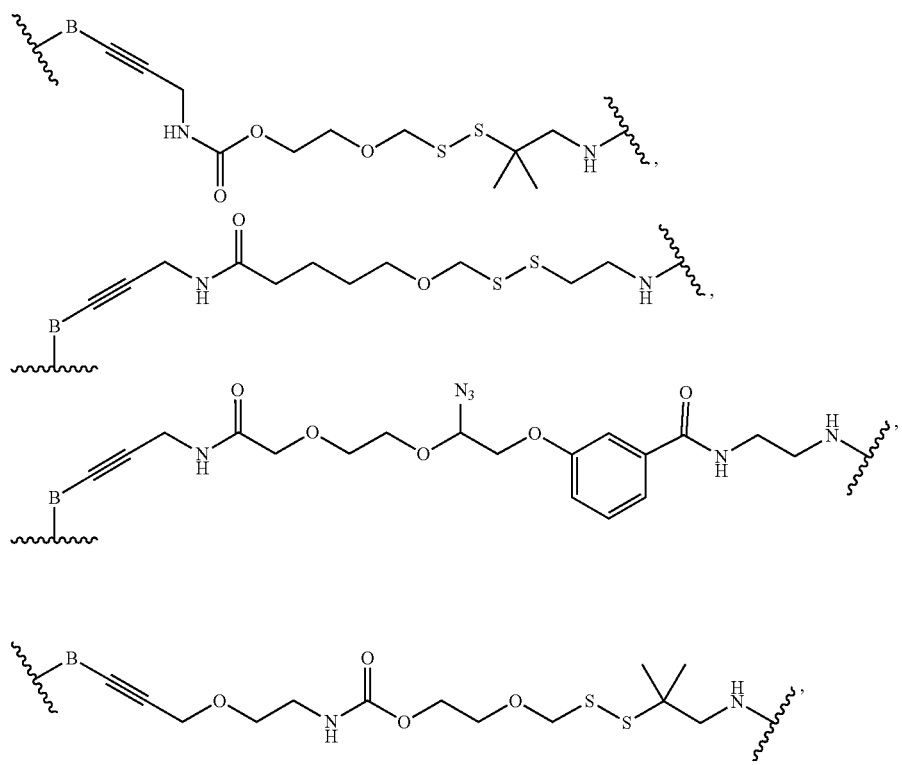

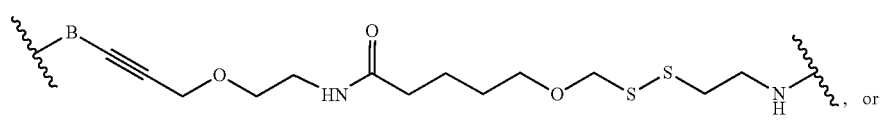

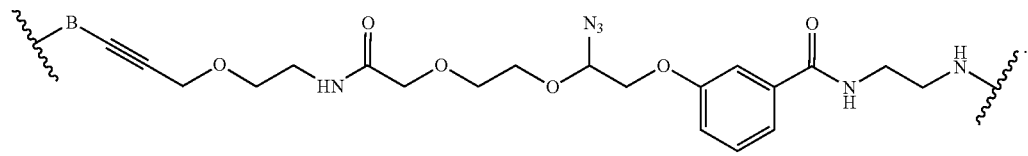

Embodiment P29. The nucleotide analogue of anyone of embodiments P1 to P28, wherein $X^1$ is hydrogen and $X^2$ is halogen.

Embodiment P30. The nucleotide analogue of anyone of embodiments P1 to P28, wherein $X^1$ is halogen and $X^2$ is hydrogen.

Embodiment P31. The nucleotide analogue of anyone of embodiments P1 to P28, wherein $X^1$ is hydrogen and $X^2$ is —F.

Embodiment P32. The nucleotide analogue of anyone of embodiments P1 to P28, wherein $X^1$ is —F and $X^2$ is hydrogen.

Embodiment P33. The nucleotide analogue of anyone of embodiments P1 to P28, wherein $X^1$ and $X^2$ are halogen.

Embodiment P34. The nucleotide analogue of anyone of embodiments P1 to P28, wherein $X^1$ is hydrogen and $X^2$ is —CN.

Embodiment P35. The nucleotide analogue of anyone of embodiments P1 to P28, wherein $X^1$ is hydrogen $X^2$ is —$N_3$.

Embodiment P36. The nucleotide analogue of anyone of embodiments P1 to P28, wherein $X^2$ is hydrogen and $X^1$ is —CN.

Embodiment P37. The nucleotide analogue of anyone of embodiments P1 to P28, wherein $X^2$ is hydrogen $X^1$ is —$N_3$.

Embodiment P38. The nucleotide analogue of anyone of embodiments P1 to P28, wherein $X^2$ is hydrogen $X^1$ is —$N_3$.

Embodiment P39. The nucleotide analogue of anyone of embodiments P1 to P28, wherein $X^1$ and $X^2$ are —F.

Embodiment P40. The nucleotide analogue of anyone of embodiments P1 to P39, wherein $R^5$ is a detectable label.

Embodiment P41. The nucleotide analogue of anyone of embodiments P1 to P39, wherein $R^5$ is a fluorescent dye.

Embodiment P42. The nucleotide analogue of any one of embodiments P1 to P39, wherein $R^5$ is

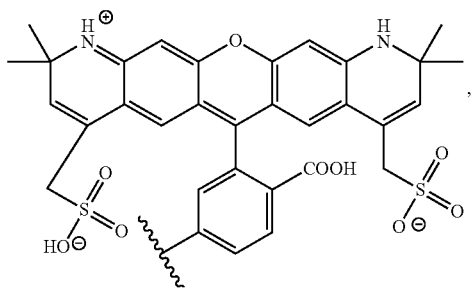

,

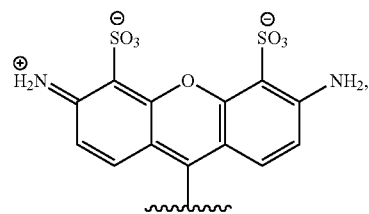

,

-continued

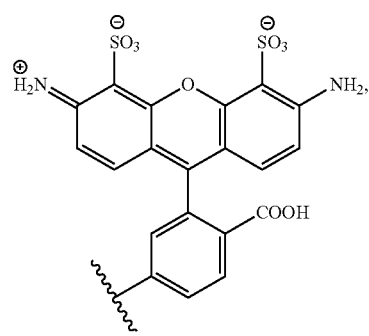

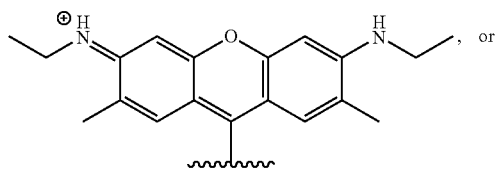

, or

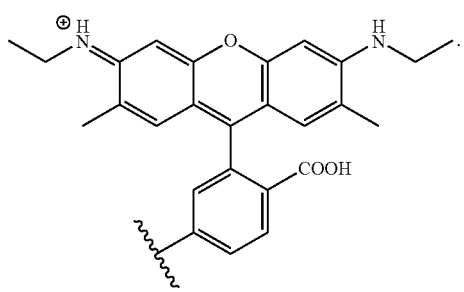

.

Embodiment P43. The nucleotide analogue of anyone of embodiments P1 to P42, wherein $R^{12}$ is a streptavidin moiety.

Embodiment P44. The nucleotide analogue of anyone of embodiments P1 to P42, wherein $R^{12}$ is selected from the group consisting of:

353

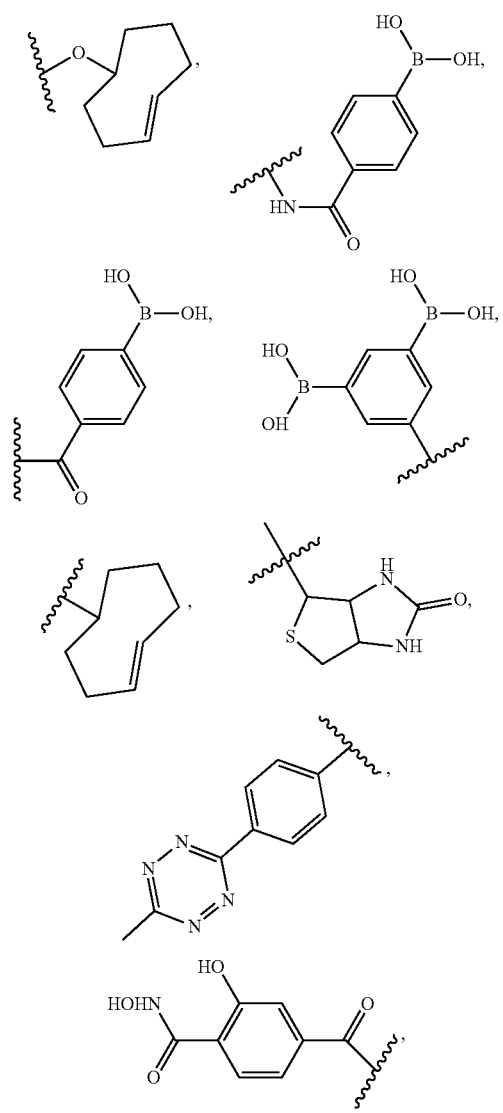

a streptavidin moiety,

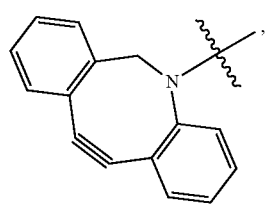 [SMILES: *CN1Cc2ccccc2C#Cc2ccccc21]

unsubstituted ethynyl,

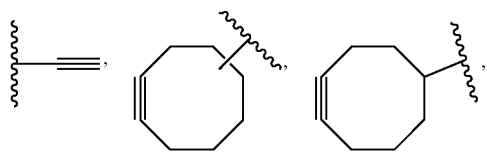

354

-continued

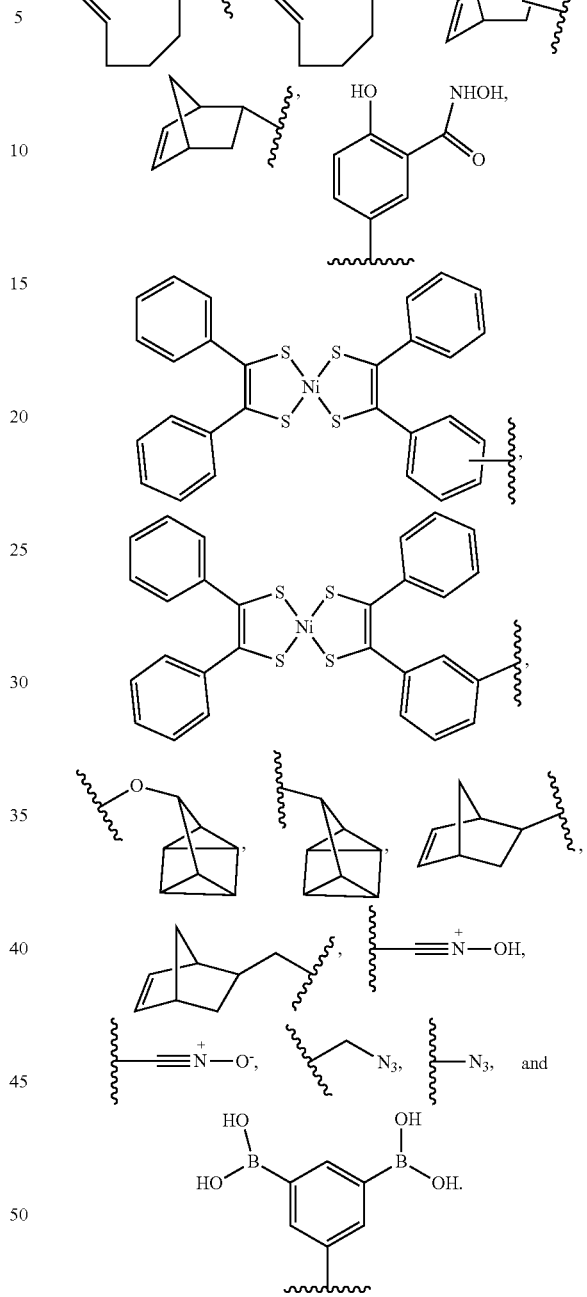

Embodiment P45. The nucleotide analogue of anyone of embodiments P1 to P43, wherein $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P46. The nucleotide analogue of anyone of embodiments P1 to P43, wherein $L^3$ is an orthogonally cleavable linker.

Embodiment P47. The nucleotide analogue of anyone of embodiments P1 to P47, wherein $L^3$ is a photocleavable linker, an acid-cleavable linker, a base-cleavable linker, an oxidant-cleavable linker, a reductant-cleavable linker, or a fluoride-cleavable linker.

Embodiment P48. The nucleotide analogue of anyone of embodiments P1 to P43, wherein $L^3$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment P49. The nucleotide analogue of anyone of embodiments P1 to P43, wherein
$L^3$ is $L^{3A}$-$L^{3B}$-$L^{3C}$-$L^{3D}$-$L^{3E}$; and
$L^{3A}$, $L^{3B}$, $L^{3C}$, $L^{3D}$, and $L^{3E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{3A}$, $L^{3B}$, $L^{3C}$, $L^{3D}$, and $L^{3E}$ is not a bond.

Embodiment P50. The nucleotide analogue of anyone of embodiments P1 to P43, wherein
$L^3$ is $L^{3A}$-$L^{3B}$-$L^{3C}$-$L^{3D}$-$L^{3E}$.
$L^{3A}$ is a bond, —NN—, —NHC(O)—, —C(O)NH—, substituted or unsubstituted alkylene, substituted or unsubstituted heteroalkylene;
$L^{3B}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{3C}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{3D}$ is a bond, —NN—, —NHC(O)—, —C(O)NH—, substituted or unsubstituted alkylene, substituted or unsubstituted heteroalkylene; and
$L^{3E}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{3A}$, $L^{3B}$, $L^{3C}$, $L^{3D}$, and $L^{3E}$ is not a bond.

Embodiment P51. The nucleotide analogue of anyone of embodiments P1 to P50, wherein $R^{13}$ is a detectable label.

Embodiment P52. The nucleotide analogue of anyone of embodiments P1 to P50, wherein $R^{13}$ is a fluorescent dye.

Embodiment P53. The nucleotide analogue of any one of embodiments P1 to P50, wherein $R^{13}$ is

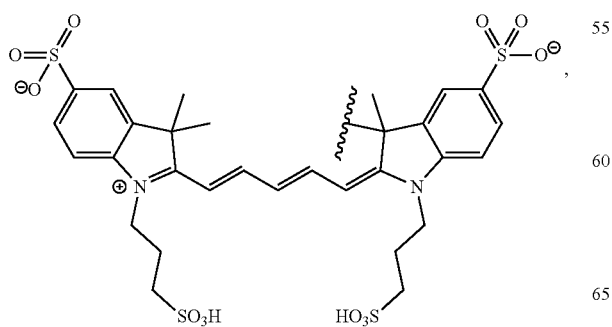

-continued

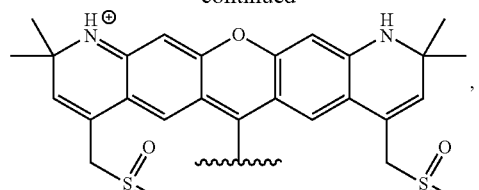

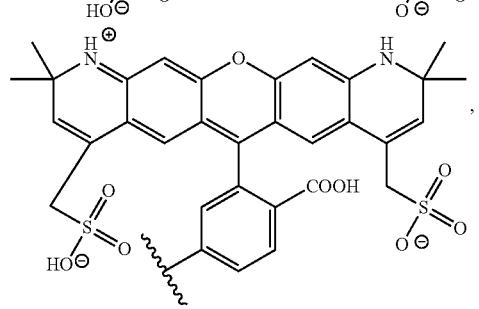

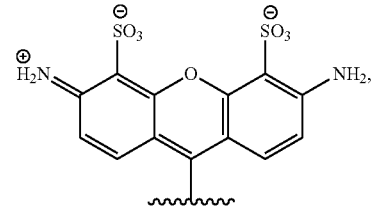

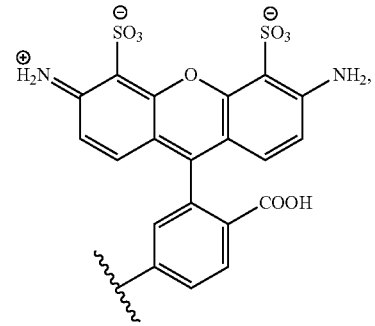

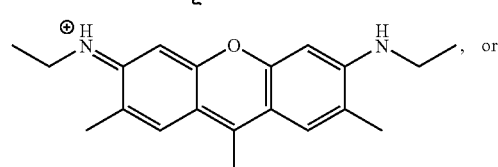

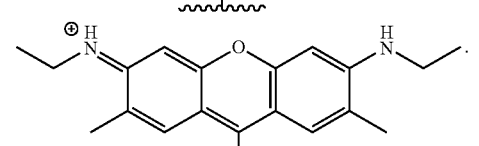

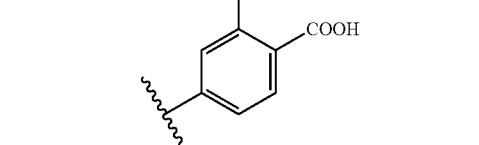

Embodiment P54. The nucleotide analogue of anyone of embodiments P1 to P53, wherein $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P55. The nucleotide analogue of anyone of embodiments P1 to P53, wherein $L^4$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment P56. The nucleotide analogue of anyone of embodiments P1 to P53, wherein $L^4$ is a substituted or unsubstituted $C_1$-$C_6$ alkylene or substituted or unsubstituted 2 to 6 membered heteroalkylene.

Embodiment P57. The nucleotide analogue of anyone of embodiments P1 to P53, wherein $L^4$ is an unsubstituted $C_1$-$C_4$ alkylene.

Embodiment P58. The nucleotide analogue of anyone of embodiments P1 to P53, wherein $L^4$ is a bond.

Embodiment P59. The nucleotide analogue of anyone of embodiments P1 to P58, wherein $R^4$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment P60. The nucleotide analogue of anyone of embodiments P1 to P58, wherein $R^4$ is substituted or unsubstituted $C_1$-$C_6$ alkyl, or substituted or unsubstituted phenyl.

Embodiment P61. The nucleotide analogue of anyone of embodiments P1 to P58, wherein $R^4$ is an unsubstituted $C_1$-$C_6$ alkyl.

Embodiment P62. The nucleotide analogue of embodiment P1, having the formula.

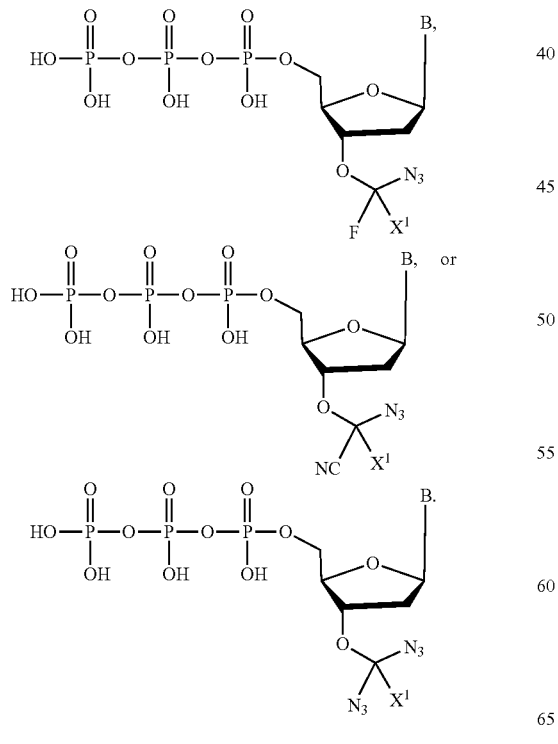

Embodiment P63. The nucleotide analogue of embodiment P1, having the formula:

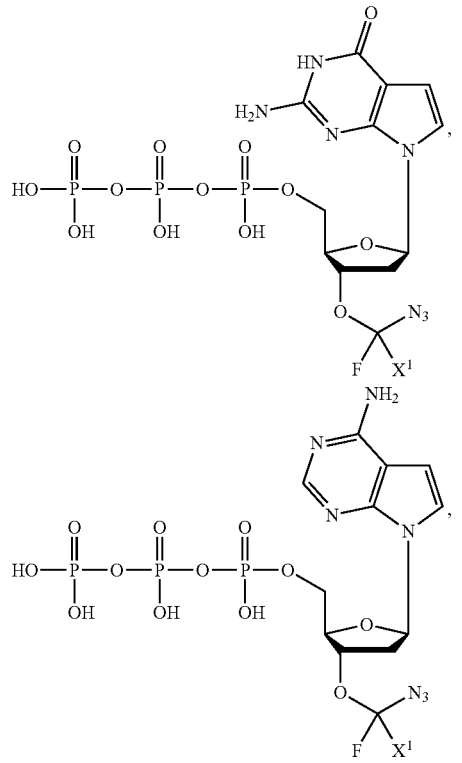

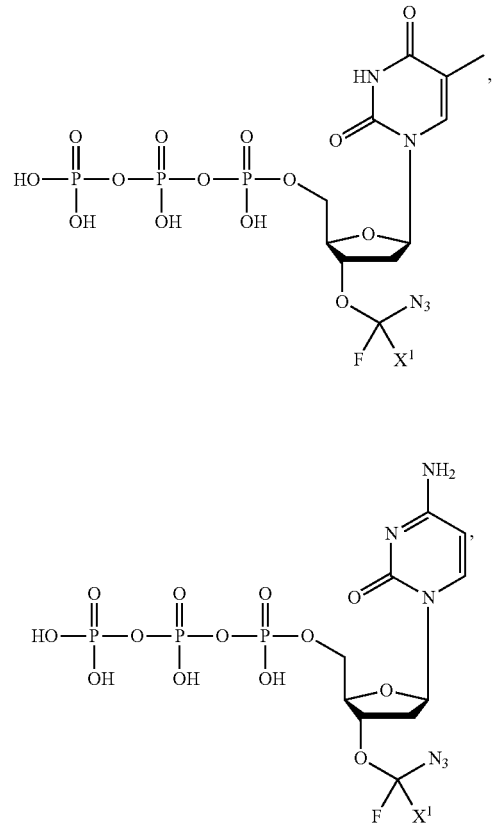

359
-continued
360
-continued
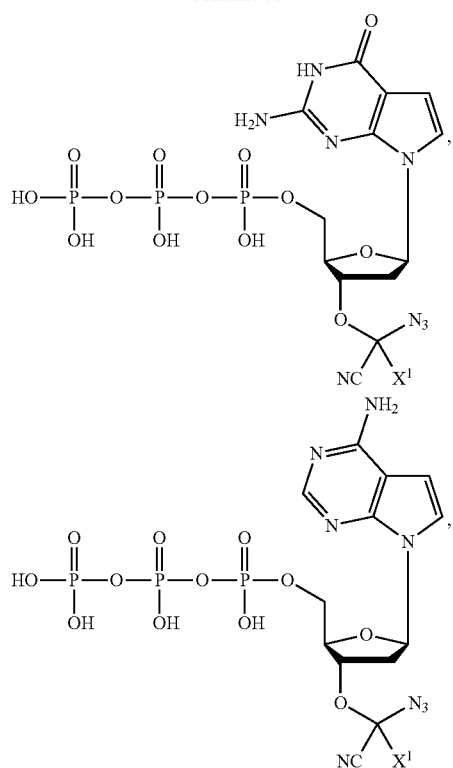
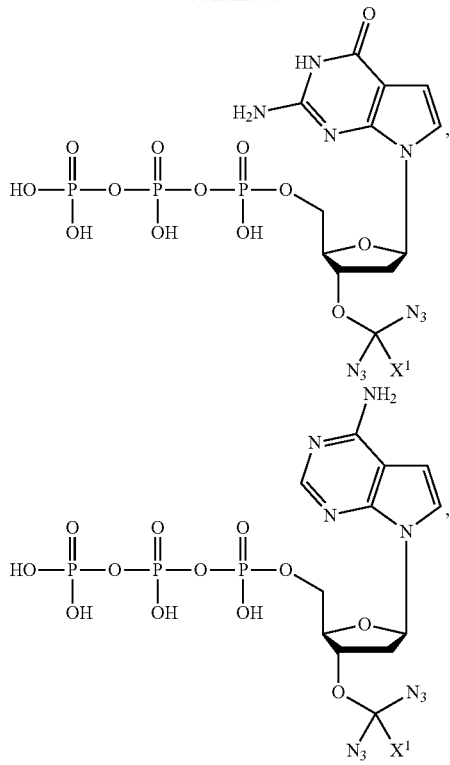

Embodiment P64. The nucleotide analogue of embodiment P1, having the formula:
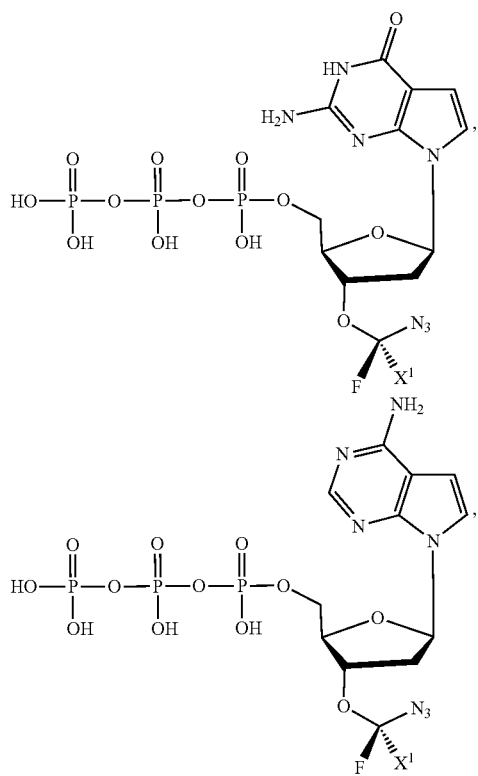
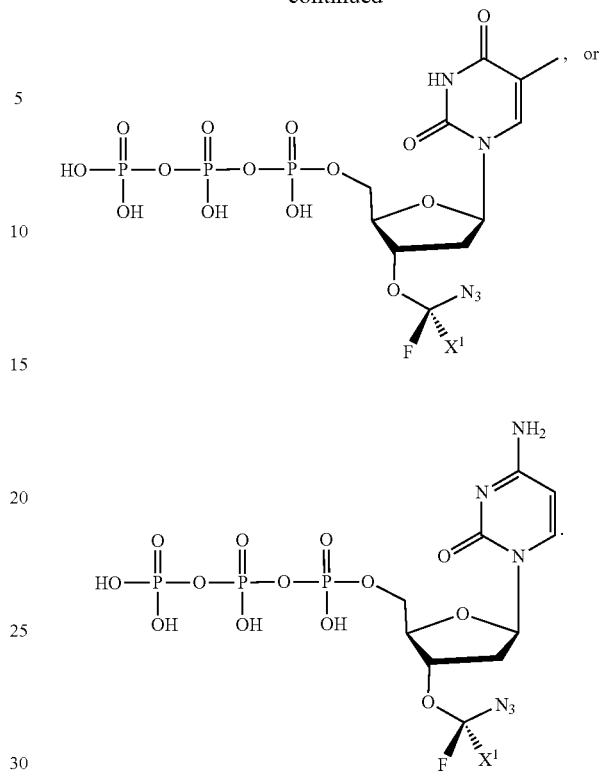
Embodiment P65. The nucleotide analogue of embodiment P1, having the formula:
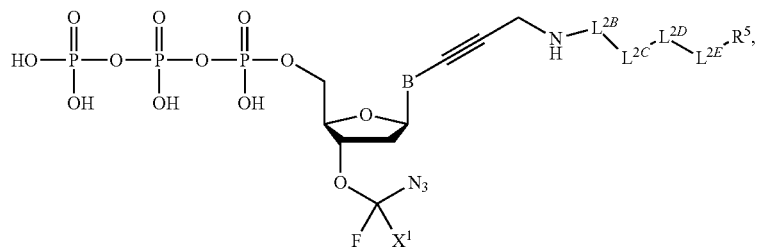
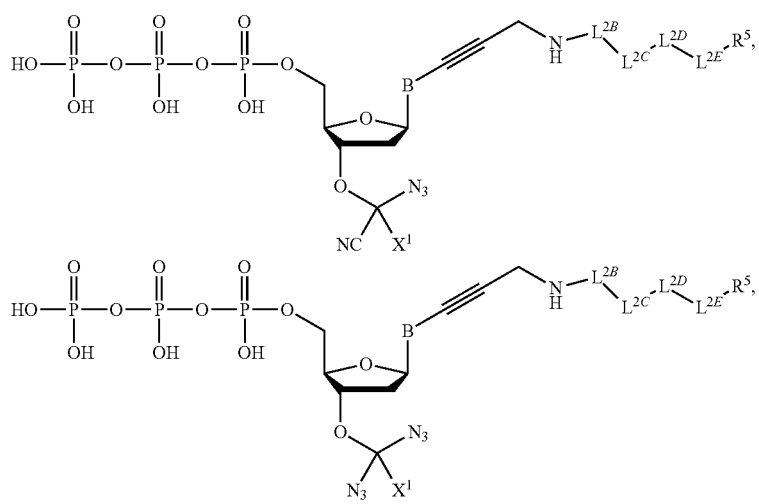

-continued
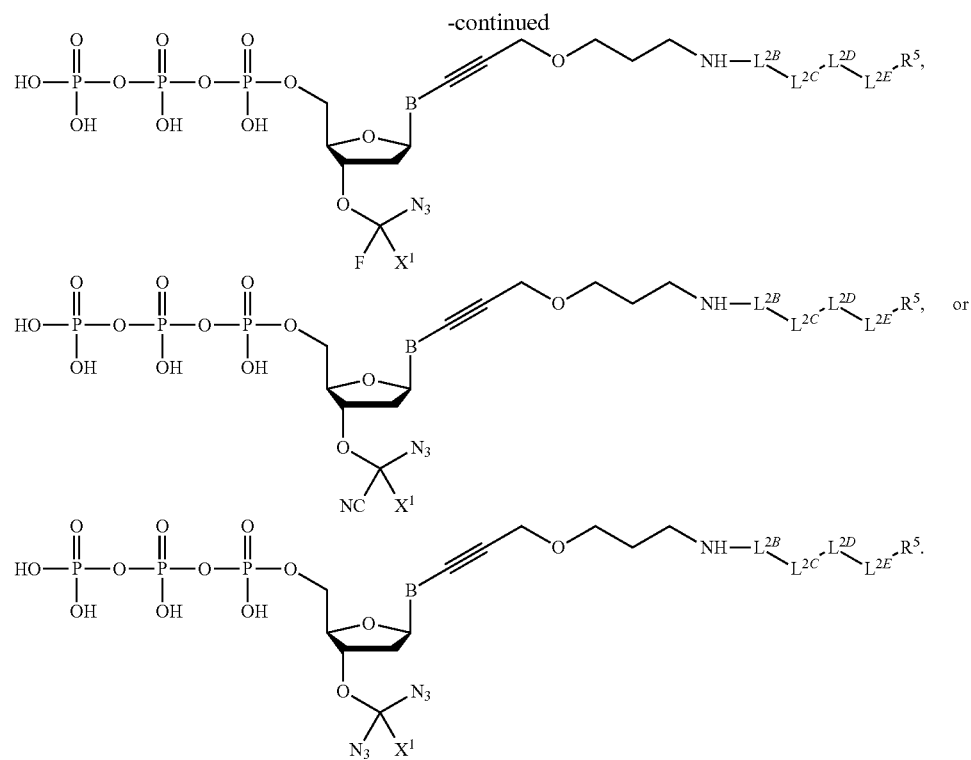
Embodiment P66. The nucleotide analogue of embodiment P1, having the formula:
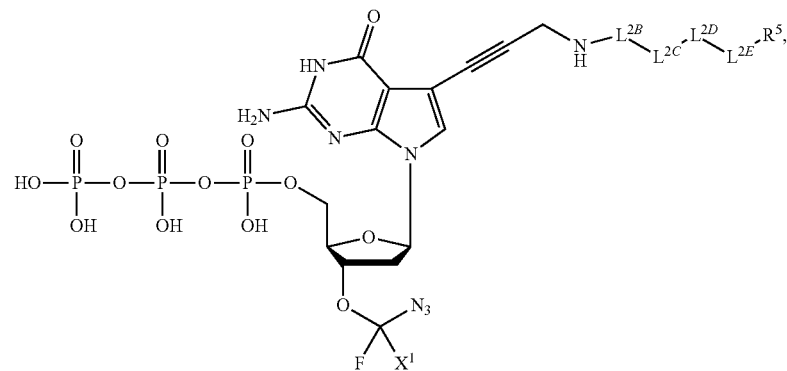
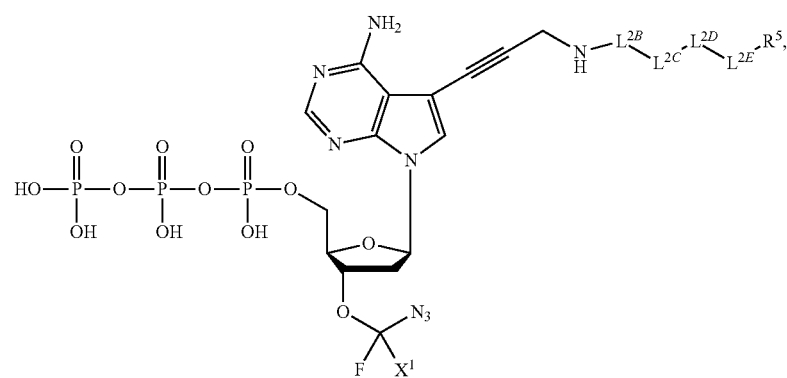

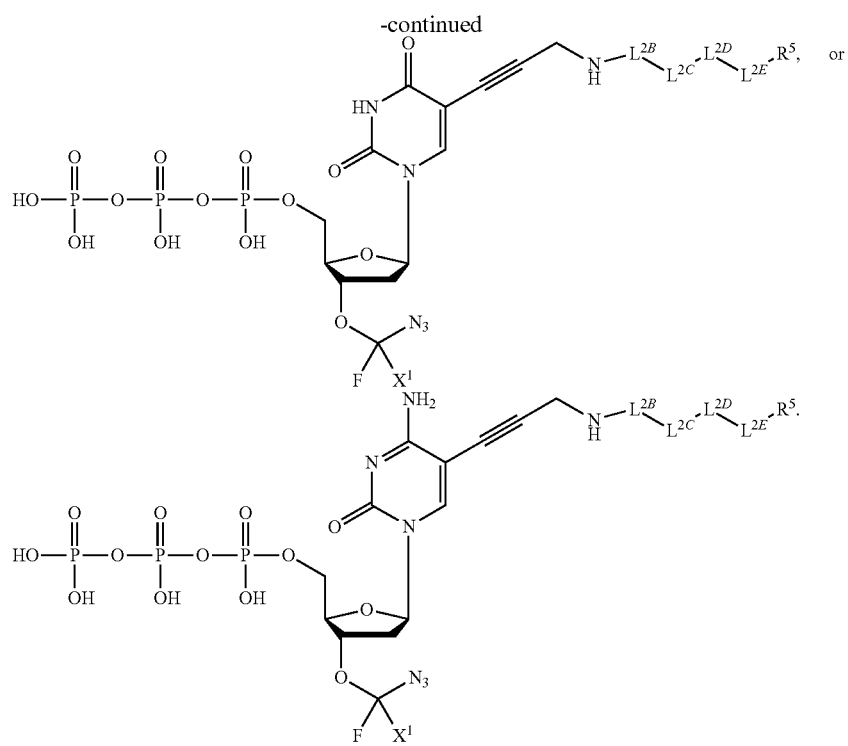
Embodiment P67. The nucleotide analogue of embodiment P1, having the formula:
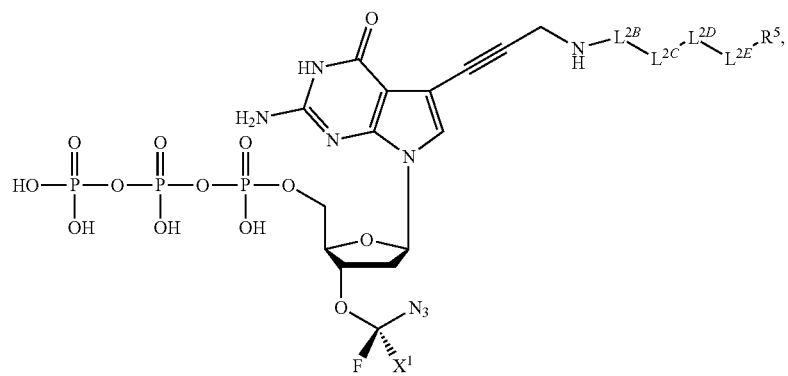
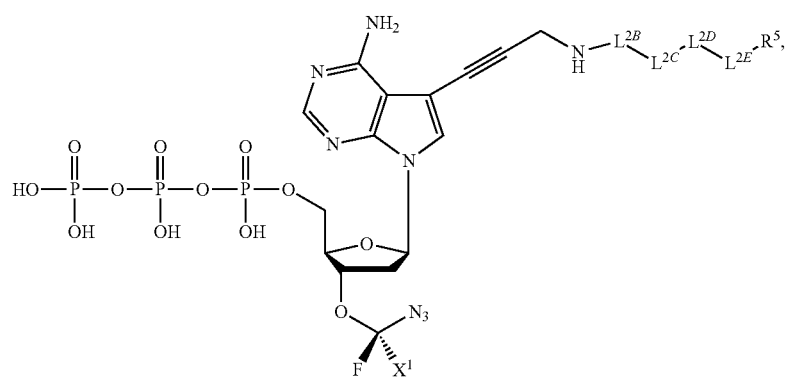

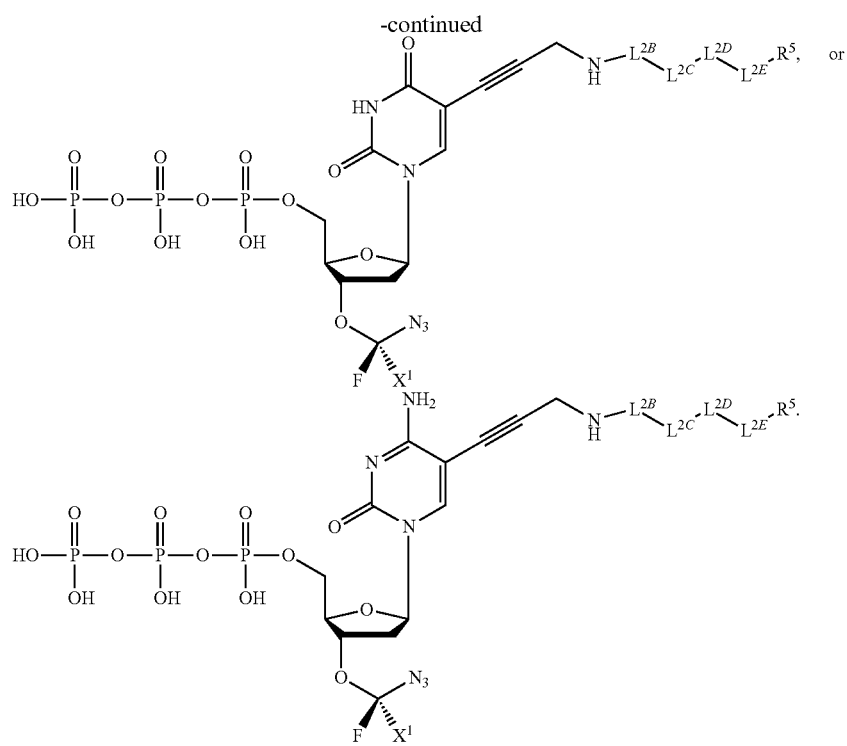
Embodiment P68. The nucleotide analogue of embodiment P1, having the formula:
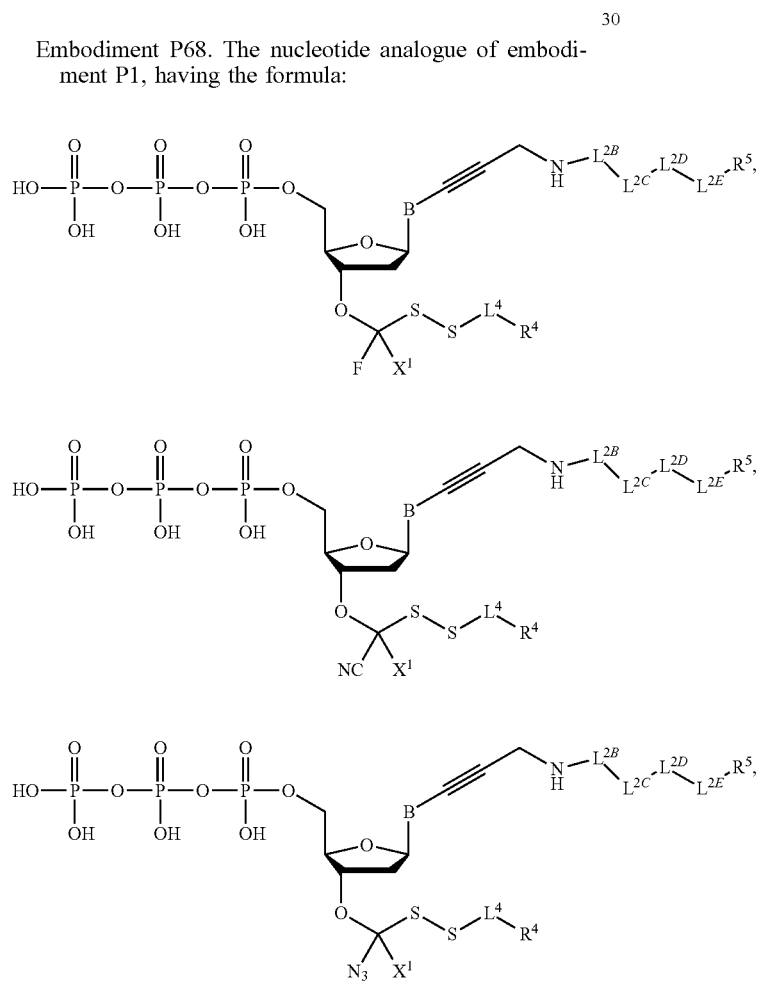

-continued
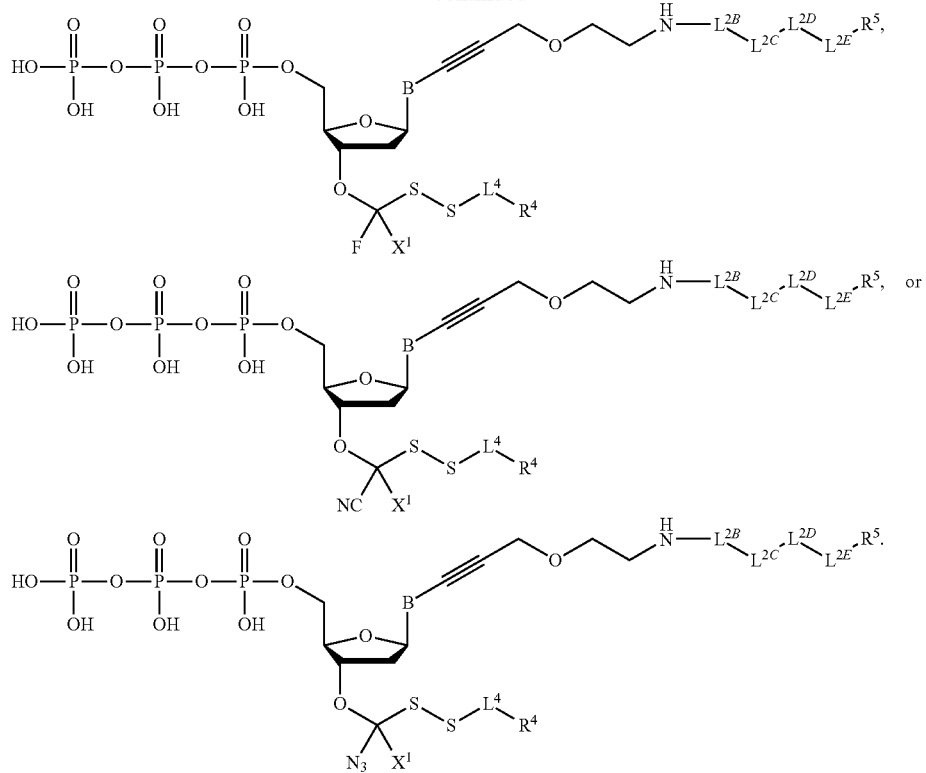
Embodiment P69. The nucleotide analogue of embodiment P1, having the formula:
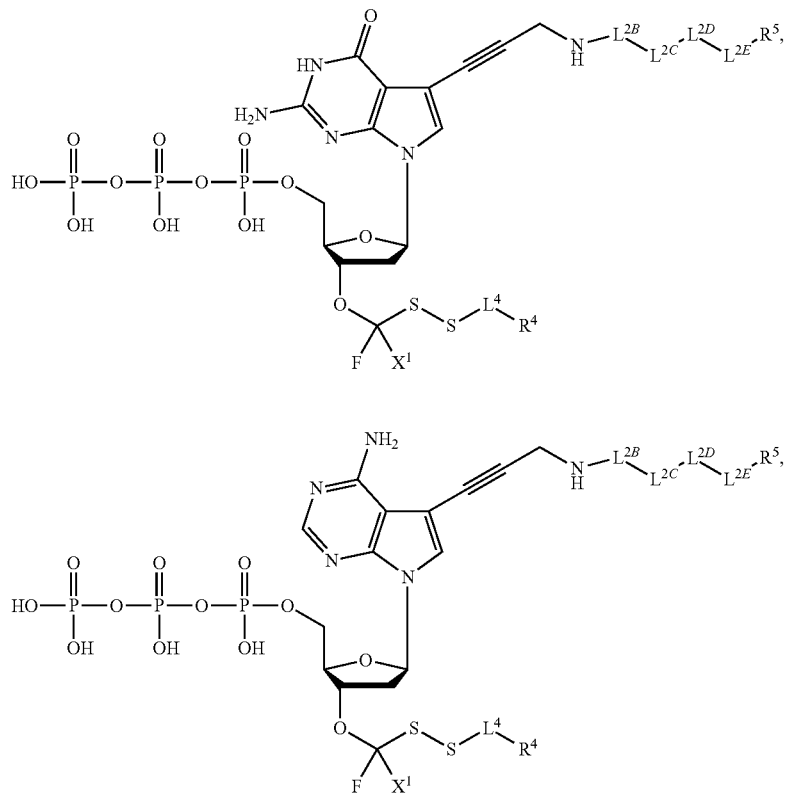

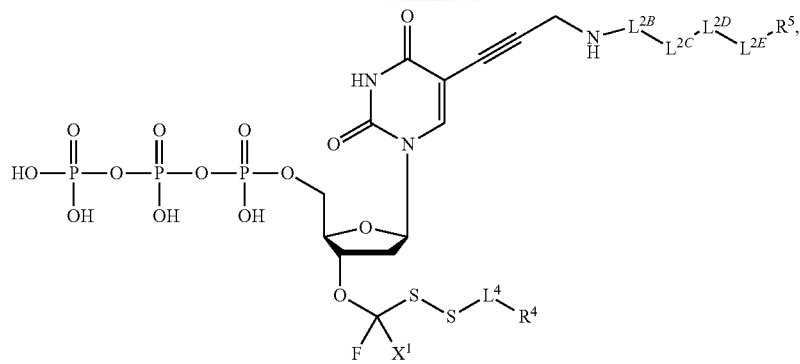
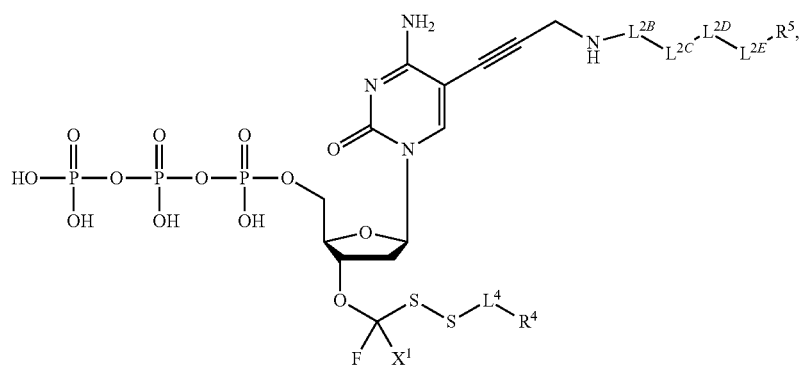
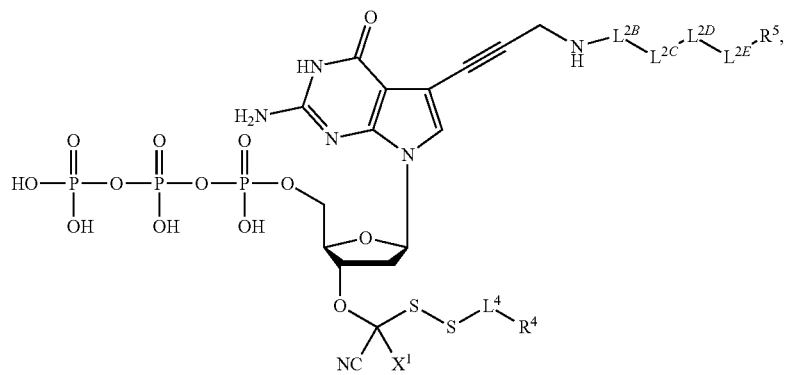
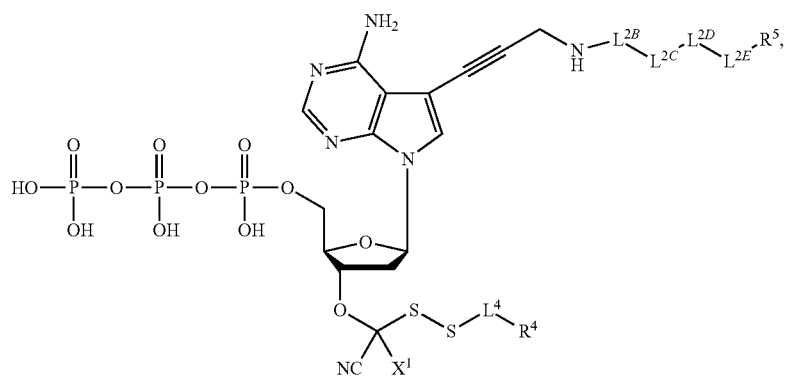

-continued
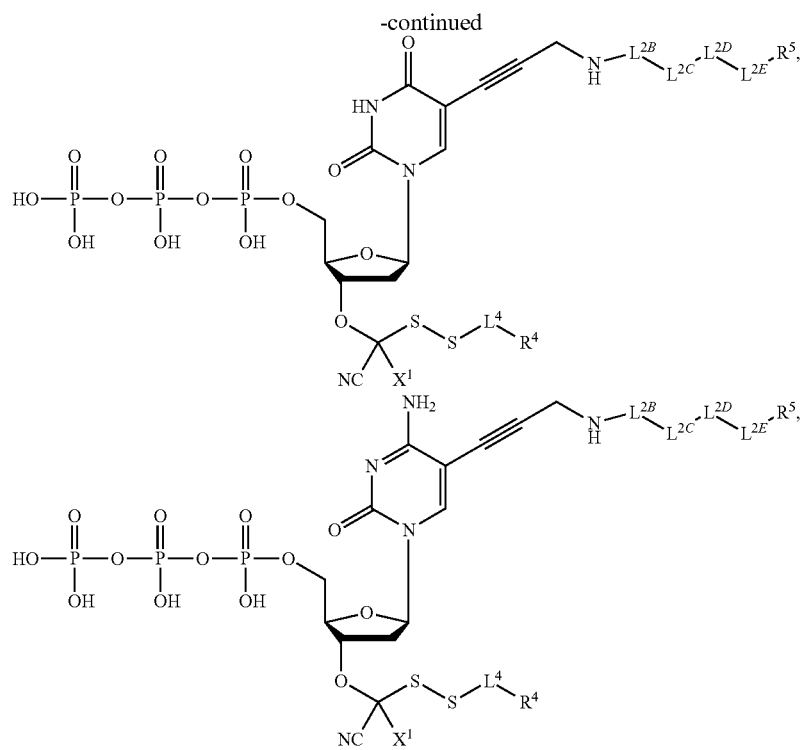
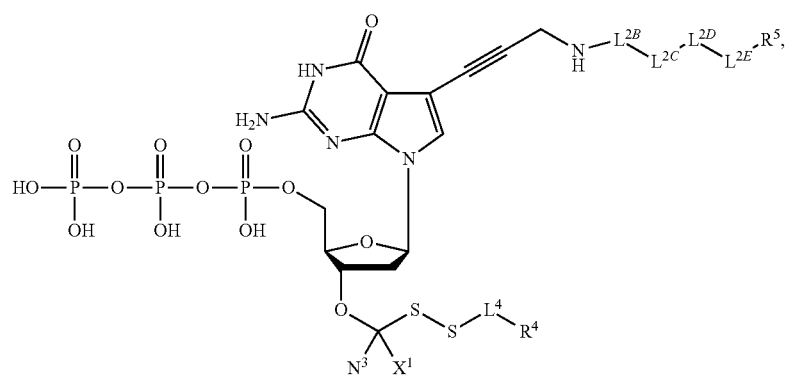
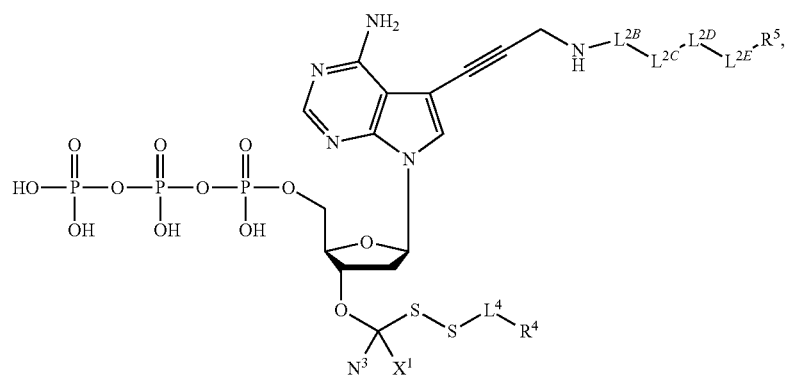

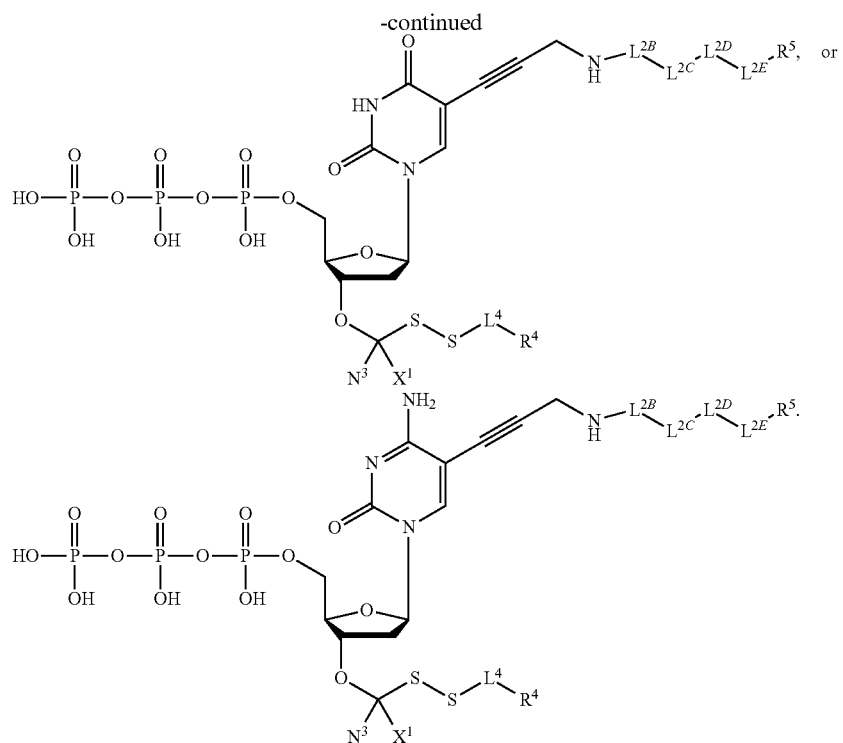
Embodiment P70. The nucleotide analogue of embodiment P1, having the formula:
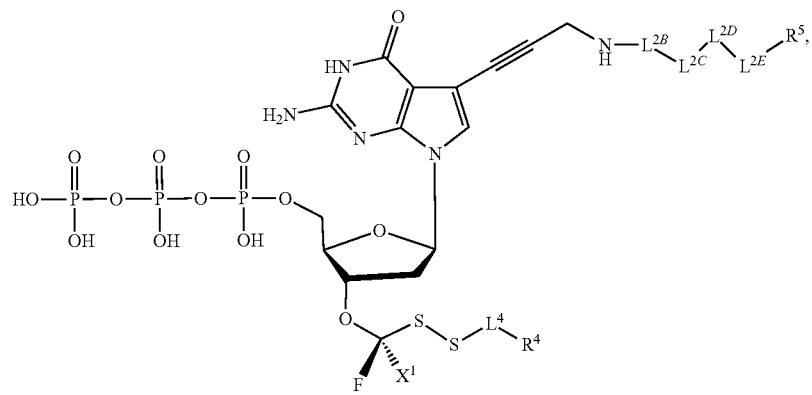
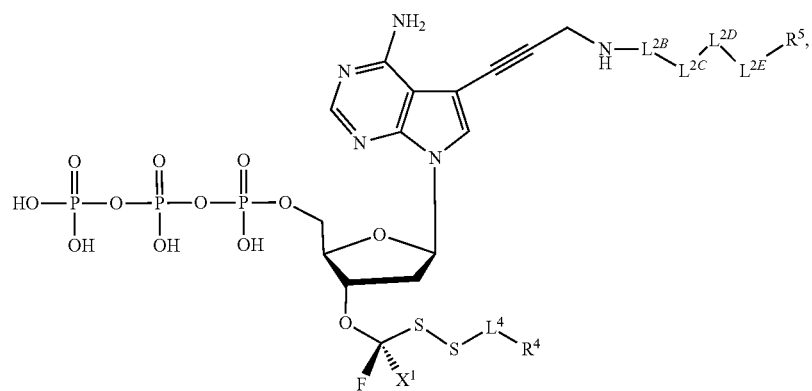

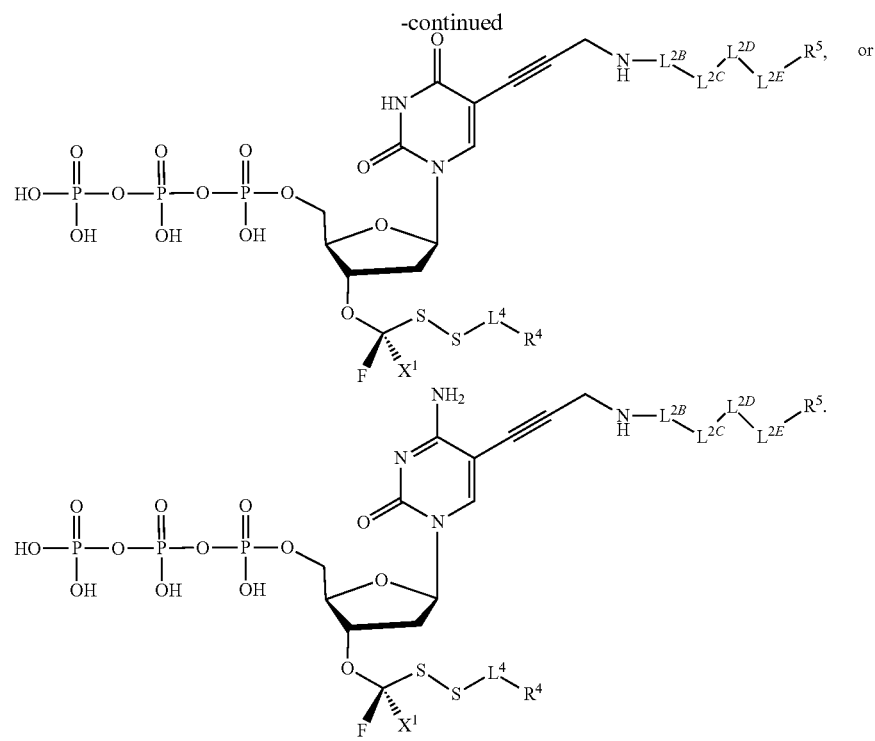
Embodiment P71. The nucleotide analogue of embodiment P1, having the formula:
Embodiment P72. The nucleotide analogue of embodiment P1, having the formula:
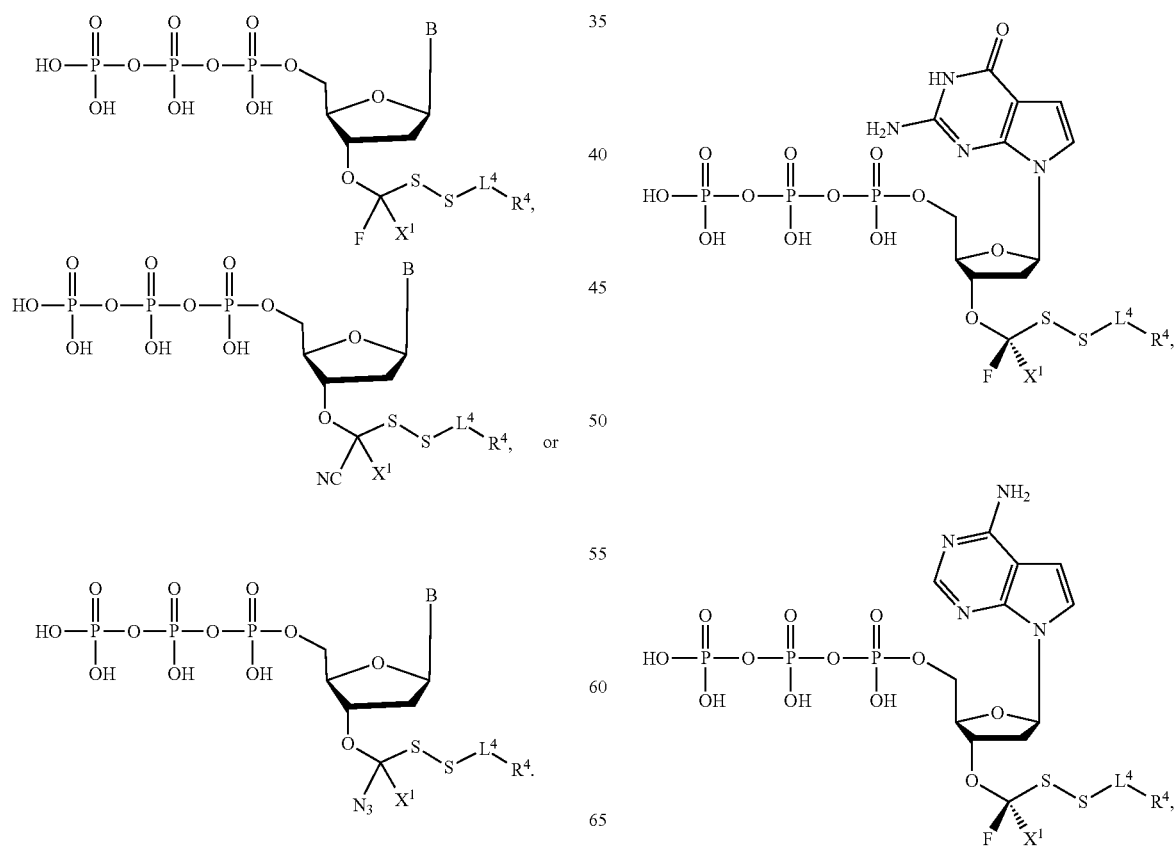

-continued
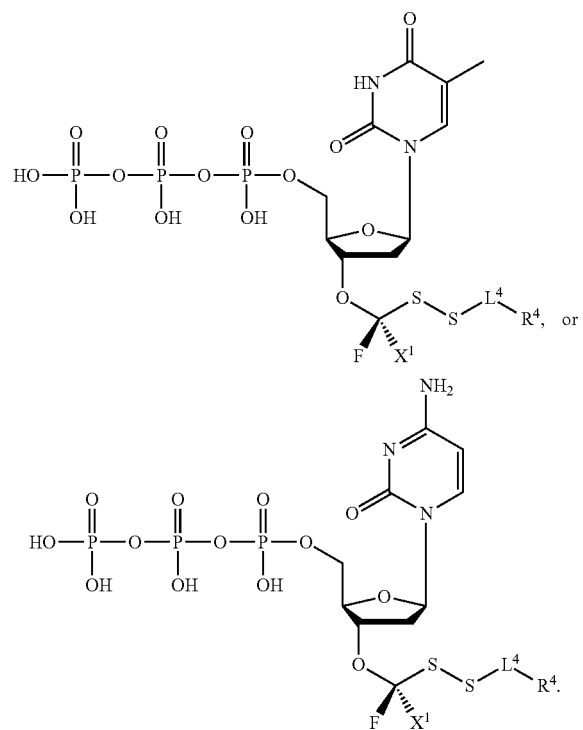
Embodiment P73. The nucleotide analogue of embodiment P1, having the formula:
Embodiment P74. The nucleotide analogue of embodiment P1, having the formula:
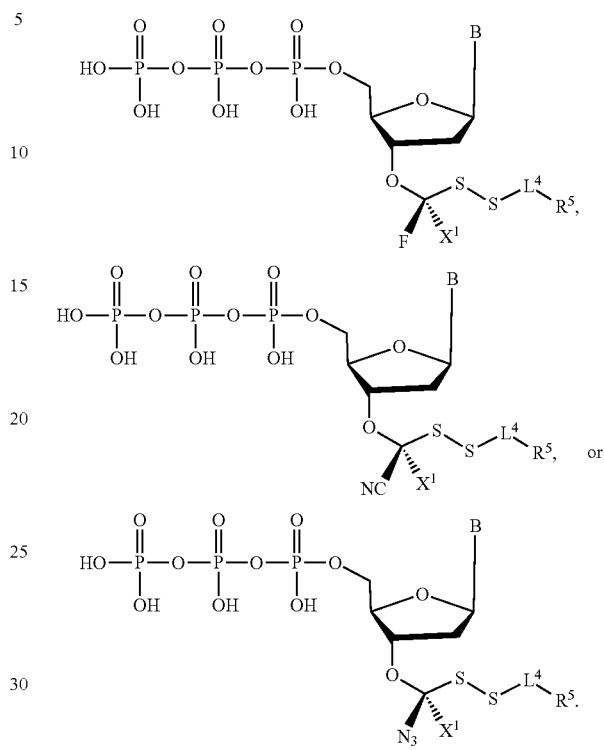
Embodiment P75. The nucleotide analogue of embodiment P1, having the formula:
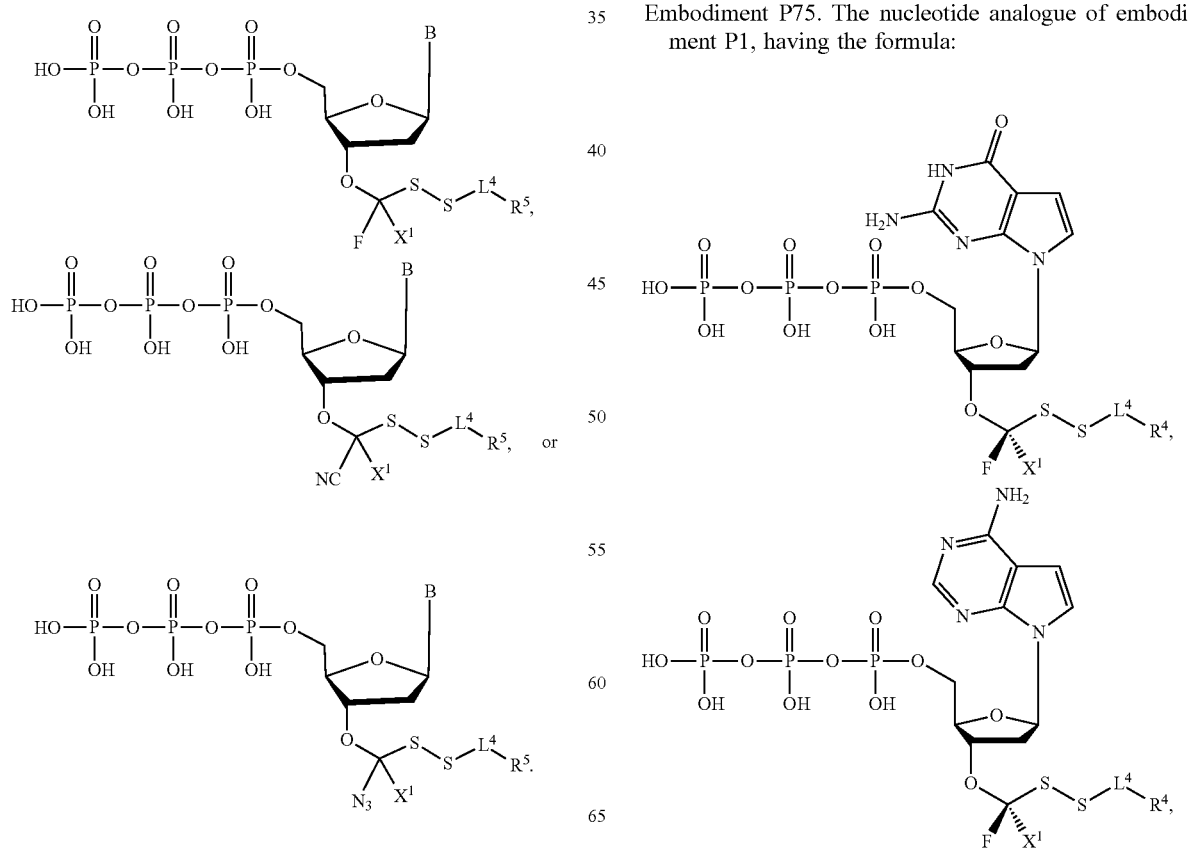

381
-continued

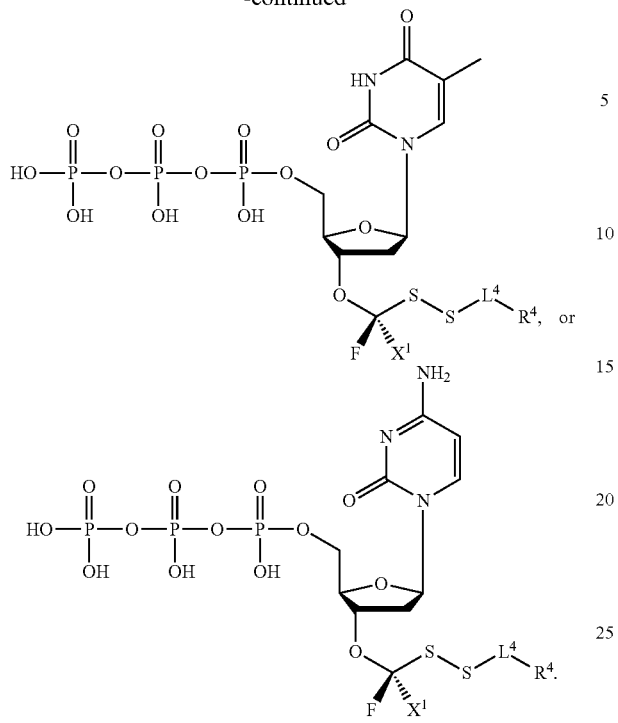

Embodiment P76. A method for sequencing a nucleic acid, including:
incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues comprise a unique detectable label;
detecting the unique detectable label of each incorporated nucleotide analogue, so as to thereby identify each incorporated nucleotide analogue in the extension strand, thereby sequencing the nucleic acid;
wherein each of the four different labeled nucleotide analogues is of the structure of one of embodiments P1 to P75.

Embodiment P77. A method of incorporating a nucleotide analogue into a primer, the method including combining a polymerase, a primer hybridized to nucleic acid template and a nucleotide analogue within a reaction vessel and allowing the polymerase to incorporate the nucleotide analogue into the primer thereby forming an extended primer, wherein the nucleotide analogue is of the structure of one of embodiments P1 to P75.

Embodiment P78. The method of embodiment P77, wherein $L^2$ is a cleavable moiety and $R^5$ is a detectable label, the method further including, after the incorporating, cleaving the cleavable moiety with a cleaving reagent.

Embodiment P79. The method of embodiment P77, wherein $R^5$ is anchor moiety, the method further including, after the incorporating, labeling the nucleotide analog with a detectable label.

Embodiment P80. A nucleic acid polymerase complex, wherein the nucleic acid polymerase is bound to a nucleotide analogue of one of embodiments P1 to P75.

382

V. Additional Embodiments

Embodiment 1. A nucleotide analogue of the formula:

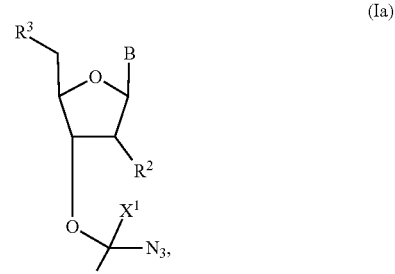
(Ia)

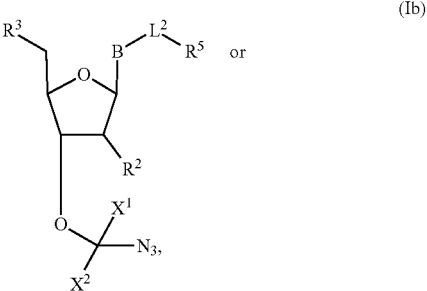
(Ib)

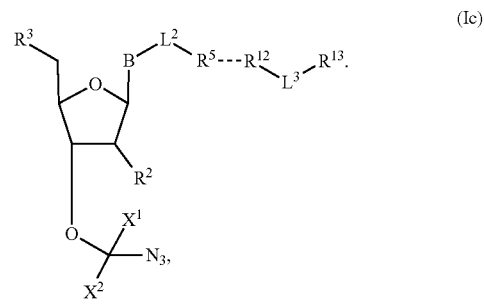
(Ic)

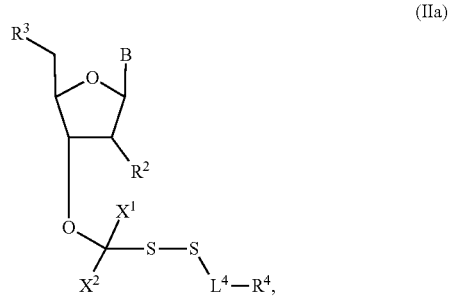
(IIa)

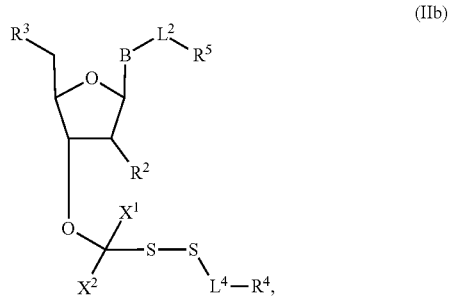
(IIb)

383

-continued

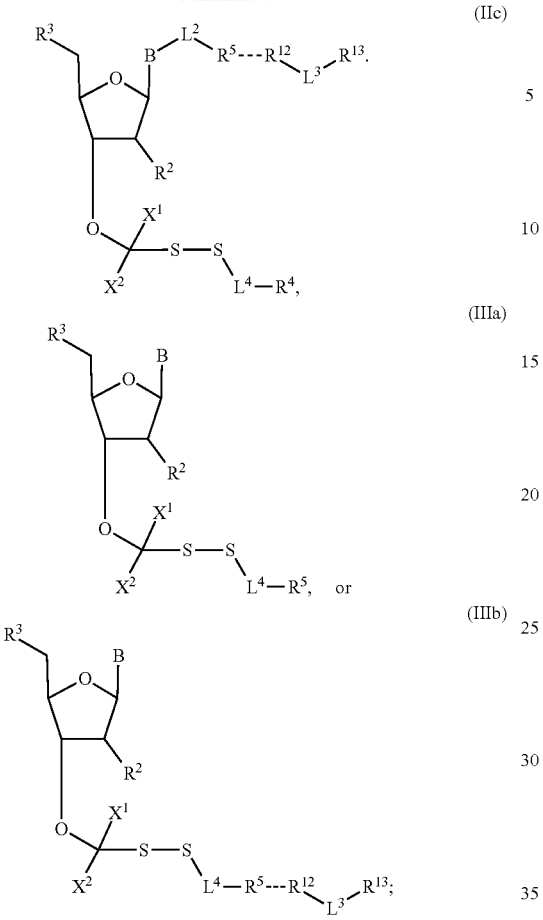

wherein
the symbol " --- " is a non-covalent bond;
B is a base or analogue thereof;
$L^2$ is a covalent linker;
$L^3$ is a covalent linker;
$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^2$ is hydrogen or —$OR^{2A}$, wherein $R^{2A}$ is hydrogen or a polymerase-compatible cleavable moiety;
$R^3$ is —OH, monophosphate, or polyphosphate or a nucleic acid;
$R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is a detectable label, an anchor moiety, or affinity anchor moiety;
$R^{12}$ is a complementary affinity anchor moiety binder;
$R^{13}$ is a detectable label; and
$X^1$ and $X^2$ are independently hydrogen, halogen, —$N_3$, or —CN; wherein at least wherein at least one of $X^1$ or $X^2$ is halogen, —$N_3$, or —CN.

Embodiment 2. The nucleotide analogue of embodiment 1, wherein the nucleotide analogue has the formula:

384

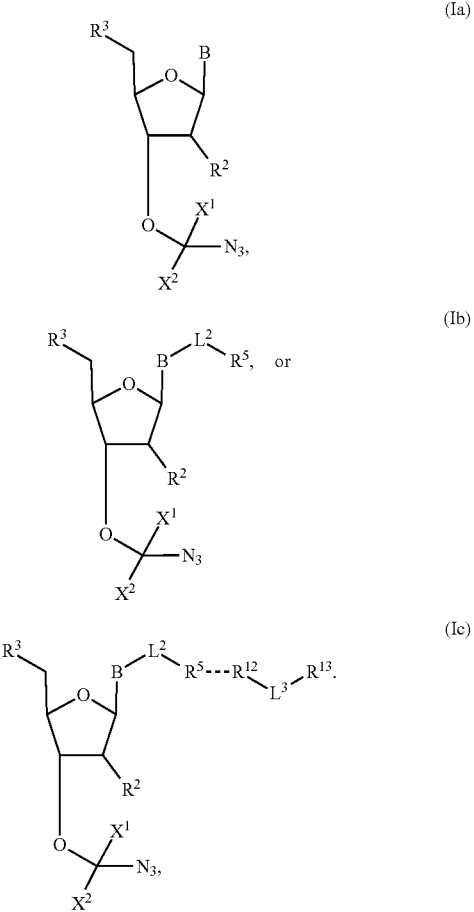

Embodiment 3. The nucleotide analogue of embodiment 1, wherein the nucleotide analogue has the formula:

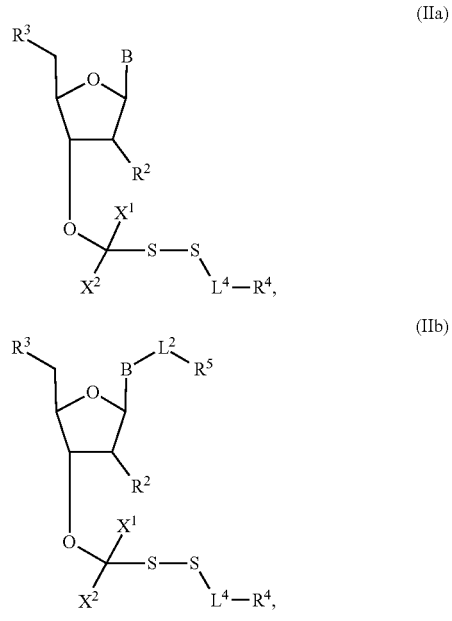

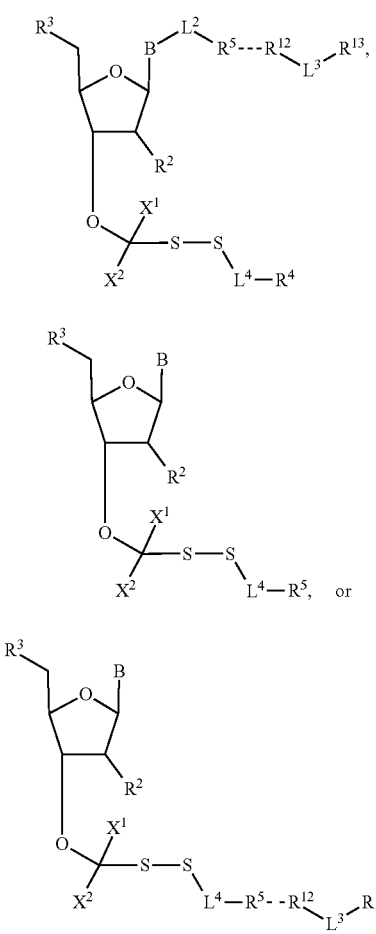

Embodiment 4. The nucleotide analogue of embodiment 1, wherein the nucleotide analogue has the formula:

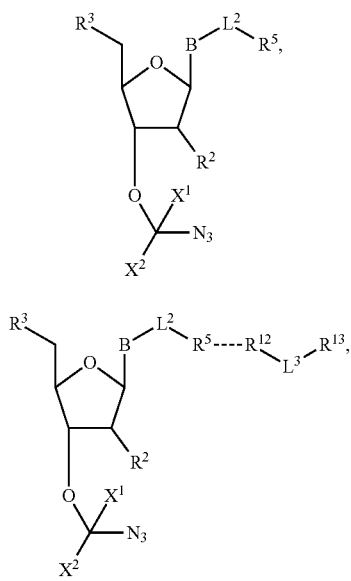

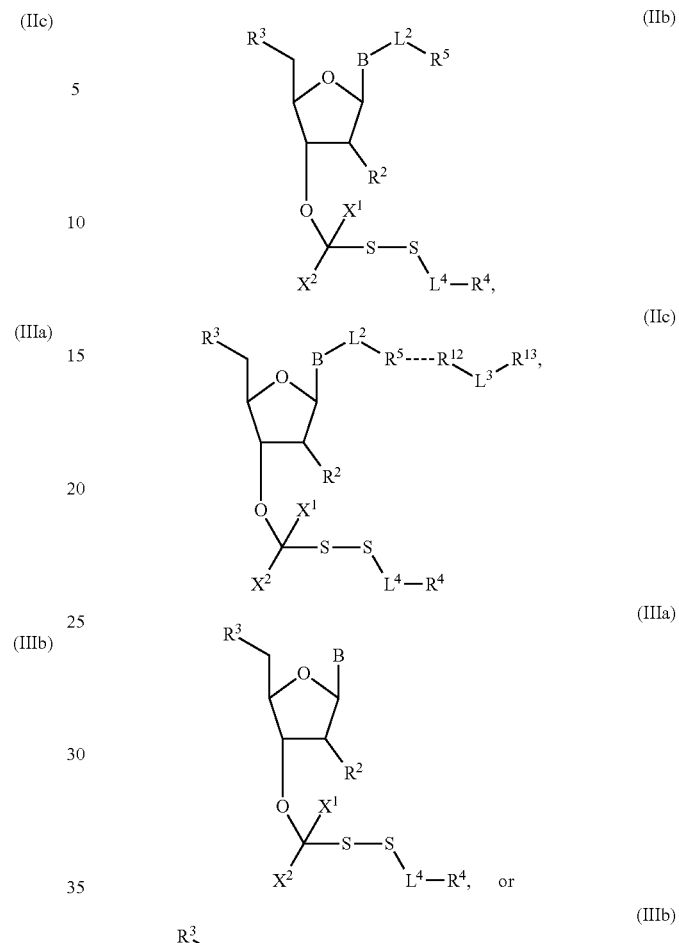

Embodiment 5. The nucleotide analogue of any one of embodiments 1 to 4 having the formula (Ia), (IIa), (IIIa), or (IIIb), wherein B is cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, deaza-adenine or a derivative thereof, deaza-guanine or a derivative thereof, deaza-hypoxanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment 6. The nucleotide analogue of any one of embodiments 1 to 4 having the formula (Ia), (IIa), (IIIa), or (IIIb), wherein B is

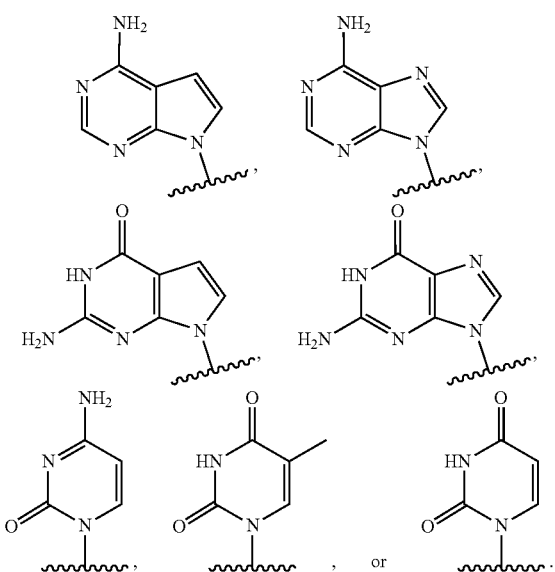

Embodiment 7. The nucleotide analogue of any one of embodiments 1 to 4 having the formula (Ib), (Ic), (IIb), (IIc), wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment 8. The nucleotide analogue of any one of c embodiments 1 to 4 having the formula (Ib), (Ic), (IIb), (IIc), wherein B is

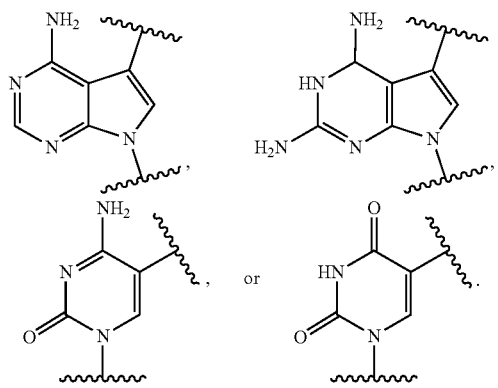

Embodiment 9. The nucleotide analogue of any one of embodiments 1 to 8, wherein $R^3$ is —OH.

Embodiment 10. The nucleotide analogue of any one of embodiments 1 to 8, wherein $R^3$ is monophosphate.

Embodiment 11. The nucleotide analogue of any one of embodiments 1 to 8, wherein $R^3$ is triphosphate, tetraphosphate, pentaphosphate, or hexaphosphate.

Embodiment 12. The nucleotide analogue of any one of embodiments 1 to 11, wherein $R^2$ is hydrogen or —OH.

Embodiment 13. The nucleotide analogue of any one of embodiments 1 to 11, wherein $R^2$ is hydrogen.

Embodiment 14. The nucleotide analogue of any one of embodiments 1 to 13, wherein $L^2$ is a cleavable linker.

Embodiment 15. The nucleotide analogue of any one of embodiments 1 to 14, wherein $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 16. The nucleotide analogue of any one of embodiments 1 to 14, wherein $L^2$ is a non-cleavable linker.

Embodiment 17. The nucleotide analogue of any one of embodiments 1 to 14, wherein $L^2$ is a chemically cleavable linker.

Embodiment 18. The nucleotide analogue of any one of embodiments 1 to 14, wherein $L^2$ is a photocleavable linker, an acid-cleavable linker, a base-cleavable linker, an oxidant-cleavable linker, a reductant-cleavable linker, or a fluoride-cleavable linker.

Embodiment 19. The nucleotide analogue of any one of embodiments 1 to 14, wherein $L^2$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment 20. The nucleotide analogue of any one of embodiments 1 to 14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$, and $L^{2E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{2A}$, $L^{2B}$, $L^{2C}$ $L^{2D}$, and $L^{2E}$ is not a bond.

Embodiment 21. The nucleotide analogue of any one of embodiments 1 to 14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene;
wherein at least one of $L^{2A}$, $L^{2B}$, $L^{2C}$ $L^{2D}$, and $L^{2E}$ is not a bond.

Embodiment 22. The nucleotide analogue of any one of embodiments 1 to 14, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene;
wherein at least one of $L^{2A}$, $L^{2B}$, $L^{2C}$ $L^{2D}$, and $L^{2E}$ is not a bond.

Embodiment 23. The nucleotide analogue of any one of embodiments 1 to 14, wherein $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{2A}$, $L^{2B}$, $L^{2C}$, $L^{2D}$, and $L^{2E}$ is not a bond.

Embodiment 24. The nucleotide analogue of any one of embodiments 1 to 14, wherein $L^2$ is $L^{2A}$-$L^{2B}$-$L^{2C}$-$L^{2D}$-$L^{2E}$.

$L^{2A}$ is a bond, substituted or unsubstituted alkylene, substituted or unsubstituted heteroalkylene;

$L^{2B}$ is a bond, substituted or unsubstituted cycloalkylene, substituted or unsubstituted heterocycloalkylene, substituted or unsubstituted arylene, substituted or unsubstituted heteroarylene;

$L^{2C}$ is a bond, substituted or unsubstituted cycloalkylene, substituted or unsubstituted heterocycloalkylene, substituted or unsubstituted arylene, substituted or unsubstituted heteroarylene;

$L^{2D}$ is a bond, substituted or unsubstituted alkylene, substituted or unsubstituted heteroalkylene; and $L^{2E}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein at least one of $L^{2A}$, $L^{2B}$, $L^{2C}$ $L^{2D}$, and $L^{2E}$ is not a bond.

Embodiment 25. The nucleotide analogue of any one of embodiments 1 to 14, wherein $L^2$ is

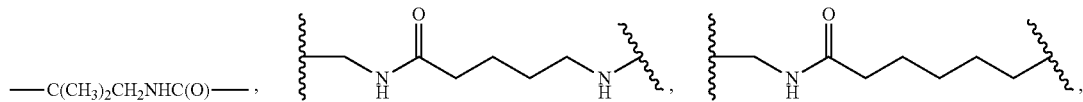

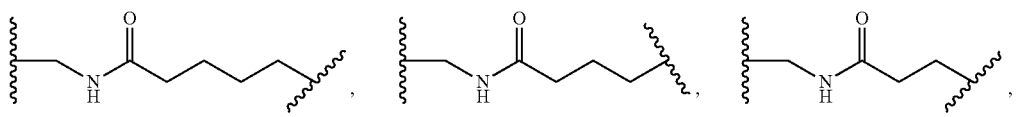

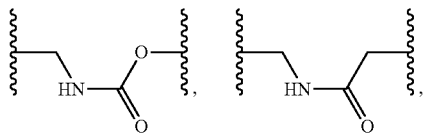

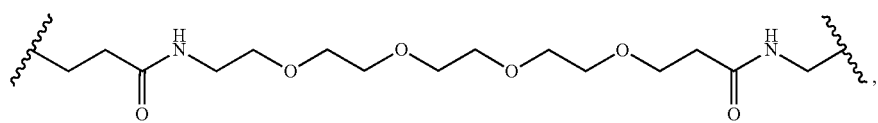

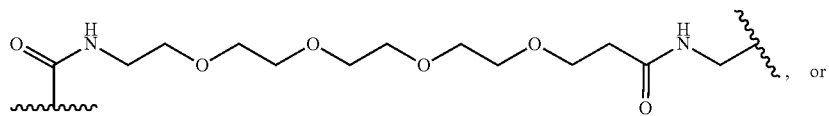, or

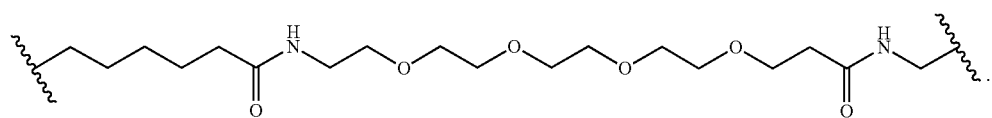

Embodiment 26. The nucleotide analogue of any one of embodiments 1 to 14, wherein —B-L$^{2A}$-L$^{2B}$-L$^{2C}$-L$^{2D}$-L$^{2E}$-R$^5$ has the formula:
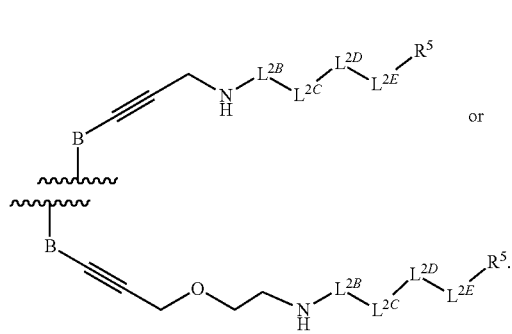
or
Embodiment 27. The nucleotide analogue of any one of embodiments 1 to 14, wherein —B-L$^{2A}$-L$^{2B}$-L$^{2C}$-L$^{2D}$-L$^{2E}$-R$^5$----R$^{12}$-L$^3$-R$^{13}$ has the formula:
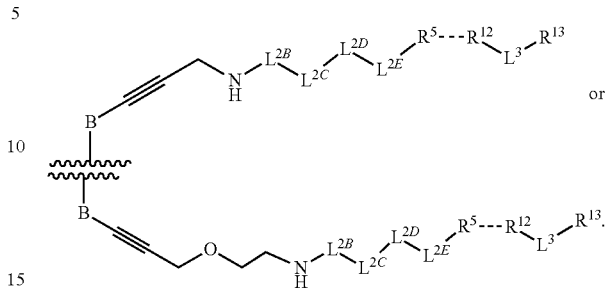
or
Embodiment 28. The nucleotide analogue of any one of embodiments 1 to 14, wherein —B-L$^2$ is
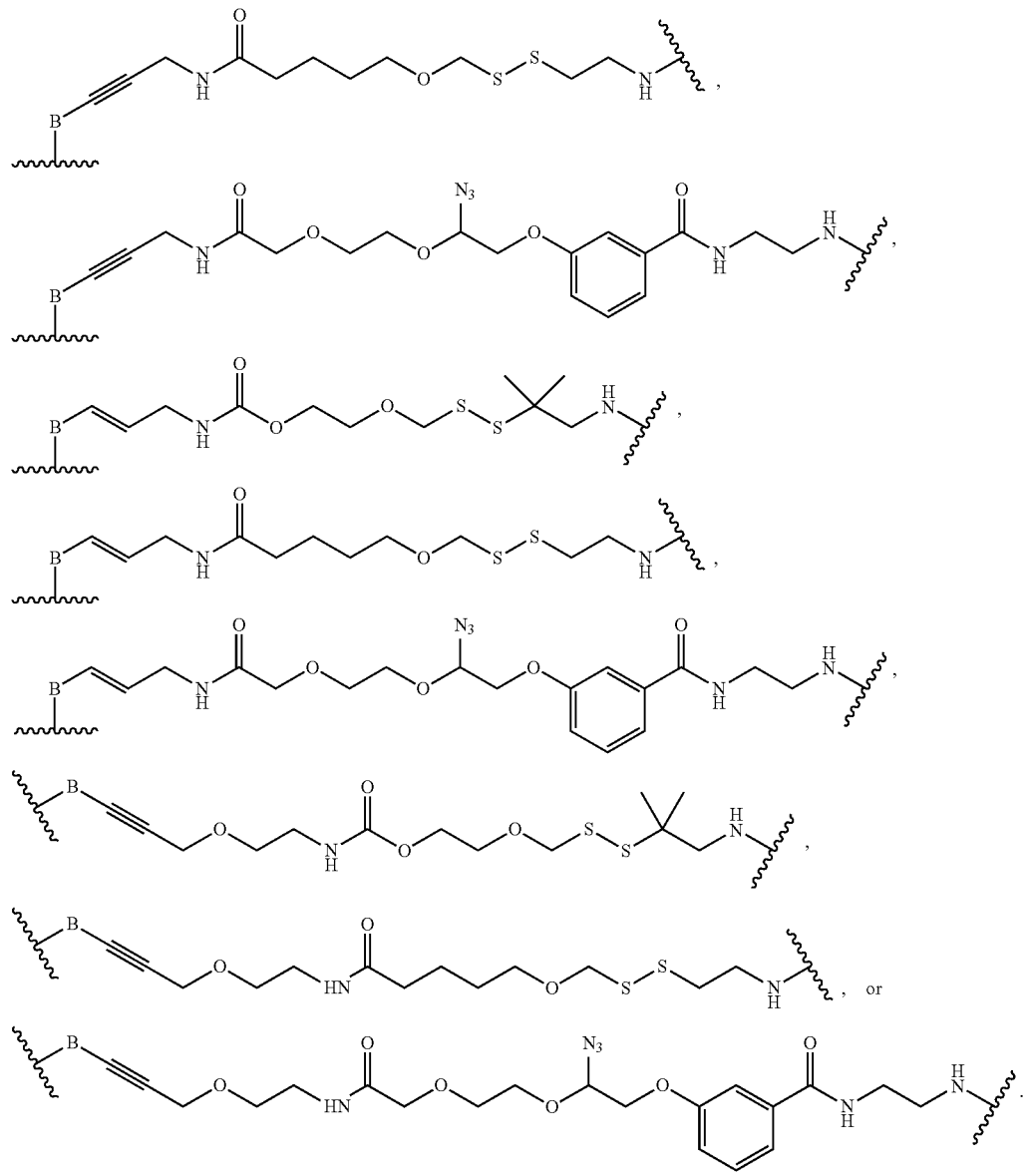

Embodiment 29. The nucleotide analogue of any one of embodiments 1 to 28, wherein $X^1$ is hydrogen and $X^2$ is halogen.

Embodiment 30. The nucleotide analogue of any one of embodiments 1 to 28, wherein $X^1$ is halogen and $X^2$ is hydrogen.

Embodiment 31. The nucleotide analogue of any one of embodiments 1 to 28, wherein $X^1$ is hydrogen and $X^2$ is —F.

Embodiment 32. The nucleotide analogue of any one of embodiments 1 to 28, wherein $X^1$ is —F and $X^2$ is hydrogen.

Embodiment 33. The nucleotide analogue of any one of embodiments 1 to 28, wherein $X^1$ and $X^2$ are halogen.

Embodiment 34. The nucleotide analogue of any one of embodiments 1 to 28, wherein $X^1$ is hydrogen and $X^2$ is —CN.

Embodiment 35. The nucleotide analogue of any one of embodiments 1 to 28, wherein $X^1$ is hydrogen $X^2$ is —$N_3$.

Embodiment 36. The nucleotide analogue of any one of embodiments 1 to 28, wherein $X^2$ is hydrogen and $X^1$ is —CN.

Embodiment 37. The nucleotide analogue of any one of embodiments 1 to 28, wherein $X^2$ is hydrogen $X^1$ is —$N_3$.

Embodiment 38. The nucleotide analogue of any one of embodiments 1 to 28, wherein $X^2$ is hydrogen $X^1$ is —$N_3$.

Embodiment 39. The nucleotide analogue of any one of embodiments 1 to 28, wherein $X^1$ and $X^2$ are —F.

Embodiment 40. The nucleotide analogue of any one of embodiments 1 to 39, wherein $R^5$ is a detectable label.

Embodiment 41. The nucleotide analogue of any one of embodiments 1 to 39, wherein $R^5$ is a fluorescent dye.

Embodiment 42. The nucleotide analogue of any one of embodiments 1 to 39, wherein $R^5$ is

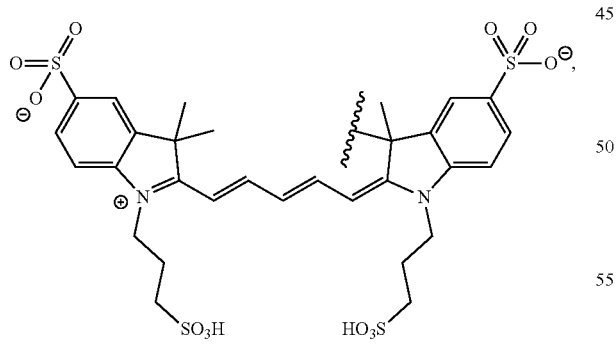

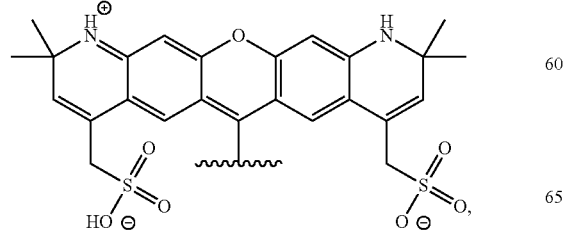

-continued

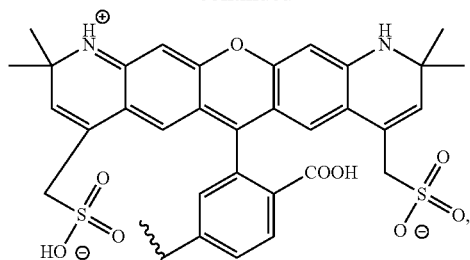

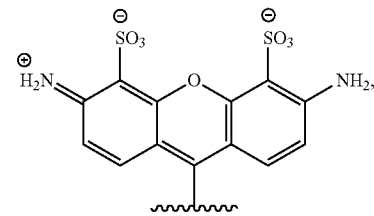

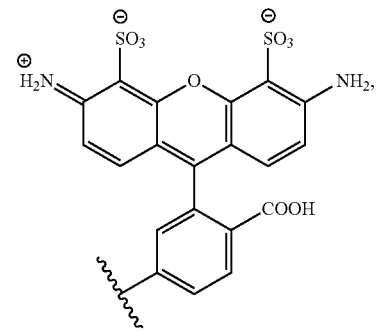

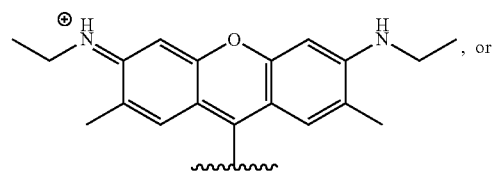, or

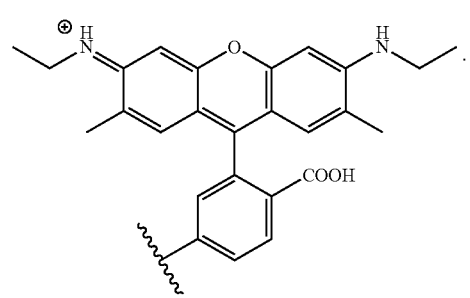.

Embodiment 43. The nucleotide analogue of any one of embodiments 1 to 42, wherein $R^{12}$ is a streptavidin moiety.

Embodiment 44. The nucleotide analogue of any one of embodiments 1 to 42, wherein $R^{12}$ is selected from the group consisting of:

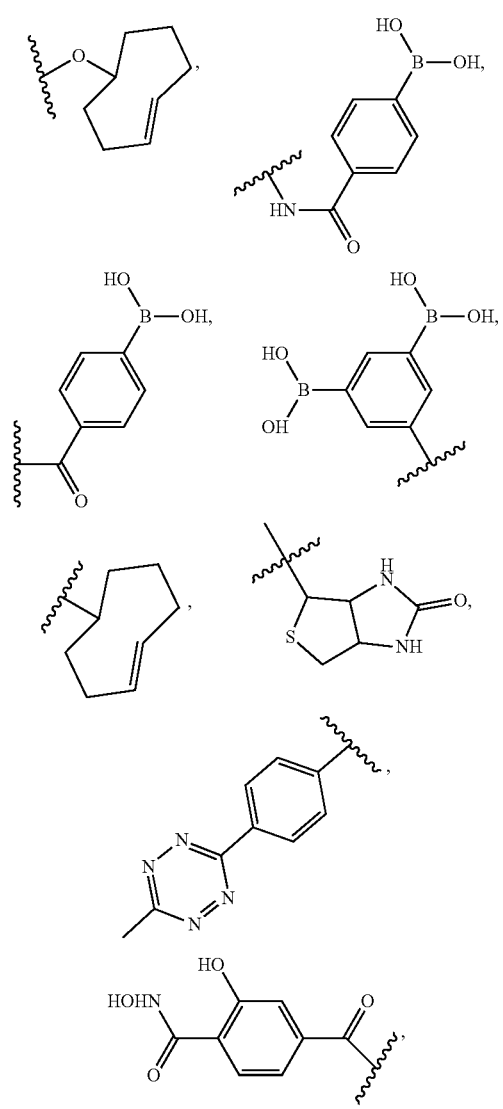

a streptavidin moiety,

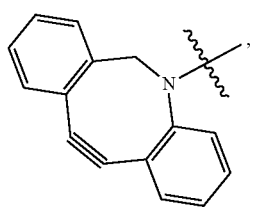 [SMILES: *N1Cc2ccccc2C#Cc2ccccc21]

unsubstituted ethynyl,

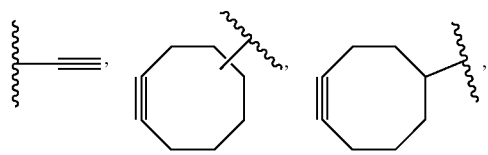

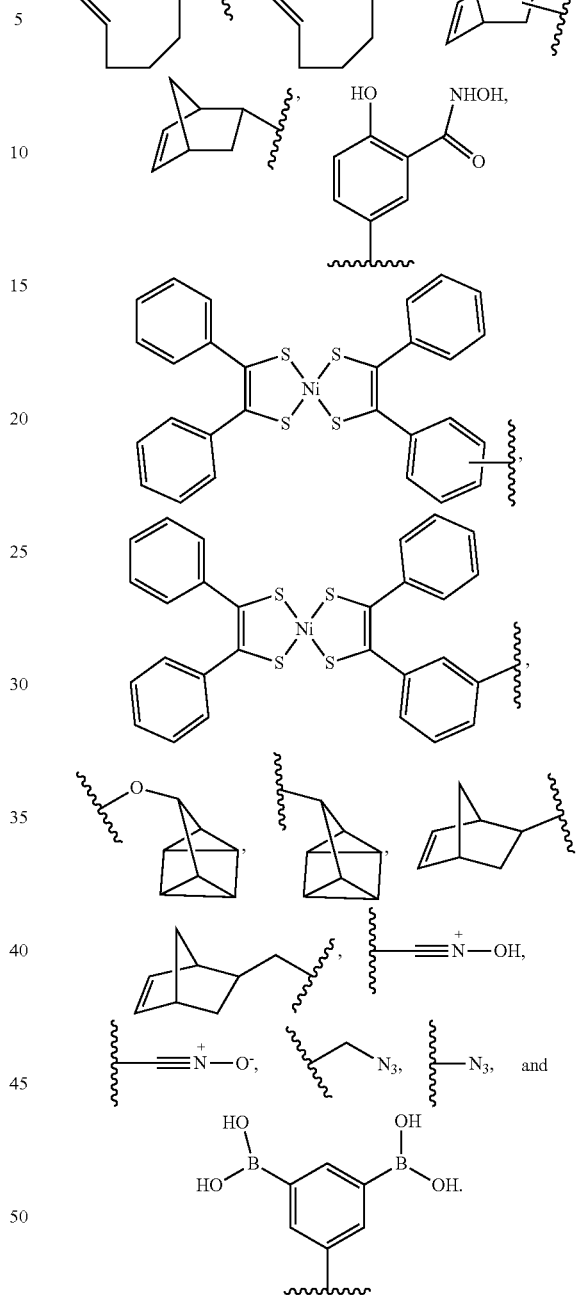

Embodiment 45. The nucleotide analogue of any one of embodiments 1 to 43, wherein $L^3$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 46. The nucleotide analogue of any one of embodiments 1 to 43, wherein $L^3$ is an orthogonally cleavable linker.

Embodiment 47. The nucleotide analogue of any one of embodiments 1 to 47, wherein $L^3$ is a photocleavable linker, an acid-cleavable linker, a base-cleavable linker, an oxidant-cleavable linker, a reductant-cleavable linker, or a fluoride-cleavable linker.

Embodiment 48. The nucleotide analogue of any one of embodiments 1 to 43, wherein $L^3$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment 49. The nucleotide analogue of any one of embodiments 1 to 43, wherein
$L^3$ is $L^{3A}$-$L^{3B}$-$L^{3C}$-$L^{3D}$-$L^{3E}$; and
$L^{3A}$, $L^{3B}$, $L^{3C}$, $L^{3D}$, and $L^{3E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{3A}$, $L^{3B}$, $L^{3C}$, $L^{3D}$, and $L^{3E}$ is not a bond.

Embodiment 50. The nucleotide analogue of any one of embodiments 1 to 43, wherein
$L^3$ is $L^{3A}$-$L^{3B}$-$L^{3C}$-$L^{3D}$-$L^{3E}$.
$L^{3A}$ is a bond, —NN—, —NHC(O)—, —C(O)NH—, substituted or unsubstituted alkylene, substituted or unsubstituted heteroalkylene;
$L^{3B}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{3C}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{3D}$ is a bond, —NN—, —NHC(O)—, —C(O)NH—, substituted or unsubstituted alkylene, substituted or unsubstituted heteroalkylene; and
$L^{3E}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{3A}$, $L^{3B}$, $L^{3C}$, $L^{3D}$, and $L^{3E}$ is not a bond.

Embodiment 51. The nucleotide analogue of any one of embodiments 1 to 50, wherein $R^{13}$ is a detectable label.

Embodiment 52. The nucleotide analogue of any one of embodiments 1 to 50, wherein $R^{13}$ is a fluorescent dye.

Embodiment 53. The nucleotide analogue of any one of embodiments 1 to 50, wherein $R^{13}$ is

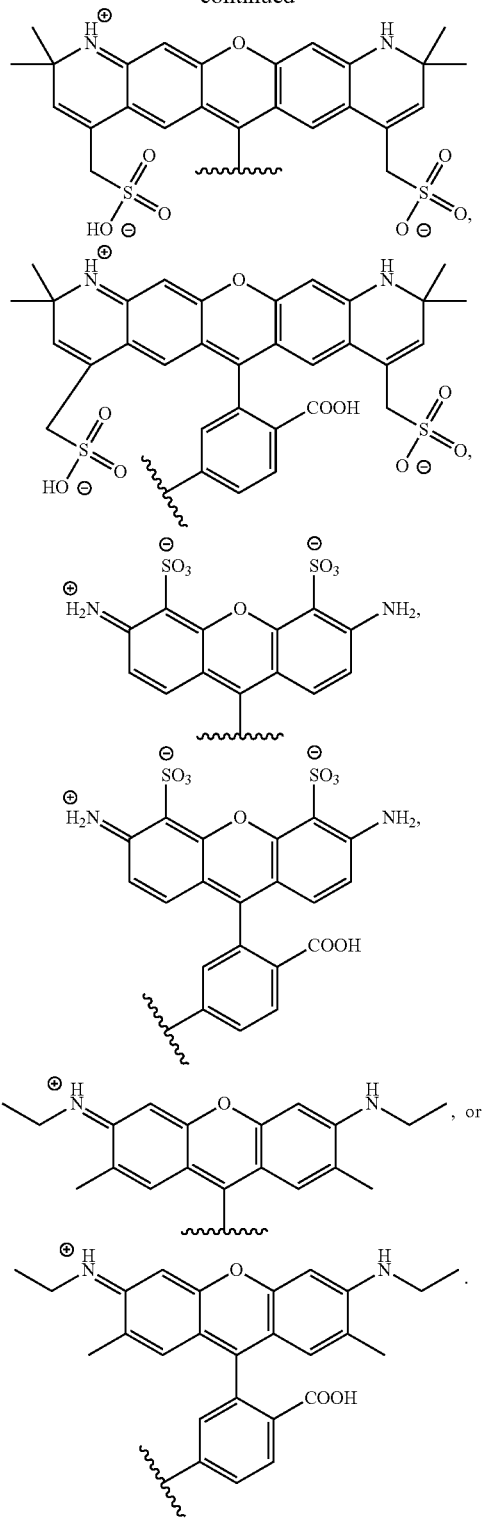

Embodiment 54. The nucleotide analogue of any one of embodiments 1 to 53, wherein $L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 55. The nucleotide analogue of any one of embodiments 1 to 53, wherein $L^4$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 56. The nucleotide analogue of any one of embodiments 1 to 53, wherein $L^4$ is a substituted or unsubstituted $C_1$-$C_6$ alkylene or substituted or unsubstituted 2 to 6 membered heteroalkylene.

Embodiment 57. The nucleotide analogue of any one of embodiments 1 to 53, wherein $L^4$ is an unsubstituted $C_1$-$C_4$ alkylene.

Embodiment 58. The nucleotide analogue of any one of embodiments 1 to 53, wherein $L^4$ is a bond.

Embodiment 59. The nucleotide analogue of any one of embodiments 1 to 58, wherein $R^4$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 60. The nucleotide analogue of any one of embodiments 1 to 58, wherein $R^4$ is substituted or unsubstituted $C_1$-$C_6$ alkyl, or substituted or unsubstituted phenyl.

Embodiment 61. The nucleotide analogue of any one of embodiments 1 to 58, wherein $R^4$ is an unsubstituted $C_1$-$C_6$ alkyl.

Embodiment 62. The nucleotide analogue of embodiment 1, having the formula:

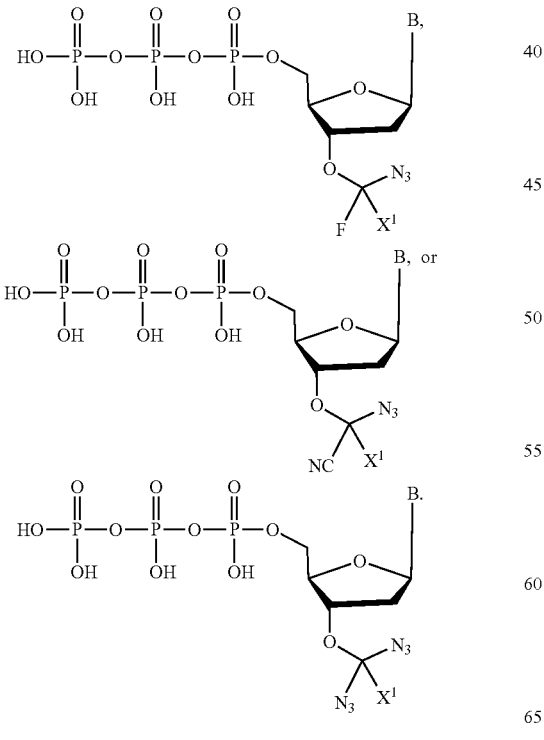

Embodiment 63. The nucleotide analogue of embodiment 1, having the formula:

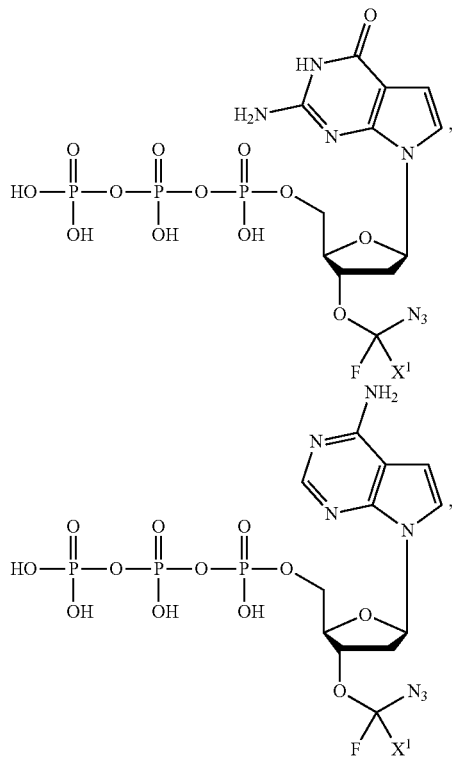

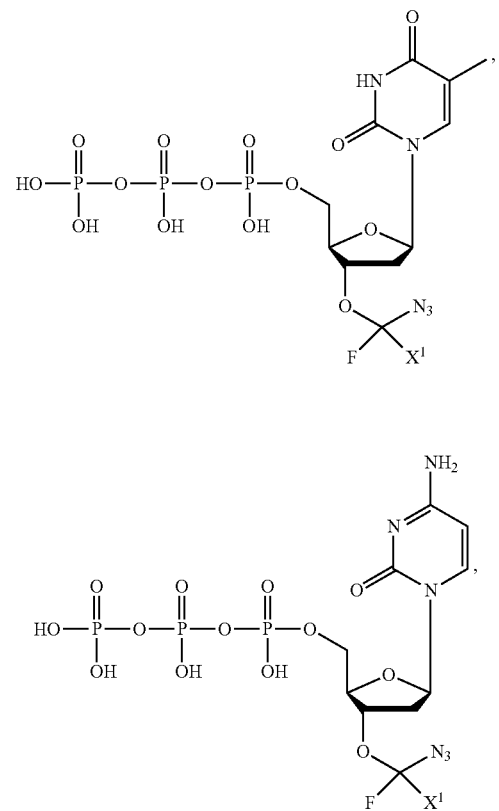

-continued
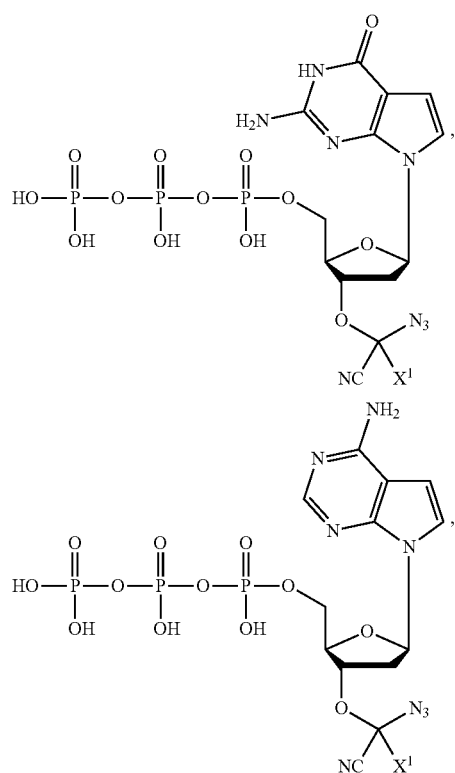
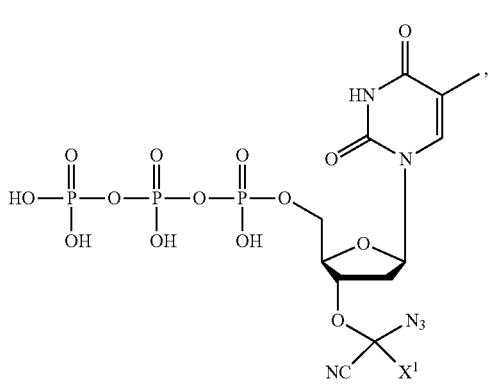
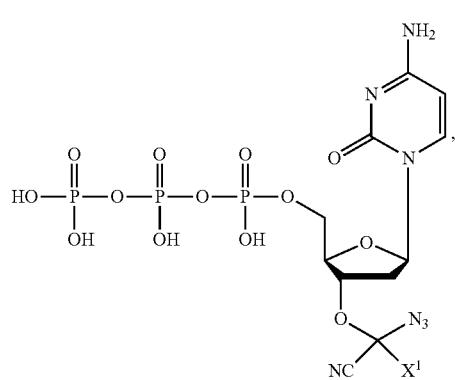
-continued
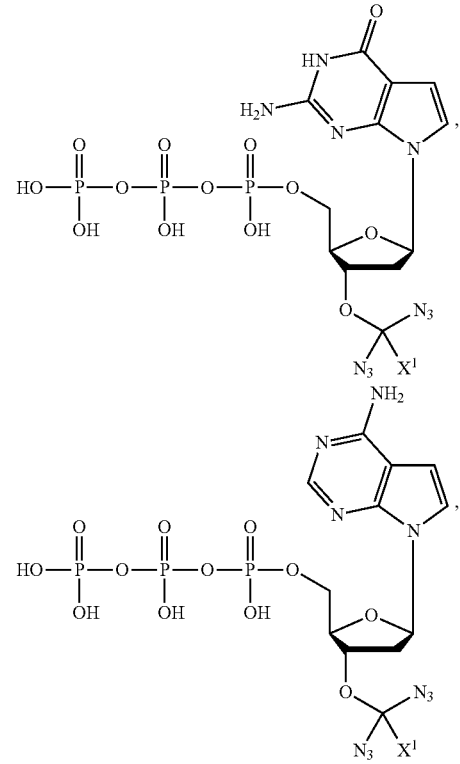
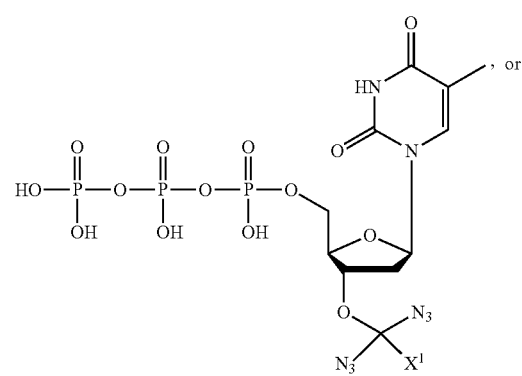

Embodiment 64. The nucleotide analogue of embodiment 1, having the formula:
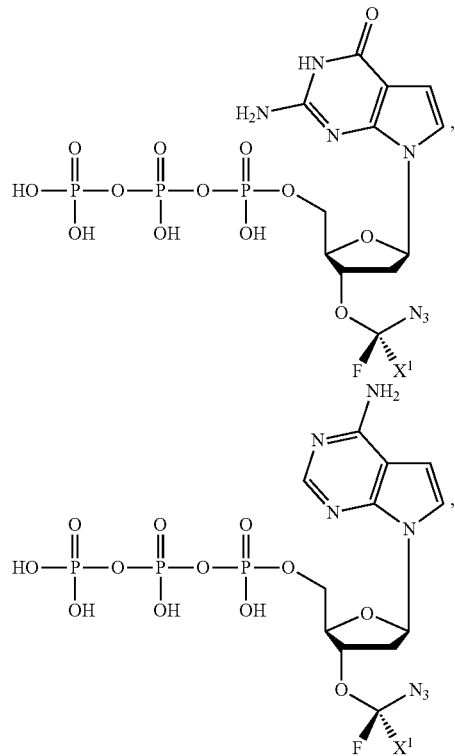
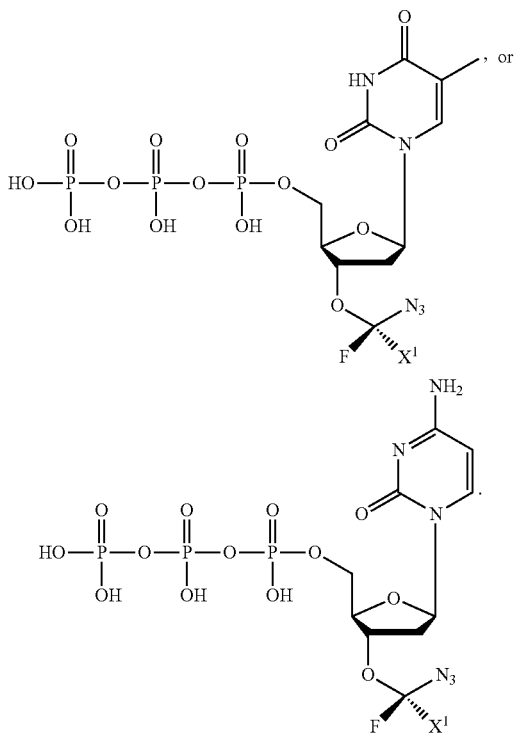
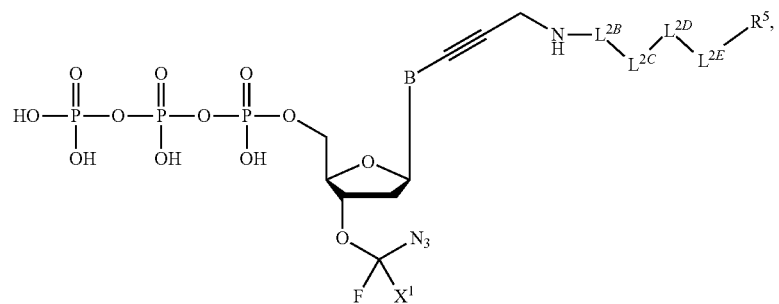
Embodiment 65. The nucleotide analogue of embodiment 1, having the formula:
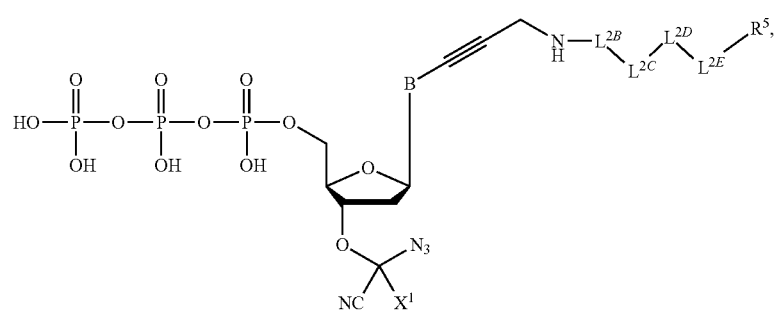

-continued
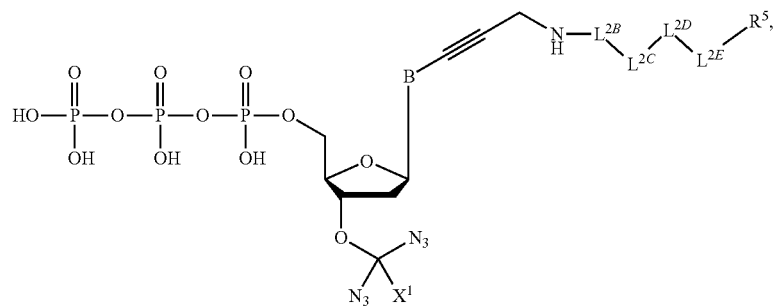
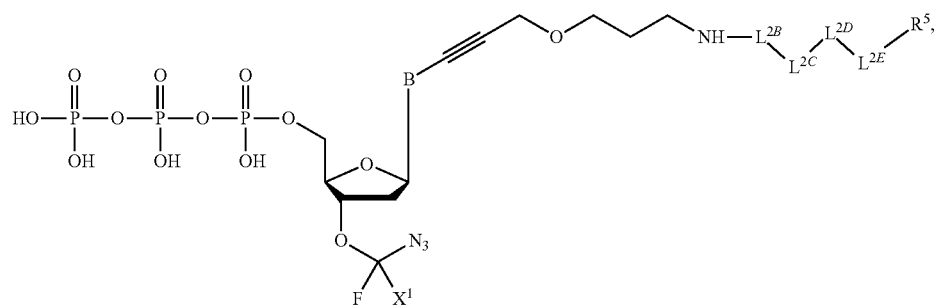
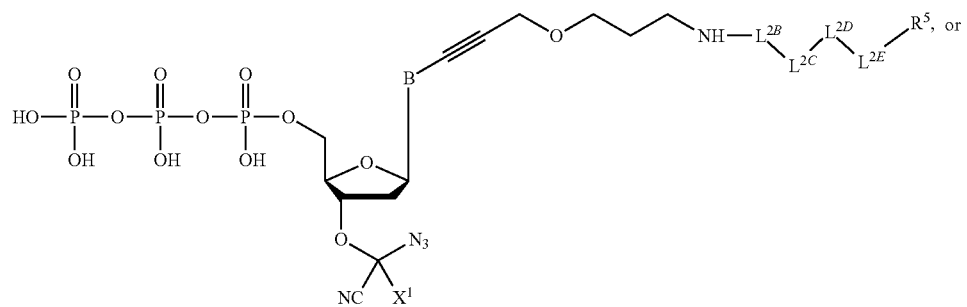
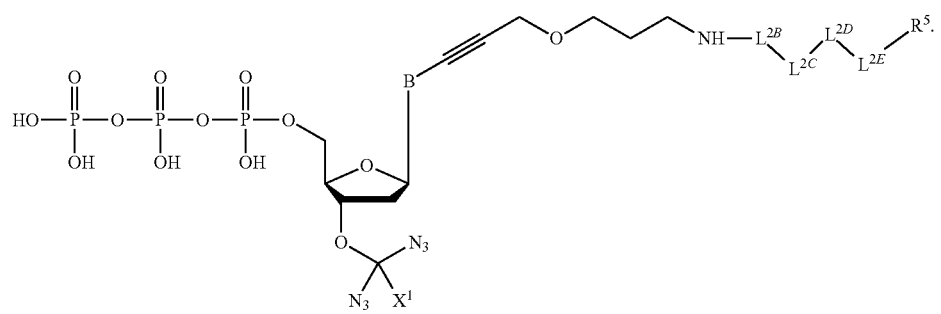

Embodiment 66. The nucleotide analogue of embodiment 1, having the formula:
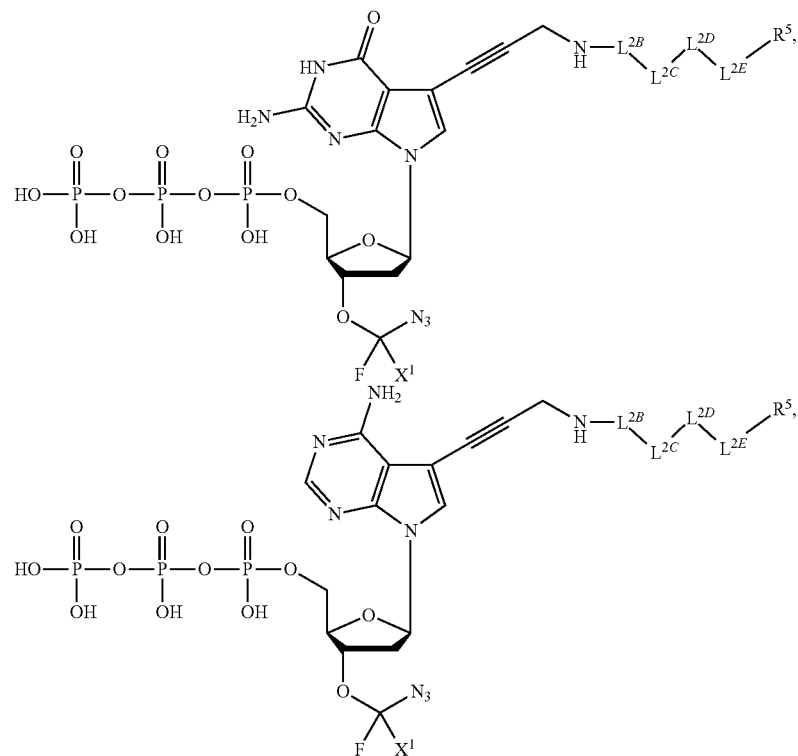
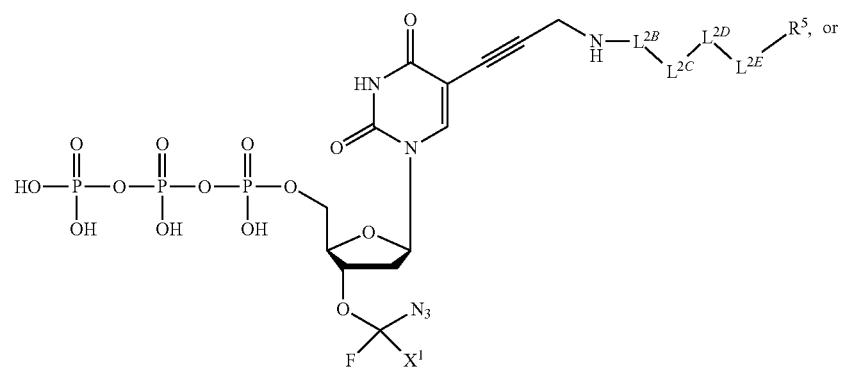
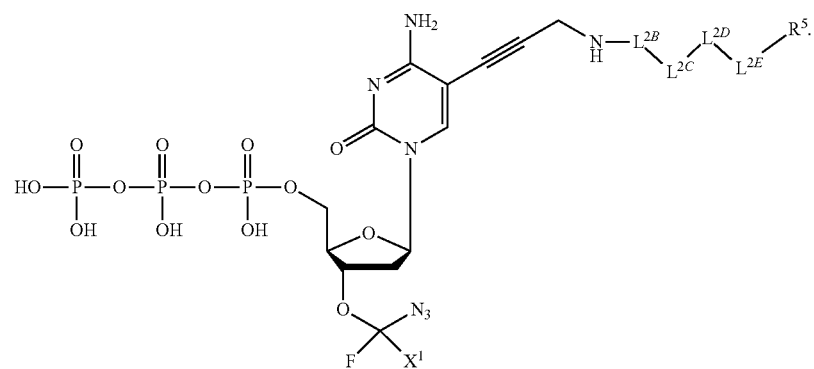

Embodiment 67. The nucleotide analogue of embodiment 1, having the formula:
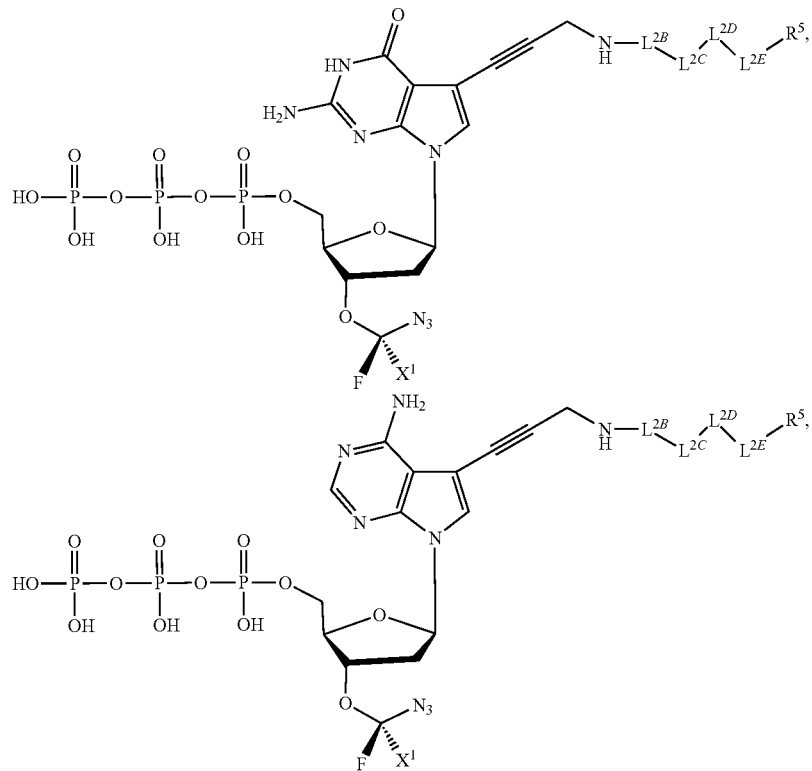
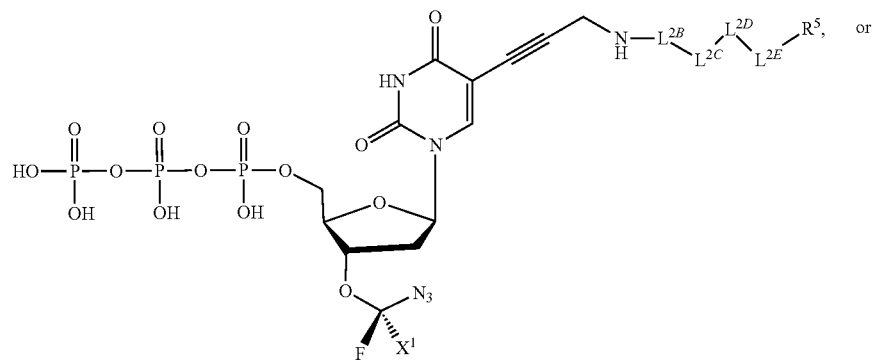
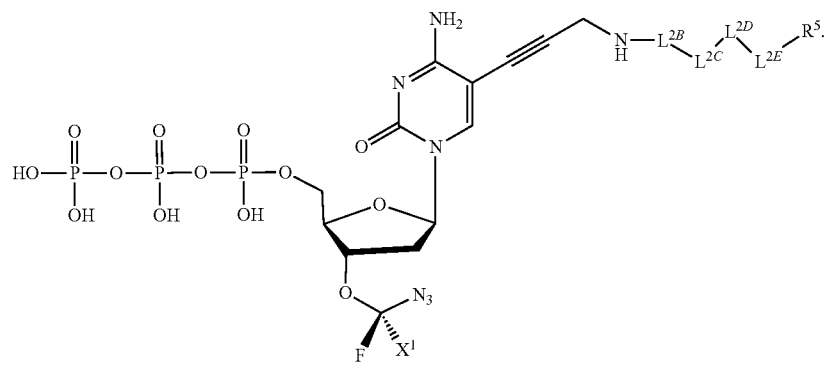

Embodiment 68. The nucleotide analogue of embodiment 1, having the formula:
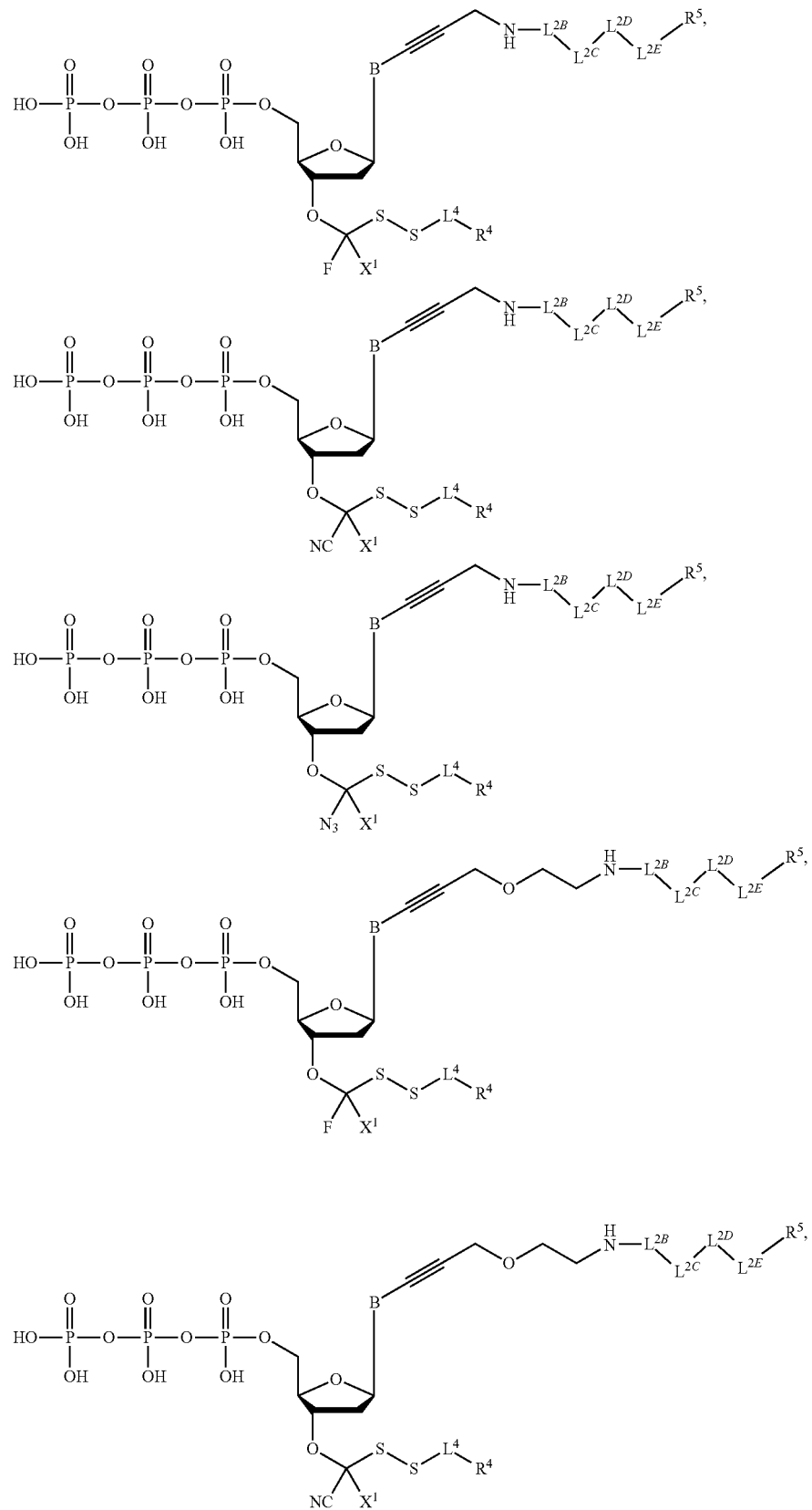

-continued
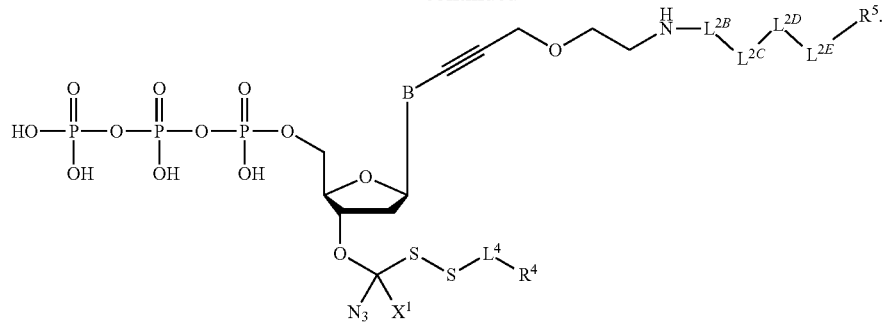
Embodiment 69. The nucleotide analogue of embodiment 1, having the formula:
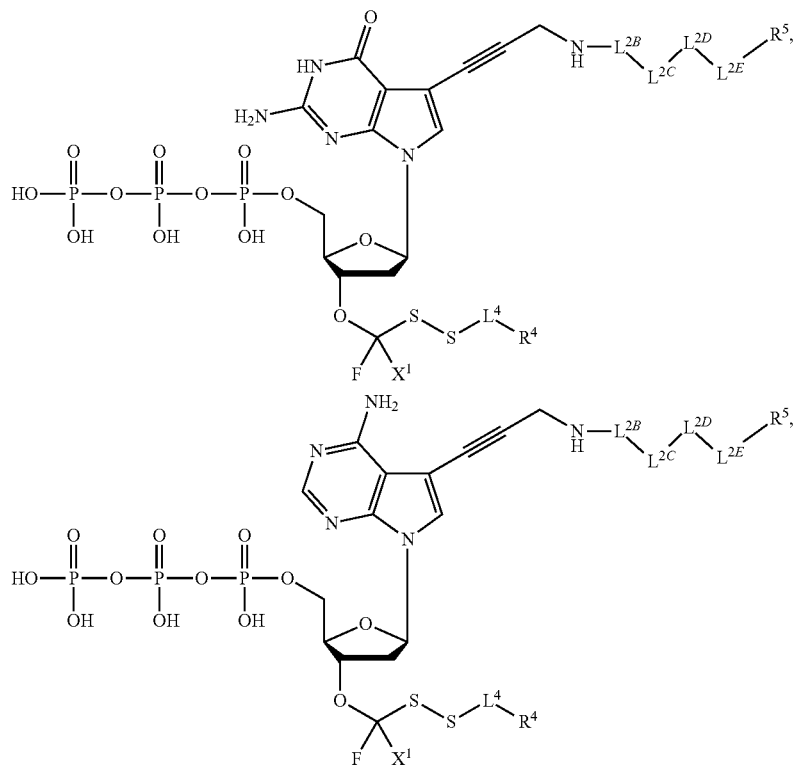
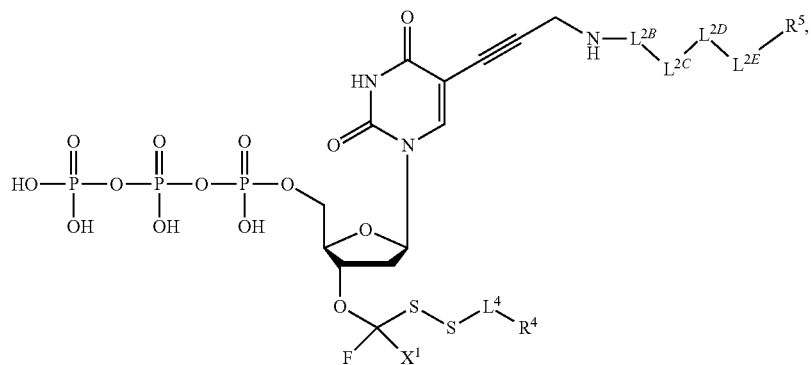

-continued
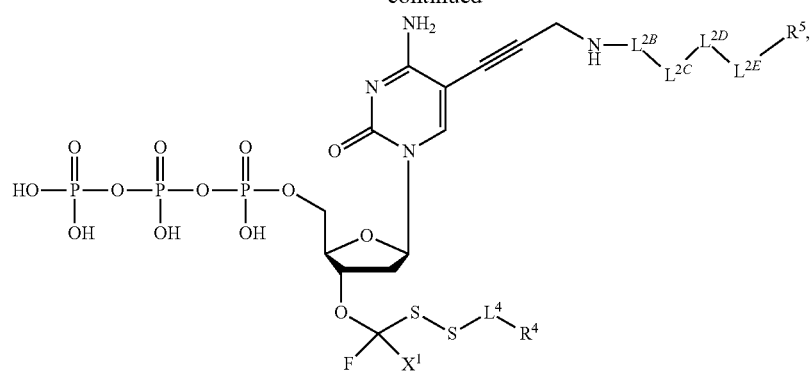
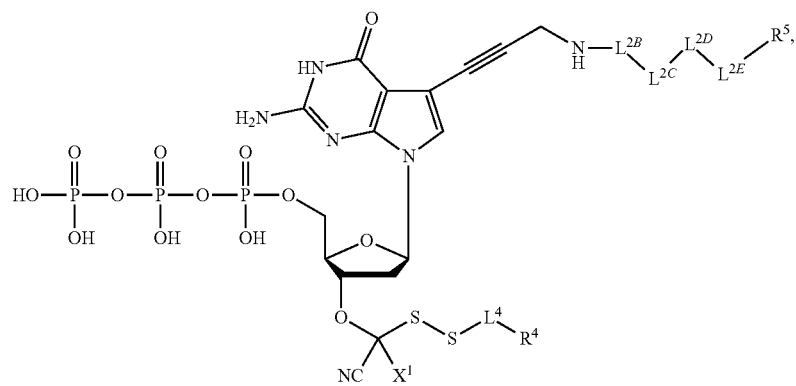
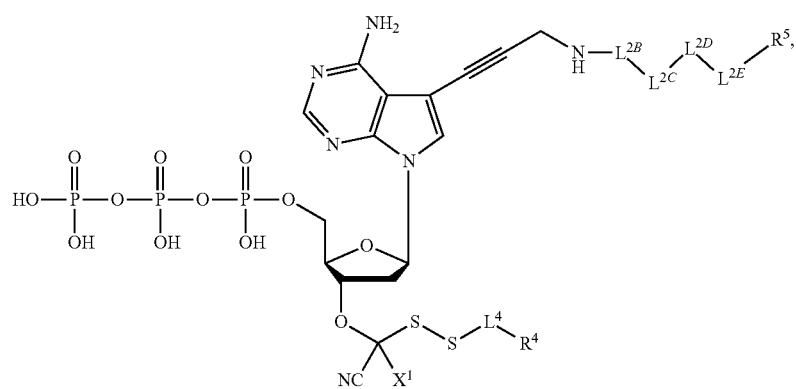
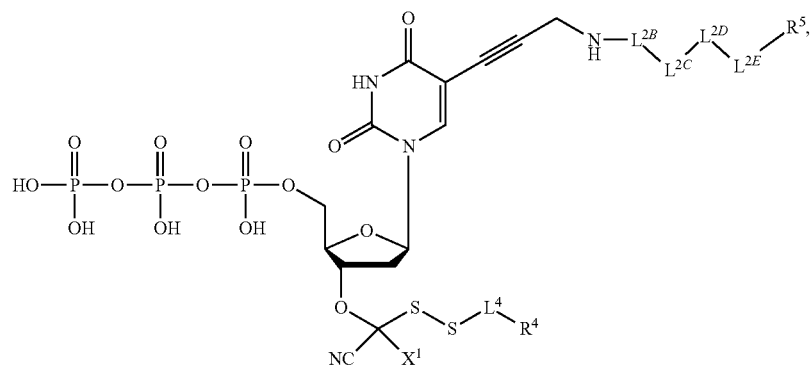

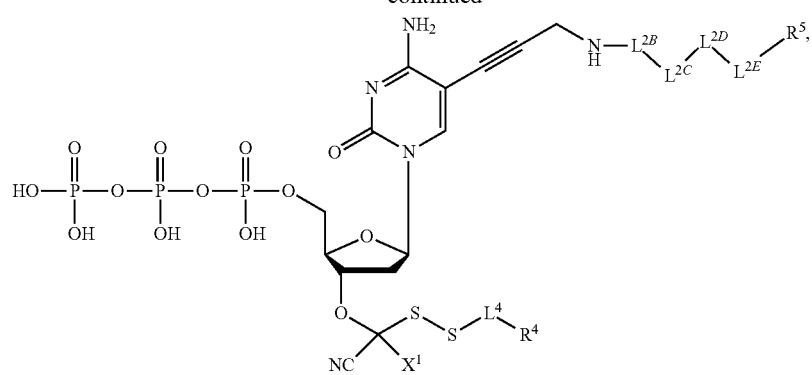
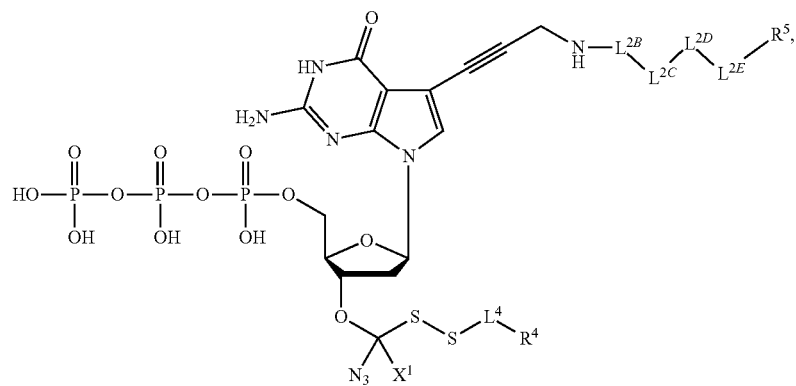
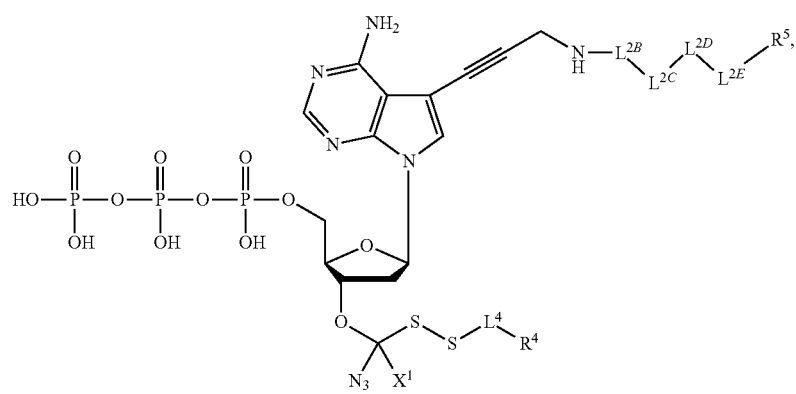
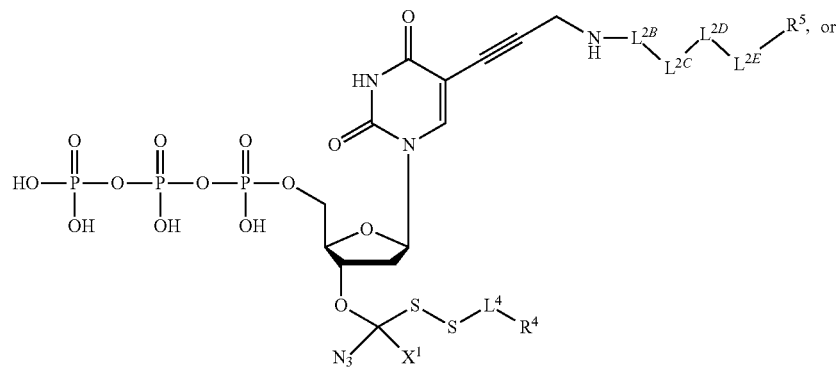

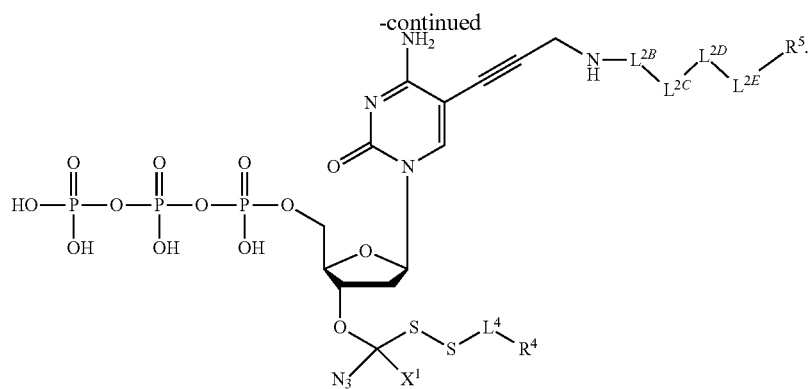
Embodiment 70. The nucleotide analogue of embodiment 1, having the formula:
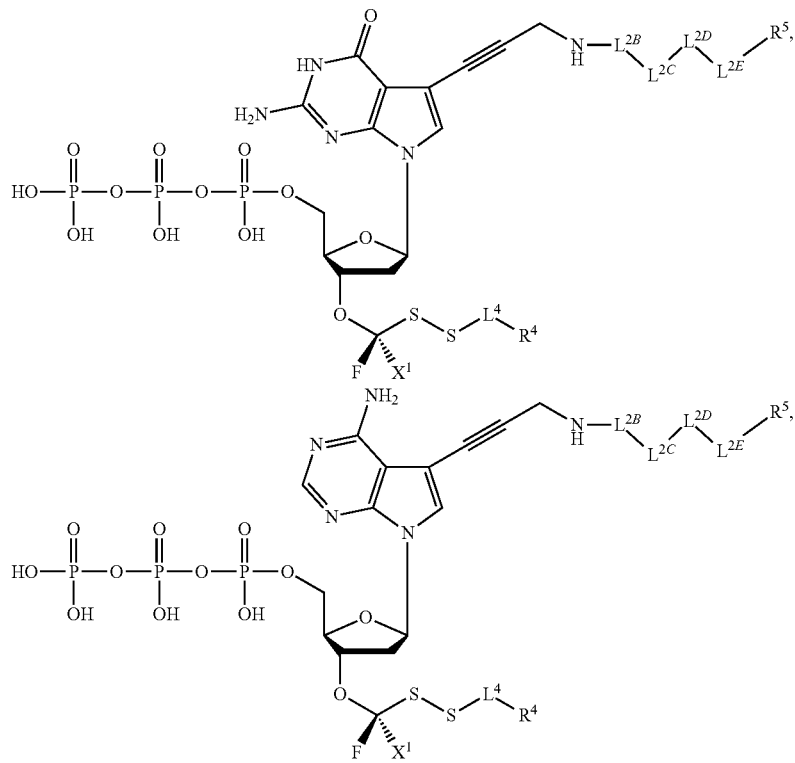
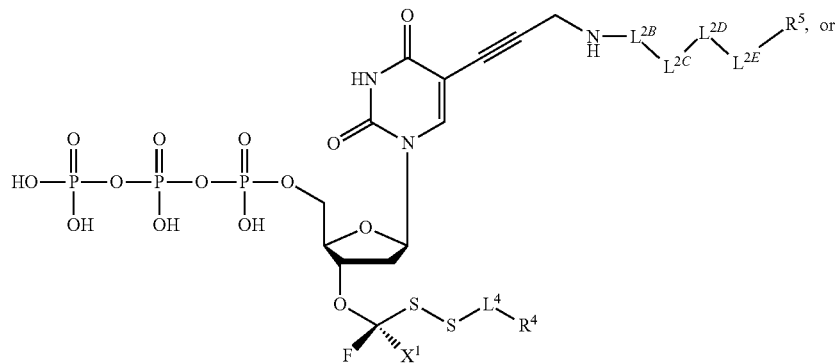

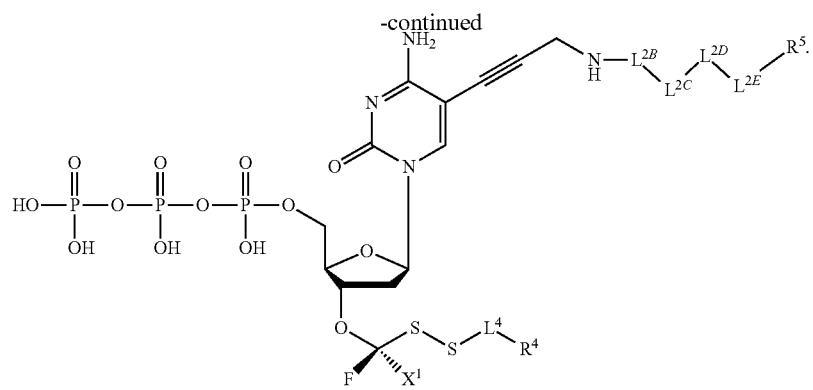
Embodiment 71. The nucleotide analogue of embodiment 1, having the formula:
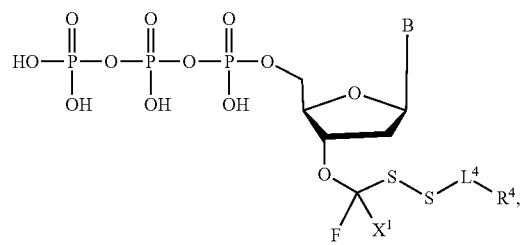
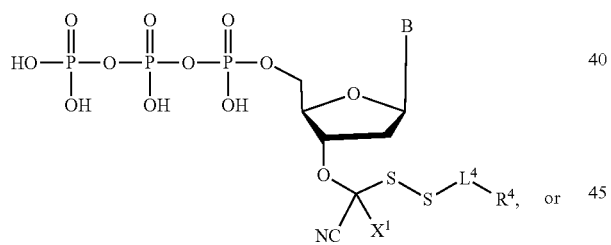
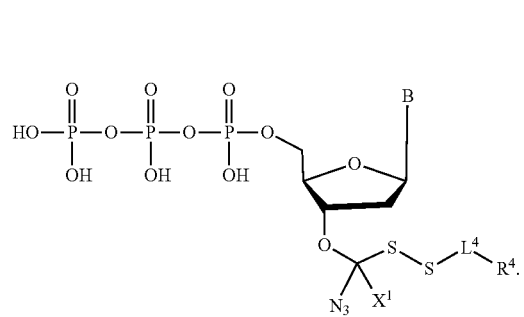
Embodiment 72. The nucleotide analogue of embodiment 1, having the formula:
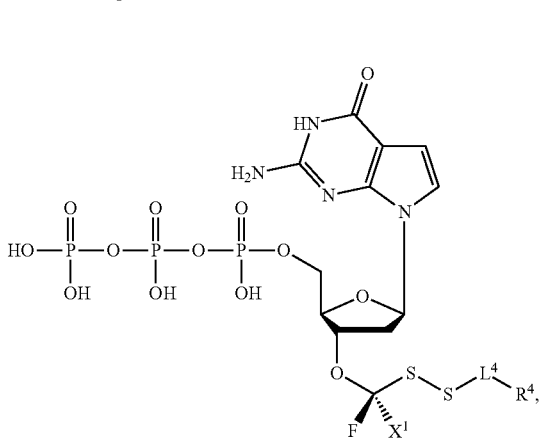
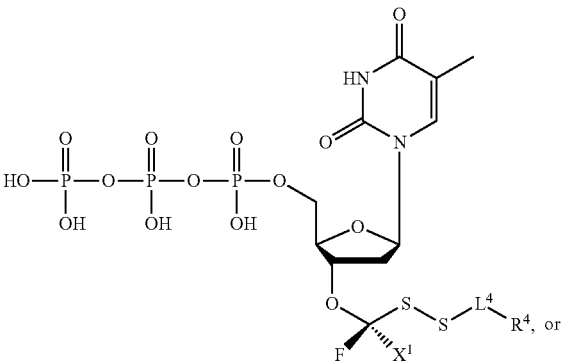

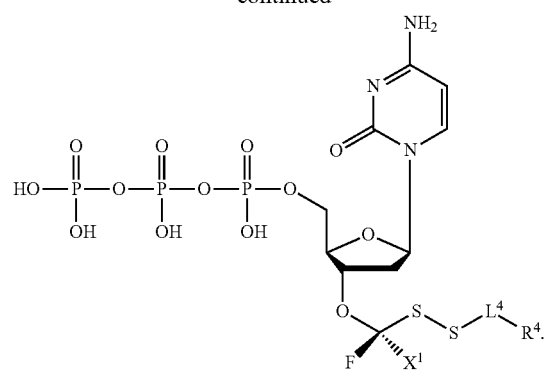
Embodiment 73. The nucleotide analogue of embodiment 1, having the formula:
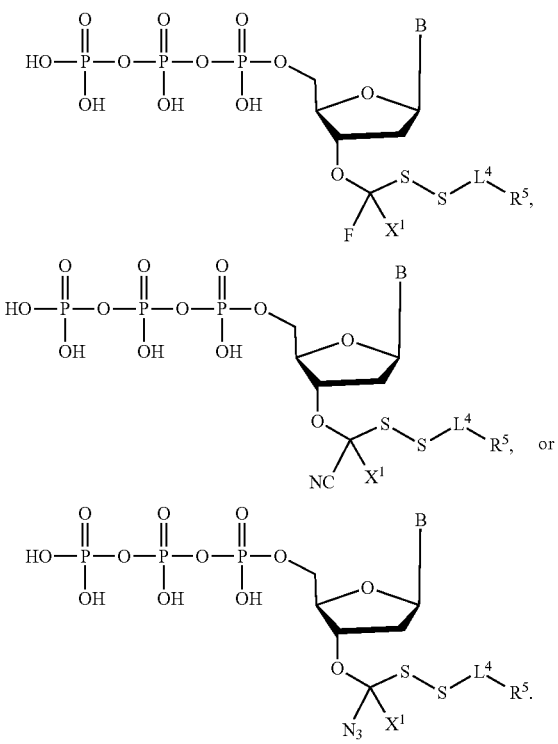
Embodiment 74. The nucleotide analogue of embodiment 1, having the formula:
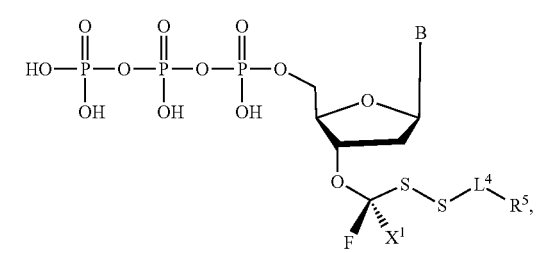
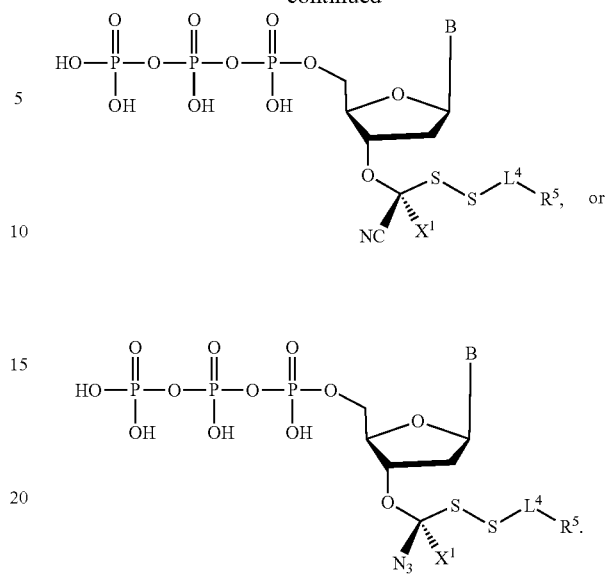
Embodiment 75. The nucleotide analogue of embodiment 1, having the formula:
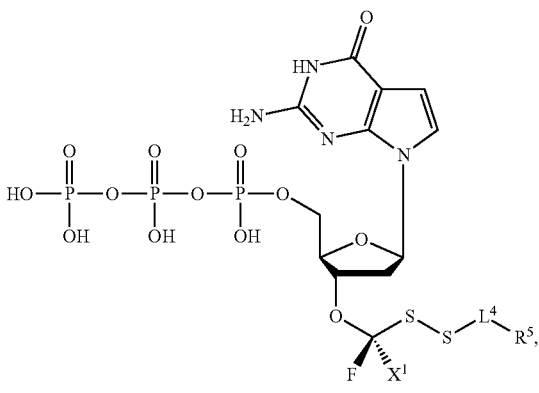
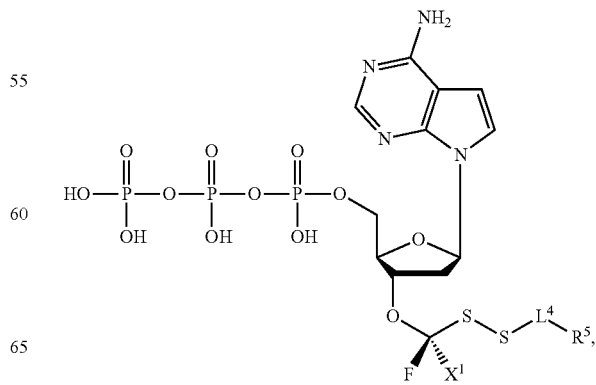

425
-continued

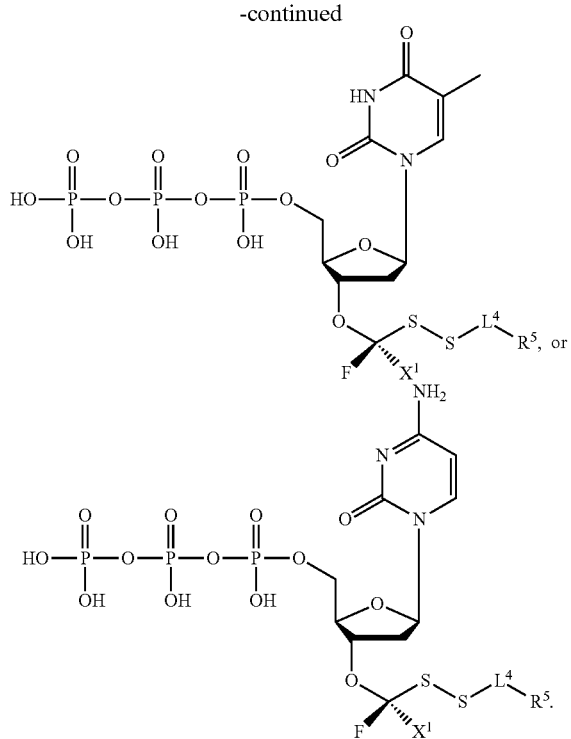

Embodiment 76. A method for sequencing a nucleic acid, including:
incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues comprise a unique detectable label;

426 detecting the unique detectable label of each incorporated nucleotide analogue, so as to thereby identify each incorporated nucleotide analogue in the extension strand, thereby sequencing the nucleic acid;
wherein each of the four different labeled nucleotide analogues is of the structure of one of embodiments 1 to 75.

Embodiment 77. A method of incorporating a nucleotide analogue into a primer, the method including combining a polymerase, a primer hybridized to a nucleic acid template and a nucleotide analogue within a reaction vessel and allowing the polymerase to incorporate the nucleotide analogue into the primer thereby forming an extended primer, wherein the nucleotide analogue is of the structure of one of embodiments 1 to 75.

Embodiment 78. The method of embodiment 77, wherein $L^2$ is a cleavable moiety and $R^5$ is a detectable label, the method further including, after the incorporating, cleaving the cleavable moiety with a cleaving reagent.

Embodiment 79. The method of embodiment 77, wherein $R^5$ is anchor moiety, the method further including, after the incorporating, labeling the nucleotide analog with a detectable label.

Embodiment 80. A nucleic acid polymerase complex, wherein the nucleic acid polymerase is bound to a nucleotide analogue of one of embodiments 1 to 75.

EXAMPLES

Example 1: 3' Reversible Terminators

One strategy is to use electron withdrawing groups (EWG) to speed up cleavage, and balance the cleavage rate and still maintain efficient DNA polymerase incorporation.

Scheme 01 shows a proposed mechanism for enhanced cleavage rate of 3' fluoro disulfide reversible terminators. In this example, the 3' monofluoro carbon atom is chiral.

Scheme 01

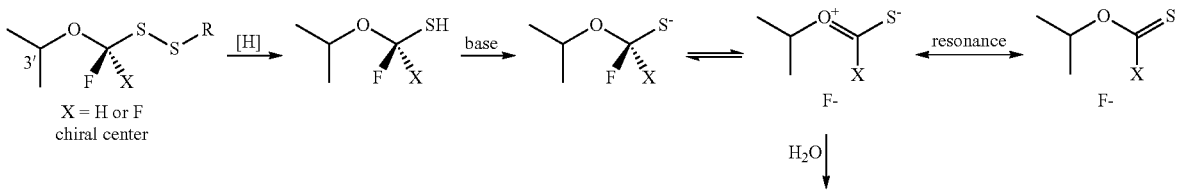

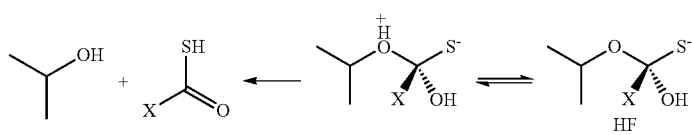

Scheme 02 shows a proposed mechanism for enhanced cleavage rate of 3' fluoro azido reversible terminators. In this example, the 3' monofluoro carbon atom is chiral.

Scheme 02:

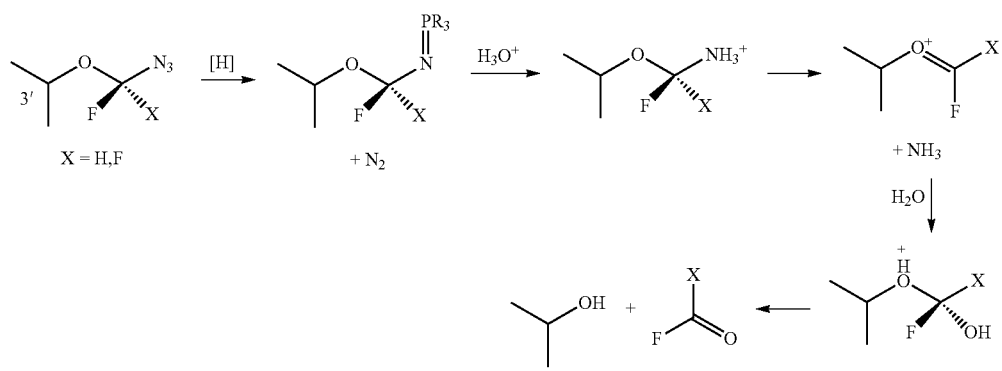

We desired to increase cleavage rate and stability without increasing steric bulk at the 3' position because polymerase efficiency is sensitive to steric crowding at this position. We reasoned that mono- or di-fluoro substitution would increase cleavage rate and stability without increasing steric bulk (see Scheme 03).

Scheme 03.

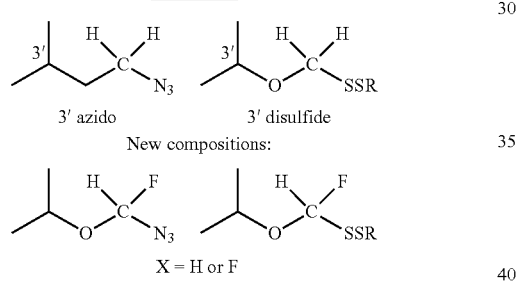

X = H or F

Scheme 04 shows synthesis of 3' mono-fluoro azido and disulfide nucleosides. The nucleosides are converted to nucleotides by standard procedures.

Scheme 04:

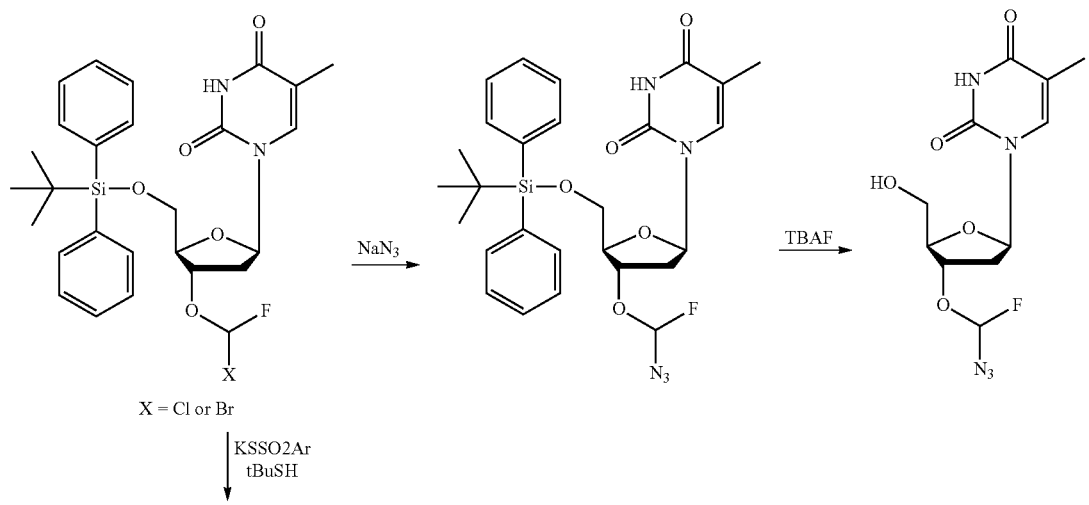

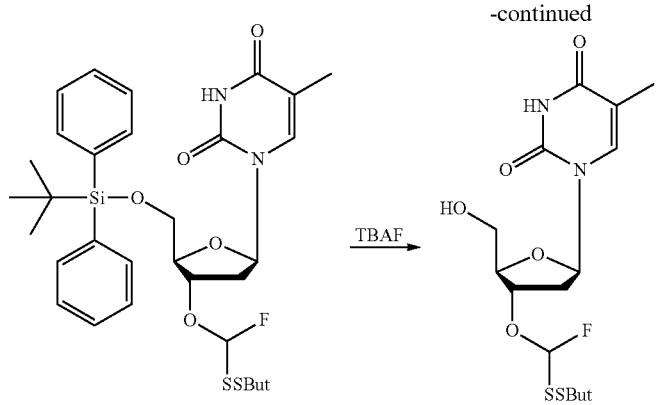

Scheme 05 shows synthesis of 3' difluoro azido and disulfide nucleosides. For synthesis of difluoro(methylthio) methyl ethers by the reaction of dithiocarbonates with IF5-pyridine-HF see: Shoji Hara and co-workers, Journal of Fluorine Chemistry, 2015, volume 179, pages 48-52, which is incorporated herein for all purposes in its entirety. The nucleosides are converted to nucleotides by standard procedures.

Scheme 05:

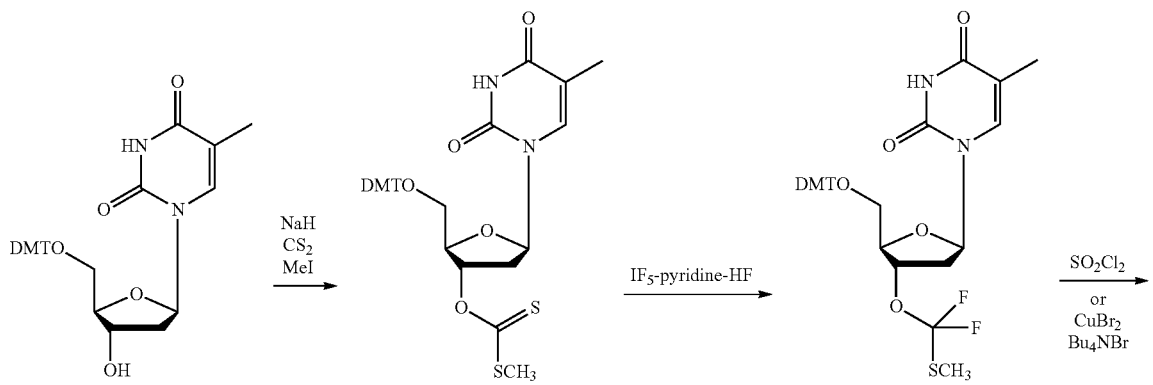

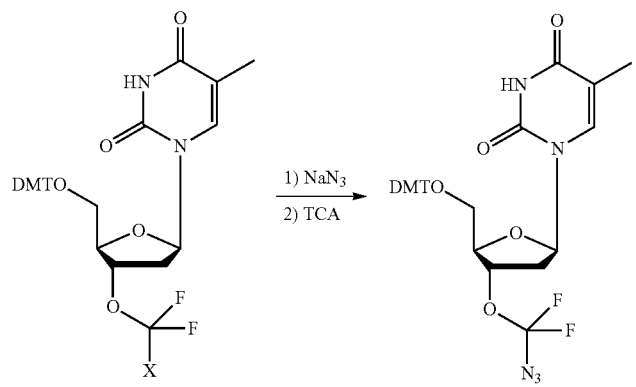

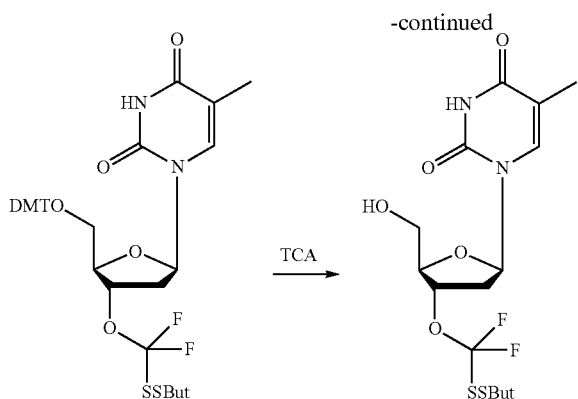
Scheme 06 below shows the outcome of the synthesis as a generalized nucleoside.
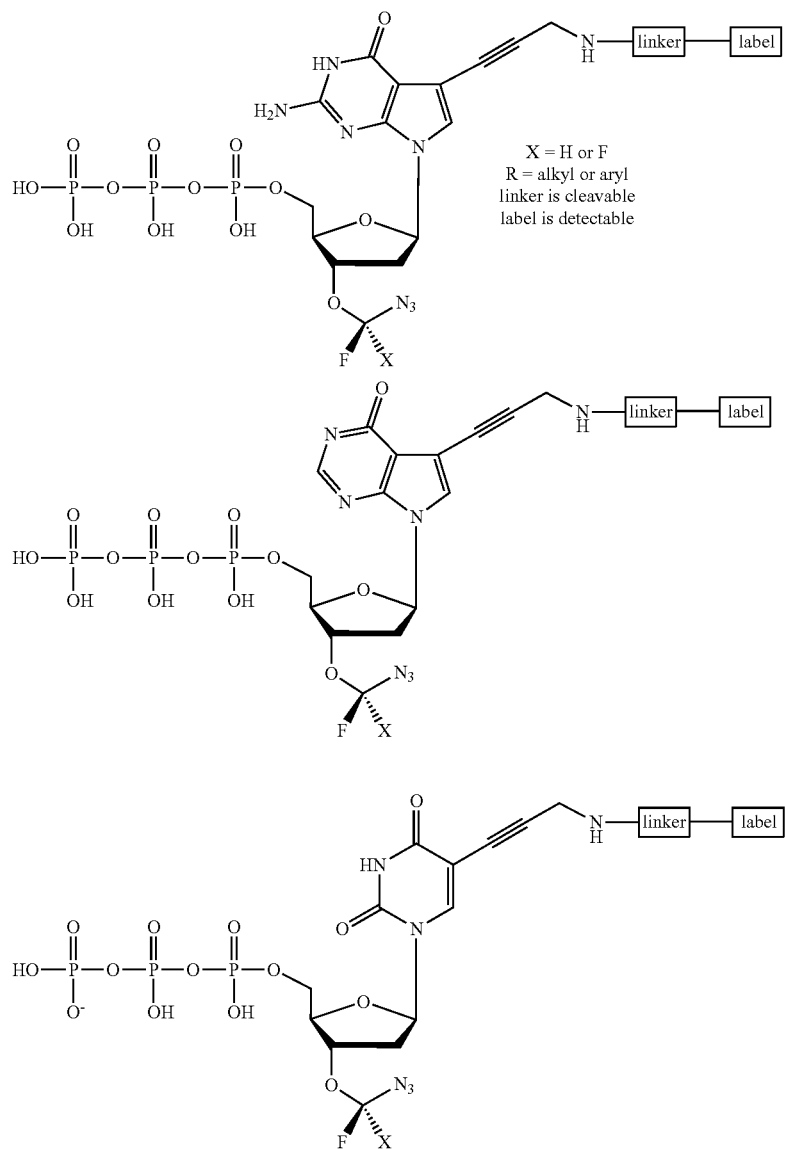

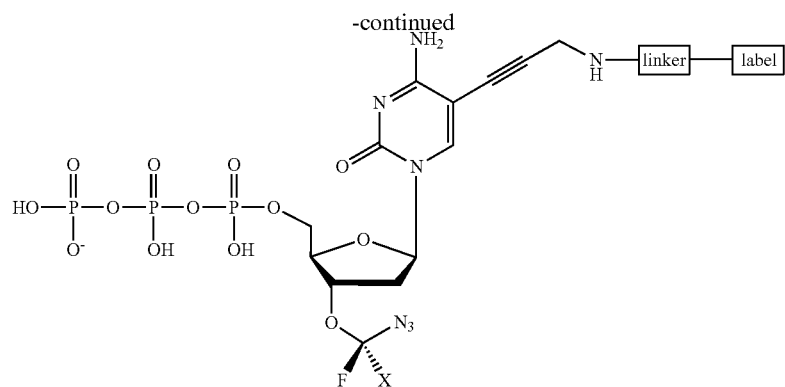
Scheme 07 below shows the outcome of the synthesis as a generalized nucleoside.
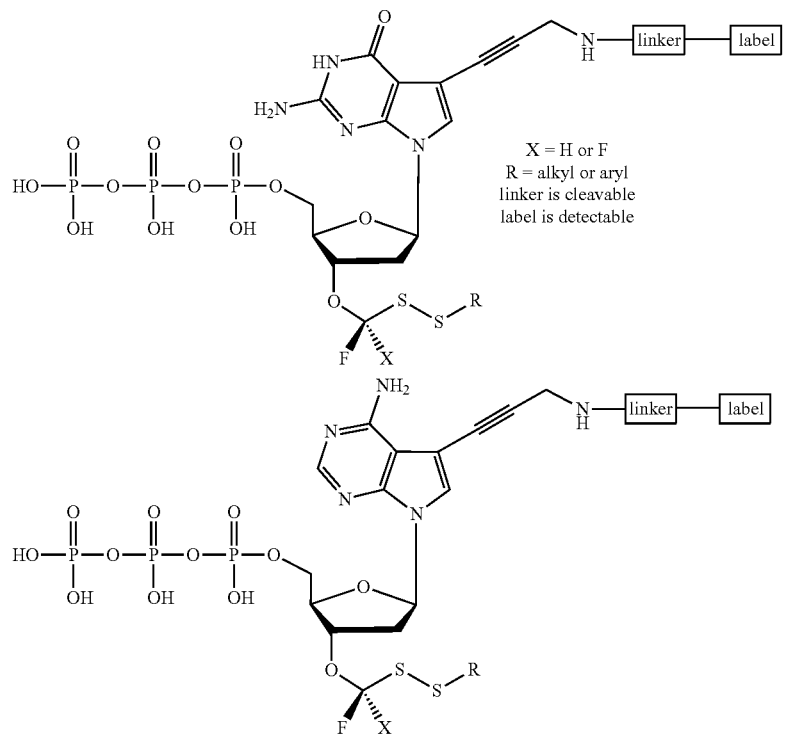
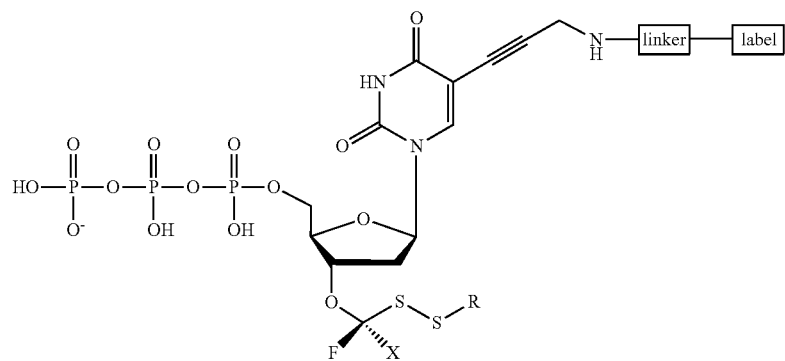

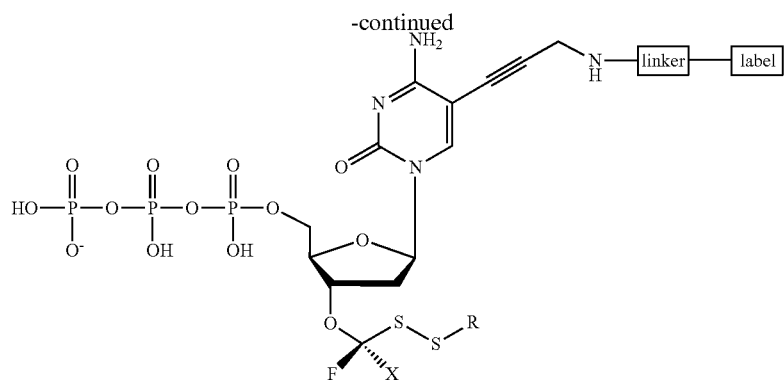

Scheme 08 below shows three examples of cleavable linkers, wherein it is understood that the terminating hydrogens (e.g., H of the hydroxyl and H of the amine) represent leaving groups to form a divalent moiety.

Scheme 08

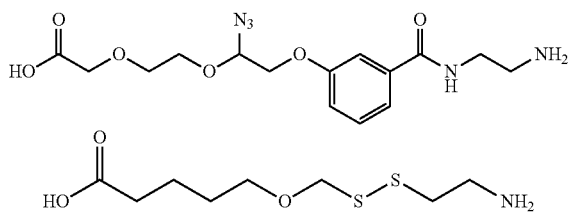

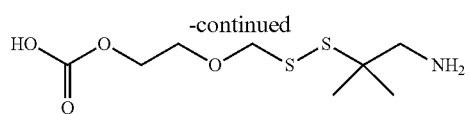

Scheme 09 shows examples of 3' mono and difluoro disulfide reversible terminators with azido linker off the base. Note the monofluoro carbon is chiral and results in a mixture of diastereoisomers which can be separated by HPLC. Either diastereoisomer can be used or the mixture can be used. (X=H or F; R=alkyl or aryl).

Scheme 09

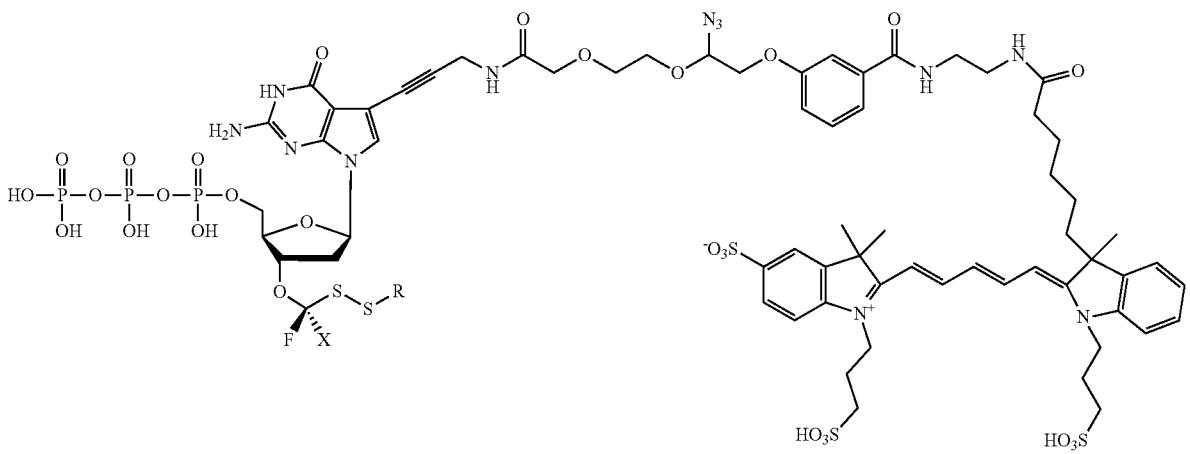

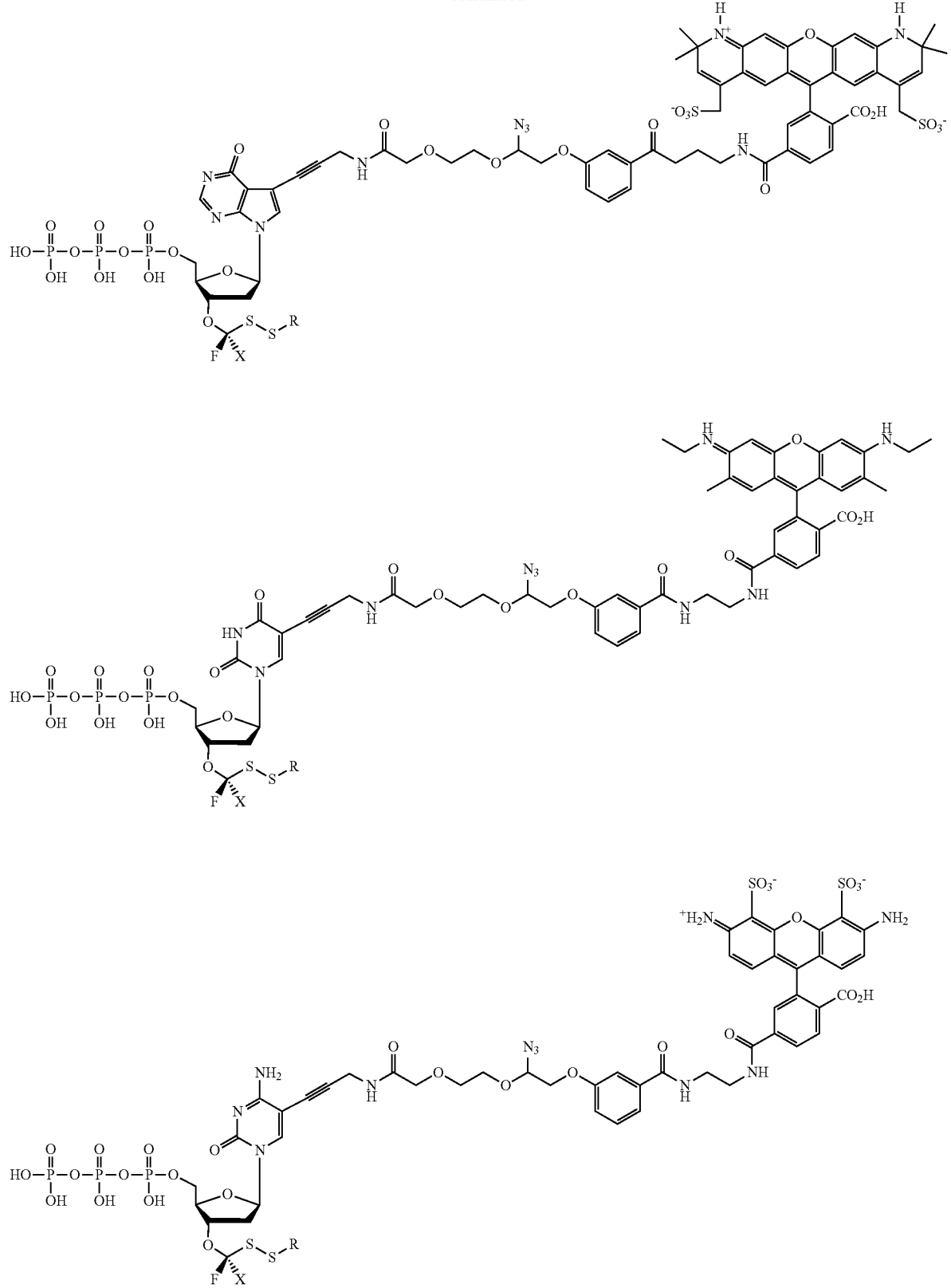
Scheme 10 shows examples of 3' mono and difluoro azido reversible terminators with azido linker off the base. Note the monofluoro carbon is chiral and results in a mixture of diastereoisomers which can be separated by HPLC. Either diastereoisomer can be used or the mixture can be used. (X=H or F; R=alkyl or aryl)

Scheme 10
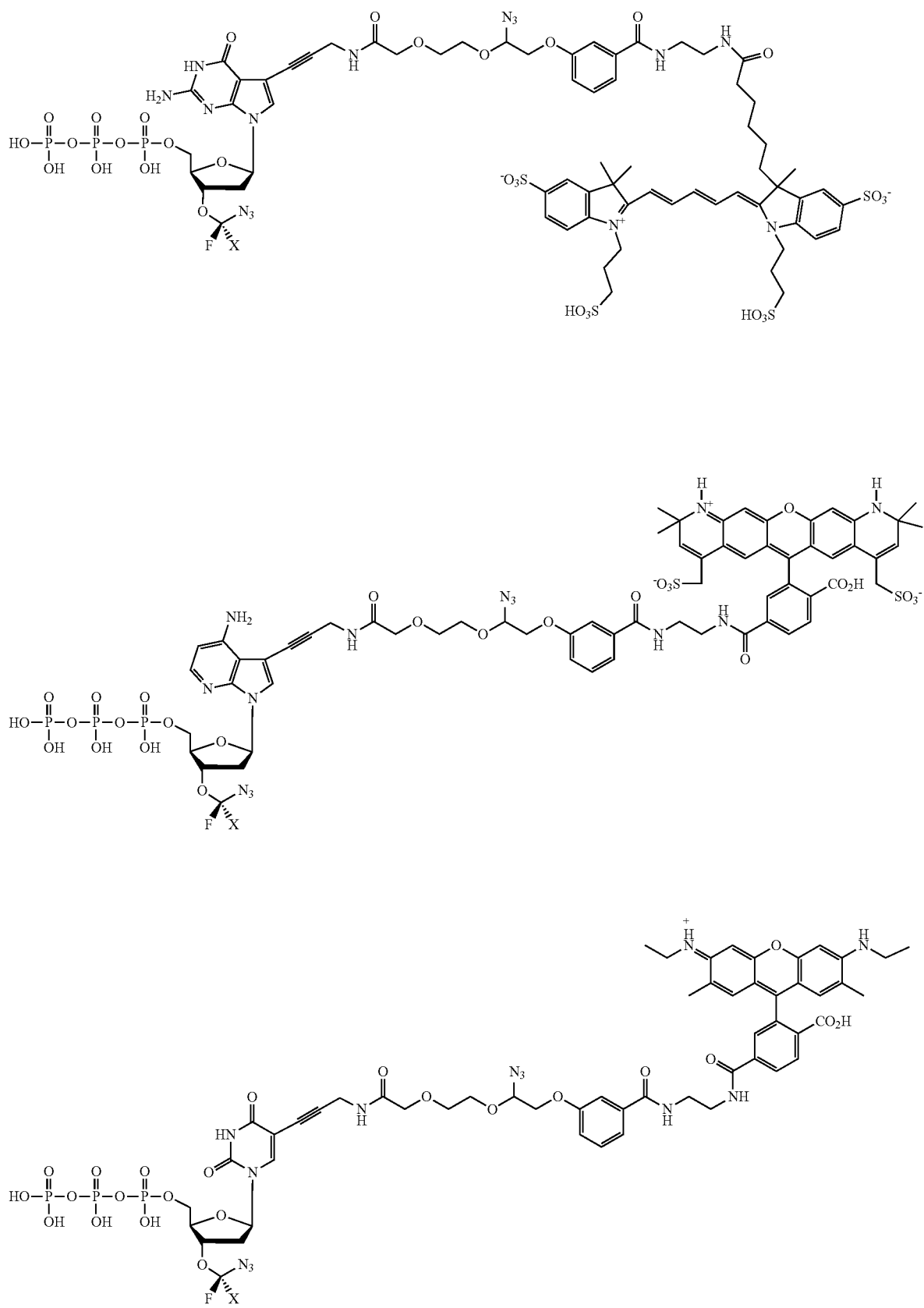

441
442
-continued
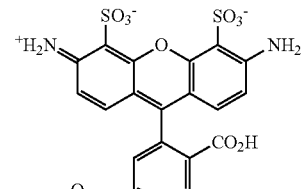
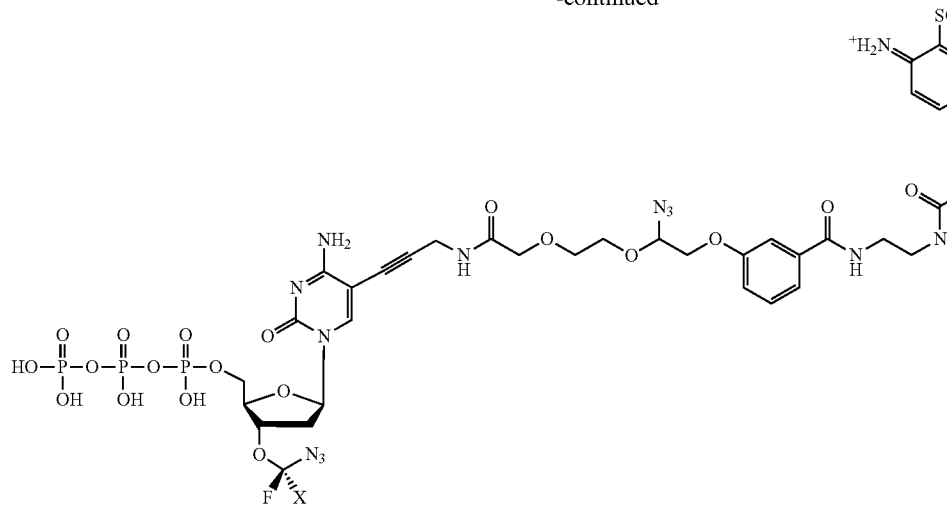
Scheme 11 shows examples of 3' mono and difluoro azido reversible terminators with disulfide linker off the base. Note the monofluoro carbon is chiral and results in a mixture of diastereoisomers which can be separated by HPLC. Either diastereoisomer can be used or the mixture can be used. (X=H or F; R=alkyl or aryl)
Scheme 11
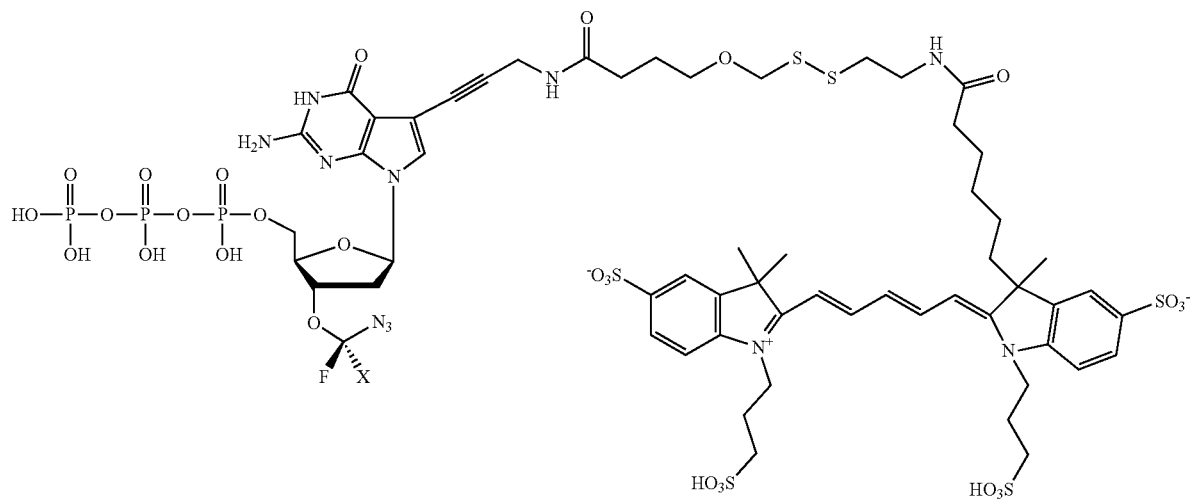

443
444
-continued
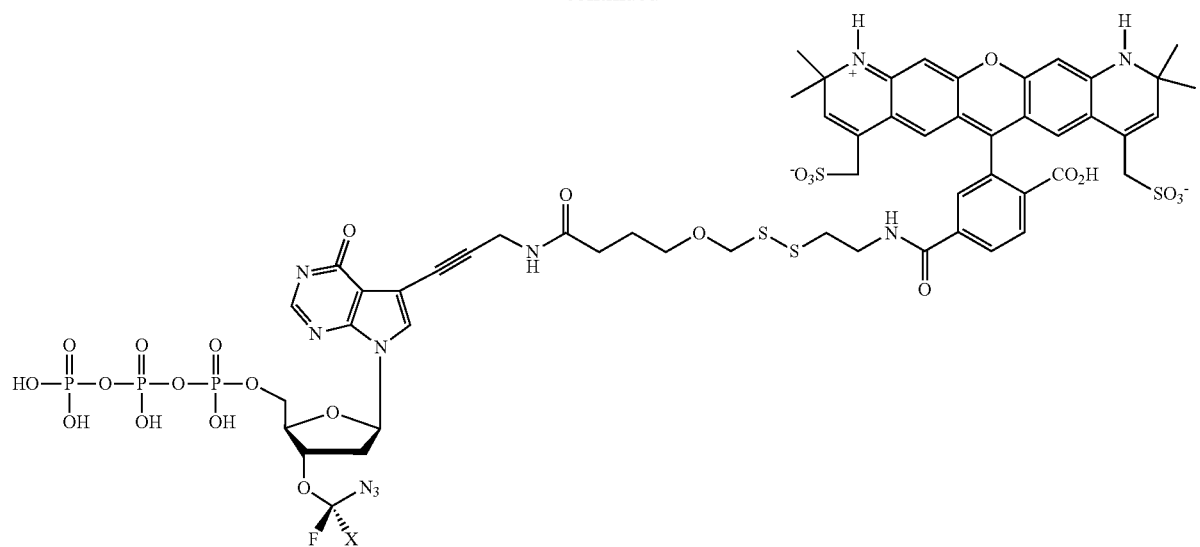
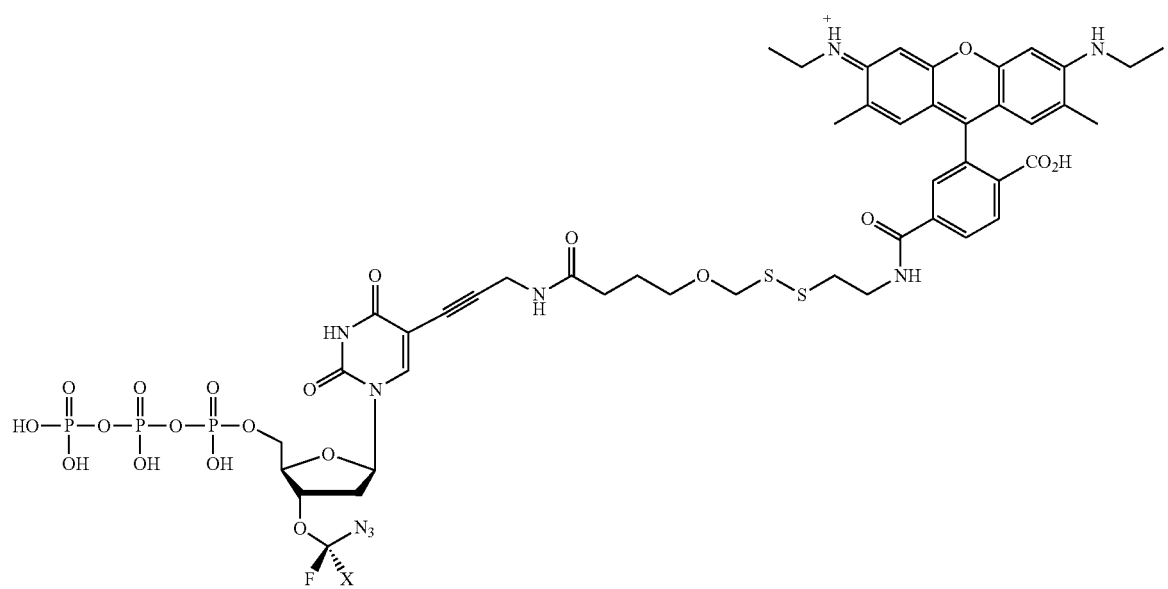

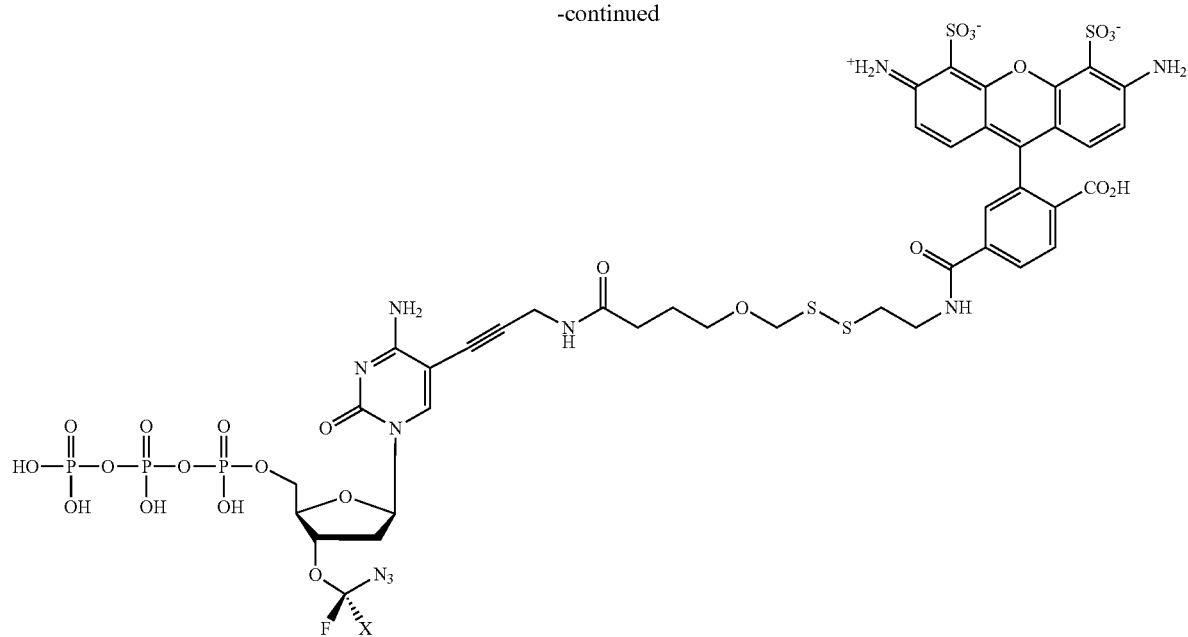
Scheme 12 below shows examples of 3' mono and difluoro disulfide reversible terminators with disulfide linker off the base. Note the monofluoro carbon is chiral and results in a mixture of diastereoisomers which can be separated by HPLC. Either diastereoisomer can be used or the mixture can be used. (X=H or F; R=alkyl or aryl).
Scheme 12
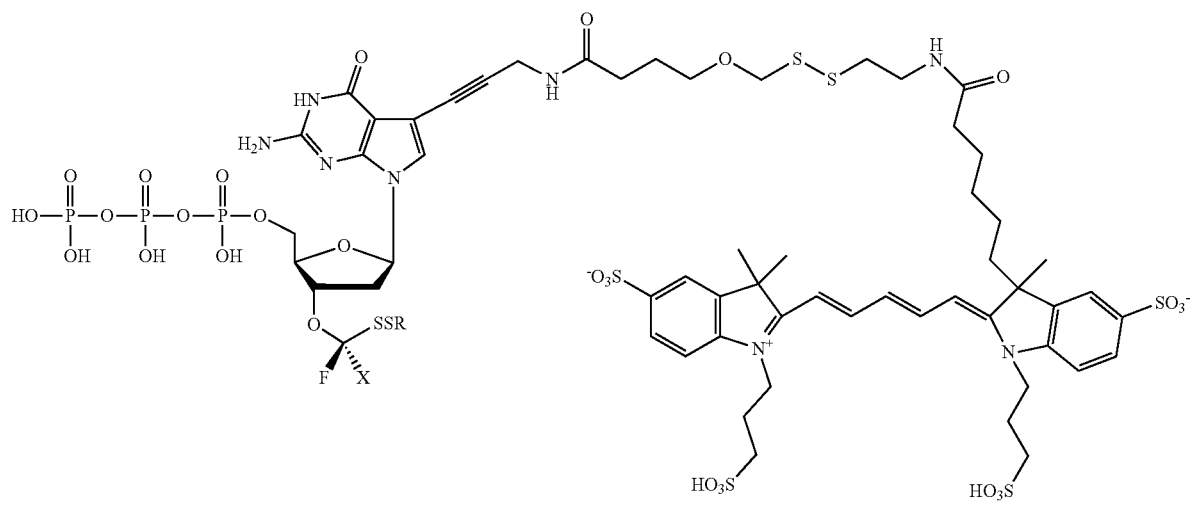

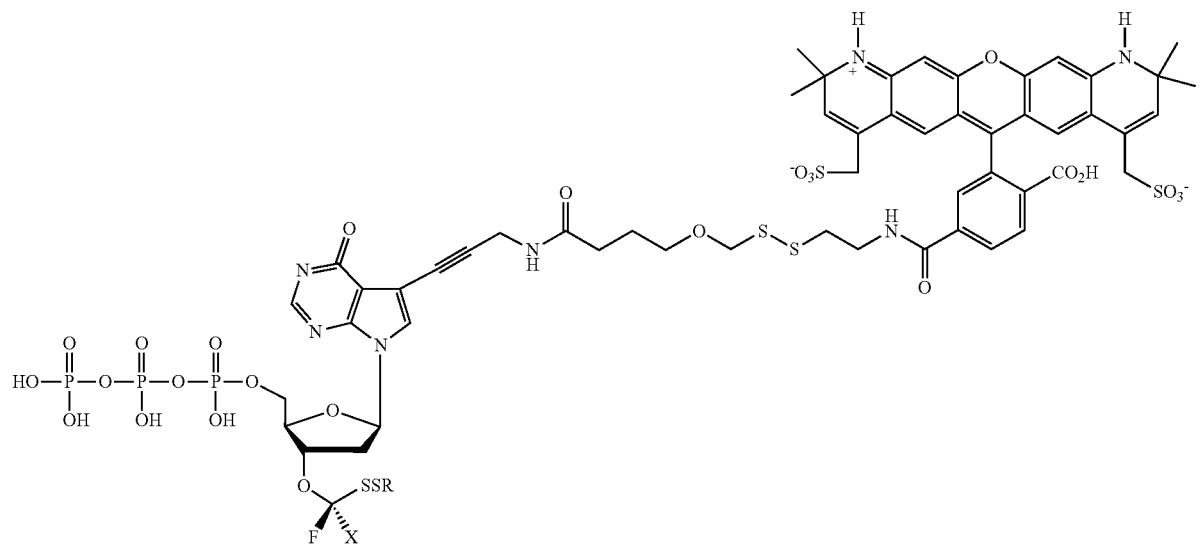
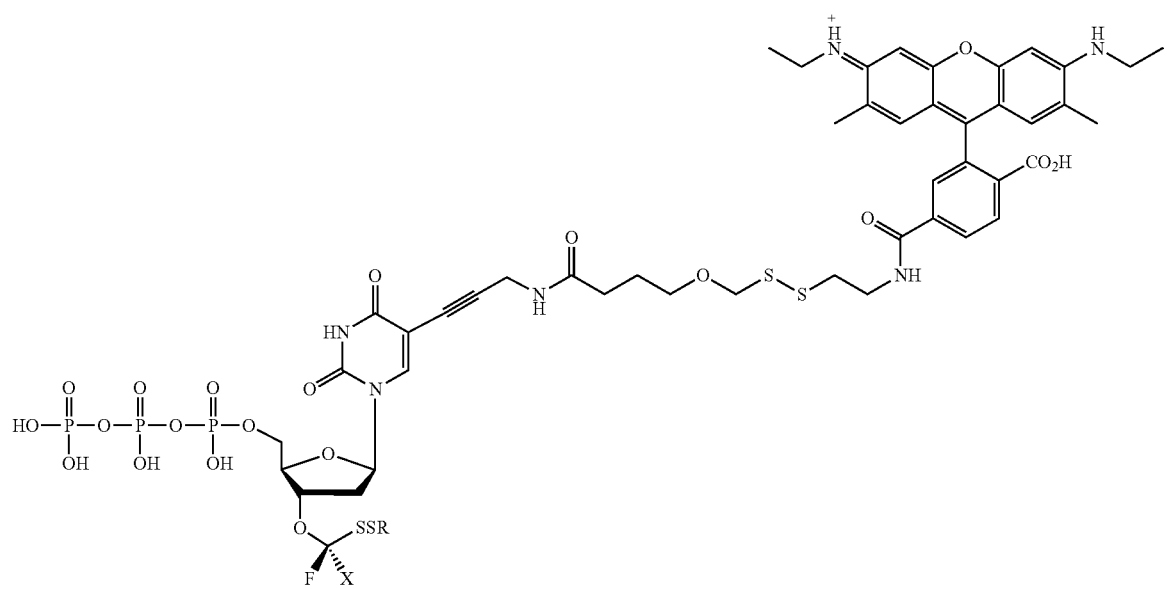

449 450
-continued
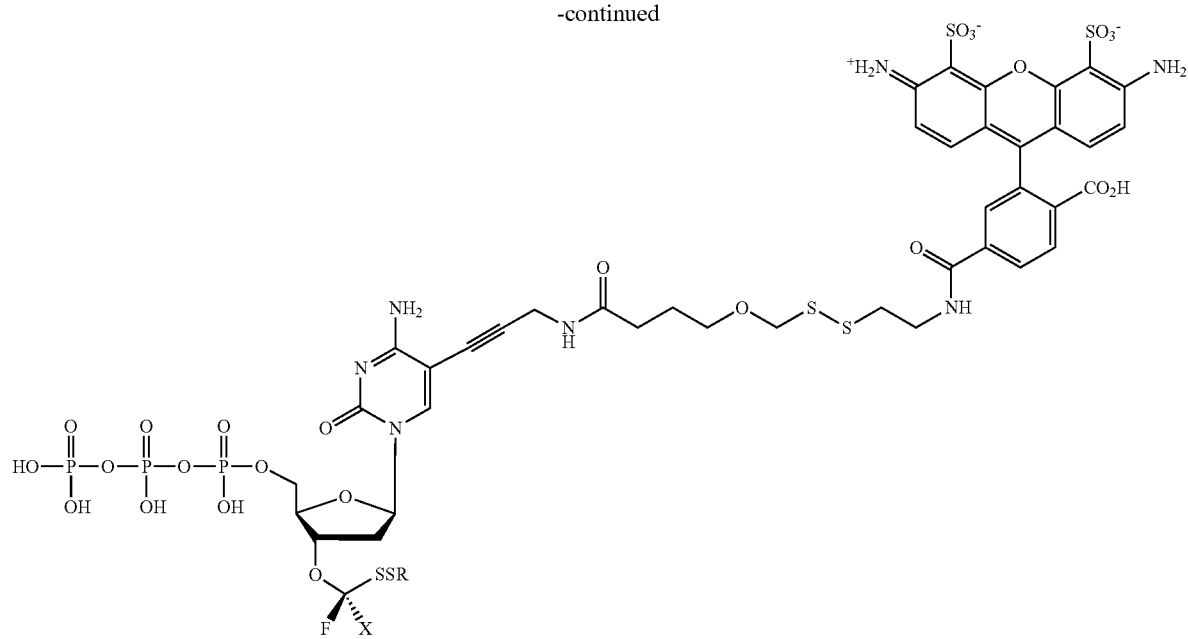
Scheme 13: Synthesis of 3'RO-CH(N₃)-N₃ nucleotides.
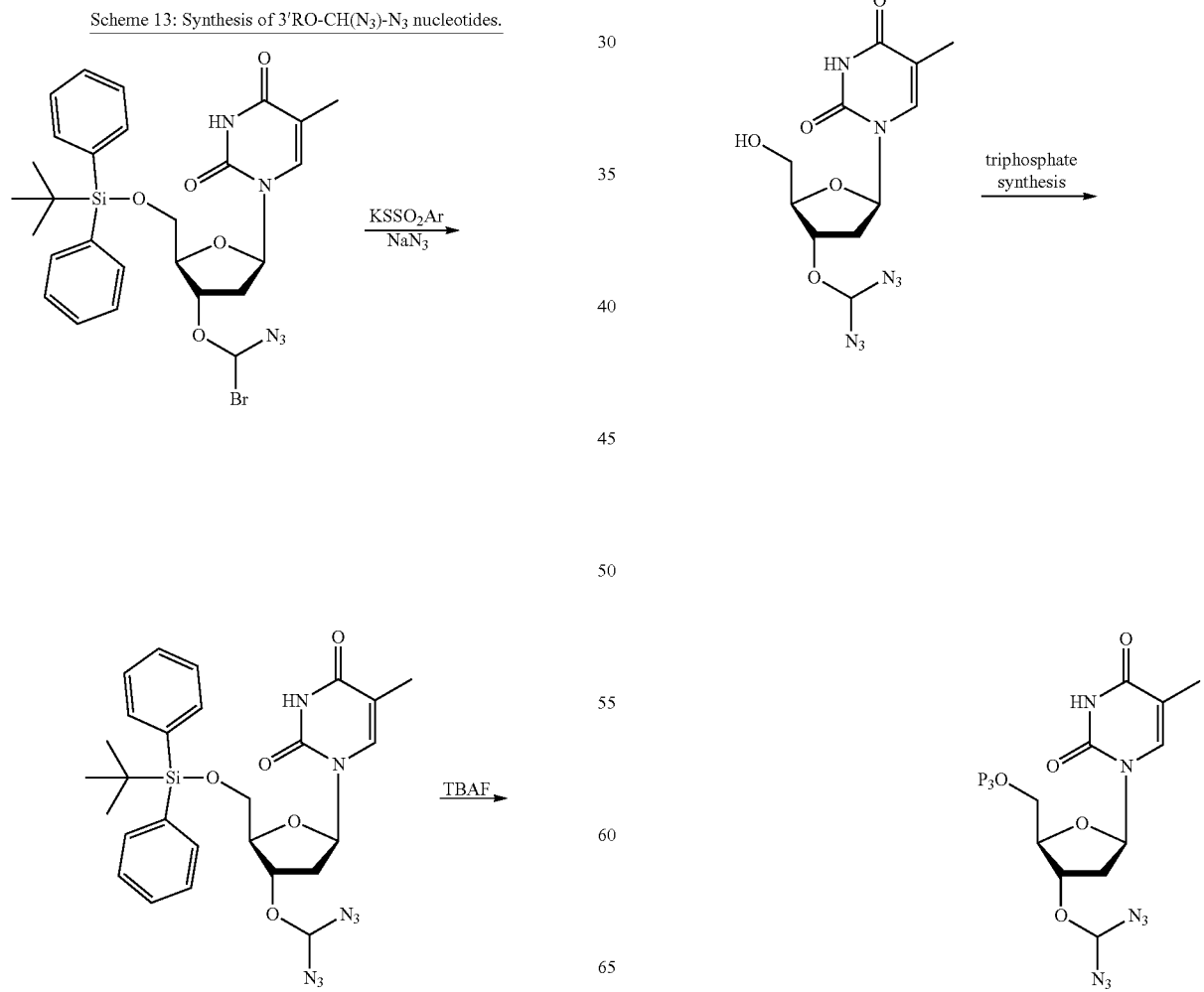

Scheme 14: Synthesis of 3'RO-CH(N₃)-SSBut nucleotides.
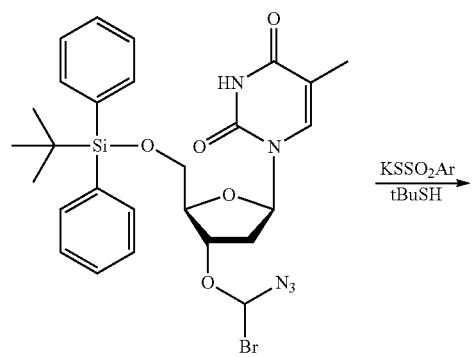
KSSO₂Ar
tBuSH
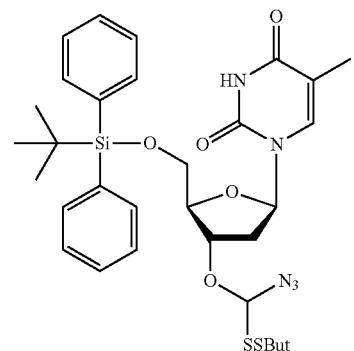
TBAF
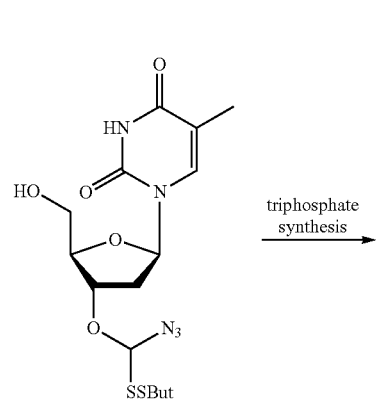
triphosphate synthesis
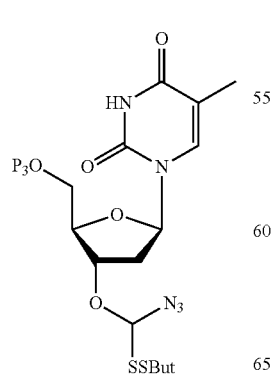
Scheme 15: Synthesis of 3'RO-CH(CN)-SSBut nucleotides.
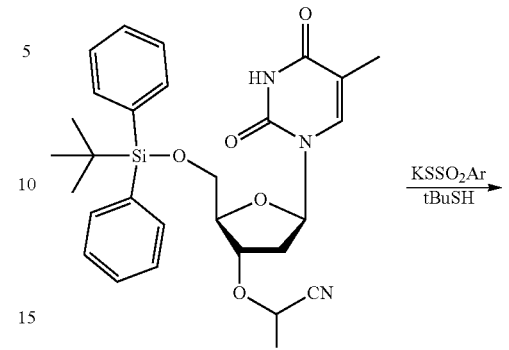
KSSO₂Ar
tBuSH
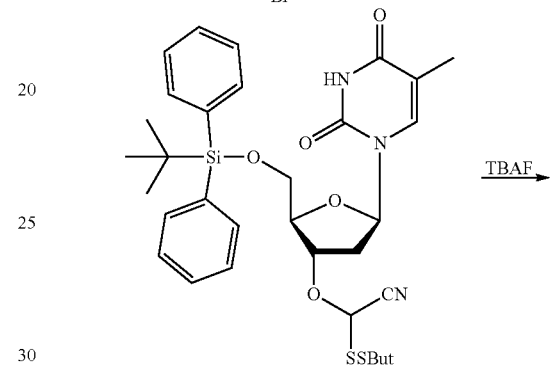
TBAF
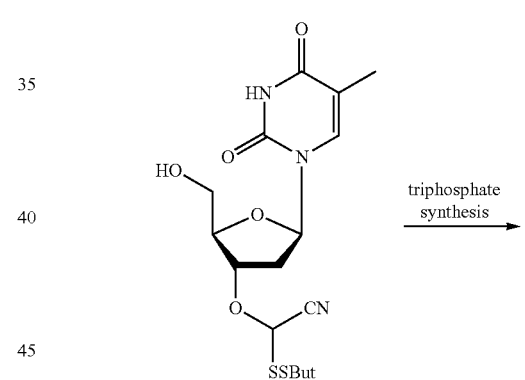
triphosphate synthesis
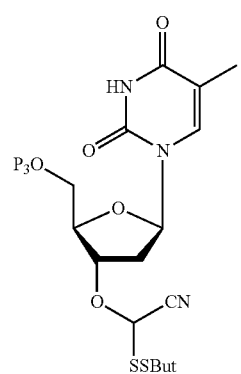

Scheme 15. Synthesis of 3'RO-CH(CN)-N₃ nucleotides.
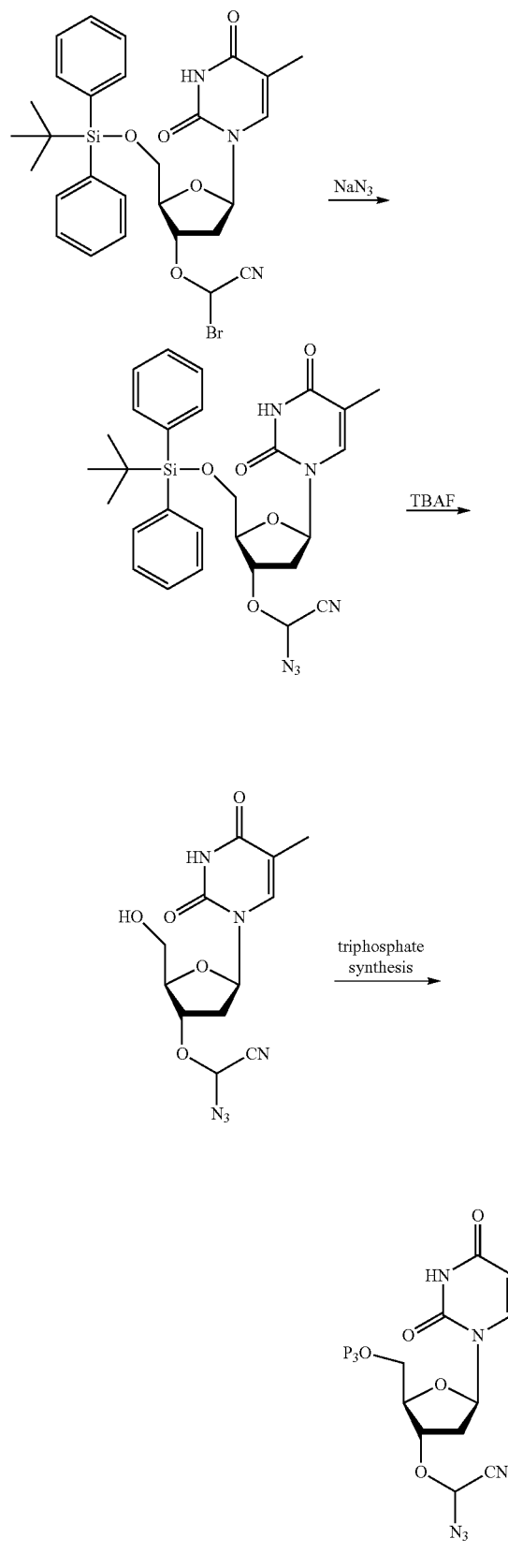
What is claimed is:
1. A nucleotide analogue having the formula:
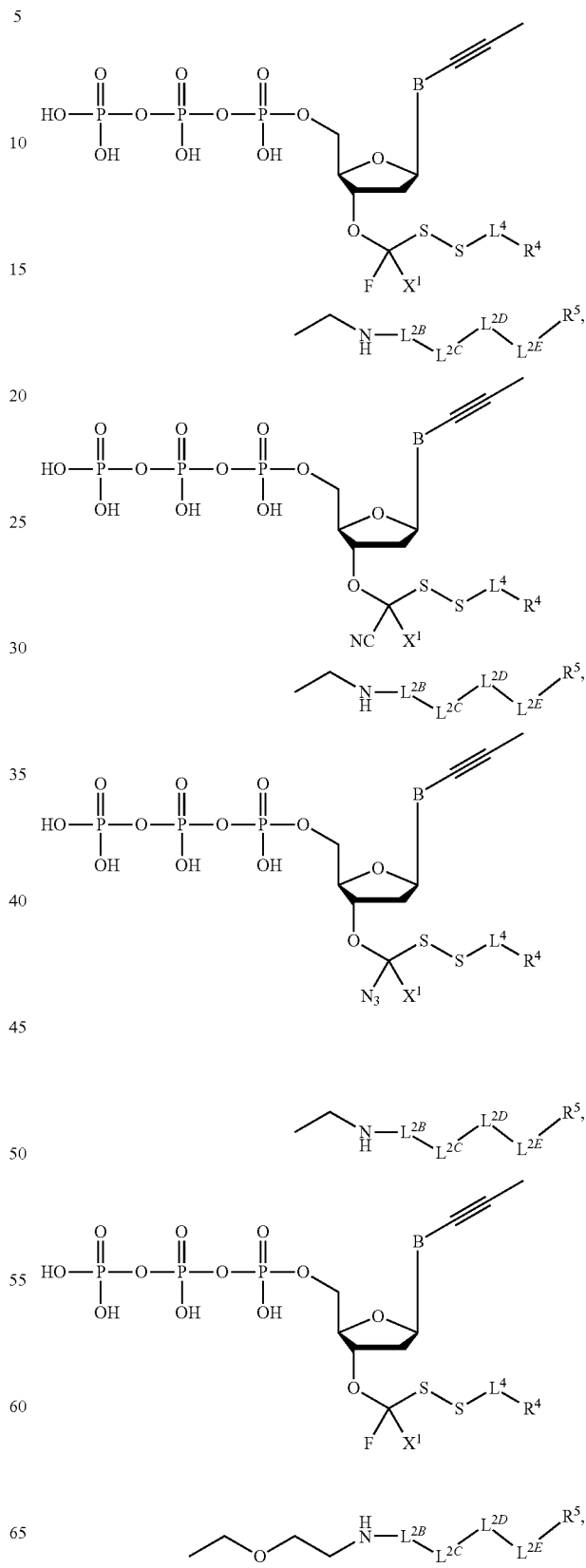

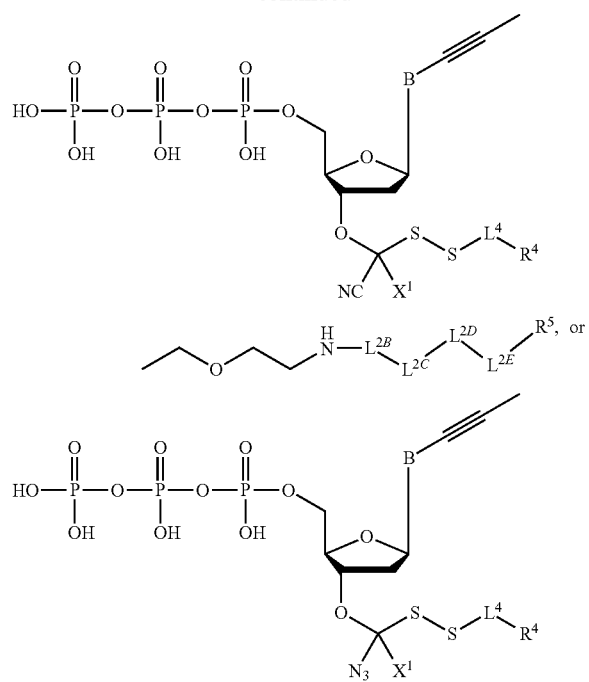

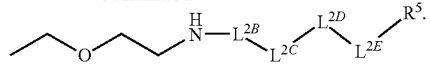

wherein
B is a base or analogue thereof;
$L^{2B}$, $L^{2C}$, $L^{2D}$, and $L^{2E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein at least one of $L^{2A}$, $L^{2B}$, $L^{2C}$, $L^{2D}$, and $L^{2E}$ is not a bond;
$L^4$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is a detectable label, an anchor moiety, or an affinity anchor moiety; and
$X^1$ is hydrogen, halogen, —N$_3$, or —CN.
2. The nucleotide analogue of claim 1, having the formula:

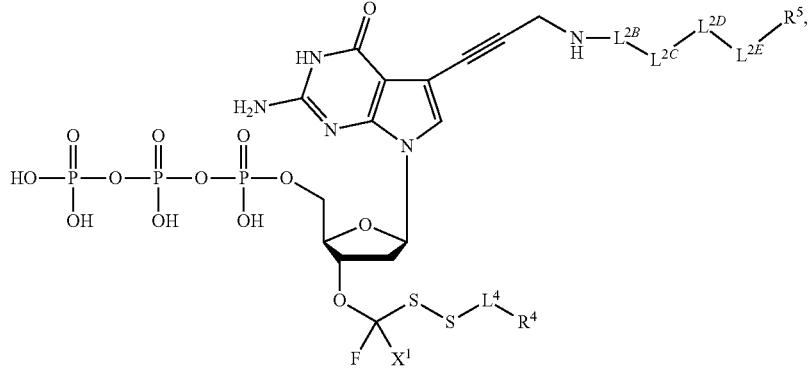

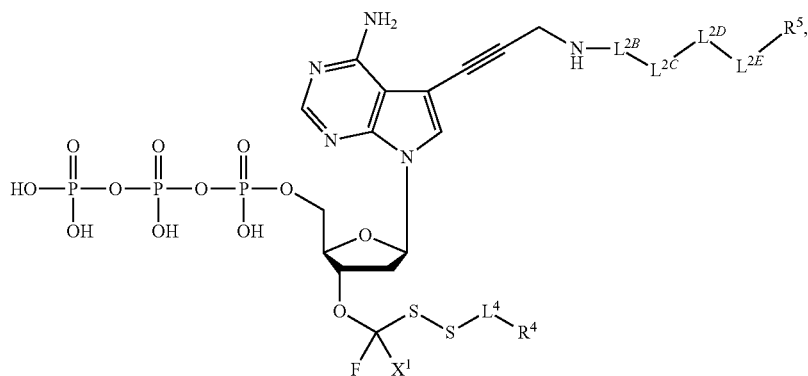

-continued
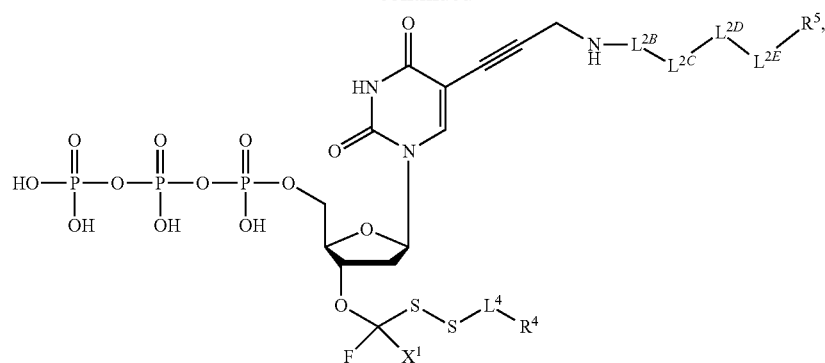
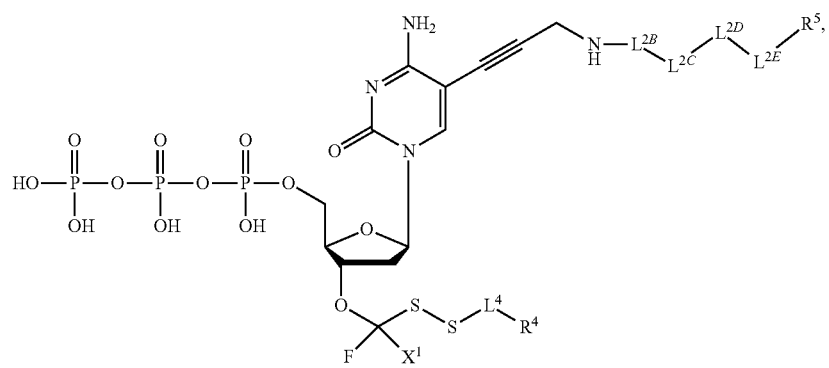
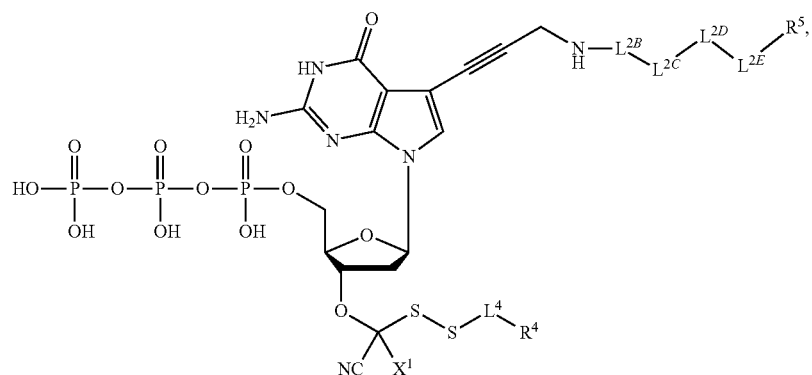
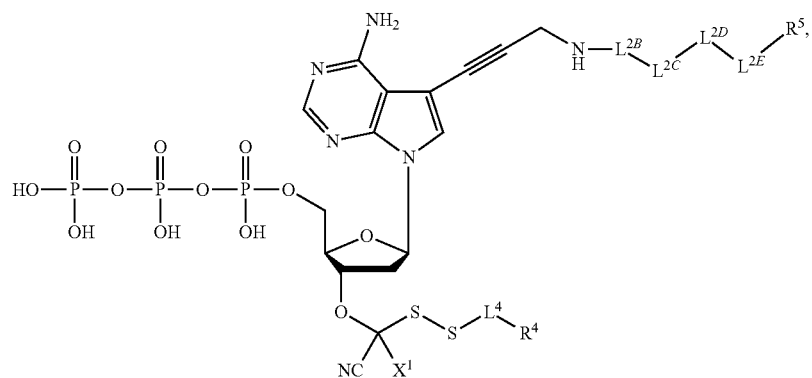

-continued
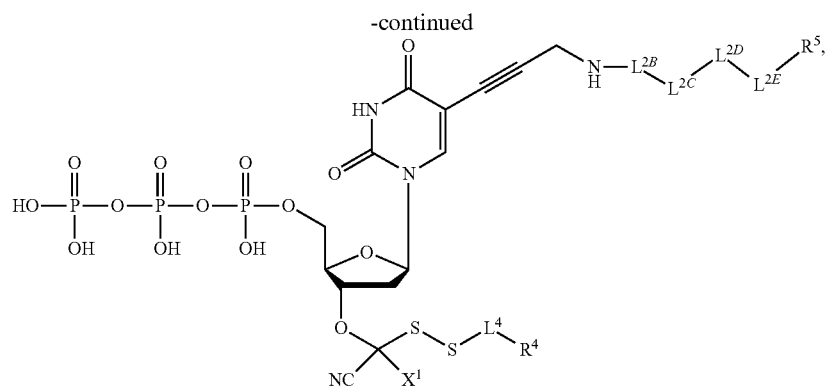
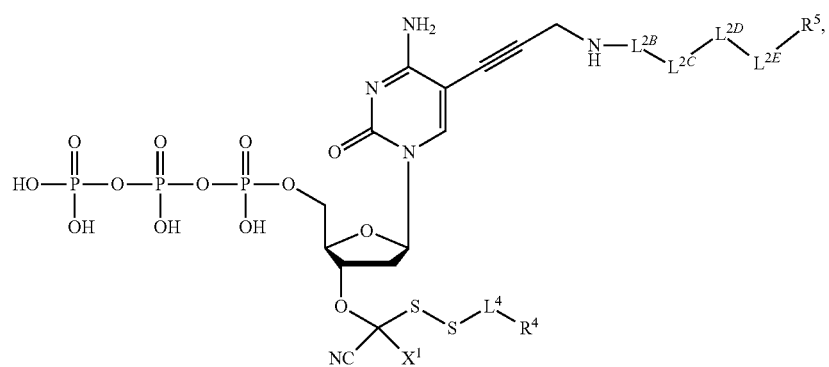
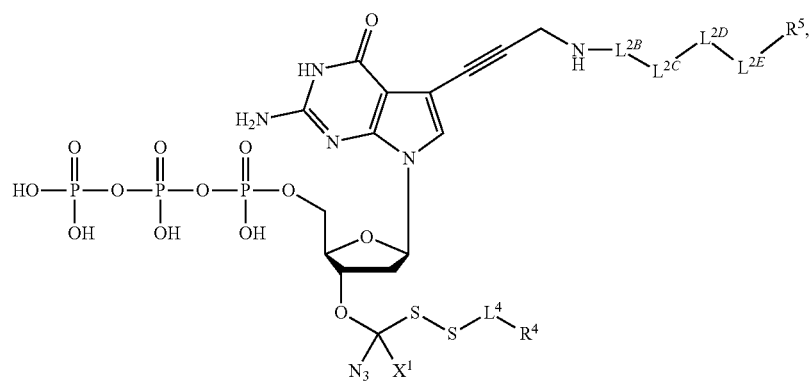
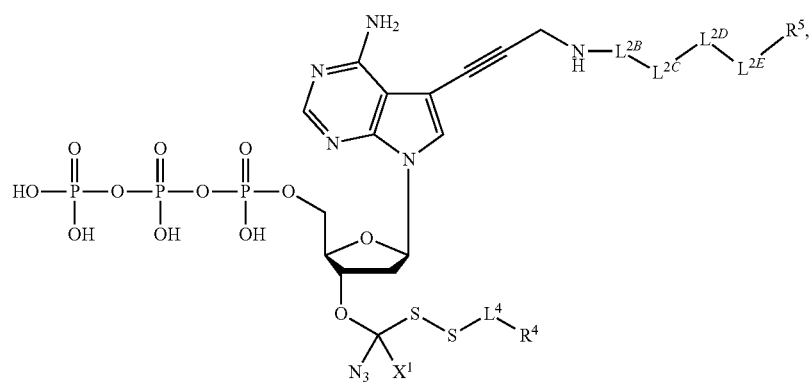

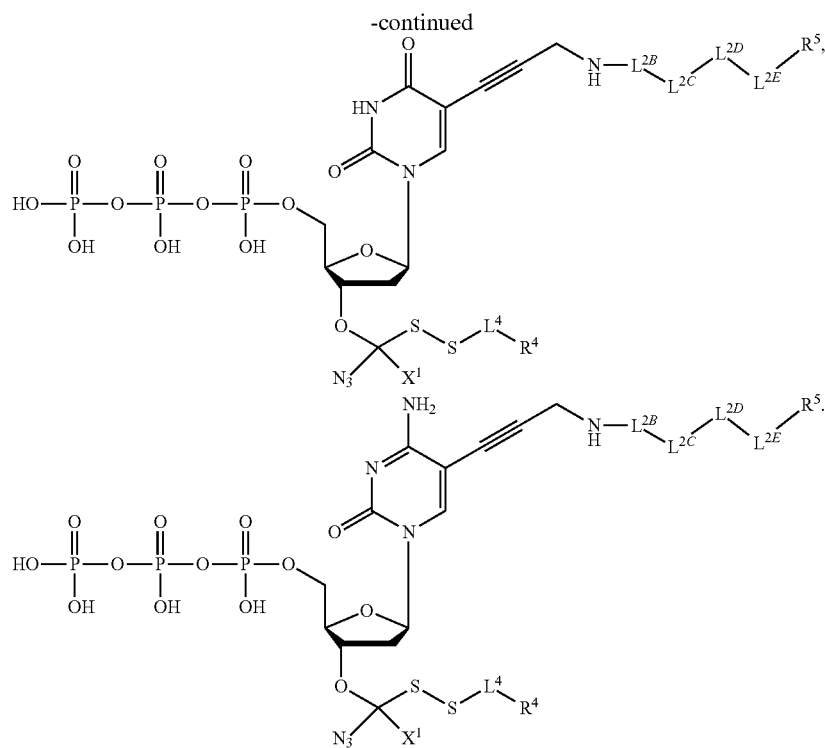

3. The nucleotide analogue of claim 1, wherein $X^1$ is —F.

4. The nucleotide analogue of claim 1, wherein $X^1$ is hydrogen.

5. The nucleotide analogue of claim 1, wherein $X^1$ is —Cl.

6. The nucleotide analogue of claim 1, wherein $X^1$ is —Br.

7. The nucleotide analogue of claim 1, wherein $X^1$ is —I.

8. The nucleotide analogue of claim 1, wherein $L^4$ is substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

9. The nucleotide analogue of claim 1, wherein $L^4$ is a bond or an unsubstituted $C_1$-$C_4$ alkylene.

10. The nucleotide analogue of claim 1, wherein $R^4$ is substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

11. The nucleotide analogue of claim 1, wherein $R^4$ is substituted $C_1$-$C_6$ alkyl.

12. The nucleotide analogue of claim 1, wherein $R^4$ is unsubstituted $C_1$-$C_6$ alkyl.

13. The nucleotide analogue of claim 1, wherein $R^4$ is substituted phenyl.

14. The nucleotide analogue of claim 1, wherein $R^4$ is unsubstituted phenyl.

15. The nucleotide analogue of claim 1, wherein $R^5$ is a detectable label.

16. A nucleic acid polymerase complex, wherein said nucleic acid polymerase is bound to a nucleotide analogue of claim 1.

17. A method for sequencing a nucleic acid, comprising:
(i) incorporating in series with a nucleic acid polymerase, within a reaction vessel, one of four different labeled nucleotide analogues into a primer to create an extension strand, wherein said primer is hybridized to said nucleic acid and wherein each of the four different labeled nucleotide analogues comprise a unique detectable label;
(ii) detecting said unique detectable label of each incorporated nucleotide analogue, so as to thereby identify each incorporated nucleotide analogue in said extension strand, thereby sequencing the nucleic acid;
wherein each of said four different labeled nucleotide analogues is of the structure of claim 1.

18. A method of incorporating a nucleotide analogue into a primer, the method comprising combining a polymerase, a primer hybridized to nucleic acid template and a nucleotide analogue within a reaction vessel and allowing said polymerase to incorporate said nucleotide analogue into said primer thereby forming an extended primer, wherein said nucleotide analogue is of the structure of claim 1.

* * * * *